(12) United States Patent
Furst et al.

(10) Patent No.: US 11,401,278 B2
(45) Date of Patent: Aug. 2, 2022

(54) MACROCYCLIC INDOLE DERIVATIVES

(71) Applicants: The Broad Institute, Inc., Cambridge, MA (US); Bayer Aktiengesellschaft, Leverkusen (DE); Bayer Pharma Aktiengesellschaft, Berlin (DE)

(72) Inventors: Laura Furst, Cambridge, MA (US); Michael H. Serrano-Wu, Cambridge, MA (US); Chris Lemke, Cambridge, MA (US); David McKinney, Cambridge, MA (US); Mark Fitzgerald, Cambridge, MA (US); Christopher Nasveschuk, Cambridge, MA (US); Kiel Lazarski, Cambridge, MA (US); Steven J. Ferrara, Cambridge, MA (US); Guo Wei, Cambridge, MA (US); Patrick R. McCarren, Cambridge, MA (US); Kai Thede, Leverkusen (DE); Anne Mengel, Leverkusen (DE); Clara Christ, Leverkusen (DE); Joachim Kuhnke, Leverkusen (DE); Sarah Anna Liesa Johannes, Leverkusen (DE); Philipp Buchgraber, Leverkusen (DE); Ulrich Klar, Leverkusen (DE); Ulrike Rauh, Leverkusen (DE); Stefan Kaulfuss, Leverkusen (DE); Amaury Ernesto Fernandez-Montalvan, Leverkusen (DE); Nicolas Werbeck, Leverkusen (DE); Ursula Mönning, Leverkusen (DE); Katrin Nowak-Reppel, Leverkusen (DE)

(73) Assignees: The Broad Institute, Inc., Cambridge, MA (US); Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/764,672

(22) PCT Filed: Nov. 15, 2018

(86) PCT No.: PCT/EP2018/081381
§ 371 (c)(1),
(2) Date: May 15, 2020

(87) PCT Pub. No.: WO2019/096911
PCT Pub. Date: May 23, 2019

(65) Prior Publication Data
US 2021/0292341 A1 Sep. 23, 2021

Related U.S. Application Data

(60) Provisional application No. 62/588,055, filed on Nov. 17, 2017.

(51) Int. Cl.
*C07D 513/14* (2006.01)
*A61P 35/02* (2006.01)
(Continued)

(52) U.S. Cl.
CPC ........ *C07D 513/14* (2013.01); *A61K 31/4162* (2013.01); *A61K 31/454* (2013.01);
(Continued)

(58) Field of Classification Search
CPC .................................................. C07D 513/14
(Continued)

(56) References Cited

U.S. PATENT DOCUMENTS 10,981,932 B2   4/2021   Johannes et al.
2015/0336925 A1   11/2015   Lee et al.
(Continued)

FOREIGN PATENT DOCUMENTS

WO   WO-2008/130970 A1   10/2008
WO   WO-2008/131000 A2   10/2008
(Continued)

OTHER PUBLICATIONS

Zhang et al., "Research progress of GSK-3 inhibitors," Progress in Chemistry, 19(4): 614-623 (2007).
(Continued)

*Primary Examiner* — Taofiq A Solola
(74) *Attorney, Agent, or Firm* — Foley Hoag LLP; David P. Halstead

(57) ABSTRACT

The present invention relates to macrocyclic indole derivatives of general formula (I):

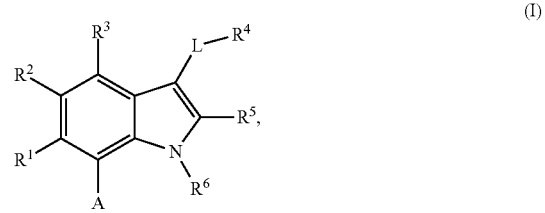

in which $R^1$, $R^2$, $R^3$, $R^4$, $R^5$, $R^6$, A and L are as defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative disorders, as a sole agent or in combination with other active ingredients.

13 Claims, No Drawings
Specification includes a Sequence Listing.

(51) Int. Cl.
    *A61P 35/00*       (2006.01)
    *A61K 31/4162*   (2006.01)
    *A61K 31/454*    (2006.01)
    *A61K 31/5377*   (2006.01)
    *A61K 45/06*    (2006.01)

(52) U.S. Cl.
    CPC .......... *A61K 31/5377* (2013.01); *A61K 45/06* (2013.01); *A61P 35/00* (2018.01); *A61P 35/02* (2018.01)

(58) Field of Classification Search
    USPC ...................................................... 514/233.2
    See application file for complete search history.

(56) References Cited

U.S. PATENT DOCUMENTS

| | | |
|---|---|---|
| 2016/0106731 A1 | 4/2016 | Lee et al. |
| 2017/0305926 A1 | 10/2017 | Hird et al. |
| 2020/0087322 A1 | 3/2020 | Johannes et al. |
| 2021/0079018 A1 | 3/2021 | Ferrara et al. |
| 2021/0253598 A1 | 8/2021 | Thede et al. |
| 2021/0269456 A1 | 9/2021 | Thede et al. |
| 2021/0277022 A1 | 9/2021 | Thede et al. |
| 2021/0292341 A1 | 9/2021 | Furst et al. |

FOREIGN PATENT DOCUMENTS

| | | |
|---|---|---|
| WO | WO-2014/047427 A2 | 3/2014 |
| WO | WO-2015/031608 A1 | 3/2015 |
| WO | WO-2015/148854 A1 | 10/2015 |
| WO | WO-2017/152076 A1 | 9/2017 |
| WO | WO-2017/182625 A1 | 10/2017 |
| WO | WO-2017/198341 A1 | 11/2017 |
| WO | WO-2018/098534 A1 | 6/2018 |
| WO | WO-2019/096905 A1 | 5/2019 |
| WO | WO-2019/096907 A1 | 5/2019 |
| WO | WO-2019/096909 A1 | 5/2019 |
| WO | WO-2019/096911 A1 | 5/2019 |
| WO | WO-2019/096914 A1 | 5/2019 |
| WO | WO-2019/096922 A1 | 5/2019 |
| WO | WO-2020/151738 A1 | 7/2020 |
| WO | WO-2020/236556 A1 | 11/2020 |

OTHER PUBLICATIONS

Adams et al., "The Bcl-2 apoptotic switch in cancer development and therapy," Oncogene, 26:1324-1337 (2007).
Beroukhim et al., "The Landscape of Somatic Copy-Number Alteration Across Human Cancers," Nature, 463(7283):899-905 (2010).
Glaser et al., "Anti-apoptotic Mcl-1 is essential for the development and sustained growth of acute myeloid leukemia," Genes Dev, 26:120-125 (2012).
Hanahan et al., "Hallmarks of Cancer: The Next Generation," Cell 144(5):646-674 (2011).
International Preliminary Report on Patentability for International Application No. PCT/EP2017/000629 dated Nov. 20, 2018.
International Preliminary Report on Patentability for International Application No. PCT/EP2018/081370 dated May 19, 2020.
International Preliminary Report on Patentability for International Application No. PCT/EP2018/081374 dated May 19, 2020.
International Preliminary Report on Patentability for International Application No. PCT/EP2018/081378 dated May 19, 2020.
International Preliminary Report on Patentability for International Application No. PCT/EP2018/081381 dated May 19, 2020.
International Preliminary Report on Patentability for International Application No. PCT/EP2018/081388 dated May 19, 2020.
International Preliminary Report on Patentability for International Application No. PCT/EP2018/081406 dated May 19, 2020.
International Search Report and Written Opinion for International Application No. PCT/EP2017/000629 dated Sep. 6, 2017.
International Search Report and Written Opinion for International Application No. PCT/EP2018/081370 dated Feb. 13, 2019.
International Search Report and Written Opinion for International Application No. PCT/EP2018/081374 dated Feb. 13, 2019.
International Search Report and Written Opinion for International Application No. PCT/EP2018/081378 dated Jan. 9, 2019.
International Search Report and Written Opinion for International Application No. PCT/EP2018/081381 dated Jan. 15, 2019.
International Search Report and Written Opinion for International Application No. PCT/EP2018/081388 dated Feb. 14, 2019.
International Search Report and Written Opinion for International Application No. PCT/EP2018/081406 dated Feb. 11, 2019.
International Search Report and Written Opinion for International Application No. PCT/US2020/033067 dated Jul. 19, 2020.
Korsmeyer, "BCL-2 Gene Family and the Regulation of Programmed Cell Death," Cancer Res Suppl, 59(7):1693s-1700s (1999).
Pelz et al., "Discovery of 2-Indole-acylsulfonamide Myeloid Cell Leukemia 1 (Mcl-1) Inhibitors Using Fragment-Based Methods," Journal of Medicinal Chemistry, 59(5): 2054-2066 (2016).
Wertz et al., "Sensitivity to antitubulin chemotherapeutics is regulated by MCL1 and FBW7," Nature, 471:110-114 (2011).
Zhou et al., "MCL1 transgenic mice exhibit a high incidence of B-cell lymphoma manifested as a spectrum of histologic subtypes," Blood, 97(12):3902-3909 (2001).
Lee et al., "Discovery and biological characterization of potent and myeloid cell leukemia-1 inhibitors," FEBS Letters. 591: 240-251 (2017).

SEQUENCE LISTING

```
<160> NUMBER OF SEQ ID NOS: 5

<210> SEQ ID NO 1
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
```

Thr Pro Asp Lys Ala Phe Gln Asp Lys Leu Tyr Pro Phe Thr Trp Asp
65                  70                  75                  80

Ala Val Arg Tyr Asn Gly Lys Leu Ile Ala Tyr Pro Ile Ala Val Glu
            85                  90                  95

Ala Leu Ser Leu Ile Tyr Asn Lys Asp Leu Leu Pro Asn Pro Pro Lys
        100                 105                 110

Thr Trp Glu Glu Ile Pro Ala Leu Asp Lys Glu Leu Lys Ala Lys Gly
    115                 120                 125

Lys Ser Ala Leu Met Phe Asn Leu Gln Glu Pro Tyr Phe Thr Trp Pro
130                 135                 140

Leu Ile Ala Ala Asp Gly Gly Tyr Ala Phe Lys Tyr Glu Asn Gly Lys
145                 150                 155                 160

Tyr Asp Ile Lys Asp Val Gly Val Asp Asn Ala Gly Ala Lys Ala Gly
            165                 170                 175

Leu Thr Phe Leu Val Asp Leu Ile Lys Asn Lys His Met Asn Ala Asp
        180                 185                 190

Thr Asp Tyr Ser Ile Ala Glu Ala Ala Phe Asn Lys Gly Glu Thr Ala
    195                 200                 205

Met Thr Ile Asn Gly Pro Trp Ala Trp Ser Asn Ile Asp Thr Ser Lys
210                 215                 220

Val Asn Tyr Gly Val Thr Val Leu Pro Thr Phe Lys Gly Gln Pro Ser
225                 230                 235                 240

Lys Pro Phe Val Gly Val Leu Ser Ala Gly Ile Asn Ala Ala Ser Pro
            245                 250                 255

Asn Lys Glu Leu Ala Lys Glu Phe Leu Glu Asn Tyr Leu Leu Thr Asp
        260                 265                 270

Glu Gly Leu Glu Ala Val Asn Lys Asp Lys Pro Leu Gly Ala Val Ala
    275                 280                 285

Leu Lys Ser Tyr Glu Glu Leu Ala Lys Asp Pro Arg Ile Ala Ala
290                 295                 300

Thr Met Glu Asn Ala Gln Lys Gly Glu Ile Met Pro Asn Ile Pro Gln
305                 310                 315                 320

Met Ser Ala Phe Trp Tyr Ala Val Arg Thr Ala Val Ile Asn Ala Ala
            325                 330                 335

Ser Gly Arg Gln Thr Val Asp Glu Ala Leu Lys Asp Ala Gln Thr Gly
        340                 345                 350

Ser Ser Glu Leu Tyr Arg Gln Ser Leu Glu Ile Ile Ser Arg Tyr Leu
    355                 360                 365

Arg Glu Gln Ala Thr Gly Ala Ala Asp Thr Ala Pro Met Gly Ala Ser
370                 375                 380

Gly Ala Thr Ser Arg Lys Ala Leu Glu Thr Leu Arg Arg Val Gly Asp
385                 390                 395                 400

Gly Val Gln Arg Asn His Glu Thr Ala Phe Gln Gly Met Leu Arg Lys
            405                 410                 415

Leu Asp Ile Lys Asn Glu Asp Val Lys Ser Leu Ser Arg Val Met
        420                 425                 430

Ile His Val Phe Ser Asp Gly Val Thr Asn Trp Gly Arg Ile Val Thr
    435                 440                 445

Leu Ile Ser Phe Gly Ala Phe Val Ala Lys His Leu Lys Thr Ile Asn
450                 455                 460

Gln Glu Ser Cys Ile Glu Pro Leu Ala Glu Ser Ile Thr Asp Val Leu
465                 470                 475                 480

485                 490                 495

```
Val Arg Thr Lys Arg Asp Trp Leu Val Lys Gln Arg Gly Trp Asp Gly
            500                 505                 510

Phe Val Glu Phe Phe His Val
        515

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Biotin-PEG-PEG-PEG-PEG
<220> FEATURE:
<221> NAME/KEY: MOD_RES
<222> LOCATION: (8)..(8)
<223> OTHER INFORMATION: Norvaline
<220> FEATURE:
<221> NAME/KEY: MOD_RES
<222> LOCATION: (26)..(26)
<223> OTHER INFORMATION: Amidation

<400> SEQUENCE: 2

Pro Ala Glu Leu Glu Val Glu Val Ala Thr Gln Leu Arg Arg Phe Gly
1               5                   10                  15

Asp Lys Leu Asn Phe Arg Gln Lys Leu Leu
            20                  25

<210> SEQ ID NO 3
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175
```

```
His Leu Glu Pro Trp Ile Gln Glu Asn Gly Gly Trp Asp Thr Phe Val
            180                 185                 190

Glu Leu Tyr Gly Asn Asn Ala Ala Glu Ser Arg Lys Gly Gln Glu
        195                 200                 205

Arg Phe Asn Arg His His His His His His
    210                 215

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Biotin-PEG-PEG-PEG-PEG
<220> FEATURE:
<221> NAME/KEY: MOD_RES
<222> LOCATION: (15)..(15)
<223> OTHER INFORMATION: Norleucine
<220> FEATURE:
<221> NAME/KEY: MOD_RES
<222> LOCATION: (25)..(25)
<223> OTHER INFORMATION: Amidation

<400> SEQUENCE: 4

Asn Leu Trp Ala Ala Gln Arg Tyr Gly Arg Glu Leu Arg Arg Leu Ser
1               5                   10                  15

Asp Glu Phe Val Asp Ser Phe Lys Lys
            20                  25

<210> SEQ ID NO 5
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160
```

```
Ser Val Asn Arg Glu Met Ser Pro Leu Val Asp Asn Ile Ala Leu Trp
            165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
            195                 200                 205

Leu Phe Asp His His His His His His
    210                 215
```

MACROCYCLIC INDOLE DERIVATIVES

RELATED APPLICATIONS

This application is the U.S. national phase of International Patent Application No. PCT/EP2018/081381, filed Nov. 15, 2018, which claims the benefit of U.S. Provisional Application No. 62/588,055 filed on Nov. 17, 2017. The International Patent Application No. PCT/EP2018/081381 is hereby incorporated by reference in its entirety.

SEQUENCE LISTING

The instant application contains a Sequence Listing, which has been submitted electronically in ASCII format and is hereby incorporated by reference in its entirety. Said ASCII copy, created on May 3, 2021, is named BRH-01901_SL.txt and is 10,063 bytes in size.

BACKGROUND

The present invention covers macrocyclic indole derivatives of general formula (I) which inhibit the antiapoptotic activity of MCL-1 by inhibiting its interaction with proapoptotic proteins.

Apoptosis, also called programmed cell death, is a natural process which allows a damaged or unwanted cell to die in a controlled manner. Deregulation of this process leads to unrestrained cell proliferation and is thus a hallmark of cancer (Hanahan and Weinberg, 2011).

Apoptosis is highly controlled by proteins of the B-cell lymphoma 2 (BCL-2) family. These proteins are characterized by their conserved regions known as BCL-2 homology (BH) domains (BH1-BH4) (Korsmeyer, 1999) through which they interact with each other. The BCL-2 family can be divided into pro-apoptotic members including BAX, BAK, BAD, BID, BIM, BMF, NOXA, and PUMA, which induce cell death, and anti-apoptotic members such as BCL-2, BCL-XL, BCL-w, Bfl1-AI, and myeloid cell leukemia-1 (MCL-1) which block apoptosis (Adams and Cory, 2007). The relative expression level of these two opponent groups of the BCL-2 family will decide if a cell will go into apoptosis or not.

MCL-1 has been identified as an important therapeutic target in cancer. MCL-1 is highly expressed in a variety of human cancers, and amplification of the MCL-1 locus is one of the most frequent somatic genetic events in human cancer, further pointing to its centrality in the pathogenesis of malignancy (Beroukhim et al., 2010). Its expression has been linked to deregulated anti-apoptotic pathways in cancer, thus leading to increased cancer cell survival, tumor development (Zhou et al., 2001) and resistance to anticancer therapies (Wertz et al., 2011). MCL-1 protein has been shown to mediate survival in models of acute myeloid leukemia (Glaser et al., 2012), lymphomas (Kelly et al., 2014) and multiple myeloma (Zhang et al., 2002). Many chemotherapeutics as well as radiation aim at inducing apoptosis in cancer cells. However, in malignant cells, apoptotic signaling is often deregulated, leading to uncontrolled growth and therapeutic resistance. One key resistance mechanism to apoptosis is to upregulate or genetically amplify MCL-1.

MCl-1 is a major inhibitor of apoptosis in cancer. MCL-1 is the largest member of the anti-apoptotic Bcl-2 proteins. Its expression is tightly controlled with a half-life of only 1-4 h. With its BH-3 domain, MCL-1 tightly binds to BH-3 only containing pro-apoptotic proteins such as BAK or BAX and hinders them from inducing pores in the mitochondrial membrane, thereby blocking the intrinsic apoptotic pathway.

Thus, the specific inhibition of the interaction of MCL-1 with BH-3 only containing pro-apoptotic proteins like BAK or BAX represents a very attractive therapeutic principle to induce apoptosis in cancer cells and to address resistance against chemotherapeutics, radiation and new targeted agents. However, from WO 2015/148854, US 2016/0106731, WO 2008/130970, some indole derivatives are known as MCL-1 inhibitors. As no inhibitors have shown efficacy in the clinic yet, there is still a need for further MCL-1 inhibitors to be provided.

SUMMARY

It has now been found that the compounds of the present invention effectively inhibit the activity of the anti-apoptotic BCL-2 family member Myeloid cell leukemia-1 (MCL-1) protein for which data are given in the biological experimental section and may therefore be used for the treatment or prophylaxis of hyperproliferative disorders, such as cancer disorders, for example, forms of acute leukemia, lymphoma and multiple myeloma.

In accordance with a first aspect, the present invention provides compounds of general formula (I):

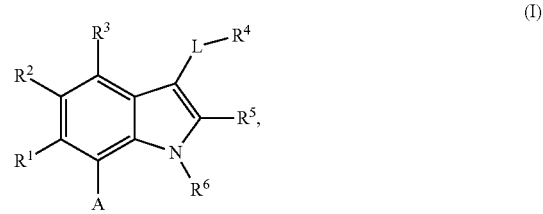

(I)

wherein
A is

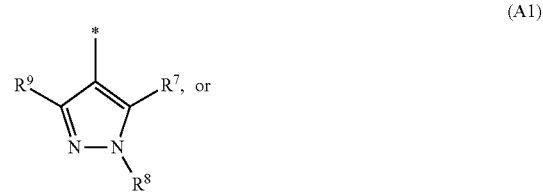

(A1)

or

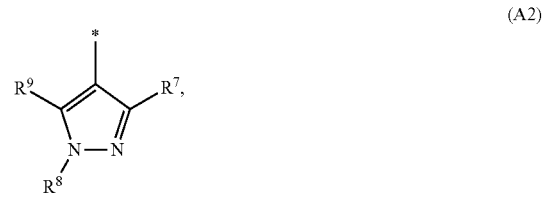

(A2)

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent;

or
A is

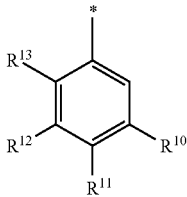
(A3)

wherein optionally one or two of the groups selected from $CR^{11}$, $CR^{12}$ and $CR^{13}$ are replaced by a nitrogen atom,
  wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;
$R^1$ and $R^2$ are each independently selected from a hydrogen atom, a halogen atom, a cyano group, a $C_1$-$C_3$-alkyl group, and a $C_1$-$C_3$-alkoxy group;
$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, a $C_1$-$C_3$-haloalkoxy group, a $C_1$-$C_3$-haloalkylthio group and a $C_3$-$C_5$-cycloalkyl group;
$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;
L is a group —(CH$_2$)$_m$-E- wherein any CH$_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-membered to 6-membered cycloalkyl ring, or a 3-membered to 8-membered saturated or partially unsaturated heterocyclic ring having 1-2 heteroatoms independently selected from an oxygen atom, a sulfur atom, a —S(O)— group, a —S(O)$_2$— group and a —NR$^{14}$— group;
E is a bond, an oxygen atom, a sulfur atom, a —S(O)— group, a —S(O)$_2$— group or a —NR$^{14}$— group and constitutes the connecting element to $R^4$;
m is 2, 3, or 4;
$R^5$ is selected from a COOH group, a

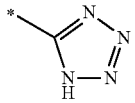

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;

—$R^6$-$R^7$— is $^\#$—(CH$_2$)$_n$—(B)$_t$—(CH$_2$)$_p$—$^{\#\#}$, wherein any —CH$_2$— group is unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a heterocycloalkyl group and a (heterocycloalkyl)-($C_1$-$C_3$-alkylene)- group, and where a double bond in any alkenylene can be replaced by a 1,2-cyclopropyl group, and said 1,2-cyclopropyl group is unsubstituted or substituted one or two times with a halogen atom or a $C_1$-$C_2$-alkyl group, wherein $^\#$ is the point of attachment with the indole nitrogen atom and $^{\#\#}$ is the point of attachment with the pyrazole carbon atom bearing the $R^7$ substituent or —$R^6$-$R^7$— is $^\#$—(CH$_2$)$_n$—(B)$_t$—CR$^{22}$R$^{23}$—$^{\#\#}$ or $^\#$—(C$_2$-C$_6$-alkenylene)-(B)$_t$—CR$^{22}$R$^{23}$—$^{\#\#}$,
  wherein $^\#$ is the point of attachment with the indole nitrogen atom and $^{\#\#}$ is the point of attachment with the pyrazole carbon atom bearing the $R^7$ substituent; and
  wherein one or more —CH$_2$— groups may be unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group;

—$R^6$-$R^{10}$— is $^\#$—(CH$_2$)$_n$—(B)$_t$—(CH$_2$)$_p$—$^{\#\#}$, where one or more CH$_2$ groups are unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a heterocycloalkyl group and a (heterocycloalkyl)-($C_1$-$C_3$-alkylene)- group, wherein $^\#$ is the point of attachment with the indole nitrogen atom and $^{\#\#}$ is the point of attachment with the carbon atom of the phenyl moiety bearing the $R^{10}$ substituent or —$R^6$-$R^{10}$— is $^\#$—(CH$_2$)$_n$—(B)$_t$—CR$^{22}$R$^{23}$—$^{\#\#}$ or $^\#$—(C$_2$-C$_6$-alkenylene)-(B)$_t$—CR$^{22}$R$^{23}$—$^{\#\#}$, where one or more —CH$_2$— groups are substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group, wherein $^\#$ is the point of attachment with the indole nitrogen atom and $^{\#\#}$ is the point of attachment with the carbon atom of the phenyl moiety bearing the $R^{19}$ substituent;
n is 1, 2, 3, 4, 5, 6, 7, or 8;
p is 1, 2, 3, 4, 5, 6, 7 or 8;
t is 1;
s is 0, 1 or 2;
where the integers selected for variables n, t, and p result in forming a 9-membered to 16-membered ring independently from the selection of variable A1, A2 or A3;
B is independently selected from a —S(O)NR$^{15}$— group, a —NR$^{15}$S(O)— group, a —S(O)$_2$NR$^{15}$— group, and a —NR$^{15}$S(O)$_2$— group;
$R^8$ is selected from a hydrogen atom,
  a $C_1$-$C_6$-alkyl group, which is unsubstituted or substituted with one or more substituents independently selected from a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group, and a $C_1$-$C_3$-haloalkyl group, a $C_3$-$C_6$-cycloalkyl group, or a $C_1$-$C_6$-alkyl group in which one or two not directly adjacent carbon atoms are independently replaced by a heteroatom independently selected from —O— and —NH—;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{18}$-(phenylene)-($C_1$-$C_3$-alkylene)-O—($C_1$-$C_3$-alkylene)- group,
a $R^{18}$-(phenylene)-O—($C_1$-$C_3$-alkylene)- group,
a $R^{18}$-(phenylene)-(heteroarylene)-O—($C_1$-$C_3$-alkylene)- group,
a ($R^{18}$)-(heterocycloalkylene)-($C_1$-$C_3$-alkylene)- group,
a ($R^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{18}$)-(heteroarylene)-($C_1$-$C_3$-alkylene)-O—($C_1$-$C_3$-alkylene)- group,
a ($R^{18}$)-(heteroarylene)-(phenylene)-O—($C_1$-$C_3$-alkylene)- group,
a ($R^{19}$)—S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{18}$)-(heteroarylene)-O—($C_1$-$C_3$-alkylene)- group,
a ($R^{19}$)—S(O)$_2$-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a $NR^{20}R^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-NR$^{15}$—C(O)—($C_1$-$C_3$-alkylene)- group, a ($C_1$-$C_3$-alkyl)-C(O)—NH—($C_1$-$C_3$-alkylene)- group,
a ($C_1$-$C_3$-alkyl)-C(O)—NR$^{15}$—($C_1$-$C_3$-alkylene)- group,
a

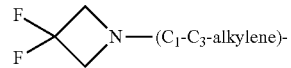

group, and a

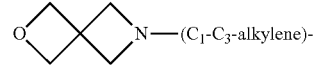

group, where the phenyl ring is unsubstituted or substituted with a halogen atom, a hydroxyl group, or a $C_1$-$C_3$-alkoxy group and
the heterocycloalkyl group is unsubstituted or substituted with an oxo (=O) group or is unsubstituted or substituted with one or more substituents independently selected from a halogen atom, a hydroxyl group, a $C_1$-$C_3$-alkyl group and a $C_1$-$C_3$-alkoxy group, or $R^8$ and $R^9$ together form a 5- or 6-membered ring optionally comprising one or two heteroatoms independently selected from —O— and —NR$^{14}$—;

$R^{11}$ and $R^{13}$ are each independently selected from a hydrogen atom, a halogen atom, a $C_1$-$C_3$-alkyl group, and a $C_1$-$C_3$-alkoxy group;

$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a $NR^{16}R^{17}$ group;

$R^{14}$ is a hydrogen atom or a $C_1$-$C_3$-alkyl group;

$R^{15}$ is independently selected from a hydrogen atom,
a $C_1$-$C_6$-alkyl group
which is unsubstituted or substituted with one or more substituents independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an unsubstituted or substituted aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O)— group, an aryl-($C_1$-$C_3$-alkylene)-NH—C(O)— group, a heterocycloalkylene-($C_1$-$C_3$-alkylene)-S(O)$_2$— group, and a heterocycloalkylene-heteroarylene-S(O)$_2$— group;
a ($C_3$-$C_7$)-cycloalkyl group and
a phenyl group;

$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;

$R^{18}$ is independently selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)OR$^{21}$ group, a —C(O)NR$^{20}R^{21}$ group, a ($C_1$-$C_3$-alkyl)-O—($C_1$-

$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a $NR^{20}R^{21}$ group;

$R^{20}$ and $R^{21}$ are independently selected from a hydrogen atom and a $C_1$-$C_6$-alkyl group;

$R^{22}$ is independently selected from,
  a halogen atom,
  a $C_1$-$C_6$-alkyl group
    which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-S(O)$_2$— group, and a heterocycloalkylene-heteroarylene-S(O)$_2$— group and a $C_1$-$C_3$-alkyl-C(O)— group;

$R^{23}$ is independently selected from a hydrogen atom, a halogen atom, a hydroxy group, a $C_1$-$C_6$-alkyl group, and a $C_1$-$C_6$-haloalkyl group, or $R^{22}$ and $R^{23}$ together with the carbon atom to which they are attached form a 3-membered to 6-membered carbocyclic ring or a 3-membered to 6-membered heterocyclic ring comprising one or two heteroatoms selected from nitrogen, oxygen or sulfur;

or a tautomer, an N-oxide, or a salt thereof, or a salt of a tautomer, or salt of an N-oxide, or a mixture of same.

DETAILED DESCRIPTION

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "unsubstituted or substituted" means that the number of substituents can be equal to or different from zero. Unless otherwise indicated, it is possible that the substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two, three, four or five identical or different substituents, particularly with one, two or three substituents.

Oxo, an oxo group or an oxo substituent means a doubly attached oxygen atom =O. Oxo may be attached to atoms of suitable valency, for example to a saturated carbon atom or to a sulfur atom. For example, but without limitation, one oxo group is can be attached to a carbon atom, resulting in the formation of a carbonyl group C(=O), or two oxo groups are can be attached to one sulfur atom, resulting in the formation of a sulfonyl group —S(=O)$_2$. The term "ring substituent" means a substituent attached to an aromatic or nonaromatic ring which replaces an available hydrogen atom on the ring.

Should a composite substituent be composed of more than one part, e.g., ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of" but does not have to be the scope indicated by "consisting of.

If within the present text any item is referred to as "as mentioned herein", it means that it may be mentioned anywhere in the present text.

If within the present text any item is referred to as "supra" within the description it indicates any of the respective disclosures made within the specification in any of the preceding pages, or above on the same page.

If within the present text any item is referred to as "infra" within the description it indicates any of the respective disclosures made within the specification in any of the subsequent pages, or below on the same page.

The terms as mentioned in the present text have the following meanings:

The term "halogen atom" means a fluorine, chlorine, bromine or iodine atom, particularly a fluorine, chlorine or bromine atom.

The term "$C_1$-$C_8$-alkyl-" means a linear or branched, saturated hydrocarbon group having 1, 2, 3, 4, 5, 6, 7 or 8 carbon atoms, e.g., a methyl-, ethyl-, propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, 1,2-dimethylbutyl-, n-heptyl-, 5-methylhexyl-, 4-methylhexyl-, 2-methylhexyl-, 1-methylhexyl-, 2-ethylpentyl-, 1-ethylpentyl-, 3,3-dimethylpentyl-, 2,2-dimethylpentyl-, 1,1-dimethylpentyl-, 2,3-dimethylpentyl-, 1,3-dimethylpentyl-, 1,2-dimethylpentyl-, n-octyl-, 6-methylheptyl-, 4-methylheptyl-, 2-methylheptyl-, 1-methylheptyl-, 2-ethylhexyl-, 1-ethylhexyl-, 3,3-dimethylhexyl-, 2,2-dimethylhexyl-, 1,1-dimethylhexyl-, 2,3-dimethylhexyl-, 1,3-dimethylhexyl-, 1,2-dimethylhexyl- group, or an isomer thereof. Preferably, said group has 1, 2, 3, 4, 5 or 6 carbon atoms ("$C_1$-$C_6$-alkyl-"), e.g., a methyl-, ethyl-, n-propyl-, iso-propyl-, n-butyl-, iso-butyl-, sec-butyl-, tert-butyl-, n-pentyl-, iso-pentyl-, 2-methylbutyl-, 1-methylbutyl-, 1-ethylpropyl-, 1,2-dimethylpropyl-, neo-pentyl-, 1,1-dimethylpropyl-, n-hexyl-, 4-methylpentyl-, 3-methylpentyl-, 2-methylpentyl-, 1-methylpentyl-, 2-ethyl-butyl-, 1-ethylbutyl-, 3,3-dimethylbutyl-, 2,2-dimethyl-butyl-, 1,1-dimethylbutyl-, 2,3-dimethylbutyl-, 1,3-dimeth-ylbutyl- or 1,2-dimethylbutyl group, or an isomer thereof. More preferably, said group has 1, 2, 3 or 4 carbon atoms ("$C_1$-$C_4$-alkyl-"), e.g., a methyl-, ethyl-, n-propyl-, iso-propyl-, n-butyl-, iso-butyl-, sec-butyl- or tert-butyl- group, 1, 2 or 3 carbon atoms ("$C_1$-$C_3$-alkyl-"), e.g., a methyl-, ethyl-, n-propyl- or iso-propyl group, or 1 or 2 carbon atoms ("$C_1$-$C_2$-alkyl-"), e.g., a methyl group, an ethyl group.

The same definitions can be applied should the alkyl group be placed within a chain as a bivalent "$C_1$-$C_6$-alkylene" moiety. All names as mentioned above then will bear an "ene" added to the end, thus e.g., a "pentyl" becomes a bivalent "pentylene" group. In addition, the term "$C_1$-$C_6$-heteroalkyl" refers to a $C_1$-$C_6$-alkyl group in which one or more of the carbon atoms have been replaced with an atom selected from N, O, S, or P, which are substituted as mentioned herein to satisfy atom valency requirements.

The term "$C_2$-$C_6$-alkylene" means a linear or branched, saturated, divalent hydrocarbon chain (or "tether") having 2, 3, 4, 5 or 6 carbon atoms, e.g., —CH$_2$—CH$_2$— ("ethylene" or "$C_2$-alkylene"), —CH$_2$—CH$_2$—CH$_2$—, —C(H)(CH$_3$)—CH$_2$— or —C(CH$_3$)$_2$— ("propylene" or "$C_3$-alkylene"), or, for example —CH$_2$—C(H)(CH$_3$)—CH$_2$—, —CH$_2$—C(CH$_3$)$_2$—, —CH$_2$—CH$_2$—CH$_2$—CH$_2$— ("butylene" or "$C_4$-alkylene"), "$C_5$-alkylene", e.g., —CH$_2$—CH$_2$—CH$_2$—CH$_2$—CH$_2$— ("n-pentylene"), or "—$C_6$-alkylene-", e.g., —CH$_2$—CH$_2$—CH$_2$—CH$_2$—CH$_2$—CH$_2$— ("n-hexylene") or a —C(CH$_3$)$_2$—C(CH$_3$)$_2$ group.

The term "hydroxy-($C_1$-$C_6$-alkyl)-" means a linear or branched, saturated, hydrocarbon group in which one or more hydrogen atoms of a "$C_1$-$C_6$-alkyl-" as defined supra are each replaced by a hydroxy group, e.g., a hydroxym-ethyl-, 1-hydroxyethyl-, 2-hydroxyethyl-, 1,2-dihydroxy-ethyl-, 3-hydroxypropyl-, 2-hydroxypropyl-, 2,3-dihydroxy-propyl-, 1,3-dihydroxypropan-2-yl-, 3-hydroxy-2-methyl-propyl-, 2-hydroxy-2-methyl-propyl-, or a 1-hydroxy-2-methyl-propyl- group. Particularly the hydroxyalkyl group means a linear or branched, saturated, monovalent hydro-carbon group has 1, 2 or 3 carbon atoms in which 1 hydrogen atom is replaced with a hydroxy group e.g. a hydroxym-ethyl-, 1-hydroxyethyl-, 2-hydroxyethyl-, 3-hydroxypro-pyl-, 2-hydroxypropyl-, 1-hydroxypropyl-, 2-hydroxy-2-methyl-ethyl group.

The term "$C_1$-$C_6$-haloalkyl" means a linear or branched, saturated, monovalent hydrocarbon group in which the term "$C_1$-$C_6$-alkyl" is as defined supra and in which one or more of the hydrogen atoms are replaced, identically or differ-ently, with a halogen atom. Preferably, said halogen atom is a fluorine atom. Said $C_1$-$C_6$-haloalkyl, particularly a $C_1$-$C_3$-haloalkyl group is, for example, fluoromethyl-, difluorom-ethyl-, trifluoromethyl-, 2-fluoroethyl-, 2,2-difluoroethyl-, 2,2,2-trifluoroethyl-, pentafluoroethyl-, 3,3,3-trifluoropro-pyl- or a 1,3-difluoropropan-2-yl group.

The term "$C_1$-$C_6$-alkoxy" means a linear or branched, saturated, monovalent group of formula ($C_1$-$C_6$-alkyl)-O—, in which the term "$C_1$-$C_6$-alkyl" group is as defined supra, e.g. methoxy-, ethoxy-, n-propoxy-, isopropoxy-, n-butoxy-, sec-butoxy-, isobutoxy-, tert-butoxy-, pentyloxy-, isopenty-loxy- or a n-hexyloxy group, or an isomer thereof.

The term "$C_1$-$C_6$-alkylthio" or "$C_1$-$C_6$-thioalkyl" means a linear or branched, saturated, monovalent group of formula ($C_1$-$C_6$-alkyl)-S—, in which the term "$C_1$-$C_6$-alkyl" is as defined supra, e.g. methylthio-, ethylthio-, n-propylthio-, isopropylthio-, n-butylthio-, sec-butylthio-, isobutylthio-, tert-butylthio-, pentylthio-, isopentylthio- or a n-hexylthio group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Preferably, said halogen atom in "$C_1$-$C_6$-haloalkoxy-" is fluorine, resulting in a group referred to herein as "$C_1$-$C_6$-fluoroalkoxy-". Representative $C_1$-$C_6$-fluoroalkoxy groups include, for example, —OCF$_3$, —OCHF$_2$, —OCH$_2$F, —OCF$_2$CF$_3$ and —OCH$_2$CF$_3$.

The term "$C_1$-$C_6$-haloalkylthio" or "$C_1$-$C_6$-halothioalkyl" or "$C_1$-$C_6$-haloalkyl-S—" means a linear or branched, satu-rated, monovalent $C_1$-$C_6$-alkylthio group, as defined supra, in which one or more of the hydrogen atoms is replaced, identically or differently, with a halogen atom. Preferably, said halogen atom in "$C_1$-$C_6$-haloalkylthio-" is fluorine.

The term "$C_2$-$C_6$-alkenyl-" means a linear or branched, monovalent hydrocarbon group, which contains one or more double bonds and which has 2, 3, 4, 5 or 6 carbon atoms, preferably 2, 3 or 4 carbon atoms ("$C_2$-$C_4$-alkenyl-") or 2 or 3 carbon atoms ("$C_2$-$C_3$-alkenyl-"), it being understood that in the case in which said alkenyl- group contains more than one double bond, then said double bonds may be isolated from, or conjugated with, each other. Representative alkenyl groups include, for example, an ethenyl-, prop-2-enyl-, (E)-prop-1-enyl-, (Z)-prop-1-enyl-, iso-propenyl-, but-3-enyl-, (E)-but-2-enyl-, (Z)-but-2-enyl-, (E)-but-1-enyl-, (Z)-but-1-enyl-, 2-methylprop-2-enyl-, 1-methylprop-2-enyl-, 2-methylprop-1-enyl-, (E)-1-methylprop-1-enyl-, (Z)-1-methylprop-1-enyl-, buta-1,3-dienyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-meth-ylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethyl-prop-2-enyl-, 1-ethylprop-1-enyl-, 1-propylvinyl-, 1-isopro-pylvinyl-, (E)-3,3-dimethylprop-1-enyl-, (Z)-3,3-dimethylprop-1-enyl-, penta-1,4-dienyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, 4-methylpent-4-enyl-, 3-methylpent-4-enyl-, 2-methylpent-4-enyl-, 1-methylpent-4-enyl-, 4-meth-ylpent-3-enyl-, (E)-3-methylpent-3-enyl-, (Z)-3-methyl-pent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-meth-ylpent-2-enyl-, (Z)-1-methylpent-2-enyl-, (E)-4-methyl-pent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl, 2-ethylbut-3-enyl-, 1-ethylbut-3-enyl-, (E)-3-ethylbut-2-enyl-, (Z)-3-eth-ylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propyl-prop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, hexa-1,5-dienyl- and a 1-(1,1-dimethylethyl-)ethenyl group. Particularly, said group is an ethenyl- or a prop-2-enyl group.

The same definitions can be applied should the alkenyl group be placed within a chain as a bivalent "$C_2$-$C_6$-alkenylene" moiety. All names as mentioned above then will bear a "ene" added to their end, thus e.g., a "pentenyl" becomes a bivalent "pentenylene" group.

The term "$C_2$-$C_6$-haloalkenyl-" means a linear or branched hydrocarbon group in which one or more of the hydrogen atoms of a "$C_2$-$C_6$-alkenyl-" as defined supra are each replaced, identically or differently, by a halogen atom. Preferably, said halogen atom is fluorine, resulting in a group referred herein as "$C_2$-$C_6$-fluoroalkenyl-". Representative $C_2$-$C_6$-fluoroalkenyl- groups include, for example, —CH=CF$_2$, —CF=CH$_2$, —CF=CF$_2$, —C(CH$_3$)=CF$_2$, —CH=C(F)—CH$_3$, —CH$_2$—CF=CF$_2$ and —CF$_2$—CH=CH$_2$.

The term "$C_2$-$C_6$-alkynyl-" means a linear or branched, monovalent hydrocarbon group which contains one or more triple bonds, and which contains 2, 3, 4, 5 or 6 carbon atoms, preferably 2, 3 or 4 carbon atoms ("$C_2$-$C_4$-alkynyl-") or 2 or 3 carbon atoms ("$C_2$-$C_3$-alkynyl-"). Representative $C_2$-$C_6$-alkynyl- groups include, for example, an ethynyl-, prop-1-ynyl-, prop-2-ynyl-, but-1-ynyl-, but-2-ynyl-, but-3-ynyl-, pent-1-ynyl-, pent-2-ynyl, pent-3-ynyl-, pent-4-ynyl-, hex-1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-, 3-methylpent-4-ynyl-, 2-methylpent-4-ynyl-, 1-methyl-pent-4-ynyl-, 2-methylpent-3-ynyl-, 1-methylpent-3-ynyl-, 4-methylpent-2-ynyl-, 1-methyl-pent-2-ynyl-, 4-methylpent-1-ynyl-, 3-methylpent-1-ynyl-, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-dimethylbut-2-ynyl- and a 3,3-dimethylbut-1-ynyl- group. Particularly, said alkynyl- group is an ethynyl-, a prop-1-ynyl- or a prop-2-ynyl- group.

The term "$C_3$-$C_{10}$-cycloalkyl-" means a saturated mono- or bicyclic hydrocarbon ring which contains 3, 4, 5, 6, 7, 8, 9 or 10 carbon atoms ("$C_3$-$C_{10}$-cycloalkyl-"). Said $C_3$-$C_{10}$-cycloalkyl- group may be, for example, a monocyclic hydrocarbon ring, e.g., a cyclopropyl-, cyclobutyl-, cyclopentyl-, cyclohexyl- or cycloheptyl- group, or a bicyclic hydrocarbon ring, such as a decalinyl- group. Preferably, said hydrocarbon ring is monocyclic and contains 3, 4, 5, 6 or 7 carbon atoms ("$C_3$-$C_7$-cycloalkyl-"), e.g., a cyclopropyl-, cyclobutyl-, cyclopentyl-, cyclohexyl- or cycloheptyl- group, or 3, 4, 5 or 6 carbon atoms ("$C_3$-$C_6$-cycloalkyl-"), e.g., a cyclopropyl-, cyclobutyl-, cyclopentyl- or a cyclohexyl- group. A cycloalkyl group may be unsubstituted or substituted as defined at the respective part wherein such term is used.

The term "$C_4$-$C_8$-cycloalkenyl" means a monovalent, mono- or bicyclic hydrocarbon ring which contains 4, 5, 6, 7 or 8 carbon atoms and one double bond. Particularly, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g., a cyclobutenyl, cyclopentenyl, cyclohexenyl, cycloheptenyl or a cyclooctenyl group, or a bicyclic hydrocarbon ring, e.g., a bicyclo[2.2.1]hept-2-enyl or a bicyclo[2.2.2]oct-2-enyl group.

If the term "heterocycloalkyl" is used without specifying a number of atoms it is meant to be a "4-membered to 10-membered heterocycloalkyl-" group, more particularly a 5-membered to 6-membered heterocycloalkyl group. The term "4- to 10-membered heterocycloalkyl-" means a saturated mono- or bicyclic hydrocarbon ring which contains 3, 4, 5, 6, 7, 8 or 9 carbon atoms, and which contains 1, 2, 3 or 4 heteroatoms which may be identical or different, said heteroatoms are preferably selected from oxygen, nitrogen or sulfur, and wherein carbon atoms and heteroatoms add up to 4, 5, 6, 7, 8, 9 or 10 ring atoms in total, it being possible for said heterocycloalkyl- group to be attached to the rest of the molecule via any one of the carbon atoms or, if present, a nitrogen atom. "Heterospirocycloalkyl-", "heterobicycloalkyl-" and "bridged heterocycloalkyl-", as defined infra, are also included within the scope of this definition.

Preferably, said "4-membered to 10-membered heterocycloalkyl-" is monocyclic and contains 3, 4, 5 or 6 carbon atoms, and one or two of the above-mentioned heteroatoms, adding up to 4, 5, 6 or 7 ring atoms in total (a "4-membered to 7-membered monocyclic heterocycloalkyl-"), or contains 3, 4 or 5 carbon atoms, and one or two of the above-mentioned heteroatoms, adding up to 4, 5 or 6 ring atoms in total (a "4-membered to 6-membered monocyclic heterocycloalkyl-"), or contains 3, 4 or 5 carbon atoms, and one or two of the above-mentioned heteroatoms, adding up to 5 or 6 ring atoms in total (a "5-membered to 6-membered monocyclic heterocycloalkyl-"); it being possible for said heterocycloalkyl- group to be attached to the rest of the molecule via any one of the carbon atoms or the nitrogen atoms, if present.

Exemplarily, without being limited thereto, said "4-membered to 7-membered monocyclic heterocycloalkyl-", can be a 4-membered ring, a "4-membered heterocycloalkyl-" group, such as an azetidinyl- or an oxetanyl group; or a 5-membered ring, a "5-membered heterocycloalkyl-" group, such as a tetrahydrofuranyl-, dioxolinyl-, pyrrolidinyl-, imidazolidinyl-, pyrazolidinyl- or a pyrrolinyl group; or a 6-membered ring, a "6-membered heterocycloalkyl-" group, such as a tetrahydropyranyl-, piperidinyl-, morpholinyl-, 3-oxomorpholin-4-yl, dithianyl-, thiomorpholinyl- or a piperazinyl group; or a 7-membered ring, a "7-membered heterocycloalkyl-" group, such as an azepanyl-, diazepanyl- or an oxazepanyl group, for example. The heterocycloalkyl groups may be one or more times substituted with $C_1$-$C_3$-alkyl, $C_1$-$C_3$-alkoxy, hydroxy, halogen or a carbonyl group.

The term "heterocycloalkenyl" or "5- to 7-membered heterocycloalkenyl" means a monocyclic, unsaturated, non-aromatic heterocycle with 5, 6, or 7 ring atoms in total, which contains one or two double bonds and one or two identical or different ring heteroatoms from the series: N, O, S; it being possible for said heterocycloalkenyl group to be attached to the rest of the molecule via any one of the carbon atoms or, if present, a nitrogen atom.

Said heterocycloalkenyl group is, for example, a 4H-pyranyl-, 3,6-dihydro-2H-pyran-4-yl-, 2H-pyranyl-, dihydropyridinyl-, tetrahydropyridinyl-, 2-oxopyridin-1(2H)-yl-, 2,5-dihydro-1H-pyrrolyl-, [1,3]dioxolyl-, 4H-[1,3,4]thiadiazinyl-, 2,5-dihydrofuranyl-, 2,3-dihydrofuranyl-, 2,5-dihydrothiophenyl-, 2,3-dihydrothiophenyl-, 4,5-dihydrooxazolyl- or a 4H-[1,4]thiazinyl group. Those heterocycloalkenyl groups may be substituted with a hydroxy group or a methoxy group.

The term "fused heterocycloalkyl" or "heterobicycloalkyl-" means a bicyclic, saturated heterocycle with 6, 7, 8, 9 or 10 ring atoms in total, in which the two rings share two adjacent ring atoms, which "fused heterocycloalkyl" contains one or two identical or different ring heteroatoms from the series: N, O, S; it being possible for said fused heterocycloalkyl group to be attached to the rest of the molecule via any one of the carbon atoms or, if present, a nitrogen atom.

Said "fused heterocycloalkyl" or "heterobicycloalkyl-" group is, for example, an azabicyclo[3.3.0]octyl, azabicyclo [4.3.0]nonyl, diazabicyclo[4.3.0]nonyl, oxazabicyclo[4.3.0] nonyl, and a thiazabicyclo[4.3.0]nonyl or an azabicyclo [4.4.0]decyl group.

The term "aryl" means a phenyl-, naphthyl-, 5,6-dihydronaphthyl-, 7,8-dihydronaphthyl-, 5,6,7,8-tetrahydronaphthyl- indanyl-, or an indenyl group, which is unsubstituted or substituted with one, two, three, four or five substituents, each substituent independently selected from halogen, cyano, $C_1$-$C_3$-alkyl, $C_1$-$C_3$-haloalkyl, $C_1$-$C_3$-alkoxy, $C_1$-$C_3$-thioalkyl, $C_1$-$C_3$-haloalkoxy, $C_1$-$C_3$-halothioalkyl, $C_3$-$C_5$-cycloalkyl, particularly halogen, $C_1$-$C_3$-alkyl, $C_1$-$C_3$-haloalkyl, $C_1$-$C_3$-alkoxy, $C_1$-$C_3$-haloalkoxy.

The term "heteroaryl-" means a monocyclic, bicyclic or tricyclic aromatic ring system having 5, 6, 7, 8, 9, 10, 11, 12, 13 or 14 ring atoms (a "5- to 14-membered heteroaryl-" group), preferably 5, 6, 9 or 10 ring atoms and which contains 1, 2, 3 or 4 heteroatoms which may be identical or different, said heteroatoms being selected from oxygen, nitrogen and sulfur. Said heteroaryl- group can be a 5-membered heteroaryl group, such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl- or a tetrazolyl group; or a 6-membered heteroaryl group, such as, for example, a pyridyl-, pyridazinyl-, pyrimidyl-, pyrazinyl- or a triazinyl group; or a benzo-fused 5-membered heteroaryl- group, such as, for example, a benzofuranyl-, benzothienyl-, benzoxazolyl-, benzisoxazolyl-, benzimidazolyl-, benzothiazolyl-, benzotriazolyl-, indazolyl-, indolyl- or a isoindolyl group; or a benzo-fused 6-membered heteroaryl group, such as, for example, a quinolinyl-, quinazolinyl-, isoquinolinyl-, cinnolinyl-, phthalazinyl- or quinoxalinyl-; or another bicyclic group, such as, for example, indolizinyl-, purinyl- or a pteridinyl group; or a tricyclic heteroaryl- group, such as, for example, a carbazolyl-, acridinyl- or a phenazinyl group Preferably, "heteroaryl-" is a monocyclic aromatic ring system having 5 or 6 ring atoms and which contains at least one heteroatom, if more than one, they may be identical or different, said heteroatom being selected from oxygen, nitrogen and sulfur a ("5- to 6-membered monocyclic heteroaryl-") group, such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl-, pyridyl-, pyridazinyl-, pyrimidyl-, pyrazinyl- or a triazinyl- group.

In general, and unless otherwise mentioned, said heteroaryl- groups include all the possible isomeric forms thereof, e.g., the positional isomers thereof. Thus, for some illustrative non-restricting examples, the term pyridyl- includes a pyridin-2-yl-, a pyridin-3-yl- and a pyridin-4-yl- group; the term thienyl- includes a thien-2-yl- and a thien-3-yl- group. Furthermore, said heteroaryl- groups can be attached to the rest of the molecule via any one of the carbon atoms, or, if applicable, a nitrogen atom, e.g., a pyrrol-1-yl-, a pyrazol-1-yl- or a imidazol-1-yl- group.

In general, and unless otherwise mentioned, the heteroaryl or heteroarylene groups include all possible isomeric forms thereof, e.g., tautomers and positional isomers with respect to the point of linkage to the rest of the molecule. Thus, for some illustrative non-restricting examples, the term pyridinyl includes a pyridin-2-yl, a pyridin-3-yl and a pyridin-4-yl group; or the term thienyl includes a thien-2-yl and a thien-3-yl group.

Particularly, the heteroaryl group is a pyridyl- or pyrimidyl- group or a imidazolyl group. including a hydroxy substitution of the pyridyl group leading e.g. to a 2-hydroxypyridine which is the tautomeric form to a 2-oxo-2(1H)-pyridine.

The term "$C_1$-$C_6$", as used throughout this text, e.g., in the context of the definition of "$C_1$-$C_6$-alkyl-", "$C_1$-$C_6$-haloalkyl-", "$C_1$-$C_6$-alkoxy-" or "$C_1$-$C_6$-haloalkoxy-" is to be understood as meaning an alkyl group having a whole number of carbon atoms from 1 to 6, i.e., 1, 2, 3, 4, 5 or 6 carbon atoms. It is to be understood further that said term "$C_1$-$C_6$" is to be interpreted as disclosing any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$ preferably $C_1$-$C_2$, $C_1$-$C_3$, $C_1$-$C_4$, $C_1$-$C_6$, $C_1$-$C_6$, more preferably $C_1$-$C_4$; in the case of "$C_1$-$C_6$-haloalkyl-" or "$C_1$-$C_6$-haloalkoxy-" even more preferably $C_1$-$C_2$.

Similarly, as used herein, the term "$C_2$-$C_6$", as used throughout this text, e.g., in the context of the definitions of "$C_2$-$C_6$-alkenyl-" and "$C_2$-$C_6$-alkynyl-", is to be understood as meaning an alkenyl- group or an alkynyl group having a whole number of carbon atoms from 2 to 6, i.e., 2, 3, 4, 5 or 6 carbon atoms. It is to be understood further that said term "$C_2$-$C_6$" is to be interpreted as disclosing any sub-range comprised therein, e.g., $C_2$-$C_6$, $C_3$-$C_5$, $C_3$-$C_4$, $C_2$-$C_3$, $C_2$-$C_6$, $C_2$-$C_5$, preferably $C_2$-$C_3$.

Further, as used herein, the term "$C_3$-$C_7$", as used throughout this text, e.g., in the context of the definition of "$C_3$-$C_7$-cycloalkyl-", is to be understood as meaning a cycloalkyl- group having a whole number of carbon atoms of 3 to 7, i.e., 3, 4, 5, 6 or 7 carbon atoms. It is to be understood further that said term "$C_3$-$C_7$" is to be interpreted as disclosing any sub-range comprised therein, e.g., $C_3$-$C_6$, $C_4$-$C_5$, $C_3$-$C_5$, $C_3$-$C_4$, $C_4$-$C_6$, $C_5$-$C_7$; preferably $C_3$-$C_6$.

As used herein, the term "leaving group" refers to an atom or a group of atoms that is displaced in a chemical reaction as stable species taking with it the bonding electrons, e.g., typically forming an anion. Preferably, a leaving group is selected from the group comprising: halo, in particular a chloro, bromo or iodo, (methylsulfonyl)oxy-, [(4-methylphenyl)sulfonyl]oxy-, [(trifluoromethyl)sulfonyl]oxy-, [(nonafluorobutyl)sulfonyl]oxy-, [(4-bromophenyl)sulfonyl]oxy-, [(4-nitrophenyl)sulfonyl]oxy-, [(2-nitrophenyl) sulfonyl]oxy-, [(4-isopropylphenyl)sulfonyl]oxy-, [(2,4,6-triisopropylphenyl)sulfonyl]oxy-, [(2,4,6-trimethylphenyl) sulfonyl]oxy-, [(4-tert-butylphenyl)sulfonyl]oxy-, (phenylsulfonyl)oxy-, and a [(4-methoxyphenyl)sulfonyl] oxy group.

As used herein, the term "protective group" is a protective group attached to an oxygen or nitrogen atom in intermediates used for the preparation of compounds of the general formula (I). Such groups are introduced e.g., by chemical modification of the respective hydroxy or amino group in order to obtain chemoselectivity in a subsequent chemical reaction. Protective groups for hydroxy and amino groups are described for example in T.W. Greene and P.G.M. Wuts in *Protective Groups in Organic Synthesis*, 4th edition, Wiley 2006; more specifically, protective groups for amino groups can be selected from substituted sulfonyl groups, such as a mesyl-, tosyl- or a phenylsulfonyl group, acyl groups such as a benzoyl-, acetyl- or a tetrahydropyranoyl group, or carbamate based groups, such as a tert-butoxycarbonyl group (Boc). Protective groups for hydroxy groups can be selected from acyl groups such as a benzoyl-, acetyl, pivaloyl- or a tetrahydropyranoyl group, or can include silicon, as in e.g., a tert-butyldimethylsilyl-, tert-butyldiphenylsilyl-, triethylsilyl- or a triisopropylsilyl group.

The term "substituent" refers to a group "substituted" on, e.g., an alkyl-, haloalkyl-, cycloalkyl-, heterocyclyl-, heterocycloalkenyl-, cycloalkenyl-, aryl-, or a heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

By "subject" is meant a mammal, including, but not limited to, a human or non-human mammal, such as a bovine, equine, canine, ovine, rodent, or feline.

It is possible for the compounds of general formula (I) to exist as isotopic variants. The invention therefore includes one or more isotopic variant(s) of the compounds of general formula (I), particularly deuterium-containing compounds of general formula (I).

The invention also includes all suitable isotopic variations of a compound of the invention.

The term "isotopic variant" of a compound or a reagent is defined as a compound exhibiting an unnatural proportion of one or more of the isotopes that constitute such a compound.

The expression "unnatural proportion" in relation to an isotope means a proportion of such isotope which is higher than its natural abundance. The natural abundances of isotopes to be applied in this context are described in "Isotopic Compositions of the Elements 1997", Pure Appl. Chem., 70(1), 217-235, 1998.

An isotopic variation of a compound of the invention is defined as one in which at least one atom is replaced by an atom having the same atomic number but an atomic mass different from the atomic mass usually or predominantly found in nature.

Examples of isotopes that can be incorporated into a compound of the invention include isotopes of hydrogen, carbon, nitrogen, oxygen, phosphorus, sulphur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Accordingly, recitation of "hydrogen" or "H" should be understood to encompass $^{1}H$ (protium), $^{2}H$ (deuterium), and $^{3}H$ (tritium) unless otherwise specified. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

With respect to the treatment and/or prophylaxis of the disorders specified herein, the isotopic variant(s) of the compounds of general formula (I) preferably contain deuterium ("deuterium-containing compounds of general formula (I)"). Isotopic variants of the compounds of general formula (I) in which one or more radioactive isotopes, such as $^{3}H$ or $^{14}C$, are incorporated are useful, e.g., in drug and/or substrate tissue distribution studies. These isotopes are particularly preferred for the ease of their incorporation and detectability. Positron-emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g., Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g., Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g., lower number of doses or lower dosage to achieve the desired effect) and/or may produce lower metabolite loads.

A compound of general formula (I) may have multiple potential sites of vulnerability to metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g., cytochrome $P_{450}$.

For example, in some embodiments, the present invention concerns a deuterium-containing compound of general formula (I), e.g.:

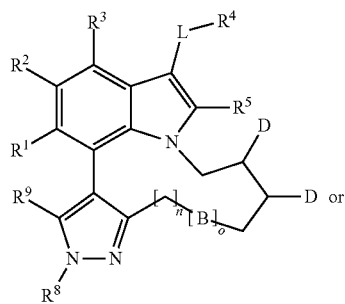

-continued

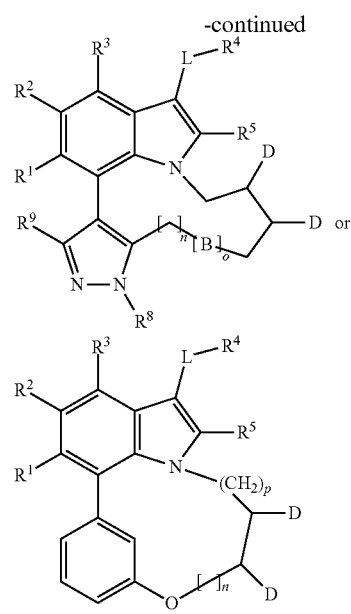

Such deuterium-containing compounds can be prepared by methods well-known to the person skilled in the art. Particularly, such deuterium-containing compounds can be prepared from the corresponding olefins, which are available by methods known to the person skilled in the art, such as ring closing metathesis reactions, as discussed e.g., in the general description of the synthesis of compounds of general formula (I), infra, in the context of Schemes 2c and 2j, respectively.

Where the plural form of the word compounds, salts, polymorphs, hydrates, solvates and the like, is used herein, this is taken to mean also a single compound, salt, polymorph, isomer, hydrate, solvate or the like. The terms "a" or "an," as used in herein means one or more.

By "stable compound" or "stable structure" is meant a compound that is sufficiently robust to survive isolation to a useful degree of purity from a reaction mixture, and formulation into an efficacious therapeutic agent.

Compounds of the present invention, as well as the corresponding macrocyclic intermediates of formula (II), are typically chiral merely as a result of restricted rotation around at least one single bond, which is due to limited comformational flexibility of their macrocyclic core as a whole or even of open chain precursors. Hence, compounds of the present invention as well as the corresponding macrocyclic intermediates of formula (II), can exist as atropisomers. Atropisomers represent a subclass of conformers which arise from restricted rotation around a single bond. The conformers (called atropisomers) can be isolated as separated species (IUPAC Gold book, http://goldbook.iupac.org/A00511.html; Pure and Appl. Chem., 2009, 68, 2193-2222). This induced chirality belongs to the axial type of chirality. The compounds of the present invention as well as the corresponding macrocyclic intermediates of formula (II), furthermore optionally contain one or more asymmetric centers, depending upon the location and nature of the various substituents desired. It is possible that one or more asymmetric carbon atoms are present in the (R) or (S) configuration, which can result in racemic mixtures in the case of a single asymmetric center, and in diastereomeric mixtures in the case of multiple asymmetric centers. Hence, compounds of the present invention, as well as the corresponding macrocyclic intermediates of formula (II), featuring the above-mentioned atropisomerism and an additional asymmetric centre can also exist as diasteromeric mixtures as described supra.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

If only one isomer (enantiomer) displays the desired biological activity, and the second isomer (enantiomer) is inactive, the preferred isomer is the one which produces the more desirable biological activity. Should one isomer (enantiomer/diastereomer) display better activity than the other isomer (enantiomer/diastreromer) the preferred isomer is the one which produces the better biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Deicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials, enantioselective catalytic reactions, and other suitable methods.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g., a single enantiomer or a single diastereomer, of a compound of the present invention may be achieved by any suitable method, such as chromatography, especially chiral chromatography, for example.

Further, it is possible for the compounds of the present invention to exist as tautomers. For example, any compound of the present invention which contains an pyrazol moiety as a heteroaryl group for example can exist as a 1H tautomer, or a 2H tautomer, or even a mixture in any amount of the two tautomers, namely:

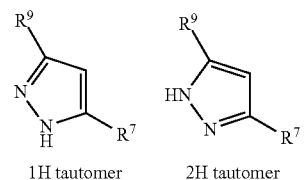

1H tautomer   2H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also includes useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention form a crystal that contains molecules of polar solvents, in particular water, methanol or ethanol, for example, as structural element of the crystal lattice of the compounds. The molecules of polar solvents, in particular water, may be present in a stoichiometric or non-stoichiometric ratio with the molecules of the compound. In the case of stoichiometric solvates, e.g., a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19. It includes any physiologically acceptable salt as referred to below.

Physiologically acceptable salts of the compounds according to the invention encompass acid addition salts of mineral acids, carboxylic acids and sulfonic acids, for example salts of hydrochloric acid, hydrobromic acid, hydroiodic acid, sulfuric acid, bisulfuric acid, phosphoric acid, and nitric acid, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalenedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

A "pharmaceutically acceptable anion" refers to the deprotonated form of a conventional acid, such as, for example, a hydroxide, a carboxylate, a sulfate, a halide, a phosphate, or a nitrate.

Physiologically acceptable salts of the compounds according to the invention also comprise salts of conventional bases, such as, by way of example and by preference, alkali metal salts (for example lithium, sodium and potassium salts), alkaline earth metal salts (for example calcium, strontium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl) aminomethane, aminopropanediol, Sovak base, and 1-amino-2,3,4-butanetriol.

Additionally, the compounds according to the invention may form salts with a quaternary ammonium ion obtainable, e.g., by quaternisation of a basic nitrogen-containing group with agents such as lower alkylhalides such as methyl-, ethyl-, propyl-, and butylchlorides, -bromides and -iodides; dialkylsulfates such as dimethyl-, diethyl-, dibutyl- and diamylsulfates, long chain halides such as decyl-, lauryl-, myristyl- and stearylchlorides, -bromides and -iodides, aralkylhalides such as benzyl- and phenethylbromides and others. Examples of suitable quaternary ammonium ions are tetramethylammonium, tetraethylammonium, tetra(n-propyl)ammonium, tetra (n-butyl)ammonium, or N-benzyl-N,N,N-trimethylammonium.

The present invention includes all possible salts of the compounds of the present invention as single salts, or as any mixture of said salts, in any ratio.

Unless specified otherwise, suffixes to chemical names or structural formulae relating to salts, such as "hydrochloride", "trifluoroacetate", "sodium salt", or "x HCl", "x $CF_3COOH$", "x Na+", for example, mean a salt form, the stoichiometry of which salt form not being specified.

Solvates and hydrates of disclosed intermediates or example compounds, or salts thereof, which have been obtained, by the preparation and/or purification processes described herein, may be formed in any ratio.

Furthermore, the present invention includes all possible crystalline forms, or polymorphs, of the compounds of the present invention, either as a single polymorph, or as a mixture of more than one polymorph, in any ratio.

Moreover, the present invention also includes prodrugs of the compounds according to the invention. The term "prodrugs" designates compounds which themselves can be biologically active or inactive, but are converted (for example metabolically or hydrolytically) into compounds according to the invention during their residence time in the body. For example, a prodrug may be in the form of an in vivo hydrolysable ester of the specified compound. Derivatives of the compounds of formula (I) and the salts thereof which are converted into a compound of formula (I) or a salt thereof in a biological system (bioprecursors or pro-drugs) are covered by the invention. Said biological system may be, for example, a mammalian organism, particularly a human subject. The bioprecursor is, for example, converted into the compound of formula (I) or a salt thereof by metabolic processes.

Further Embodiments of the First Aspect of the Present Invention

In accordance with a further aspect, the present invention provides compounds of general formula (I) wherein
A is

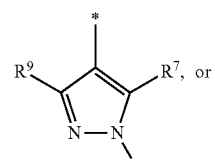

(A1)

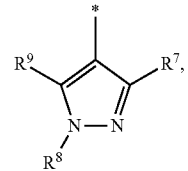

(A2)

wherein $R^6$ and $R^7$, together with two carbon atoms of the pyrazole ring, two carbon atoms of the indole moiety and the nitrogen atom to which $R^6$ is attached, form a 9-membered to 13-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

$R^4$ is selected from an aryl group and a heteroaryl group, each of which is unsubstituted or substituted with one, two, or three substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group;

E is a bond, an oxygen atom, a sulfur atom, or a —$NR^{14}$— group and constitutes the connecting element to $R^4$;

m is 2, 3, or 4;

$R^5$ is selected from a COOH group and a

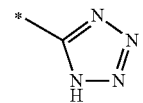

group;

—$R^6$-$R^7$— is $^\#$—$(CH_2)_n$—$(B)_t$—$(CH_2)_p$—$^{\#\#}$, wherein any —$CH_2$— group is unsubstituted or substituted with one or more substituents selected from a halogen atom, a hydroxyl group, a $NR^{16}R^{17}$ group, a $C_1$-$C_3$-alkyl group, a $C_1$-$C_3$-haloalkyl group, a heterocycloalkyl group and a $C_1$-$C_3$-alkoxy group, wherein $^\#$ is the point of attachment with the indole nitrogen atom and $^{\#\#}$ is the point of attachment with the pyrazole carbon atom bearing the $R^7$ substituent or —$R^6$-$R^7$— is $^\#$—$(CH_2)_n$—$(B)_t$—$CR^{22}R^{23}$—$^{\#\#}$ or $^\#$—$(C_2$-$C_9$-alkenylene)-$(B)_t$—$CR^{22}R^{23}$—$^{\#\#}$, wherein $^\#$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group;

n is 1, 2, 3, 4, or 5;
p is 1, 2, 3, or 4;
t is 1;
where the integers selected for variables n, t, and p result in forming a 9-membered to 13-membered ring independently from the selection of variable A1 or A2;

B is independently selected from a —$S(O)_2NR^{15}$— group and a —$NR^{15}S(O)_2$— group, $R^8$ is selected from a hydrogen atom, and
  a $C_1$-$C_6$-alkyl group, which is unsubstituted or substituted with one or more substituents independently selected from
    a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group;

$R^9$ is selected from a hydrogen atom,
  a $C_1$-$C_4$-alkyl group,
  a $C_1$-$C_3$-hydroxyalkyl group,
  a $C_1$-$C_4$-haloalkyl group,
  a $C_1$-$C_4$-haloalkyl-NH—C(O)—O—($C_1$-$C_3$-alkylene)- group,
  a $C_2$-$C_6$-haloalkenyl group,
  a $C_1$-$C_6$-alkyl-O— group,
  a $C_1$-$C_4$-haloalkoxy group,
  a $C_1$-$C_6$-alkyl-O—($C_1$-$C_3$-alkylene)- group,
  a ($C_1$-$C_3$-alkyl)-NH—($C_1$-$C_3$-alkylene)- group,
  a ($C_3$-$C_7$)-cycloalkyl group, and
  a ($C_3$-$C_7$)-cycloalkyl-O—($C_1$-$C_3$-alkylene)- group;

$R^{14}$ is a hydrogen atom or a $C_1$-$C_3$-alkyl group;

$R^{15}$ is independently selected from a hydrogen atom,
  a $C_1$-$C_6$-alkyl group
    which is unsubstituted or substituted with one or more substituents selected from a $C_1$-$C_3$-alkyl group, a heterocycloalkyl group, and an unsubstituted or substituted aryl group,
  a ($C_3$-$C_7$)-cycloalkyl group and
  a phenyl group;

$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)_2$— group and a $C_1$-$C_3$-alkyl-O—C(=O)— group;

$R^{19}$ is selected from a $C_1$-$C_3$-alkyl group, a $C_3$-$C_6$-cycloalkyl group and a $NR^{20}R^{21}$ group;

$R^{20}$ and $R^{21}$ are independently from a hydrogen atom and a $C_1$-$C_6$-alkyl group;

$R^{22}$ is independently selected from
  a halogen atom
  a $C_1$-$C_6$-alkyl group which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, and a phenyl group,
  a $C_3$-$C_6$-cycloalkyl group,
  a heterocycloalkyl group,
  a phenyl group, and
  a heteroaryl group;

$R^{23}$ is independently selected from a hydrogen atom, a halogen atom, a hydroxy group, and a $C_1$-$C_4$-alkyl group; or $R^{22}$ and $R^{23}$ together with the carbon atom to which they are attached form a 3-6-membered carbocyclic ring or a 3-6-membered heterocyclic ring comprising one or two heteroatoms selected from nitrogen, oxygen or sulfur;

or a tautomer, an N-oxide, or a salt thereof, or a salt of a tautomer, or salt of an N-oxide, or a mixture of same.

In accordance with a further aspect, the present invention provides compounds of general formula (I) wherein A is

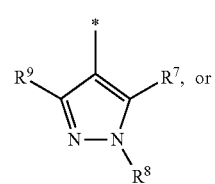

(A1)

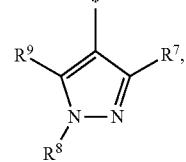

(A2)

wherein $R^6$ and $R^7$, together with two carbon atoms of the pyrazole ring, two carbon atoms of the indole moiety and the nitrogen atom to which $R^6$ is attached, form a 10-membered to 13-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one, two, or three, substituents and each substituent is independently selected from a halogen atom and a $C_1$-$C_3$-alkyl group;

L is a group —$(CH_2)_m$-E-;

E is a bond or an oxygen atom and constitutes the connecting element to $R^4$;

m is 2, 3, or 4;

$R^5$ is a COOH group;

—$R^6$-$R^7$— is $^\#$—$(CH_2)_n$—$(B)_t$—$(CH_2)_p$—$^{\#\#}$, wherein any —$CH_2$— group is unsubstituted or substituted with one or more substituents selected from a halogen atom, a hydroxyl group, a $NR^{16}R^{17}$ group, a $C_1$-$C_3$-alkyl group, a $C_1$-$C_3$-haloalkyl group, a heterocycloalkyl group and a $C_1$-$C_3$-alkoxy group, wherein $^\#$ is the point of attachment with the indole nitrogen atom and $^{\#\#}$ is the point of attachment with the pyrazole carbon atom bearing the $R^7$ substituent or —$R^6$-$R^7$— is $^\#$—$(CH_2)_n$—$(B)_t$—$CR^{22}R^{23}$—$^{\#\#}$ or $^\#$—$(C_2$-$C_9$-alkenylene)-$(B)_t$—$CR^{22}R^{23}$—$^{\#\#}$, wherein $^\#$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group;

n is 2, 3 or 4;

p is 1, 2, or 3;

t is 1;

where the integers selected for variables n, t, and p result in forming a 10-membered to 13-membered ring independently from the selection of variable A1 or A2;

B is selected from a —$S(O)_2NR^{15}$— group and a —$NR^{15}S(O)_2$— group;

$R^8$ is selected from a hydrogen atom, and
  a $C_1$-$C_6$-alkyl group, which is unsubstituted or substituted with one or more substituents independently selected from
    a halogen atom, a hydroxy group, a $C_3$-$C_6$-cycloalkyl group and a heterocycloalkyl group;

$R^9$ is selected from a hydrogen atom,
  a $C_1$-$C_4$-alkyl group,
  a $C_1$-$C_3$-hydroxyalkyl group,
  a $C_1$-$C_4$-haloalkyl group,
  a $C_1$-$C_6$-alkyl-O— group,
  a $C_1$-$C_4$-haloalkoxy group, and
  a $C_1$-$C_6$-alkyl-O—($C_1$-$C_3$-alkylene)- group;

$R^{15}$ is independently selected from a hydrogen atom,
  a $C_1$-$C_6$-alkyl group
    which is unsubstituted or substituted with a substituent selected from a heterocycloalkyl group and an unsubstituted or substituted aryl group, and
  a ($C_3$-$C_7$)-cycloalkyl group;

$R^{16}$ and $R^{17}$ are each independently selected from a hydrogen atom, a $C_1$-$C_6$-alkyl group and a $C_1$-$C_6$-haloalkyl group;

$R^{22}$ is independently selected from
  a halogen atom
  a $C_1$-$C_4$-alkyl group which is unsubstituted or substituted with a group selected from a hydroxy group, $NR^{16}R^{17}$ group, a $C_1$-$C_4$-alkoxy group, a $C_3$-$C_6$-cycloalkyl group, a heterocycloalkyl group and a phenyl group,
  a phenyl group,
  a heteroaryl group,
  a $C_3$-$C_6$-cycloalkyl group, and
  a heterocycloalkyl group, $R^{23}$ is independently selected from a hydrogen atom, a halogen atom, a hydroxy group, and a $C_1$-$C_4$-alkyl group, or $R^{22}$ and $R^{23}$ together form a 3-6-membered carbocyclic ring;

or a tautomer, an N-oxide, or a salt thereof, or a salt of a tautomer, or salt of an N-oxide, or a mixture of same.

In accordance with a further aspect, the present invention provides compounds of general formula (I)
wherein
A is

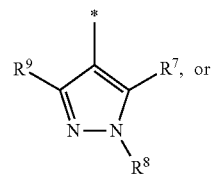

(A1)

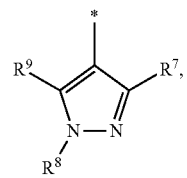

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group which is unsubstituted or substituted with one, two, or three substituents and each substituent is independently selected from a halogen atom, and a $C_1$-$C_3$-alkyl group;

L is a group —$(CH_2)_m$-E-;

E is a bond or an oxygen atom and constitutes the connecting element to $R^4$;

m is 3;

$R^5$ is a COOH group;

—$R^6$-$R^7$— is $^\#$—$(CH_2)_n$—$(B)_t$—$(CH_2)_p$—$^{\#\#}$, wherein $^\#$ is the point of attachment with the indole nitrogen atom and $^{\#\#}$ is the point of attachment with the pyrazole carbon atom bearing the $R^7$ substituent or —$R^6$-$R^7$— is $^\#$—$(CH_2)_n$—$(B)_t$—$CR^{22}R^{23}$—$^{\#\#}$ or $^\#$—$(C_2$-$C_9$-alkenylene)-$(B)_t$—$CR^{22}R^{23}$—$^{\#\#}$, wherein $^\#$ is the point of attachment with the indole nitrogen atom and $^{\#\#}$ is the point of attachment with the pyrazole carbon atom bearing the $R^7$ substituent;

n is 3;

t is 1;

p is 1;

where the integers selected for variables n, t, and p result in forming a 11-membered ring independently from the selection of variable A1 or A2;

B is a —$S(O)_2NR^{15}$— group;

$R^8$ is selected from a hydrogen atom, and
  a $C_1$-$C_6$-alkyl group which is unsubstituted or substituted with a heterocycloalkyl group;

$R^9$ is selected from a hydrogen atom,
  a $C_1$-$C_4$-alkyl group, and
  a $C_1$-$C_6$-alkyl-O—($C_1$-$C_3$-alkylene)- group;

$R^{15}$ is independently selected from a hydrogen atom,
  a $C_1$-$C_6$-alkyl group
    which is unsubstituted or substituted with an unsubstituted or substituted aryl group or with a heterocycloalkyl group, and
  a ($C_3$-$C_7$)-cycloalkyl group;
$R^{22}$ is independently selected from
  a halogen atom,
  a phenyl group,
  a $C_3$-$C_6$-cycloalkyl group,
  a $C_1$-$C_3$-alkyl group which is unsubstituted or substituted with one or more substituents selected from a hydroxy group, a $NR^{17}R^{18}$ group, a $C_1$-$C_3$-haloalkyl group, a $C_1$-$C_3$-alkoxy group, a $C_3$-$C_6$-cycloalkyl group, a heterocycloalkyl group and a phenyl group;
$R^{23}$ is independently selected from a hydrogen atom, a halogen atom, a hydroxy group and a $C_1$-$C_3$-alkyl group
or
$R^{22}$ and $R^{23}$ together form a 3-6-membered carbocyclic ring;
or a tautomer, an N-oxide, or a salt thereof, or a salt of a tautomer, or salt of an N-oxide, or a mixture of same.

In accordance with a further aspect, the present invention provides compounds of general formula (I)
wherein
A is

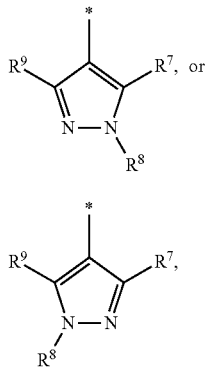

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a hydrogen atom or a halogen atom;
$R^2$ is a hydrogen atom;
$R^3$ is a hydrogen atom;
$R^4$ is an aryl group, which is unsubstituted or substituted with one, two or three substituents independently selected from a halogen atom and a methyl group;
L is a group $(CH_2)_3$—O—;
$R^5$ is a COOH group;
—$R^6$-$R^7$— is $^{\#}$—$(CH_2)_n$—$S(O)_2NR^{15}$—$(CH_2)_p$—$^{\#\#}$, wherein $^{\#}$ is the point of attachment with the indole nitrogen atom and $^{\#\#}$ is the point of attachment with the pyrazole carbon atom bearing the $R^7$ substituent or
—$R^6$-$R^7$— is $^{\#}$—$(CH_2)_n$—$(B)_t$—$CR^{22}R^{23}$—$^{\#\#}$,
wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming a 11-membered ring independently from the selection of variable A1 or A2;
B is a —$S(O)_2NR^{15}$— group;
$R^8$ is a methyl group;
$R^9$ is selected from a methyl group and an ethyl group,
$R^{15}$ is independently selected from a hydrogen atom,
  a $C_1$-$C_3$-alkyl group which is unsubstituted or substituted with an unsubstituted or a substituted aryl group or with an unsubstituted or substituted heterocycloalkyl group and
  a ($C_3$-$C_7$)-cycloalkyl group;
$R^{22}$ is independently selected from a $C_1$-$C_3$-haloalkyl group and a $C_1$-$C_3$-alkyl group which is unsubstituted or substituted with a hydroxyl group, a $C_3$-$C_5$-cycloalkyl group, or a heterocyclyl group;
$R^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein
A is

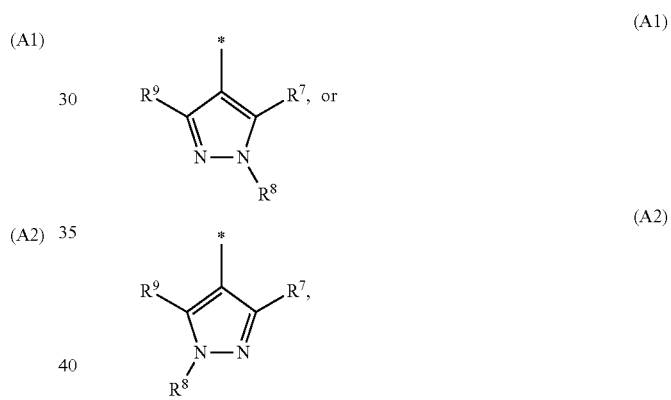

wherein $R^6$ and $R^7$, together with two carbon atoms of the pyrazole ring, two carbon atoms of the indole moiety and the nitrogen atom to which $R^6$ is attached, form a 11-membered to 13-membered ring and * is the point of attachment of these moieties to the indole carbon atom bearing the A substituent;
$R^1$ and $R^2$ are each independently selected from a hydrogen atom and a halogen atom;
$R^3$ is a hydrogen atom;
$R^4$ is selected from an aryl group which is unsubstituted or substituted with one, two, or three substituents and each substituent is independently selected from a halogen atom, and a $C_1$-$C_3$-alkyl group;
L is a group —$(CH_2)_m$-E-;
E is a bond or an oxygen atom and constitutes the connecting element to $R^4$;
m is 3;
$R^5$ is a COOH group;
—$R^6$-$R^7$— is $^{\#}$—$(CH_2)_n$—$(B)_t$—$(CH_2)_p$—$^{\#\#}$, wherein any —$CH_2$— group is unsubstituted or substituted with one heterocycloalkyl group, wherein $^{\#}$ is the point of attachment with the indole nitrogen atom and $^{\#\#}$ is the point of attachment with the pyrazole carbon atom bearing the $R^7$ substituent or —$R^6$-$R^7$— is $^{\#}$—(CH$_2$)$_n$—(B)$_t$—CR$^{22}$R$^{23}$—$^{\#\#}$ or $^{\#}$—(C$_2$-C$_9$-alkenylene)-(B)$_t$—CR$^{22}$R$^{23}$—$^{\#\#}$,
wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1, 2 or 3;
where the integers selected for variables n, t, and p result in forming a 11-membered to 13-membered ring independently from the selection of variable A1 or A2;
B is a —S(O)$_2$NR$^{15}$— group;
$R^8$ is selected from a hydrogen atom, and
a $C_1$-$C_6$-alkyl group which is unsubstituted or substituted with a heterocycloalkyl group;
$R^9$ is selected from a hydrogen atom,
a $C_1$-$C_4$-alkyl group, and
a $C_1$-$C_6$-alkyl-O—($C_1$-$C_3$-alkylene)- group;
$R^{15}$ is independently selected from a hydrogen atom,
a $C_1$-$C_6$-alkyl group
which is unsubstituted or substituted with an unsubstituted or substituted aryl group or with a heterocycloalkyl group, and
a ($C_3$-$C_7$)-cycloalkyl group;
$R^{22}$ is independently selected from
a halogen atom,
a phenyl group,
a $C_3$-$C_6$-cycloalkyl group, and
a $C_1$-$C_3$-alkyl group which is unsubstituted or substituted with one or more substituents selected from a hydroxy group, a NR$^{17}$R$^{18}$ group, a $C_1$-$C_3$-haloalkyl group, a $C_1$-$C_3$-alkoxy group, a $C_3$-$C_6$-cycloalkyl group, a heterocycloalkyl group and a phenyl group;
$R^{23}$ is independently selected from a hydrogen atom, a halogen atom, a hydroxy group and a $C_1$-$C_3$-alkyl group or
$R^{22}$ and $R^{23}$ together form a 3-6-membered carbocyclic ring;
or a tautomer, an N-oxide, or a salt thereof, or a salt of a tautomer, or salt of an N-oxide, or a mixture of same.

In accordance with a further aspect, the present invention provides compounds of general formula (I)
wherein
A is

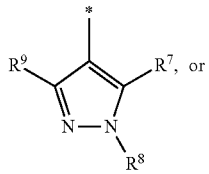

(A1)

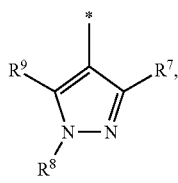

(A2)

wherein $R^6$ and $R^7$, together with two carbon atoms of the pyrazole ring, two carbon atoms of the indole moiety and the nitrogen atom to which $R^6$ is attached, form a 11-membered to 13-membered ring and * is the point of attachment of these moieties to the indole carbon atom bearing the A substituent;

$R^1$ is a hydrogen atom or a halogen atom;
$R^2$ is a hydrogen atom;
$R^3$ is a hydrogen atom;
$R^4$ is an aryl group, which is unsubstituted or substituted with one, two or three substituents independently selected from a halogen atom and a methyl group;
L is a group (CH$_2$)$_3$—O—;
$R^5$ is a COOH group;
—$R^6$-$R^7$— is $^{\#}$—(CH$_2$)$_n$—S(O)$_2$NR$^{15}$—(CH$_2$)$_p$—$^{\#\#}$,
wherein any —CH$_2$— group is unsubstituted or substituted with one heterocycloalkyl group, wherein $^{\#}$ is the point of attachment with the indole nitrogen atom and $^{\#\#}$ is the point of attachment with the pyrazole carbon atom bearing the $R^7$ substituent or
—$R^6$-$R^7$— is $^{\#}$—(CH$_2$)$_n$—(B)$_t$—CR$^{22}$R$^{23}$—$^{\#\#}$,
wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1, 2 or 3;
where the integers selected for variables n, t and p result in forming a 11-membered to 13-membered ring independently from the selection of variable A1 or A2;
B is a —S(O)$_2$NR$^{15}$— group;
$R^8$ is a methyl group;
$R^9$ is selected from a methyl group and an ethyl group;
$R^{15}$ is independently selected from a hydrogen atom,
a $C_1$-$C_3$-alkyl group which is unsubstituted or substituted with an unsubstituted or a substituted aryl group or with an unsubstituted or substituted heterocycloalkyl group, and
a ($C_3$-$C_7$)-cycloalkyl group,
$R^{22}$ is independently selected from a $C_1$-$C_3$-haloalkyl group and a $C_1$-$C_3$-alkyl group which is unsubstituted or substituted with a hydroxyl group, a $C_3$-$C_5$-cycloalkyl group, or a heterocyclyl group;
$R^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I):

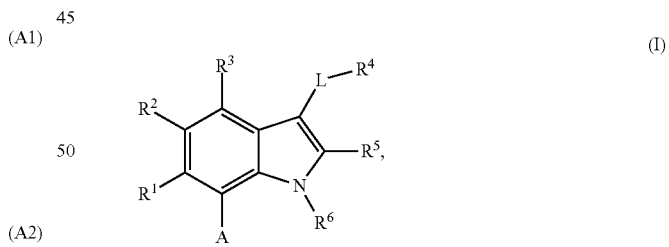

(I)

wherein
A is

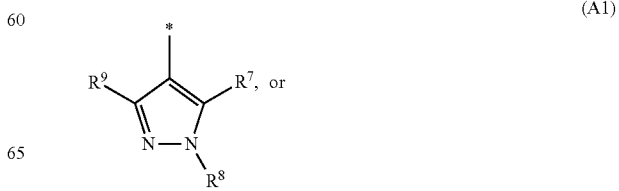

(A1)

-continued (A2)

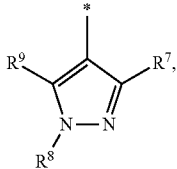

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent;
or
A is (A3)

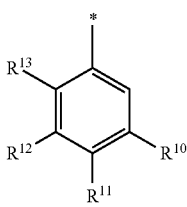

wherein optionally one or two of the groups selected from $CR^{11}$, $CR^{12}$ and $CR^{13}$ are replaced by a nitrogen atom,
wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;
$R^1$ and $R^2$ are each independently selected from a hydrogen atom, a halogen atom, a cyano group, a $C_1$-$C_3$-alkyl group, and a $C_1$-$C_3$-alkoxy group;
$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, a $C_1$-$C_3$-haloalkoxy group, a $C_1$-$C_3$-haloalkylthio group and a $C_3$-$C_5$-cycloalkyl group;
$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;
L is a group —(CH$_2$)$_m$-E- wherein any CH$_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8-membered saturated or partially unsaturated heterocyclic ring having 1-2 heteroatoms independently selected from an oxygen atom, a sulfur atom, a S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to $R^4$;
m is 2, 3, or 4;
$R^5$ is selected from a COOH group, a

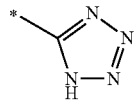

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;
—$R^6$-$R^7$— is $^{\#}$—(CH$_2$)$_n$—(B)$_t$—(CH$_2$)$_p$—$^{\#\#}$, wherein any —CH$_2$— group is unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a heterocycloalkyl group and a (heterocycloalkyl)-($C_1$-$C_3$-alkylene)- group, and where a double bond in any alkenylene can be replaced by a 1,2-cyclopropyl group, and said 1,2-cyclopropyl group is unsubstituted or substituted one or two times with a halogen atom or a $C_1$-$C_2$-alkyl group, wherein $^{\#}$ is the point of attachment with the indole nitrogen atom and $^{\#\#}$ is the point of attachment with the pyrazole carbon atom bearing the $R^7$ substituent or
—$R^6$-$R^{10}$— is $^{\#}$—(CH$_2$)$_n$—(B)$_t$—(CH$_2$)$_p$—$^{\#\#}$, where one or more CH$_2$ groups are unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a heterocycloalkyl group and a (heterocycloalkyl)-($C_1$-$C_3$alkylene)- group, wherein $^{\#}$ is the point of attachment with the indole nitrogen atom and $^{\#\#}$ is the point of attachment with the carbon atom of the phenyl moiety bearing the $R^{10}$ substituent;
n is 1, 2, 3, 4, 5, 6, 7, or 8;
p is 1, 2, 3, 4, 5, 6, 7 or 8;
t is 1;
s is 0, 1 or 2;
where the integers selected for variables n, t, and p result in forming a 9-membered to 16-membered ring independently from the selection of variable A1, A2 or A3;
B is independently selected from a —S(O)NR$^{15}$— group, a —NR$^{15}$S(O)— group, a —S(O)$_2$NR$^{15}$— group, and a —NR$^{15}$S(O)$_2$— group;
$R^8$ is selected from a hydrogen atom,
a $C_1$-$C_6$-alkyl group, which is unsubstituted or substituted with one or more substituents independently selected from
a halogen atom, a hydroxyl group, a $C_1$-$C_3$-alkoxy group, a $C_1$-$C_3$-haloalkoxy group,
a $C_3$-$C_6$-cycloalkyl group, a heterocycloalkyl group, and a NR$^{20}$R$^{21}$ group, and
a $C_1$-$C_3$-haloalkyl group, a $C_3$-$C_6$-cycloalkyl group, or a $C_1$-$C_6$-alkyl group in which one or two not directly adjacent carbon atoms are independently replaced by a heteroatom independently selected from —O— and —NH—;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{18}$-(phenylene)-($C_1$-$C_3$-alkylene)-O—($C_1$-$C_3$-alkylene)- group,
a $R^{18}$-(phenylene)-O—($C_1$-$C_3$-alkylene)- group,
a $R^{18}$-(phenylene)-(heteroarylene)-O—($C_1$-$C_3$-alkylene)- group,
a ($R^{18}$)-(heterocycloalkylene)-($C_1$-$C_3$-alkylene)- group,
a ($R^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{18}$)-(heteroarylene)-($C_1$-$C_3$-alkylene)-O—($C_1$-$C_3$-alkylene)- group,
a ($R^{18}$)-(heteroarylene)-(phenylene)-O—($C_1$-$C_3$-alkylene)- group,
a ($R^{19}$)—S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{18}$)-(heteroarylene)-O—($C_1$-$C_3$-alkylene)- group,
a ($R^{19}$)—S(O)$_2$-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a NR$^{20}$R$^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-NR$^{19}$—C(O)—($C_1$-$C_3$-alkylene)- group,
a ($C_1$-$C_3$-alkyl)-C(O)—NH—($C_1$-$C_3$-alkylene)- group,
a ($C_1$-$C_3$-alkyl)-C(O)—NR$^{19}$—($C_1$-$C_3$-alkylene)- group,
a

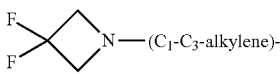

group, and a

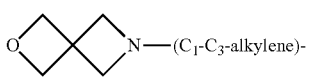

group, where the phenyl ring is unsubstituted or substituted with a halogen atom, a hydroxyl group, or a $C_1$-$C_3$-alkoxy group and
the heterocycloalkyl group is unsubstituted or substituted with an oxo (=O) group or is unsubstituted or substituted with one or more substituents independently selected from a halogen atom, a hydroxyl group, a $C_1$-$C_3$-alkyl group and a $C_1$-$C_3$-alkoxy group,
or $R^8$ and $R^9$ together form a 5- or 6-membered ring optionally comprising one or two heteroatoms independently selected from —O— and —NR$^{14}$—;
$R^{11}$ and $R^{13}$ are each independently selected from a hydrogen atom, a halogen atom, a $C_1$-$C_3$-alkyl group, and a $C_1$-$C_3$-alkoxy group;
$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a NR$^{16}$R$^{17}$ group;
$R^{14}$ is a hydrogen atom or a $C_1$-$C_3$-alkyl group;
$R^{15}$ is independently selected from a hydrogen atom,
a $C_1$-$C_6$-alkyl group
which is unsubstituted or substituted with one or more substituents independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an unsubstituted or substituted aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-S(O)$_2$— group, and a heterocycloalkylene-heteroarylene-S(O)$_2$— group,
a ($C_3$-$C_7$)-cycloalkyl group and
a phenyl group;
$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;
$R^{18}$ is independently selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a R$^{21}$OC(O)—($C_1$-$C_3$-alkylene)- group, a —C(O)OR$^{21}$ group, a —C(O)NR$^{20}$R$^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;
$R^{19}$ is selected from a $C_1$-$C_3$-alkyl group, a $C_3$-$C_6$-cycloalkyl group and a NR$^{20}$R$^{21}$ group; and
$R^{20}$ and $R^{21}$ are independently selected from a hydrogen atom and a $C_1$-$C_6$-alkyl group; or a tautomer, an N-oxide, or a salt thereof, or a salt of a tautomer, or salt of an N-oxide, or a mixture of same.

In accordance with a further aspect, the present invention provides compounds of general formula (I) wherein
A is

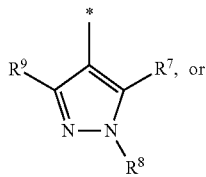
(A1)

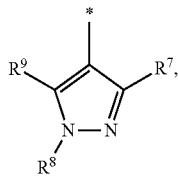
(A2)

wherein $R^6$ and $R^7$, together with two carbon atoms of the pyrazole ring, two carbon atoms of the indole moiety and the nitrogen atom to which $R^6$ is attached, form a 9-membered to 13-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

$R^4$ is selected from an aryl group and a heteroaryl group, each of which is unsubstituted or substituted with one, two, or three substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group;

E is a bond, an oxygen atom, a sulfur atom, or a —$NR^{14}$— group and constitutes the connecting element to $R^4$;

m is 2, 3, or 4;

$R^5$ is selected from a COOH group and a

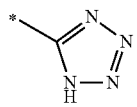

group;

—$R^6$-$R^7$— is #—$(CH_2)_n$—$(B)_t$—$(CH_2)_p$—##, wherein any —$CH_2$— group is unsubstituted or substituted with one or more substituents selected from a halogen atom, a hydroxyl group, a $NR^{16}R^{17}$ group, a $C_1$-$C_3$-alkyl group, a $C_1$-$C_3$-haloalkyl group, a heterocycloalkyl group and a $C_1$-$C_3$-alkoxy group, wherein # is the point of attachment with the indole nitrogen atom and ## is the point of attachment with the pyrazole carbon atom bearing the $R^7$ substituent;

n is 1, 2, 3, 4, or 5;
p is 1, 2, 3, or 4;
t is 1;
where the integers selected for variables n, t, and p result in forming a 9-membered to 13-membered ring independently from the selection of variable A1 or A2;

B is independently selected from a —$S(O)_2NR^{15}$— group and a —$NR^{15}S(O)_2$— group, $R^8$ is selected from a hydrogen atom, and
a $C_1$-$C_6$-alkyl group, which is unsubstituted or substituted with one or more substituents independently selected from
a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_1$-$C_3$-alkyl)-NH—($C_1$-$C_3$-alkylene)- group,
a ($C_3$-$C_7$)-cycloalkyl group, and
a ($C_3$-$C_7$)-cycloalkyl-O—($C_1$-$C_3$-alkylene)- group;

$R^{14}$ is a hydrogen atom or a $C_1$-$C_3$-alkyl group;

$R^{15}$ is independently selected from a hydrogen atom,
a $C_1$-$C_6$-alkyl group
which is unsubstituted or substituted with one or more substituents selected from a $C_1$-$C_3$-alkyl group, a heterocycloalkyl group, and an unsubstituted or substituted aryl group,
a ($C_3$-$C_7$)-cycloalkyl group and
a phenyl group;

$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;

$R^{19}$ is selected from a $C_1$-$C_3$-alkyl group, a $C_3$-$C_6$-cycloalkyl group and a $NR^{20}R^{21}$ group; and $R^{29}$ and $R^{21}$ are independently selected from a hydrogen atom and a $C_1$-$C_6$-alkyl group;

or a tautomer, an N-oxide, or a salt thereof, or a salt of a tautomer, or salt of an N-oxide, or a mixture of same.

In accordance with a further aspect, the present invention provides compounds of general formula (I) wherein
A is

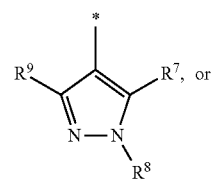
(A1)

-continued

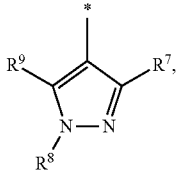
(A2)

wherein R⁶ and R⁷, together with two carbon atoms of the pyrazole ring, two carbon atoms of the indole moiety and the nitrogen atom to which R⁶ is attached, form a 10-membered to 13-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one, two, or three, substituents and each substituent is independently selected from a halogen atom and a $C_1$-$C_3$-alkyl group;

L is a group —$(CH_2)_m$-E-;

E is a bond or an oxygen atom and constitutes the connecting element to $R^4$;

m is 2, 3, or 4;

$R^5$ is a COOH group;

—$R^6$-$R^7$— is $^{\#}$—$(CH_2)_n$—(B)$_t$—$(CH_2)_p$—$^{\#\#}$, wherein any —$CH_2$— group is unsubstituted or substituted with one or more substituents selected from a halogen atom, a hydroxyl group, a $NR^{16}R^{17}$ group, a $C_1$-$C_3$-alkyl group, a $C_1$-$C_3$-haloalkyl group, a heterocycloalkyl group and a $C_1$-$C_3$-alkoxy group, wherein $^{\#}$ is the point of attachment with the indole nitrogen atom and $^{\#\#}$ is the point of attachment with the pyrazole carbon atom bearing the $R^7$ substituent;

n is 2, 3 or 4;

p is 1, 2, or 3;

t is 1;

where the integers selected for variables n, t, and p result in forming a 10-membered to 13-membered ring independently from the selection of variable A1 or A2;

B is selected from a —$S(O)_2NR^{15}$— group and a —$NR^{15}S(O)_2$— group;

$R^8$ is selected from a hydrogen atom, and
a $C_1$-$C_6$-alkyl group, which is unsubstituted or substituted with one or more substituents independently selected from
a halogen atom, a hydroxy group, a $C_3$-$C_6$-cycloalkyl group and a heterocycloalkyl group;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_6$-alkyl-O— group,
a $C_1$-$C_4$-haloalkoxy group, and
a $C_1$-$C_6$-alkyl-O—($C_1$-$C_3$-alkylene)- group;

$R^{15}$ is independently selected from a hydrogen atom,
a $C_1$-$C_6$-alkyl group
which is unsubstituted or substituted with a substituent selected from a heterocycloalkyl group and an unsubstituted or substituted aryl group, and
a ($C_3$-$C_7$)-cycloalkyl group;

$R^{16}$ and $R^{17}$ are each independently selected from a hydrogen atom, a $C_1$-$C_6$-alkyl group and a $C_1$-$C_6$-haloalkyl group; or a tautomer, an N-oxide, or a salt thereof, or a salt of a tautomer, or salt of an N-oxide, or a mixture of same.

In accordance with a further aspect, the present invention provides compounds of general formula (I) wherein
A is

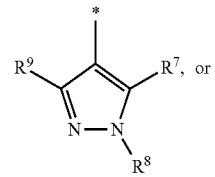
(A1)

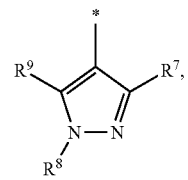
(A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group which is unsubstituted or substituted with one, two, or three substituents and each substituent is independently selected from a halogen atom, and a $C_1$-$C_3$-alkyl group;

L is a group —$(CH_2)_m$-E-;

E is a bond or an oxygen atom and constitutes the connecting element to $R^4$;

m is 3;

$R^5$ is a COOH group;

—$R^6$-$R^7$— is $^{\#}$—$(CH_2)_n$—(B)$_t$—$(CH_2)_p$—$^{\#\#}$, wherein $^{\#}$ is the point of attachment with the indole nitrogen atom and $^{\#\#}$ is the point of attachment with the pyrazole carbon atom bearing the $R^7$ substituent;

n is 3;

t is 1;

p is 1;

where the integers selected for variables n, t, and p result in forming a 11-membered ring independently from the selection of variable A1 or A2;

B is a —$S(O)_2NR^{15}$— group;

$R^5$ is selected from a hydrogen atom, and
a $C_1$-$C_6$-alkyl group which is unsubstituted or substituted with a heterocycloalkyl group;

$R^9$ is selected from a hydrogen atom,
a $C_1$-$C_4$-alkyl group, and
a $C_1$-$C_6$-alkyl-O—($C_1$-$C_3$-alkylene)- group;

$R^{15}$ is independently selected from a hydrogen atom,
a $C_1$-$C_6$-alkyl group
which is unsubstituted or substituted with an unsubstituted or substituted aryl group or with a heterocycloalkyl group; and
a ($C_3$-$C_7$)-cycloalkyl group;

or a tautomer, an N-oxide, or a salt thereof, or a salt of a tautomer, or salt of an N-oxide, or a mixture of same.

In accordance with a further aspect, the present invention provides compounds of general formula (I)
wherein
A is

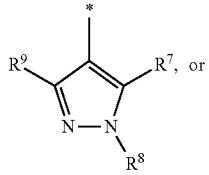

(A1)

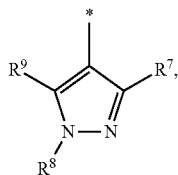

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a hydrogen atom or a halogen atom;
$R^2$ is a hydrogen atom;
$R^3$ is a hydrogen atom;
$R^4$ is an aryl group, which is unsubstituted or substituted with one, two or three substituents independently selected from a halogen atom and a methyl group;
L is a group $(CH_2)_3$—O—;
$R^5$ is a COOH group;
—$R^6$-$R^7$— is $^{\#}$—$(CH_2)_n$—$S(O)_2NR^{15}$—$(CH_2)_p$—$^{\#\#}$, wherein $^{\#}$ is the point of attachment with the indole nitrogen atom and $^{\#\#}$ is the point of attachment with the pyrazole carbon atom bearing the $R^7$ substituent;
n is 3;
p is 1;
where the integers selected for variables n and p result in forming a 11-membered ring independently from the selection of variable A1 or A2;
$R^8$ is a methyl group;
$R^9$ is selected from a methyl group and an ethyl group;
$R^{15}$ is independently selected from a hydrogen atom,
a $C_1$-$C_3$-alkyl group which is unsubstituted or substituted with an unsubstituted or a substituted aryl group or with an unsubstituted or substituted heterocycloalkyl group and a $(C_3$-$C_7)$-cycloalkyl group,
or a tautomer, an N-oxide, or a salt thereof, or a salt of a tautomer, or salt of an N-oxide, or a mixture of same.

In accordance with a further aspect, the present invention provides compounds of general formula (I)
wherein
A is

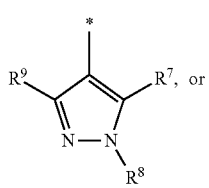

(A1)

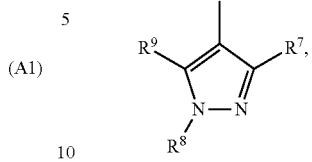

(A2)

wherein $R^6$ and $R^7$, together with two carbon atoms of the pyrazole ring, two carbon atoms of the indole moiety and the nitrogen atom to which $R^6$ is attached, form a 11-membered to 13-membered ring and * is the point of attachment of these moieties to the indole carbon atom bearing the A substituent;
$R^1$ and $R^2$ are each independently selected from a hydrogen atom and a halogen atom;
$R^3$ is a hydrogen atom;
$R^4$ is selected from an aryl group which is unsubstituted or substituted with one, two, or three substituents and each substituent is independently selected from a halogen atom and a $C_1$-$C_3$-alkyl group;
L is a group —$(CH_2)_m$-E-;
E is a bond or an oxygen atom and constitutes the connecting element to $R^4$;
m is 3;
$R^5$ is a COOH group;
—$R^6$-$R^7$— is $^{\#}$—$(CH_2)_n$—(B)$_t$—$(CH_2)_p$—$^{\#\#}$, wherein any —$CH_2$— group is unsubstituted or substituted with one heterocycloalkyl group, wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1, 2 or 3;
where the integers selected for variables n, t, and p result in forming a 11-membered to 13-membered ring independently from the selection of variable A1 or A2;
B is a —$S(O)_2NR^{15}$— group;
$R^8$ is selected from a hydrogen atom, and
a $C_1$-$C_6$-alkyl group which is unsubstituted or substituted with a heterocycloalkyl group;
$R^9$ is selected from a hydrogen atom,
a $C_1$-$C_4$-alkyl group, and
a $C_1$-$C_6$-alkyl-O—$(C_1$-$C_3$-alkylene)- group;
$R^{15}$ is independently selected from a hydrogen atom,
a $C_1$-$C_6$-alkyl group
which is unsubstituted or substituted with an unsubstituted or substituted aryl group or with a heterocycloalkyl group, and
a $(C_3$-$C_7)$-cycloalkyl group;
or a tautomer, an N-oxide, or a salt thereof, or a salt of a tautomer, or salt of an N-oxide, or a mixture of same.

In accordance with a further aspect, the present invention provides compounds of general formula (I)
wherein
A is

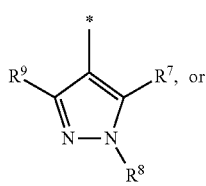
(A1)

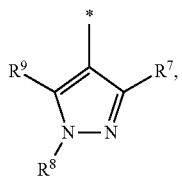
(A2)

wherein $R^6$ and $R^7$, together with two carbon atoms of the pyrazole ring, two carbon atoms of the indole moiety and the nitrogen atom to which $R^6$ is attached, form a 11-membered to 13-membered ring and * is the point of attachment of these moieties to the indole carbon atom bearing the A substituent;

$R^1$ is a hydrogen atom or a halogen atom;

$R^2$ is a hydrogen atom;

$R^3$ is a hydrogen atom;

$R^4$ is an aryl group, which is unsubstituted or substituted with one, two or three substituents independently selected from a halogen atom and a methyl group;

L is a group $(CH_2)_3$—O—;

$R^5$ is a COOH group;

—$R^6$-$R^7$— is #—$(CH_2)_n$—$S(O)_2NR^{15}$—$(CH_2)_p$—##, wherein any —$CH_2$— group is unsubstituted or substituted with one heterocycloalkyl group, wherein # is the point of attachment with the indole nitrogen atom and ## is the point of attachment with the pyrazole carbon atom bearing the $R^7$ substituent;

n is 3;

p is 1, 2 or 3;

where the integers selected for variables n and p result in forming a 11-membered to 13-membered ring independently from the selection of variable A1 or A2;

$R^8$ is a methyl group;

$R^9$ is selected from a methyl group and an ethyl group;

$R^{15}$ is independently selected from a hydrogen atom,
a $C_1$-$C_3$-alkyl group which is unsubstituted or substituted with an unsubstituted or a substituted aryl group or with an unsubstituted or substituted heterocycloalkyl group, and
a $(C_3$-$C_7)$-cycloalkyl group;

or a tautomer, an N-oxide, or a salt thereof, or a salt of a tautomer, or salt of an N-oxide, or a mixture of same.

In accordance with a further aspect, the present invention provides compounds of general formula (I)

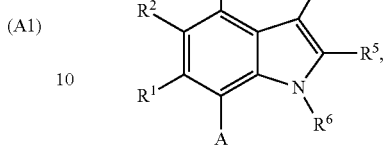
(I)

wherein
A is

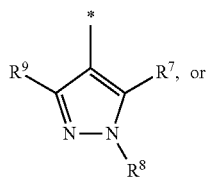
(A1)

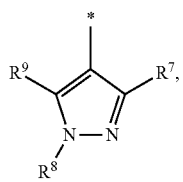
(A2)

wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent;
or
A is

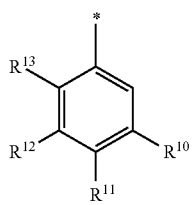
(A3)

wherein optionally one or two of the groups selected from $CR^{11}$, $CR^{12}$ and $CR^{13}$ are replaced by a nitrogen atom,
wherein $R^6$ and $R^{10}$, together with three carbon atoms of the phenyl ring, two carbon atoms of the indole moiety and the nitrogen atom to which $R^6$ is attached, form a 9-membered to 16-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group, and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, a $C_1$-$C_3$-haloalkoxy group, a $C_1$-$C_3$-haloalkylthio group and a $C_3$-$C_5$-cycloalkyl group;

$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;

L is a group —(CH$_2$)$_m$-E- wherein any CH$_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to $R^4$;

m is 2, 3, or 4;

$R^5$ is selected from a COOH group, a

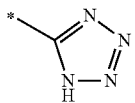

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;

—$R^6$-$R^7$— is #—(CH$_2$)$_n$—(B)$_t$—CR$^{22}$R$^{23}$—## or #—(C$_2$-C$_9$-alkenylene)-(B)$_t$—CR$^{22}$R$^{23}$—##, wherein # is the point of attachment with the indole nitrogen atom and ## is the point of attachment with the pyrazole carbon atom bearing the $R^7$ substituent; and wherein one or more —CH$_2$— groups may be unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group;

—$R^6$-$R^{10}$— is #—(CH$_2$)$_n$—(B)$_t$—CR$^{22}$R$_{23}$—## or #—(C$_2$-C$_9$-alkenylene)-(B)$_t$—CR$^{22}$R$^{23}$—##, where one or more —CH$_2$— groups are substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group, wherein # is the point of attachment with the indole nitrogen atom and ## is the point of attachment with the carbon atom of the phenyl moiety bearing the $R^{10}$ substituent;

n is 1, 2, 3, 4, 5, 6, 7, or 8;

p is 1, 2, 3, 4, 5, 6, 7 or 8;

t is 1;

s is 0, 1 or 2;

where the integers selected for variables n, t, and p result in forming a 9-membered to 16-membered ring independently from the selection of variable A1, A2 or A3;

B is independently selected from a —S(O)NR$^{15}$— group, a —NR$^{15}$S(O)— group, a —S(O)$_2$NR$^{15}$— group, and a —NR$^{15}$S(O)$_2$— group;

$R^8$ is selected from a hydrogen atom,
a $C_1$-$C_6$-alkyl group, which is unsubstituted or substituted with one or more substituents independently selected from
a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group, and a NR$^{20}$R$^{21}$ group, and
a $C_1$-$C_3$-haloalkyl group, a $C_3$-$C_6$-cycloalkyl group, or a $C_1$-$C_6$-alkyl group in which one or two not directly adjacent carbon atoms are independently replaced by a heteroatom independently selected from —O— and NH—;

$R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a R$^{18}$-(phenylene)-($C_1$-$C_3$-alkylene)-O—($C_1$-$C_3$-alkylene)- group,
a R$^{18}$-(phenylene)-O—($C_1$-$C_3$-alkylene)- group,
a R$^{18}$-(phenylene)-(heteroarylene)-O—($C_1$-$C_3$-alkylene)- group,
a (R$^{18}$)-(heterocycloalkylene)-($C_1$-$C_3$-alkylene)- group,
a (R$^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a (R$^{18}$)-(heteroarylene)-($C_1$-$C_3$-alkylene)-O—($C_1$-$C_3$-alkylene)- group,
a (R$^{18}$)-(heteroarylene)-(phenylene)-O—($C_1$-$C_3$-alkylene)- group,
a (R$^{19}$)—S(O)$_2$-(phenylene)-O—($C_1$-$C_3$-alkylene)- group,
a (R$^{19}$)—S(O)$_2$—NH-(phenylene)-O—($C_1$-$C_3$-alkylene)- group,
a (R$^{19}$)—S(O)$_2$—NH-(phenylene)-O—($C_1$-$C_3$-alkylene)- group,
a (R$^{19}$)—S(O)$_2$—N($C_1$-$C_6$-alkyl)-(phenylene)-O—($C_1$-$C_3$-alkylene)- group,
a (R$^{19}$)—S(O)$_2$-(heterocycloalkylene)-(phenylene)-O—($C_1$-$C_3$-alkylene)- group,
a (R$^{18}$)-(heterocycloalkylene)-(heteroarylene)-O—($C_1$-$C_3$-alkylene)- group,
a (R$^{19}$)-(heteroarylene)-O—($C_1$-$C_3$-alkylene)- group,
a (R$^{18}$)-(heteroarylene)-O—($C_1$-$C_3$-alkylene)- group,
a (R$^{19}$)—S(O)$_2$-(heteroarylene)-O—($C_1$-$C_3$-alkylene)- group,
a (R$^{19}$)—S(O)$_2$-(heterocycloalkylene)-(heteroarylene)-O—($C_1$-$C_3$-alkylene)- group, a NR$^{20}$R$^{21}$—(C$_1$-C$_3$-alkylene)- group,
a (C$_1$-C$_3$-alkyl)-NH—(C$_1$-C$_3$-alkylene)- group,
a (C$_1$-C$_3$-haloalkyl)-(C$_1$-C$_3$-alkylene)-NH—(C$_1$-C$_3$-alkylene)- group,
a (C$_1$-C$_3$-haloalkyl)-NH—(C$_1$-C$_3$-alkylene)- group,
a (C$_1$-C$_3$-alkyl)-NH—C(O)—(C$_1$-C$_3$-alkylene)- group,
a (C$_1$-C$_3$-alkyl)-NR$^{15}$—C(O)—(C$_1$-C$_3$-alkylene)- group,
a (C$_1$-C$_3$-alkyl)-C(O)—NH—(C$_1$-C$_3$-alkylene)- group,
a (C$_1$-C$_3$-alkyl)-C(O)—NR$^{19}$—(C$_1$-C$_3$-alkylene)- group,
a

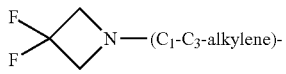

group, and a

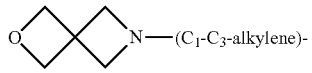

group, where the phenyl ring is unsubstituted or substituted with a halogen atom, a hydroxyl group, or a C$_1$-C$_3$-alkoxy group and
the heterocycloalkyl group is unsubstituted or substituted with an oxo (=O) group or is unsubstituted or substituted with one or more substituents independently selected from a halogen atom, a hydroxyl group, a C$_1$-C$_3$-alkyl group and a C$_1$-C$_3$-alkoxy group,
or R$^8$ and R$^9$ together form a 5- or 6-membered ring optionally comprising one or two heteroatoms independently selected from —O— and —NR$^{14}$—;
R$^{11}$ and R$^{13}$ are each independently selected from a hydrogen atom, a halogen atom, a C$_1$-C$_3$-alkyl group, and a C$_1$-C$_3$-alkoxy group;
R$^{12}$ is selected from a hydrogen atom, a C$_1$-C$_3$-alkoxy group, a C$_1$-C$_3$-alkyl group, a C$_1$-C$_3$-haloalkyl group, a C$_1$-C$_3$-haloalkoxy group, and a NR$^{16}$R$^{17}$ group;
R$^{14}$ is a hydrogen atom or a C$_1$-C$_3$-alkyl group;
R$^{15}$ is independently selected from a hydrogen atom,
a C$_1$-C$_6$-alkyl group
which is unsubstituted or substituted with one or more substituents independently selected from a halogen atom, a C$_1$-C$_3$-alkyl group, a C$_1$-C$_3$-haloalkyl group, a C$_1$-C$_3$-hydroxyalkyl group, a C$_1$-C$_3$-alkoxy group, a C$_1$-C$_3$-haloalkoxy group, a heterocycloalkyl group, an unsubstituted or substituted aryl group, a (R$^{18}$)-(heterocycloalkylene)-(arylene)-O— group, a (heterocycloalkyl)-(arylene)-O— group, an aryl-O— group, an aryl-(C$_1$-C$_3$-alkylene)-O— group, a (R$^{19}$)—S(O)$_2$-arylene-O— group, a (R$^{19}$)S(O)$_2$-heterocycloalkylene-arylene-O— group, an aryl-heteroarylene-O— group, an aryl-heteroarylene-O—(C$_1$-C$_3$-alkylene)- group, a heterocycloalkyl-(C$_1$-C$_3$-alkylene)-C(O)— group, a heterocycloalkyl-NH—C(O) group, an aryl-(C$_1$-C$_3$-alkylene)-NH—C(O)— group, a heterocycloalkylene-(C$_1$-C$_3$-alkylene)-S(O)$_2$— group, and a heterocycloalkylene-heteroarylene-S(O)$_2$— group;
a (C$_3$-C$_7$)-cycloalkyl group and
a phenyl group;
R$^{16}$ and R$^{17}$ are each independently selected from a hydrogen atom, a C$_1$-C$_6$-alkyl group, a C$_1$-C$_6$-haloalkyl group, a C$_3$-C$_5$-cycloalkyl group, a C$_1$-C$_3$-alkyl-C(O)— group, a C$_1$-C$_3$-alkylS(O)$_2$— group and a C$_1$-C$_3$-alkyl-O—C(=O)— group;
R$^{18}$ is independently selected from a hydrogen atom, a hydroxyl group, a cyano group, a C$_1$-C$_3$-alkyl group, a C$_1$-C$_6$-hydroxyalkyl group, a C$_1$-C$_3$-alkoxy group, a R$^{21}$OC(O)—(C$_1$-C$_3$-alkylene)- group, a —C(O)OR$^{21}$ group, a —C(O)NR$^{20}$R$^{21}$ group, a (C$_1$-C$_3$-alkyl)-O—(C$_1$-C$_3$-alkylene)-C(O)— group, a (C$_1$-C$_6$-alkyl)-C(O)— group and a C$_3$-C$_6$-cycloalkyl-C(O)— group;
R$^{19}$ is selected from a C$_1$-C$_3$-alkyl group, a C$_3$-C$_6$-cycloalkyl group and a NR$^{20}$R$^{21}$ group;
R$^{20}$ and R$^{21}$ are independently selected from a hydrogen atom and a C$_1$-C$_6$-alkyl group;
R$^{22}$ is independently selected from,
a halogen atom,
a C$_1$-C$_6$-alkyl group
which is unsubstituted or substituted with one or more substituents selected from a halogen atom, a hydroxy group, a NR$^{16}$R$^{17}$ group, a C$_1$-C$_3$-alkyl group, a C$_1$-C$_3$-haloalkyl group, a C$_1$-C$_3$-hydroxyalkyl group, a C$_1$-C$_3$-alkoxy group, a C$_1$-C$_3$-haloalkoxy group, a C$_3$-C$_6$-cycloalkyl group, a heterocycloalkyl group, an aryl group, a (R$^{18}$)-(heterocycloalkylene)-(arylene)-O— group, a (heterocycloalkyl)-(arylene)-O— group, an aryl-O— group, an aryl-(C$_1$-C$_3$-alkylene)-O— group, a (R$^{19}$)—S(O)$_2$-arylene-O— group, a (R$^{19}$)S(O)$_2$-heterocycloalkylene-arylene-O— group, an aryl-heteroarylene-O— group, an aryl-heteroarylene-O—(C$_1$-C$_3$-alkylene)- group, a heterocycloalkyl-(C$_1$-C$_3$-alkylene)-C(O)— group, a heterocycloalkyl-NH—C(O) group, an aryl-(C$_1$-C$_3$-alkylene)-NH—C(O)— group, a heterocycloalkylene-(C$_1$-C$_3$-alkylene)-S(O)$_2$— group, and a heterocycloalkylene-heteroarylene-S(O)$_2$— group and a C$_1$-C$_3$-alkyl-C(O)— group;
R$^{23}$ is independently selected from a hydrogen atom, a halogen atom, a hydroxy group, a C$_1$-C$_6$-alkyl group, and a C$_1$-C$_6$-haloalkyl group,
or
R$^{22}$ and R$^{23}$ together with the carbon atom to which they are attached form a 3-6-membered carbocyclic ring or a 3-6-membered heterocyclic ring comprising one or two heteroatoms selected from nitrogen, oxygen or sulfur;
or a tautomer, an N-oxide, or a salt thereof, or a salt of a tautomer, or salt of an N-oxide, or a mixture of same.
In accordance with a further aspect, the present invention provides compounds of general formula (I) wherein
A is

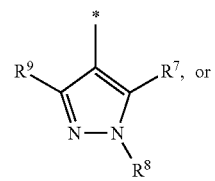

(A1)

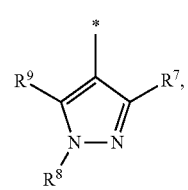

(A2)

wherein R⁶ and R⁷, together with two carbon atoms of the pyrazole ring, two carbon atoms of the indole moiety and the nitrogen atom to which R⁶ is attached, form a 9-membered to 13-membered ring and * is the point of attachment of these moieties to the indole carbon atom bearing the A substituent;

R¹ and R² are each independently selected from a hydrogen atom, a halogen atom, a cyano group, a $C_1$-$C_3$-alkyl group and a $C_1$-$C_3$-alkoxy group;

R³ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

R⁴ is selected from an aryl group and a heteroaryl group, each of which is unsubstituted or substituted with one, two, or three substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

L is a group —$(CH_2)_m$-E- wherein any $CH_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group;

E is a bond, an oxygen atom, a sulfur atom, or a —NR¹⁴— group and constitutes the connecting element to R⁴;

m is 2, 3, or 4;

R⁵ is selected from a COOH group and a

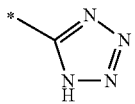

group;

—R⁶-R⁷— is #—$(CH_2)_n$—(B)$_t$—$CR^{22}R^{23}$—## or #—($C_2$-$C_9$-alkenylene)-(B)$_t$—$CR^{22}R^{23}$—##, wherein # is the point of attachment with the indole nitrogen atom and ## is the point of attachment with the pyrazole carbon atom bearing the R⁷ substituent; and wherein one or more —$CH_2$— groups may be unsubstituted or substituted with one or more substituents independently selected from a halogen atom, a hydroxyl group, a NR¹⁶R¹⁷ group, a $C_1$-$C_3$-alkyl group, a $C_1$-$C_3$-haloalkyl group, a $C_1$-$C_3$-alkoxy group, and a $C_1$-$C_3$-haloalkoxy group;

n is 1, 2, 3, 4, or 5;

p is 1, 2, 3, or 4;

t is 1;

where the integers selected for variables n, t, and p result in forming a 9-membered to 13-membered ring independently from the selection of variable A1 or A2;

B is independently selected from a —S(O)₂NR¹⁵— group and a —NR¹⁵S(O)₂— group;

R⁹ is selected from a hydrogen atom, and
a $C_1$-$C_6$-alkyl group, which is unsubstituted or substituted with one or more substituents independently selected from
a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a NR²⁰R²¹ group;

R⁹ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_1$-$C_3$-alkyl)-NH—($C_1$-$C_3$-alkylene)- group,
a ($C_3$-$C_7$)-cycloalkyl group, and
a ($C_3$-$C_7$)-cycloalkyl-O—($C_1$-$C_3$-alkylene)- group;

R¹⁴ is a hydrogen atom or a $C_1$-$C_3$-alkyl group;

R¹⁵ is independently selected from a hydrogen atom,
a $C_1$-$C_6$-alkyl group
which is unsubstituted or substituted with one or more substituents selected from a $C_1$-$C_3$-alkyl group, a heterocycloalkyl group, and an unsubstituted or substituted aryl group,
a ($C_3$-$C_7$)-cycloalkyl group and
a phenyl group;

R¹⁶ and R¹⁷ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)₂— group and a $C_1$-$C_3$-alkyl-O—C(=O)— group;

R¹⁹ is selected from a $C_1$-$C_3$-alkyl group, a $C_3$-$C_6$-cycloalkyl group and a NR²⁰R²¹ group;

R²⁰ and R²¹ are independently selected from a hydrogen atom and a $C_1$-$C_6$-alkyl group;

R²² is independently selected from
a halogen atom,
a $C_1$-$C_6$-alkyl group which is unsubstituted or substituted with one or more substituents selected from a halogen atom, a hydroxy group, a NR¹⁶R¹⁷ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, and a phenyl group,
a $C_3$-$C_6$-cycloalkyl group,
a heterocycloalkyl group,
a phenyl group, and
a heteroaryl group;

R²³ is independently selected from a hydrogen atom, a halogen atom, a hydroxy group, and a $C_1$-$C_4$-alkyl group;

or

R²² and R²³ together with the carbon atom to which they are attached form a 3-6-membered carbocyclic ring or a 3-6-membered heterocyclic ring comprising one or two heteroatoms selected from nitrogen, oxygen or sulfur;

or a tautomer, an N-oxide, or a salt thereof, or a salt of a tautomer, or salt of an N-oxide, or a mixture of same.

In accordance with a further aspect, the present invention provides compounds of general formula (I) wherein A is

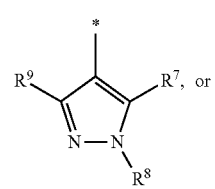

(A1)

-continued

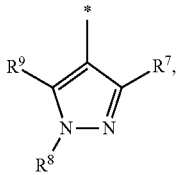
(A2)

wherein R⁶ and R⁷, together with two carbon atoms of the pyrazole ring, two carbon atoms of the indole moiety and the nitrogen atom to which R⁶ is attached, form a 10-membered to 13-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one, two, or three, substituents and each substituent is independently selected from a halogen atom and a $C_1$-$C_3$-alkyl group;

L is a group —(CH₂)$_m$-E-;

E is a bond or an oxygen atom and constitutes the connecting element to $R^4$;

m is 2, 3, or 4;

$R^5$ is a COOH group;

—R⁶-R⁷— is #—(CH₂)$_n$—(B)$_t$—CR²²R²³—## or #—(C₂-C₉-alkenylene)-(B)$_t$—CR²²R²³—##, wherein # is the point of attachment with the indole nitrogen atom and ## is the point of attachment with the pyrazole carbon atom bearing the $R^7$ substituent; and wherein one or more —CH₂— groups may be unsubstituted or substituted with one or more substituents independently selected from a halogen atom, a hydroxyl group, a NR¹⁶R¹⁷ group, a $C_1$-$C_3$-alkyl group, a $C_1$-$C_3$-haloalkyl group, a $C_1$-$C_3$-alkoxy group, a $C_1$-$C_3$-haloalkoxy group;

n is 2, 3 or 4;

p is 1, 2, or 3;

t is 1;

where the integers selected for variables n, t, and p result in forming a 10-membered to 13-membered ring independently from the selection of variable A1 or A2;

B is selected from a —S(O)₂NR¹⁵— group and a —NR¹⁵S(O)₂— group;

$R^9$ is selected from a hydrogen atom, and a $C_1$-$C_6$-alkyl group, which is unsubstituted or substituted with one or more substituents independently selected from a halogen atom, a hydroxy group, a $C_3$-$C_6$-cycloalkyl group and a heterocycloalkyl group;

$R^9$ is selected from a hydrogen atom, a $C_1$-$C_4$-alkyl group, a $C_1$-$C_3$-hydroxyalkyl group, a $C_1$-$C_4$-haloalkyl group, a $C_1$-$C_6$-alkyl-O— group, a $C_1$-$C_4$-haloalkoxy group, and a $C_1$-$C_6$-alkyl-O—($C_1$-$C_3$-alkylene)- group;

$R^{15}$ is independently selected from a hydrogen atom, a $C_1$-$C_6$-alkyl group which is unsubstituted or substituted with a substituent selected from a heterocycloalkyl group and an unsubstituted or substituted aryl group and a ($C_3$-$C_7$)-cycloalkyl group;

$R^{16}$ and $R^{17}$ are each independently selected from a hydrogen atom, a $C_1$-$C_6$-alkyl group and a $C_1$-$C_6$-haloalkyl group;

$R^{22}$ is independently selected from a halogen atom, a $C_1$-$C_4$-alkyl group which is unsubstituted or substituted with a group selected from a hydroxy group, NR¹⁶R¹⁷ group, a $C_1$-$C_4$-alkoxy group, a $C_3$-$C_6$-cycloalkyl group, a heterocycloalkyl group and a phenyl group;

a phenyl group, a heteroaryl group, a $C_3$-$C_6$-cycloalkyl group, a heterocycloalkyl group, $R^{23}$ is independently selected from a hydrogen atom, a halogen atom, a hydroxy group, and a $C_1$-$C_4$-alkyl group or $R^{22}$ and $R^{23}$ together form a 3-6-membered carbocyclic ring;

or a tautomer, an N-oxide, or a salt thereof, or a salt of a tautomer, or salt of an N-oxide, or a mixture of same.

In accordance with a further aspect, the present invention provides compounds of general formula (I) wherein A is

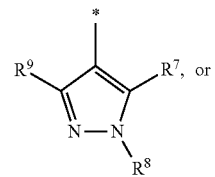
(A1)

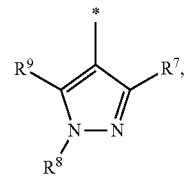
(A2)

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group which is unsubstituted or substituted with one, two, or three substituents and each substituent is independently selected from a halogen atom, and a $C_1$-$C_3$-alkyl group;

L is a group —(CH₂)$_m$-E-;

E is a bond or an oxygen atom and constitutes the connecting element to $R^4$;

m is 3;

$R^5$ is a COOH group;

—R⁶-R⁷— is #—(CH₂)$_n$—(B)$_t$—CR²²R²³—## or #—(C₂-C₉-alkenylene)-(B)$_t$—CR²²R²³—##, wherein # is the point of attachment with the indole nitrogen atom and ## is the point of attachment with the pyrazole carbon atom bearing the $R^7$ substituent;

n is 3;
t is 1;
p is 1;
where the integers selected for variables n, t, and p result in forming a 11-membered ring independently from the selection of variable A1 or A2;
B is a —S(O)$_2$NR$^{15}$— group;
R$^8$ is selected from a hydrogen atom, and
a C$_1$-C$_6$-alkyl group which is unsubstituted or substituted with a heterocycloalkyl group;
R$^9$ is selected from a hydrogen atom,
a C$_1$-C$_4$-alkyl group, and
a C$_1$-C$_6$-alkyl-O—(C$_1$-C$_3$-alkylene)- group;
R$^{15}$ is independently selected from a hydrogen atom,
a C$_1$-C$_6$-alkyl group
which is unsubstituted or substituted with an unsubstituted or substituted aryl group or with a heterocycloalkyl group, and
a (C$_3$-C$_7$)-cycloalkyl group;
R$^{22}$ is independently selected from
a halogen atom,
a phenyl group,
a C$_3$-C$_6$-cycloalkyl group,
a C$_1$-C$_3$-alkyl group which is unsubstituted or substituted with one or more substituents selected from a hydroxy group, a NR$^{17}$R$^{18}$ group, a C$_1$-C$_3$-haloalkyl group, a C$_1$-C$_3$-alkoxy group, a C$_3$-C$_6$-cycloalkyl group, a heterocycloalkyl group and a phenyl group;
R$^{23}$ is independently selected from a hydrogen atom, a halogen atom, a hydroxy group and a C$_1$-C$_3$-alkyl group or
R$^{22}$ and R$^{23}$ together form a 3-6-membered carbocyclic ring;
or a tautomer, an N-oxide, or a salt thereof, or a salt of a tautomer, or salt of an N-oxide, or a mixture of same.

In accordance with a further aspect, the present invention provides compounds of general formula (I) wherein A is

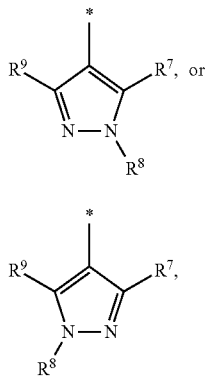

(A1)

(A2)

wherein R$^6$ and R$^7$, together with two carbon atoms of the pyrazole ring, two carbon atoms of the indole moiety and the nitrogen atom to which R$^6$ is attached, form a 11-membered ring and * is the point of attachment of these moieties to the indole carbon atom bearing the A substituent;
R$^1$ is a hydrogen atom or a halogen atom;
R$^2$ is a hydrogen atom;
R$^3$ is a hydrogen atom;
R$^4$ is an aryl group, which is unsubstituted or substituted with one, two or three substituents independently selected from a halogen atom and a methyl group;
L is a group (CH$_2$)$_3$—O—;
R$^5$ is a COOH group;
—R$^6$-R$^7$— is $^\#$—(CH$_2$)$_n$—(B)$_t$—CR$^{22}$R$^{23}$—$^{\#\#}$,
wherein $^\#$ is the point of attachment with the indole nitrogen atom and $^{\#\#}$ is the point of attachment with the pyrazole carbon atom bearing the R$^7$ substituent;
n is 3;
t is 1;
p is 1;
where the integers selected for variables n, t and p result in forming a 11-membered ring independently from the selection of variable A1 or A2;
B is a —S(O)$_2$NR$^{15}$— group;
R$^8$ is a methyl group;
R$^9$ is selected from a methyl group and an ethyl group,
R$^{15}$ is independently selected from a hydrogen atom,
a C$_1$-C$_3$-alkyl group which is unsubstituted or substituted with an unsubstituted or a substituted aryl group or with an unsubstituted or substituted heterocycloalkyl group and
a (C$_3$-C$_7$)-cycloalkyl group,
R$^{22}$ is independently selected from a C$_1$-C$_3$-haloalkyl group and a C$_1$-C$_3$-alkyl group which is unsubstituted or substituted with a hydroxyl group, a C$_3$-C$_5$-cycloalkyl group, or a heterocyclyl group;
R$^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I) wherein A is

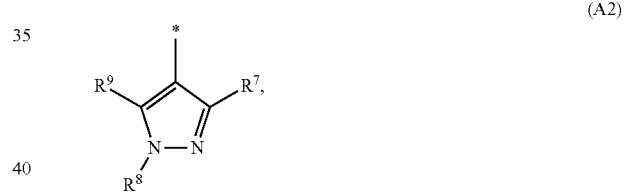

(A2)

wherein R$^6$ and R$^7$, together with two carbon atoms of the pyrazole ring, two carbon atoms of the indole moiety and the nitrogen atom to which R$^6$ is attached, form a 11-membered to 13-membered ring and * is the point of attachment of these moieties to the indole carbon atom bearing the A substituent;
R$^1$ is a hydrogen atom or a chlorine atom;
R$^2$ is a hydrogen atom;
R$^3$ is a hydrogen atom;
R$^4$ is a naphthyl or a 6-fluoronaphthyl group;
L is a group (CH$_2$)$_3$—O—;
R$^5$ is a COOH group;
—R$^6$-R$^7$— is $^\#$—(CH$_2$)$_n$—S(O)$_2$NR$^{15}$—(CH$_2$)$_p$—$^{\#\#}$,
wherein any —CH$_2$— group is unsubstituted or substituted with one heterocycloalkyl group, wherein $^\#$ is the point of attachment with the indole nitrogen atom and $^{\#\#}$ is the point of attachment with the pyrazole carbon atom bearing the R$^7$ substituent or
—R$^6$-R$^7$— is $^\#$—(CH$_2$)$_n$—(B)$_t$—CR$^{22}$R$^{23}$—$^{\#\#}$,
wherein $^\#$ is the point of attachment with the indole nitrogen atom and $^{\#\#}$ is the point of attachment with the pyrazole carbon atom bearing the R$^7$ substituent;
n is 3;
t is 1;
p is 1, 2 or 3;

where the integers selected for variables n, t and p result in forming a 11-membered to 13-membered ring;
B is a —S(O)$_2$NR$^{15}$— group;
R$^8$ is a methyl group;
R$^9$ is selected from a methyl group and an ethyl group;
R$^{15}$ is independently selected from hydrogen, a methyl group, an ethyl group and a cyclopropyl group;
R$^{22}$ is a C$_1$-C$_3$-alkyl group which is substituted with a heterocyclyl group;
R$^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein A is

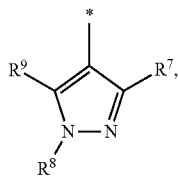
(A2)

wherein R$^6$ and R$^7$, together with two carbon atoms of the pyrazole ring, two carbon atoms of the indole moiety and the nitrogen atom to which R$^6$ is attached, form a 11-membered to 13-membered ring and * is the point of attachment of these moieties to the indole carbon atom bearing the A substituent;
R$^1$ is a hydrogen atom or a chlorine atom;
R$^2$ is a hydrogen atom;
R$^3$ is a hydrogen atom;
R$^4$ is a naphthyl or a 6-fluoronaphthyl group;
L is a group (CH$_2$)$_3$—O—;
R$^5$ is a COOH group;
—R$^6$-R$^7$— is $^\#$—(CH$_2$)$_n$—S(O)$_2$NR$^{15}$—(CH$_2$)$_p$—$^{\#\#}$, wherein any —CH$_2$— group is unsubstituted or substituted with one heterocycloalkyl group, wherein $^\#$ is the point of attachment with the indole nitrogen atom and $^{\#\#}$ is the point of attachment with the pyrazole carbon atom bearing the R$^7$ substituent or
—R$^6$-R$^7$— is $^\#$—(CH$_2$)$_n$—(B)$_t$—CR$^{22}$R$^{23}$—$^{\#\#}$,
wherein $^\#$ is the point of attachment with the indole nitrogen atom and $^{\#\#}$ is the point of attachment with the pyrazole carbon atom bearing the R$^7$ substituent;
n is 3;
t is 1;
p is 1, 2 or 3;
where the integers selected for variables n, t and p result in forming a 11-membered to 13-membered ring;
B is a —S(O)$_2$NR$^{15}$— group;
R$^8$ is a methyl group;
R$^9$ is selected from a methyl group and an ethyl group;
R$^{15}$ is independently selected from hydrogen, a methyl group, an ethyl group and a cyclopropyl group;
R$^{22}$ is a C$_1$-C$_3$-alkyl group which is substituted with a heterocycloalkyl group;
R$^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein A is

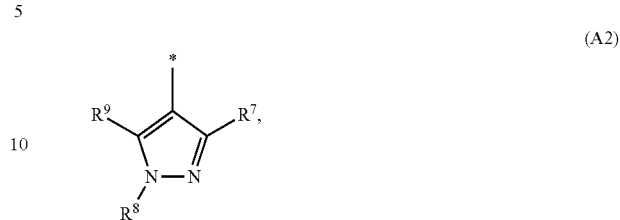
(A2)

wherein R$^6$ and R$^7$, together with two carbon atoms of the pyrazole ring, two carbon atoms of the indole moiety and the nitrogen atom to which R$^6$ is attached, form an 11-membered ring and * is the point of attachment of these moieties to the indole carbon atom bearing the A substituent;
R$^1$ is a hydrogen atom or a chlorine atom;
R$^2$ is a hydrogen atom;
R$^3$ is a hydrogen atom;
R$^4$ is a naphthyl or a 6-fluoronaphthyl group;
L is a group (CH$_2$)$_3$—O—;
R$^5$ is a COOH group;
—R$^6$-R$^7$— is $^\#$—(CH$_2$)$_n$—S(O)$_2$NR$^{15}$—(CH$_2$)$_p$—$^{\#\#}$, wherein $^\#$ is the point of attachment with the indole nitrogen atom and $^{\#\#}$ is the point of attachment with the pyrazole carbon atom bearing the R$^7$ substituent or
—R$^6$-R$^7$— is $^\#$—(CH$_2$)$_n$—(B)$_t$—CR$^{22}$R$^{23}$—$^{\#\#}$,
wherein $^\#$ is the point of attachment with the indole nitrogen atom and $^{\#\#}$ is the point of attachment with the pyrazole carbon atom bearing the R$^7$ substituent;
n is 3;
t is 1;
p is 1;
where the integers selected for variables n, t and p result in forming an 11-membered ring;
B is a —S(O)$_2$NR$^{15}$— group;
R$^8$ is a methyl group;
R$^9$ is selected from a methyl group and an ethyl group;
R$^{15}$ is independently selected from hydrogen, a methyl group, an ethyl group and a cyclopropyl group;
R$^{22}$ is a C$_1$-C$_3$-alkyl group which is substituted with a heterocycloalkyl group;
R$^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein A is

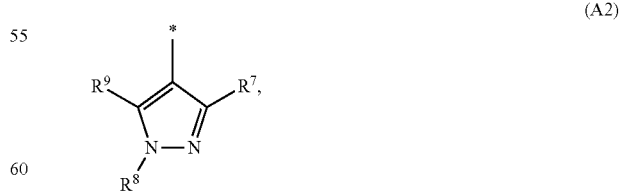
(A2)

wherein R$^6$ and R$^7$, together with two carbon atoms of the pyrazole ring, two carbon atoms of the indole moiety and the nitrogen atom to which R$^6$ is attached, form an 11-membered ring and * is the point of attachment of these moieties to the indole carbon atom bearing the A substituent;

$R^1$ is a hydrogen atom or a chlorine atom;
$R^2$ is a hydrogen atom;
$R^3$ is a hydrogen atom;
$R^4$ is a naphthyl or a 6-fluoronaphthyl group;
L is a group $(CH_2)_3$—O—;
$R^5$ is a COOH group;
—$R^6$-$R^7$— is $^{\#}$—$(CH_2)_n$—$S(O)_2NR^{15}$—$(CH_2)_p$—$^{\#\#}$,
  wherein $^{\#}$ is the point of attachment with the indole nitrogen atom and $^{\#\#}$ is the point of attachment with the pyrazole carbon atom bearing the $R^7$ substituent or
—$R^6$-$R^7$— is $^{\#}$—$(CH_2)_n$—$(B)_t$—$CR^{22}R^{23}$—$^{\#\#}$,
  wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming an 11-membered ring;
B is a —$S(O)_2NR^{15}$— group;
$R^8$ is a methyl group;
$R^9$ is selected from a methyl group and an ethyl group;
$R^{15}$ is independently selected from hydrogen, a methyl group, an ethyl group and a cyclopropyl group;
$R^{22}$ is a $C_1$-$C_3$-alkyl group which is substituted with a morpholin-4-yl or a tetrahydropyran-4-yl group;
$R^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein A is

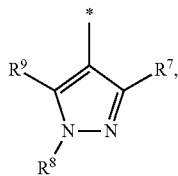
(A2)

wherein $R^6$ and $R^7$, together with two carbon atoms of the pyrazole ring, two carbon atoms of the indole moiety and the nitrogen atom to which $R^6$ is attached, form an 11-membered ring and * is the point of attachment of these moieties to the indole carbon atom bearing the A substituent;
$R^1$ is a chlorine atom;
$R^2$ is a hydrogen atom;
$R^3$ is a hydrogen atom;
$R^4$ is a 6-fluoronaphthyl group;
L is a group $(CH_2)_3$—O—;
$R^5$ is a COOH group;
—$R^6$-$R^7$— is $^{\#}$—$(CH_2)_n$—$S(O)_2NR^{15}$—$(CH_2)_p$—$^{\#\#}$,
  wherein $^{\#}$ is the point of attachment with the indole nitrogen atom and $^{\#\#}$ is the point of attachment with the pyrazole carbon atom bearing the $R^7$ substituent or
—$R^6$-$R^7$— is $^{\#}$—$(CH_2)_n$—$(B)_t$—$CR^{22}R^{23}$—$^{\#\#}$,
  wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming an 11-membered ring;
B is a —$S(O)_2NR^{15}$— group;
$R^9$ is a methyl group;
$R^9$ is selected from a methyl group and an ethyl group;
$R^{15}$ is independently selected from a methyl group, an ethyl group and a cyclopropyl group;
$R^{22}$ is a $C_1$-$C_3$-alkyl group which is substituted with a heterocyclyl group;
$R^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein A is

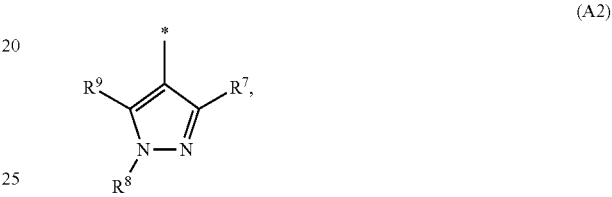
(A2)

wherein $R^6$ and $R^7$, together with two carbon atoms of the pyrazole ring, two carbon atoms of the indole moiety and the nitrogen atom to which $R^6$ is attached, form an 11-membered ring and * is the point of attachment of these moieties to the indole carbon atom bearing the A substituent;
$R^1$ is a chlorine atom;
$R^2$ is a hydrogen atom;
$R^3$ is a hydrogen atom;
$R^4$ is a 6-fluoronaphthyl group;
L is a group $(CH_2)_3$—O—;
$R^5$ is a COOH group;
—$R^6$-$R^7$— is $^{\#}$—$(CH_2)_n$—$S(O)_2NR^{15}$—$(CH_2)_p$—$^{\#\#}$,
  wherein $^{\#}$ is the point of attachment with the indole nitrogen atom and $^{\#\#}$ is the point of attachment with the pyrazole carbon atom bearing the $R^7$ substituent or
—$R^6$-$R^7$— is $^{\#}$—$(CH_2)_n$—$(B)_t$—$CR^{22}R^{23}$—$^{\#\#}$,
  wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming an 11-membered ring;
B is a —$S(O)_2NR^{15}$— group;
$R^8$ is a methyl group;
$R^9$ is selected from a methyl group and an ethyl group;
$R^{15}$ is independently selected from a methyl group, an ethyl group and a cyclopropyl group;
$R^{22}$ is a $C_1$-$C_3$-alkyl group which is substituted with a heterocycloalkyl group;
$R^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I) wherein A is

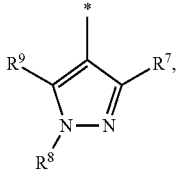
(A2)

wherein $R^6$ and $R^7$, together with two carbon atoms of the pyrazole ring, two carbon atoms of the indole moiety and the nitrogen atom to which $R^6$ is attached, form an 11-membered ring and * is the point of attachment of these moieties to the indole carbon atom bearing the A substituent;
$R^1$ is a chlorine atom;
$R^2$ is a hydrogen atom;
$R^3$ is a hydrogen atom;
$R^4$ is a 6-fluoronaphthyl group;
L is a group $(CH_2)_3$—O—;
$R^5$ is a COOH group;
—$R^6$-$R^7$— is $^{\#}$—$(CH_2)_n$—$S(O)_2NR^{15}$—$(CH_2)_p$—$^{\#\#}$, wherein $^{\#}$ is the point of attachment with the indole nitrogen atom and $^{\#\#}$ is the point of attachment with the pyrazole carbon atom bearing the $R^7$ substituent or
—$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming an 11-membered ring;
B is a —$S(O)_2NR^{15}$— group;
$R^9$ is a methyl group;
$R^9$ is selected from a methyl group and an ethyl group;
$R^{15}$ is independently selected from a methyl group, an ethyl group and a cyclopropyl group;
$R^{22}$ is a $C_1$-$C_3$-alkyl group which is substituted with a morpholin-4-yl or a tetrahydropyran-4-yl group;
$R^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I) wherein A is

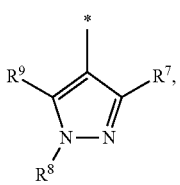
(A2)

wherein $R^6$ and $R^7$, together with two carbon atoms of the pyrazole ring, two carbon atoms of the indole moiety and the nitrogen atom to which $R^6$ is attached, form an 11-membered ring and * is the point of attachment of these moieties to the indole carbon atom bearing the A substituent;
$R^1$ is a chlorine atom;
$R^2$ is a hydrogen atom;
$R^3$ is a hydrogen atom;
$R^4$ is a 6-fluoronaphthyl group;
L is a group $(CH_2)_3$—O—;
$R^5$ is a COOH group;
—$R^6$-$R^7$— is $^{\#}$—$(CH_2)_n$—$S(O)_2NR^{15}$—$(CH_2)_p$—$^{\#\#}$, wherein $^{\#}$ is the point of attachment with the indole nitrogen atom and $^{\#\#}$ is the point of attachment with the pyrazole carbon atom bearing the $R^7$ substituent or
—$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming an 11-membered ring;
B is a —$S(O)_2NR^{15}$— group;
$R^8$ is a methyl group;
$R^9$ is selected from a methyl group and an ethyl group;
$R^{15}$ is independently selected from a methyl group and an ethyl group;
$R^{22}$ is a $C_1$-$C_3$-alkyl group which is substituted with a heterocyclyl group;
$R^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I) wherein A is

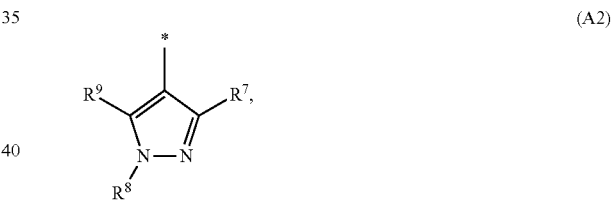
(A2)

wherein $R^6$ and $R^7$, together with two carbon atoms of the pyrazole ring, two carbon atoms of the indole moiety and the nitrogen atom to which $R^6$ is attached, form an 11-membered ring and * is the point of attachment of these moieties to the indole carbon atom bearing the A substituent;
$R^1$ is a chlorine atom;
$R^2$ is a hydrogen atom;
$R^3$ is a hydrogen atom;
$R^4$ is a 6-fluoronaphthyl group;
L is a group $(CH_2)_3$—O—;
$R^5$ is a COOH group;
—$R^6$-$R^7$— is $^{\#}$—$(CH_2)_n$—$S(O)_2NR^{15}$—$(CH_2)_p$—$^{\#\#}$, wherein $^{\#}$ is the point of attachment with the indole nitrogen atom and $^{\#\#}$ is the point of attachment with the pyrazole carbon atom bearing the $R^7$ substituent or
—$R^6$-$R^7$— is $^{\#}$—$(CH_2)_n$—$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming an 11-membered ring;

B is a —S(O)$_2$NR$^{15}$— group;

R$^8$ is a methyl group;

R$^9$ is selected from a methyl group and an ethyl group;

R$^{15}$ is independently selected from a methyl group and an ethyl group;

R$^{22}$ is a C$_1$-C$_3$-alkyl group which is substituted with a heterocycloalkyl group;

R$^{23}$ is a hydrogen atom;

or a tautomer, an N-oxide, or a salt thereof, or a salt of a tautomer, or salt of an N-oxide, or a mixture of same.

In accordance with a further aspect, the present invention provides compounds of general formula (I) wherein A is

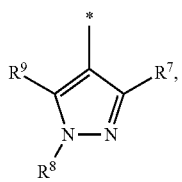

(A2)

wherein R$^6$ and R$^7$, together with two carbon atoms of the pyrazole ring, two carbon atoms of the indole moiety and the nitrogen atom to which R$^6$ is attached, form an 11-membered ring and * is the point of attachment of these moieties to the indole carbon atom bearing the A substituent;

R$^1$ is a chlorine atom;

R$^2$ is a hydrogen atom;

R$^3$ is a hydrogen atom;

R$^4$ is a 6-fluoronaphthyl group;

L is a group (CH$_2$)$_3$—O—;

R$^5$ is a COOH group;

—R$^6$-R$^7$— is $^{\#}$—(CH$_2$)$_n$—S(O)$_2$NR$^{15}$—(CH$_2$)$_p$—$^{\#\#}$, wherein $^{\#}$ is the point of attachment with the indole nitrogen atom and $^{\#\#}$ is the point of attachment with the pyrazole carbon atom bearing the R$^7$ substituent or —R$^6$-R$^7$— is $^{\#}$—(CH$_2$)$_n$—(B)$_t$—CR$^{22}$R$^{23}$—$^{\#\#}$, wherein $^{\#}$ is the point of attachment with the indole nitrogen atom and $^{\#\#}$ is the point of attachment with the pyrazole carbon atom bearing the R$^7$ substituent;

n is 3;

t is 1;

p is 1;

where the integers selected for variables n, t and p result in forming an 11-membered ring;

B is a —S(O)$_2$NR$^{15}$— group;

R$^8$ is a methyl group;

R$^9$ is selected from a methyl group and an ethyl group;

R$^{15}$ is independently selected from a methyl group and an ethyl group;

R$^{22}$ is a C$_1$-C$_3$-alkyl group which is substituted with a morpholin-4-yl or a tetrahydropyran-4-yl group;

R$^{23}$ is a hydrogen atom;

or a tautomer, an N-oxide, or a salt thereof, or a salt of a tautomer, or salt of an N-oxide, or a mixture of same.

In accordance with a further aspect, the present invention provides compounds of general formula (I) wherein A is

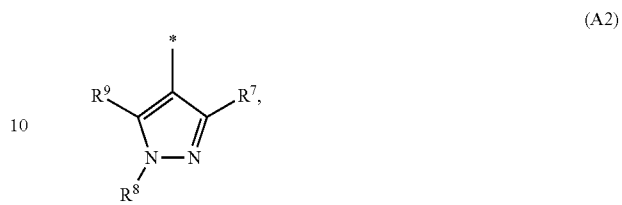

(A2)

wherein R$^6$ and R$^7$, together with two carbon atoms of the pyrazole ring, two carbon atoms of the indole moiety and the nitrogen atom to which R$^6$ is attached, form an 11-membered ring and * is the point of attachment of these moieties to the indole carbon atom bearing the A substituent;

R$^1$ is a chlorine atom;

R$^2$ is a hydrogen atom;

R$^3$ is a hydrogen atom;

R$^4$ is a 6-fluoronaphthyl group;

L is a group (CH$_2$)$_3$—O—;

R$^5$ is a COOH group;

—R$^6$-R$^7$— is $^{\#}$—(CH$_2$)$_n$—(B)$_t$—CR$^{22}$R$^{23}$—$^{\#\#}$, wherein $^{\#}$ is the point of attachment with the indole nitrogen atom and $^{\#\#}$ is the point of attachment with the pyrazole carbon atom bearing the R$^7$ substituent;

n is 3;

t is 1;

p is 1;

where the integers selected for variables n, t and p result in forming an 11-membered ring;

B is a —S(O)$_2$NR$^{15}$— group;

R$^8$ is a methyl group;

R$^9$ is selected from a methyl group and an ethyl group;

R$^{15}$ is a methyl group;

R$^{22}$ is a C$_1$-C$_3$-alkyl group which is substituted with a morpholin-4-yl or a tetrahydropyran-4-yl group;

R$^{23}$ is a hydrogen atom;

or a tautomer, an N-oxide, or a salt thereof, or a salt of a tautomer, or salt of an N-oxide, or a mixture of same.

In accordance with a further aspect, the present invention provides compounds of general formula (I) wherein A is

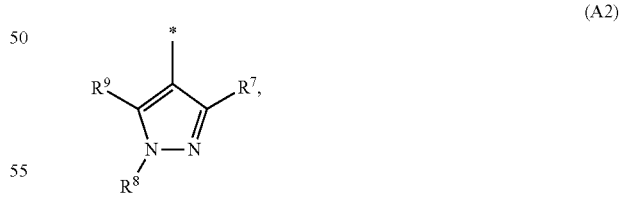

(A2)

wherein R$^6$ and R$^7$, together with two carbon atoms of the pyrazole ring, two carbon atoms of the indole moiety and the nitrogen atom to which R$^6$ is attached, form an 11-membered ring and * is the point of attachment of these moieties to the indole carbon atom bearing the A substituent;

R$^1$ is a chlorine atom;

R$^2$ is a hydrogen atom;

R$^3$ is a hydrogen atom;

R$^4$ is a 6-fluoronaphthyl group;

L is a group (CH$_2$)$_3$—O—;

R⁵ is a COOH group;
—R⁶-R⁷— is #—(CH$_2$)$_n$—(B)$_t$—CR$^{22}$R$^{23}$—##,
  wherein # is the point of attachment with the indole nitrogen atom and ## is the point of attachment with the pyrazole carbon atom bearing the R⁷ substituent;
n is 3;
t is 1;
p is 1;
where the integers selected for variables n, t and p result in forming an 11-membered ring;
B is a —S(O)$_2$NR$^{15}$— group;
R⁸ is a methyl group;
R⁹ is selected from a methyl group and an ethyl group;
R¹⁵ is a methyl group;
R²² is a C$_1$-C$_3$-alkyl group which is substituted with a morpholin-4-yl group;
R²³ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein A is

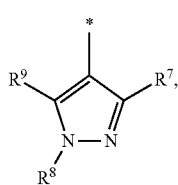

(A2)

wherein R⁶ and R⁷, together with two carbon atoms of the pyrazole ring, two carbon atoms of the indole moiety and the nitrogen atom to which R⁶ is attached, form an 11-membered ring and * is the point of attachment of these moieties to the indole carbon atom bearing the A substituent;
R¹ is a chlorine atom;
R² is a hydrogen atom;
R³ is a hydrogen atom;
R⁴ is a 6-fluoronaphthyl group;
L is a group (CH$_2$)$_3$—O—;
R⁵ is a COOH group;
—R⁶-R⁷— is #—(CH$_2$)$_n$—(B)$_t$—CR$^{22}$R$^{23}$—##,
  wherein # is the point of attachment with the indole nitrogen atom and ## is the point of attachment with the pyrazole carbon atom bearing the R⁷ substituent;
n is 3;
t is 1;
p is 1;
where the integers selected for variables n, t and p result in forming an 11-membered ring;
B is a —S(O)$_2$NR$^{15}$— group;
R⁸ is a methyl group;
R⁹ is a methyl group;
R¹⁵ is a methyl group;
R²² is a C$_1$-C$_3$-alkyl group which is substituted with a morpholin-4-yl group;
R²³ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein A is

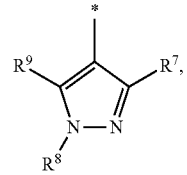

(A2)

wherein R⁶ and R⁷, together with two carbon atoms of the pyrazole ring, two carbon atoms of the indole moiety and the nitrogen atom to which R⁶ is attached, form an 11-membered ring and * is the point of attachment of these moieties to the indole carbon atom bearing the A substituent;
R¹ is a chlorine atom;
R² is a hydrogen atom;
R³ is a hydrogen atom;
R⁴ is a 6-fluoronaphthyl group;
L is a group (CH$_2$)$_3$—O—;
R⁵ is a COOH group;
—R⁶-R⁷— is #—(CH$_2$)$_n$—(B)$_t$—CR$^{22}$R$^{23}$—##,
  wherein # is the point of attachment with the indole nitrogen atom and ## is the point of attachment with the pyrazole carbon atom bearing the R⁷ substituent;
n is 3;
t is 1;
p is 1;
where the integers selected for variables n, t and p result in forming an 11-membered ring;
B is a —S(O)$_2$NR$^{15}$— group;
R⁸ is a methyl group;
R⁹ is an ethyl group;
R¹⁵ is a methyl group;
R²² is a C$_1$-C$_3$-alkyl group which is substituted with a tetrahydropyran-4-yl group;
R²³ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein A is

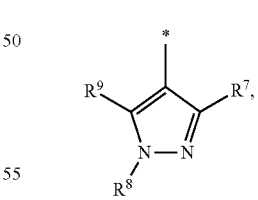

(A2)

wherein R⁶ and R⁷, together with two carbon atoms of the pyrazole ring, two carbon atoms of the indole moiety and the nitrogen atom to which R⁶ is attached, form an 11-membered ring and * is the point of attachment of these moieties to the indole carbon atom bearing the A substituent;
R¹ is a chlorine atom;
R² is a hydrogen atom;
R³ is a hydrogen atom;
R⁴ is a 6-fluoronaphthyl group;
L is a group (CH$_2$)$_3$—O—;

$R^5$ is a COOH group;
—$R^6$-$R^7$— is $^{\#}$—(CH$_2$)$_n$—(B)$_t$—CR$^{22}$R$^{23}$—$^{\#\#}$,
  wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming an 11-membered ring;
B is a —S(O)$_2$NR$^{15}$— group;
$R^8$ is a methyl group;
$R^9$ is an ethyl group;
$R^{15}$ is a methyl group;
$R^{22}$ is a $C_1$-$C_3$-alkyl group which is substituted with a morpholin-4-yl or a tetrahydropyran-4-yl group;
$R^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein A is

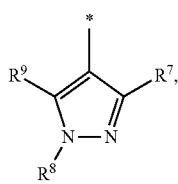

(A2)

wherein $R^6$ and $R^7$, together with two carbon atoms of the pyrazole ring, two carbon atoms of the indole moiety and the nitrogen atom to which $R^6$ is attached, form an 11-membered ring and * is the point of attachment of these moieties to the indole carbon atom bearing the A substituent;
$R^1$ is a chlorine atom;
$R^2$ is a hydrogen atom;
$R^3$ is a hydrogen atom;
$R^4$ is a 6-fluoronaphthyl group;
L is a group (CH$_2$)$_3$—O—;
$R^5$ is a COOH group;
—$R^6$-$R^7$— is $^{\#}$—(CH$_2$)$_n$—(B)$_t$—CR$^{22}$R$^{23}$—$^{\#\#}$,
  wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming an 11-membered ring;
B is a —S(O)$_2$NR$^{15}$— group;
$R^8$ is a methyl group;
$R^9$ is an ethyl group;
$R^{15}$ is a methyl group;
$R^{22}$ is a $C_1$-$C_3$-alkyl group which is substituted with a morpholin-4-yl group;
$R^{23}$ is a hydrogen atom;
or a tautomer, an N-oxide, or a salt thereof, or a salt of a tautomer, or salt of an N-oxide, or a mixture of same.

In accordance with a further aspect, the present invention provides compounds of general formula (I)
wherein A is

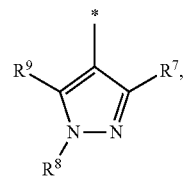

(A2)

wherein $R^6$ and $R^7$, together with two carbon atoms of the pyrazole ring, two carbon atoms of the indole moiety and the nitrogen atom to which $R^6$ is attached, form an 11-membered ring and * is the point of attachment of these moieties to the indole carbon atom bearing the A substituent;
$R^1$ is a chlorine atom;
$R^2$ is a hydrogen atom;
$R^3$ is a hydrogen atom;
$R^4$ is a 6-fluoronaphthyl group;
L is a group (CH$_2$)$_3$—O—;
$R^5$ is a COOH group;
—$R^6$-$R^7$— is $^{\#}$—(CH$_2$)$_n$—S(O)$_2$NR$^{15}$—(CH$_2$)$_p$—$^{\#\#}$,
  wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming an 11-membered ring;
$R^8$ is a methyl group;
$R^9$ is an ethyl group;
$R^{15}$ is independently selected from a methyl group and an ethyl group;
or a tautomer, an N-oxide, or a salt thereof, or a salt of a tautomer, or salt of an N-oxide, or a mixture of same.

In accordance with a further aspect, the present invention provides compounds of general formula (I)
wherein A is

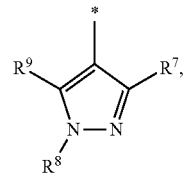

(A2)

wherein $R^6$ and $R^7$, together with two carbon atoms of the pyrazole ring, two carbon atoms of the indole moiety and the nitrogen atom to which $R^6$ is attached, form an 11-membered ring and * is the point of attachment of these moieties to the indole carbon atom bearing the A substituent;
$R^1$ is a chlorine atom;
$R^2$ is a hydrogen atom;
$R^3$ is a hydrogen atom;
$R^4$ is a 6-fluoronaphthyl group;
L is a group (CH$_2$)$_3$—O—;
$R^5$ is a COOH group;
—$R^6$-$R^7$— is $^{\#}$—(CH$_2$)$_n$—S(O)$_2$NR$^{15}$—(CH$_2$)$_p$—$^{\#\#}$,
  wherein $^{\#}$ is the point of attachment with the indole nitrogen atom and ## is the point of attachment with the pyrazole carbon atom bearing the $R^7$ substituent or n is 3;
t is 1;
p is 1;
where the integers selected for variables n, t and p result in forming an 11-membered ring;
$R^8$ is a methyl group;
$R^9$ is an ethyl group;
$R^{15}$ is a methyl group;
or a tautomer, an N-oxide, or a salt thereof, or a salt of a tautomer, or salt of an N-oxide, or a mixture of same.

In accordance with a further aspect, the present invention provides compounds of general formula (I) wherein A is

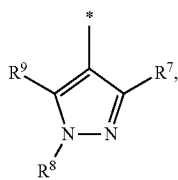

(A2)

wherein $R^6$ and $R^7$, together with two carbon atoms of the pyrazole ring, two carbon atoms of the indole moiety and the nitrogen atom to which $R^6$ is attached, form an 11-membered ring and * is the point of attachment of these moieties to the indole carbon atom bearing the A substituent;
$R^1$ is a chlorine atom;
$R^2$ is a hydrogen atom;
$R^3$ is a hydrogen atom;
$R^4$ is a 6-fluoronaphthyl group;
L is a group $(CH_2)_3$—O—;
$R^5$ is a COOH group;
—$R^6$-$R^7$— is #—$(CH_2)_n$—$S(O)_2NR^{15}$—$(CH_2)_p$—##, wherein # is the point of attachment with the indole nitrogen atom and ## is the point of attachment with the pyrazole carbon atom bearing the $R^7$ substituent or
n is 3;
t is 1;
p is 1;
where the integers selected for variables n, t and p result in forming an 11-membered ring;
$R^8$ is a methyl group;
$R^9$ is an ethyl group;
$R^{15}$ is an ethyl group;
or a tautomer, an N-oxide, or a salt thereof, or a salt of a tautomer, or salt of an N-oxide, or a mixture of same.

In accordance with a further aspect, the present invention provides compounds of general formula (I):

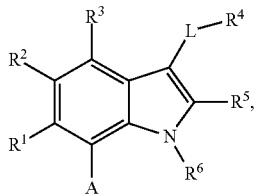

(I)

wherein
A is

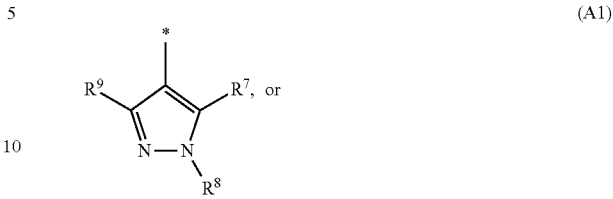

(A1)

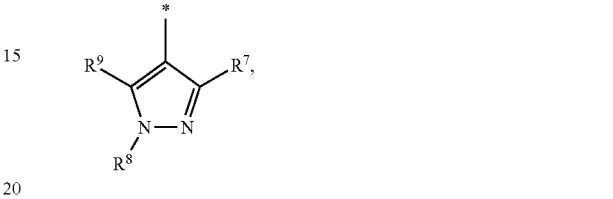

(A2)

wherein $R^6$ and $R^7$, together with two carbon atoms of the pyrazole ring, two carbon atoms of the indole moiety and the nitrogen atom to which $R^6$ is attached, form a 9- to 16-membered ring and * is the point of attachment of these moieties to the indole carbon atom bearing the A substituent;
or
A is

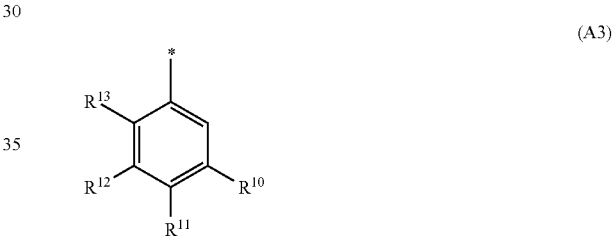

(A3)

wherein optionally one or two of the groups selected from $CR^{11}$, $CR^{12}$ and $CR^{13}$ are replaced by a nitrogen atom,
wherein $R^6$ and $R^{10}$, together with three carbon atoms of the phenyl ring, two carbon atoms of the indole moiety and the nitrogen atom to which $R^6$ is attached, form a 9- to 16-membered ring and * is the point of attachment of these moieties to the indole carbon atom bearing the A substituent;
$R^1$ and $R^2$ are each independently selected from a hydrogen atom, a halogen atom, a cyano group, a $C_1$-$C_3$-alkyl group, and a $C_1$-$C_3$-alkoxy group;
$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —$S(O)_2$—($C_1$-$C_3$-alkyl) group, a $C_1$-$C_3$-haloalkoxy group, a $C_1$-$C_3$-haloalkylthio group and a $C_3$-$C_5$-cycloalkyl group;
$R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group;
L is a group —$(CH_2)_m$-E- wherein any $CH_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a S(O)— group, a —S(O)$_2$— group and a —NR$^{14}$— group;

E is a bond, an oxygen atom, a sulfur atom, a —S(O)— group, a —S(O)$_2$— group or a —NR$^{14}$— group and constitutes the connecting element to R$^4$;

m is 2, 3, or 4;

R$^5$ is selected from a COOH group, a

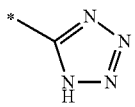

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO($C_1$-$C_6$-alkyl) group, a —C(O)—NHS(O)$_2$(CH$_2$)$_s$NHCO($C_3$-$C_6$-cycloalkyl) group and a —C(O)—NHS(O)$_2$(CH$_2$)$_s$NHCO(aryl) group;

—R$^6$-R$^7$— is $^\#$—(CH$_2$)$_n$—(B)$_t$—(CH$_2$)$_p$—$^{\#\#}$, wherein any —CH$_2$— group is unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, and a (heterocycloalkyl)-($C_1$-$C_3$-alkylene)- group, and where a double bond in any alkenylene can be replaced by a 1,2-cyclopropyl group, and said 1,2-cyclopropyl group is unsubstituted or substituted one or two times with a halogen atom or a $C_1$-$C_2$-alkyl group, wherein $^\#$ is the point of attachment with the indole nitrogen atom and $^{\#\#}$ is the point of attachment with the pyrazole carbon atom bearing the R$^7$ substituent;

—R$^6$-R$^{10}$— is $^\#$—(CH$_2$)$_n$—(B)$_t$—(CH$_2$)$_p$—$^{\#\#}$, where one or more CH$_2$ groups are unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group and a (heterocycloalkyl)-($C_1$-$C_3$-alkylene)- group, wherein $^\#$ is the point of attachment with the indole nitrogen atom and $^{\#\#}$ is the point of attachment with the carbon atom of the phenyl moiety bearing the R$^{19}$ substituent;

n is 1, 2, 3, 4, 5, 6, 7, or 8;

p is 1, 2, 3, 4, 5, 6, 7 or 8;

t is 1;

s is 0, 1 or 2;

where the integers selected for variables n, t, and p result in forming a 9- to 16-membered ring independently from the selection of variable A1, A2 or A3;

B is independently selected from a —S(O)NR$^{15}$— group, a —NR$^{15}$S(O)— group, a —S(O)$_2$NR$^{15}$— group, and a —NR$^{15}$S(O)$_2$— group;

R$^8$ is selected from a hydrogen atom,
a $C_1$-$C_6$-alkyl group, which is unsubstituted or substituted with one or more substituents independently selected from
a halogen atom, a hydroxyl group, a $C_1$-$C_3$-alkoxy group, a $C_1$-$C_3$-haloalkoxy group,
a $C_3$-$C_6$-cycloalkyl group, a heterocycloalkyl group, and a NR$^{20}$R$^{21}$ group, and
a $C_1$-$C_3$-haloalkyl group, a $C_3$-$C_6$-cycloalkyl group, or a $C_1$-$C_6$-alkyl group in which one or two not directly adjacent carbon atoms are independently replaced by a heteroatom independently selected from —O— and NH—;

R$^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O— group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a R$^{18}$-(phenylene)-($C_1$-$C_3$-alkylene)-O—($C_1$-$C_3$-alkylene)- group,
a R$^{18}$-(phenylene)-O—($C_1$-$C_3$-alkylene)- group,
a R$^{18}$-(phenylene)-(heteroarylene)-O—($C_1$-$C_3$-alkylene)- group,
a (R$^{18}$)-(heterocycloalkylene)-($C_1$-$C_3$-alkylene)- group,
a (R$^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a (R$^{18}$)-(heteroarylene)-($C_1$-$C_3$-alkylene)-O—($C_1$-$C_3$-alkylene)- group,
a (R$^{18}$)-(heteroarylene)-(phenylene)-O—($C_1$-$C_3$-alkylene)- group,
a (R$^{19}$)—S(O)$_2$-(phenylene)-O—($C_1$-$C_3$-alkylene)- group,
a (R$^{19}$)—S(O)$_2$—NH-(phenylene)-O—($C_1$-$C_3$-alkylene)- group,
a (R$^{19}$)—S(O)$_2$—NH-(phenylene)-O—($C_1$-$C_3$-alkylene)- group,
a (R$^{19}$)—S(O)$_2$—N($C_1$-$C_6$-alkyl)-(phenylene)-O—($C_1$-$C_3$-alkylene)- group,
a (R$^{19}$)—S(O)$_2$-(heterocycloalkylene)-(phenylene)-O—($C_1$-$C_3$-alkylene)- group,
a (R$^{18}$)-(heterocycloalkylene)-(heteroarylene)-O—($C_1$-$C_3$-alkylene)- group,
a (R$^{19}$)-(heteroarylene)-O—($C_1$-$C_3$-alkylene)- group,
a (R$^{18}$)-(heteroarylene)-O—($C_1$-$C_3$-alkylene)- group,
a (R$^{19}$)—S(O)$_2$-(heteroarylene)-O—($C_1$-$C_3$-alkylene)- group,
a (R$^{19}$)—S(O)$_2$-(heterocycloalkylene)-(heteroarylene)-O—($C_1$-$C_3$-alkylene)- group,
a NR$^{20}$R$^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-NR$^{19}$—C(O)—($C_1$-$C_3$-alkylene)- group, a ($C_1$-$C_3$-alkyl)-C(O)—NH—($C_1$-$C_3$-alkylene)- group,
a ($C_1$-$C_3$-alkyl)-C(O)—$NR^{19}$—($C_1$-$C_3$-alkylene)- group,
a

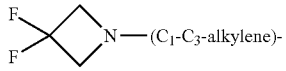

group, and a

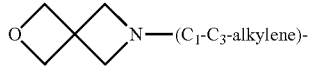

group, where the phenyl ring is unsubstituted or substituted with a halogen atom, a hydroxyl group, or a $C_1$-$C_3$-alkoxy group and
the heterocycloalkyl group is unsubstituted or substituted with an oxo (=O) group or is unsubstituted or substituted with one or more substituents independently selected from a halogen atom, a hydroxyl group, a $C_1$-$C_3$-alkyl group and a $C_1$-$C_3$-alkoxy group,
or $R^8$ and $R^9$ together form a 5- or 6-membered ring optionally comprising one or two heteroatoms independently selected from —O— and —$NR^{14}$—;
$R^{11}$ and $R^{13}$ are each independently selected from a hydrogen atom, a halogen atom, a $C_1$-$C_3$-alkyl group, and a $C_1$-$C_3$-alkoxy group;
$R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group, and a $NR^{16}R^{17}$ group;
$R^{14}$ is a hydrogen atom or a $C_1$-$C_3$-alkyl group;
$R^{15}$ is independently selected from a hydrogen atom,
a $C_1$-$C_6$-alkyl group
which is unsubstituted or substituted with one or more substituents independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—$S(O)_2$-arylene-O— group, a ($R^{19}$)$S(O)_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-$S(O)_2$— group, and a heterocycloalkylene-heteroarylene-$S(O)_2$— group; and
a phenyl group;
$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;
$R^{18}$ is independently selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)O$R^{21}$ group, a —C(O)N$R^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a $NR^{20}R^{21}$ group; and
$R^{20}$ and $R^{21}$ are independently selected from a hydrogen atom and a $C_1$-$C_6$-alkyl group;
or a tautomer, an N-oxide, or a salt thereof, or a salt of a tautomer, or salt of an N-oxide, or a mixture of same.
In accordance with a further aspect, the present invention provides compounds of general formula (I): wherein A is

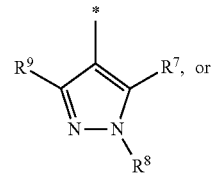 (A1)

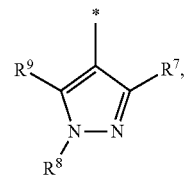 (A2)

wherein $R^6$ and $R^7$, together with two carbon atoms of the pyrazole ring, two carbon atoms of the indole moiety and the nitrogen atom to which $R^6$ is attached, form a 9- to 13-membered ring and * is the point of attachment of these moieties to the indole carbon atom bearing the A substituent;
$R^1$ and $R^2$ are each independently selected from a hydrogen atom, a halogen atom, a cyano group, a $C_1$-$C_3$-alkyl group and a $C_1$-$C_3$-alkoxy group;
$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;
$R^4$ is selected from an aryl group and a heteroaryl group, each of which is unsubstituted or substituted with one, two, or three substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;
L is a group —(CH$_2$)$_m$-E- wherein any CH$_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group;
E is a bond, an oxygen atom, a sulfur atom, or a —$NR^{14}$— group and constitutes the connecting element to $R^4$;
m is 2, 3, or 4;
$R^5$ is selected from a COOH group and a

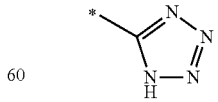

group;
—$R^6$-$R^7$— is #—(CH$_2$)$_n$—(B)$_t$—(CH$_2$)$_p$—##, wherein any —CH$_2$— group is unsubstituted or substituted with one or more substituents selected from a halogen atom, a hydroxyl group, a $NR^{16}R^{17}$ group, a $C_1$-$C_3$-alkyl group, a $C_1$-$C_3$-haloalkyl group, and a $C_1$-$C_3$-alkoxy group, wherein # is the point of attachment with the indole nitrogen atom and ## is the point of attachment with the pyrazole carbon atom bearing the $R^7$ substituent;

n is 1, 2, 3, 4, or 5;

p is 1, 2, 3, or 4;

t is 1;

where the integers selected for variables n, t, and p result in forming a 9- to 13-membered ring independently from the selection of variable A1 or A2;

B is independently selected from a —S(O)$_2$NR$^{15}$— group and a —NR$^{15}$S(O)$_2$— group;

$R^8$ is selected from a hydrogen atom, and
- a $C_1$-$C_6$-alkyl group, which is unsubstituted or substituted with one or more substituents independently selected from
  - a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a NR$^{20}$R$^{21}$ group;

$R^9$ is selected from a hydrogen atom,
- a $C_1$-$C_4$-alkyl group,
- a $C_1$-$C_3$-hydroxyalkyl group,
- a $C_1$-$C_4$-haloalkyl group,
- a $C_1$-$C_4$-haloalkyl-NH—C(O)—O—($C_1$-$C_3$-alkylene)-group,
- a $C_2$-$C_6$-haloalkenyl group,
- a $C_1$-$C_6$-alkyl-O— group,
- a $C_1$-$C_4$-haloalkoxy group,
- a $C_1$-$C_6$-alkyl-O—($C_1$-$C_3$-alkylene)- group,
- a ($C_1$-$C_3$-alkyl)-NH—($C_1$-$C_3$-alkylene)- group,
- a ($C_3$-$C_7$)-cycloalkyl group, and
- a ($C_3$-$C_7$)-cycloalkyl-O—($C_1$-$C_3$-alkylene)- group;

$R^{14}$ is a hydrogen atom or a $C_1$-$C_3$-alkyl group;

$R^{15}$ is independently selected from a hydrogen atom,
- a $C_1$-$C_6$-alkyl group
  - which is unsubstituted or substituted with one or more substituents selected from a $C_1$-$C_3$-alkyl group, a heterocycloalkyl group, and an aryl group, and a phenyl group;

$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;

$R^{19}$ is selected from a $C_1$-$C_3$-alkyl group, a $C_3$-$C_6$-cycloalkyl group and a NR$^{20}$R$^{21}$ group; and $R^{29}$ and $R^{21}$ are independently selected from a hydrogen atom and a $C_1$-$C_6$-alkyl group;

or a tautomer, an N-oxide, or a salt thereof, or a salt of a tautomer, or salt of an N-oxide, or a mixture of same.

In accordance with a further aspect, the present invention provides compounds of general formula (I): wherein A is

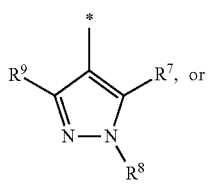

(A1)

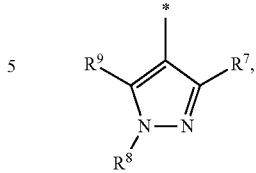

(A2)

wherein $R^6$ and $R^7$, together with two carbon atoms of the pyrazole ring, two carbon atoms of the indole moiety and the nitrogen atom to which $R^6$ is attached, form a 10- to 12-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one, two, or three, substituents and each substituent is independently selected from a halogen atom, and a $C_1$-$C_3$-alkyl group;

L is a group —(CH$_2$)$_m$-E-;

E is a bond or an oxygen atom and constitutes the connecting element to $R^4$;

m is 2, 3, or 4;

$R^5$ is a COOH group;

—R$^6$-R$^7$— is #—(CH$_2$)$_n$—(B)$_t$—(CH$_2$)$_p$—##, wherein any —CH$_2$— group is unsubstituted or substituted with one or more substituents selected from a halogen atom, a hydroxyl group, a NR$^{16}$R$^{17}$ group, a $C_1$-$C_3$-alkyl group, a $C_1$-$C_3$-haloalkyl group, and a $C_1$-$C_3$-alkoxy group, wherein # is the point of attachment with the indole nitrogen atom and ## is the point of attachment with the pyrazole carbon atom bearing the $R^7$ substituent;

n is 2, 3 or 4;

p is 1, 2, or 3;

t is 1;

where the integers selected for variables n, t, and p result in forming a 9- to 12-membered ring independently from the selection of variable A1 or A2;

B is selected from a —S(O)$_2$NR$^{15}$— group and a —NR$^{15}$S(O)$_2$— group;

$R^9$ is selected from a hydrogen atom, and
- a $C_1$-$C_6$-alkyl group, which is unsubstituted or substituted with one or more substituents independently selected from
  - a halogen atom, a hydroxy group, a $C_3$-$C_6$-cycloalkyl group and a heterocycloalkyl group;

$R^9$ is selected from a hydrogen atom,
- a $C_1$-$C_4$-alkyl group,
- a $C_1$-$C_3$-hydroxyalkyl group,
- a $C_1$-$C_4$-haloalkyl group,
- a $C_1$-$C_6$-alkyl-O— group,
- a $C_1$-$C_4$-haloalkoxy group, and
- a $C_1$-$C_6$-alkyl-O—($C_1$-$C_3$-alkylene)- group;

$R^{15}$ is independently selected from a hydrogen atom, and
- a $C_1$-$C_6$-alkyl group
  - which is unsubstituted or substituted with a substituent selected from a heterocycloalkyl group and an aryl group;

$R^{16}$ and $R^{17}$ are each independently selected from a hydrogen atom, a $C_1$-$C_6$-alkyl group and a $C_1$-$C_6$-haloalkyl group;

or a tautomer, an N-oxide, or a salt thereof, or a salt of a tautomer, or salt of an N-oxide, or a mixture of same.

In accordance with a further aspect, the present invention provides compounds of general formula (I): wherein
A is

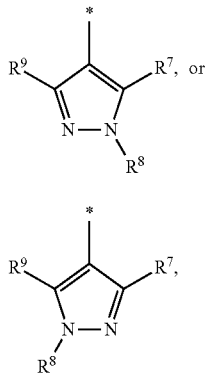

(A1)

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group which is unsubstituted or substituted with one, two, or three substituents and each substituent is independently selected from a halogen atom, and a $C_1$-$C_3$-alkyl group;

L is a group —$(CH_2)_m$-E-;

E is a bond or an oxygen atom and constitutes the connecting element to $R^4$;

m is 3;

$R^5$ is a COOH group;

—$R^6$-$R^7$— is $^{\#}$—$(CH_2)_n$—$(B)_t$—$(CH_2)_p$—$^{\#\#}$, wherein $^{\#}$ is the point of attachment with the indole nitrogen atom and $^{\#\#}$ is the point of attachment with the pyrazole carbon atom bearing the $R^7$ substituent;

n is 3;

t is 1;

p is 1;

where the integers selected for variables n, t, and p result in forming a 11-membered ring independently from the selection of variable A1 or A2;

B is a —$S(O)_2NR^{15}$— group;

$R^8$ is selected from a hydrogen atom, and
a $C_1$-$C_6$-alkyl group, which is unsubstituted or substituted with a heterocycloalkyl group;

$R^9$ is selected from a hydrogen atom,
a $C_1$-$C_4$-alkyl group, and
a $C_1$-$C_6$-alkyl-O—($C_1$-$C_3$-alkylene)- group;

$R^{15}$ is independently selected from a hydrogen atom, and
a $C_1$-$C_6$-alkyl group
which is unsubstituted or substituted with a heterocycloalkyl group;

or a tautomer, an N-oxide, or a salt thereof, or a salt of a tautomer, or salt of an N-oxide, or a mixture of same.

In accordance with a further aspect, the present invention provides compounds of general formula (I): wherein in which
A is

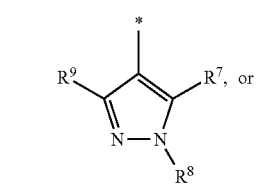

(A1)

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ is a hydrogen atom or a halogen atom;

$R^2$ is a hydrogen atom;

$R^3$ is a hydrogen atom;

$R^4$ is an aryl group, which is unsubstituted or substituted with one, two or three substituents independently selected from a halogen atom and a methyl group;

L is a group $(CH_2)_3$—O—;

$R^5$ is a COOH group;

—$R^6$-$R^7$— is $^{\#}$—$(CH_2)_n$—$S(O)_2NR^{15}$—$(CH_2)_p$—$^{\#\#}$, wherein $^{\#}$ is the point of attachment with the indole nitrogen atom and $^{\#\#}$ is the point of attachment with the pyrazole carbon atom bearing the $R^7$ substituent;

n is 3;

p is 1;

where the integers selected for variables n and p result in forming a 11-membered ring independently from the selection of variable A1 or A2;

$R^8$ is a methyl group;

$R^9$ is selected from a methyl group and an ethyl group;

$R^{15}$ is a $C_1$-$C_3$-alkyl group which is unsubstituted or substituted with an unsubstituted or a substituted heterocycloalkyl group;

or a tautomer, an N-oxide, or a salt thereof, or a salt of a tautomer, or salt of an N-oxide, or a mixture of same.

In accordance with a further aspect, the present invention provides compounds of general formula (I): wherein
A is

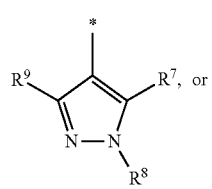

(A1)

-continued (A2)

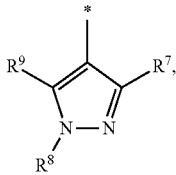

wherein R⁶ and R⁷, together with two carbon atoms of the pyrazole ring, two carbon atoms of the indole moiety and the nitrogen atom to which R⁶ is attached, form a 11-membered ring and * is the point of attachment of these moieties to the indole carbon atom bearing the A substituent;
R¹ is a hydrogen atom, a chlorine atom or a fluorine atom;
R² is a hydrogen atom;
R³ is a hydrogen atom;
R⁴ is a naphthalene-1-yl group, a 6-fluoro-naphthalene-1-yl group, a 4-fluoro-naphthalin-1-yl group, a (5,6,7,8-tetrahydronaphthalene-1-yl) group, a 2,3-dihydro-1H-inden-4-yl group, or a 4-chloro-3,5-dimethylphen-1-yl group;
L is a group (CH₂)₃—O—;
R⁵ is a COOH group;
—R⁶-R⁷— is $^{\#}$—(CH₂)$_n$—S(O)₂NR¹⁵—(CH₂)$_p$—$^{\#\#\#}$, wherein # is the point of attachment with the indole nitrogen atom and ### is the point of attachment with the pyrazole carbon atom bearing the R⁷ substituent;
n is 3;
p is 1;
where the integers selected for variables n and p result in forming a 11-membered ring independently from the selection of variable A1 or A2;
R⁸ is a methyl group;
R⁹ is selected from a methyl group and an ethyl group; and
R¹⁵ is a C₁-C₃-alkyl group which is unsubstituted or substituted with a pyrrolidin-1-yl group, a 2-oxopyrrolidin-1-yl group, a piperidin-1-yl group or a morpholin-4-yl group;
or a tautomer, an N-oxide, or a salt thereof, or a salt of a tautomer, or salt of an N-oxide, or a mixture of same.

In some embodiments, the present invention includes compounds of general formula (I) selected from:
(rac)-2,3-dimethyl-14-[2-(morpholin-4-yl)ethyl]-7-{3-[(naphthalen-1-yl)oxy]propyl}-13,13-dioxo-10,11,12,13,14,15-hexahydro-2H-13lambda⁶-pyrazolo[3',4':4,5][1,2,8]thiadiazacycloundecino-[6,7,8-hi]indole-8-carboxylic acid,
2,3-dimethyl-14-[2-(morpholin-4-yl)ethyl]-7-{3-[(naphthalen-1-yl)oxy]propyl}-13,13-dioxo-10,11,12,13,14,15-hexahydro-2H-13lambda⁶-pyrazolo[3',4':4,5][1,2,8]thiadiazacycloundecino-[6,7,8-hi]indole-8-carboxylic acid-N-ethylethanamine (enantiomer 1),
2,3-dimethyl-14-[2-(morpholin-4-yl)ethyl]-7-{3-[(naphthalen-1-yl)oxy]propyl}-13,13-dioxo-10,11,12,13,14,15-hexahydro-2H-13lambda⁶-pyrazolo[3',4':4,5][1,2,8]thiadiazacycloundecino-[6,7,8-hi]indole-8-carboxylic acid-N-ethylethanamine (enantiomer 2),
(rac)-4-chloro-2,3,14-trimethyl-7-{3-[(naphthalen-1-yl)oxy]propyl}-13,13-dioxo-10,11,12,13,14,15-hexahydro-2H-13lambda⁶-pyrazolo[3',4':4,5][1,2,8]thiadiazacycloundecino-[6,7,8-hi]indole-8-carboxylic acid,
4-chloro-2,3,14-trimethyl-7-{3-[(naphthalen-1-yl)oxy]propyl}-13,13-dioxo-10,11,12,13,14,15-hexahydro-2H-13lambda⁶-pyrazolo[3',4':4,5][1,2,8]thiadiazacycloundecino[6,7,8-hi]indole-8-carboxylic acid-N-ethylethanamine (enantiomer 1),
4-chloro-2,3,14-trimethyl-7-{3-[(naphthalen-1-yl)oxy]propyl}-13,13-dioxo-10,11,12,13,14,15-hexahydro-2H-13lambda⁶-pyrazolo[3',4':4,5][1,2,8]thiadiazacycloundecino[6,7,8-hi]indole-8-carboxylic acid-N-ethylethanamine (enantiomer 2),
(rac)-12-ethyl-13-fluoro-1-(3-((6-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide,
3-ethyl-4-fluoro-7-{3-[(6-fluoronaphthalen-1-yl)oxy]propyl}-2,14-dimethyl-13,13-dioxo-10,11,12,13,14,15-hexahydro-2H-13lambda⁶-pyrazolo[3',4':4,5][1,2,8]thiadiazacycloundecino-[6,7,8-hi]indole-8-carboxylic acid (enantiomer 1),
3-ethyl-4-fluoro-7-{3-[(6-fluoronaphthalen-1-yl)oxy]propyl}-2,14-dimethyl-13,13-dioxo-10,11,12,13,14,15-hexahydro-2H-13lambda⁶-pyrazolo[3',4':4,5][1,2,8]thiadiazacycloundecino-[6,7,8-hi]indole-8-carboxylic acid (enantiomer 2),
(rac)-8,11,12-trimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide,
2,3,14-trimethyl-7-{3-[(naphthalen-1-yl)oxy]propyl}-13,13-dioxo-10,11,12,13,14,15-hexahydro-2H-13lambda⁶-pyrazolo[3',4':4,5][1,2,8]thiadiazacycloundecino[6,7,8-hi]indole-8-carboxylic acid-N-ethylethanamine (enantiomer 1),
2,3,14-trimethyl-7-{3-[(naphthalen-1-yl)oxy]propyl}-13,13-dioxo-10,11,12,13,14,15-hexahydro-2H-13lambda⁶-pyrazolo[3',4':4,5][1,2,8]thiadiazacycloundecino[6,7,8-hi]indole-8-carboxylic acid-N-ethylethanamine (enantiomer 2),
(rac)-12-ethyl-11-methyl-1-(3-(naphthalen-1-yloxy)propyl)-8-(3-(2-oxopyrrolidin-1-yl)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-12-ethyl-11-methyl-1-(3-(naphthalen-1-yloxy)propyl)-8-(2-(piperidin-1-yl)ethyl)-4,5,6,8,9,11-hexahydropyrazolo[3',4':4,5][1,2,8]thiadiazacycloundecino[6,7,8-hi]indole-2-carboxylic acid 7,7-dioxide 2,2,2-trifluoroacetic acid salt,
(rac)-12-ethyl-11-methyl-8-(3-morpholinopropyl)-1-(3-(naphthalen-1-yloxy)propyl)-4,5,6,8,9,11-hexahydropyrazolo[3',4':4,5][1,2,8]thiadiazacycloundecino[6,7,8-hi]indole-2-carboxylic acid 7,7-dioxide 2,2,2-trifluoroacetic acid salt,
(rac)-12-ethyl-11-methyl-1-(3-(naphthalen-1-yloxy)propyl)-8-(3-(pyrrolidin-1-yl)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-12-ethyl-11-methyl-1-(3-(naphthalen-1-yloxy)propyl)-4,5,6,8,9,11-hexahydropyrazolo[3',4':4,5][1,2,8]thiadiazacycloundecino[6,7,8-hi]indole-2-carboxylic acid 7,7-dioxide,
(rac)-12-ethyl-8,9,11-trimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-13-chloro-12-ethyl-1-(3-((6-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide, (rac)-13-chloro-12-ethyl-8,11-dimethyl-1-(3-(naphthalen-1-yloxy)propyl)-5,6,9,11-tetrahydro-4H,8H-pyrazolo[3',4': 4,5][1]thia[2,8]diazacycloundecino[6,7,8-hi]indole-2-carboxylic acid 7,7-dioxide,
(rac)-13-chloro-1-(3-((2,3-dihydro-1H-inden-4-yl)oxy)propyl)-12-ethyl-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-13-chloro-1-(3-(4-chloro-3,5-dimethylphenoxy)propyl)-12-ethyl-8,11-dimethyl-4,5,6,8,9,11-hexahydropyrazolo[3',4':4,5][1,2,8]thiadiazacycloundecino[6,7,8-hi]indole-2-carboxylic acid 7,7-dioxide,
(rac)-13-chloro-12-ethyl-8,11-dimethyl-1-(3-((5,6,7,8-tetrahydronaphthalen-1-yl)oxy)propyl)-4,5,6,8,9,11-hexahydropyrazolo[3',4':4,5][1,2,8]thiadiazacycloundecino[6,7,8-hi]indole-2-carboxylic acid 7,7-dioxide,
(rac)-13-chloro-12-ethyl-1-(3-((4-fluoronaphthalen-1-yl)oxy)propyl)-8,11-dimethyl-4,5,6,8,9,11-hexahydropyrazolo[3',4':4,5][1,2,8]thiadiazacycloundecino[6,7,8-hi]indole-2-carboxylic acid 7,7-dioxide,
(rac)-13-fluoro-1-(3-((6-fluoronaphthalen-1-yl)oxy)propyl)-8,11,12-trimethyl-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-13-fluoro-8,11,12-trimethyl-1-(3-(naphthalen-1-yloxy)propyl)-5,6,9,11-tetrahydro-4H,8H-pyrazolo[3',4': 4,5][1]thia[2,8]diazacycloundecino[6,7,8-hi]indole-2-carboxylic acid 7,7-dioxide,
(rac)-1-(3-((2,3-dihydro-1H-inden-4-yl)oxy)propyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-1-(3-(4-chloro-3,5-dimethylphenoxy)propyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-13-fluoro-8,11,12-trimethyl-1-(3-((5,6,7,8-tetrahydronaphthalen-1-yl)oxy)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-13-fluoro-1-(34(4-fluoronaphthalen-1-yl)oxy)propyl)-8,11,12-trimethyl-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-12-ethyl-13-fluoro-8,11-dimethyl-1-(3-(naphthalen-1-yloxy)propyl)-5,6,9,11-tetrahydro-4H,8H-pyrazolo[3',4': 4,5][1]thia[2,8]diazacycloundecino[6,7,8-hi]indole-2-carboxylic acid 7,7-dioxide,
(rac)-1-(3-((2,3-dihydro-1H-inden-4-yl)oxy)propyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-1-(3-(4-chloro-3,5-dimethylphenoxy)propyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide,
(rac)-12-ethyl-13-fluoro-8,11-dimethyl-1-(3-((5,6,7,8-tetrahydronaphthalen-1-yl)oxy)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide and
(rac)-12-ethyl-13-fluoro-1-(3-((4-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide,
wherein lambda$^6$ means λ6;
or a tautomer, an N-oxide, or a salt thereof, or a salt of a tautomer, or salt of an N-oxide, or a mixture of same.

In some embodiments, the present invention includes compounds of general formula (I) selected from:
(+)-4-chloro-3-ethyl-7-{3-[(6-fluoronaphthalen-1-yl)oxy]propyl}-2,14-dimethyl-13,13-dioxo-10,11,12,13,14,15-hexahydro-2H-13lambda$^6$-pyrazolo[3',4':4,5][1,2,8]thiadiazacycloundecino-[6,7,8-hi]indole-8-carboxylic acid (enantiomer 1),
(−)-4-chloro-3-ethyl-7-{3-[(6-fluoronaphthalen-1-yl)oxy]propyl}-2,14-dimethyl-13,13-dioxo-10,11,12,13,14,15-hexahydro-2H-13lambda$^6$-pyrazolo[3',4':4,5][1,2,8]thiadiazacycloundecino-[6,7,8-hi]indole-8-carboxylic acid (enantiomer 2),
(−)-4-fluoro-7-{3-[(6-fluoronaphthalen-1-yl)oxy]propyl}-2,3,14-trimethyl-13,13-dioxo-10,11,12,13,14,15-hexahydro-2H-13lambda$^6$-pyrazolo[3',4':4,5][1,2,8]thiadiazacycloundecino-[6,7,8-hi]indole-8-carboxylic acid (enantiomer 1),
(+)-4-fluoro-7-{3-[(6-fluoronaphthalen-1-yl)oxy]propyl}-2,3,14-trimethyl-13,13-dioxo-10,11,12,13,14,15-hexahydro-2H-13lambda$^6$-pyrazolo[3',4':4,5][1,2,8]thiadiazacycloundecino-[6,7,8-hi]indole-8-carboxylic acid (enantiomer 2),
(rac)-4-chloro-14-cyclopropyl-2,3-dimethyl-7-[3-(1-naphthyloxy)propyl]-11,12,14,15-tetrahydro-2H,10H-pyrazolo[3',4':4,5][1,2,8]thiadiazacycloundecino[6,7,8-hi]indole-8-carboxylic acid 13,13-dioxide,
(rac)-4-chloro-14-cyclopropyl-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide,
(−)-4-chloro-14-cyclopropyl-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide N-diethylamine salt (enantiomer 1),
(+)-4-chloro-14-cyclopropyl-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide N-diethylamine salt (enantiomer 2),
(rac)-2,3,14-trimethyl-15-[2-(morpholin-4-yl)ethyl]-7-[3-(1-naphthyloxy)propyl]-11,12,14,15-tetrahydro-2H,10H-pyrazolo[3',4':4,5][1,2,8]thiadiazacycloundecino[6,7,8-hi]indole-8-carboxylic acid 13,13-dioxide,
2,3,14-trimethyl-15-[2-(morpholin-4-yl)ethyl]-7-{3-[(naphthalen-1-yl)oxy]propyl}-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine salt (enantiomer 1),
2,3,14-trimethyl-15-[2-(morpholin-4-yl)ethyl]-7-{3-[(naphthalen-1-yl)oxy]propyl}-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine salt (enantiomer 2),
(rac)-4-chloro-7-{3-[(6-fluoro-1-naphthyl)oxy]propyl}-2,3,14-trimethyl-15-[2-(morpholin-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide,
(rac)-4-chloro-7-{3-[(6-fluoro-1-naphthyl)oxy]propyl}-2,3,14-trimethyl-15-[2-(morpholin-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide,
(rac)-4-chloro-14-(2,4-dimethoxybenzyl)-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide, (rac)-4-chloro-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide, 4-chloro-7-{3-[(6-fluoronaphthalen-1-yl)oxy]propyl}-2,3-dimethyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 1), 4-chloro-7-{3-[(6-fluoronaphthalen-1-yl)oxy]propyl}-2,3-dimethyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 2), (rac)-4-chloro-14-cyclopropyl-3-ethyl-7-{3-[(6-fluoro-1-naphthyl)oxy]propyl}-2-methyl-11,12,14,15-tetrahydro-2H,10H-pyrazolo[3',4':4,5][1,2,8]thiadiazacycloundecino[6,7,8-hi]indole-8-carboxylic acid 13,13-dioxide, (−) 4-chloro-14-cyclopropyl-3-ethyl-7-{3-[(6-fluoronaphthalen-1-yl)oxy]propyl}-2-methyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine salt (enantiomer 1), (+)4-chloro-14-cyclopropyl-3-ethyl-7-{3-[(6-fluoronaphthalen-1-yl)oxy]propyl}-2-methyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine salt (enantiomer 2), (rac)-4-chloro-3,14-diethyl-7-{3-[(6-fluoro-1-naphthyl)oxy]propyl}-2-methyl-11,12,14,15-tetrahydro-2H,10H-pyrazolo[3',4':4,5][1,2,8]thiadiazacycloundecino[6,7,8-hi]indole-8-carboxylic acid 13,13-dioxide, (+)-4-chloro-3,14-diethyl-7-{3-[(6-fluoronaphthalen-1-yl)oxy]propyl}-2-methyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine salt (enantiomer 1), (−)-4-chloro-3,14-diethyl-7-{3-[(6-fluoronaphthalen-1-yl)oxy]propyl}-2-methyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine salt (enantiomer 2), (rac)-4-chloro-3-ethyl-7-{3-[(6-fluoro-1-naphthyl)oxy]propyl}-2,14-dimethyl-15-[2-(tetrahydro-2H-pyran-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide (racemate 2), (rac)-4-chloro-3-ethyl-7-{3-[(6-fluoro-1-naphthyl)oxy]propyl}-2,14-dimethyl-15-[2-(tetrahydro-2H-pyran-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide (racemate 1), (+)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 1), (−)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 2), (+)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 3), (−)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 4), (rac)-4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid, 4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 1), 4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 2), (rac)4-chloro-3-ethyl-7-{3-[(6-fluoro-1-naphthyl)oxy]propyl}-2,14-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide, (rac)-15-chloro-14-ethyl-1-(3-((6-fluoronaphthalen-1-yl)oxy) propyl)-8,13-dimethyl-11-morpholino-5,6,9,10,11,13-hexahydro-4H,8H-pyrazolo[3',4':6,7][1]thia[2,10]diazacyclotridecino[8,9,10-hi]indole-2-carboxylic acid 7,7-dioxide, (+)-4-chloro-3-ethyl-7-{3-[(6-fluoro-1-naphthyl)oxy]propyl}-2,14-dimethyl-17-(morpholin-4-yl)-11,12,14,15,16,17-hexahydro-2H,10H-pyrazolo[3',4':6,7][1,2,10]thiadiazacyclotridecino[8,9,10-hi]indole-8-carboxylic acid 13,13-dioxide trifluoroacetate salt (enantiomer 1), (−)-4-chloro-3-ethyl-7-{3-[(6-fluoro-1-naphthyl)oxy]propyl}-2,14-dimethyl-17-(morpholin-4-yl)-11,12,14,15,16,17-hexahydro-2H,10H-pyrazolo[3',4':6,7][1,2,10]thiadiazacyclotridecino[8,9,10-hi]indole-8-carboxylic acid 13,13-dioxide trifluoroacetate salt (enantiomer 2), (rac)-4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda6-pyrazolo[3',4':4,5][1,2,8]thiadiazacycloundecino[6,7,8-hi]indole-8-carboxylic acid, (15S)-4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid, (rac)-4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda6-pyrazolo[3',4':4,5][1,2,8]thiadiazacycloundecino[6,7,8-hi]indole-8-carboxylic acid, 4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid-N-ethylethanamine salt (enantiomer 1), 4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda$^6$- pyrazolo[3',4':4,5][1,2,8]thiadiazacycloundecino[6,7,8-hi]indole-8-carboxylic acid-N-ethylethanamine salt (enantiomer 2) and (rac)-13-chloro-12-ethyl-1-(3-((6-fluoronaphthalen-1-yl)oxy)propyl)-11-methyl-8-(2-morpholinoethyl)-5,6,9,11-tetrahydro-4H,8H-pyrazolo[3',4':4,5][1]thia[2,8]diazacycloundecino[6,7,8-hi]indole-2-carboxylic acid 7,7-dioxide wherein lambda$^6$ means A6;

or a tautomer, an N-oxide, or a salt thereof, or a salt of a tautomer, or salt of an N-oxide, or a mixture of same.

In some embodiments, the present invention includes compounds of general formula (I) selected from:

(rac)-13-chloro-12-ethyl-1-(3-((6-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide, (+)-4-chloro-3-ethyl-7-{3-[(6-fluoronaphthalen-1-yl)oxy]propyl}-2,14-dimethyl-13,13-dioxo-10,11,12,13,14,15-hexahydro-2H-13lambda$^6$-pyrazolo[3',4':4,5][1,2,8]thiadiazacycloundecino-[6,7,8-hi]indole-8-carboxylic acid (enantiomer 1), (−)-4-chloro-3-ethyl-7-{3-[(6-fluoronaphthalen-1-yl)oxy]propyl}-2,14-dimethyl-13,13-dioxo-10,11,12,13,14,15-hexahydro-2H-13lambda$^6$-pyrazolo[3',4':4,5][1,2,8]thiadiazacycloundecino-[6,7,8-hi]indole-8-carboxylic acid (enantiomer 2), (rac)-4-chloro-7-{3-[(6-fluoro-1-naphthyl)oxy]propyl}-2,3,14-trimethyl-15-[2-(morpholin-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide, (rac)-4-chloro-7-{3-[(6-fluoro-1-naphthyl)oxy]propyl}-2,3,14-trimethyl-15-[2-(morpholin-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide, (rac)-4-chloro-3,14-diethyl-7-{3-[(6-fluoro-1-naphthyl)oxy]propyl}-2-methyl-11,12,14,15-tetrahydro-2H,10H-pyrazolo[3',4':4,5][1,2,8]thiadiazacycloundecino[6,7,8-hi]indole-8-carboxylic acid 13,13-dioxide, (+)-4-chloro-3,14-diethyl-7-{3-[(6-fluoronaphthalen-1-yl)oxy]propyl}-2-methyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine salt (enantiomer 1), (−)-4-chloro-3,14-diethyl-7-{3-[(6-fluoronaphthalen-1-yl)oxy]propyl}-2-methyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine salt (enantiomer 2), (rac)-4-chloro-3-ethyl-7-{3-[(6-fluoro-1-naphthyl)oxy]propyl}-2,14-dimethyl-15-[2-(tetrahydro-2H-pyran-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide (racemate 2), (rac)-4-chloro-3-ethyl-7-{3-[(6-fluoro-1-naphthyl)oxy]propyl}-2,14-dimethyl-15-[2-(tetrahydro-2H-pyran-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide (racemate 1), (+)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 1), (−)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 2), (+)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 3), (−)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 4), (rac)-4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid, 4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 1), 4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (enantiomer 2), (rac) 4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda6-pyrazolo[3',4':4,5][1,2,8]thiadiazacycloundecino[6,7,8-hi]indole-8-carboxylic acid, (15S)-4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid, (rac) 4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda6-pyrazolo[3',4':4,5][1,2,8]thiadiazacycloundecino[6,7,8-hi]indole-8-carboxylic acid and 4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid-N-ethylethanamine salt (enantiomer 1) and 4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid-N-ethylethanamine salt (enantiomer 2), wherein lambda$^6$ means A6;

or a tautomer, an N-oxide, or a salt thereof, or a salt of a tautomer, or salt of an N-oxide, or a mixture of same.

In some embodiments, the present invention includes compounds of general formula (I) selected from:

(rac)-13-chloro-12-ethyl-1-(3-((6-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide, (+)-4-chloro-3-ethyl-7-{3-[(6-fluoronaphthalen-1-yl)oxy]
propyl}-2,14-dimethyl-13,13-dioxo-10,11,12,13,14,15-
hexahydro-2H-13lambda$^6$-pyrazolo[3',4':4,5][1,2,8]thia-
diazacycloundecino-[6,7,8-hi]indole-8-carboxylic acid
(enantiomer 1), (−)-4-chloro-3-ethyl-7-{3-[(6-fluoronaphthalen-1-yl)oxy]
propyl}-2,14-dimethyl-13,13-dioxo-10,11,12,13,14,15-
hexahydro-2H-13lambda$^6$-pyrazolo[3',4':4,5][1,2,8]thia-
diazacycloundecino-[6,7,8-hi]indole-8-carboxylic acid
(enantiomer 2), (rac)-4-chloro-7-{3-[(6-fluoro-1-naphthyl)oxy]propyl}-2,3,
14-trimethyl-15-[2-(morpholin-4-yl)ethyl]-11,12,14,15-
tetrahydro-2H,10H-pyrazolo[3',4':4,5][1,2,8]thiadiazacy-
cloundecino[6,7,8-hi]indole-8-carboxylic acid 13,13-
dioxide, (rac)-4-chloro-7-{3-[(6-fluoro-1-naphthyl)oxy]propyl}-2,3,
14-trimethyl-15-[2-(morpholin-4-yl)ethyl]-11,12,14,15-
tetrahydro-2H,10H-pyrazolo[3',4':4,5][1,2,8]thiadiazacy-
cloundecino[6,7,8-hi]indole-8-carboxylic acid 13,13-
dioxide, (rac)-4-chloro-3,14-diethyl-7-{3-[(6-fluoro-1-naphthyl)
oxy]propyl}-2-methyl-11,12,14,15-tetrahydro-2H,10H-
pyrazolo[3',4':4,5][1,2,8]thiadiazacycloundecino[6,7,8-
hi]indole-8-carboxylic acid 13,13-dioxide, (+)-4-chloro-3,14-diethyl-7-{3-[(6-fluoronaphthalen-1-yl)
oxy]propyl}-2-methyl-13,13-dioxo-10,11,12,13,14,15-
hexahydro-2H-13lambda$^6$-pyrazolo[3',4':4,5][1,2,8]thia-
diazacycloundecino[6,7,8-hi]indole-8-carboxylic acid
N-ethylethanamine salt (enantiomer 1), (−)-4-chloro-3,14-diethyl-7-{3-[(6-fluoronaphthalen-1-yl)
oxy]propyl}-2-methyl-13,13-dioxo-10,11,12,13,14,15-
hexahydro-2H-13lambda$^6$-pyrazolo[3',4':4,5][1,2,8]thia-
diazacycloundecino[6,7,8-hi]indole-8-carboxylic acid
N-ethylethanamine salt (enantiomer 2), (rac)-4-chloro-3-ethyl-7-{3-[(6-fluoro-1-naphthyl)oxy]pro-
pyl}-2,14-dimethyl-15-[2-(tetrahydro-2H-pyran-4-yl)
ethyl]-11,12,14,15-tetrahydro-2H,10H-pyrazolo[3',4':4,5]
[1,2,8]thiadiazacycloundecino[6,7,8-hi]indole-8-
carboxylic acid 13,13-dioxide (racemate 2) and (rac)-4-chloro-3-ethyl-7-{3-[(6-fluoro-1-naphthyl)oxy]pro-
pyl}-2,14-dimethyl-15-[2-(tetrahydro-2H-pyran-4-yl)
ethyl]-11,12,14,15-tetrahydro-2H,10H-pyrazolo[3',4':4,5]
[1,2,8]thiadiazacycloundecino[6,7,8-hi]indole-8-
carboxylic acid 13,13-dioxide (racemate 1), wherein lambda$^6$ means A6;
or a tautomer, an N-oxide, or a salt thereof, or a salt of a
tautomer, or salt of an N-oxide, or a mixture of same.

In some embodiments, the present invention includes
compounds of general formula (I) selected from:

(+)-4-chloro-3-ethyl-7-{3-[(6-fluoronaphthalen-1-yl)oxy]
propyl}-2,14-dimethyl-15-[2-(oxan-4-yl)ethyl]-13,13-di-
oxo-10,11,12,13,14,15-hexahydro-2H-13lambda$^6$-pyra-
zolo[3',4':4,5][1,2,8]thiadiazacycloundecino[6,7,8-hi]
indole-8-carboxylic acid (enantiomer 1), (−)-4-chloro-3-ethyl-7-{3-[(6-fluoronaphthalen-1-yl)oxy]
propyl}-2,14-dimethyl-15-[2-(oxan-4-yl)ethyl]-13,13-di-
oxo-10,11,12,13,14,15-hexahydro-2H-13lambda$^6$-pyra-
zolo[3',4':4,5][1,2,8]thiadiazacycloundecino[6,7,8-hi]
indole-8-carboxylic acid (enantiomer 2), (+)-4-chloro-3-ethyl-7-{3-[(6-fluoronaphthalen-1-yl)oxy]
propyl}-2,14-dimethyl-15-[2-(oxan-4-yl)ethyl]-13,13-di-
oxo-10,11,12,13,14,15-hexahydro-2H-13lambda$^6$-pyra-
zolo[3',4':4,5][1,2,8]thiadiazacycloundecino[6,7,8-hi]
indole-8-carboxylic acid (enantiomer 3), (−)-4-chloro-3-ethyl-7-{3-[(6-fluoronaphthalen-1-yl)oxy]
propyl}-2,14-dimethyl-15-[2-(oxan-4-yl)ethyl]-13,13-di-
oxo-10,11,12,13,14,15-hexahydro-2H-13lambda$^6$-pyra-
zolo[3',4':4,5][1,2,8]thiadiazacycloundecino[6,7,8-hi]
indole-8-carboxylic acid (enantiomer 4), (rac)-4-chloro-7-{3-[(6-fluoronaphthalen-1-yl)oxy]propyl}-
2,3,14-trimethyl-15-[2-(morpholin-4-yl)ethyl]-13,13-di-
oxo-10,11,12,13,14,15-hexahydro-2H-13lambda$^6$-pyra-
zolo[3',4':4,5][1,2,8]thiadiazacycloundecino[6,7,8-hi]
indole-8-carboxylic acid, 4-chloro-7-{3-[(6-fluoronaphthalen-1-yl)oxy]propyl}-2,3,
14-trimethyl-15-[2-(morpholin-4-yl)ethyl]-13,13-dioxo-
10,11,12,13,14,15-hexahydro-2H-13lambda$^6$-pyrazolo
[3',4':4,5][1,2,8]thiadiazacycloundecino[6,7,8-hi]indole-
8-carboxylic acid (enantiomer 1), 4-chloro-7-{3-[(6-fluoronaphthalen-1-yl)oxy]propyl}-2,3,
14-trimethyl-15-[2-(morpholin-4-yl)ethyl]-13,13-dioxo-
10,11,12,13,14,15-hexahydro-2H-13lambda$^6$-pyrazolo
[3',4':4,5][1,2,8]thiadiazacycloundecino[6,7,8-hi]indole-
8-carboxylic acid (enantiomer 2), (rac) 4-chloro-3-ethyl-7-{3-[(6-fluoronaphthalen-1-yl)oxy]
propyl}-2,14-dimethyl-15-[2-(morpholin-4-yl)ethyl]-13,
13-dioxo-10,11,12,13,14,15-hexahydro-2H-13lambda6-
pyrazolo[3',4':4,5][1,2,8]thiadiazacycloundecino[6,7,8-
hi]indole-8-carboxylic acid, (15S)-4-chloro-3-ethyl-7-{3-[(6-fluoronaphthalen-1-yl)
oxy]propyl}-2,14-dimethyl-15-[2-(morpholin-4-yl)
ethyl]-13,13-dioxo-10,11,12,13,14,15-hexahydro-2H-
13lambda$^6$-pyrazolo[3',4':4,5][1,2,8]
thiadiazacycloundecino[6,7,8-hi]indole-8-carboxylic
acid, (rac) 4-chloro-3-ethyl-7-{3-[(6-fluoronaphthalen-1-yl)oxy]
propyl}-2,14-dimethyl-15-[2-(morpholin-4-yl)ethyl]-13,
13-dioxo-10,11,12,13,14,15-hexahydro-2H-13lambda6-
pyrazolo[3',4':4,5][1,2,8]thiadiazacycloundecino[6,7,8-
hi]indole-8-carboxylic acid, 4-chloro-3-ethyl-7-{3-[(6-fluoronaphthalen-1-yl)oxy]pro-
pyl}-2,14-dimethyl-15-[2-(morpholin-4-yl)ethyl]-13,13-
dioxo-10,11,12,13,14,15-hexahydro-2H-13lambda$^6$-
pyrazolo[3',4':4,5][1,2,8]thiadiazacycloundecino[6,7,8-
hi]indole-8-carboxylic acid-N-ethylethanamine salt
(enantiomer 1) and 4-chloro-3-ethyl-7-{3-[(6-fluoronaphthalen-1-yl)oxy]pro-
pyl}-2,14-dimethyl-15-[2-(morpholin-4-yl)ethyl]-13,13-
dioxo-10,11,12,13,14,15-hexahydro-2H-13lambda$^6$-
pyrazolo[3',4':4,5][1,2,8]thiadiazacycloundecino[6,7,8-
hi]indole-8-carboxylic acid-N-ethylethanamine salt
(enantiomer 2), wherein lambda$^6$ means A6;
or a tautomer, an N-oxide, or a salt thereof, or a salt of a
tautomer, or salt of an N-oxide, or a mixture of same.

In some embodiments, the present invention includes com-
pounds of general formula (I) selected from:

(rac)-4-chloro-14-cyclopropyl-3-ethyl-7-{3-[(6-fluoro-1-
naphthyl)oxy]propyl}-2-methyl-11,12,14,15-tetrahydro-
2H,10H-pyrazolo[3',4':4,5][1,2,8]thiadiazacycloundecino
[6,7,8-hi]indole-8-carboxylic acid 13,13-dioxide, (−)-4-chloro-14-cyclopropyl-3-ethyl-7-{3-[(6-fluoronaph-
thalen-1-yl)oxy]propyl}-2-methyl-13,13-dioxo-10,11,12,
13,14,15-hexahydro-2H-13lambda$^6$-pyrazolo[3',4':4,5][1,
2,8]thiadiazacycloundecino[6,7,8-hi]indole-8-carboxylic
acid N-ethylethanamine salt (enantiomer 1) and (+)-4-chloro-14-cyclopropyl-3-ethyl-7-{3-[(6-fluoronaph-
thalen-1-yl)oxy]propyl}-2-methyl-13,13-dioxo-10,11,12,
13,14,15-hexahydro-2H-13lambda$^6$-pyrazolo[3',4':4,5][1,
2,8]thiadiazacycloundecino[6,7,8-hi]indole-8-carboxylic
acid N-ethylethanamine salt (enantiomer 2), wherein lambda$^6$ means A6;
or a tautomer, an N-oxide, or a salt thereof, or a salt of a
tautomer, or salt of an N-oxide, or a mixture of same.

In some embodiments, the present invention includes compounds of general formula (I) selected from:

(rac)-4-chloro-14-cyclopropyl-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide, (−)-4-chloro-14-cyclopropyl-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide N-diethylamine salt (enantiomer 1), (+)-4-chloro-14-cyclopropyl-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide N-diethylamine salt (enantiomer 2), (rac)-2,3,14-trimethyl-15-[2-(morpholin-4-yl)ethyl]-7-[3-(1-naphthyloxy)propyl]-11,12,14,15-tetrahydro-2H,10H-pyrazolo[3',4':4,5][1,2,8]thiadiazacycloundecino[6,7,8-hi]indole-8-carboxylic acid 13,13-dioxide, 2,3,14-trimethyl-15-[2-(morpholin-4-yl)ethyl]-7-{3-[(naphthalen-1-yl)oxy]propyl}-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine salt (enantiomer 1), 2,3,14-trimethyl-15-[2-(morpholin-4-yl)ethyl]-7-{3-[(naphthalen-1-yl)oxy]propyl}-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine salt (enantiomer 2), (rac)4-chloro-3-ethyl-7-{3-[(6-fluoro-1-naphthyl)oxy]propyl}-2,14-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide, (rac)-15-chloro-14-ethyl-1-(3-((6-fluoronaphthalen-1-yl)oxy)propyl)-8,13-dimethyl-11-morpholino-5,6,9,10,11,13-hexahydro-4H,8H-pyrazolo[3',4':6,7][1]thia[2,10]diazacyclotridecino[8,9,10-hi]indole-2-carboxylic acid 7,7-dioxide, (+)-4-chloro-3-ethyl-7-{3-[(6-fluoro-1-naphthyl)oxy]propyl}-2,14-dimethyl-17-(morpholin-4-yl)-11,12,14,15,16,17-hexahydro-2H,10H-pyrazolo[3',4':6,7][1,2,10]thiadiazacyclotridecino[8,9,10-hi]indole-8-carboxylic acid 13,13-dioxide trifluoroacetate salt (enantiomer 1) and (−)-4-chloro-3-ethyl-7-{3-[(6-fluoro-1-naphthyl)oxy]propyl}-2,14-dimethyl-17-(morpholin-4-yl)-11,12,14,15,16,17-hexahydro-2H,10H-pyrazolo[3',4':6,7][1,2,10]thiadiazacyclotridecino[8,9,10-hi]indole-8-carboxylic acid 13,13-dioxide trifluoroacetate salt (enantiomer 2)

wherein lambda$^6$ means A6;
or a tautomer, an N-oxide, or a salt thereof, or a salt of a tautomer,
or salt of an N-oxide, or a mixture of same.

In some embodiments, the present invention includes compounds of general formula (I) selected from example 001 example 035, or a tautomer, an N-oxide, or a salt thereof, or a salt of a tautomer, or a salt of an N-oxide, or a mixture of same.

In some embodiments, the present invention includes compounds of general formula (I) selected from example 036 example 077, or a tautomer, an N-oxide, or a salt thereof, or a salt of a tautomer, or a salt of an N-oxide, or a mixture of same.

In some embodiments, the present invention includes compounds of general formula (I) selected from example 001 example 077, or a tautomer, an N-oxide, or a salt thereof, or a salt of a tautomer, or salt of an N-oxide, or a mixture of same.

In some embodiments, the present invention includes compounds of formula (I), supra, in which an aryl group can be a substituted or unsubstituted single-ring aromatic group in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls.

In some embodiments, the present invention includes compounds of formula (I), supra, in which a heterocyclyoalkyl group can be a 4- to 10-membered heterocycloalkyl group. Preferably, the heterocycloalkyl group is a 6-membered heterocycloalkyl group containing one or two heteroatoms selected from —O— and —N—. More preferably, the heterocycloalkyl group is a monocyclic heterocycloalkyl group and contains 5 carbon atoms and one heteroatom selected from —O— and —N—, particularly an oxygen atom. More preferably, the heterocycloalkyl group is a monocyclic heterocycloalkyl group and contains 4 carbon atoms and two heteroatoms selected from —O— and —N—, said two heteroatoms being preferably one oxygen atom and one nitrogen atom. More preferably, the heterocycloalkyl group is a tetrahydropyran group. More preferably, the heterocycloalkyl group is a morpholino group. Most preferably, the heterocycloalkyl group is a tetrahydropyran-4-yl group. Most preferably, the heterocycloalkyl group is a morpholin-4-yl group.

In some embodiments, the present invention includes compounds of formula (I), supra, in which $R^1$ and $R^2$ are each selected from a hydrogen atom, a halogen atom, a cyano group, a $C_1$-$C_3$-alkoxy group and a $C_1$-$C_3$-alkyl group, or a tautomer, an N-oxide, or a salt thereof, or a salt of a tautomer, or salt of an N-oxide, or a mixture of same.

In some embodiments, the present invention includes compounds of formula (I), supra, in which $R^1$ and $R^2$ are each selected from a hydrogen atom, a halogen atom, a cyano group and a $C_1$-$C_3$-alkyl group, or a tautomer, an N-oxide, or a salt thereof, or a salt of a tautomer, or salt of an N-oxide, or a mixture of same.

In some embodiments, the present invention includes compounds of formula (I), supra, in which $R^1$ and $R^2$ are each selected from a hydrogen atom, a halogen atom and a $C_1$-$C_3$-alkyl group, or a tautomer, an N-oxide, or a salt thereof, or a salt of a tautomer, or salt of an N-oxide, or a mixture of same.

In some embodiments, the present invention includes compounds of formula (I), supra, in which $R^1$ and $R^2$ are each selected from a hydrogen atom and a halogen atom, or a tautomer, an N-oxide, or a salt thereof, or a salt of a tautomer, or salt of an N-oxide, or a mixture of same.

In some embodiments, the present invention includes compounds of formula (I), supra, in which $R^1$ and $R^2$ are each selected from a hydrogen atom, a fluorine atom and a chlorine atom, or a tautomer, an N-oxide, or a salt thereof, or a salt of a tautomer, or salt of an N-oxide, or a mixture of same.

In some embodiments, the present invention includes compounds of formula (I), supra, in which $R^1$, $R^2$, and $R^3$ are each selected from a hydrogen atom and a halogen atom, or a tautomer, an N-oxide, or a salt thereof, or a salt of a tautomer, or salt of an N-oxide, or a mixture of same.

In some embodiments, the present invention includes compounds of formula (I), supra, in which $R^1$ and $R^2$ are each a hydrogen atom, or a tautomer, an N-oxide, or a salt thereof, or a salt of a tautomer, or salt of an N-oxide, or a mixture of same.

In some embodiments, the present invention includes compounds of formula (I), supra, in which $R^1$ is a hydrogen atom, or a tautomer, an N-oxide, or a salt thereof, or a salt of a tautomer, or salt of an N-oxide, or a mixture of same.

In some embodiments, the present invention includes compounds of formula (I), supra, in which $R^1$ is a hydrogen atom and $R^2$ is a halogen atom, or a tautomer, an N-oxide, or a salt thereof, or a salt of a tautomer, or salt of an N-oxide, or a mixture of same.

In some embodiments, the present invention includes compounds of formula (I), supra, in which $R^2$ is a hydrogen atom, or a tautomer, an N-oxide, or a salt thereof, or a salt of a tautomer, or salt of an N-oxide, or a mixture of same.

In some embodiments, the present invention includes compounds of formula (I), supra, in which $R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, a $C_1$-$C_3$-haloalkoxy group, a $C_1$-$C_3$-haloalkylthio group and a $C_3$-$C_5$-cycloalkyl group, or a tautomer, an N-oxide, or a salt thereof, or a salt of a tautomer, or a salt of an N-oxide, or a mixture of same.

In some embodiments, the present invention includes compounds of formula (I), supra, in which $R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a $C_1$-$C_3$-haloalkoxy group, a $C_1$-$C_3$-haloalkylthio group, and a $C_3$-$C_5$-cycloalkyl group, or a tautomer, an N-oxide, or a salt thereof, or a salt of a tautomer, or a salt of an N-oxide, or a mixture of same.

In some embodiments, the present invention includes compounds of formula (I), supra, in which $R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group, or a tautomer, an N-oxide, or a salt thereof, or a salt of a tautomer, or salt of an N-oxide, or a mixture of same.

In some embodiments, the present invention includes compounds of formula (I), supra, in which $R^3$ is a hydrogen atom or a tautomer, an N-oxide, or a salt thereof, or a salt of a tautomer, or salt of an N-oxide, or a mixture of same.

In some embodiments, the present invention includes compounds of formula (I), supra, in which $R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S— group and a $C_3$-$C_5$-cycloalkyl group, or a tautomer, an N-oxide, or a salt thereof, or a salt of a tautomer or salt of an N-oxide or a mixture of same.

In some embodiments, the present invention includes compounds of formula (I), supra, in which $R^4$ is an aryl group and a heteroaryl group, each of which is unsubstituted or substituted with one, two, or three substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group, or a tautomer, an N-oxide, or a salt thereof, or a salt of a tautomer, or a salt of an N-oxide, or a mixture of same.

In other embodiments, the present invention includes compounds of formula (I), supra, in which $R^4$ is selected from an aryl group and a heteroaryl group, each of which is unsubstituted or substituted with one, two, or three, substituents and each substituent is independently selected from a halogen atom and a $C_1$-$C_3$-alkyl group, or a tautomer, an N-oxide, or a salt thereof, or a salt of a tautomer, or a salt of an N-oxide, or a mixture of same.

In other embodiments, the present invention includes compounds of formula (I), supra, in which $R^4$ is an aryl group or a heteroaryl group, which is unsubstituted or substituted with one, two, or three, substituents and each substituent is independently selected from a halogen atom and a $C_1$-$C_3$-alkyl group, or a tautomer, an N-oxide, or a salt thereof, or a salt of a tautomer, or a salt of an N-oxide, or a mixture of same.

In other embodiments, the present invention provides compounds of formula (I), supra, in which $R^4$ is an aryl group which is unsubstituted or substituted with one, two, or three, substituents and each substituent is independently selected from a halogen atom and a $C_1$-$C_3$-alkyl group, or a tautomer, an N-oxide, or a salt thereof, or a salt of a tautomer, or a salt of an N-oxide, or a mixture of same.

In other embodiments, the present invention includes compounds of formula (I), supra, in which $R^4$ is a group selected from a naphthalene-1-yl group, a 6-fluoro-naphthalene-1-yl group, a 4-fluoro-naphthalin-1-yl group, a (5,6,7,8-tetrahydronaphthalen-1-yl) group, a 2,3-dihydro-1H-inden-4-yl group, and a 4-chloro-3,5-dimethylphen-1-yl, or a tautomer, an N-oxide, or a salt thereof, or a salt of a tautomer, or a salt of an N-oxide, or a mixture of same.

In other embodiments, the present invention includes compounds of formula (I), supra, in which $R^4$ is selected from a phenyl group, a naphthyl group, and a 5,6,7,8-tetrahydronaphthyl group, each of which are optionally substituted with one, two or three substituents, and each substituent independently selected from a halogen atom and a $C_1$-$C_3$-alkyl group, or a tautomer, an N-oxide, or a salt thereof, or a salt of a tautomer, or a salt of an N-oxide, or a mixture of same.

In other embodiments, the present invention includes compounds of formula (I), supra, in which $R^4$ is selected from a phenyl group, a naphthyl group, a 5,6,7,8-tetrahydronaphthyl group and an indenyl group, each of which are optionally substituted with one, two or three substituents, and each substituent independently selected from a halogen atom, more particularly a fluorine atom or a chlorine atom, and a $C_1$-$C_3$-alkyl group, more particularly a methyl group, or a tautomer, an N-oxide, or a salt thereof, or a salt of a tautomer, or a salt of an N-oxide, or a mixture of same.

In other embodiments, the present invention includes compounds of formula (I), supra, in which $R^4$ has one, two or three optional substituents, or a tautomer, an N-oxide, or a salt thereof or a salt of a tautomer or a salt of an N-oxide or a mixture of same.

In other embodiments, the present invention includes compounds of formula (I), supra, in which $R^4$ has one or two optional substituents, or a tautomer, an N-oxide, or a salt thereof, or a salt of a tautomer, or a salt of an N-oxide, or a mixture of same.

In other embodiments, the present invention includes compounds of formula (I), supra, in which $R^4$ has one optional substituent, or a tautomer, an N-oxide, or a salt thereof, or a salt of a tautomer, or a salt of an N-oxide, or a mixture of same.

In other embodiments, the present invention includes compounds of formula (I), supra, in which L is a group —(CH$_2$)$_m$-E- wherein any CH$_2$ group is unsubstituted or substituted with one or two substituents and each substituent is independently selected from a halogen atom, a cyano group, a hydroxyl group, a C$_1$-C$_3$-alkyl group, and a C$_1$-C$_3$-alkoxy group, or two substituents are optionally taken together with their intervening atoms to form a saturated or partially unsaturated 3-6-membered cycloalkyl ring, or a 3-8 membered saturated or partially unsaturated heterocyclic ring having 1-2 heteroatoms independently selected from an oxygen atom, a sulfur atom, a S(O)— group, a —S(O)$_2$— group and a —NR$^{14}$— group, or a tautomer, an N-oxide, or a salt thereof, or a salt of a tautomer, or a salt of an N-oxide, or a mixture of same.

In other embodiments, the present invention includes compounds of formula (I), supra, in which L is a group —(CH$_2$)$_m$-E- wherein any CH$_2$ group is unsubstituted or substituted with one or two substituents and each substituent is independently selected from a halogen atom, a cyano group, a hydroxyl group, a C$_1$-C$_3$alkyl group, and a C$_1$-C$_3$-alkoxy group, or a tautomer, an N-oxide, or a salt thereof, or a salt of a tautomer, or a salt of an N-oxide, or a mixture of same.

In other embodiments, the present invention includes compounds of formula (I), supra, in which L is a —(CH$_2$)$_m$-E- group which is optionally substituted with a C$_1$-C$_3$-alkyl group, particularly with a methyl group, or a tautomer, an N-oxide, or a salt thereof, or a salt of a tautomer, or a salt of an N-oxide, or a mixture of same.

In other embodiments, the present invention includes compounds of formula (I), supra, in which L is an unsubstituted group —(CH$_2$)$_m$-E-, or a tautomer, an N-oxide, or a salt thereof, or a salt of a tautomer, or a salt of an N-oxide, or a mixture of same.

In further embodiments the present invention includes compounds of formula (I), supra, in which E is an oxygen atom, or a tautomer, an N-oxide, or a salt thereof, or a salt of a tautomer, or a salt of an N-oxide, or a mixture of same.

In other embodiments, the present invention includes compounds of formula (I), supra, in which L is a —(CH$_2$)$_m$-E- group which is optionally substituted with a C$_1$-C$_3$-alkyl group, particularly with a methyl group, and E is a oxygen atom, or a tautomer, an N-oxide, or a salt thereof, or a salt of a tautomer, or a salt of an N-oxide, or a mixture of same.

In other embodiments, the present invention includes compounds of formula (I), supra, in which L is an unsubstituted group —(CH$_2$)$_m$-E- and E is an oxygen atom, or a tautomer, an N-oxide, or a salt thereof, or a salt of a tautomer, or a salt of an N-oxide, or a mixture of same.

In yet further embodiments, the present invention includes compounds of formula (I), supra, in which R$^5$ is selected from a COOH group, a

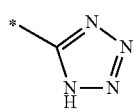

group, a —C(O)—NHS(O)$_2$(C$_1$-C$_6$-alkyl) group, a —C(O)—NHS(O)$_2$(C$_3$-C$_6$-cycloalkyl) group, a —C(O)—NHS(O)$_2$(aryl) group, a —C(O)—NHS(O)$_2$(CH$_2$)$_s$NHCO(C$_1$-C$_6$-alkyl) group, a —C(O)—NHS(O)$_2$(CH$_2$)$_s$NHCO(C$_3$-C$_6$-cycloalkyl) group and a —C(O)—NHS(O)$_2$(CH$_2$)$_s$NHCO(aryl) group, or a tautomer, an N-oxide, or a salt thereof, or a salt of a tautomer, or a salt of an N-oxide, or a mixture of same.

In further embodiments, the present invention includes compounds of formula (I), supra, in R$^5$ is selected from a COOH group and or a

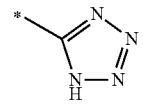

group, or a tautomer, an N-oxide, or a salt thereof, or a salt of a tautomer, or a salt of an N-oxide, or a mixture of same.

In further embodiments, the present invention includes compounds of formula (I), supra, in R$^5$ is a COOH group, or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is $^{\#}$—(CH$_2$)$_n$—(B)$_t$—(CH$_2$)$_p$—$^{\#\#}$, wherein any —CH$_2$— group is unsubstituted or substituted with one or more substituents independently selected from a halogen atom, a hydroxyl group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, and a (heterocycloalkyl)-(C$_1$-C$_3$-alkylene)- group, and where a double bond in any alkenylene can be replaced by a 1,2-cyclopropyl group, and said 1,2-cyclopropyl group is unsubstituted or substituted one or two times with a halogen atom or a C$_1$-C$_2$-alkyl group, wherein $^{\#}$ is the point of attachment with the indole nitrogen atom and $^{\#\#}$ is the point of attachment with the pyrazole carbon atom bearing the R$^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —R$^6$-R$^7$— is $^{\#}$—(CH$_2$)$_n$—(B)$_t$—(CH$_2$)$_p$—$^{\#\#}$, wherein any —CH$_2$— group is unsubstituted or substituted with one or more substituents independently selected from a halogen atom, a hydroxyl group, a NR$^{16}$R$^{17}$ group, a C$_1$-C$_3$-alkyl group, a C$_1$-C$_3$-haloalkyl group, a C$_1$-C$_3$-alkoxy group, a C$_1$-C$_3$-haloalkoxy group, a heterocycloalkyl group and a (heterocycloalkyl)-(C$_1$-C$_3$alkylene)- group, and where a double bond in any alkenylene can be replaced by a 1,2-cyclopropyl group, and said 1,2-cyclopropyl group is unsubstituted or substituted one or two times with a halogen atom or a C$_1$-C$_2$-alkyl group, wherein $^{\#}$ is the point of attachment with the indole nitrogen atom and $^{\#\#}$ is the point of attachment with the pyrazole carbon atom bearing the R$^7$ substituent, or a tautomer, an N-oxide, or a salt thereof, or a salt of a tautomer, or a salt of an N-oxide, or a mixture of same.

In further embodiments, the present invention includes compounds of formula (I), supra, in which —R$^6$-R$^7$— is $^{\#}$—(CH$_2$)$_n$—(B)$_t$—(CH$_2$)$_p$—$^{\#\#}$, wherein any —CH$_2$— group is unsubstituted or substituted with one or more substituents selected from a halogen atom, a hydroxyl group, a NR$^{16}$R$^{17}$ group, a C$_1$-C$_3$-alkyl group, a C$_1$-C$_3$-haloalkyl group and a C$_1$-C$_3$-alkoxy group, wherein $^{\#}$ is the point of attachment with the indole nitrogen atom and $^{\#\#}$ is the point of attachment with the pyrazole carbon atom bearing the R$^7$ substituent, or a tautomer, an N-oxide, or a salt thereof, or a salt of a tautomer, or a salt of an N-oxide or a mixture of same.

In further embodiments, the present invention includes compounds of formula (I), supra, in which —$R^6$-$R^7$— is $^\#$—$(CH_2)_n$—$(B)_t$—$(CH_2)_p$—$^{\#\#}$, wherein any —$CH_2$— group is unsubstituted or substituted with one or more substituents selected from a halogen atom, a hydroxyl group, a $NR^{16}R^{17}$ group, a $C_1$-$C_3$-alkyl group, a $C_1$-$C_3$-haloalkyl group, a heterocycloalkyl group and a $C_1$-$C_3$-alkoxy group, wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In further embodiments, the present invention includes compounds of formula (I), supra, in which —$R^6$-$R^7$— is $^\#$—$(CH_2)_n$—$(B)_t$—$(CH_2)_p$—$^{\#\#}$, wherein any —$CH_2$— group is unsubstituted or substituted with a heterocycloalkyl group, wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_n$—$(B)_t$—$(CH_2)_p$—$^{\#\#}$, wherein any —$CH_2$— group is unsubstituted and wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_n$—$S(O)_2NR^{15}$—$(CH_2)_p$—$^{\#\#}$ wherein any —$CH_2$— group is unsubstituted and wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^\#$—$(CH_2)_3$—$SO_2$—$NH$—$CH_2$—$^{\#\#}$, $^\#$—$(CH_2)_3$—$SO_2$—$N(CH_3)$—$CH_2$—$^{\#\#}$, $^\#$—$(CH_2)_3$—$SO_2$—$N[(CH_2CH_2)$-morpholino]-$CH_2$—$^{190\,\#}$, $^\#$—$(CH_2)_3$—$SO_2$—$N[(CH_2)_3$-morpholino]-$CH_2$-—$^{\#\#}$, $^\#$—$(CH_2)_3$—$SO_2$—$N[(CH_2)_3$-pyrrolidin-1-yl]-$CH_2$—$^{\#\#}$, $^\#$—$(CH_2)_3$—$SO_2$—$N[(CH_2)_3$-(2-oxopyrrolidin-1-yl)]-$CH_2$—$^{\#\#}$, $^\#$—$(CH_2)_3$—$SO_2$—$N[(CH_2)_3$-piperidin-1-yl]-$CH_2$-—$^{\#\#}$, and wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^\#$—$(CH_2)_3$—$SO_2$—$NH$—$CH_2$—$^{\#\#}$, $^\#$—$(CH_2)_3$—$SO_2$—$N(CH_3)$—$CH_2$—$^{\#\#}$, $^\#$—$(CH_2)_3$—$SO_2$—$N(CH_2CH_3)$—$CH_2$—$^{190\,\#}$, $^\#$—$(CH_2)_3$—$SO_2$—$N[(CH_2)_2$-morpholino]-$CH_2$—$^{\#\#}$, $^\#$—$(CH_2)_3$—$SO_2$—$N[(CH_2)_3$-morpholino]-$CH_2$—$^{\#\#}$, $^\#$—$(CH_2)_3$—$SO_2$—$N[(CH_2)_3$-pyrrolidin-1-yl]-$CH_2$—$^{\#\#}$, $^\#$—$(CH_2)_3$—$SO_2$—$N[(CH_2)_3$-(2-oxopyrrolidin-1-yl)]-$CH_2$—$^{\#\#}$, $^\#$—$(CH_2)_3$—$SO_2$—$N[(CH_2)_3$-piperidin-1-yl]-$CH_2$—$^{\#\#}$, $^\#$—$(CH_2)_3$—$SO_2$—$N(CH_3)$—$(CH_2)_2$—$CH$(morpholin-4-yl)-$^{\#\#}$, $^\#$—$(CH_2)_3$—$SO_2$—$N(CH_3)$—$CH[(CH_2)_2$(morpholin-4-yl)]-$^{\#\#}$, and $^\#$—$(CH_2)_3$—$SO_2$—$N(CH_3)$—$CH[(CH_2)_2$(tetrahydropyran-4-yl)]-$^{\#\#}$, and wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_3$—$SO_2$—$N(CH_3)$—$CH_2$—$^{\#\#}$ and wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_3$—$SO_2$—$N(CH_2CH_3)$—$CH_2$—$^{\#\#}$ and wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_3$—$SO_2$—$N(CH_3)$—$CH[(CH_2)_2$(morpholin-4-yl)]-$^{\#\#}$, and wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_3$—$SO_2$—$N(CH_2CH_3)$—$CH[(CH_2)_2$(morpholin-4-yl)]-$^{\#\#}$, and wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_3$—$SO_2$—$N(CH_3)$—$CH[(CH_2)_2$(tetrahydropyran-4-yl)]-$^{\#\#}$, and wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^\#$—$(CH_2)_3$—$SO_2$—$N(CH_3)$—$(CH_2)_2$—$CH$(morpholin-4-yl)-$^{\#\#}$, and wherein $^\#$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^\#$—$(CH_2)_3$—$SO_2$—$NH$—$CH_2$—$^{\#\#}$, $^\#$—$(CH_2)_3$—$SO_2$—$N(CH_3)$—$CH_2$—$^{\#\#}$, $^\#$—$(CH_2)_3$—$SO_2$—$N(CH_2CH_3)$—$CH_2$—$^{\#\#}$, $^\#$—$(CH_2)_3$—$SO_2$—$N[(CH_2)_2$-morpholino]-$CH_2$—$^{\#\#}$, $^\#$—$(CH_2)_3$—$SO_2$—$N[(CH_2)_3$-morpholino]-$CH_2$—$^{\#\#}$, $^\#$—$(CH_2)_3$—$SO_2$—$N[(CH_2)_3$-pyrrolidin-1-yl]-$CH_2$—$^{\#\#}$, $^\#$—$(CH_2)_3$—$SO_2$—$N[(CH_2)_3$-(2-oxopyrrolidin-1-yl)]-$CH_2$—$^{\#\#}$, $^\#$—$(CH_2)_3$—$SO_2$—$N[(CH_2)_3$-piperidin-1-yl]-$CH_2$—$^{\#\#}$, and $^\#$—$(CH_2)_3$—$SO_2$—$N(CH_3)$—$(CH_2)_2$—$CH$(morpholin-4-yl)-$^{\#\#}$ and wherein $^\#$ is the point of attachment with the indole nitrogen atom and $^{\#\#}$ is the point of attachment with the pyrazole carbon atom bearing the $R^7$ substituent;
$R^8$ is a $C_1$-$C_3$-alkyl group;
$R^9$ is a $C_1$-$C_3$-alkyl group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^{\#}$—$(CH_2)_3$—$SO_2$—NH—$CH_2$—$^{\#\#}$, $^{\#}$—$(CH_2)_3$—$SO_2$—$N(CH_3)$—$CH_2$—$^{\#\#}$, $^{\#}$—$(CH_2)_3$—$SO_2$—$N(CH_2CH_3)$—$CH_2$—$^{\#\#}$, $^{\#}$—$(CH_2)_3$—$SO_2$—$N[(CH_2)_2$-morpholino]-$CH_2$—$^{\#\#}$, $^{\#}$—$(CH_2)_3$—$SO_2$—$N[(CH_2)_2$-morpholino]-$CH_2$—$^{\#\#}$, $^{\#}$—$(CH_2)_3$—$SO_2$—$N[(CH_2)_3$-pyrrolidin-1-yl]-$CH_2$—$^{\#\#}$, $^{\#}$—$(CH_2)_3$—$SO_2$—$N[(CH_2)_3$-(2-oxopyrrolidin-1-yl)]-$CH_2$—$^{\#\#}$, $^{\#}$—$(CH_2)_3$—$SO_2$—$N[(CH_2)_3$-piperidin-1-yl]-$CH_2$—$^{\#\#}$, and $^{\#}$—$(CH_2)_3$—$SO_2$—$N(CH_3)$—$(CH_2)_2$—CH(morpholin-4-yl)-$^{\#\#}$ and wherein $^{\#}$ is the point of attachment with the indole nitrogen atom and $^{\#\#}$ is the point of attachment with the pyrazole carbon atom bearing the $R^7$ substituent;
$R^8$ is selected from a methyl group and an ethyl group;
$R^9$ is selected from a methyl group and an ethyl group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^{\#}$—$(CH_2)_3$—$SO_2$—NH—$CH_2$—$^{\#\#}$, $^{\#}$—$(CH_2)_3$—$SO_2$—$N(CH_3)$—$CH_2$—$^{\#\#}$, $^{\#}$—$(CH_2)_3$—$SO_2$—$N(CH_2CH_3)$—$CH_2$—$^{\#\#}$, $^{\#}$—$(CH_2)_3$—$SO_2$—$N[(CH_2)_2$-morpholino]-$CH_2$—$^{\#\#}$, $^{\#}$—$(CH_2)_3$—$SO_2$—$N[(CH_2)_2$-morpholino]-$CH_2$—$^{\#\#}$, $^{\#}$—$(CH_2)_3$—$SO_2$—$N[(CH_2)_3$-pyrrolidin-1-yl]-$CH_2$—$^{\#\#}$, $^{\#}$—$(CH_2)_3$—$SO_2$—$N[(CH_2)_3$-(2-oxopyrrolidin-1-yl)]-$CH_2$—$^{\#\#}$, $^{\#}$—$(CH_2)_3$—$SO_2$—$N[(CH_2)_3$-piperidin-1-yl]-$CH_2$—$^{\#\#}$, and $^{\#}$—$(CH_2)_3$—$SO_2$—$N(CH_3)$—$(CH_2)_2$—CH(morpholin-4-yl)-$^{\#\#}$ and wherein $^{\#}$ is the point of attachment with the indole nitrogen atom and $^{\#\#}$ is the point of attachment with the pyrazole carbon atom bearing the $R^7$ substituent;
$R^8$ is a methyl group;
$R^9$ is an ethyl group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—$(CH_2)_3$—$SO_2$—$N(CH_3)$—$CH_2$—$^{\#\#}$ and wherein $^{\#}$ is the point of attachment with the indole nitrogen atom and $^{\#\#}$ is the point of attachment with the pyrazole carbon atom bearing the $R^7$ substituent;
$R^8$ is a methyl group;
$R^9$ is an ethyl group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—$(CH_2)_3$—$SO_2$—$N(CH_2CH_3)$—$CH_2$—$^{\#\#}$ and wherein $^{\#}$ is the point of attachment with the indole nitrogen atom and $^{\#\#}$ is the point of attachment with the pyrazole carbon atom bearing the $R^7$ substituent;
$R^8$ is a methyl group;
$R^9$ is an ethyl group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—$(CH_2)_3$—$SO_2$—$N(CH_3)$—CH[$(CH_2)_2$(morpholin-4-yl)]-$^{\#\#}$ and wherein $^{\#}$ is the point of attachment with the indole nitrogen atom and $^{\#\#}$ is the point of attachment with the pyrazole carbon atom bearing the $R^7$ substituent;
$R^8$ is a $C_1$-$C_3$-alkyl group;
$R^9$ is a $C_1$-$C_3$-alkyl group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—$(CH_2)_3$—$SO_2$—$N(CH_3)$—CH[$(CH_2)_2$(morpholin-4-yl)]-$^{\#\#}$ and wherein $^{\#}$ is the point of attachment with the indole nitrogen atom and $^{\#\#}$ is the point of attachment with the pyrazole carbon atom bearing the $R^7$ substituent;
$R^8$ is a methyl group;
$R^9$ is a methyl group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—$(CH_2)_3$—$SO_2$—$N(CH_3)$—CH[$(CH_2)_2$(morpholin-4-yl)]-$^{\#\#}$ and wherein $^{\#}$ is the point of attachment with the indole nitrogen atom and $^{\#\#}$ is the point of attachment with the pyrazole carbon atom bearing the $R^7$ substituent;
$R^8$ is a methyl group;
$R^9$ is an ethyl group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—$(CH_2)_3$—$SO_2$—$N(CH_3)$—CH[$(CH_2)_2$(tetrahydropyran-4-yl)]-$^{\#\#}$ and wherein $^{\#}$ is the point of attachment with the indole nitrogen atom and $^{\#\#}$ is the point of attachment with the pyrazole carbon atom bearing the $R^7$ substituent;
$R^8$ is a methyl group;
$R^9$ is an ethyl group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^{10}$— is $^{\#}$—$(CH_2)_n$—$(B)_t$—$(CH_2)_p$—$^{\#\#}$, where one or more $CH_2$ groups are unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group and a (heterocycloalkyl)-($C_1$-$C_3$-alkylene)- group, wherein $^{\#}$ is the point of attachment with the indole nitrogen atom and $^{\#\#}$ is the point of attachment with the carbon atom of the phenyl moiety bearing the $R^{10}$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^{10}$— is $^{\#}$—$(CH_2)_n$—$(B)_t$—$(CH_2)_p$—$^{\#\#}$, where one or more $CH_2$ groups are unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, wherein $^{\#}$ is the point of attachment with the indole nitrogen atom and $^{\#\#}$ is the point of attachment with the carbon atom of the phenyl moiety bearing the $R^{10}$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—$(CH_2)_n$—$(B)_t$—$CR^{22}R^{23}$—$^{\#\#}$ or $^{\#}$—$(C_2$-$C_9$-alkenylene)-$(B)_t$—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent; and
wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$alkylene)-group, or a tautomer, an N-oxide, or a salt thereof, or a salt of a tautomer, or a salt of an N-oxide, or a mixture of same.

In further embodiments, the present invention includes compounds of formula (I), supra, in which —$R^6$-$R^7$— is $^{\#}$—($CH_2$)$_n$—(B)$_t$—$CR^{22}R^{23}$—$^{\#\#}$ or $^{\#}$—($C_2$-$C_9$-alkenylene)-(B)$_t$—$CR^{22}R^{23}$—$^{\#\#}$,
wherein $^{\#}$ is the point of attachment with the indole nitrogen atom and $^{\#\#}$ is the point of attachment with the pyrazole carbon atom bearing the $R^7$ substituent; and
wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—($CH_2$)$_n$—(B)$_t$—$CR^{22}R^{23}$—$^{\#\#}$ or $^{\#}$—($C_2$-$C_9$-alkenylene)-(B)$_t$—$CR^{22}R^{23}$—$^{\#\#}$,
wherein $^{\#}$ is the point of attachment with the indole nitrogen atom and $^{\#\#}$ is the point of attachment with the pyrazole carbon atom bearing the $R^7$ substituent; and
wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group;
or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—($CH_2$)$_n$—(B)$_t$—$CR^{22}R^{23}$—$^{\#\#}$ or $^{\#}$—($C_2$-$C_9$-alkenylene)-(B)$_t$—$CR^{22}R^{23}$—$^{\#\#}$,
wherein $^{\#}$ is the point of attachment with the indole nitrogen atom and $^{\#\#}$ is the point of attachment with the pyrazole carbon atom bearing the $R^7$ substituent; and
wherein one or more —$CH_2$— groups may be unsubstituted or substituted with one or more substituents independently selected from a halogen atom, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—($CH_2$)$_n$—(B)$_t$—$CR^{22}R^{23}$—$^{\#\#}$ or $^{\#}$—($C_2$-$C_9$-alkenylene)-(B)$_t$—$CR^{22}R^{23}$—$^{\#\#}$,
wherein $^{\#}$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—($CH_2$)$_n$—(B)$_t$—$CR^{22}R^{23}$—$^{\#\#}$ or $^{\#}$—($C_2$-$C_9$-alkenylene)-(B)$_t$—$CR^{22}R^{23}$—$^{\#\#}$,
wherein $^{\#}$ is the point of attachment with the indole nitrogen atom and $^{\#\#}$ is the point of attachment with the pyrazole carbon atom bearing the $R^7$ substituent, and wherein one or more —$CH_2$— groups may be unsubstituted or substituted with one or more substituents independently selected from a halogen atom, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—($CH_2$)$_4$—O—$CR^{22}R^{23}$—$^{\#\#}$ wherein $^{\#}$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—($C_2$-$C_9$-alkenylene)-(B)$_t$—$CR^{22}R^{23}$—$^{\#\#}$,
wherein $^{\#}$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—($C_2$-$C_9$-alkenylene)-(B)$_t$—$CR^{22}R^{23}$—$^{\#\#}$,
wherein $^{\#}$ is the point of attachment with the indole nitrogen atom and $^{\#\#}$ is the point of attachment with the pyrazole carbon atom bearing the $R^7$ substituent, and wherein one or more —$CH_2$— groups may be unsubstituted or substituted with one or more substituents independently selected from a halogen atom, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—($CH_2$)$_4$—N($R^{15}$)—$CR^{22}R^{23}$—$^{\#\#}$ wherein $^{\#}$ is the point of attachment with the indole nitrogen atom and $^{\#\#}$ is the point of attachment with the pyrazole carbon atom bearing the $R^7$ substituent, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is $^{\#}$—($CH_2$)$_4$—N($R^{15}$)—$CR^{22}R^{23}$—$^{\#\#}$, wherein $^{\#}$ is the point of attachment with the indole nitrogen atom and $^{\#\#}$ is the point of attachment with the pyrazole carbon atom bearing the $R^7$ substituent, and wherein one or more —$CH_2$— groups may be unsubstituted or substituted with one or more substituents independently selected from a halogen atom, or a tautomer, an N-oxide, or a salt thereof, or a salt of a tautomer, or a salt of an N-oxide, or a mixture of same.

In other embodiments, the present invention includes compounds of formula (I), supra, in which —$R^6$-$R^7$— is selected from $^{\#}$—($CH_2$)$_4$—O—$CH(CH_3)$—$^{\#}$, $^{\#}$—($CH_2$)$_4$—O—$CH[(CH_2)_2$-morpholino]-$^{\#\#}$, $^{\#}$—($CH_2$)$_4$—O—$CH[(CH_2)_2$—N-methylpiperazino]—$^{\#\#}$, $^{\#}$—($CH_2$)$_4$—O—$CH[(CH_2)_2$-pyrrolidino]—$^{\#\#}$, $^{\#}$—($CH_2$)$_4$—O—$CH[(CH_2)_2$-cyclopropyl]-$^{\#\#}$, $^{\#}$—($CH_2$)$_4$—O—$CH$(cyclopropyl)-$^{\#\#}$, $^{\#}$—($CH_2$)$_4$—O—$CH[(CH_2)_2$—O—$CH_3$]—$^{\#\#}$, $^{\#}$—($CH_2$)$_4$—O—$CH[(CH_2)_2$—OH]—$^{\#\#}$, $^{\#}$—($CH_2$)$_4$—O—$CH(CH_2CH_3)$—$^{\#\#}$, and $^{\#}$—($CH_2$)$_4$—O—$CH(CF_3)$—$^{\#\#}$, and wherein $^{\#}$ is the point of attachment with the indole nitrogen atom and $^{\#\#}$ is the point of attachment with the pyrazole carbon atom bearing the $R^7$ substituent, or a tautomer, or a salt thereof, or a salt of a tautomer, or a mixture of same.

In other embodiments, the present invention includes compounds of formula (I), supra, in which —$R^6$-$R^7$— is selected from $^{\#}$—($CH_2$)$_4$—O—$CH(CH_3)$—$^{\#\#}$, $^{\#}$—($CH_2$)$_4$—

O—CH[(CH$_2$)$_2$-morpholino]-##, #—(CH$_2$)$_4$—O—CH(cyclopropyl)-##, #—(CH$_2$)$_4$—O—CH[(CH$_2$)$_2$—OH]—##, #—(CH$_2$)$_4$—O—CH(CH$_2$CH$_3$)—##, and #—(CH$_2$)$_4$—O—CH(CF$_3$)—##, and wherein # is the point of attachment with the indole nitrogen atom and ## is the point of attachment with the pyrazole carbon atom bearing the R$^7$ substituent, or a tautomer, or a salt thereof, or a salt of a tautomer, or a mixture of same.

In other embodiments, the present invention includes compounds of formula (I), supra, in which —R$^6$-R$^{10}$ is #—(CH$_2$)$_n$—(B)$_r$CR$^{22}$R$^{23}$—## or #—(C$_2$-C$_9$-alkenylene)-(B)$_t$—CR$^{22}$R$^{23}$—##, where one or more —CH$_2$— groups are substituted with one or more substituents independently selected from a halogen atom, a hydroxyl group, a NR$^{16}$R$^{17}$ group, a C$_1$-C$_3$-alkyl group, a C$_1$-C$_3$-haloalkyl group, a C$_1$-C$_3$-alkoxy group, and a C$_1$-C$_3$-haloalkoxy group, wherein # is the point of attachment with the indole nitrogen atom and ## is the point of attachment with the carbon atom of the phenyl moiety bearing the R$^{10}$ substituent;
or a tautomer, an N-oxide, or a salt thereof, or a salt of a tautomer, or a salt of an N-oxide, or a mixture of same.

In further embodiments, the present invention includes compounds of formula (I), supra, in which B is independently selected from a —S(O)NR$^{15}$— group, a —NR$^{15}$S(O)— group, a —S(O)$_2$NR$^{15}$— group, a —NR$^{15}$S(O)$_2$— group, or a tautomer, an N-oxide, or a salt thereof, or a salt of a tautomer, or a salt of an N-oxide, or a mixture of same.

In further embodiments, the present invention includes compounds of formula (I), supra, in which B is selected from a —S(O)$_2$NR$^{15}$— group and a —NR$^{15}$S(O)$_2$— group, or a tautomer, an N-oxide, or a salt thereof, or a salt of a tautomer, or a salt of an N-oxide, or a mixture of same.

In further embodiments, the present invention includes compounds of formula (I), supra, in which B is a —S(O)$_2$NR$^{15}$— group, or a tautomer, an N-oxide, or a salt thereof, or a salt of a tautomer, or a salt of an N-oxide, or a mixture of same.

In other embodiments, the present invention includes compounds of formula (I), supra, in which A is A1 or a tautomer, an N-oxide, or a salt thereof, or a salt of a tautomer, or a salt of an N-oxide, or a mixture of same.

In further embodiments, the present invention includes compounds of formula (I), supra, in which A is A2, or a tautomer, an N-oxide, or a salt thereof, or a salt of a tautomer, or a salt of an N-oxide, or a mixture of same.

In yet other embodiments, the present invention includes compounds of formula (I), supra, in which A is A3, or a tautomer, an N-oxide, or a salt thereof, or a salt of a tautomer, or a salt of an N-oxide, or a mixture of same.

In yet other embodiments, the present invention includes compounds of formula (I), supra, in which A is A3 and the macrocyclic ring is a 9-membered, a 10-membered, a 11-membered, a 12-membered, a 13-membered, a 14-membered, a 15-membered or a 16-membered ring, particularly a 9-membered, a 10-membered, a 11-membered, or a 12-membered ring, more particularly a 12-membered ring, or a tautomer, an N-oxide, or a salt thereof, or a salt of a tautomer, or a salt of an N-oxide, or a mixture of same.

In yet other embodiments, the present invention includes compounds of formula (I), supra, in which A is A3 whereby optionally one or two of the groups selected from CR$^{11}$, CR$^{12}$ or CR$^{13}$ may be replaced by a nitrogen atom, wherein R$^6$ and R$^{10}$, together with three carbon atoms of the phenyl ring, two carbon atoms of the indole moiety and the nitrogen atom to which R$^6$ is attached, form a 9- to 16-membered ring and * is the point of attachment of these moieties to the indole carbon atom bearing the A substituent; or a tautomer, an N-oxide, or a salt thereof, or a salt of a tautomer, or a salt of an N-oxide, or a mixture of same.

In yet other embodiments, the present invention includes compounds of formula (I), supra, in which A is A3 wherein R$^6$ and R$^{10}$, together with three carbon atoms of the phenyl ring, two carbon atoms of the indole moiety and the nitrogen atom to which R$^6$ is attached, form a 9- to 16-membered ring and * is the point of attachment of these moieties to the indole carbon atom bearing the A substituent; or a tautomer, an N-oxide, or a salt thereof, or a salt of a tautomer, or a salt of an N-oxide, or a mixture of same.

In yet other embodiments, the present invention includes compounds of formula (I), supra, in which A is A3 wherein R$^6$ and R$^{10}$, together with three carbon atoms of the phenyl ring, two carbon atoms of the indole moiety and the nitrogen atom to which R$^6$ is attached, form a 11- to 16-membered ring and * is the point of attachment of these moieties to the indole carbon atom bearing the A substituent; or a tautomer, an N-oxide, or a salt thereof, or a salt of a tautomer, or a salt of an N-oxide, or a mixture of same.

In yet other embodiments, the present invention includes compounds of formula (I), supra, in which A is A3 wherein R$^6$ and R$^{10}$, together with three carbon atoms of the phenyl ring, two carbon atoms of the indole moiety and the nitrogen atom to which R$^6$ is attached, form a 12-membered ring and * is the point of attachment of these moieties to the indole carbon atom bearing the A substituent; or a tautomer, an N-oxide, or a salt thereof, or a salt of a tautomer, or a salt of an N-oxide, or a mixture of same.

In further embodiments, the present invention includes compounds of formula (I), supra, in which A is A1 or A2, or a tautomer, an N-oxide, or a salt thereof, or a salt of a tautomer, or a salt of an N-oxide, or a mixture of same.

In other embodiments, the present invention includes compounds of formula (I), supra, in which A is A1 or A2 and the macrocyclic ring is a 9-membered, a 10-membered, a 11-membered, a 12-membered, a 13-membered, a 14-membered, a 15-membered or a 16-membered ring, particularly a 9- to 12-membered ring or a 12- or a 13-membered ring, more particularly a 10- to 12-membered ring, and even more particularly a 11-membered ring, or a tautomer, an N-oxide, or a salt thereof, or a salt of a tautomer, or a salt of an N-oxide, or a mixture of same.

In other embodiments, the present invention includes compounds of formula (I), supra, in which A is A1 or A2, which together with the indole moiety and the R$^6$-R$^7$ form a 9-membered, a 10-membered, a 11-membered or a 12-membered macrocyclic ring, or a tautomer, an N-oxide, or a salt thereof, or a salt of a tautomer, or a salt of an N-oxide, or a mixture of same.

In yet other embodiments, the present invention includes compounds of formula (I), supra, in which A is A1, which together with the indole moiety and the R$^6$-R$^7$ form a 9-membered, a 10-membered, a 11-membered or a 12-membered macrocyclic ring, or a tautomer, an N-oxide, or a salt thereof, or a salt of a tautomer, or a salt of an N-oxide, or a mixture of same.

In yet other embodiments, the present invention includes compounds of formula (I), supra, in which A is A2, which together with the indole moiety and the R$^6$-R$^7$ form a 9-membered, a 10-membered, a 11-membered or a 12-membered macrocyclic ring, or a tautomer, an N-oxide, or a salt thereof, or a salt of a tautomer, or a salt of an N-oxide, or a mixture of same.

In yet other embodiments, the present invention includes compounds of formula (I), supra, in which A is A1 or A2, which together with the indole moiety and the R$^6$-R$^7$ form a 10-membered or a 11-membered macrocyclic ring, or a tautomer, an N-oxide, or a salt thereof, or a salt of a tautomer, or a salt of an N-oxide, or a mixture of same.

In particular embodiments, the present invention includes compounds of formula (I), supra, in which A is A1 or A2, which together with the indole moiety and the $R^6$-$R^7$ form a 11-membered macrocyclic ring, or a tautomer, an N-oxide, or a tautomer, an N-oxide, or a salt thereof, or a salt of a tautomer, or a salt of an N-oxide, or a mixture of same.

In yet other embodiments, the present invention includes compounds of formula (I), supra, in which A is A1 and $R^8$ and $R^9$ are $C_1$-$C_3$-alkyl, or a tautomer, an N-oxide, or a tautomer, an N-oxide, or a salt thereof, or a salt of a tautomer, or a salt of an N-oxide, or a mixture of same.

In still other embodiments, the present invention includes compounds of formula (I), supra, in which A is A2 and $R^8$ and $R^9$ are independently selected from $C_1$-$C_3$-alkyl, particularly from methyl or ethyl, or a tautomer, an N-oxide, or a tautomer, an N-oxide, or a salt thereof, or a salt of a tautomer, or a salt of an N-oxide, or a mixture of same.

The integers selected for variables n, s, t, and p may result in different ring sizes but still the rings obtained have to fulfill the rule that only rings of a ring size of 9 members up to a ring size of 16 members including 9 and 16 are encompassed.

In further embodiments, the present invention includes compounds of formula (I), supra, in which
n is 1, 2, 3, 4, 5, 6, 7, or 8;
s is 0, 1 or 2;
t is 1;
p is 1, 2, 3, 4, 5, 6, 7 or 8;
where the integers selected for variables n, t, and p, result in forming a 9- to 16-membered ring independently from the selection of variable A1, A2 or A3;
or a tautomer, an N-oxide, or a salt thereof, or a salt of a tautomer, or a salt of an N-oxide, or a mixture of same.

In further embodiments, the present invention includes compounds of formula (I), supra, in which
n is 1, 2, 3, 4, or 5;
t is 1;
p is 1, 2, 3, or 4;
where the integers selected for variables n, t, and p, result in forming a 9- to 13-membered ring independently from the selection of variable A1, or A2;
or a tautomer, an N-oxide, or a salt thereof, or a salt of a tautomer, or a salt of an N-oxide, or a mixture of same.

In further embodiments, the present invention includes compounds of formula (I), supra, in which
n is 2, 3 or 4;
t is 1;
p is 1, 2, or 3;
where the integers selected for variables n, t, and p, result in forming a 9- to 12-membered ring independently from the selection of variable A1 or A2;
or a tautomer, an N-oxide, or a salt thereof, or a salt of a tautomer, or a salt of an N-oxide, or a mixture of same.

In further embodiments, the present invention includes compounds of formula (I), supra, in which
n is 3;
t is 1;
p is 1;
where the integers selected for variables n, t, and p, result in forming a 11-membered ring independently from the selection of variable A1, or A2;
or a tautomer, an N-oxide, or a salt thereof, or a salt of a tautomer, or a salt of an N-oxide, or a mixture of same.

In further embodiments, the present invention includes compounds of formula (I), supra, in which
n is 3;
t is 1;
p is 3;
where the integers selected for variables n, t, and p, result in forming a 13-membered ring independently from the selection of variable A1 or A2;
or a tautomer, an N-oxide, or a salt thereof, or a salt of a tautomer, or a salt of an N-oxide, or a mixture of same.

The limitations relating to A1 and A2 are independent from the limitations relating to A3.

In further embodiments, the present invention includes compounds of formula (I), supra, in which
$R^8$ selected from a hydrogen atom,
a $C_1$-$C_6$-alkyl group, which is unsubstituted or substituted with one or more substituents independently selected from
a halogen atom, a hydroxyl group, a $C_1$-$C_3$-alkoxy group, a $C_1$-$C_3$-haloalkoxy group,
a $C_3$-$C_6$-cycloalkyl group, a heterocycloalkyl group, and a $NR^{20}R^{21}$ group, and
a $C_1$-$C_3$-haloalkyl group, a $C_3$-$C_6$-cycloalkyl group, or a $C_1$-$C_6$-alkyl group in which one or two not directly adjacent carbon atoms are independently replaced by a heteroatom independently selected from —O— and NH—,
or a tautomer, an N-oxide, or a salt thereof, or a salt of a tautomer, or a salt of an N-oxide, or a mixture of same.

In further embodiments, the present invention includes compounds of formula (I), supra, in which $R^8$ is selected from
a hydrogen atom,
a $C_1$-$C_6$-alkyl group which is unsubstituted or substituted with one or more substituents independently selected from
a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group, or a tautomer, an N-oxide, or a salt thereof, or a salt of a tautomer, or a salt of an N-oxide, or a mixture of same.

In further embodiments, the present invention includes compounds of formula (I), supra, in which $R^8$ is selected from
a hydrogen atom,
a $C_1$-$C_6$-alkyl group, which is unsubstituted or substituted with one or more substituents independently selected from
a halogen atom, a hydroxy group, a $C_3$-$C_6$-cycloalkyl group and a heterocycloalkyl group,
or a tautomer, an N-oxide, or a salt thereof, or a salt of a tautomer, or a salt of an N-oxide, or a mixture of same.

In further embodiments, the present invention includes compounds of formula (I), supra, in which $R^8$ is a $C_1$-$C_6$-alkyl group which is unsubstituted or substituted with a heterocycloalkyl group, or a tautomer, an N-oxide, or a salt thereof, or a salt of a tautomer, or a salt of an N-oxide, or a mixture of same.

In further embodiments, the present invention includes compounds of formula (I), supra, in which $R^8$ is a $C_1$-$C_6$-alkyl group, or a tautomer, an N-oxide, or a salt thereof, or a salt of a tautomer, or a salt of an N-oxide, or a mixture of same.

In further embodiments, the present invention includes compounds of formula (I), supra, in which
   $R^8$ is selected from a $C_1$-$C_3$-alkyl group, or a tautomer, an N-oxide, or a salt thereof, or a salt of a tautomer, or a salt of an N-oxide, or a mixture of same.

In further embodiments, the present invention includes compounds of formula (I), supra, in which
   $R^8$ is selected from a methyl group, or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from
   a hydrogen atom,
   a $C_1$-$C_4$-alkyl group,
   a $C_1$-$C_3$-hydroxyalkyl group,
   a $C_1$-$C_4$-haloalkyl group,
   a $C_1$-$C_4$-haloalkyl-NH—C(O)—O—($C_1$-$C_3$-alkylene)- group,
   a $C_2$-$C_6$-haloalkenyl group,
   a $C_1$-$C_6$-alkyl-O— group,
   a $C_1$-$C_4$-haloalkoxy group,
   a $C_1$-$C_6$-alkyl-O—($C_1$-$C_3$-alkylene)- group,
   a ($C_3$-$C_7$)-cycloalkyl group,
   a ($C_3$-$C_7$)-cycloalkyl-O—($C_1$-$C_3$-alkylene)- group,
   a phenyl-O—($C_1$-$C_3$-alkylene)- group,
   a phenyl-($C_1$-$C_3$-alkylene)-O—($C_1$-$C_3$-alkylene)- group,
   a $R^{18}$-(phenylene)-($C_1$-$C_3$-alkylene)-O—($C_1$-$C_3$-alkylene)- group,
   a $R^{18}$-(phenylene)-O—($C_1$-$C_3$-alkylene)- group,
   a $R^{18}$-(phenylene)-(heteroarylene)-O—($C_1$-$C_3$-alkylene) group,
   a ($R^{18}$)-(heterocycloalkylene)-($C_1$-$C_3$-alkylene)- group,
   a ($R^{18}$)-(heterocycloalkylene)-(phenylene)-O—($C_1$-$C_3$-alkylene)- group,
   a (heterocycloalkenyl)-(phenylene)-O—($C_1$-$C_3$-alkylene)- group,
   a ($R^{18}$)-(heteroarylene)-($C_1$-$C_3$-alkylene)-O—($C_1$-$C_3$-alkylene)- group,
   a ($R^{18}$)-(heteroarylene)-(phenylene)-O—($C_1$-$C_3$-alkylene)- group,
   a ($R^{19}$)—S(O)$_2$-(phenylene)-O—($C_1$-$C_3$-alkylene)- group,
   a ($R^{19}$)—S(O)$_2$—NH-(phenylene)-O—($C_1$-$C_3$-alkylene)- group,
   a ($R^{19}$)—S(O)$_2$—NH-(phenylene)-O—($C_1$-$C_3$-alkylene)- group,
   a ($R^{19}$)—S(O)$_2$—N($C_1$-$C_6$-alkyl)-(phenylene)-O—($C_1$-$C_3$-alkylene)- group,
   a ($R^{19}$)—S(O)$_2$-(heterocycloalkylene)-(phenylene)-O—($C_1$-$C_3$-alkylene)- group,
   a ($R^{18}$)-(heterocycloalkylene)-(heteroarylene)-O—($C_1$-$C_3$-alkylene)- group,
   a ($R^{19}$)-(heteroarylene)-O—($C_1$-$C_3$-alkylene)- group,
   a ($R^{18}$)-(heteroarylene)-O—($C_1$-$C_3$-alkylene)- group,
   a ($R^{19}$)—S(O)$_2$-(heteroarylene)-O—($C_1$-$C_3$-alkylene)- group,
   a ($R^{19}$)—S(O)$_2$-(heterocycloalkylene)-(heteroarylene)-O—($C_1$-$C_3$-alkylene)- group,
   a $NR^{20}R^{21}$—($C_1$-$C_3$-alkylene)- group,
   a ($C_1$-$C_3$-alkyl)-NH—($C_1$-$C_3$-alkylene)- group,
   a ($C_1$-$C_3$-haloalkyl)-($C_1$-$C_3$-alkylene)-NH—($C_1$-$C_3$-alkylene)- group,
   a ($C_1$-$C_3$-haloalkyl)-NH—($C_1$-$C_3$-alkylene)- group,
   a ($C_1$-$C_3$-alkyl)-NH—C(O)—($C_1$-$C_3$-alkylene)- group
   a ($C_1$-$C_3$-alkyl)-NR$^{15}$—C(O)—($C_1$-$C_3$-alkylene)- group
   a ($C_1$-$C_3$-alkyl)-C(O)—NH—($C_1$-$C_3$-alkylene)- group
   a ($C_1$-$C_3$-alkyl)-C(O)—NR$^{15}$—($C_1$-$C_3$-alkylene)- group,
   a

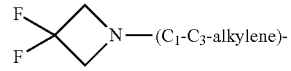

group, and a

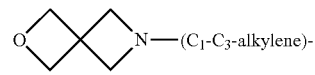

group, where the phenyl ring is unsubstituted or substituted with a halogen atom, a hydroxyl group, or a $C_1$-$C_3$-alkoxy group and
   the heterocycloalkyl group is unsubstituted or substituted with an oxo (=O) group or is unsubstituted or substituted with one or more substituents independently selected from a halogen atom, a hydroxyl group, a $C_1$-$C_3$-alkyl group and a $C_1$-$C_3$-alkoxy group,
or a tautomer, an N-oxide, or a salt thereof, or a salt of a tautomer, or a salt of an N-oxide, or a mixture of same.

In further embodiments, the present invention includes compounds of formula (I), supra, in which
   $R^9$ is selected from
   a hydrogen atom,
      a $C_1$-$C_4$-alkyl group,
      a $C_1$-$C_3$-hydroxyalkyl group,
      a $C_1$-$C_4$-haloalkyl group,
      a $C_1$-$C_4$-haloalkyl-NH—C(O)—O—($C_1$-$C_3$-alkylene)- group,
      a $C_2$-$C_6$-haloalkenyl group,
      a $C_1$-$C_6$-alkyl-O— group,
      a $C_1$-$C_4$-haloalkoxy group,
      a $C_1$-$C_6$-alkyl-O—($C_1$-$C_3$-alkylene)- group,
      a ($C_1$-$C_3$-alkyl)-NH—($C_1$-$C_3$-alkylene)- group,
      a ($C_3$-$C_7$)-cycloalkyl group, and
a ($C_3$-$C_7$)-cycloalkyl-O—($C_1$-$C_3$-alkylene)- group, or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from
a hydrogen atom,
   a $C_1$-$C_4$-alkyl group,
   a $C_1$-$C_3$-hydroxyalkyl group,
   a $C_1$-$C_4$-haloalkyl group,
   a $C_1$-$C_6$-alkyl-O— group,
   a $C_1$-$C_4$-haloalkoxy group, and
   a $C_1$-$C_6$-alkyl-O—($C_1$-$C_3$-alkylene)- group,
or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from
a hydrogen atom,
   a $C_1$-$C_4$-alkyl group,
and a $C_1$-$C_6$-alkyl-O—($C_1$-$C_3$-alkylene)- group, or a tautomer, an N-oxide, or a salt thereof, or a salt of a tautomer, or a salt of an N-oxide, or a mixture of same.

In further embodiments, the present invention includes compounds of formula (I), supra, in which $R^9$ is a $C_1$-$C_3$-alkyl group,
or a tautomer, an N-oxide, or a salt thereof, or a salt of a tautomer, or a salt of an N-oxide, or a mixture of same.

In further embodiments, the present invention includes compounds of formula (I), supra, in which $R^9$ is selected from a methyl group and an ethyl group, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 5- or 6-membered ring optionally containing one or two heteroatoms selected from —O—, and —NR$^{14}$—, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 5- or 6-membered ring optionally containing one or two oxygen atoms, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 6-membered ring optionally containing one or two oxygen atoms, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together form a 6-membered ring optionally containing one oxygen atom, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together are *—(CH$_2$—)$_3$—O—**, *—(CH$_2$)$_2$—O—CH$_2$—**, —(CH$_2$)$_4$—, where * means the point of attachment at the pyrazole nitrogen atom ($R^8$ site) and ** means the point of attachment to the carbon atom ($R^9$ site) of the pyrazole, or a tautomer, an N-oxide, or a salt thereof, or a salt of a tautomer, or a salt of an N-oxide, or a mixture of same.

In further embodiments, the present invention includes compounds of formula (I), supra, in which $R^8$ and $R^9$ together do not form a ring.

In further embodiments, the present invention includes compounds of formula (I), supra, in which $R^{11}$ and $R^{13}$ are each independently selected from a hydrogen atom, a halogen atom, a $C_1$-$C_3$-alkyl group, and a $C_1$-$C_3$-alkoxy group, or a tautomer, an N-oxide, or a salt thereof, or a salt of a tautomer, or a salt of an N-oxide, or a mixture of same.

In further embodiments, the present invention includes compounds of formula (I), supra, in which $R^{12}$ is selected from a hydrogen atom, a $C_1$-$C_3$-alkoxy group, a $C_1$-$C_3$-alkyl group, a $C_1$-$C_3$-haloalkyl group, a $C_1$-$C_3$-haloalkoxy group and a NR$^{16}$R$^{17}$ group, or a tautomer, an N-oxide, or a salt thereof, or a salt of a tautomer, or a salt of an N-oxide, or a mixture of same.

In further embodiments, the present invention includes compounds of formula (I), supra, in which $R^{12}$ is hydrogen or a methoxy group, or a tautomer, an N-oxide, or a salt thereof, or a salt of a tautomer, or a salt of an N-oxide, or a mixture of same.

In further embodiments, the present invention includes compounds of formula (I), supra, in which $R^{11}$ and $R^{13}$ are each independently a hydrogen or a methyl group, or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
a hydrogen atom,
a $C_1$-$C_6$-alkyl group
which is unsubstituted or substituted with one or more substituents independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)—S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, a aryl-($C_1$-$C_3$-alkylene)-NH—C(O)— group, a heterocycloalkylene-($C_1$-$C_3$-alkylene)-S(O)$_2$— group, and a heterocycloalkylene-heteroarylene-S(O)$_2$— group;
a phenyl group,
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is independently selected from a hydrogen atom,
a $C_1$-$C_6$-alkyl group
which is unsubstituted or substituted with one or more substituents independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an unsubstituted or substituted aryl group, a ($R^{18}$)-(heterocycloalkylene)-(arylene)-O— group, a (heterocycloalkyl)-(arylene)-O— group, an aryl-O— group, an aryl-($C_1$-$C_3$-alkylene)-O— group, a ($R^{19}$)-S(O)$_2$-arylene-O— group, a ($R^{19}$)S(O)$_2$-heterocycloalkylene-arylene-O— group, an aryl-heteroarylene-O— group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-S(O)$_2$— group, and a heterocycloalkylene-heteroarylene-S(O)$_2$— group;
a ($C_3$-$C_7$)-cycloalkyl group and
a phenyl group;

In further embodiments, the present invention includes compounds of formula (I), supra, in which $R^{15}$ is selected from
selected from a hydrogen atom,
a $C_1$-$C_6$-alkyl group
which is unsubstituted or substituted with one or more substituents selected from a $C_1$-$C_3$-alkyl group, a heterocycloalkyl group, and an aryl group,
a phenyl group,
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
a hydrogen atom,
a $C_1$-$C_6$-alkyl group
  which is unsubstituted or substituted with one or more substituents selected from a $C_1$-$C_3$-alkyl group, a heterocycloalkyl group, and an unsubstituted or substituted aryl group;
a ($C_3$-$C_7$)-cycloalkyl group and
a phenyl group,
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
a hydrogen atom,
a $C_1$-$C_6$-alkyl group
  which is unsubstituted or substituted with a substituent selected from a heterocycloalkyl group and an aryl group;
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
a hydrogen atom,
a $C_1$-$C_6$-alkyl group
  which is unsubstituted or substituted with a substituent selected from a heterocycloalkyl group and an unsubstituted or substituted aryl group, and
a ($C_3$-$C_7$)-cycloalkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
a hydrogen atom, and
a $C_1$-$C_6$-alkyl group
  which is unsubstituted or substituted with a heterocycloalkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
a hydrogen atom,
a $C_1$-$C_6$-alkyl group
  which is unsubstituted or substituted with a heterocycloalkyl group, and a ($C_3$-$C_7$)-cycloalkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
a hydrogen atom,
a $C_1$-$C_6$-alkyl group
  which is unsubstituted or substituted with an unsubstituted or substituted aryl group, and
a ($C_3$-$C_7$)-cycloalkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
a hydrogen atom,
a $C_1$-$C_3$-alkyl group
  which is unsubstituted or substituted with an unsubstituted or substituted aryl group, and
a ($C_3$-$C_7$)-cycloalkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
a hydrogen atom,
a $C_1$-$C_3$-alkyl group
  which is unsubstituted or substituted with a 2,4-dimethoxyphenyl group, and a ($C_3$-$C_7$)-cycloalkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from
a hydrogen atom,
a $C_1$-$C_3$-alkyl group
  which is unsubstituted or substituted with a 2,4-dimethoxyphenyl group, and a ($C_3$-$C_5$)-cycloalkyl group;
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is selected from a hydrogen atom, and a $C_1$-$C_3$-alkyl group which is unsubstituted or substituted with a pyrrolidin-1-yl group, a 2-oxopyrrolidin-1-yl group, a piperidin-1-yl group and a morpholin-4-yl group, or a tautomer, an N-oxide, or a salt thereof or a salt of a tautomer or a salt of an N-oxide or a mixture of same.

In further embodiments, the present invention includes compounds of formula (I), supra, in which $R^{15}$ is selected from a hydrogen atom, and a $C_1$-$C_3$-alkyl group which is unsubstituted or substituted with a pyrrolidin-1-yl group, a 2-oxopyrrolidin-1-yl group, a piperidin-1-yl group, a 2,4-dimethoxyphenyl group and a morpholin-4-yl group, or a tautomer, an N-oxide, or a salt thereof or a salt of a tautomer or a salt of an N-oxide or a mixture of same.

In further embodiments, the present invention includes compounds of formula (I), supra, in which $R^{15}$ is a $C_1$-$C_3$-alkyl group which is unsubstituted or substituted with a pyrrolidin-1-yl group, a 2-oxopyrrolidin-1-yl group, a piperidin-1-yl group and a morpholin-4-yl group, or a tautomer, an N-oxide, or a salt thereof or a salt of a tautomer or a salt of an N-oxide or a mixture of same.

In further embodiments, the present invention includes compounds of formula (I), supra, in which $R^{15}$ is a $C_1$-$C_3$-alkyl group which is unsubstituted or substituted with a pyrrolidin-1-yl group, a 2-oxopyrrolidin-1-yl group, a piperidin- 1-yl group, a 2,4-dimethoxyphenyl group and a morpholin-4-yl group, or a tautomer, an N-oxide, or a salt thereof or a salt of a tautomer or a salt of an N-oxide or a mixture of same.

In further embodiments, the present invention includes compounds of formula (I), supra, in which $R^{15}$ is a ($C_3$-$C_5$)-cycloalkyl group
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is a cyclopropyl group
or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is a methyl group or an ethyl group or a tautomer, an N-oxide, or a salt thereof, or a salt of a tautomer, or a salt of an N-oxide, or a mixture of same.

In further embodiments, the present invention includes compounds of formula (I), supra, in which $R^{15}$ is a [(CH$_2$)$_2$(morpholin-4-yl)] group
or a tautomer, an N-oxide, or a salt thereof, or a salt of a tautomer, or a salt of an N-oxide, or a mixture of same.

In further embodiments, the present invention includes compounds of formula (I), supra, in which $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group; or a tautomer, an N-oxide, or a salt thereof, or a salt of a tautomer, or a salt of an N-oxide, or a mixture of same.

In further embodiments, the present invention includes compounds of formula (I), supra, in which $R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group; or a tautomer, an N-oxide, or a salt thereof, or a salt of a tautomer, or a salt of an N-oxide, or a mixture of same.

In further embodiments, the present invention includes compounds of formula (I), supra, in which $R^{16}$ and $R^{17}$ are each independently selected from a hydrogen atom, a $C_1$-$C_6$-alkyl group and a $C_1$-$C_6$-haloalkyl group; or a tautomer, an N-oxide, or a salt thereof, or a salt of a tautomer, or a salt of an N-oxide, or a mixture of same.

In further embodiments, the present invention includes compounds of formula (I), supra, in which $R^{16}$ and $R^{17}$ are taken together with the nitrogen atom to which they are attached to form a heterocyclyl, preferably a 4-morpholinyl group, or a tautomer, an N-oxide, or a salt thereof, or a salt of a tautomer, or a salt of an N-oxide, or a mixture of same.

In yet further embodiments, the present invention includes compounds of formula (I), supra, in which $R^{18}$ is independently selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a C(O)OR$^{21}$— (C$_1$-$C_3$-alkylene)- group, a —C(O)OR$^{21}$ group, a —C(O)NR$^{20}$R$^{21}$ group, a (C$_1$-$C_3$-alkyl)-O—(C$_1$-$C_3$-alkylene)-C(O)— group, a (C$_1$-$C_6$-alkyl)-C(O)— group and a $C_3$-$C_6$-cycloalkyl-C(O)— group; or a tautomer, an N-oxide, or a salt thereof, or a salt of a tautomer, or a salt of an N-oxide, or a mixture of same.

In further embodiments, the present invention includes compounds of formula (I), supra, in which $R^{19}$ is selected from a $C_1$-$C_3$-alkyl group, a $C_3$-$C_6$-cycloalkyl group and a NR$^{20}$R$^{21}$ group; or a tautomer, an N-oxide, or a salt thereof, or a salt of a tautomer, or a salt of an N-oxide, or a mixture of same.

In further embodiments, the present invention includes compounds of formula (I), supra, wherein $R^{20}$ and $R^{21}$ are independently selected from a hydrogen atom and a $C_1$-$C_6$-alkyl group; or a tautomer, an N-oxide, or a salt thereof, or a salt of a tautomer, or a salt of an N-oxide, or a mixture of same.

In yet further embodiments, the present invention includes compounds of formula (I), supra, in which $R^{22}$ is independently selected from
  a halogen atom,
  a $C_1$-$C_6$-alkyl group
    which is unsubstituted or substituted with one or more substituents selected from a halogen atom, a hydroxy group, NR$^{16}$R$^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a (R$^{18}$)-(heterocycloalkylene)-(arylene)-O— group, a (heterocycloalkyl)-(arylene)-O— group, an aryl-O— group, an aryl-(C$_1$-$C_3$-alkylene)-O— group, a (R$^{19}$)—S(O)$_2$-arylene-O— group, a (R$^{19}$)S(O)$_2$-heterocycloalkylene-arylene-O— group, an aryl-heteroarylene-O— group, an aryl-heteroarylene-O—(C$_1$-$C_3$-alkylene)- group, a heterocycloalkyl-(C$_1$-$C_3$-alkylene)-C(O)— group, a heterocycloalkyl-NH—C(O) group, a aryl-(C$_1$-$C_3$-alkylene)-NH—C(O)— group, a heterocycloalkylene-(C$_1$-$C_3$-alkylene)-S(O)$_2$— group, and a heterocycloalkylene-heteroarylene-S(O)$_2$— group;
  a $C_1$-$C_3$-alkylene-C(O)— group,
or a tautomer, an N-oxide, or a salt thereof, or a salt of a tautomer, or a salt of an N-oxide, or a mixture of same.

In further embodiments, the present invention includes compounds of formula (I), supra, wherein $R^{22}$ is independently selected from
  a halogen atom,
  a $C_1$-$C_6$-alkyl group which is unsubstituted or substituted with one or more substituents selected from a halogen atom, a hydroxy group, NR$^{16}$R$^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, and a phenyl group,
  a $C_3$-$C_6$-cycloalkyl group,
  a heterocycloalkyl group,
  a phenyl group, and
  a heteroaryl group,
or a tautomer, an N-oxide, or a salt thereof, or a salt of a tautomer, or a salt of an N-oxide, or a mixture of same.

In further embodiments, the present invention includes compounds of formula (I), supra, wherein $R^{22}$ is independently selected from
  a halogen atom,
  a $C_1$-$C_4$-alkyl group which is unsubstituted or substituted with a group selected from a hydroxy group, NR$^{16}$R$^{17}$ group, a $C_1$-$C_4$-alkoxy group, a $C_3$-$C_6$-cycloalkyl group, a heterocycloalkyl group and a phenyl group;
  a phenyl group,
  a heteroaryl group,
  a $C_3$-$C_6$-cycloalkyl group, and
  a heterocycloalkyl group,
or a tautomer, an N-oxide, or a salt thereof, or a salt of a tautomer, or a salt of an N-oxide, or a mixture of same.

In further embodiments, the present invention includes compounds of formula (I), supra, in which $R^{22}$ is independently selected from
  a halogen atom,
  a phenyl group,
  a $C_3$-$C_6$-cycloalkyl group,
  a $C_1$-$C_3$-alkyl group which is unsubstituted or substituted with one or more substituents selected from a hydroxy group, NR$^{17}$R$^{18}$ group, a $C_1$-$C_3$-haloalkyl group, a $C_1$-$C_3$-alkoxy group, a $C_3$-$C_6$-cycloalkyl group, a heterocycloalkyl group and a phenyl group;
or a tautomer, an N-oxide, or a salt thereof, or a salt of a tautomer, or a salt of an N-oxide, or a mixture of same.

In yet further embodiments, the present invention includes compounds of formula (I), supra, wherein $R^{22}$ is independently selected from a $C_1$-$C_3$-haloalkyl- group and a $C_1$-$C_3$-alkyl group which is unsubstituted or substituted with a hydroxyl group, a $C_3$-$C_5$-cycloalkyl group, and a heterocyclyl group; or a tautomer, an N-oxide, or a salt thereof, or a salt of a tautomer, or a salt of an N-oxide, or a mixture of same.

In yet further embodiments, the present invention includes compounds of formula (I), supra, wherein $R^{22}$ is independently selected from a $C_1$-$C_3$-haloalkyl- group and a $C_1$-$C_3$-alkyl group which is unsubstituted or substituted with a hydroxyl group, a $C_3$-$C_5$-cycloalkyl group, a heterocycloalkyl group, and a heterocyclyl group; or a tautomer, an N-oxide, or a salt thereof, or a salt of a tautomer, or a salt of an N-oxide, or a mixture of same.

In yet further embodiments, the present invention includes compounds of formula (I), supra, wherein $R^{22}$ is a $C_1$-$C_3$-alkyl group which is unsubstituted or substituted with a heterocycloalkyl group; or a tautomer, an N-oxide, or a salt thereof, or a salt of a tautomer, or a salt of an N-oxide, or a mixture of same.

In yet further embodiments, the present invention includes compounds of formula (I), supra, wherein $R^{22}$ is a $C_1$-$C_3$-alkyl group which is unsubstituted or substituted with a morpholin-4-yl or a tetrahydropyran-4-yl group; or a tautomer, an N-oxide, or a salt thereof, or a salt of a tautomer, or a salt of an N-oxide, or a mixture of same.

In other embodiments, the present invention includes compounds of formula (I), supra, wherein $R^{22}$ is independently selected from a methyl group, an ethyl group, a hydroxyethyl group, a —$(CH_2)_2$-morpholino group, trifluoromethyl group and a cyclopropyl group; or a tautomer, an N-oxide, or a salt thereof, or a salt of a tautomer, or a salt of an N-oxide, or a mixture of same.

In other embodiments, the present invention includes compounds of formula (I), supra, wherein $R^{22}$ is independently selected from a methyl group, an ethyl group, a hydroxyethyl group, a —$(CH_2)_2$-morpholino group, a —$(CH_2)_2$-tetrahydropyrano group, a trifluoromethyl group and a cyclopropyl group; or a tautomer, an N-oxide, or a salt thereof, or a salt of a tautomer, or a salt of an N-oxide, or a mixture of same.

In other embodiments, the present invention includes compounds of formula (I), supra, wherein $R^{22}$ is independently selected from a —$(CH_2)_2$-morpholino group and a —$(CH_2)_2$-tetrahydropyrano group; or a tautomer, an N-oxide, or a salt thereof, or a salt of a tautomer, or a salt of an N-oxide, or a mixture of same.

In other embodiments, the present invention includes compounds of formula (I), supra, wherein $R^{22}$ is independently selected from a —$(CH_2)_2$-morpholin-4-yl group and a —$(CH_2)_2$-tetrahydropyran-4-yl group; or a tautomer, an N-oxide, or a salt thereof, or a salt of a tautomer, or a salt of an N-oxide, or a mixture of same.

In other embodiments, the present invention includes compounds of formula (I), supra, wherein $R^{22}$ is a —$(CH_2)_2$-morpholin-4-yl group; or a tautomer, an N-oxide, or a salt thereof, or a salt of a tautomer, or a salt of an N-oxide, or a mixture of same.

In yet further embodiments, the present invention includes compounds of formula (I), supra, wherein $R^{23}$ is independently selected from a hydrogen atom, a halogen atom, a hydroxy group, a $C_1$-$C_6$-alkyl group, and a $C_1$-$C_6$-haloalkyl group, or a tautomer, an N-oxide, or a salt thereof, or a salt of a tautomer, or a salt of an N-oxide, or a mixture of same.

In yet further embodiments, the present invention includes compounds of formula (I), supra, wherein $R^{23}$ is independently selected from a hydrogen atom, a halogen atom, a hydroxy group, and a $C_1$-$C_4$-alkyl group, or a tautomer, an N-oxide, or a salt thereof, or a salt of a tautomer, or a salt of an N-oxide, or a mixture of same.

In yet further embodiments, the present invention includes compounds of formula (I), supra, wherein $R^{23}$ is independently selected from a hydrogen atom, a halogen atom, a hydroxy group, and a $C_1$-$C_4$-alkyl group, or a salt thereof, or a salt of a tautomer, or a salt of an N-oxide, or a mixture of same.

In further embodiments, the present invention includes compounds of formula (I), wherein $R^{23}$ is independently selected from a hydrogen atom, a halogen atom, a hydroxy group, and a $C_1$-$C_3$-alkyl group, or a tautomer, an N-oxide, or a salt thereof, or a salt of a tautomer, or a salt of an N-oxide, or a mixture of same.

In further embodiments, the present invention includes compounds of formula (I), wherein $R^{23}$ is independently selected from a hydrogen atom and a $C_1$-$C_3$-alkyl group, or a tautomer, an N-oxide, or a salt thereof, or a salt of a tautomer, or a salt of an N-oxide, or a mixture of same.

In yet further embodiments, the present invention includes compounds of formula (I), supra, wherein $R^{22}$ and $R^{23}$ together with the carbon atom to which they are attached form a 3-6-membered carbocyclic ring or a 3-6-membered heterocyclic ring comprising one or two heteroatoms selected from nitrogen, oxygen or sulfur, or a tautomer, an N-oxide, or a salt thereof, or a salt of a tautomer, or a salt of an N-oxide, or a mixture of same.

In further embodiments, the present invention includes compounds of formula (I), wherein $R^{22}$ and $R^{23}$ together form a 3-6-membered carbocyclic ring; or a tautomer, an N-oxide, or a salt thereof, or a salt of a tautomer, or a salt of an N-oxide, or a mixture of same.

In yet further embodiments, the present invention includes compounds of formula (I), supra, wherein $R^{22}$ and $R^{23}$ together with the carbon atom to which they are attached form a 3-6-membered heterocyclic ring comprising one or two heteroatoms selected from nitrogen, oxygen or sulfur, or a tautomer, an N-oxide, or a salt thereof, or a salt of a tautomer, or a salt of an N-oxide, or a mixture of same.

In further embodiments, the present invention includes compounds of formula (I), which are salts.

In further embodiments, the present invention includes compounds of formula (I), which are a tautomer or a salt thereof or a salt of a tautomer or a mixture of same.

In further embodiments, the present invention includes compounds of formula (I), which are a an N-oxide, or a salt thereof or a salt of an N-oxide or a mixture of same.

In a particular further embodiment of the first aspect, the present invention provides combinations of two or more of the above mentioned embodiments under the heading "further embodiments of the first aspect of the present invention".

Furthermore, it is understood that the invention includes any subcombination of the disclosed single embodiments herein for certain residues or subcombination of residues of formula (I).

The present invention includes any sub-combination within any embodiments or aspects of the present invention of compounds of general formula (I), supra.

The present invention includes any sub-combination within any embodiments or aspects of the present invention of compounds or intermediate compounds of general formula (I or II). The present invention includes the compounds of general formula (I) which are disclosed in the Example Section of this text, infra.

GENERAL SYNTHESIS OF COMPOUNDS OF GENERAL FORMULA (I) OF THE PRESENT INVENTION

A. General Synthesis Route

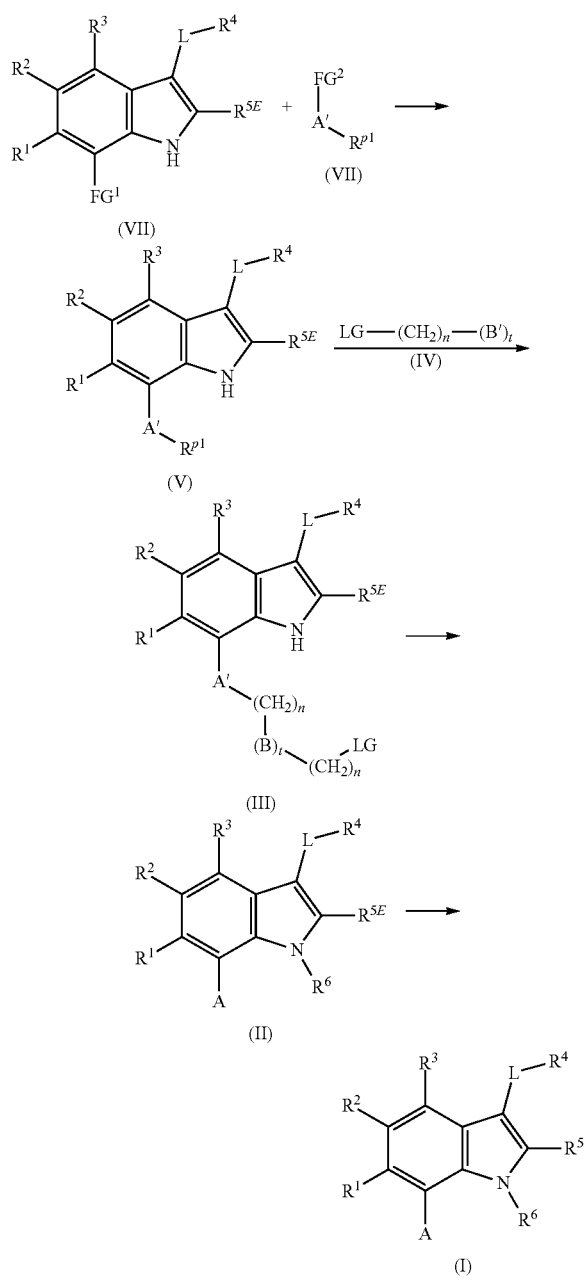

Scheme 1

Compounds of general formula (I) can be synthesized using various synthesis routes, e.g. according to the general synthesis route depicted in Scheme 1, encompassing a Suzuki coupling of starting materials of formulae (VII) and (VI) to give intermediates of formula (V), followed by elaboration of the macrocylic core by (i) extension of a group $R^{p1}$ attached to A', in which A', together with the group $R^{p1}$ attached to it, represents a group suitable to act as precursor of a group A as defined for the compounds of general formula (I), by reaction with compounds of formula (IV), in which LG represents a leaving group as defined herein and $(B')_t$ represents a precursor group of the group $(B)_t$ as defined for the compounds of general formula (I), followed by (ii) macrocyclisation of the resulting intermediates of formula (III), e.g. by intramolecular nucleophilic substitution, to give macrocyclic intermediates of formula (II). It is, alternatively, also possible to attach a group $-(CH_2)_n-(B')_t$ to the indole nitrogen present in said intermediates of formula (V), and to accomplish macrocyclisation from there (not shown in Scheme 1 but discussed in context of Scheme 2b). For details of the various routes from intermediates of formula (V) to macrocyclic intermediates of formula (II), see e.g. the Schemes 2a-2c, infra. Finally, conversion of $R^{5E}$ into $R^5$, e.g. by ester saponification, optionally followed by conversion of the resulting carboxylic acid into an acylsulfonamide according to methods known to the person skilled in the art (see for example: *Bioorg. Med. Chem. Lett.* 2006, 16, 3639-3641; *Bioorg. Med Chem. Lett.* 2012, 22, 713-717; *Org. Lett.* 2012, 14(2), 556-559), yields the compounds of formula (I).

Said general synthesis route commences with a well-known Suzuki coupling of compounds of formula (VII), in which $R^1, R^2, R^3, R^4$ and L are as defined for the compounds of general formula (I), wherein any —$CH_2$— group is unsubstituted or substituted with one or more substituents as defined for the compounds of general formula (I), and in which $R^{5E}$ represents a group suitable to act as a precursor of a —C(=O)OH or a tetrazol-5-yl group, preferably a group —C(=O)O—$C_{1-4}$-alkyl, with compounds of formula (VI), in which A', together with the group $R^{p1}$ attached to it, represents a group suitable to act as precursor of a group A as defined for the compounds of general formula (I), to give compounds of formula (V). The group $R^4$, constituting the terminus of the side chain attached to C-3 of the indole core in formula (VII), can alternatively be established on later stage (see e.g. Scheme 2c and its discussion for details). Examples of groups A' are exemplified further below in this chapter.

In formulae (VI) and (VII), $FG^1$ in combination with $FG^2$ represents a pair of functional groups together enabling a Suzuki coupling; either $FG^1$ represents chloro, bromo, iodo or a trifluoromethanesulfonyl- group, preferably bromo or iodo, and $FG^2$ represents a group —$B(OR^B)_2$, or vice versa. Said group $B(OR^B)_2$ may be a boronic acid moiety ($R^B$=H) or an alkyl ester of the boronic acid, e.g. its isopropyl ester ($R^B$=$C_1$-$C_4$-alkyl, e.g. —$CH(CH_3)_2$), or an ester derived from a diol such as pinacol in which the boronic acid intermediate forms a cyclic boronic ester, preferably a 4,4,5,5-tetramethyl-1,3,2-dioxaborolane ($R^B$-$R^B$=$C_2$-$C_6$-alkylene, preferably $C(CH_3)_2$—$C(CH_3)_2$—). Many boronic acids and their esters are commercially available and their synthesis is well-known to the person skilled in the art; see e.g. D. G. Hall, Boronic Acids, 2005 WILEY-VCH Verlag GmbH & Co. KGaA, Weinheim, ISBN 3-527-30991-8 and references cited therein, and Journal of Medicinal Chemistry, 2015, 58, 2180-2194. Alternatively to boronic acid derivatives, also tetrafluoroborates, in which —$BF_4^-$ replaces the —$B(OR^B)_2$ moiety, can also be employed.

Said Suzuki coupling reaction can be catalysed by palladium catalysts, exemplified by but not limited to by Pd(0) catalysts such as e.g. tetrakis(triphenylphosphine)palladium (0) [Pd(PPh$_3$)$_4$], tris(dibenzylideneacetone)di-palladium(0) [Pd$_2$(dba)$_3$] in combination with a ligand, e.g. a phosphine such as triphenylphosphine, or by Pd(II) catalysts such as e.g. dichlorobis(triphenylphosphine)-palladium(II) [Pd(PPh$_3$)$_2$Cl$_2$], dichloropalladium-tricyclohexylphosphine (1:2), palladium(II) acetate in combination with a ligand, e.g. a phosphine such as e.g. triphenylphosphine, chloro(2-dicyclohexylphosphino-2',4',6'-triisopropyl-1,1'-biphenyl)[2-(2'-amino-1,1'-biphenyl)]palladium(II) (herein also referred to as XPhos Pd G2), (2-Dicyclohexylphosphino-2',4',6'-triisopropyl-1,1'-biphenyl)[2-(2'-amino-1,1'-biphenyl)] palladium(II) methanesulfonate (herein also referred to as XPhos Pd G3), or by [1,1'-bis(diphenylphosphino)ferrocene]-palladium dichloride, in free form [Pd(dppf)Cl$_2$] or as dichloromethane adduct [Pd(dppf)Cl$_2$×CH$_2$Cl$_2$].

The reaction is preferably carried out in solvents such as e.g. 1,2-dimethoxyethane, 1,4-dioxane, DMF, THF, or n-propanol, or mixtures thereof, optionally also in mixture with water, and in the presence of a base such as e.g. aqueous potassium carbonate, aqueous sodium carbonate or aqueous potassium triphosphate.

The reaction is performed at temperatures ranging from room temperature (i.e. 20° C.) to the boiling point of the solvent. Additionally, the reaction can be performed at temperatures above the boiling point using pressure tubes and a microwave oven. (for a review on Suzuki couplings see: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

Synthetic approaches to starting materials of formulae (VI) and (VII) are discussed in paragraph D. of this chapter, infra.

Compounds of formula (II) can be obtained using various methods described in more detail below, e.g. by reacting compounds of formula (V) with compounds of formula (IV), in which LG represents a leaving group, preferably chloro, in which the index "n" is as defined for the compounds of general formula (I), and in which (B')$_t$ represents a reactive precursor group, e.g. the group —S(O)$_2$Cl, of the group (B)$_t$ as defined for the compounds of general formula (I), followed by intramolecular nucleophilic displacement of said leaving group LG by the indole nitrogen. The following paragraphs outline more specific examples of various conversions inter alia of compounds of formula (Va), constituting a sub-compartment of formula (V), into compounds of (IIa), (IIb), and (IIc), all of them constituting sub-compartments of formula (II).

Said macrocyclic intermediates of formula (II) can finally be converted into the compounds of general formula (I) as described in further detail in context with Scheme 3, infra.

B. More Specific Synthesis Routes for Establishing the Macrocyclic Core, Schemes 2a 2d:

Scheme 2a

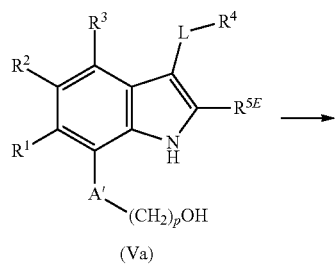

(Va)

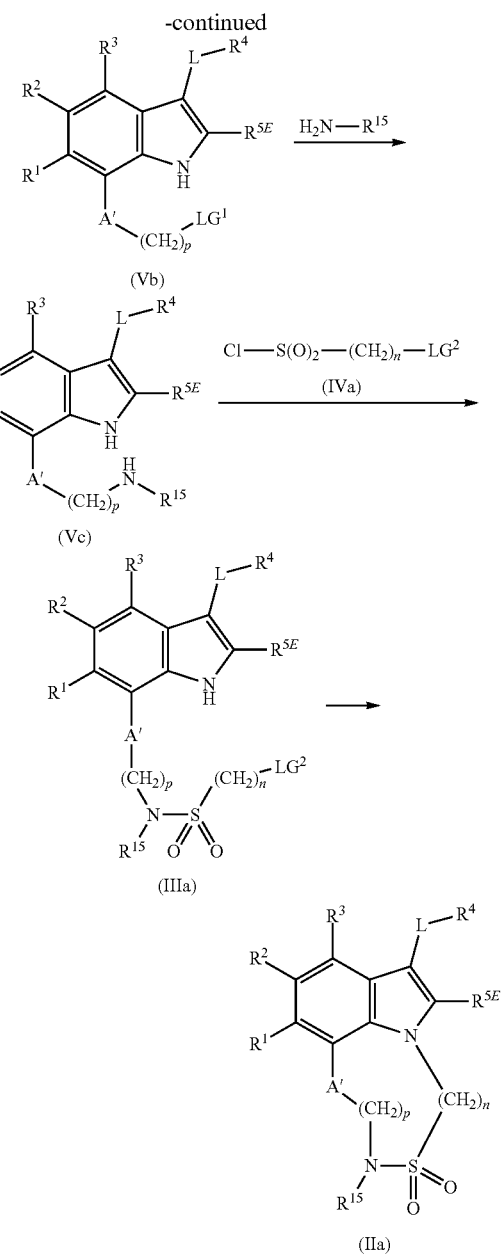

According to Scheme 2a, compounds of formula (IIa), in which R$^7$ (which is a feature of group A as defined for the compounds of general formula (I)) and R$^6$ together form a $^{\#\#}$—(CH$_2$)$_p$—N(R$^{15}$)—S(O)$_2$—(CH$_2$)$_n$—$^{\#}$ group, in which $^{\#}$ represents the point of attachment to the indole nitrogen atom and $^{\#\#}$ represents the point of attachment to the pyrazole carbon atom bearing the R$^7$ substituent, wherein any —CH$_2$— group is unsubstituted or substituted with one or more substituents as defined for the compounds of general formula (I), can be obtained from compounds of formula (Va), in which A' is A or represents a group suitable to act as precursor of a group A as defined for the compounds of general formula (I), in which R$^1$, R$^2$, R$^3$, R$^4$ and L are as defined for the compounds of general formula (I), in which R$^{5E}$ represents a group suitable to act as a precursor of a —C(═O)OH or a tetrazol-5-yl group, preferably a group —C(═O)O—C$_{1-4}$-alkyl, in which R$^{p1}$ (see General Synthesis Route, Scheme 1) represents a —(CH$_2$)$_p$—OH group, in which index "p" is as defined for the compounds of general formula (I), by (i) conversion of said compounds of formula (Va) into compounds of formula (Vb) featuring a group —(CH$_2$)$_p$-LG$^1$, in which LG$^1$ represents a leaving group as defined herein, such as chloro, bromo or iodo, by methods well known to the person skilled in the art, followed by (ii) reacting with primary amines of the formula H$_2$N—R$^{15}$, in which R$^{15}$ is as defined for the compounds of formula (I) but preferably different from a hydrogen atom, to give compounds of the formula (Vc), and (iii) reacting said compounds of formula (Vc) with compounds of formula (IVa), in which LG$^2$ represents a leaving group as defined herein, such as chloro, bromo or iodo, preferably chloro, and in which index "n" is as defined for the compounds of general formula (I), with the proviso that the sum of the integers represented by indices "p" and "n" is at least 2 and does not exceed 9, to give rise to intermediates of formula (IIIa). Said intermediates of formula (IIIa) can be, in turn, subjected to intramolecular nucleophilic substitution to yield the corresponding macrocyclic intermediates of formula (IIa).

The abovementioned transformations can be advantageously accomplished by reacting a compound of formula (Va) with an alkylsulfonyl chloride, such as e.g. methylsulfonyl chloride in the presence of a suitable base, such as e.g. a tertiary aliphatic amine of the formula (C$_1$-C$_3$-alkyl)$_3$N, e.g. N,N-diisopropylethylamine, in a halogenated aliphatic hydrocarbon, such as dichloromethane, to give a compound of formula (Vb), which can be reacted, optionally in situ, with a primary amine of the formula H$_2$N—R$^{15}$, optionally in the presence of an alkali iodide, such as e.g. sodium iodide or potassium iodide, in order to effect in situ interconversion of LG$^1$ into iodo, to give a compound of formula (Vc). Said compound of formula (Vc) can be advantageously reacted with a compound of formula (IVa), defined as supra, in the presence of a suitable base, such as e.g. a tertiary aliphatic amine of the formula (C$_1$-C$_3$-alkyl)$_3$N, e.g. N,N-diisopropylethylamine, in a halogenated aliphatic hydrocarbon, such as e.g. dichloromethane, at a temperature ranging from 0° C. to 30° C., to give a compound of formula (IIIa). Said compound of formula (IIIa) can be advantageously subjected to intramolecular nucleophilic substitution in the presence of a base such as e.g. an alkali hydride, preferably sodium hydride, in a solvent such as e.g. N,N-dimethylformamide, N,N-dimethylacetamide, or N-methylpyrrolidin-2-one, preferably N,N-dimethylformamide, at a temperature ranging from 0° C. to 100° C., preferably 0° C. to 60° C., to give a macrocyclic intermediate of formula (IIa). Specific examples are given in the Experimental section, infra.

Scheme 2a'

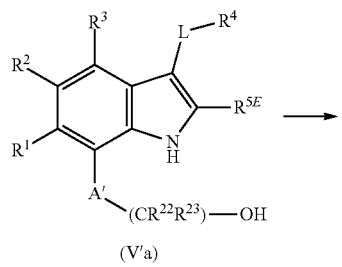

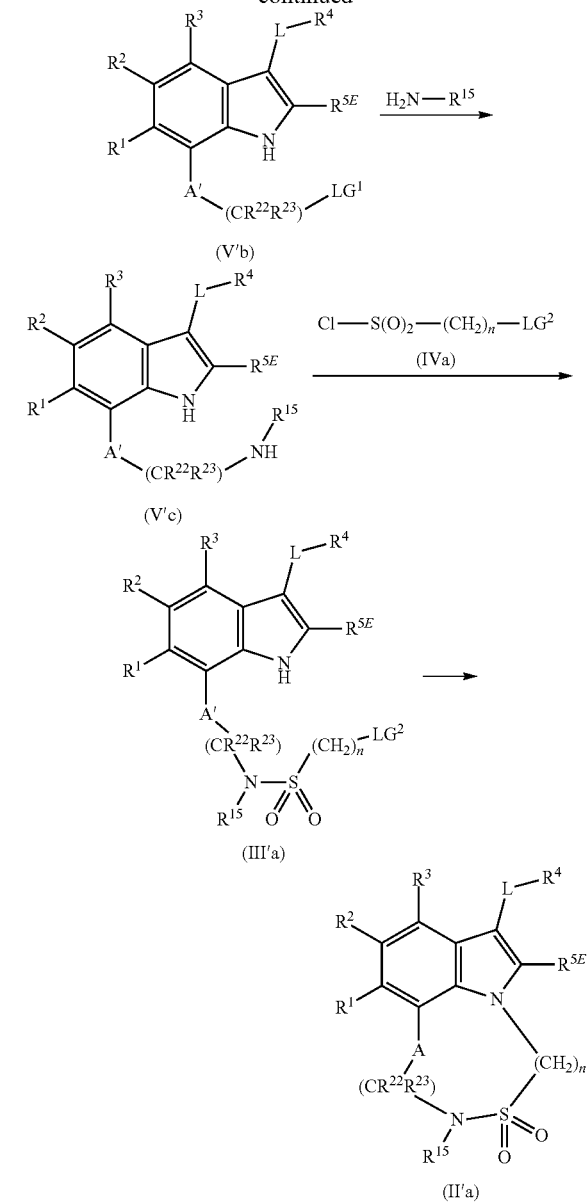

According to Scheme 2a', compounds of formula (II'a), in which R$^7$ (which is a feature of group A as defined for the compounds of general formula (I)) and R$^6$ together form a $^{\#\#}$—(CR$^{22}$R$^{23}$)—N(R$^{15}$)—S(O)$_2$—(CH$_2$)$_n$—$^\#$ group, in which $^\#$ represents the point of attachment to the indole nitrogen atom and $^{\#\#}$ represents the point of attachment to the pyrazole carbon atom bearing the R$^7$ substituent, can be obtained from compounds of formula (V'a), in which A' is A or represents a group suitable to act as precursor of a group A as defined for the compounds of general formula (I), in which R$^1$, R$^2$, R$^3$, R$^4$, R$^{22}$, R$^{23}$ and L are as defined for the compounds of general formula (I), in which R$^{5E}$ represents a group suitable to act as a precursor of a —C(O)OH or a tetrazol-5-yl group, preferably a group —C(=O)O—C$_{1-4}$-alkyl, in which R$^{p1}$ (see General Synthesis Route, Scheme 1) represents a (CR$^{22}$R$^{23}$)—OH group, by (i) conversion of said compounds of formula (V'a) into compounds of formula (V'b) featuring a group —(CR$^{22}$R$^{23}$)-LG$^1$, in which LG$^1$ represents a leaving group as defined herein, such as chloro, bromo or iodo, by methods well known to the person skilled in the art, followed by (ii) reacting with primary amines of the formula H₂N—R¹⁵, in which R¹⁵ is as defined for the compounds of formula (I) but preferably different from a hydrogen atom, to give compounds of the formula (V'c), and (iii) reacting said compounds of formula (V'c) with compounds of formula (IVa), in which LG² represents a leaving group as defined herein, such as chloro, bromo or iodo, preferably chloro, and in which index "n" is as defined for the compounds of general formula (I), with the proviso that the sum of the integers represented by indices "p" and "n" is at least 2 and does not exceed 9, to give rise to intermediates of formula (III'a). Said intermediates of formula (III'a) can be, in turn, subjected to intramolecular nucleophilic substitution to yield the corresponding macrocyclic intermediates of formula (II'a).

The abovementioned transformations can be advantageously accomplished by reacting a compound of formula (V'a) with an alkylsulfonyl chloride, such as e.g. methylsulfonyl chloride in the presence of a suitable base, such as e.g. a tertiary aliphatic amine of the formula $(C_1$-$C_3$-alkyl$)_3$N, e.g. N,N-diisopropylethylamine, in a halogenated aliphatic hydrocarbon, such as e.g. dichloromethane, to give a compound of formula (V'b), which can be reacted, optionally in situ, with a primary amine of the formula H₂N—R¹⁵, optionally in the presence of an alkali iodide, such as e.g. sodium iodide or potassium iodide, in order to effect in situ interconversion of LG¹ into iodo, to give a compound of formula (V'c). Said compound of formula (V'c) can be advantageously reacted with a compound of formula (IVa), defined as supra, in the presence of a suitable base, such as e.g. a tertiary aliphatic amine of the formula $(C_1$-$C_3$-alkyl$)_3$N, e.g. N,N-diisopropylethylamine, in a halogenated aliphatic hydrocarbon, such as e.g. dichloromethane, at a temperature ranging from 0° C. to 30° C., to give a compound of formula (III'a). Said compound of formula (III'a) can be advantageously subjected to intramolecular nucleophilic substitution in the presence of a base such as e.g. an alkali hydride, preferably sodium hydride, in a solvent such as e.g. N,N-dimethylformamide, N,N-dimethylacetamide, or N-methylpyrrolidin-2-one, preferably N,N-dimethylformamide, at a temperature ranging from 0° C. to 100° C., preferably 0° C. to 60° C., to give a macrocyclic intermediate of formula (II'a). Specific examples are given in the Experimental section, infra.

Scheme 2b

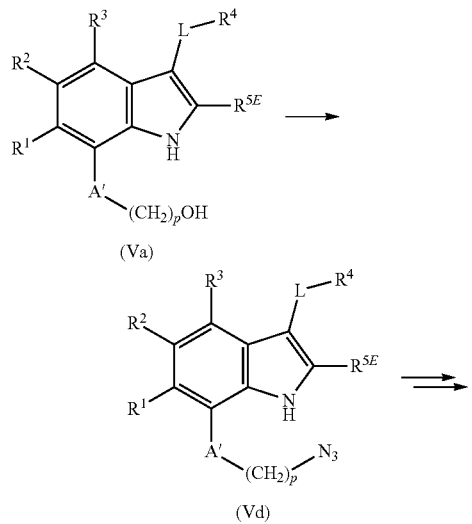

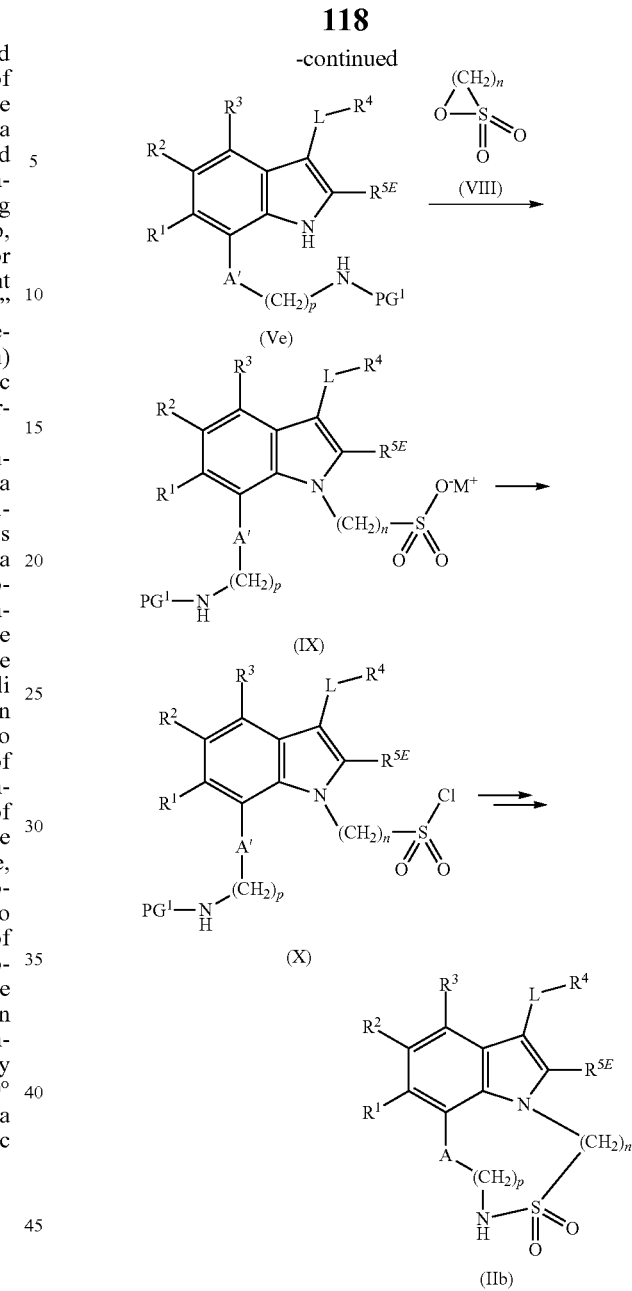

In a somewhat complementary approach shown in Scheme 2b, compounds of formula (IIb), in which R⁷ (which is a feature of group A as defined for the compounds of general formula (I)) and R⁶ together form a ¹⁹⁰ #—(CH₂)$_p$—NH—S(O)₂—(CH₂)$_n$—## group, in which # represents the point of attachment to the indole nitrogen atom and ## represents the point of attachment to the pyrazole carbon atom bearing the R⁷ substituent, can be obtained from compounds of formula (Va), in which R¹, R², R³, R⁴ and L are as defined for the compounds of general formula (I), in which R⁵ᴱ represents a group suitable to act as a precursor of a —C(=O)OH or a tetrazol-5-yl group, preferably a group —C(=O)O—C$_{1-4}$-alkyl, in which R$^{P1}$ represents a —(CH₂)$_p$—OH group, in which index "p" is as defined for the compounds of general formula (I), by (i) conversion of said compounds of formula (Va) into compounds of formula (Vb) featuring an azidoalkyl group —(CH₂)$_p$—N₃, followed by (ii) reduction using well-known methods to give compounds featuring an aminoalkyl group —(CH$_2$)$_p$—NH$_2$, and (iii) attachment of a protective group PG$^1$ to said aminoalkyl group —(CH$_2$)$_p$—NH$_2$, to give compounds of the formula (Ve). Said compounds of formula (Ve) can be reacted with compounds of formula (VIII), in which the index "n" is as defined for the compounds of general formula (I), in the presence of an alkali hydride M$^+$H$^-$, to give sulfonate salts of formula (IX), which in turn can be converted into the corresponding sulfonyl chlorides of formula (X). Removal of said protective group PG$^1$ by known methods, followed by intramolecular nucleophilic substitution in some analogy to Scheme 2a and its discussion can be used to obtain macrocyclic intermediates of formula (IIb).

The abovementioned sequence of transformations can be advantageously performed by reacting a compound of formula (Va) with diphenylphosphoryl azide in the presence of 1,8-diazabicyclo[5.4.0]undec-7-ene in toluene as a solvent, to give a compound of formula (Vd), which, in turn, can be reduced e.g. using palladium on carbon to a compound under an atmosphere of hydrogen, in an aliphatic alcohol of the formula C$_1$-C$_3$-alkyl-OH, such as e.g. ethanol, or in tetrahydrofuran, or in a mixture thereof, as a solvent, followed by reaction e.g. with benzyl chloroformate in the presence of a tertiary aliphatic amine of the formula (C$_1$-C$_3$-alkyl)$_3$N, such as e.g. trimethylamine, to give a compound of formula (Ve), in which PG$^1$ represents a protective group for amino groups, as defined herein, e.g. a benzyloxycarbonyl group. Said compound of formula (Ve) can be reacted with a compound of formula (VIII), as defined supra, in the presence of a strong base such as e.g. an alkali hydride, preferably sodium hydride, to give a compound of formula (IX) in which M$^+$ preferably represents a sodium cation Na$^+$. Reaction with a chlorinating reagent, preferably oxalyl chloride, can be advantageously used to convert said compound of formula (IX) into a compound of formula (X), from which the protective group PG$^1$ can be removed using methods well known to the person skilled in the art (see e.g. T.W. Greene and P.G.M. Wuts in Protective Groups in Organic Synthesis, 4$^{th}$ edition, Wiley 2006), such as reacting said compound of formula (X) with a solution of hydrogen bromide in acetic acid in dichloromethane as a solvent in case PG$^1$ represents a benzyloxycarbonyl group. Intramolecular nucleophilic substitution of the crude product thus obtained is favourably accomplished by reacting with a tertiary aliphatic amine, e.g. of the formula (C$_1$-C$_3$-alkyl)$_3$N, such as N,N-diisopropylamine, at a temperature between 0° C. and 50° C., in a halogenated aliphatic hydrocarbon, such as e.g. dichloromethane, as a solvent, to yield a macrocyclic intermediate of formula (IIb). Specific examples are given in the Experimental section, infra.

Scheme 2c

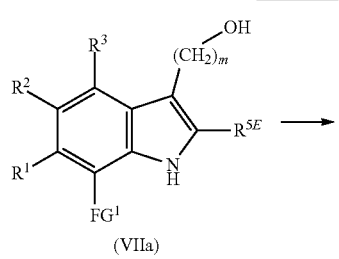

(VIIa)

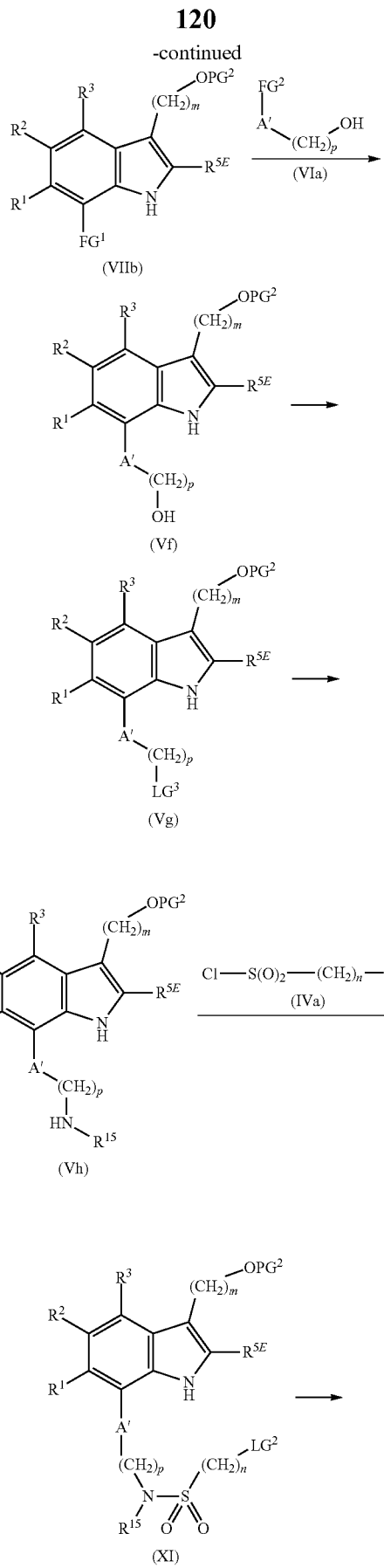

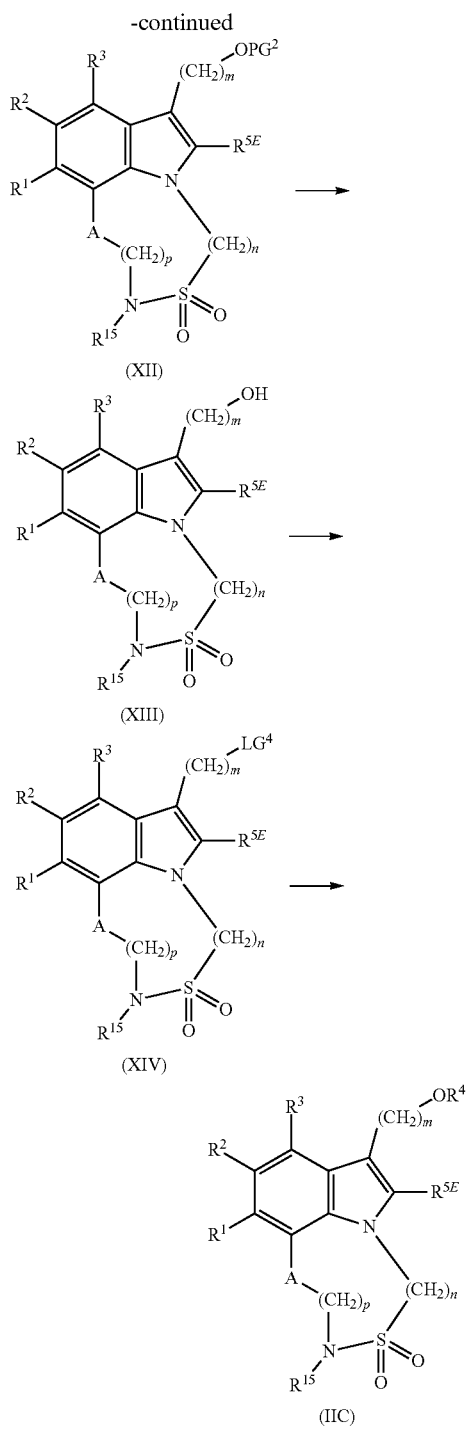

Scheme 2c outlines a modified general synthesis route for certain macrocyclic intermediates of general formula (IIc), constituting a sub-compartment of formula (II), supra, in which E represents an oxygen atom, which employs indole starting materials of formula (VIIa), in turn constituting a sub-compartment of formula (VII), supra. The approach differs from the ones described in the preceding Schemes 2a and 2b in that the group $R^4$ is only introduced on late stage, after elaboration of the macrocyclic core, and hence is particularly useful for preparing multiple compounds of the present invention with many different $R^4$ groups.

As shown in Scheme 2c, indole starting materials of formula (VIIa), in which $R^1$, $R^2$, $R^3$, and m are as defined for the compounds of general formula (I), in which $R^E$ represents a group suitable to act as a precursor of a —C(=O)OH or a tetrazol-5-yl group, preferably a group —C(=O)O—$C_{1-4}$-alkyl, and in which $FG^1$ represents chloro, bromo, iodo, a trifluoromethanesulfonyl- group, or a group —B(OR$^B$)$_2$, preferably bromo or iodo, more preferably a group —B(OR$^B$)$_2$, are protected at their free hydroxy group attached to —(CH$_2$)$_m$— with PG$^2$, a protective group for hydroxy groups as defined herein, such as tert-butyldimethylsilyl-, by reaction with a suitable reagent such as e.g. tert-butylchlorodimethylsilane, in the presence of a base such as e.g. imidazole, using a halogenated aliphatic hydrocarbon, such as e.g. dichloromethane, as a solvent, to give indole derivatives of formula (VIIb). It is well possible to elaborate said —B(OR$^B$)$_2$ group, if not present already in the compounds of formula (VIIa), from bromo upon introduction of the protective group PG$^2$. Specific examples are given in the Experimental Section, infra. In formulae (VIa), (VIIa) and (VIIb), $FG^1$ in combination with $FG^2$ represents a pair of functional groups together enabling a Suzuki coupling; either $FG^1$ represents chloro, bromo, iodo or a trifluoromethanesulfonyl- group, preferably bromo or iodo, and $FG^2$ represents a group —B(OR$^B$)$_2$, or vice versa. Said group —B(OR$^B$)$_2$ may be a boronic acid moiety ($R^B$=—H) or an alkyl ester of the boronic acid, e.g. its isopropyl ester ($R^B$=$C_1$-$C_4$-alkyl, e.g. CH(CH$_3$)$_2$), or an ester derived from a diol such as pinacol in which the boronic acid intermediate forms a cyclic boronic ester, preferably a 4,4,5,5-tetramethyl-1,3,2-dioxaborolane ($R^B$-$R^B$=$C_2$-$C_6$-alkylene, preferably —C(CH$_3$)$_2$—C(CH$_3$)$_2$—).

Said indole derivatives of formula (VIIb) can, in analogy to the methods discussed in the context of Scheme 1, be reacted in a well-known Suzuki coupling with compounds of formula (VIa), in which p is as defined for the compound of general formula (I), in which $FG^2$ is as discussed above and in and in which A', together with the group (CH$_2$)$_p$—OH attached to it, represents a group suitable to act as precursor of a group A as defined for the compounds of general formula (I), to give compounds of formula (Vf). Said indole starting materials of formula (VIIc) are well known to the person skilled in the art and can be prepared as described infra.

In a subsequent step, the macrocyclic core can be elaborated using approaches such as those outlined and discussed in the context of Scheme 2a, by (i) conversion of said compounds of formula (Vf) into compounds of formula (Vg) featuring a group —(CH$_2$)$_p$-LG$^3$, in which LG$^3$ represents a leaving group as defined herein, such as chloro, bromo or iodo, by methods well known to the person skilled in the art, followed by (ii) reacting with primary amines of the formula H$_2$N—R$^{15}$, in which R$^{15}$ is as defined for the compounds of formula (I) but preferably different from a hydrogen atom, to give compounds of the formula (Vh), and (iii) reacting said compounds of formula (Vh) with compounds of formula (IVa), in which LG$^2$ represents a leaving group as defined herein, such as chloro, bromo or iodo, preferably chloro, and in which index "n" is as defined for the compounds of general formula (I), with the proviso that the sum of the integers represented by indices "p" and "n" is at least 2 and does not exceed 9, to give rise to intermediates of formula (XI). Said intermediates of formula (XI) can be, in turn, be subjected to intramolecular nucleophilic substitution to yield the corresponding macrocyclic intermediates of formula (XII), e.g. by reacting said intermediates of formula (XI) in the presence of a base, such as e.g. cesium carbonate, in a solvent such as e.g. acetonitrile, and in the optional presence of an alkali iodide such as e.g. sodium iodide, to give macrocyclic intermediates of the formula (XII). Said macrocyclic intermediate compounds of formula (XII) can be subsequently subjected to a cleavage of the protective group $PG^2$, according to methods known to the person skilled in the art (see e.g. T.W. Greene and P.G.M. Wuts in Protective Groups in Organic Synthesis, 4th edition, Wiley 2006), e.g. by reacting with tetrabutylammonium fluoride in tetrahydrofuran in case $PG^2$ represents a tert-butyldimethylsilyl-group, to give compounds of the formula (XIII). The hydroxy group present in said compounds of formula (XIII) can then be converted into $LG^4$, representing a leaving group as defined herein, such as bromo, by methods known to the person skilled in the art, such as the reaction with tetrabromomethane in the presence of triphenylphosphine, in a suitable solvent such as e.g. a halogenated aliphatic hydrocarbon, e.g. dichloromethane, giving rise to compounds of the formula (XIV). The group $R^4$ can finally be introduced by reaction of said compounds of the formula (XIV) with a compound of the formula $R^4$—OH, in which $R^4$ is as defined for the compounds of formula (I), in the presence of a base, such as e.g. sodium hydride or cesium carbonate, in a solvent such as e.g. tetrahydrofuran or N,N-dimethylformamide (DMF), to give compounds of formula (IIc). Specific examples are given in the Experimental section, infra.

suitable protecting group strategies, if needed (see e.g. T.W. Greene and P.G.M. Wuts in Protective Groups in Organic Synthesis, $4^{th}$ edition, Wiley 2006).

Said compounds of formula (IVb) can be converted into the corresponding sulfinic acid derivatives of formula (IVc), e.g. using an aqueous solution of sodium sulfite and sodium carbonate in water at elevated temperature, such as 80° C. (see e.g. Angew. Chem. Int. Ed. Engl. 2017, 56 (32), 9608-9613; Chemistry—A European Journal 2016, 22(50), 18085-18091; Chemistry—A European Journal, 2016, 22(25), 8694-8699; Organic Letters, 2016, 18(16), 4144-4147).

Said sulfinic acid derivatives of formula (IVc) can subsequently be converted into sulfinylamides of formula (IVf) featuring said group —$S(O)NR^{15}$— either by chlorination, e.g. with thionyl chloride (see e.g. Synthesis, 1987, (2), 173), to give sulfinyl chlorides of formula (IVd), which in turn can be subjected to aminolysis with amines $R^{S2}R^{15}NH$ (see e.g. Angewandte Chemie, International Edition, 2011, 50(14), 3236-3239, S3236/1-S3236/135), in which $R^{15}$ is as defined for the compound of general formula (I), and in which $R^{S2}$ represents a suitable portion of the respective compound of the present invention, or an intermediate thereof, to give said sulfinylamides of formula (IVf). Alternatively, said sulfinic acid derivatives of formula (IVc) can be esterified e.g. using the corresponding alcohol $R^E$—OH,

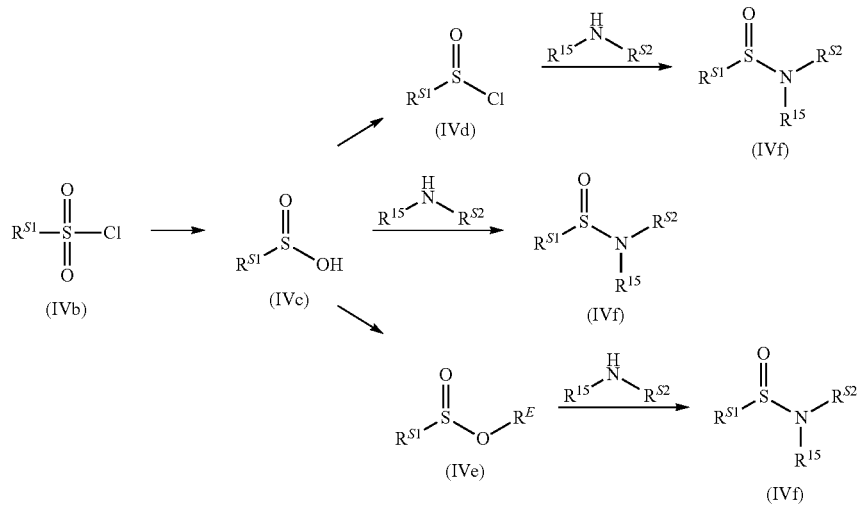

Scheme 2d

It is readily recognised by the person skilled in the art that the synthesis routes as described in the preceding Schemes 2a, 2b and 2c also enable for the introduction of —(B)$_t$ groups other than —$S(O)_2NR^{15}$—, such as —$S(O)NR^{15}$—, as exemplarily outlined in Scheme 2d. Such approaches can be applied to synthesis intermediate featuring a chlorosulfonyl group, as present in intermediates such as (IVa) and (X), supra, herein collectively referred to by formula (IVb), in which $R^{S1}$ represents a suitable portion of the respective compound of the present invention, or an intermediate thereof, featuring no intervening reactive groups, using in which $R^E$ represents a $C_1$-$C_6$-alkyl group, in the presence of concentrated sulfuric acid (see e.g. Tetrahedron Letters 2017, 58(13), 1265-1268), to give sulfinate esters of formula (IVd), followed by reaction with amines $R^{S2}R^{15}NH$, as defined supra, in the presence of a strong base such as e.g. butyllithium (see e.g. Synthesis 2008 (2), 311-319), to give said sulfinylamides of formula (IVf). Also, a direct coupling reaction of said sulfinic acid derivatives of formula (IVc) with amines $R^{S2}R^{15}NH$, as defined supra, in the presence of well-known peptide coupling reagents such as e.g. dicyclohexyl carbodiimide (DCC) can be used (see e.g. Chemical &

Pharmaceutical Bulletin 1980, 28(1), 134-41) to prepare said sulfinylamides of formula (IVf).

C. Conversion into Compounds of Formula (I), Scheme 3:

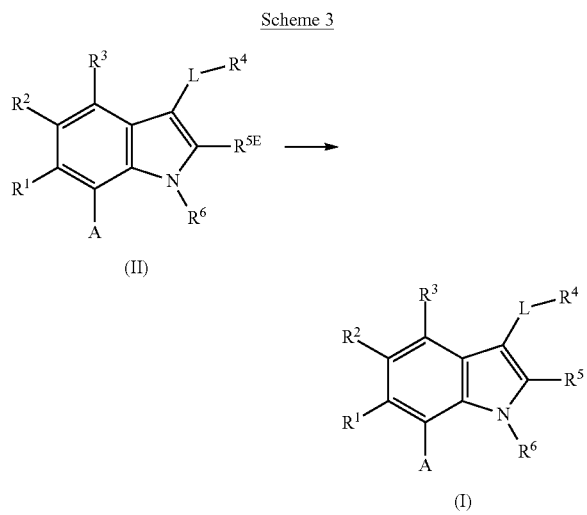

Scheme 3

(II)

(I)

According to Scheme 3, compounds of formula (II) (such as the compounds of the formulae (IIa), (IIb) and (IIc)), in which $R^1$, $R^2$, $R^3$, $R^4$, $R^6$, A and L are as defined for the compounds of general formula (I), and in which $R^{5E}$ represents a group suitable to act as a precursor of a —C(=O)OH or a tetrazol-5-yl group, preferably a carboxylic ester group, such as e.g. a —C(=O)O—$C_{1-4}$-alkyl group or a benzyl ester, can be readily converted into compounds of formula (I) by transforming group $R^{5E}$ into group $R^5$ as defined for the compounds of general formula (I), preferably by reacting with an alkali hydroxide, such as e.g. potassium hydroxide, sodium hydroxide, lithium hydroxide, preferably lithium hydroxide, in a mixture of water with THF and/or an aliphatic alcohol of the formula $C_1$-$C_3$-alkyl-OH, preferably methanol or ethanol, at a temperature in the range from 0° C. to 100° C., preferably in the range from 50° C. to 70° C., and subsequent usual workup as known by the person skilled in the art and as for example disclosed in the experimental section.

Said compounds of general formula (I) may be obtained as free acids or converted into pharmaceutically acceptable salts thereof, such as alkali salts, e.g. sodium or potassium salts, earth alkali salts, e.g. magnesium or calcium salts, and ammonium salts, e.g. ammonium ($NH_4+$), diethylammonium (herein also referred to as N-ethylethanamine salts) or triethylammonium salts, by methods known to the person skilled in the art. Compounds of the invention featuring a basic nitrogen atom, e.g. within the group $R^{15}$, can be isolated as salts with a counteranion of the basic nitrogen, such as e.g. trifluoroacetate, and the like, or as inner carboxylate salts. Further, compounds of formula (I) in which $R^5$ represents a free carboxylic acid group can be optionally converted into an acylsulfonamide according to methods known to the person skilled in the art (see for example: Bioorg. Med. Chem. Lett. 2006, 16, 3639-3641; Bioorg. Med Chem. Lett. 2012, 22, 713-717; Org. Lett. 2012, 14(2), 556-559).

Further, single enantiomers of said compounds of general formula (I) may be obtained by methods known to the person skilled in the art, such as preparative HPLC on a chiral stationary phase, as described supra, and as exemplified in the Experimental Section, infra.

D. Synthesis Routes to Starting Materials of Formulae (VI) and (VII); Schemes 4a-4c:

As outlined in Schemes 4a, 4b and 4c below, several approaches, which are intended to illustrate but not to limit the synthetic routes available to the person skilled in the art for this purpose, can be followed in order to prepare starting materials of the formula (VI), as defined in the context of Scheme 1, supra, i.e. in which A', together with the group $R^{P1}$ attached to it, represents a group suitable to act as precursor of a group A as defined for the compounds of general formula (I), and in which $FG^2$, in combination with the group $FG^1$ present in formula (VII), represents a pair of functional groups together enabling a Suzuki coupling; either $FG^1$ represents chloro, bromo, iodo or a trifluoromethanesulfonyl- group, preferably bromo or iodo, and $FG^2$ represents a group —$B(OR^B)_2$ as defined supra, or vice versa. Preferably in particular, $FG^2$ represents bromo. Conversion of compounds, in which $FG^2$ represents bromo, into compounds in which $FG^2$ represents a group —$B(OR^B)_2$, is possible on various steps of the outlined synthesis routes using methods well known to the person skilled in the art.

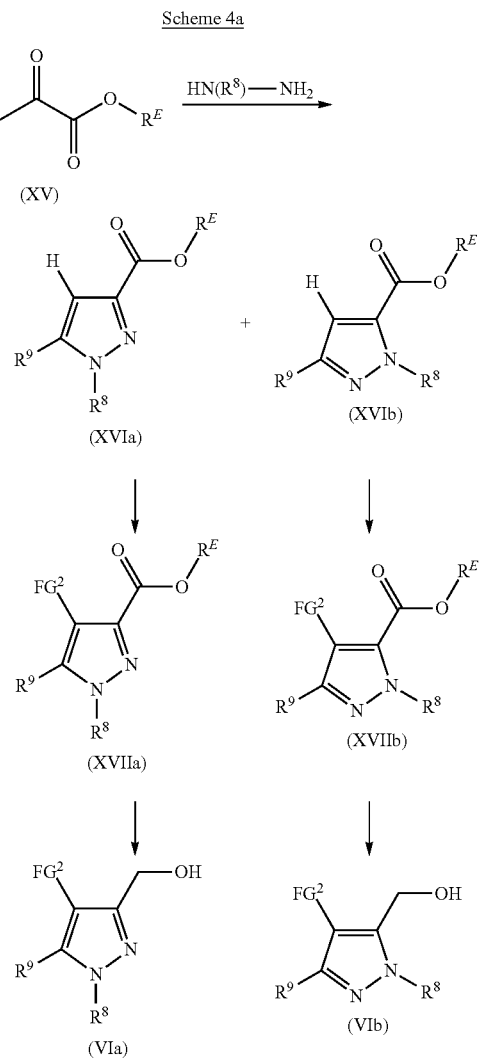

Scheme 4a

Scheme 4a illustrates the synthesis route enabling the preparation of compounds of formula (VI), in which A' is derived from pyrazole, namely compounds of formulae (VIb) and (VIc), both of them constituting sub-compartments for formula (VI).

Said compounds of formulae (VIb) and (VIc) can be prepared from well-known α,γ-diketoesters of formula (XV), in which $R^9$ is as defined for the compounds of general formula (I), and in which $R^E$ represents a $C_1$-$C_6$-alkyl group, by reaction with hydrazines $HN(R^8)$—$NH_2$, in which $R^8$ is as defined for the compounds of general formula (I), to give regioisomeric mixtures of pyrazole derivatives of formulae (XVIa) and (XVIb), which can be separated on this step or on one of the steps described below. If unsubstituted hydrazine ($R^8$=H) is used, $R^8$ groups different from a hydrogen atom can be introduced into compounds of formulae (XVIa) and (XVIb) e.g. by suitable alkylating agents such as a $C_1$-$C_6$-alkyl halide or a di($C_1$-$C_6$-alkyl)sulfate in the presence of a base, such as e.g. sodium carbonate, in a solvent such as e.g. dichloromethane or N,N-dimethylformamide.

Said pyrazole derivatives of formulae (XVIa) and (XVIb) can subsequently be reacted with reagents suitable to introduce $FG^2$, such as N-halo succinimides or solutions of elemental halogens, to give pyrazole derivatives of formulae (XVIIa) and (XVIIb); preferably, N-bromo succinimide in a halogenated hydrocarbon, such as e.g. 1,2-dichloroethane, as a solvent, or bromine in a solvent such as e.g. glacial acetic acid or a halogenated hydrocarbon, such as e.g. dichloromethane, can be used. Said pyrazole derivatives of formulae (XVIIa) and (XVIIb) can subsequently be reduced by a suitable reducing agent not interfering with the groups $FG^2$, such as lithium borohydride, in a solvent such as e.g. tetrahydrofurane, to give pyrazolyl methanols of formulae (VIb) and (VIc). Specific examples are given in the Experimental section, infra. It is readily recognised by the person skilled in the art that the $CH_2OH$ group present in said pyrazolyl methanols of formulae (VIb) and (VIc) can be converted in various other $R^{p1}$ groups (see formula (VI)).

Scheme 4b

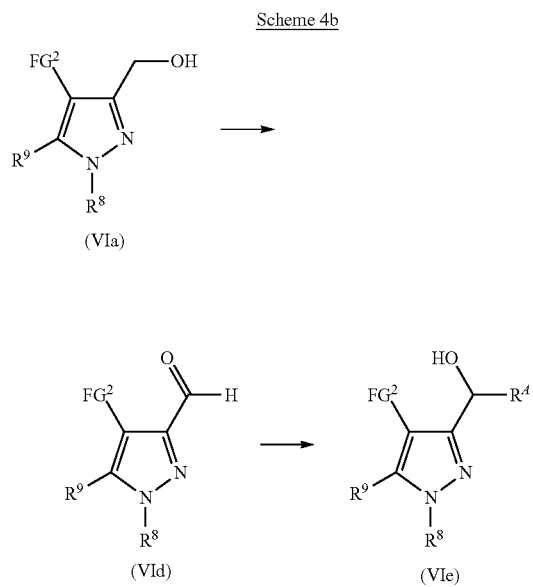

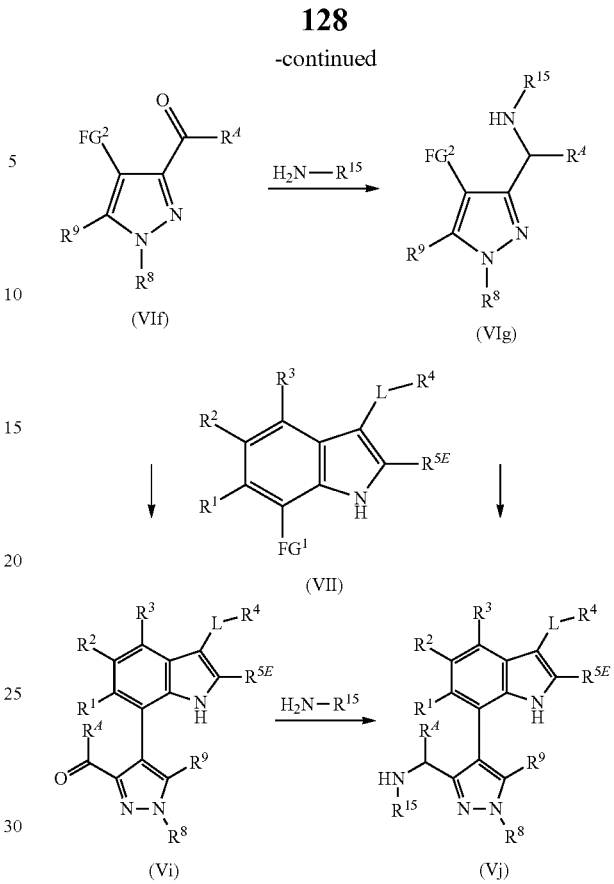

One exemplary series of such conversions is shown in Scheme 4b. As shown therein, pyrazolyl methanols of formula (VIa) can be oxidised by well-known methods, e.g. by reacting with oxalyl chloride and dimethylsulfoxide in the presence of a base such as e.g. trimethylamine (the so-called Swern oxidation), to give the corresponding aldehydes of formula (VId), which can be reacted with reagents of the formula $R^A$—Mg-$LG^5$, in which $LG^5$ represents a leaving group selected from chloro, bromo and iodo, and in which $R^A$ represents a $C_1$-$C_3$-alkyl group, in a solvent such as e.g. tetrahydrofuran or diethyl ether, to give secondary pyrazolyl carbinols of formula (VIe). Said secondary pyrazolyl carbinols of formula (VIe), in turn, can be oxidised again, using well-known methodology, such as a reaction with hypervalent iodine species, e.g. 1,1-bis(acetyloxy)-3-oxo-3H-1λ$^5$,2-benziodaoxol-1-yl acetate, in a solvent such as e.g. dichloromethane, to give the corresponding ketones of formula (VIf). Said ketones of formula (VIf), or the corresponding compounds of formula (Vi), obtainable according to the methods described e.g. in context of Scheme 1 by Suzuki coupling with indole derivatives of formula (VII) as defined supra, can readily be subjected to a well-known reductive amination, i.e. a reaction with an amine of the formula $H_2N$—$R^{15}$, in which $R^{15}$ is as defined for the compounds of formula (I) but preferably different from a hydrogen atom, in the presence of a reagent such as e.g. sodium triacetoxyborohydride or sodium cyanoborohydride, in a solvent such as e.g. a halogenated aliphatic hydrocarbon such as e.g. dichloromethane, 1,2-dichloroethane, or chloroform, or acetonitrile or methanol, to give amine compounds of formulae (VIg) or (Vj), respectively, featuring a substituted $CH_2$ group as defined e.g. for groups $R^6$-$R^7$ in compounds of the general formula (I). It is also possible to obtain compounds of general formula (Vj) according to the methods described e.g. in context of Scheme 1 by Suzuki coupling of amine compounds of formula (VIg), obtained as described above, with indole derivatives of formula (VII) as defined supra.

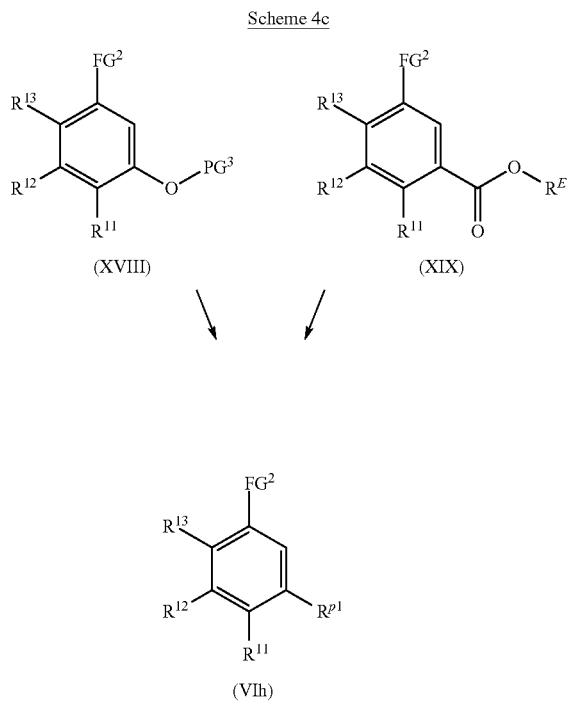

Scheme 4c (XVIII)

(XIX)

(VIh)

Scheme 4c illustrates synthesis routes enabling the preparation of compounds of formula (VI), in which A' is derived from phenyl, pyridinyl, pyrimidinyl or pyridazinyl, namely compounds of formula (VIh), constituting yet another subcompartment of formula (VI).

$R^{12}$, Starting from compounds of formula (XVIII), in which $R^{11}$, and $R^{13}$ are as defined for the compounds of general formula (I), and wherein one or two of the groups selected from $CR^{11}$, $CR^{12}$ or $CR^{13}$ may be replaced by a nitrogen atom, and in which $FG^2$, in combination with the group $FG^1$ present in formula (VII), represents a pair of functional groups together enabling a Suzuki coupling; either $FG^1$ represents chloro, bromo, iodo or a trifluoromethanesulfonyl- group, preferably bromo or iodo, and $FG^2$ represents a group —$B(OR^B)_2$ as defined supra, or vice versa, and in which $PG^3$ represents a protective group, compounds of formula (VIh), in which $R^{p1}$ represents a hydroxy group, can be readily obtained. Likewise, compounds of formula (XIX) in which $R^{11}$, $R^{12}$, and $R^{13}$ are as defined for the compounds of general formula (I), and wherein one or two of the groups selected from $CR^{11}$, $CR^{12}$ or $CR^{13}$ may be replaced by a nitrogen atom, and in which $FG^2$, in combination with the group $FG^1$ present in formula (VII), represents a pair of functional groups together enabling a Suzuki coupling; either $FG^1$ represents chloro, bromo, iodo or a trifluoromethanesulfonyl- group, preferably bromo or iodo, and $FG^2$ represents a group —$B(OR^B)_2$ as defined supra, or vice versa, and $R^E$ represents a group —$C_1$-$C_6$-alkyl, can be converted into compounds of formula (VIh), in which $R_{p1}$ represents a —$CH_2$—OH group, a —C(=O)H group, or a —$CH_2$-$LG^6$ group, in which $LG^6$ represents a leaving group, preferably bromo, in analogy to the methods discussed in the context of the preceding Schemes.

Compounds of formulae (XVIII) and (XIX) are commercially available, and known to the person skilled in the art, in considerable variety. Using known methods, groups $R^{11}$, $R^{12}$ and $R^{13}$ can be broadly modified using known methods at various stages of the synthesis. Protective groups as present in compounds of formula (XVIII), and methods of their removal, are well known to the person skilled in the art, see e.g. T.W. Greene and P.G.M. Wuts in Protective Groups in Organic Synthesis, 4th edition, Wiley 2006.

Indole based starting materials of formula (VII), in which $R^1$, $R^2$, $R^3$, $R^4$ and L are as defined for the compounds of general formula (I), in which $R^{5E}$ represents a group suitable to act as a precursor of a —C(=O)OH or a tetrazol-5-yl group, preferably a group —C(=O)O—$C_{1-4}$-alkyl, and in which $FG^1$ represents chloro, bromo, iodo, a trifluoromethanesulfonyl- group, or a group —$B(OR^B)_2$, preferably bromo or iodo, more preferably group —$B(OR^B)_2$, can be prepared using methods well known to the person skilled in the art, see e.g. Journal of Medicinal Chemistry, 2015, 58, 2180-2194. Said group —$B(OR^B)_2$ may be a boronic acid moiety ($R^B$=—H) or an alkyl ester of the boronic acid, e.g. its isopropyl ester ($R^B$=$C_1$-$C_4$-alkyl, e.g. —$CH(CH_3)_2$), or an ester derived from a diol such as pinacol in which the boronic acid intermediate forms a cyclic boronic ester, preferably a 4,4,5,5-tetramethyl-1,3,2-dioxaborolane ($R^B$-$R^B$=$C_2$-$C_6$-alkylene, preferably —$C(CH_3)_2$—$C(CH_3)_2$—). Alternatively to boronic acid derivatives, also tetrafluoroborates, in which $BF_4^-$ replaces the —$B(OR^B)_2$ moiety, can also be employed.

Modification of any of the substituents, such as $R^1$, $R^2$, $R^3$, $R^4$, $R^5$, $R^{5E}$, $R^6$, $R^7$, $R^8$, $R^9$, $R^{10}$, $R^{11}$, $R^{12}$, $R^{13}$ and $R^{p1}$ can be achieved before and/or after the exemplified transformation. However, also other routes may be used to synthesize the target compounds, in accordance with common general knowledge of a person skilled in the art of organic synthesis. Also, suitable and optionally protected precursor groups of said substituents can be carried through the synthesis routes described in context of the Schemes above, to be elaborated into the actual substituents as defined for the general formula (I) on late stage, as exemplified e.g. for $R^4$ in Intermediates 44 to 85 in the Experimental Section below.

Said modifications can be such as the introduction of protective groups, cleavage of protective groups, reduction or oxidation of functional groups, formation or cleavage of esters or carboxamides, halogenation, metallation, substitution or other reactions known to a person skilled in the art. These transformations include those which introduce a functionality which allows for further interconversion of substituents. Appropriate protective groups and their introduction and cleavage are well-known to a person skilled in the art (see for example T.W. Greene and P.G.M. Wuts in Protective Groups in Organic Synthesis, 4$^{th}$ edition, Wiley 2006). Further, it is possible that two or more successive steps may be performed without work-up being performed between said steps, e.g. a "one-pot" reaction, as it is well-known to a person skilled in the art.

In accordance with a further aspect, the present invention provides a method of preparing a compound of general formula (I) according to any one of claims 1 to 5, said method comprising the step of reacting an intermediate compound of general formula (II):

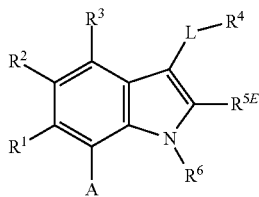
(II)

wherein $R^1$, $R^2$, $R^3$, $R^4$, $R^6$, A and L are as defined for the compound of general formula (I) according to any one of claims 1 to 5, and $R^{5E}$ represents a carboxylic ester group or a benzyl ester group,
with an alkali hydroxide in a mixture of water and THF and/or an aliphatic alcohol of formula $C_1$-$C_3$-alkyl-OH, at a temperature from 0° C. to 100° C. to transform the group $R^{5E}$ into a group $R^5$ as defined for the compounds of general formula (I), and
subsequently optionally to convert the free acid group $R^5$ into a pharmaceutically acceptable salt thereof to obtain a compound of general formula (I)

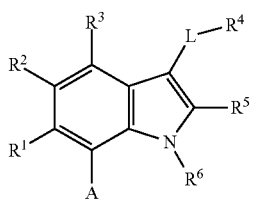
(I)

wherein $R^1$, $R^2$, $R^3$, $R^4$, $R^5$, $R^6$, A and L are as defined for the compound of general formula (I) according to any one of claims 1 to 6 or a stereoisomer, a tautomer, an N-oxide, a hydrate, a solvate, as a salt thereof, or a mixture of same, and subsequently, or as a step preceding the salt conversion, optionally separating enantiomers by means of preparative HPLC on a chiral stationary phase.

In accordance with a further aspect, the present invention covers a method of preparing compounds of general formula (I) according to any one of claims 1 to 5, said method comprising the step of reacting an intermediate compound of general formula (II)

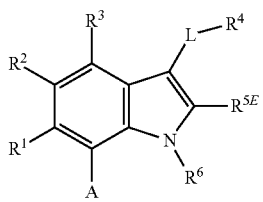
(II)

wherein $R^1$, $R^2$, $R^3$, $R^4$, $R^6$, A and L are as defined for the compound of general formula (I) according to any one of claims 1 to 5, and $R^{5E}$ represents a —C(=O)O—$C_{1-4}$-alkyl group or a benzyl ester with an alkali hydroxide such as e.g. potassium hydroxide, sodium hydroxide, lithium hydroxide, preferably lithium hydroxide, in a mixture of water and THF and/or an aliphatic alcohol of the formula $C_1$-$C_3$-alkyl-OH, preferably methanol or ethanol, at a temperature from 0° C. to 100° C., preferably from 20° C. to 60° C., to transform the group $R^{5E}$ into a group $R^5$ as defined for the compounds of general formula (I), and subsequently optionally to convert the free acid group $R^5$ into a pharmaceutically acceptable salt thereof to obtain a compound of general formula (I)

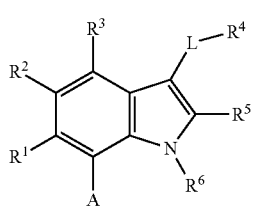
(I)

wherein $R^1$, $R^2$, $R^3$, $R^4$, $R^5$, $R^6$, A and L are as defined for the compound of general formula (I) according to any one of claims 1 to 5 or a stereoisomer, a tautomer, an N-oxide, a hydrate, a solvate, or a salt thereof, or a mixture of same and subsequently or as a step preceding the salt conversion optionally separating enantiomers by means of preparative HPLC on a chiral stationary phase.

The present invention provides methods of preparing compounds of the present invention of general formula (I), said methods comprising the steps as described in the Experimental Section herein.

In accordance with a further aspect, the present invention provides intermediate compounds which are useful for the preparation of the compounds of general formula (I), supra.

Particularly, the invention provides the intermediate compounds of general formula (II)

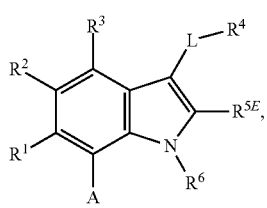
(II)

in which $R^1$, $R^2$, $R^3$, $R^4$, $R^6$, A and L are as defined for the compound of general formula (I) according to any one of claims 1 to 5, and $R^{5E}$ represents a carboxylic ester group, more particularly a —C(=O)O—$C_{1-4}$-alkyl group, or a benzyl group.

In accordance with another aspect, the present invention provides the use of said intermediate compounds for the preparation of a compound of general formula (I) as defined supra.

In accordance with another aspect, the present invention provides a method of using the intermediate compound of general formula (II) for the preparation of a compound of general formula (I).

The present invention provides the intermediate compounds which are disclosed in the Example Section of this text, infra.

The present invention provides any sub-combination within any embodiment or aspect of the present invention of intermediate compounds of general formula (II), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Methods and Administration

Compounds of general formula (I) of the present invention demonstrate a valuable pharmacological spectrum of action and pharmacokinetic profile, both of which could not have been predicted. Compounds of the present invention have surprisingly been found to effectively inhibit MCL-1 activity, and it is possible therefore that said compounds can be used for the treatment or prophylaxis of diseases, preferably hyperproliferative disorders in humans and animals.

As used herein, "prophylaxis" includes a use of the compound that, in a statistical sample, reduces the occurrence of the disorder or condition in the treated sample relative to an untreated control sample, or delays the onset or reduces the severity of one or more symptoms of the disorder or condition relative to the untreated control sample, when administered to prior to the onset of the disorder or condition.

Compounds of the present invention can be utilized to inhibit, block, reduce, and/or decrease cell proliferation and/or cell division, and/or induce apoptosis. Disclosed methods include administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disorder.

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumours.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, basal cell carcinoma, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell lymphoma DLBCL, double-hit lymphoma and double-expressor lymphoma; anaplastic large cell lymphoma, B-cell lymphoma, cutaneous T-cell lymphoma, Burkitt's lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma and Sezary syndrome.

Sarcomas include, but are not limited to, sarcoma of the soft tissue, osteosarcoma, malignant fibrous histiocytoma, lymphosarcoma, and rhabdomyosarcoma.

Leukemias include, but are not limited to acute lymphoblastic leukemia, acute myeloid leukemia, (acute) T-cell leukemia, acute lymphoblastic leukemia, acute lymphocytic leukemia (ALL), acute monocytic leukemia (AML), acute promyelocytic leukemia (APL), bisphenotypic B myelomonocytic leukemia, chronic lymphocytic leukemia, chronic myelogenous leukemia, chronic myeloid leukemia (CML), chronic myelomonocytic leukemia (CMML), large granular lymphocytic leukemia, plasma cell leukemia, and also myelodysplastic syndrome (MDS), which can develop into an acute myeloid leukemia.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opthalmol. Vis. Sci., 1996, 37, 855], neovascular glaucoma, psoriasis, retrolental fibroplasias, angiofibroma, inflammation, rheumatoid arthritis (RA), restenosis, in-stent restenosis, and vascular graft restenosis. In addition, the increased blood supply associated with cancerous and neoplastic tissue encourages growth, leading to rapid tumour enlargement and metastasis. Moreover, the growth of new blood and lymph vessels in a tumour provides an escape route for rapidly dividing cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, and/or decreasing endothelial cell proliferation, or other pathways involved in angiogenesis, as well as causing cell death or apoptosis of such cell types.

These disorders have been well characterized in humans, but also exist with a similar etiology in other mammals, and can be treated by administering pharmaceutical compositions of the present invention.

By "subject" is meant a mammal, including, but not limited to, a human or non-human mammal, such as a bovine, equine, canine, ovine, or feline.

The term "treating" or "treatment" as stated throughout this document is used conventionally, for example the management or care of a subject for the purpose of combating, alleviating, reducing, relieving, and/or improving the condition of a disease or disorder, such as a carcinoma.

The compounds of the present invention can be used in particular in therapy and prevention, i.e., prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:
1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In some embodiments of the present invention, the compounds of general formula (I) of the present invention may be used to sensitize a cell to radiation, i.e., treatment of a cell with a compound of the present invention prior to radiation treatment of the cell renders the cell more susceptible to DNA damage and cell death than the cell would be in the absence of any treatment with a compound of the present invention. In some embodiments, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In some embodiments, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e., after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g., cisplatin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In some embodiments, a compound of general formula (I) of the present invention is administered to a cell prior to the radiation or other induction of DNA damage in the cell. In some embodiments, a compound of general formula (I) of the present invention is administered to a cell concomitantly with the radiation or other induction of DNA damage in the cell. In some embodiments, a compound of general formula (I) of the present invention is administered to a cell immediately after radiation or other induction of DNA damage in the cell has begun.

In some embodiments, the cell is in vitro. In some embodiments, the cell is in vivo.

Thus in some embodiments, the present invention includes a method of inhibiting proliferation of a cell and/or the induction of apoptosis in a cell, comprising contacting the cell with a compound of formula (I) according to any one of claims 1-6.

Another aspect of the invention is a method for controlling cancer (e.g., through treatment and/or prophylaxis) in a subject (e.g., human, other mammal, such as rat, etc.) by administering an effective amount of at least one compound of general formula (I), or a pharmaceutically acceptable salt, polymorph, metabolite, hydrate, solvate or ester thereof to the subject.

In some embodiments, the subject may be administered a medicament, comprising at least one compound of general formula (I) and one or more pharmaceutically acceptable carriers, excipients, and/or diluents.

Furthermore in some embodiments, the present invention includes a method of using a compound of general formula (I) for the treatment of diseases.

Particularly in some embodiments, the present invention includes a method of treating a hyperproliferative disease, more particularly cancer, comprising administering an effective amount of at least one compound of general formula (I) according to any one of claims 1-6.

In some embodiments, the method of treatment and/or prophylaxis of a hyperproliferative disorder in a subject may comprise administering to the subject an effective amount of a compound of general formula (I). The hyperproliferative disorder may be, for example, cancer (e.g., breast cancer, leukemia, lymphoma, multiple myeloma, ovarian cancer etc.).

A method of inhibiting dihydroorotate dehydrogenase activity in a cancer cell is also provided, wherein the method comprises contacting a cancer cell with a compound of general formula (I). The cancer cell may be in vitro or in vivo.

Furthermore in some embodiments, the present invention includes a method of treating cancer, particularly lymphoma, non-Hodgkin-lymphoma type, diffuse large B-cell lymphoma subtype, acute leukemia, acute myeloid leukemia type, multiple myeloma, and ovarian cancer, comprising administering an effective amount of at least one compound of formula (I) according to any one of claims 1-6.

Furthermore in some embodiments, the present invention includes a method of treating cancer, particularly breast cancer, leukemia, lymphoma, multiple myeloma, and ovarian cancer comprising administering an effective amount of at least one compound of formula (I) according to any one of claims 1-6.

Furthermore in some embodiments, the present invention includes a method of treating cancer, particularly breast cancer, leukemia, liver cancer, lung cancer, lymphoma, melanoma, multiple myeloma, squamous cell carcinoma, stomach cancer and ovarian cancer comprising administering an effective amount of at least one compound of formula (I) according to any one of claims 1-6.

Furthermore in some embodiments, the present invention includes a method of treating cancer, particularly breast cancer, triple-negative breast cancer type, Her2-positive breast cancer type, leukemia, acute monocytic leukemia type, liver cancer, lung cancer, small cell lung cancer type, non-small cell lung cancer type, lymphoma, B-cell lymphoma type, mantle cell lymphoma type, melanoma, multiple myeloma, squamous cell carcinoma, stomach cancer and ovarian cancer comprising administering an effective amount of at least one compound of formula (I) according to any one of claims 1-6.

Furthermore in some embodiments, the present invention includes a method of treating cancer, particularly multiple myeloma, ovarian carcinoma, acute monocytic leukemia, melanoma and lung cancer, comprising administering an effective amount of at least one compound of formula (I) according to any one of claims 1-6.

In some embodiments the present invention provides for compounds of general formula (I) for use in a method of treating cancer, particularly where the cancer disease is multiple myeloma, ovarian carcinoma, acute monocytic leukemia, melanoma or lung cancer.

In some embodiments the present invention provides for compounds of general formula (I) for use in a method of treating cancer, particularly where the cancer disease is breast cancer, leukemia, lymphoma, multiple myeloma, or ovarian cancer.

In some embodiments the present invention provides for compounds of general formula (I) for use in a method of treating cancer, particularly where the cancer disease is breast cancer, leukemia, liver cancer, lung cancer, lymphoma, melanoma, multiple myeloma, squamous cell carcinoma, stomach cancer or ovarian cancer.

In some embodiments the present invention provides for compounds of general formula (I) for use in a method of treating cancer, particularly where the cancer disease is breast cancer, triple-negative breast cancer type, Her2-positive breast cancer type, leukemia, acute monocytic leukemia type, liver cancer, lung cancer, small cell lung cancer type, non-small cell lung cancer type, lymphoma, B-cell lymphoma type, mantle cell lymphoma type, melanoma, multiple myeloma, squamous cell carcinoma, stomach cancer or ovarian cancer.

Furthermore in some embodiments, the present invention includes a method of treating cancer, particularly breast cancer; lung cancer; lymphoma including non-Hodgkin-lymphoma type, diffuse large B-cell lymphoma subtype including GC-DLBCL* and ABC-DLBCL subtypes, and mantle cell lymphoma; acute leukemia, acute myeloid leukemia type, acute monocytic leukemia; melanoma; multiple myeloma; ovarian cancer; and pancreas cancer comprising administering an effective amount of at least one compound of formula (I) according to any one of claims 1-6. GC-DLBCL means Germinal B-cell Diffuse Large B-Cell Lymphoma and  ABC-DLBCL means Activated B-cell Diffuse Large B-Cell Lymphoma.

Furthermore in some embodiments, the present invention includes a method of treating cancer, particularly breast cancer, lung cancer, diffuse large B-cell lymphoma subtype including GC-DLBCL* and ABC-DLBCL subtypes, mantle cell lymphoma, acute monocytic leukemia, melanoma, ovarian cancer, and pancreas cancer comprising administering an effective amount of at least one compound of formula (I) according to any one of claims 1-6**. Furthermore in accordance with another aspect, the present invention provides a compound of formula (I) for use of treating diseases.

In some embodiments, the present invention includes a compound of general formula (I) for use in a method of inhibiting proliferation of a cell and/or the induction of apoptosis in a cell, comprising contacting the cell with a compound of formula (I) according to any one of claims 1-6.

Furthermore in some embodiments, the present invention includes a method of treating acute monocytic leukemia in a subject, the method comprising administering to the subject an effective amount of a compound of formula (I).

Particularly in some embodiments, the present invention includes compounds of general formula (I) for use in a method of treating a hyperproliferative disease, more particularly wherein the hyperproliferative disease is cancer, and yet even more particularly wherein the cancer disease is lymphoma, non-Hodgkin-lymphoma type, diffuse large B-cell lymphoma subtype, ovarian cancer, multiple myeloma, acute leukemia, or acute myeloid leukemia.

Particularly in some embodiments, the present invention includes compounds of general formula (I) for use in a method of treating a hyperproliferative disease, more particularly wherein the hyperproliferative disease is cancer, and yet even more particularly wherein the cancer disease is breast cancer; lung cancer; lymphoma including non-Hodgkin-lymphoma type, diffuse large B-cell lymphoma subtype including GC-DLBCL* and ABC-DLBCL** subtypes, and mantle cell lymphoma; acute leukemia, acute myeloid leukemia type, acute monocytic leukemia; melanoma; multiple myeloma; ovarian cancer; or pancreas cancer.

In some embodiments, the present invention includes use of the compounds of general formula (I) for the manufacture of a medicament for the treatment of a hyperproliferative disease, particularly cancer and more particularly breast cancer, leukemia, lymphoma, multiple myeloma and ovarian cancer.

In some embodiments, the present invention includes use of the compounds of general formula (I) for the manufacture of a medicament for the treatment of a hyperproliferative disease, particularly cancer and more particularly breast cancer, leukemia, liver cancer, lung cancer, lymphoma, melanoma, multiple myeloma, squamous cell carcinoma, stomach cancer and ovarian cancer.

In some embodiments, the present invention includes use of the compounds of general formula (I) for the manufacture of a medicament for the treatment of a hyperproliferative disease, particularly cancer and more particularly breast cancer, triple-negative breast cancer type, Her2-positive breast cancer type, leukemia, acute monocytic leukemia type, liver cancer, lung cancer, small cell lung cancer type, non-small cell lung cancer type, lymphoma, B-cell lymphoma type, mantle cell lymphoma type, melanoma, multiple myeloma, squamous cell carcinoma, stomach cancer and ovarian cancer.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, or otic route or as an implant or stent.

For these administration routes, it is possible for the compounds according to the invention to be administered in suitable administration forms.

For oral administration, it is possible to formulate the compounds according to the invention into dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatin capsules), sugar-coated tablets, granules, pellets, powders, emulsions, suspensions, aerosols or solutions. It is possible to incorporate the compounds according to the invention in crystalline and/or amorphous and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation (inter alia powder inhalers, nebulizers), nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example, cellulose, microcrystalline cellulose (such as, for example, Avicel®), lactose, mannitol, starch, calcium phosphate (such as, for example)) Di-Cafos®)),
  ointment bases (for example petroleum jelly, paraffins, triglycerides, waxes, wool wax, wool wax alcohols, lanolin, hydrophilic ointment, polyethylene glycols), bases for suppositories (for example, polyethylene glycols, cacao butter, hard fat),
solvents (for example, water, ethanol, isopropanol, glycerol, propylene glycol, medium chain-length triglycerides, fatty oils, liquid polyethylene glycols, paraffins),
surfactants, emulsifiers, dispersants or wetters (for example, sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxyethylene fatty acid esters, polyoxyethylene fatty alcohol ethers, glycerol fatty acid esters, poloxamers (such as, for example, Pluronic®),
buffers, acids and bases (for example, phosphates, carbonates, citric acid, acetic acid, hydrochloric acid, sodium hydroxide solution, ammonium carbonate, trometamol, triethanolamine),
isotonicity agents (for example, glucose, sodium chloride),
adsorbents (for example, highly-disperse silicas),
viscosity-increasing agents, gel formers, thickeners and/or binders (for example, polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatin),
disintegrants (for example, modified starch, carboxymethylcellulose-sodium, sodium starch glycolate (such as, for example, Explotab®), cross- linked polyvinylpyrrolidone, croscarmellose-sodium (such as, for example, AcDiSol®)),
flow regulators, lubricants, glidants and mould release agents (for example, magnesium stearate, stearic acid, talc, highly-disperse silicas (such as, for example, Aerosil®)),
coating materials (for example, sugar, shellac) and film formers for films or diffusion membranes which dissolve rapidly or in a modified manner (for example, polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)),
capsule materials (for example, gelatin, hydroxypropylmethylcellulose),
synthetic polymers (for example, polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers),
plasticizers (for example, polyethylene glycols, propylene glycol, glycerol, triacetine, triacetyl citrate, dibutyl phthalate),
penetration enhancers,
stabilisers (for example, antioxidants such as, for example, ascorbic acid, ascorbyl palmitate, sodium ascorbate, butylhydroxyanisole, butylhydroxytoluene, propyl gallate),
preservatives (for example, parabens, sorbic acid, thiomersal, benzalkonium chloride, chlorhexidine acetate, sodium benzoate),
colourants (for example, inorganic pigments such as, for example, iron oxides, titanium dioxide), and flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In some embodiments, the present invention includes pharmaceutical combinations, in particular medicaments, comprising at least one compound of general formula (I) of the present invention and at least one or more further active ingredients, in particular for the treatment and/or prophylaxis of a hyperproliferative disorder, particularly cancer.

Particularly, the present invention includes a pharmaceutical combination, which comprises:
- one or more first active ingredients, in particular compounds of general formula (I) as defined supra, and
- one or more further active ingredients, in particular for the treatment and/or prophylaxis of hyperproliferative disorder, particularly cancer.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent, or in combination with one or more other pharmaceutically active ingredients where the combination causes no unacceptable adverse effects. The present invention also includes such pharmaceutical combinations. For example, the compounds of the present invention can be combined with known anti-cancer agents.

Examples of anti-cancer agents include:
131I-chTNT, abarelix, abemaciclib, abiraterone, acalabrutinib, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, apalutamide, aprepitant, arcitumomab, arglabin, arsenic trioxide, asparaginase, atezolizumab, avelumab, axicabtagene ciloleucel, axitinib, azacitidine, basiliximab, belotecan, bendamustine, besilesomab, belinostat, bevacizumab, bexarotene, bicalutamide, bisantrene, bleomycin, blinatumomab, bortezomib, bosutinib, buserelin, brentuximab vedotin, brigatinib, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, durvalumab, eculizumab, edrecolomab, elliptinium acetate, elotuzumab, eltrombopag, enasidenib, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, inotuzumab ozogamicin, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, lutetium Lu 177 dotatate, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, midostaurin, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, mvasi, nabilone, nabiximols, nafarelin, naloxone+pentazocine, naltrexone, nartograstim, necitumumab, nedaplatin, nelarabine, neratinib, neridronic acid, netupitant/palonosetron, nivolumab, pentetreotide, nilotinib, nilutamide, nimorazole, nimotuzumab, nimustine, nintedanib, niraparib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide- K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, ribociclib, risedronic acid, rhenium-186 etidronate, rituximab, rolapitant, romidepsin, romiplostim, romurtide, rucaparib, samarium (153Sm) lexidronam, sargramostim, sarilumab, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tisagenlecleucel, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, and zorubicin.

Based upon standard laboratory techniques known to evaluate compounds useful for the treatment of hyperproliferative diseases, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 40 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 3000 mg of active ingredient, or from about 0.5 mg to about 1500 mg (e.g. about 0.5 mg to about 5 mg, about 5 mg to about 50 mg, about 50 mg to about 500 mg, about 500 mg to about 1500 mg, etc.) and can be administered one or more times per day or less than once a day. The average daily dosage for administration by injection, including intravenous, intramuscular, subcutaneous and parenteral injections, and use of infusion techniques will preferably be from about 0.01 to about 200 mg/kg of total body weight. The average daily rectal dosage regimen will preferably be from about 0.01 to about 200 mg/kg of total body weight. The average daily vaginal dosage regimen will preferably be from about 0.01 to about 200 mg/kg of total body weight. The average daily topical dosage regimen will preferably be from about 0.1 to about 200 mg administered between one to four times daily. The transdermal concentration will preferably be that required to maintain a daily dose of from about 0.01 to about 200 mg/kg. The average daily inhalation dosage regimen will preferably be from about 0.01 to about 100 mg/kg of total body weight.

In one embodiment the average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from about 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

Experimental Section—NMR Spectra

To the extent NMR peak forms and multiplicities are specified, they are stated as they appear in the spectra, possible higher order effects have not been considered.

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$), . . . , $δ_i$ (intensity$_i$), . . . , $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Experimental Section—Abbreviations

The following table lists the abbreviations used in this paragraph and in the Intermediates and Examples section as far as they are not explained within the text body. Other abbreviations have their meanings customary per se to the skilled person. A comprehensive list of the abbreviations utilized by organic chemists of ordinary skill in the art appears presented in the first issue of each volume of the Journal of Organic Chemistry; this list is typically presented in a table titled "Standard List of Abbreviations". In case of doubt, the abbreviations and/or their meaning according to the following table shall prevail.

TABLE 1

Abbreviations

| Abbreviation | Meaning |
| --- | --- |
| br. | broad signal (NMR) |
| BPR | Back Pressure Regulator |
| d | doublet (NMR) |
| DAD | Diode array detector |
| dd | doublet of doublet (NMR) |
| dt | doublet of triplet (NMR) |
| DMF | N,N-Dimethylformamide |
| DMSO | dimethylsulfoxide |
| EDC | N-[3-(dimethylamino)propyl]-N'-ethylcarbodiimide hydrochloride |
| EDTA | ethylenediaminetetraacetic acid |
| ee | enantiomeric excess |
| ESI | electrospray (ES) ionisation |
| h, hr (hrs) | hour(s) |
| HCl | hydrogen chloride, hydrochloric acid |
| HPLC | high performance liquid chromatography |
| HRP | horseradish peroxidase |
| LC-MS | liquid chromatography-mass spectrometry |
| m | multiplet (NMR) |
| Min | minute(s) |
| MS | mass spectrometry |
| MTP | microtiter plate |
| MWD | Multiple wavelength detector |
| NHS | N-Hydroxysuccinimide |
| Na—K-tartrate | Sodium potassium tartrate |
| NMR | nuclear magnetic resonance spectroscopy: chemical shifts (δ) are given in ppm. The chemical shifts were corrected by setting the DMSO signal to 2.50 ppm using dmso-d6 unless otherwise stated. |
| NAD$^+$ | nicotinamide adenine dinucleotide |
| PBS | phosphate buffered saline |
| Pd(dppf)Cl$_2$x CH$_2$Cl$_2$ | [1,1'-Bis-(diphenylphosphino)-ferrocen]-dichloropalladium(II), complex with dichloromethanen |
| q | quartet (NMR) |
| quin | quintet (NMR) |
| rt | room temperature |
| R$_t$, Rt | retention time |
| s | singulet (NMR) |
| SFC | Supercritical Fluid Chromatography |
| SPA | Scintillation proximity assay |
| t | triplet (NMR) |
| td | triplet of doublet (NMR) |
| TFA | trifluoroacetic acid |
| THF | tetrahydrofuran |
| TLC | thin layer chromatography |
| wt-% | percent of weight |
| UPLC | ultra performance liquid chromatography |
| UV | ultraviolet |
| [$^3$H]- | tritium |
| δ | chemical shift |
| XPhos Pd G2 | Chloro(2-dicyclohexylphosphino-2',4',6'-triisopropyl-1,1'-biphenyl)[2-(2'-amino-1,1'-biphenyl)]palladium(II) (Cas No: 1310584-14-5) |

TABLE 1-continued

Abbreviations

| Abbreviation | Meaning |
|---|---|
| XPhos Pd G3 | (2-Dicyclohexylphosphino-2',4',6'-triisopropyl-1,1'-biphenyl)[2-(2'-amino-1,1'-biphenyl)]palladium(II) methanesulfonate (Cas No: 1445085-55-1) |
| SPhos Pd G3 | (2-Dicyclohexylphosphino-2',6'-dimethoxybiphenyl) [2-(2'-amino-1,1'-biphenyl)]palladium(II) methanesulfonate (CAS No: 1445085-82-4) |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art. Reactions were set up and started, e.g. by the addition of reagents, at temperatures as specified in the protocols; if no temperature is specified, the respective working step was performed at ambient temperature, i.e. between 18 and 25° C.

"Silicone filter" or "water resistant filter" refers to filter papers which are made hydrophobic (impermeable to water) by impregnation with a silicone. With the aid of these filters, water can be separated from water-immiscible organic solvents by means of a filtration (i.e. filter paper type MN 617 WA, Macherey-Nagel).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be removed by trituration using a suitable solvent or solvent mixture. In some cases, the compounds may be purified by chromatography, particularly flash column chromatography, using for example prepacked silica gel cartridges, e.g. Biotage SNAP cartridges KP-Sil® or KP-NH®, preferably in combination with a partially or fully automated column chromatography device, such as a Biotage autopurifier system (SP4® or Isolera Four®) or an ISCO column chromatography device, and eluents such as gradients of hexane/ethyl acetate or DCM/ethanol. In flash column chromatography, unmodified ("regular") silica gel may be used as well as aminophase functionalized silica gel. As used herein, "Biotage SNAP cartridge silica" refers to the use of regular silica gel; "Biotage SNAP cartridge $NH_2$ silica" refers to the use of aminophase functionalized silica gel. If reference is made to flash column chromatography or to flash chromatography in the experimental section without specification of a stationary phase, regular silica gel was used. Further, column chromatography can also be used advantageously in the reversed-phase mode, using materials such as C-18 silica gel as stationary phase, and using eluents such as gradients of water and acetonitrile which may contain additives such as trifluoroacetic acid, formic acid, diethylamine or aqueous ammonia. If reference is made to reversed phase column chromatography in the experimental section without specification of a stationary phase, C-18 silica gel was used.

In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid, diethylamine or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI−).

Analytical UPLC Methods:

Method 1:

Instrument: Waters Acquity UPLCMS SingleQuad; Column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; DAD scan: 210-400 nm.

Method 2:

Instrument: Waters Acquity UPLCMS SingleQuad; Column: Acquity UPLC BEH C18 1.7 µm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

Method 3:

Instrument: Waters Alliance HT; Column: Waters Cortecs 30 mm×3 mm×2.7 µm; eluent A: Water (MilliQ)+0.01 vol % formic acid, eluent B: acetonitrile+0.01 vol % formic acid; gradient: 0-1.7 min 3-95% B, 1.7-2.2 min 95% B; 2.3-2.5 3% B; flow: 1.75 mL/mn; temperature: 45° C.; DAD scan: 200-500 nm.

Method 4:

Instrument: Waters Alliance HT; Column: Waters Cortecs 30 mm×3 mm×2.7 µm; eluent A: Water (MilliQ)+0.01 vol % formic acid, eluent B: acetonitrile+0.01 vol % formic acid; gradient: 0-6.8 min 5-95% B, 6.8-7.3 min 95% B; 7.3-7.5 5% B; flow: 1.75 mL/mn; temperature: 45° C.; DAD scan: 200-500 nm.

Method 5:

Instrument: Waters Acquity; Column: Waters Acquity BEH C18 50 mm×2.1 mm×1.7 µm; eluent A: Water (MilliQ)+0.01 vol % formic acid, eluent B: acetonitrile+0.01 vol % formic acid; gradient: 0-0.3 min 3-4% B, 0.3-1.5 min 4-95% B, 1.5-1.9 min 95% B; 1.9-2.0 min 5% B; flow: 0.65 mL/min; temperature: 50° C.; DAD scan: 200-500 nm.

Method 6:

Instrument: Waters Acquity; Column: Waters Acquity BEH C18 50 mm×2.1 mm×1.7 µm; eluent A: Water (MilliQ)+0.01 vol % formic acid, eluent B: acetonitrile+0.01 vol % formic acid; gradient: 0-0.5 min 2% B, 0.5-1.5 min 2-95% B, 1.5-1.9 min 95% B; 1.9-2.0 min 95-2% B, 2.0-2.5 min, 2% B; flow: 0.65 mL/min; temperature: 45° C.; DAD scan: 200-500 nm.

Method 7:

Instrument: Waters Acquity; Column: Waters Acquity BEH C18 50 mm×2.1 mm×1.7 µm; eluent A: Water (MilliQ)+0.01 vol % formic acid, eluent B: acetonitrile+0.01 vol % formic acid; gradient: 0-0.5 min 2-5% B, 0.5-4.0 min 5-95% B, 4.0-4.5 min 95% B, 4.5-5.0 min 95-2% B; flow: 0.65 mL/min; temperature: 45° C.; DAD scan: 200-500 nm.

Preparative HPLC Methods:

Method P1:

Instrument: Waters Autopurification MS SingleQuad; Column: Waters XBrigde C18 5µ 100×30 mm; eluent A: water+0.1 vol % formic acid (99%), eluent B: acetonitrile; gradient: 0-5.5 min 5-100% B; flow 70 mL/min; temperature: 25° C.; DAD scan: 210-400 nm.

Method P2:

Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; solvent A: water+0.1 vol-% formic acid, solvent B: acetonitrile; gradient: 0.00-0.50 min 40% B (150 mL/min), 0.50-6.00 min 40-80% B (150 mL/min), 6.00-6.10 min 80-100% B (150 mL/min), 6.10-8.00 min 100% B (150 mL/min), UV-Detection.

Method P3:

Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: Chromatorex RP C-18 10 µm, 125×30 mm; solvent A: water+0.1 vol-% formic acid, solvent B: acetonitrile; gradient: 0.00-0.50 min 65% B (150 mL/min), 0.50-6.00 min 65-100% B (150 mL/min), 6.00-8.00 min 100% B (150 mL/min), UV-Detection.

Method P4:

Instrument: Pump: Labomatic HD-5000 or HD-3000, Head HDK 280, low pressure gradient module ND-B1000; Manual injection valve: Rheodyne 3725i038; Detector: Knauer Azura UVD 2.15; Collector: Labomatic Labocol Vario-4000; Column: XBridge, RP C18 5 µm, 100×30 mm; Solvent A: water+0.2 Vol-% ammonia (32%), Solvent B: acetonitrile, gradient: 0.00-2.00 min 10% B (60 mL/min), 2.00-14.00 min 10-50% B (60 mL/min), 14.00-14.10 min 50-100% B (60 mL/min), 14.10-17.00 min 100% B (60 mL/min), UV-Detection.

Specific Optical Rotation Methods:

Method O1: Instrument: JASCO P2000 Polarimeter; wavelength 589 nm; temperature: 20° C.; integration time 10 s; path length 100 mm.

INTERMEDIATES

Intermediate 1

Ethyl 3-[3-(naphthalen-1-yloxy)propyl]-7-(4,4,5,5-tetramethyl-1,3,2-dioxaborolan-2-yl)-1H-indole-2-carboxylate

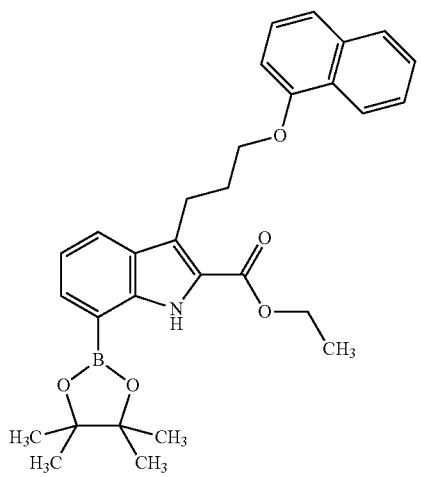 [SMILES: CCOC(=O)c1[nH]c2c(B3OC(C)(C)C(C)(C)O3)cccc2c1CCCOc1cccc2ccccc12]

Ethyl-3-[3-(naphthalen-1-yloxy)propyl]-7-(4,4,5,5-tetramethyl-1,3,2-dioxaborolan-2-yl)-1H-indole-2-carboxylate was prepared as described in the literature (Journal of Medicinal Chemistry, 2015, 58, 2180-2194).

Intermediate 2

Ethyl 7-bromo-6-chloro-3-(3-hydroxpropyl)-1H-indole-2-carboxylate

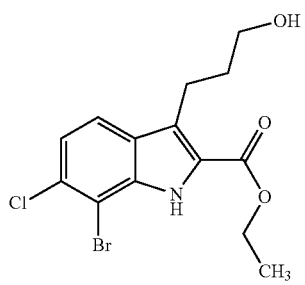 [SMILES: CCOC(=O)c1[nH]c2c(Br)c(Cl)ccc2c1CCCO]

The title compound was prepared as described in J. Med. Chem. 2015, 58, 3794-3805.

Intermediate 3

Ethyl 7-bromo-6-chloro-3-[3-(naphthalen-1-yloxy)propyl]-1H-indole-2-carboxylate

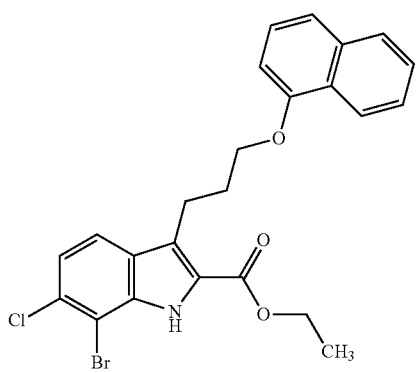 [SMILES: CCOC(=O)c1[nH]c2c(Br)c(Cl)ccc2c1CCCOc1cccc2ccccc12]

To a mixture of ethyl 7-bromo-6-chloro-3-(3-hydroxpropyl)-1H-indole-2-carboxylate (see intermediate 2, 6.62 g, 18.4 mmol), naphthalen-1-ol (CAS 90-15-3, 3.21 g, 99% purity, 22.0 mmol) and triphenylphosphine (5.84 g, 22.0 mmol) in THF (150 mL) was added diisopropyl azodicarboxylate (4.4 mL, 22 mmol) at 10° C. and the mixture was stirred for 24 hours at room temperature. For work-up, the mixture was diluted with ethyl acetate and was washed with aqueous sodium bicarbonate solution and brine. The organic phase was dried over sodium sulfate, filtered and the filtrate was concentrated under reduced pressure. The crude product was purified by flash chromatography (20-100% dichloromethane/hexane gradient) to give, after subsequent trituration with methanol, the title compound (3.5 g).

Intermediate 4

Ethyl 6-chloro-3-[3-(naphthalen-1-yloxy)propyl]-7-(4,4,5,5-tetramethyl-1,3,2-dioxaborolan-2-yl)-1H-indole-2-carboxylate

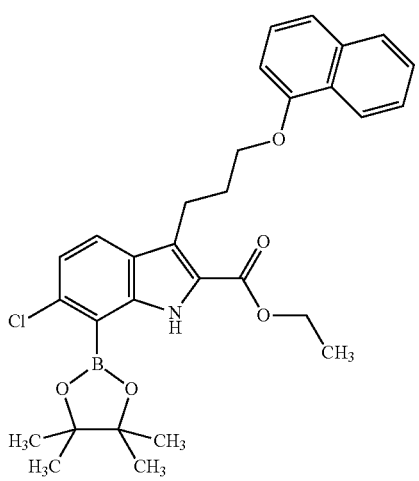 [SMILES: CCOC(=O)c1[nH]c2c(B3OC(C)(C)C(C)(C)O3)c(Cl)ccc2c1CCCOc1cccc2ccccc12]

To a degassed mixture of ethyl 7-bromo-6-chloro-3-[3-(naphthalen-1-yloxy)propyl]-1H-indole-2-carboxylate (see Intermediate 3 5.50 g, 11.3 mmol) and 4,4,4',4',5,5,5',5'-octamethyl-2,2'-bi-1,3,2-dioxaborolane (CAS 78183-34-3, 8.61 g, 33.9 mmol) in 1,4-dioxane (97 mL) was added potassium acetate (4.44 g, 45.2 mmol) and to the mixture was added 1,1'-Bis(diphenylphosphino)ferrocenpalladium (II)chloride (827 mg, 1.13 mmol), and the reaction mixture was purged with argon for 10 minutes. The mixture was stirred for 24 hours at 80° C. For work-up the mixture was concentrated and the residue was purified by flash chromatography (Biotage SNAP cartridge silica, 7%→25% ethyl acetate/hexane gradient) to give the title compound (1.5 g).

Intermediate 5

Ethyl 4-bromo-1,5-dimethyl-1H-pyrazole-3-carboxylate

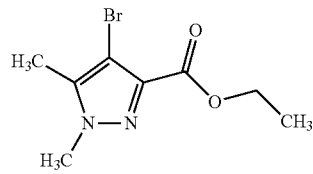

N-Bromosuccinimide (16.3 g, 90.5 mmol) was added to a solution of ethyl 1,5-dimethyl-1H-pyrazole-3-carboxylate (7.25 g, 43.1 mmol, CAS No 5744-51-4) in 1,2-dichloroethane (150 mL) and the mixture was stirred for 15 h at 80° C. For work-up, the mixture was diluted with dichloromethane, washed with water and the organic phase was filtered through a silicone filter and concentrated. The residue was purified by flash chromatography (Biotage SNAP cartridge silica 340 g, 0→100% dichloromethane//hexane gradient) to give the title compound (6.49 g, 61 yield).

$^1$H-NMR (400 MHz, DMSO-d6) δ[ppm]: 1.261 (4.14), 1.278 (8.78), 1.296 (4.21), 2.268 (14.94), 2.518 (0.74), 2.523 (0.49), 3.857 (16.00), 4.229 (1.31), 4.247 (4.03), 4.264 (3.94), 4.282 (1.24).

Intermediate 6

(4-Bromo-1,5-dimethyl-1H-pyrazol-3-yl)methanol

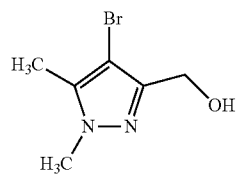

Lithium borohydride (711 mg, 32.6 mmol) was added to a solution of ethyl 4-bromo-1,5-dimethyl-1H-pyrazole-3-carboxylate (see intermediate 5, 6.45 g, 26.1 mmol) in THF (150 mL) and the mixture was stirred for 1 h at room temperature, followed by stirring for 7 h at 60° C. The reaction was stopped by addition of saturated aqueous ammonium chloride solution and the mixture was extracted with ethyl acetate. The organic phase was filtered through a silicone filter and concentrated. The residue was purified by flash chromatography (50%→100% ethyl acetate/hexane gradient) to give the title compound (4.07 g, 76% yield).

¹H-NMR (400 MHz, DMSO-d6) δ[ppm]: 2.205 (16.00), 2.518 (0.43), 3.330 (10.35), 4.285 (3.97), 4.299 (4.13), 4.933 (1.00), 4.946 (2.22), 4.960 (0.93).

Intermediate 7

Ethyl 5-ethyl-1-methyl-1H-pyrazole-3-carboxylate

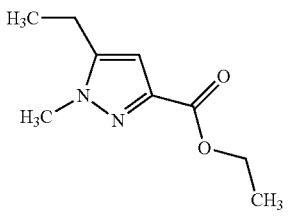

Ethyl 2,4-dioxohexanoate (CAS 13246-52-1, 5.00 g, 29.0 mmol) was dissolved in 20 mL of acetic acid. Under ice cooling methylhydrazine (1.5 mL, 29.0 mmol) was added and the mixture was stirred at rt for 23 hours. Another portion of methylhydrazine (0.5 mL, 10.0 mmol) was added and stirring was continued at rt for 24 hours. The reaction mixture was poured into ice water and extracted with ethyl acetate. The combined organic layers were washed with brine, dried using a water resistant filter and concentrated under reduced pressure. The crude material was purified by flash chromatography using silica gel (gradient hexane/ethyl acetate) to obtain the title compound (2.13 g, 40% yield).

LC-MS (Method 1): $R_t$=0.92 min; MS (ESIpos): m/z=183 [M+H]⁺

¹H-NMR (400 MHz, DMSO-d6) δ[ppm]: 1.170 (6.09), 1.188 (12.55), 1.208 (6.57), 1.245 (7.14), 1.263 (16.00), 1.280 (7.23), 2.601 (1.10), 2.602 (1.08), 2.619 (3.24), 2.621 (3.35), 2.638 (3.29), 2.640 (3.34), 2.657 (1.02), 2.659 (1.03), 3.331 (8.78), 4.200 (1.95), 4.218 (6.25), 4.236 (6.29), 4.254 (1.95), 5.759 (0.98), 6.518 (4.92).

Intermediate 8

Ethyl 4-bromo-5-ethyl-1-methyl-1H-pyrazole-3-carboxylate

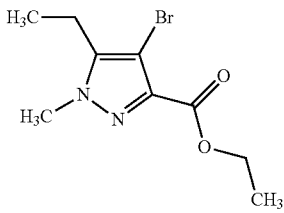

Ethyl 5-ethyl-1-methyl-1H-pyrazole-3-carboxylate (see intermediate 7, 2.10 g, 11.5 mmol) was dissolved in 15 mL of acetic acid. A solution of bromine in acetic acid (23 mL, 1.0 M, 23 mmol) was added dropwise and the reaction mixture was stirred for 18 hours at rt. The mixture was poured into ice water and aqueous sodium thiosulfate solution (10%) was added. The mixture was extracted with ethyl acetate, and the combined organic layers were washed with brine, dried using a water resistant filter and concentrated under reduced pressure to obtain 2.97 g of the title compound. The crude material was used without further purification in the next step.

LC-MS (Method 1): $R_t$=1.08 min; MS (ESIpos): m/z=261 [M+H]⁺

¹H-NMR (400 MHz, DMSO-d6) δ[ppm]: 1.077 (2.69), 1.096 (6.29), 1.115 (2.81), 1.260 (3.48), 1.278 (7.87), 1.295 (3.68), 1.907 (1.63), 2.518 (0.62), 2.523 (0.41), 2.673 (0.89), 2.692 (2.71), 2.711 (2.65), 2.730 (0.75), 3.894 (16.00), 4.231 (1.11), 4.249 (3.60), 4.266 (3.59), 4.284 (1.10).

Intermediate 9

(4-Bromo-5-ethyl-1-methyl-1H-pyrazol-3-yl)methanol

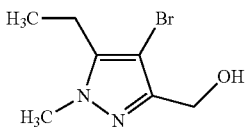

Ethyl 4-bromo-5-ethyl-1-methyl-1H-pyrazole-3-carboxylate (see intermediate 8, 2.97 g) was dissolved in 45 mL of THF and lithium borohydride (310 mg, 14.2 mmol) was added portionwise. This mixture was stirred for 20 hours at rt and for 22 hours at 60° C. Another portion of lithium borohydride (50 mg, 2.3 mmol) was added and stirring was continued for 24 hours at rt, and subsequently for 3 hours at 60° C. The reaction mixture was diluted with saturated aqueous ammonium chloride solution and extracted with ethyl acetate. The combined organic layers were washed with brine, dried using a water resistant filter and concentrated under reduced pressure to obtain the title compound (2.18 g). The crude material was used without further purification in the next step.

LC-MS (Method 1): $R_t$=0.79 min; MS (ESIpos): m/z=219 [M+H]⁺

¹H-NMR (400 MHz, DMSO-d6) δ[ppm]: 1.068 (3.21), 1.087 (7.19), 1.105 (3.37), 2.518 (0.44), 2.609 (1.02), 2.628 (3.36), 2.647 (3.29), 2.666 (1.04), 3.761 (16.00), 4.287 (4.77), 4.301 (4.91), 4.941 (1.34), 4.955 (2.69), 4.969 (1.21).

Intermediate 10

Ethyl 7-[3-(hydroxymethyl)-1,5-dimethyl-1H-pyrazol-4-yl]-3-[3-(naphthalen-1-yloxy)propyl]-1H-indole-2-carboxylate

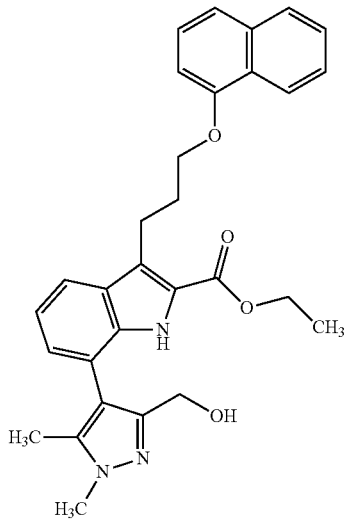 [SMILES: CCOC(=O)c1[nH]c2c(-c3c(CO)nn(C)c3C)cccc2c1CCCOc1cccc2ccccc12]

XPhos Pd G2 (see abbreviations; 483 mg, 613 µmol) was added to a degassed mixture of ethyl-3-[3-(naphthalen-1-yloxy)propyl]-7-(4,4,5,5-tetramethyl-1,3,2-dioxaborolan-2-yl)-1H-indole-2-carboxylate (see intermediate 1; 10.0 g, 20.0 mmol), (4-bromo-1,5-dimethyl-1H-pyrazol-3-yl)methanol (3.73 g, 18.2 mmol, see intermediate 6), aqueous potassium phosphate solution (73 mL, 0.50 M, 36 mmol) and THF (220 mL). The mixture was stirred for 2 h at 45° C. For work-up, ethyl acetate was added, the mixture was filtered through a pad of celite, eluted with ethyl acetate and the organic phase was washed with brine, filtered through a silicone filter and concentrated. The residue was purified by flash chromatography (Biotage SNAP cartridge silica 340 g, 50%→100% ethyl acetate/hexane gradient) to give the title compound (6.26 g, 63% yield).

LC-MS (Method 1): $R_t$=1.53 min; MS (ESIpos): m/z=498 [M+H]$^+$ $^1$H-NMR (400 MHz, DMSO-d6) δ[ppm]: 1.155 (0.41), 1.173 (0.87), 1.190 (0.43), 1.256 (4.82), 1.273 (10.89), 1.291 (4.91), 1.988 (1.61), 2.164 (15.76), 2.205 (5.25), 2.213 (1.06), 2.231 (1.35), 2.250 (1.03), 2.518 (4.03), 2.523 (2.82), 3.355 (2.05), 3.373 (1.25), 3.726 (4.77), 3.802 (16.00), 4.199 (1.49), 4.214 (3.13), 4.222 (2.24), 4.229 (1.83), 4.240 (5.74), 4.249 (2.82), 4.258 (5.54), 4.275 (1.50), 4.286 (1.45), 4.300 (1.40), 4.947 (0.67), 5.705 (1.59), 6.907 (1.76), 6.925 (1.90), 7.060 (0.72), 7.077 (2.44), 7.090 (2.89), 7.096 (5.04), 7.108 (0.79), 7.373 (1.28), 7.394 (2.46), 7.413 (2.02), 7.450 (2.56), 7.471 (1.40), 7.492 (0.58), 7.505 (1.56), 7.509 (1.42), 7.514 (1.62), 7.521 (3.30), 7.529 (1.74), 7.533 (1.54), 7.538 (1.62), 7.551 (0.63), 7.656 (1.49), 7.662 (1.33), 7.674 (1.37), 7.679 (1.33), 7.861 (1.49), 7.868 (0.80), 7.879 (1.35), 7.884 (1.25), 8.230 (1.30), 8.236 (1.23), 8.254 (1.25), 11.324 (1.73).

Intermediate 11

Ethyl 6-chloro-7-[3-(hydroxymethyl)-1,5-dimethyl-1H-pyrazol-4-yl]-3-[3-(naphthalen-1-yloxy)-propyl]-1H-indole-2-carboxylate

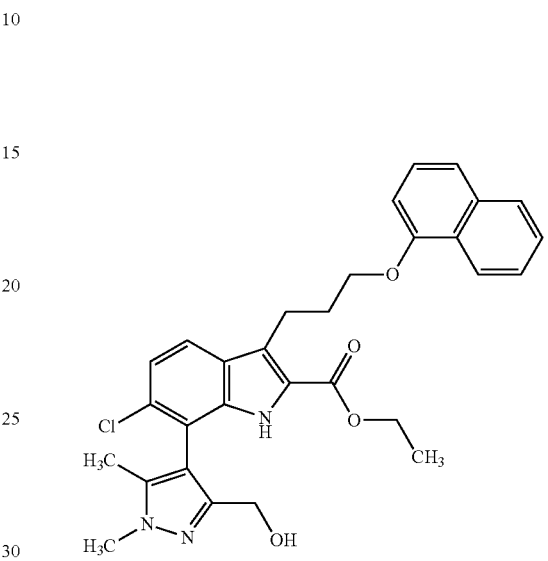

The reaction was performed in four identical preparations using a quarter of all materials.

Ethyl 6-chloro-3-[3-(naphthalen-1-yloxy)propyl]-7-(4,4,5,5-tetramethyl-1,3,2-dioxaborolan-2-yl)-1H-indole-2-carboxylate (see intermediate 4, 10.0 g, 18.7 mmol) and (4-bromo-1,5-dimethyl-1H-pyrazol-3-yl)methanol (see intermediate 6, 3.84 g, 18.7 mmol) were dissolved in 40 mL of 1,4-dioxane and 20 mL of water and purged with argon for 5 min. Potassium phosphate (9.54 g, 45.0 mmol) and Xphos Pd G3 (1.90 g, 2.25 mmol) were added and the mixture was purged with argon for 5 min and heated for 30 min. to 100° C. in a microwave reactor. The four reaction mixtures were diluted with water and extracted with ethyl acetate. The combined organic phases were washed with brine, dried using a water resistant filter, and concentrated under reduced pressure. The crude product was purified by flash chromatography using silica gel (gradient dichloromethane/ethanol) to obtain the title compound (6.58 g, 59% yield).

LC-MS (Method 1): $R_t$=1.57 min; MS (ESIpos): m/z=532 [M+H]$^+$ $^1$H-NMR (400 MHz, DMSO-d6) δ[ppm]: 1.066 (16.00), 1.138 (1.09), 1.241 (1.06), 1.259 (2.41), 1.277 (1.08), 1.997 (3.38), 2.116 (0.49), 2.205 (0.91), 2.518 (0.47), 3.565 (3.58), 3.725 (0.74), 3.800 (3.23), 3.939 (2.88), 4.214 (0.62), 4.241 (0.56), 4.244 (0.63), 4.259 (0.59), 4.261 (0.56), 7.162 (0.91), 7.183 (0.92), 7.398 (0.52), 7.417 (0.43), 7.453 (0.53), 7.521 (0.74), 7.693 (0.59), 7.715 (0.55), 10.885 (0.44).

Intermediate 12

Ethyl 7-[1,5-dimethyl-3-({[2-(morpholin-4-yl)ethyl]amino}methyl)-1H-pyrazol-4-yl]-3-{3-[(naphthalen-1-yl)oxy]propyl}-1H-indole-2-carboxylate

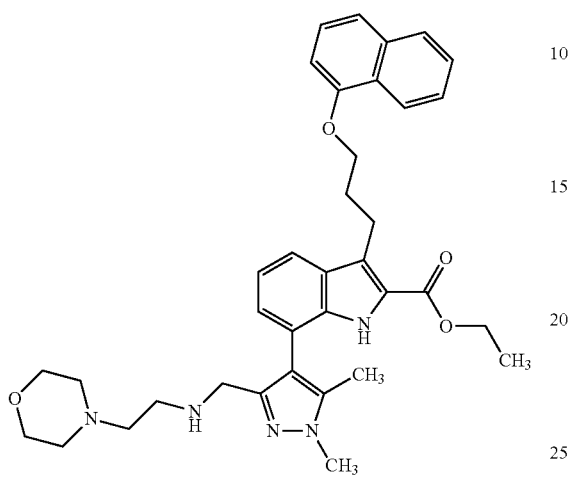

To a solution of ethyl 7-[3-(hydroxymethyl)-1,5-dimethyl-1H-pyrazol-4-yl]-3-[3-(1-naphthyloxy)propyl]-1H-indole-2-carboxylate (see intermediate 10, 100 mg, 201 μmol) in 2 mL of dry dichloromethane was added N,N-diisopropylethylamine (70 μL, 400 μmol), followed by methanesulfonyl chloride (23 μL, 300 μmol), at a temperature of 0° C. under a stream of nitrogen. After 1 hour, additional portions of N,N-diisopropylethylamine (70 μL, 400 μmol) and methanesulfonyl chloride (23 μL, 300 μmol) were added and the mixture was stirred for an additional hour. 2-(Morpholin-4-yl)ethan-1-amine (CAS 2038-03-1, 130 μL, 1.0 mmol) was then added and the mixture was stirred overnight at room temperature. The reaction mixture was diluted with dichloromethane and washed with saturated aqueous sodium bicarbonate solution, followed by brine. The organic phase was dried using a water resistant filter and was concentrated under reduced pressure. The crude residue was purified by flash chromatography on silica gel (0-10% ethanol/dichloromethane) to give the title compound (106 mg, 86% yield) as an oil.

LC-MS (Method 1): $R_t$=1.96 min; MS (ESIpos): m/z=611 [M+H]$^+$ $^1$H-NMR (400 MHz, CHLOROFORM-d) δ [ppm]: 1.041 (1.33), 1.058 (1.36), 1.252 (4.45), 1.269 (9.03), 1.288 (4.44), 1.321 (0.59), 1.338 (0.99), 1.347 (2.70), 1.359 (1.39), 1.365 (5.57), 1.383 (2.86), 1.587 (4.79), 2.056 (16.00), 2.092 (1.23), 2.097 (1.41), 2.190 (1.27), 2.221 (0.54), 2.262 (9.76), 2.332 (0.62), 2.347 (1.31), 2.365 (1.47), 2.384 (1.01), 2.475 (2.14), 2.605 (0.79), 2.620 (1.75), 2.635 (1.15), 2.743 (1.11), 2.758 (1.75), 2.774 (0.74), 3.153 (0.59), 3.411 (1.31), 3.430 (2.04), 3.448 (1.45), 3.497 (0.52), 3.605 (0.91), 3.652 (0.62), 3.671 (1.54), 3.696 (2.40), 3.707 (3.46), 3.718 (2.47), 3.815 (0.95), 3.838 (1.45), 3.866 (9.71), 3.876 (0.88), 4.105 (1.28), 4.122 (3.76), 4.140 (3.66), 4.159 (1.23), 4.221 (1.39), 4.236 (2.78), 4.252 (1.35), 4.317 (0.93), 4.334 (2.08), 4.352 (1.99), 4.369 (0.70), 5.310 (10.12), 6.773 (1.19), 6.791 (1.39), 7.059 (1.07), 7.074 (1.62), 7.077 (1.61), 7.113 (1.25), 7.133 (1.48), 7.151 (0.76), 7.335 (0.85), 7.355 (1.64), 7.364 (0.46), 7.374 (1.23), 7.411 (1.80), 7.431 (1.00), 7.481 (1.19), 7.486 (1.86), 7.495 (2.35), 7.505 (2.26), 7.510 (1.58), 7.516 (0.89), 7.521 (0.50), 7.528 (0.47), 7.683 (1.35), 7.702 (1.11), 7.801 (1.15), 7.811 (0.77), 7.818 (0.94), 7.824 (0.95), 8.352 (0.74), 8.359 (0.66), 8.376 (0.81), 12.407 (0.61).

Intermediate 13

Ethyl 7-[3-({(3-chloropropane-1-sulfonyl)[2-(morpholin-4-yl)ethyl]amino}methyl)-1,5-dimethyl-1H-pyrazol-4-yl]-3-{3-[(naphthalen-1-yl)oxy]propyl}-1H-indole-2-carboxylate

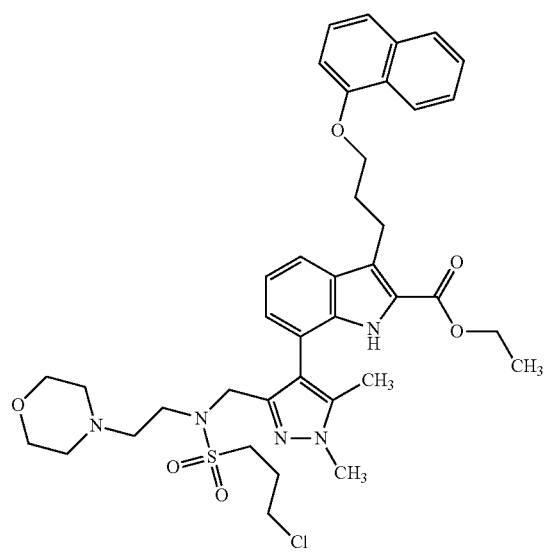 [SMILES: CCOC(=O)c1[nH]c2c(-c3c(CN(CCN4CCOCC4)S(=O)(=O)CCCCl)nn(C)c3C)cccc2c1CCCOc1cccc2ccccc12]

To a solution of ethyl 7-[1,5-dimethyl-3-({[2-(morpholin-4-yl)ethyl]amino}methyl)-1H-pyrazol-4-yl]-3-{3-[(naphthalen-1-yl)oxy]propyl}-1H-indole-2-carboxylate (see intermediate 12, 104 mg, 171 μmol) in 980 μL dry dichloromethane was added N,N-diisopropylethylamine (59 μL, 340 μmol), followed by 3-chloropropane-1-sulfonyl chloride (CAS 1633-82-5, 25 μL, 200 μmol), at a temperature of 0° C. under a stream of nitrogen. The mixture was stirred at room temperature for 2 hours, and was then concentrated under reduced pressure. The crude residue was purified by flash chromatography on silica gel (0-20% ethanol/dichloromethane) to obtain the desired sulfonamide (66 mg, 52% yield) as an oil.

LC-MS (Method 1): $R_t$=1.39 min; MS (ESIpos): m/z=751 [M+H]$^+$ $^1$H-NMR (400 MHz, CHLOROFORM-d) δ [ppm]: 1.040 (1.21), 1.049 (1.12), 1.057 (1.40), 1.067 (2.24), 1.086 (1.16), 1.213 (1.26), 1.220 (1.40), 1.229 (1.44), 1.237 (9.15), 1.254 (16.00), 1.271 (9.06), 1.320 (0.53), 1.337 (0.83), 1.356 (0.45), 1.366 (3.57), 1.383 (7.73), 1.401 (3.63), 1.585 (7.01), 2.056 (0.41), 2.091 (1.01), 2.115 (0.91), 2.122 (0.73), 2.131 (1.23), 2.136 (1.32), 2.152 (14.08), 2.167 (2.36), 2.209 (0.87), 2.220 (1.19), 2.226 (1.70), 2.243 (0.89), 2.340 (0.93), 2.357 (1.44), 2.373 (0.94), 2.456 (0.68), 2.475 (0.67), 3.050 (0.88), 3.065 (1.04), 3.071 (1.06), 3.086 (0.76), 3.129 (0.44), 3.145 (0.93), 3.162 (0.90), 3.396 (0.43), 3.414 (0.81), 3.439 (0.83), 3.457 (0.48), 3.485 (1.90), 3.496 (2.78), 3.507 (1.83), 3.548 (1.56), 3.564 (2.90), 3.580 (1.46), 3.701 (0.81), 3.718 (1.58), 3.730 (1.60), 3.736 (1.59), 3.747 (1.45), 3.764 (0.51), 3.814 (1.09), 3.881 (11.25), 4.214 (1.30), 4.230 (2.61), 4.245 (1.18), 4.356 (0.78), 4.371 (1.80), 4.374 (1.69), 4.389 (1.49), 4.392 (1.41), 4.407 (0.58), 4.454 (0.66), 5.310 (3.73), 6.778

(1.27), 6.795 (1.28), 7.096 (0.72), 7.100 (0.83), 7.114 (1.70), 7.117 (1.52), 7.132 (1.69), 7.152 (1.79), 7.169 (0.84), 7.342 (0.90), 7.363 (1.70), 7.382 (1.42), 7.422 (1.78), 7.443 (0.91), 7.483 (0.48), 7.495 (1.48), 7.497 (1.53), 7.500 (1.38), 7.508 (1.78), 7.516 (1.32), 7.519 (1.49), 7.521 (1.44), 7.706 (1.12), 7.724 (1.04), 7.809 (1.04), 7.813 (0.72), 7.822 (0.93), 7.826 (0.62), 7.832 (0.79), 8.361 (0.82), 8.371 (0.72), 8.385 (0.80), 8.523 (1.04).

Intermediate 14

(rac)-Ethyl 2,3-dimethyl-14-[2-(morpholin-4-yl)ethyl]-7-{3-[(naphthalen-1-yl)oxy]propyl}-13,13-dioxo-10,11,12,13,14,15-hexahydro-2H-13$\lambda^6$-pyrazolo[3',4':4,5][1,2,8]thiadiazacyclo-undecino-[6,7,8-hi]indole-8-carboxylate

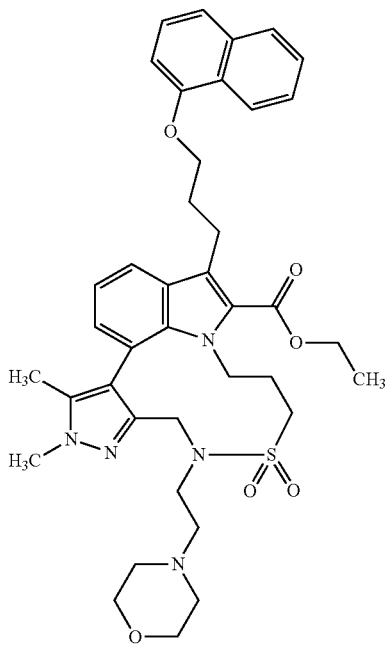 [SMILES: CCOC(=O)c1c(CCCOc2cccc3ccccc23)c2cccc3c2n1CCCS(=O)(=O)N(CCN1CCOCC1)Cc1nn(C)c(C)c1-3]

To a solution of ethyl-7-[3-({(3-chloropropane-1-sulfonyl)[2-(morpholin-4-yl)ethyl]amino}-methyl)-1,5-dimethyl-1H-pyrazol-4-yl]-3-{3-[(naphthalen-1-yl)oxy]propyl}-1H-indole-2-carboxylate (see intermediate 13, 64.0 mg, 85.3 μmol) in 4.2 mL dry N,N-dimethylformamide was added sodium hydride (6.82 mg, 60% purity, 171 μmol) at a temperature of 0° C. under a stream of nitrogen, and the mixture was warmed to room temperature. After stirring for 5 minutes, the mixture was heated to 60° C. and stirred for 3.5 hours. The reaction mixture was cooled, and the reaction was stopped by the addition of water (1 mL). N,N-Dimethylformamide was removed in vacuo and the residue was diluted with water. The mixture was extracted three times with ethyl acetate and the combined organic phases were washed with brine, passed through a water resistant filter, and concentrated under reduced pressure to give the title compound. The crude product was used directly in the next step without purification.

LC-MS (Method 2): $R_t$=1.61 min; MS (ESIpos): m/z=714 [M+H]$^+$

Intermediate 15

Ethyl 6-chloro-7-{1,5-dimethyl-3-[(methylamino)methyl]-1H-pyrazol-4-yl}-3-{3-[(naphthalen-1-yl)oxy]propyl}-1H-indole-2-carboxylate

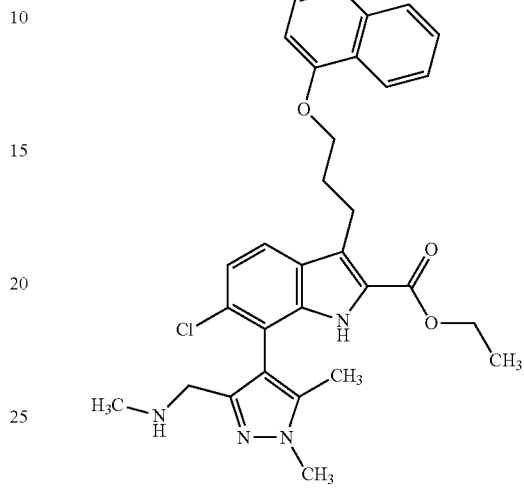

To a solution of ethyl 6-chloro-7-[3-(hydroxymethyl)-1,5-dimethyl-1H-pyrazol-4-yl]-3-{3-[(naphthalen-1-yl)oxy]propyl}-1H-indole-2-carboxylate (see intermediate 11, 1 g, 84% purity, 1.58 mmol) in 16 mL of dry dichloromethane was added N,N-diisopropylethylamine (550 μL, 3.2 mmol), followed by methanesulfonyl chloride (180 μL, 2.4 mmol), at a temperature of 0° C. under a stream of nitrogen. After 4 hours, additional portions of N,N-diisopropylethylamine (138 μL, 0.8 mmol) and methanesulfonyl chloride (60 μL, 0.8 mmol) were added every subsequent hour to drive the reaction towards completion. After 3 hours, a solution of methylamine (CAS 74-89-5, 2-molar in tetrahydrofurane, 7.9 mL, 16 mmol) was then added, and the mixture was stirred at room temperature overnight. The reaction mixture was diluted with dichloromethane and washed with saturated aqueous sodium bicarbonate solution, followed by brine. The organic phase was dried using a water resistant filter and concentrated under reduced pressure. The crude residue was purified by flash chromatography on silica gel (0-20% ethanol/dichloromethane) to give the title compound (280 mg, 95% purity, 31% yield) as a foam.

LC-MS (Method 2): $R_t$=1.72 min; MS (ESIpos): m/z=545 [M+H]$^+$ $^1$H-NMR (400 MHz, CHLOROFORM-d) δ [ppm]: 1.252 (0.74), 1.254 (0.56), 1.349 (4.59), 1.367 (9.65), 1.385 (4.60), 1.553 (0.53), 2.130 (16.00), 2.186 (0.72), 2.246 (5.86), 2.307 (0.62), 2.321 (0.58), 2.339 (1.18), 2.355 (1.83), 2.371 (1.21), 2.389 (0.50), 2.440 (13.83), 3.378 (1.07), 3.398 (1.19), 3.412 (2.32), 3.418 (1.97), 3.432 (1.01), 3.435 (0.96), 3.656 (0.52), 3.670 (0.75), 3.728 (2.34), 3.760 (2.06), 3.790 (5.36), 3.867 (15.57), 4.202 (1.09), 4.214 (2.13), 4.218 (2.42), 4.230 (1.05), 4.233 (1.02), 4.309 (0.54), 4.319 (0.59), 4.327 (0.57), 4.336 (2.28), 4.355 (3.28), 4.373 (2.19), 4.382 (0.59), 4.391 (0.58), 4.400 (0.54), 6.764 (1.60), 6.782 (1.69), 7.155 (3.24), 7.176 (3.53), 7.333 (1.17), 7.353 (2.28), 7.373 (1.94), 7.412 (2.25), 7.433 (1.23), 7.468 (0.46), 7.480 (1.36), 7.487 (1.90), 7.495 (3.18), 7.504 (2.21), 7.511 (1.60), 7.523

(0.54), 7.598 (3.44), 7.620 (3.05), 7.802 (1.27), 7.811 (0.68), 7.820 (0.95), 7.825 (1.10), 8.320 (1.09), 8.327 (0.94), 8.335 (0.48), 8.344 (1.07).

Intermediate 16

Ethyl 6-chloro-7-(3-{[(3-chloropropane-1-sulfonyl)(methyl)amino]methyl}-1,5-dimethyl-1H-pyrazol-4-yl)-3-{3-[(naphthalen-1-yl)oxy]propyl}-1H-indole-2-carboxylate

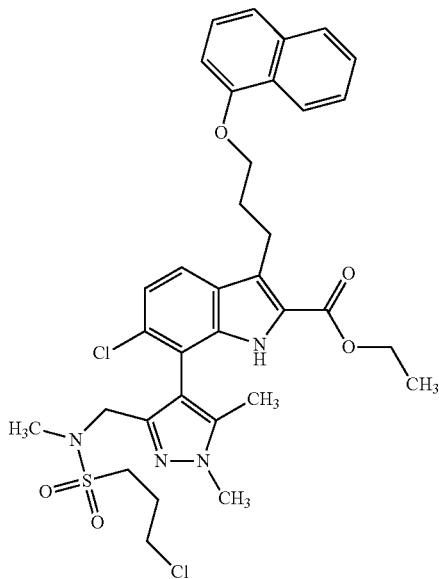 [SMILES: CCOC(=O)c1[nH]c2c(-c3c(CN(C)S(=O)(=O)CCCCl)nn(C)c3C)c(Cl)ccc2c1CCCOc1cccc2ccccc12]

To a solution of ethyl 6-chloro-7-{1,5-dimethyl-3-[(methylamino)methyl]-1H-pyrazol-4-yl}-3-{3-[(naphthalen-1-yl)oxy]propyl}-1H-indole-2-carboxylate (see intermediate 15, 280 mg, 514 µmol) in 3 mL of dry dichloromethane was added N,N-diisopropylethylamine (180 µL, 1.0 mmol), followed by 3-chloropropane-1-sulfonyl chloride (CAS 1633-82-5, 75 µL, 620 µmol), at a temperature of 0° C. under a stream of nitrogen. The mixture was stirred at room temperature for 3 hours, was then diluted with saturated aqueous sodium bicarbonate solution, and was extracted three times with dichloromethane. The combined organic phases were washed with brine, dried over a water resistant filter, and were concentrated under reduced pressure. The crude residue was purified by flash chromatography on silica gel (50-100% ethyl acetate/hexane) to obtain the desired sulfonamide (260 mg, 98% purity, 72% yield) as a foam.

LC-MS (Method 1): $R_t$=1.66 min; MS (ESIpos): m/z=685 [M+H]$^+$ $^1$H-NMR (400 MHz, CHLOROFORM-d) δ [ppm]: 1.270 (0.41), 1.357 (1.95), 1.375 (4.31), 1.392 (2.05), 1.566 (16.00), 2.056 (0.61), 2.090 (0.56), 2.107 (7.75), 2.123 (0.60), 2.332 (0.46), 2.348 (0.81), 2.364 (0.48), 2.707 (7.02), 2.879 (0.45), 2.899 (0.48), 2.965 (0.44), 3.397 (0.71), 3.404 (0.73), 3.532 (0.68), 3.534 (0.72), 3.549 (1.46), 3.563 (0.66), 3.566 (0.68), 3.910 (6.75), 4.080 (0.79), 4.118 (1.07), 4.188 (0.68), 4.203 (1.48), 4.218 (0.67), 4.302 (1.01), 4.340 (0.80), 4.344 (0.73), 4.362 (1.78), 4.380 (1.73), 4.398 (0.53), 6.765 (0.70), 6.784 (0.73), 7.165 (1.47), 7.186 (1.59), 7.339 (0.52), 7.359 (0.99), 7.378 (0.82), 7.421 (0.95), 7.442 (0.54), 7.494 (0.64), 7.499 (1.00), 7.509 (1.23), 7.518 (1.01), 7.523 (0.74), 7.616 (1.01), 7.638 (0.92), 7.811 (0.54), 7.834 (0.46), 8.348 (0.48), 8.373 (0.55), 8.385 (0.72).

Intermediate 17

(rac)-Ethyl 4-chloro-2,3,14-trimethyl-7-{3-[(naphthalen-1-yl)oxy]propyl}-13,13-dioxo-10,11,12,13,14,15-hexahydro-2H-13λ$^6$-pyrazolo[3',4':4,5][1,2,8]thiadiazacyclo-undecino[6,7,8-hi]indole-8-carboxylate

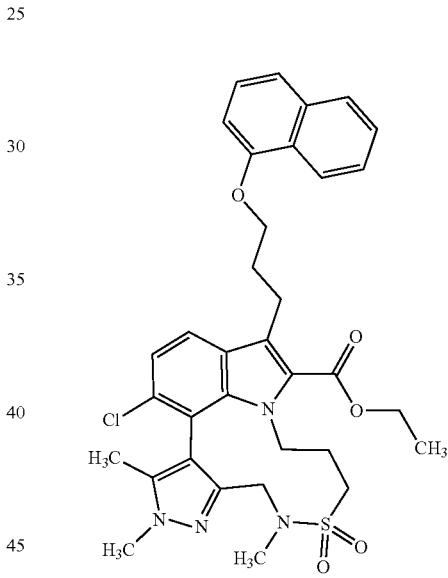

To a solution of ethyl 6-chloro-7-(3-{[(3-chloropropane-1-sulfonyl)(methyl)amino]methyl}-1,5-dimethyl-1H-pyrazol-4-yl)-3-{3-[(naphthalen-1-yl)oxy]propyl}-1H-indole-2-carboxylate (see intermediate 16, 255 mg, 71% purity, 264 µmol) in 13 mL of dry N,N-dimethylformamide at 0° C. under a stream of nitrogen was added sodium hydride (21.1 mg, 60% purity, 528 µmol) at a temperature of 0° C. under a stream of nitrogen, and the mixture was warmed to room temperature. After stirring for 5 minutes, the mixture was heated to 60° C. and stirred for 72 hours. The reaction mixture was cooled, and the reaction was stopped by the addition of water (1 mL). N,N-Dimethylformamide was removed in vacuo, using azeotropic evaporation with toluene, and the residue was used directly in the next reaction.

Intermediate 18

Ethyl 7-(1,5-dimethyl-3-((methylamino)methyl)-1H-pyrazol-4-yl)-3-(3-(naphthalen-1-yloxy)propyl)-1H-indole-2-carboxylate

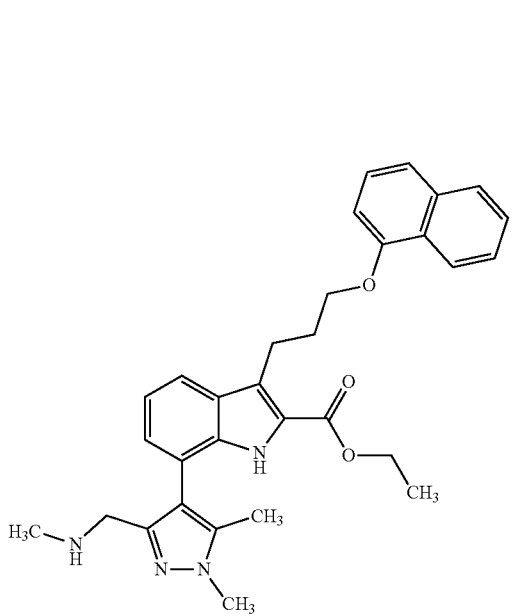 [SMILES: CCOC(=O)c1[nH]c2c(-c3c(CNC)nn(C)c3C)cccc2c1CCCOc1cccc2ccccc12]

To a solution of ethyl 7-(3-(hydroxymethyl)-1,5-dimethyl-1H-pyrazol-4-yl)-3-(3-(naphthalen-1-yloxy)propyl)-1H-indole-2-carboxylate (see intermediate 10, 0.868 g, 1.74 mmol) in dichloromethane (35 mL) was added N,N-diisopropylethylamine (605 μL, 3.48 mmol), followed by methanesulfonyl chloride (201 μL, 2.61 mmol), at a temperature of 0° C. The resulting mixture was stirred at 0° C. for 1 h, at which point a solution of methylamine (8.70 mL, 17.4 mmol, 2 M in tetrahydrofuran) was added and the reaction was then stirred overnight. Subsequently, the mixture was diluted with dichloromethane and washed with saturated aqueous sodium bicarbonate and brine. The combined organic phases were dried over sodium sulfate, filtered, and concentrated. The residue was purified by flash column chromatography on silica gel (0-10% methanol/dichloromethane) to obtain the title compound (0.687 g) as an off-white solid.

LC-MS (Method 3): $R_t$=1.39 min; MS (ESIpos): m/z=512 [M+H]$^+$ $^1$H NMR (400 MHz, Chloroform-d) δ [ppm]: δ 12.70 (s, 1H), 8.39-8.32 (m, 1H), 7.83-7.76 (m, 1H), 7.69 (dd, 1H), 7.54-7.42 (m, 2H), 7.44-7.30 (m, 2H), 7.16-7.03 (m, 2H), 6.77 (dd, 1H), 4.36 (q, 2H), 4.23 (t, 2H), 3.85 (s, 3H), 3.58 (s, 2H), 3.49-3.40 (m, 2H), 2.49 (s, 3H), 2.48 2.31 (m, 1H), 2.37 (s, 2H), 2.26 (s, 3H), 1.37 (t, 3H).

Intermediate 19 ethyl 7-(3-((3-chloro-N-methylpropylsulfonamido)methyl)-1,5-dimethyl-1H-pyrazol-4-yl)-3-(3-(naphthalen-1-yloxy)propyl)-1H-indole-2-carboxylate

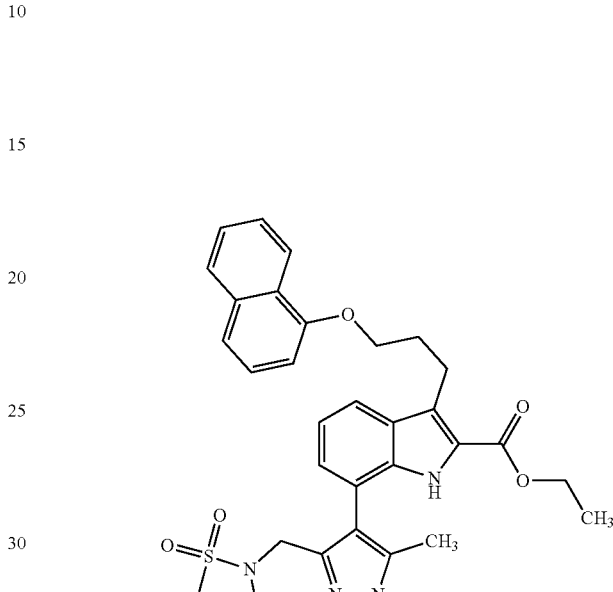

To a solution of ethyl 7-(1,5-dimethyl-3-((methylamino)methyl)-1H-pyrazol-4-yl)-3-(3-(naphthalen-1-yloxy)propyl)-1H-indole-2-carboxylate (see Intermediate 18, 0.25 g, 489 μmol) in dichloromethane (2.44 mL) was added N,N-diisopropylethylamine (169 μL, 978 μmol), followed by 3-chloropropane-1-sulfonyl chloride (CAS 1633-82-5, 70.7 μL, 586 μmol), at a temperature of 0° C. The mixture was stirred at room temperature for 2 h, and was then concentrated. The crude residue was purified by flash column chromatography on silica gel (20-100% ethyl acetate/hexanes) to obtain the title compound (314 mg) as a white solid.

LC-MS (Method 3): $R_t$=1.99 min; MS (ESIpos): m/z=651 [M+H]$^+$ $^1$H NMR (300 MHz, Chloroform-d) δ [ppm]: δ: 8.48 (s, 1H), 8.43-8.33 (m, 1H), 7.86-7.80 (m, 1H), 7.79-7.69 (m, 1H), 7.55-7.33 (m, 5H), 7.22-7.08 (m, 2H), 6.79 (d, 1H), 4.38 (q, 2H), 4.24 (t, 3H), 3.91 (s, 3H), 3.48 (dt, 5H), 2.95-2.83 (m, 2H), 2.73 (s, 4H), 2.38 (h, 2H), 2.19-2.00 (m, 5H), 1.39 (t, 3H)

Intermediate 20

Ethyl 7-(5-ethyl-3-(hydroxymethyl)-1-methyl-1H-pyrazol-4-yl)-3-(3-(naphthalen-1-yloxy)propyl)-1H-indole-2-carboxylate

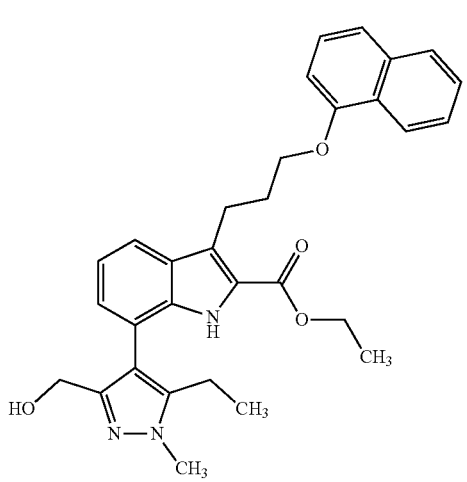 [SMILES: CCOC(=O)c1[nH]c2c(-c3c(CO)nn(C)c3CC)cccc2c1CCCOc1cccc2ccccc12]

A round-bottom flask equipped with a stirrer bar was charged with ethyl 3-(3-(naphthalen-1-yloxy)propyl)-7-(4,4,5,5-tetramethyl-1,3,2-dioxaborolan-2-yl)-1H-indole-2-carboxylate (see intermediate 1, 8.39 g, 16.7 mmol), (4-bromo-5-ethyl-1-methyl-1H-pyrazol-3-yl)methanol (see intermediate 9, 3.44 g, 15.8 mmol), potassium phosphate (7.08 g, 33.4 mmol), and XPhos Pd G3 (777 mg, 918 µmol). The flask was purged with nitrogen and filled with degassed tetrahydrofuran (166 mL) and water (66.8 mL) via cannula. The mixture was stirred at 50° C. for 2 h, and was then cooled to room temperature and diluted with ethyl acetate and water. The layers were separated and the aqueous phase was extracted twice with ethyl acetate. The combined organic phases were washed with brine, dried over sodium sulfate, filtered, and concentrated. The crude residue was suspended in dichloromethane and filtered to remove a white precipitate. The filtrate was evaporated and the residue was purified by flash column chromatography on silica gel (0-100% ethyl acetate/hexanes), followed by reverse-phase chromatography on C18-silica gel (10-100% acetonitrile/water with 0.1% formic acid) to obtain the title compound (5.35 g) as a white solid.

LC-MS (Method 3): $R_t$=1.81 min; MS (ESIpos): m/z=512 [M+H]$^+$ $^1$H NMR (300 MHz, Chloroform-d) δ [ppm]: 9.75 (s, 1H), 8.42-8.32 (m, 1H), 7.85-7.76 (m, 1H), 7.72 (dd, 1H), 7.54-7.44 (m, 2H), 7.46-7.29 (m, 2H), 7.19-7.08 (m, 2H), 6.78 (dd, 1H), 4.54 (s, 2H), 4.35 (q, 2H), 4.23 (t, 2H), 3.96 (s, 3H), 3.44 (t, 2H), 2.88 (s, 4H), 2.63 (d, 1H), 2.42-2.31 (m, 2H), 1.36 (t, 3H), 1.14 (t, 3H).

Intermediate 21

Ethyl 7-(5-ethyl-1-methyl-3-(((3-(2-oxopyrrolidin-1-yl)propyl)amino)methyl)-1H-pyrazol-4-yl)-3-(3-(naphthalen-1-yloxy)propyl)-1H-indole-2-carboxylate To a solution of ethyl 7-(5-ethyl-3-(hydroxymethyl)-1-methyl-1H-pyrazol-4-yl)-3-(3-(naphthalen-1-yloxy)propyl)-1H-indole-2-carboxylate (see intermediate 20, 0.3 g, 586 µmol) in dichloromethane (11.7 mL) was added N,N-diisopropylethylamine (152 µL, 878 µmol), followed by methanesulfonyl chloride (90.5 µL, 1.17 mmol), at a temperature of 0° C. The resulting mixture was stirred at 0° C. for 1 h, at which point a solution of 1-(3-aminopropyl)pyrrolidin-2-one (CAS 7663-77-6, 415 mg, 2.92 mmol) in dichloromethane (586 µL) was added, and the reaction was then stirred for 24 h at room temperature. Subsequently, the mixture was washed with saturated aqueous sodium bicarbonate solution, and was extracted three times with dichloromethane. The combined organic phases were washed with brine, dried over sodium sulfate, filtered and concentrated. The residue was purified by flash column chromatography on silica gel (0-15% (7 N ammonia in methanol)/dichloromethane) to obtain the title compound (0.37 g) as a foam.

LC-MS (Method 3): $R_t$=1.50 min; MS (ESIpos): m/z=636 [M+1]$^+$ $^1$H NMR (300 MHz, Chloroform-d) δ [ppm]: 8.41-8.32 (m, 1H), 7.86-7.73 (m, 1H), 7.69 (dd, 1H), 7.54-7.44 (m, 2H), 7.44-7.31 (m, 2H), 7.16-7.04 (m, 2H), 6.78 (dd, 1H), 4.33 (q, 2H), 4.24 (t, 2H), 3.88 (s, 3H), 3.61 (s, 2H), 3.37 (m, 6H), 2.73 (s, 2H), 2.60 (d, 1H), 2.36 (q, 4H), 2.00 (m, 2H), 1.85 (s, 2H), 1.77-1.43 (m, 4H), 1.36 (t, 3H), 1.14 (t, 2H).

167

Intermediate 22

Ethyl 7-(3-((3-chloro-N-(3-(2-oxopyrrolidin-1-yl)propyl)propylsulfonamido)methyl)-5-ethyl-1-methyl-1H-pyrazol-4-yl)-3-(3-(naphthalen-1-yloxy)propyl)-1H-indole-2-carboxylate

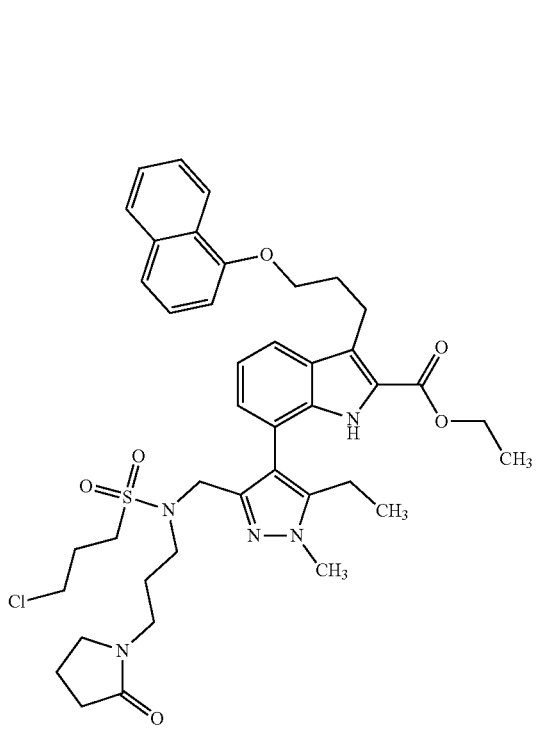 [SMILES: CCOC(=O)c1[nH]c2c(-c3c(CN(CCCN4CCCC4=O)S(=O)(=O)CCCCl)nn(C)c3CC)cccc2c1CCCOc1cccc2ccccc12]

To a solution of ethyl 7-(5-ethyl-1-methyl-3-(((3-(2-oxopyrrolidin-1-yl)propyl)amino)methyl)-1H-pyrazol-4-yl)-3-(3-(naphthalen-1-yloxy)propyl)-1H-indole-2-carboxylate (see Intermediate 21, 0.18 g, 283 µmol) in dichloromethane (1.41 mL) was added N,N-diisopropylethylamine (98.5 µL, 566 µmol), followed by 3-chloropropane-1-sulfonyl chloride (CAS 1633-82-5, 41.2 µL, 339 µmol), at a temperature of 0° C. The mixture was stirred at room temperature for 30 min and was then concentrated. The crude residue was purified by flash column chromatography on silica gel (0-100% acetone/dichloromethane) to obtain the title compound (0.189 g) as an oil.

LC-MS (Method 3): $R_t$=1.89 min; MS (ESIpos): m/z=776 [M+H]$^+$ $^1$H NMR (300 MHz, Chloroform-d) δ [ppm]: 8.74 (s, 1H), 8.44-8.31 (m, 1H), 7.86-7.77 (m, 1H), 7.76-7.69 (m, 1H), 7.54-7.44 (m, 2H), 7.45-7.31 (m, 2H), 7.20-7.08 (m, 2H), 6.78 (dd, 1H), 4.55-4.30 (m, 3H), 4.30-4.12 (m, 3H), 3.94 (s, 3H), 3.52 (t, 2H), 3.41 (m, 2H), 3.21 (t, 2H), 3.03 (q, 4H), 2.85 (m, 2H), 2.70-2.44 (m, 2H), 2.44-2.24 (m, 4H), 2.17 (s, 1H), 2.12-1.83 (m, 4H), 1.47 (q, 1H), 1.37 (t, 3H), 1.06 (t, 3H).

168

Intermediate 23

(rac)-Ethyl 12-ethyl-11-methyl-1-(3-(naphthalen-1-yloxy)propyl)-8-(3-(2-oxopyrrolidin-1-yl)propyl)-4,5,6,8,9,11-hexahydropyrazolo[3',4':4,5][1,2,8]thiadiazacycloundecino[6,7,8-hi]indole-2-carboxylate 7,7-dioxide

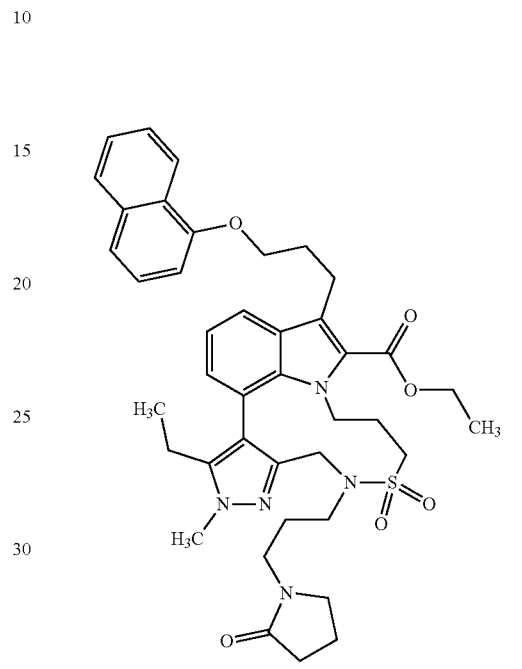

To a solution of ethyl 7-(3-((3-chloro-N-(3-(2-oxopyrrolidin-1-yl)propyl)propylsulfonamido)-methyl)-5-ethyl-1-methyl-1H-pyrazol-4-yl)-3-(3-(naphthalen-1-yloxy)propyl)-1H-indole-2-carboxylate (see Intermediate 22, 0.3 g, 386 µmol) in dry dimethylformamide (15.4 mL) at room temperature was added 60% sodium hydride (30.8 mg, 772 µmol) as a dispersion in oil and the mixture was stirred at 60° C. overnight. An additional portion of sodium hydride (30.8 mg, 772 µmol) was added and the mixture stirred for further 6 h. Subsequently, the mixture was cooled, and the reaction was stopped by the addition of water (1 mL), and was then concentrated. The residue was diluted with ethyl acetate and washed with water. The aqueous phase was extracted twice with ethyl acetate and the combined organic phases were washed with brine, dried over sodium sulfate, filtered, and concentrated. The crude residue was purified by flash column chromatography on silica gel (0-10% methanol/dichloromethane) to obtain the title compound (0.23 g) as an oil.

LC-MS (Method 3): $R_t$=1.86 min; MS (ESIpos): m/z=741 [M+H]$^+$ $^1$H NMR (300 MHz, Chloroform-d) δ [ppm]: 8.50-8.36 (m, 1H), 7.83 (m, 1H), 7.74 (dd, 1H), 7.58-7.48 (m, 2H), 7.48-7.34 (m, 2H), 7.10 (dd, 1H), 7.01-6.89 (m, 1H), 6.79 (dd, 1H), 4.55 (d, 1H), 4.42-4.09 (m, 6H), 3.89 (s, 3H), 3.56-3.20 (m, 5H), 2.43 (t, 3H), 2.39-2.16 (m, 3H), 2.07 (p, 3H), 1.84 (s, 3H), 1.58 (s, 10H), 1.38 (t, 3H), 0.90 (t, 3H).

169

Intermediate 24

Ethyl 7-(5-ethyl-1-methyl-3-(((2-(piperidin-1-yl)ethyl)amino)methyl)-1H-pyrazol-4-yl)-3-(3-(naphthalen-1-yloxy)propyl)-1H-indole-2-carboxylate

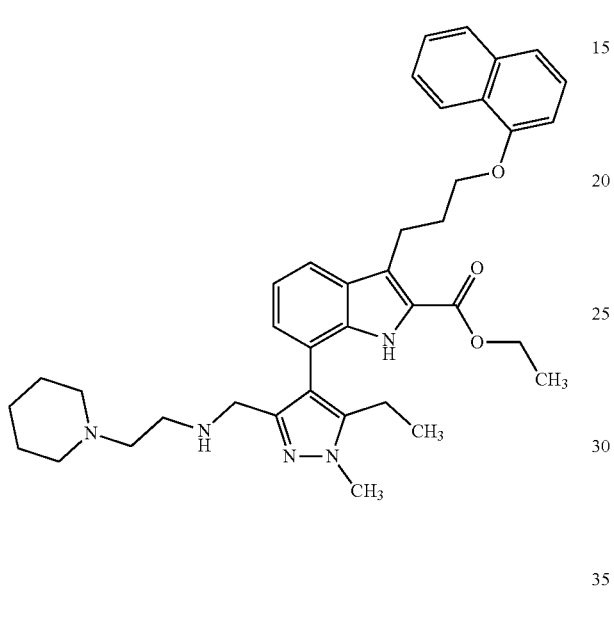

To a solution of ethyl 7-(5-ethyl-3-(hydroxymethyl)-1-methyl-1H-pyrazol-4-yl)-3-(3-(naphthalen-1-yloxy)propyl)-1H-indole-2-carboxylate (see Intermediate 20, 0.3 g, 586 µmol) in dichloromethane (11.7 mL) was added N,N-diisopropylethylamine (152 µL, 878 µmol), followed by methanesulfonyl chloride (90.5 µL, 1.17 mmol), at a temperature of 0° C. The resulting mixture was stirred at 0° C. for 1 h, at which point a solution of 2-(piperidin-1-yl)ethanamine (CAS 27578-60-5, 374 mg, 2.92 mmol) in dichloromethane (586 µL) was added. The mixture was degassed by sparging with nitrogen for 5 min, treated with sodium iodide (175 mg, 1.17 mmol), and stirred overnight at room temperature. The resulting mixture was diluted with saturated aqueous sodium bicarbonate solution and was extracted three times with ethyl acetate. The combined organic phases were washed with water and brine, dried over sodium sulfate, filtered and concentrated. The residue was purified by flash column chromatography on silica gel (0-15% (7 N ammonia in methanol)/dichloromethane) to obtain the title compound (0.344 g) as a foam.

$^1$H NMR (300 MHz, Chloroform-d) δ [ppm]: 12.18 (s, 1H), 8.43-8.31 (m, 1H), 7.86-7.74 (m, 1H), 7.69 (dd, 1H), 7.56-7.29 (m, 4H), 7.18-7.04 (m, 2H), 6.78 (dd, 1H), 4.35 (q, 2H), 4.23 (t, 2H), 3.88 (s, 3H), 3.57 (s, 2H), 3.49-3.33 (m, 2H), 2.76 (t, 2H), 2.58 (m, 4H), 2.38 (q, 6H), 1.56 (q, 4H), 1.38 (q, 5H), 1.16 (t, 3H).

170

Intermediate 25

Ethyl 7-(3-((3-chloro-N-(2-(piperidin-1-yl)ethyl)propylsulfonamido)methyl)-5-ethyl-1-methyl-1H-pyrazol-4-yl)-3-(3-(naphthalen-1-yloxy)propyl)-1H-indole-2-carboxylate

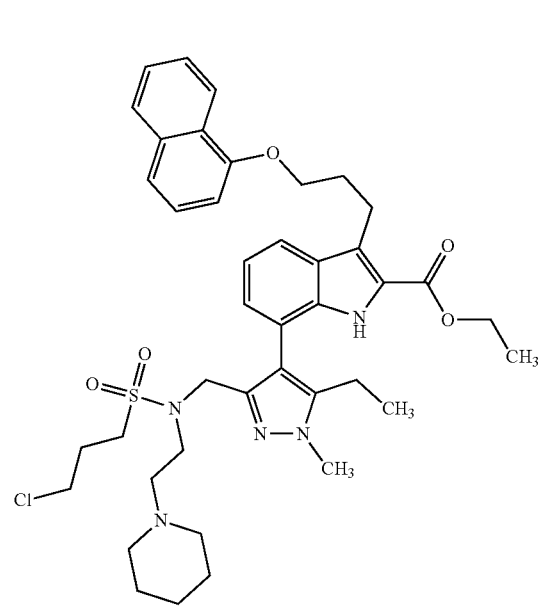 [SMILES: CCOC(=O)c1[nH]c2c(-c3c(CN(CCN4CCCCC4)S(=O)(=O)CCCCl)nn(C)c3CC)cccc2c1CCCOc1cccc2ccccc12]

To a solution of ethyl 7-(5-ethyl-1-methyl-3-(((2-(piperidin-1-yl)ethyl)amino)methyl)-1H-pyrazol-4-yl)-3-(3-(naphthalen-1-yloxy)propyl)-1H-indole-2-carboxylate (see Intermediate 24 0.18 g, 289 µmol) in dichloromethane (1.44 mL) was added N,N-diisopropylethylamine (100 µL, 578 µmol), followed by 3-chloropropane-1-sulfonyl chloride (CAS 1633-82-5, 42.0 µL, 346 µmol), at a temperature of 0° C. The mixture was stirred at room temperature for 30 min and was then concentrated. The crude residue was purified by flash column chromatography on silica gel (0-100% acetone/dichloromethane) to obtain the title compound (0.185 g) as an oil.

LC-MS (Method 3): $R_t$=1.93 min; MS (ESIpos): m/z=762 [M+H]$^+$ $^1$H NMR (300 MHz, Chloroform-d) δ [ppm]: 8.57 (s, 1H), 8.42-8.31 (m, 1H), 7.87-7.74 (m, 1H), 7.71 (dd, 1H), 7.56-7.29 (m, 4H), 7.20-7.06 (m, 2H), 6.78 (dd, 1H), 4.47-4.30 (m, 3H), 4.30-4.17 (m, 3H), 3.90 (s, 3H), 3.54 (t, 2H), 3.48-3.36 (m, 2H), 3.18 (t, 2H), 3.01 (hept, 2H), 2.53 (m, 2H), 2.36 (p, 2H), 2.25-2.06 (m, 3H), 1.40 (m, 9H), 1.05 (t, 3H).

171
Intermediate 26

(rac)-Ethyl 12-ethyl-11-methyl-1-(3-(naphthalen-1-yloxy)propyl)-8-(2-(piperidin-1-yl)ethyl)-4,5,6,8,9,11-hexahydropyrazolo[3',4':4,5][1,2,8]thiadiazacycloundecino[6,7,8-hi]indole-2-carboxylate 7,7-dioxide

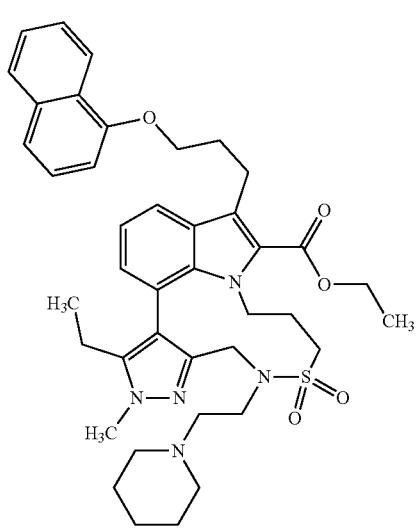 [SMILES: CCOC(=O)c1c(CCCOc2cccc3ccccc23)c2cccc3c2n1CCCS(=O)(=O)N(CCN1CCCCC1)Cc1nn(C)c(CC)c1-3]

172
Intermediate 27

Ethyl 7-(5-ethyl-1-methyl-3-(((3-morpholinopropyl)amino)methyl)-1H-pyrazol-4-yl)-3-(3-(naphthalen-1-yloxy)propyl)-1H-indole-2-carboxylate

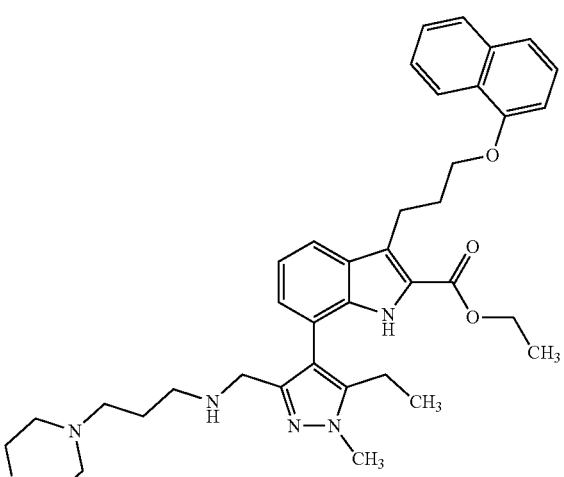

To a solution of ethyl 7-(3-((3-chloro-N-(2-(piperidin-1-yl)ethyl)propylsulfonamido)methyl)-5-ethyl-1-methyl-1H-pyrazol-4-yl)-3-(3-(naphthalen-1-yloxy)propyl)-1H-indole-2-carboxylate (see Intermediate 25, 0.309 g, 405 μmol) in dry dimethylformamide (16.2 mL) at room temperature was added 60% sodium hydride (32.3 mg, 810 μmol) as a dispersion in oil and the mixture was stirred at 60° C. overnight. An additional portion of sodium hydride (32.3 mg, 810 μmol) was added and the mixture was then stirred for further 5 h. The resulting mixture was cooled, the reaction was stopped by the addition of water (1 mL), and the mixture was concentrated. The residue was diluted with ethyl acetate and washed with water. The aqueous phase was extracted twice with ethyl acetate and the combined organic phases were washed with brine, dried over sodium sulfate, filtered, and concentrated. The crude residue was purified by flash column chromatography on silica gel (0-10% methanol/dichloromethane) to obtain the title compound (0.203 g) as an oil.

LC-MS (Method 4): $R_t$=5.50 min; MS (ESIpos): m/z=726 [M+H]$^+$ $^1$H NMR (300 MHz, Chloroform-d) δ [ppm]: 8.44-8.31 (m, 1H), 7.87-7.66 (m, 2H), 7.57-7.29 (m, 4H), 7.19-7.03 (m, 1H), 6.97 (dd, 1H), 6.78 (dd, 1H), 4.62-4.50 (m, 1H), 4.46-4.14 (m, 5H), 3.89 (d, 3H), 3.58-3.28 (m, 2H), 2.54 (d, 4H), 2.40-2.04 (m, 4H), 1.86 (s, 2H), 1.69 (s, 6H), 1.37 (m, 3H), 0.89 (t, 2H).

To a solution of ethyl 7-(5-ethyl-3-(hydroxymethyl)-1-methyl-1H-pyrazol-4-yl)-3-(3-(naphthalen-1-yloxy)propyl)-1H-indole-2-carboxylate (see Intermediate 20, 306 mg, 0.6 mmol) in dichloromethane (11.9 mL) was added N,N-diisopropylethylamine (229 μL, 1.32 mmol), followed by methanesulfonyl chloride (92.5 μL, 1.20 mmol), at a temperature of 0° C. The resulting mixture was stirred at 0° C. for 1 h, at which point a solution of 3-morpholinopropan-1-amine (CAS 123-00-2, 431 mg, 2.99 mmol) in dichloromethane (600 μL) was added, followed by sodium iodide (179 mg, 1.20 mmol). After stirring for 20 h, the mixture was diluted with dichloromethane, washed with 1:1 aqueous saturated aqueous sodium bicarbonate solution/brine mixture, and extracted three times with dichloromethane. The combined organic phases were dried over sodium sulfate, filtered and concentrated. The residue was purified by flash column chromatography on silica gel (0-15% (7 N ammonia in methanol)/dichloromethane) to obtain the title compound (361 mg) as an oil.

$^1$H NMR (Chloroform-d) δ [ppm]: 8.44-8.31 (m, 1H), 7.85-7.75 (m, 1H), 7.69 (dd, 1H), 7.55 7.44 (m, 2H), 7.46-7.29 (m, 2H), 7.18-6.92 (m, 2H), 6.78 (dd, 1H), 6.60 (s, 1H), 4.40-4.19 (m, 4H), 3.88 (s, 2H), 3.76-3.62 (m, 4H), 3.56 (s, 1H), 3.42 (t, 3H), 3.25 (q, 1H), 2.92 (s, 2H), 2.65-2.47 (m, 2H), 2.48 (s, 9H), 2.37 (q, 2H), 1.76 (p, 1H), 1.36 (t, 3H), 1.15 (m, 4H).

Intermediate 28

Ethyl 7-(3-((3-chloro-N-(3-morpholinopropyl)propylsulfonamido)methyl)-5-ethyl-1-methyl-1H-pyrazol-4-yl)-3-(3-(naphthalen-1-yloxy)propyl)-1H-indole-2-carboxylate

Intermediate 29

Ethyl 7-(5-ethyl-1-methyl-3-(((3-(pyrrolidin-1-yl)propyl)amino)methyl)-1H-pyrazol-4-yl)-3-(3-(naphthalen-1-yloxy)propyl)-1H-indole-2-carboxylate

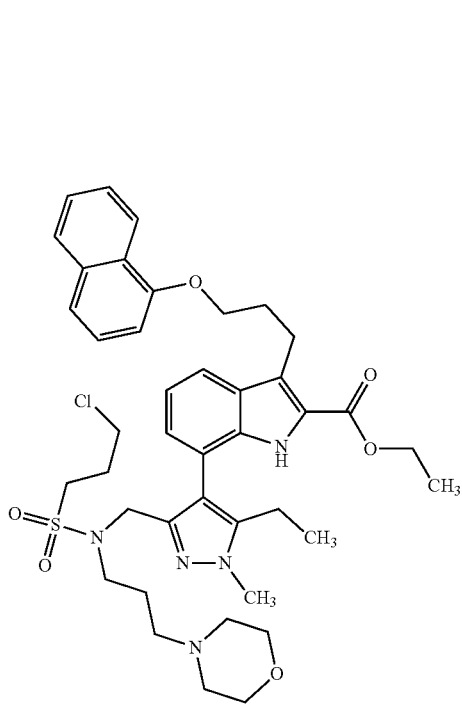 [SMILES: CCOC(=O)c1[nH]c2c(-c3c(CN(CCCN4CCOCC4)S(=O)(=O)CCCCl)nn(C)c3CC)cccc2c1CCCOc1cccc2ccccc12]

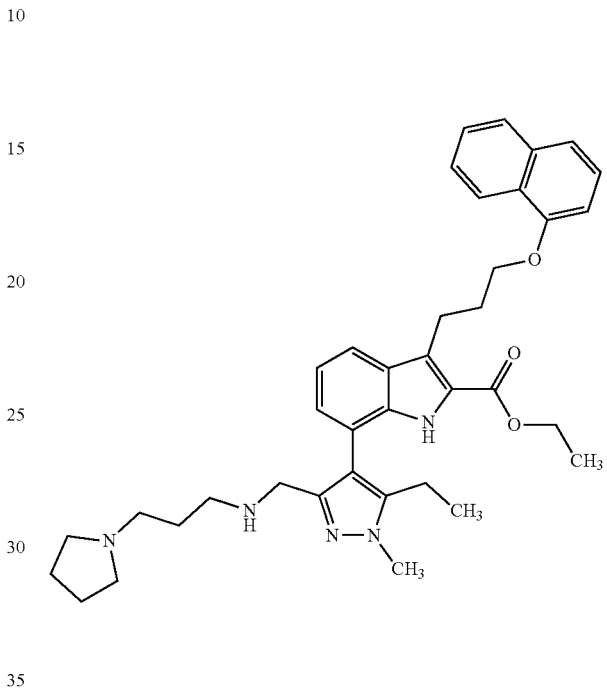

To a solution of ethyl 7-(5-ethyl-1-methyl-3-(((3-morpholinopropyl)amino)methyl)-1H-pyrazol-4-yl)-3-(3-(naphthalen-1-yloxy)propyl)-1H-indole-2-carboxylate (see Intermediate 27, 0.35 g, 547 µmol) in dichloromethane (2.73 mL) was added N,N-diisopropylethylamine (188 µL, 1.09 mmol), followed by 3-chloropropane-1-sulfonyl chloride (CAS 1633-82-5, 79.6 µL, 656 µmol), at a temperature of 0° C. The mixture was stirred at room temperature for 18 h and was then concentrated. The crude residue was purified by flash column chromatography on silica gel (0-100% acetone/dichloromethane) to obtain the title compound (246 mg) as an oil.

LC-MS (Method 3): $R_t$=1.57 min; MS (ESIpos): m/z=779 [M+H]$^+$ $^1$H NMR (300 MHz, Chloroform-d) δ [ppm]: 8.56 (s, 1H), 8.41-8.32 (m, 1H), 7.87-7.76 (m, 1H), 7.71 (d, 1H), 7.56-7.45 (m, 1H), 7.38 (dt, 2H), 7.18-7.05 (m, 2H), 6.78 (dd, 1H), 4.44-4.29 (m, 2H), 4.22 (q, 3H), 3.90 (s, 3H), 3.64 (s, 4H), 3.55 (t, 2H), 3.41 (q, 2H), 3.09 (s, 1H), 2.96 (q, 1H), 2.67-2.39 (m, 1H), 2.32 (m, 5H), 2.18-1.98 (m, 3H), 1.37 (t, 6H), 1.05 (t, 3H).

To a solution of ethyl 7-(5-ethyl-3-(hydroxymethyl)-1-methyl-1H-pyrazol-4-yl)-3-(3-(naphthalen-1-yloxy)propyl)-1H-indole-2-carboxylate (see Intermediate 20, 0.3 g, 586 µmol) in dichloromethane (11.7 mL) was added N,N-diisopropylethylamine (172 µL, 996 µmol), followed by methanesulfonyl chloride (172 µL, 1.17 mmol), at a temperature of 0° C. The resulting mixture was stirred at 0° C. for 1 h and was then concentrated. The crude residue was re-dissolved in acetonitrile (5.85 mL) and treated with 3-(pyrrolidin-1-yl)propan-1-amine (CAS 23159-07-1, 374 mg, 2.92 mmol) and sodium iodide (175 mg, 1.17 mmol). The mixture was heated to 60° C. and stirred overnight. The reaction was cooled to room temperature, concentrated, and diluted with 1:1 saturated aqueous sodium bicarbonate solution/brine mixture. The resulting mixture was extracted three times with dichloromethane, and the combined organic phases were dried over sodium sulfate, filtered and concentrated. The residue was purified by flash column chromatography on silica gel (0-15% (7 N ammonia in methanol)/dichloromethane) to obtain the title compound (122 mg) as an oil.

$^1$H NMR (Chloroform-d) δ [ppm]: 8.39-8.29 (m, 1H), 7.85-7.76 (m, 1H), 7.69 (dd, 1H), 7.56 7.29 (m, 4H), 7.19-7.04 (m, 2H), 6.78 (dd, 1H), 4.40-4.17 (m, 4H), 3.89 (s, 3H), 3.60 (s, 3H), 3.42 (t, 2H), 3.05 (s, 1H), 2.97 (s, 7H), 2.84 (t, 2H), 2.61 (d, 1H), 2.36 (p, 2H), 1.97 (s, 6H), 1.37 (t, 3H), 1.15 (t, 3H)

Intermediate 30

Ethyl 7-(3-((3-chloro-N-(3-(pyrrolidin-1-yl)propyl)propylsulfonamido)methyl)-5-ethyl-1-methyl-1H-pyrazol-4-yl)-3-(3-(naphthalen-1-yloxy)propyl)-1H-indole-2-carboxylate

Intermediate 31

Ethyl 7-(3-(azidomethyl)-5-ethyl-1-methyl-1H-pyrazol-4-yl)-3-(3-(naphthalen-1-yloxy)propyl)-1H-indole-2-carboxylate

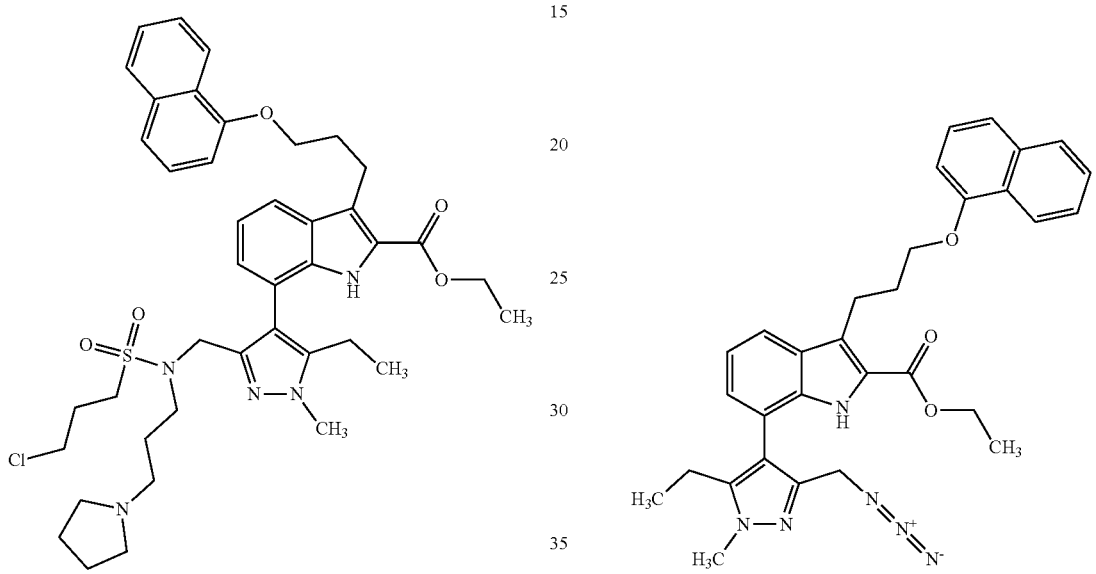

To a solution of ethyl 7-(5-ethyl-1-methyl-3-(((3-(pyrrolidin-1-yl)propyl)amino)methyl)-1H-pyrazol-4-yl)-3-(3-(naphthalen-1-yloxy)propyl)-1H-indole-2-carboxylate (see Intermediate 29, 122 mg, 196 μmol) in dichloromethane (980 μL) was added N,N-diisopropylethylamine (51.0 μL, 294 μmol), followed by 3-chloropropane-1-sulfonyl chloride (CAS 1633-82-5, 28.5 μL, 235 μmol), at a temperature of 0° C. The mixture was stirred at room temperature for 1 h. Celite was added to the resulting mixture, volatiles were removed under reduced pressure, and the residue was subjected to flash column chromatography on silica gel (0-20% methanol/dichloromethane) to obtain the title compound (88 mg) as an oil.

LC-MS (Method 3): $R_t$=1.57 min; MS (ESIneg): m/z=761 [M–H]⁻

¹H NMR (Chloroform-d) δ [ppm]: 11.53 (s, 1H), 8.75 (s, 1H), 8.40-8.29 (m, 1H), 7.80 (dt, 1H), 7.72 (d, 1H), 7.54-7.45 (m, 2H), 7.37 (dt, 2H), 7.23-7.09 (m, 2H), 6.78 (dd, 1H), 4.48-4.30 (m, 3H), 4.22 (t, 2H), 4.10 (d, 1H), 3.91 (s, 3H), 3.66 (q, 0H), 3.52 (t, 2H), 3.47-3.35 (m, 2H), 3.23 (t, 2H), 3.10 (q, 1H), 2.96-2.81 (m, 2H), 2.66-2.47 (m, 1H), 2.35 (p, 2H), 2.20-1.87 (m, 5H), 1.76 (s, 4H), 1.57-1.42 (m, 4H), 1.37 (t, 3H), 1.05 (t, 3H)

To a solution of ethyl 7-(5-ethyl-3-(hydroxymethyl)-1-methyl-1H-pyrazol-4-yl)-3-(3-(naphthalen-1-yloxy)propyl)-1H-indole-2-carboxylate (see Intermediate 20, 1.5 g, 2.93 mmol) in toluene (29.3 mL) was added 1,8-diazabicyclo[5.4.0]undec-7-ene (524 μL, 3.51 mmol), followed by diphenylphosphoryl azide (CAS 26386-88-9, 755 μL, 3.51 mmol). The mixture was stirred overnight at room temperature and then concentrated under vacuum. Purified by flash column chromatography on silica gel (0-50% ethyl acetate/hexanes) to obtain the title compound (1.34 g) as a white foam.

LC-MS (Method 3): $R_t$=2.01 min; MS (ESIneg): m/z=535 [M–H]⁻

¹H NMR (300 MHz, Chloroform-d) δ [ppm]: 8.79 (s, 1H), 8.39-8.32 (m, 1H), 7.84-7.76 (m, 1H), 7.76-7.67 (m, 1H), 7.56-7.44 (m, 2H), 7.38 (dt, 2H), 7.17-7.09 (m, 2H), 6.78 (dd, 1H), 4.36 (q, 2H), 4.23 (t, 2H), 4.13 (d, 2H), 3.94 (s, 3H), 3.44 (t, 2H), 2.57 (s, 2H), 2.37 (p, 2H), 1.37 (t, 3H), 1.24 (s, 7H), 1.09 (t, 3H).

Intermediate 32

Ethyl 7-(3-(aminomethyl)-5-ethyl-1-methyl-1H-pyrazol-4-yl)-3-(3-(naphthalen-1-yloxy)propyl)-1H-indole-2-carboxylate

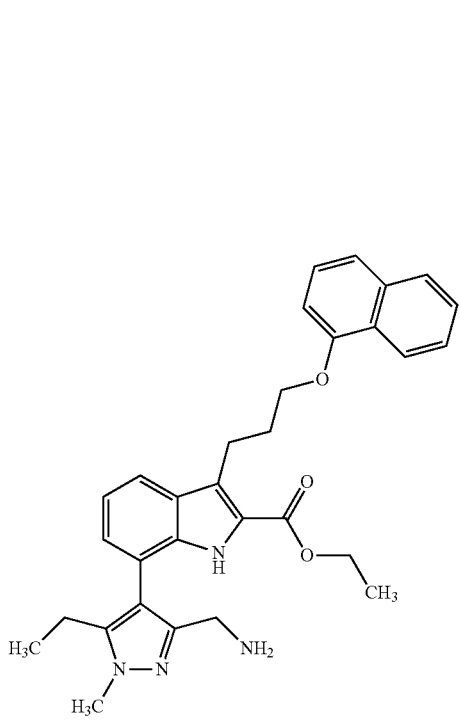 [SMILES: CCOC(=O)c1[nH]c2c(-c3c(CN)nn(C)c3CC)cccc2c1CCCOc1cccc2ccccc12]

A solution of ethyl 7-(3-(azidomethyl)-5-ethyl-1-methyl-1H-pyrazol-4-yl)-3-(3-(naphthalen-1-yloxy)propyl)-1H-indole-2-carboxylate (see intermediate 31, 1.34 g, 2.49 mmol) in ethanol (49.8 mL) was purged with nitrogen. To the resulting mixture was carefully added 10% palladium (263 mg, 249 μmol) on carbon, and the mixture was stirred under an atmosphere of hydrogen for 3 h. The solution was degassed, filtered over Celite, and concentrated to obtain the title compound (1.2 g).

LC-MS (Method 3): $R_t$=1.50 min; MS (ESIpos): m/z=512 [M+H]$^+$ $^1$H NMR (300 MHz, Chloroform-d) δ [ppm]: 8.42-8.32 (m, 1H), 7.84-7.77 (m, 1H), 7.69 (dd, 1H), 7.54-7.45 (m, 2H), 7.37 (dt, 2H), 7.16-7.05 (m, 2H), 6.78 (dd, 1H), 4.34 (q, 2H), 4.23 (t, 2H), 3.87 (s, 3H), 3.43 (t, 2H), 2.62 (q, 2H), 2.37 (p, 2H), 2.19-1.79 (m, 7H), 1.35 (t, 3H), 1.24 (s, 7H), 1.15 (t, 3H).

Intermediate 33

Ethyl 7-(3-((((benzyloxy)carbonyl)amino)methyl)-5-ethyl-1-methyl-1H-pyrazol-4-yl)-3-(3-(naphthalen-1-yloxy)propyl)-1H-indole-2-carboxylate To a solution of ethyl 7-(3-(aminomethyl)-5-ethyl-1-methyl-1H-pyrazol-4-yl)-3-(3-(naphthalen-1-yloxy)propyl)-1H-indole-2-carboxylate (see Intermediate 32, 1.2 g, 2.07 mmol) and triethylamine (431 μL, 3.10 mmol) in dichloromethane (20.6 mL) was added benzyl chloroformate (CAS 501-53-1, 323 μL, 2.27 mmol) at 0° C. under a stream of nitrogen, and the mixture was stirred overnight at room temperature. The mixture was then diluted with dichloromethane and washed with saturated aqueous sodium bicarbonate solution and brine. The organic phase was dried over sodium sulfate, filtered, and concentrated. The residue was purified by flash column chromatography on silica gel (40-100% ethyl acetate/hexanes) to obtain the title compound (0.7 g) as a white foam.

LC-MS (Method 3): $R_t$=1.99 min; MS (ESIpos): m/z=646 [M+H]$^+$ $^1$H NMR (300 MHz, Chloroform-d) δ [ppm]: 8.71 (s, 1H), 8.44-8.31 (m, 1H), 7.80 (dt, 1H), 7.73-7.63 (m, 1H), 7.54-7.45 (m, 2H), 7.45-7.27 (m, 7H), 7.16-7.04 (m, 2H), 6.78 (dd, 1H), 5.30 (s, 1H), 5.02 (s, 2H), 4.45-4.28 (m, 2H), 4.22 (q, 4H), 3.89 (s, 3H), 3.42 (t, 2H), 2.64 2.42 (m, 2H), 2.36 (p, 2H), 1.35 (t, 3H), 1.06 (t, 3H).

Intermediate 34

3-(7-(3-((((Benzyloxy)carbonyl)amino)methyl)-5-ethyl-1-methyl-1H-pyrazol-4-yl)-2-(ethoxycarbonyl)-3-(3-(naphthalen-1-yloxy)propyl)-1H-indol-1-yl)propane-1-sulfonic acid-sodium Salt

Intermediate 35

Ethyl 7-(3-((((benzyloxy)carbonyl)amino)methyl)-5-ethyl-1-methyl-1H-pyrazol-4-yl)-1-(3-(chlorosulfonyl)propyl)-3-(3-(naphthalen-1-yloxy)propyl)-1H-indole-2-carboxylate

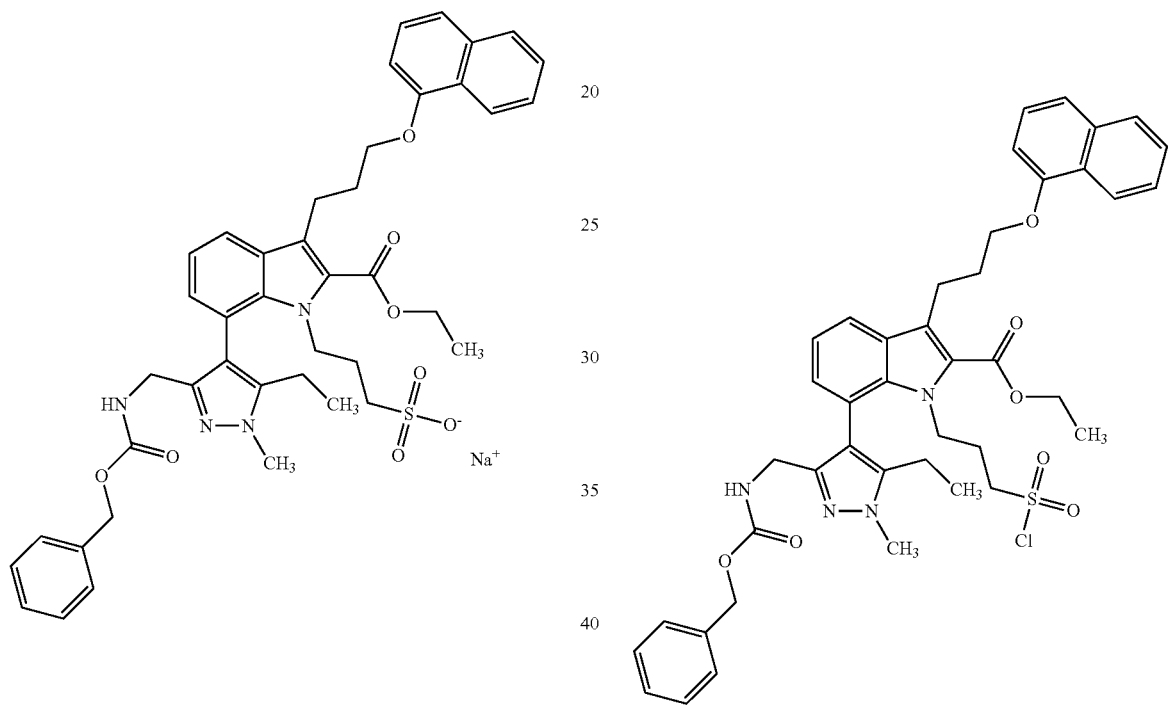

To a solution of ethyl 7-(3-((((benzyloxy)carbonyl)amino)methyl)-5-ethyl-1-methyl-1H-pyrazol-4-yl)-3-(3-(naphthalen-1-yloxy)propyl)-1H-indole-2-carboxylate (see Intermediate 33, 0.57 g, 882 µmol) in dry tetrahydrofuran (5.88 mL) was added 60% sodium hydride (41.8 mg, 1.05 mmol) at a temperature of 0° C. under an atmosphere of nitrogen. The mixture was stirred for 30 min before adding 1,2-oxathiolane 2,2-dioxide (128 mg, 1.05 mmol). The reaction mixture was heated to reflux and stirred overnight. Excess 60% sodium hydride (41.8 mg, 1.05 mmol) was added and the mixture was heated to reflux for further 24 h. The mixture was cooled to room temperature and volatiles were removed under vacuum. The crude residue was purified by reverse-phase chromatography on C18 silica gel (10-100% acetonitrile/water with 0.1% TFA) to obtain the title compound (306 mg) as a foam.

LC-MS (Method 3): $R_t$=1.63 min; MS (ESIneg): m/z=765 [M−Na]⁻

To a stirred solution of 3-(7-(3-((((benzyloxy)carbonyl)amino)methyl)-5-ethyl-1-methyl-1H-pyrazol-4-yl)-2-(ethoxycarbonyl)-3-(3-(naphthalen-1-yloxy)propyl)-1H-indol-1-yl)propane-1-sulfonic acid- sodium salt (see Intermediate 34, 0.3 g, 380 µmol) in anhydrous dichloromethane (3.79 mL) was added oxalyl dichloride (CAS 79-37-8, 36.4 µL, 418 µmol) dropwise at a temperature of 0° C. The resulting mixture was stirred at room temperature overnight and concentrated under reduced pressure to obtain the title compound (0.316 g, 63% purity) as a foam.

LC-MS (Method 3): $R_t$=2.09 min; MS (ESIpos): m/z=785 [M+1]⁺

181

Intermediate 36

(rac)-Ethyl 12-ethyl-11-methyl-1-(3-(naphthalen-1-yloxy)propyl)-4,5,6,8,9,11-hexahydropyrazolo[3',4':4,5][1,2,8]thiadiazacycloundecino[6,7,8-hi]indole-2-carboxylate 7,7-dioxide

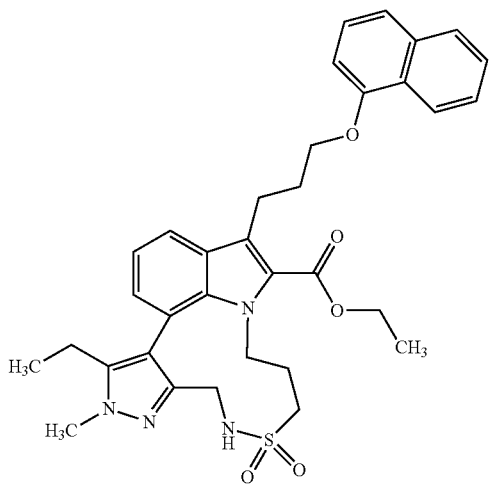 [SMILES: CCOC(=O)c1c(CCCOc2cccc3ccccc23)c2cccc3c2n1CCCS(=O)(=O)NCc1nn(C)c(CC)c1-3]

To a solution of ethyl 7-(3-((((benzyloxy)carbonyl)amino)methyl)-5-ethyl-1-methyl-1H-pyrazol-4-yl)-1-(3-(chlorosulfonyl)propyl)-3-(3-(naphthalen-1-yloxy)propyl)-1H-indole-2-carboxylate (see Intermediate 35, 0.1 g, 114 µmol) in dichloromethane (1.14 mL) at 0° C. was added 33% by wt hydrogen bromide (24.5 µL, 136 µmol) in acetic acid. The mixture was stirred for 1 h, and was then gradually warmed up to room temperature. Excess hydrogen bromide (33% by wt hydrogen bromide in acetic acid; 24.5 µL, 136 µmol) was added and the mixture was stirred for an additional 1 h before being concentrated. Under a stream of nitrogen, the crude residue was re-dissolved in dry dichloromethane (6.30 mL) and treated with N,N-diisopropylethylamine (218 µL, 1.26 mmol). The mixture was stirred at room temperature for 2 days, diluted with dichloromethane, and washed with saturated aqueous sodium bicarbonate. The organic phase was dried over sodium sulfate, filtered, and concentrated. The residue was purified by flash column chromatography on silica gel (0-20% methanol/dichloromethane and then 0-100% ethyl acetate/hexanes) to obtain the title compound (23 mg, 77% purity) as an oil.

LC-MS (Method 3): $R_t$=1.85 min; MS (ESIpos): m/z=615 [M+1]$^+$ $^1$H NMR (Chloroform-d) δ [ppm]: 8.44-8.35 (m, 1H), 7.87-7.78 (m, 1H), 7.74 (td, 1H), 7.54-7.47 (m, 2H), 7.47-7.33 (m, 2H), 7.10 (ddd, 1H), 6.99 (dd, 1H), 6.79 (dd, 1H), 4.79 (s, 1H), 4.62 (dt, 1H), 4.49-4.03 (m, 10H), 3.88 (s, 4H), 3.52-3.26 (m, 3H), 2.48 (ddd, 1H), 2.38-2.19 (m, 5H), 1.92 (d, 4H), 1.37 (t, 4H), 0.96-0.86 (m, 4H)

182

Intermediate 37

4-Bromo-5-ethyl-1-methyl-1H-pyrazole-3-carbaldehyde

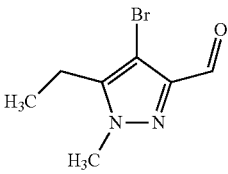

To a stirred solution of oxalyl chloride (CAS 79-37-8, 1.28 mL, 15.0 mmol) in anhydrous dichloromethane (15 mL, 1.00 M) was added dimethylsulfoxide (2.12 mL, 30.0 mmol) dropwise at a temperature of 78° C. After stirring for 15 min, a solution of (4-bromo-5-ethyl-1-methyl-1H-pyrazol-3-yl)methanol (see intermediate 9, 2.19 g, 10 mmol) in dichloromethane (14.2 mL) was added dropwise, followed by triethylamine (8.36 mL, 60.0 mmol). The resulting slurry was warmed to room temperature and stirred for 2 h. The mixture was diluted with water and extracted with dichloromethane. The combined organic extracts were washed with water, dried over sodium sulfate, filtered and concentrated under reduced pressure. The residue was purified by flash column chromatography on silica gel (0-50% ethyl acetate/hexanes) to give the title compound (1.9 g) as a white solid.

LC-MS (Method 3): $R_t$=1.05 min; MS (ESIpos): m/z=219 [M+1]$^+$ $^1$H NMR (300 MHz, Chloroform-d) δ [ppm]: 9.91 (d, 1H), 3.94 (s, 3H), 2.74 (q 2H), 1.21 (t, 3H).

Intermediate 38

(rac)-1-(4-Bromo-5-ethyl-1-methyl-1H-pyrazol-3-yl)ethanol

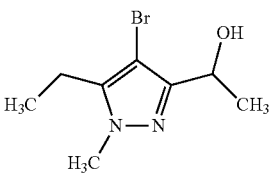

To a stirred solution of 4-bromo-5-ethyl-1-methyl-1H-pyrazole-3-carbaldehyde (intermediate 37, 1.9 g, 8.75 mmol) in anhydrous tetrahydrofuran (87.5 mL) was added a solution of methylmagnesium bromide (3.50 mL, 10.5 mmol, 3 M in ether) dropwise at a temperature of 0° C. The resulting mixture was stirred at room temperature for 4 h. Excess methylmagnesium bromide (3.50 mL, 10.5 mmol, 3 M in ether) was added and the mixture was stirred overnight before being concentrated under reduced pressure. The mixture was diluted with saturated aqueous ammonium chloride solution and was extracted three times with ethyl acetate. The combined organic extracts were washed with brine, dried over sodium sulfate, filtered and concentrated. The residue was purified by flash column chromatography on silica gel (0-100% ethyl acetate/hexanes) to obtain the title compound (1.77 g) as an oil.

LC-MS (Method 3): $R_t$=0.96 min; MS (ESIpos): m/z=235 [M+1]$^+$ $^1$H NMR (300 MHz, Chloroform-d) δ [ppm]: 4.92 (q, 1H), 3.80 (s, 3H), 2.66 (q, 2H), 2.07 (d, 2H), 1.56 (d, 3H), 1.17 (t, 3H).

Intermediate 39

1-(4-Bromo-5-ethyl-1-methyl-1H-pyrazol-3-yl)ethanone

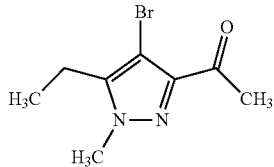

To a solution of (rac)-1-(4-bromo-5-ethyl-1-methyl-1H-pyrazol-3-yl)ethanol (see Intermediate 38, 1.19 g, 5.10 mmol) in dichloromethane (25.4 mL) was added 1,1-bis(acetyloxy)-3-oxo-3H-1λ$^5$,2-benziodaoxol-1-ylacetate (2.59 g, 6.11 mmol). The resulting mixture was stirred for 18 h at room temperature, diluted with dichloromethane, and washed with aqueous saturated sodium thiosulfate, followed by aqueous saturated sodium bicarbonate solution. The combined organic extracts were washed with water, dried over sodium sulfate, filtered and concentrated under reduced pressure. The residue was purified by flash column chromatography on silica gel (0-50% ethyl acetate/hexanes gradient) to give the title compound (1.08 g) as a white solid.

LC-MS (Method 3): $R_t$=1.12 min; MS (ESIpos): m/z=233 [M+1]$^+$ $^1$H NMR (300 MHz, Chloroform-d) δ [ppm]: 3.90 (s, 3H), 2.72 (q, 2H), 2.56 (s, 3H), 1.55 (d, 2H), 1.19 (t, 3H).

Intermediate 40

Ethyl 7-(3-acetyl-5-ethyl-1-methyl-1H-pyrazol-4-yl)-3-(3-(naphthalen-1-yloxy)propyl)-1H-indole-2-carboxylate

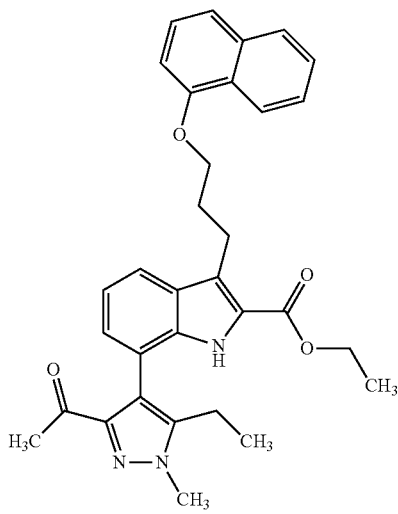 [SMILES: CCOC(=O)c1[nH]c2c(-c3c(C(C)=O)nn(C)c3CC)cccc2c1CCCOc1cccc2ccccc12]

A round-bottom flask equipped with a stirrer bar was charged with ethyl 3-(3-(naphthalen-1-yloxy)propyl)-7-(4,4,5,5-tetramethyl-1,3,2-dioxaborolan-2-yl)-1H-indole-2-carboxylate (see intermediate 1, 1.5 g, 3.00 mmol), 1-(4-bromo-5-ethyl-1-methyl-1H-pyrazol-3-yl)ethanone (see Intermediate 39, 658 mg, 2.85 mmol), potassium phosphate (1.27 g, 6.00 mmol), and XPhos Pd G3 (139 mg, 165 μmol). The flask was purged with nitrogen and filled with degassed tetrahydrofuran (30.0 mL) and water (12.0 mL). The mixture was stirred at 50° C. for 3 h, and was then cooled to room temperature and diluted with ethyl acetate and water. The layers were separated and the aqueous phase was extracted twice more with ethyl acetate. The combined organic phases were washed with brine, dried over sodium sulfate, filtered, and concentrated. The crude residue was purified by flash column chromatography on silica gel (ISCO, 0-100% ethyl acetate/hexanes, then 20% methanol/dichloromethane). The residue was suspended in dimethylsulfoxide and the resulting precipitate was filtered off, washed with acetonitrile, and kept aside. The filtrate was evaporated and the residue was purified by reverse-phase chromatography on C18-silica gel (0-100% acetonitrile/water with 0.1% TFA) and combined with the precipitate to obtain the title compound (0.7 g) as a solid.

LC-MS (Method 3): $R_t$=1.90 min; MS (ESIpos): m/z=524 [M+1]$^+$ $^1$H NMR (Chloroform-d) δ [ppm]: 8.42-8.35 (m, 1H), 8.32 (s, 1H), 7.87-7.76 (m, 1H), 7.76-7.66 (m, 1H), 7.56-7.43 (m, 2H), 7.44-7.30 (m, 2H), 7.18-7.04 (m, 2H), 6.78 (dd, 1H), 4.33 (q, 2H), 4.23 (t, 2H), 4.00 (s, 3H), 3.41 (t, 2H), 2.51 (d, 2H), 2.46 (s, 3H), 2.41-2.28 (m, 2H), 1.34 (t, 3H), 1.06 (t, 3H)

Intermediate 41

(rac)-Ethyl 7-(5-ethyl-1-methyl-3-(1-(methylamino)ethyl)-1H-pyrazol-4-yl)-3-(3-(naphthalen-1-yloxy)propyl)-1H-indole-2-carboxylate

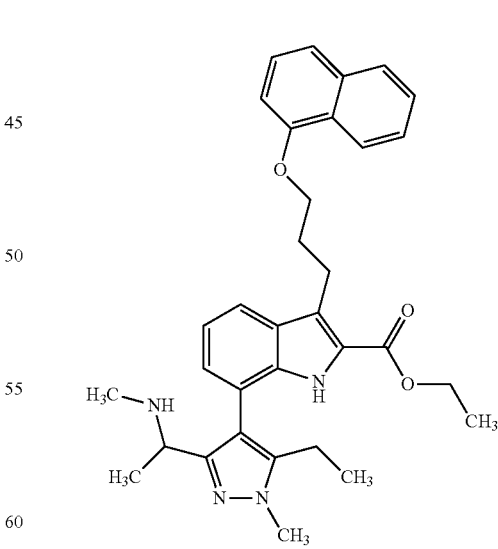

To a solution of ethyl 7-(3-acetyl-5-ethyl-1-methyl-1H-pyrazol-4-yl)-3-(3-(naphthalen-1-yloxy)propyl)-1H-indole-2-carboxylate (see Intermediate 40, 0.342 g, 653 μmol), methylamine (489 μL, 979 μmol, 2 M in tetrahydrofuran), and acetic acid (44.8 μL, 783 μmol) in 1,2-dichloroethane

185

(4.35 mL) was added sodium triacetoxyborohydride (207 mg, 979 µmol) under a stream of nitrogen. The mixture was stirred overnight at room temperature, then heated to 60° C. and stirred for 2 days. The mixture was cooled, poured into saturated aqueous sodium bicarbonate solution and extracted three times with ethyl acetate. The combined organic layers were dried over sodium sulfate, filtered, and concentrated. The crude residue was purified by flash column chromatography on silica gel (0-20% (7N ammonia in methanol)/dichloromethane) to obtain the title compound (0.2 g).

LC-MS (Method 4): $R_t$=3.86 min; MS (ESIpos): m/z=539 $[M+1]^+$

Intermediate 42

(rac)-Ethyl 7-(3-(1-(3-chloro-N-methylpropylsulfonamido)ethyl)-5-ethyl-1-methyl-1H-pyrazol-4-yl)-3-(3-(naphthalen-1-yloxy)propyl)-1H-indole-2-carboxylate

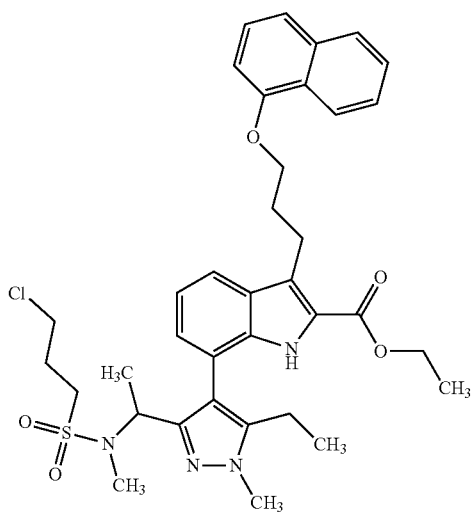 [SMILES: CCOC(=O)c1[nH]c2c(-c3c(C(C)N(C)S(=O)(=O)CCCCl)nn(C)c3CC)cccc2c1CCCOc1cccc2ccccc12]

To a solution of (rac)-ethyl 7-(5-ethyl-1-methyl-3-(1-(methylamino)ethyl)-1H-pyrazol-4-yl)-3-(3-(naphthalen-1-yloxy)propyl)-1H-indole-2-carboxylate (see intermediate 41, 0.2 g, 371 µmol) in anhydrous dichloromethane (1.85 mL) was added N,N-diisopropylethylamine (129 µL, 742 µmol) dropwise, followed by 3-chloropropane-1-sulfonyl chloride (CAS 1633-82-5, 54.0 µL, 445 µmol), at a temperature of at 0° C. The resulting mixture was warmed to room temperature and stirred for 2 h. Celite was added to the resulting mixture, volatiles were removed under reduced pressure, and the residue was subjected to flash column chromatography on silica gel (0-30% acetone/dichloromethane gradient) to give the title compound (142 mg).

LC-MS (Method 4): $R_t$=5.45 min; MS (ESIpos): m/z=679 $[M+1]^+$

Intermediate 43

Ethyl 12-ethyl-8,9,11-trimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide (Mixture of Stereoisomers)

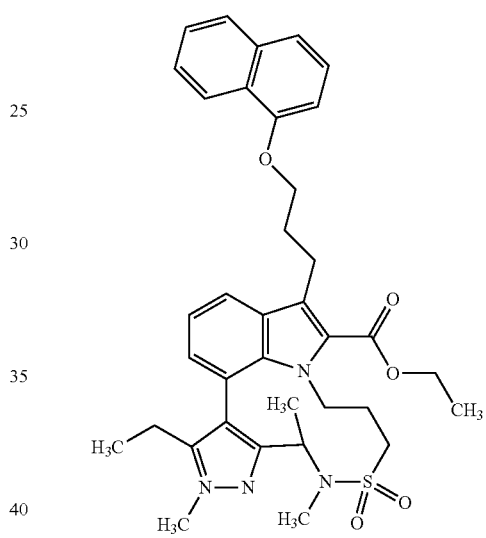

To a solution of (rac)-ethyl 7-(3-(1-(3-chloro-N-methylpropylsulfonamido)ethyl)-5-ethyl-1-methyl-1H-pyrazol-4-yl)-3-(3-(naphthalen-1-yloxy)propyl)-1H-indole-2-carboxylate (see Intermediate 42, 142 mg, 209 µmol) in anhydrous acetonitrile degassed with argon (4.18 mL) was added cesium carbonate (272 mg, 836 µmol). The resulting suspension was stirred at 60° C. for 18 h and cooled to room temperature. Celite was added to the resulting suspension, volatiles were removed under reduced pressure, and the residue was subjected to flash column chromatography on silica gel (0-50% ethyl acetate/dichloromethane) to give the title compound (110 mg).

LC-MS (Method 3): $R_t$=2.03 min; MS (ESIpos): m/z=643 $[M+1]^+$

Intermediate 44

Ethyl 7-bromo-3-(3-((tert-butyldimethylsilyl)oxy)propyl)-6-chloro-1H-indole-2-carboxylate

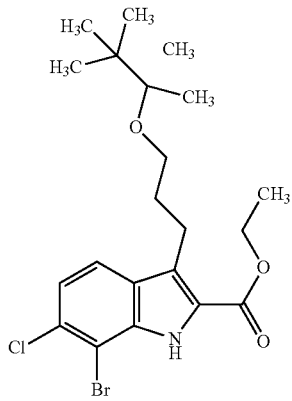

To a stirred solution of ethyl 7-bromo-6-chloro-3-(3-hydroxypropyl)-1H-indole-2-carboxylate (see intermediate 2, 10.0 g, 27.7 mmol) in anhydrous dichloromethane (110 mL) was added 1H-imidazole (2.82 g, 41.5 mmol) and tert-butylchlorodimethylsilane (CAS 18162-48-6, 5.00 g, 33.2 mmol) at a temperature of 0° C. The resulting mixture was warmed to room temperature and stirred for 2 h. The mixture was diluted with water and extracted three times with dichloromethane. The combined organic extracts were dried over sodium sulfate, filtered, and concentrated under reduced pressure. The residue was purified by flash column chromatography on silica gel (0-20% ethyl acetate/hexanes gradient) to give the title compound (12.73 g) as a white solid.

LC-MS (Method 4): $R_t$=6.45 min; MS (ESIpos): m/z=476 [M+1]$^+$ $^1$H NMR (300 MHz, Chloroform-d) δ [ppm]: 8.77 (s, 1H), 7.59 (dd, 1H), 7.20 (d, 1H), 4.43 (q, 2H), 3.65 (t, 2H), 3.20-3.05 (m, 2H), 2.00-1.75 (m, 2H), 1.43 (t, 3H), 0.92 (s, 9H), 0.05 (s, 6H).

Intermediate 45

Ethyl 3-(3-((tert-butyldimethylsilyl)oxy)propyl)-6-chloro-7-(4,4,5,5-tetramethyl-1,3,2-dioxaborolan-2-yl)-1H-indole-2-carboxylate

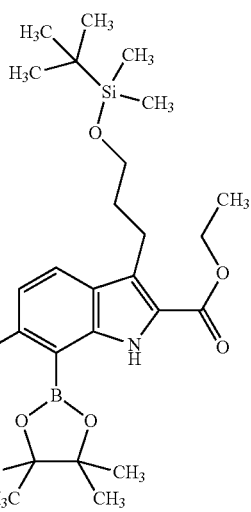

To a mixture of ethyl 7-bromo-3-(3-((tert-butyldimethylsilyl)oxy)propyl)-6-chloro-1H-indole-2-carboxylate (see Intermediate 44, 7 g, 14.7 mmol), Bis(pinacolato)diboron (CAS 78183-34-3, 4.46 g, 17.6 mmol), potassium acetate (2.88 g, 29.4 mmol) and Pd(dppf)Cl$_2$×CH$_2$Cl$_2$ (600 mg, 735 μmol) under a nitrogen atmosphere was added 1,4-dioxane sparged with nitrogen (29.4 mL). The resulting red suspension was heated to 90° C. for 9 days and cooled to room temperature. Celite was added to the resulting suspension, volatiles were removed under reduced pressure, and the residue was subjected to flash column chromatography on silica gel (5-20% ethyl acetate/hexanes) to give the title compound (4.98 g).

LC-MS (Method 4): $R_t$=7.06 min; MS (ESIpos): m/z=522 [M+1]$^+$ $^1$H NMR (300 MHz, Chloroform-d) δ [ppm]: 9.85 (s, 1H), 7.69 (dd, 1H), 7.12 (d, 1H), 4.40 (q, 2H), 3.64 (t, J=6.3 Hz, 2H), 3.17-3.02 (m, 2H), 1.93-1.74 (m, 2H), 1.43 (s, 16H), 0.92 (s, 10H), 0.05 (s, 6H).

189
Intermediate 46

Ethyl 3-(3-((tert-butyldimethylsilyl)oxy)propyl)-6-chloro-7-(5-ethyl-3-(hydroxymethyl)-1-methyl-1H-pyrazol-4-yl)-1H-indole-2-carboxylate

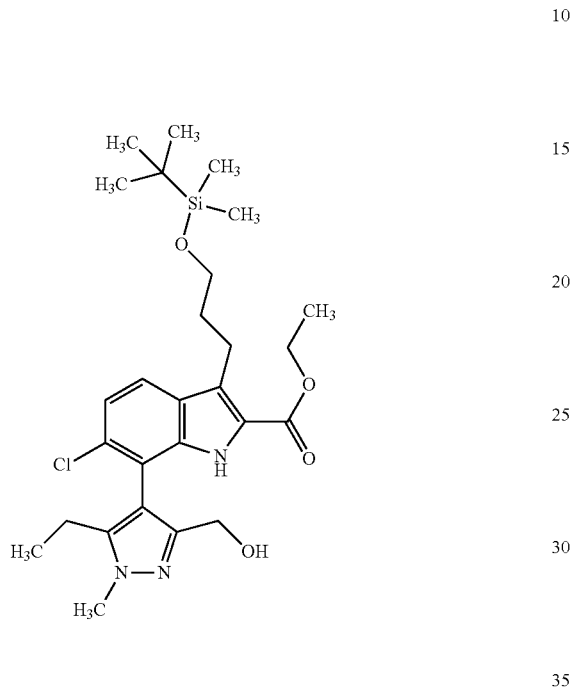

To a stirred suspension of (4-bromo-5-ethyl-1-methyl-1H-pyrazol-3-yl)methanol (see intermediate 9, 1.61 g, 7.35 mmol), XPhos Pd G3 (see abbreviations, 334 mg, 429 µmol) and potassium phosphate (2.58 g, 12.2 mmol) in degassed toluene (10.2 mL) and water (4.90 mL) was slowly added dropwise (over a period of approximately 1h), a solution of ethyl 3-(3-((tert-butyldimethylsilyl)oxy)propyl)-6-chloro-7-(4,4,5,5-tetramethyl-1,3,2-dioxaborolan-2-yl)-1H-indole-2-carboxylate (see Intermediate 45, 6.13 mL, 6.13 mmol, 1 M in degassed toluene) at a temperature of 60° C. The resulting dark mixture was heated at 60° C. for 30 minutes, cooled to room temperature and extracted with ethyl acetate. The organic phase was separated, dried over sodium sulfate, filtered and concentrated. The residue was purified by flash column chromatography on silica gel (0-100% ethyl acetate/hexanes) and by reverse-phase flash column chromatography on C18-silica gel (10-100% acetonitrile/water) to obtain the title compound (561 mg) as a white solid.

LC-MS (Method 3): $R_t$=2.04 min; MS (ESIpos): m/z=534 [M+1]$^+$ $^1$H NMR (300 MHz, Chloroform-d) δ [ppm]: 8.77 (s, 1H), 7.63 (dd, 1H), 7.23 (d, 1H), 4.52 (d, 1H), 4.37 (q, 3H), 3.93 (s, 3H), 3.69 (t, 2H), 3.21-3.07 (m, 2H), 2.50 (m, 2H), 2.07 (d, 1H), 1.96-1.81 (m, 2H), 1.38 (t, 3H), 1.00 (t, 3H), 0.93 (s, 9H), 0.07 (s, 6H).

190
Intermediate 47

Ethyl 3-(3-((tert-butyldimethylsilyl)oxy)propyl)-6-chloro-7-(5-ethyl-1-methyl-3-((methylamino)methyl)-1H-pyrazol-4-yl)-1H-indole-2-carboxylate

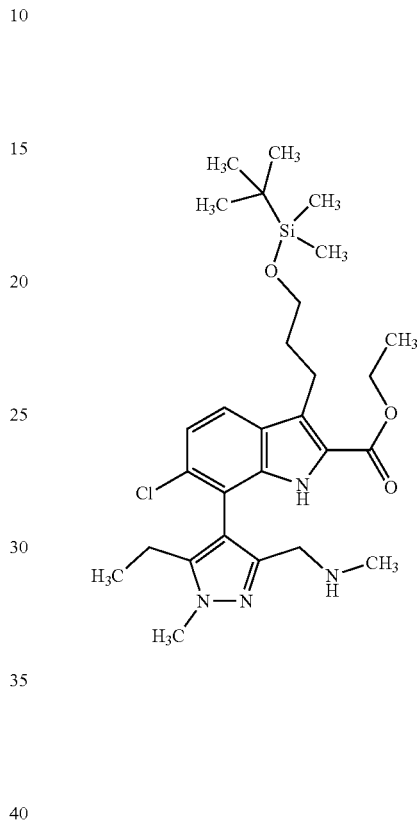

To a stirred solution of ethyl 3-(3-((tert-butyldimethylsilyl)oxy)propyl)-6-chloro-7-(5-ethyl-3-(hydroxymethyl)-1-methyl-1H-pyrazol-4-yl)-1H-indole-2-carboxylate (see Intermediate 46, 0.85 g, 1.59 mmol) in anhydrous dichloromethane (15.9 mL) was added N,N-diisopropylethylamine (553 µL, 3.18 mmol), followed by dropwise addition of methanesulfonyl chloride (158 µL, 2.06 mmol), under a stream of nitrogen at a temperature of 0° C. The resulting mixture was stirred at 0° C. for 2 h, at which point a solution of methylamine (7.95 mL, 15.9 mmol, 2 M in tetrahydrofuran) was added quickly. The mixture was warmed to room temperature and stirred overnight. Celite was added to the resulting mixture, volatiles were removed under reduced pressure, and the residue was purified by flash column chromatography on silica gel (0-20% methanol/dichloromethane) to give the title compound (0.74 g) as a white solid.

LC-MS (Method 3): $R_t$=1.64 min; MS (ESIpos): m/z=547 [M+1]$^+$ $^1$H NMR (300 MHz, Chloroform-d) δ [ppm]: 9.90 (s, 1H), 7.63 (d, 1H), 7.21 (d, 1H), 4.36 (q, 2H), 3.90 (s, 3H), 3.80-3.59 (m, 4H), 3.11 (m, 2H), 2.64-2.32 (m, 5H), 1.97-1.80 (m, 2H), 1.54 (m, 2H), 1.38 (t, 3H), 0.98 (t, 3H), 0.93 (s, 8H), 0.07 (s, 7H).

191

Intermediate 48

Ethyl 3-(3-((tert-butyldimethylsilyl)oxy)propyl)-6-chloro-7-(3-((3-chloro-N-methylpropylsulfonamido)methyl)-5-ethyl-1-methyl-1H-pyrazol-4-yl)-1H-indole-2-carboxylate

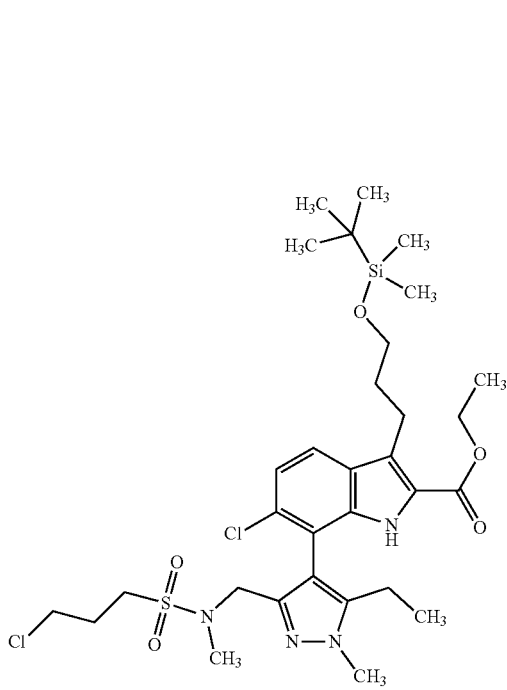 [SMILES: CCOC(=O)c1[nH]c2c(-c3c(CN(C)S(=O)(=O)CCCCl)nn(C)c3CC)c(Cl)ccc2c1CCCO[Si](C)(C)C(C)(C)C]

To a solution of ethyl 3-(3-((tert-butyldimethylsilyl)oxy)propyl)-6-chloro-7-(5-ethyl-1-methyl-3-((methylamino)methyl)-1H-pyrazol-4-yl)-1H-indole-2-carboxylate (see Intermediate 47, 0.735 g, 1.34 mmol) in anhydrous dichloromethane (6.70 mL) was added N,N-diisopropylethylamine (346 mg, 2.68 mmol), followed by dropwise addition of 3-chloropropane-1-sulfonyl chloride (CAS 1633-82-5, 194 µL, 1.60 mmol), at a temperature of 0° C. The resulting mixture was warmed to room temperature and stirred for 1 h. Celite was added to the resulting mixture, volatiles were removed under reduced pressure, and the residue was purified by flash column chromatography on silica gel (0-30% acetone/dichloromethane) to give the title compound (0.777 g).

LC-MS (Method 3): $R_t$=2.18 min; MS (ESIpos): m/z=689 [M+1]$^+$ $^1$H NMR (300 MHz, Chloroform-d) δ [ppm]: 8.31 (s, 1H), 7.64 (dd, 1H), 7.24 (d, 1H), 4.46-4.21 (m, 3H), 4.07 (d, 1H), 3.92 (s, 3H), 3.69 (t, 2H), 3.57 (t, 2H), 3.12 (m, 2H), 3.06-2.80 (m, 2H), 2.71 (s, 3H), 2.48 (m, 2H), 2.20-2.05 (m, 2H), 1.89 (p, 2H), 1.40 (t, 3H), 1.01 (t, 3H), 0.93 (s, 8H), 0.07 (s, 6H).

192

Intermediate 49

(rac)-Ethyl 1-(3-((tert-butyldimethylsilyl)oxy) propyl)-13-chloro-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide

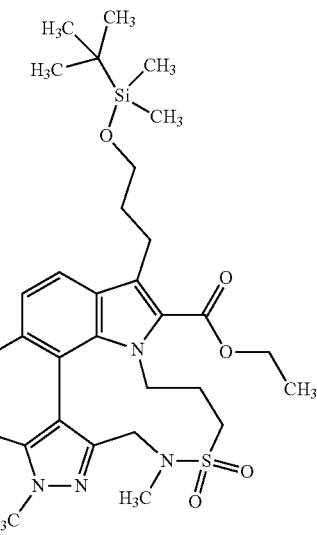

To a solution of ethyl 3-(3-((tert-butyldimethylsilyl)oxy)propyl)-6-chloro-7-(3-((3-chloro-N-methylpropylsulfonamido)methyl)-5-ethyl-1-methyl-1H-pyrazol-4-yl)-1H-indole-2-carboxylate (see Intermediate 48, 0.777 g, 1.12 mmol) in anhydrous acetonitrile degassed with argon (22.4 mL) was added cesium carbonate (1.45 g, 4.48 mmol). The resulting suspension was stirred at 60° C. for 18 h, and then cooled to room temperature. Celite was added to the resulting mixture, volatiles were removed under reduced pressure, and the residue was purified by flash column chromatography on silica gel (0-100% ethyl acetate/hexanes) to give the title compound (0.544 g).

LC-MS (Method 3): $R_t$=2.19 min; MS (ESIpos): m/z=651 [M+1]$^+$ $^1$H NMR (300 MHz, Chloroform-d) δ [ppm]: 7.68 (d, 1H), 7.28 (d, 1H), 4.59-4.03 (m, 6H), 3.90 (s, 3H), 3.67 (t, 2H), 3.28-2.94 (m, 2H), 2.90 (s, 3H), 2.58-2.40 (m, 1H), 2.22 (m, 2H), 2.12-1.97 (m, 1H), 1.95-1.67 (m, 4H), 1.40 (t, 3H), 0.93 (s, 8H), 0.89 (t, 3H), 0.07 (d, J=0.8 Hz, 6H).

Intermediate 50

(rac)-Ethyl 13-chloro-12-ethyl-1-(3-hydroxpropyl)-8,11-dimethyl-4,5,6,8,9,11-hexahydropyrazolo[3',4':4,5][1,2,8]thiadiazacycloundecino[6,7,8-hi]indole-2-carboxylate 7,7-dioxide

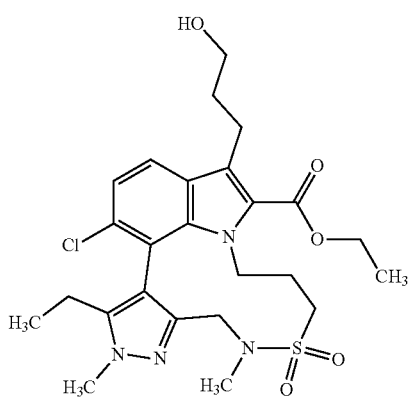 [SMILES: CCOC(=O)c1c(CCCO)c2ccc(Cl)c3c2n1CCCS(=O)(=O)N(C)Cc1nn(C)c(CC)c1-3]

To a solution of (rac)-ethyl 1-(3-((tert-butyldimethylsilyl)oxy)propyl)-13-chloro-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide (see Intermediate 49, 0.544 g, 835 μmol) in anhydrous tetrahydrofuran (16.6 mL) was added a solution of tetrabutylammonium fluoride (1 mL, 1.00 mmol, 1 M in tetrahydrofuran) at a temperature of 0° C. The resulting mixture was warmed to room temperature, stirred for 3 h and then concentrated under reduced pressure. The residue was re-suspended in 1 N aqueous hydrochloric acid and extracted three times with ethyl acetate. The combined organic extracts were washed with brine, dried over sodium sulfate, filtered and concentrated under reduced pressure. The crude product was purified by flash column chromatography on silica gel (0-20% acetone/dichloromethane) to give the title compound (327 mg).

LC-MS (Method 3): $R_t$=1.36 min; MS (ESIpos): m/z=537 [M+1]$^+$ $^1$H NMR (300 MHz, Chloroform-d) δ [ppm]: 7.65 (d, 1H), 7.30 (d, 1H), 4.52-4.18 (m, 4H), 4.11 (d, 1H), 3.91 (s, 3H), 3.71-3.51 (m, 2H), 3.18 (t, 2H), 2.92 (s, 3H), 2.51 (dd, 1H), 2.31-2.14 (m, 3H), 1.94 (m, 5H), 1.40 (t, 3H), 0.90 (t, 3H).

Intermediate 51

(rac)-Ethyl 1-(3-bromopropyl)-13-chloro-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide

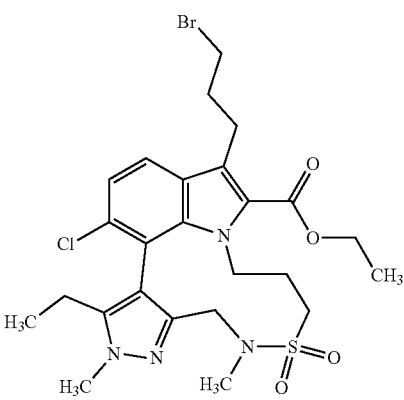 [SMILES: CCOC(=O)c1c(CCCBr)c2ccc(Cl)c3c2n1CCCS(=O)(=O)N(C)Cc1nn(C)c(CC)c1-3]

To a solution of (rac)-ethyl 13-chloro-12-ethyl-1-(3-hydroxypropyl)-8,11-dimethyl-4,5,6,8,9,11-hexahydropyrazolo[3',4':4,5][1,2,8]thiadiazacycloundecino[6,7,8-hi]indole-2-carboxylate 7,7-dioxide (see Intermediate 50, 327 mg, 608 μmol) and triphenylphosphine (175 mg, 668 μmol) in anhydrous dichloromethane (6.07 mL) was added tetrabromomethane (CAS 558-13-4, 221 mg, 668 μmol) in one portion at a temperature of 0° C. The resulting mixture was warmed to room temperature and stirred for 4 h. Celite was added to the resulting mixture, volatiles were removed under reduced pressure, and the residue was purified by flash column chromatography on silica gel (0-20% acetone/dichloromethane) and was then further purified by reverse-phase column chromatography on C18-silica gel (10-100% acetonitrile/water with 0.1% formic acid) to give the title compound (0.334 g) as a solid.

LC-MS (Method 3): $R_t$=1.77 min; MS (ESIpos): m/z=601 [M+1]$^+$ $^1$H NMR (300 MHz, Chloroform-d) δ [ppm]: 7.68 (d, 1H), 7.31 (d, 1H), 4.61-4.06 (m, 7H), 3.91 (s, 3H), 3.46 (m, 2H), 3.36-3.07 (m, 2H), 2.91 (s, 3H), 2.57-2.43 (m, 1H), 2.33-2.13 (m, 4H), 2.05 (dd, 1H), 1.42 (t, 3H), 0.89 (t, 3H).

195

Intermediate 52

(rac)-Ethyl 13-chloro-12-ethyl-1-(3-((6-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

196

Intermediate 53

(rac)-Ethyl 13-chloro-12-ethyl-8,11-dimethyl-1-(3-(naphthalen-1-yloxy)propyl)-4,5,6,8,9,11-hexahydropyrazolo[3',4':4,5][1,2,8]thiadiazacycloundecino[6,7,8-hi]indole-2-carboxylate 7,7-dioxide

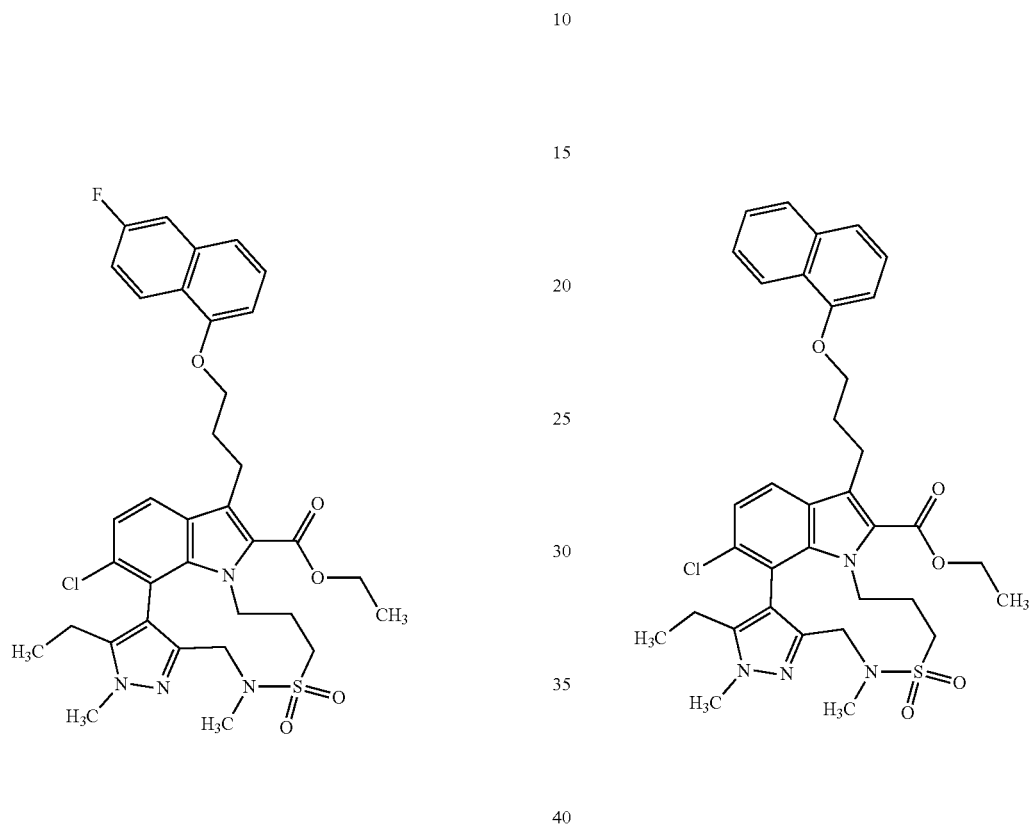

To a solution of (rac)-ethyl 1-(3-bromopropyl)-13-chloro-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide (see Intermediate 51, 155 mg, 0.26 mmol) in anhydrous tetrahydrofuran (2.59 mL) were added cesium carbonate (508 mg, 1.56 mmol) and 6-fluoronaphthalen-1-ol (CAS 804498-72-4, 84.3 mg, 520 µmol). The resulting suspension was heated to 60° C. for 20 h, and then cooled to room temperature. Celite was added to the resulting mixture, volatiles were removed under reduced pressure, and the residue was purified by reverse phase column chromatography on C18-silica gel (10-100% acetonitrile/water with 0.1% formic acid) to give the title compound (171 mg).

LC-MS (Method 3): $R_t$=2.01 min; MS (ESIpos): m/z=681 [M+1]$^+$ $^1$H NMR (Chloroform-d) δ [ppm]: 7.46-7.32 (m, 3H), 8.36 (dd, 1H), 7.63 (d, 1H), 7.26 (s, 4H), 7.20 (d, 1H), 6.71 (dd, 1H), 4.58-4.45 (m, 1H), 4.45-4.07 (m, 7H), 3.91 (s, 3H), 3.48-3.22 (m, 2H), 2.91 (s, 3H), 2.57-2.46 (m, 1H), 2.34-2.16 (m, 5H), 2.13-2.03 (m, 1H), 1.36 (t, 3H), 0.88 (t, 3H).

To a solution of (rac)-ethyl 1-(3-bromopropyl)-13-chloro-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide (see Intermediate 51 45.0 mg, 75.0 µmol) in anhydrous tetrahydrofuran (749 µL) were added cesium carbonate (146 mg, 450 µmol) and naphthalen-1-ol (CAS 90-15-3, 21.6 mg, 150 µmol). The resulting suspension was heated to 60° C. for 20 h and cooled to room temperature. Celite was added to the resulting mixture, volatiles were removed under reduced pressure, and the residue was purified by reverse phase column chromatography on C18-silica gel (10-100% acetonitrile/water with 0.1% formic acid) to give the title compound (48.8 mg).

LC-MS (Method 3): $R_t$=2.00 min; MS (ESIpos): m/z=663 [M+1]$^+$ $^1$H NMR (300 MHz, Chloroform-d) δ [ppm]: 8.43-8.33 (m, 1H), 7.88-7.78 (m, 1H), 7.65 (d, 1H), 7.56-7.48 (m, 2H), 7.48-7.30 (m, 2H), 7.20 (d, 1H), 6.80-6.73 (m, 1H), 4.61-4.49 (m, 1H), 4.47-4.08 (m, 7H), 3.91 (s, 3H), 3.53-3.24 (m, 2H), 2.90 (s, 3H), 2.62-2.44 (m, 1H), 2.37-2.03 (m, 5H), 1.95-1.72 (m, 2H), 1.37 (t, 3H), 0.89 (t, 3H).

197
Intermediate 54

(rac)-Ethyl 13-chloro-1-(3-((2,3-dihydro-1H-inden-4-yl)oxy)propyl)-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide

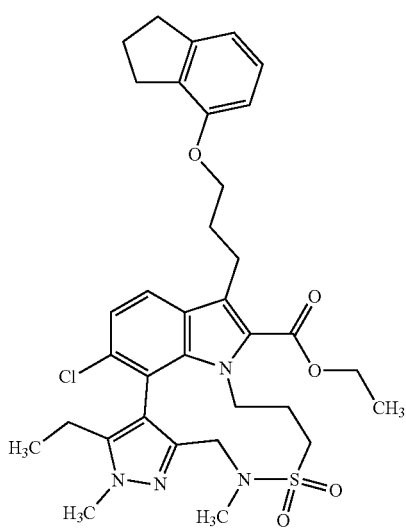 [SMILES: CCOC(=O)c1c(CCCOc2cccc3c2CCC3)c2ccc(Cl)c3c2n1CCCS(=O)(=O)N(C)Cc1nn(C)c(CC)c1-3]

To a solution of (rac)-ethyl 1-(3-bromopropyl)-13-chloro-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide (see Intermediate 51, 45.0 mg, 75.0 µmol) in anhydrous tetrahydrofuran (749 µL) under a stream of nitrogen were added cesium carbonate (146 mg, 450 µmol) and 2,3-dihydro-1H-inden-4-ol (CAS 1641-41-4, 20.1 mg, 150 µmol). The resulting suspension was heated to 60 C for 20 h and cooled to room temperature. Celite was added to the resulting mixture, volatiles were removed under reduced pressure, and the residue was purified by reverse-phase column chromatography on C18-silica gel (10-100% acetonitrile/water with 0.1% formic acid gradient) to give the title compound (46 mg).

LC-MS (Method 3): $R_t$=2.04 min; MS (ESIpos): m/z=653 [M+1]$^+$ $^1$H NMR (300 MHz, Chloroform-d) δ [ppm]: 7.64 (d, 1H), 7.26 (s, 10H), 7.10 (t, 1H), 6.94-6.83 (m, 1H), 6.62 (d, 1H), 4.52 (d, 1H), 4.46-4.09 (m, 5H), 4.04 (t, 2H), 3.91 (s, 3H), 3.39-3.10 (m, 2H), 3.00-2.81 (m, 8H), 2.50 (dd, 1H), 2.32-2.02 (m, 4H), 1.84 (s, 2H), 1.39 (t 3H), 0.89 (t, 3H).

198
Intermediate 55

(rac)-Ethyl 13-chloro-1-(3-(4-chloro-3,5-dimethylphenoxy)propyl)-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide

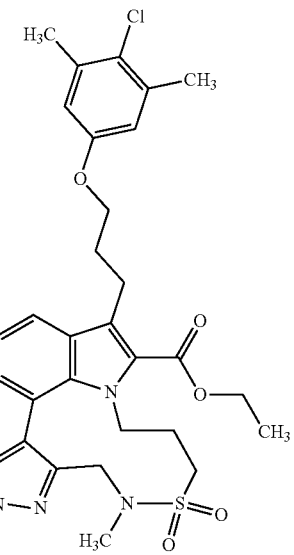

To a solution of (rac)-ethyl 1-(3-bromopropyl)-13-chloro-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide (see Intermediate 51, 45.0 mg, 75.0 µmol) in anhydrous tetrahydrofuran (766 µL) under a stream of nitrogen were added cesium carbonate (24.9 mg, 76.7 µmol) and 4-chloro-3,5-dimethylphenol (CAS 88-04-0, 23.9 mg, 153 µmol). The resulting suspension was heated to 60° C. for 24 h and cooled to room temperature. Celite was added to the resulting mixture, volatiles were removed under reduced pressure, and the residue was purified by reverse-phase column chromatography on C18-silica gel (10-100% acetonitrile/water with 0.1% formic acid gradient) to give the title compound (50 mg).

LC-MS (Method 3): $R_t$=2.09 min; MS (ESIpos): m/z=675 [M+1]$^+$ $^1$H NMR (300 MHz, Chloroform-d) δ [ppm]: 7.63 (d, 1H), 7.34-7.26 (m, 4H), 6.64 (s, 2H), 4.62-4.05 (m, 6H), 3.95 (t, 2H), 3.91 (s, 3H), 3.23 (m, 2H), 2.90 (s, 3H), 2.50 (dd, 1H), 2.35 (s, 6H), 2.22 (m, 2H), 2.09 (q, 2H), 1.84 (d, 1H), 1.41 (t, 3H), 0.89 (t, 3H).

Intermediate 56

(rac)-Ethyl 13-chloro-12-ethyl-8,11-dimethyl-1-(3-((5,6,7,8-tetrahydronaphthalen-1-yl)oxy)propyl)-4,5,6,8,9,11-hexahydropyrazolo[3',4':4,5][1,2,8]thiadiazacycloundecino[6,7,8-hi]indole-2-carboxylate 7,7-dioxide

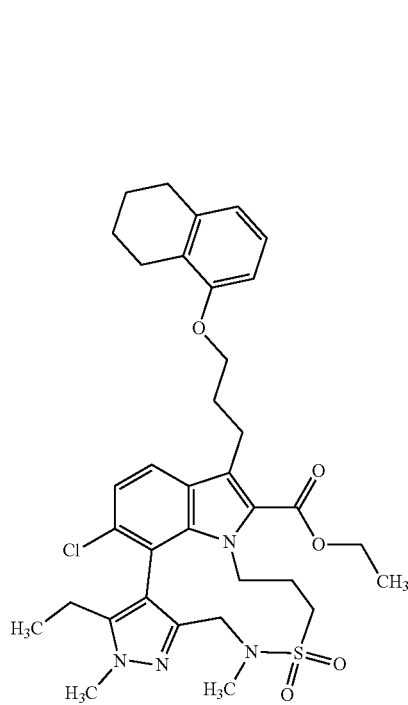 [SMILES: CCOC(=O)c1c(CCCOc2cccc3c2CCCC3)c2ccc(Cl)c3c2n1CCCS(=O)(=O)N(C)Cc1nn(C)c(CC)c1-3]

To a solution of (rac)-ethyl 1-(3-bromopropyl)-13-chloro-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide (see Intermediate 51, 45.0 mg, 75.0 µmol) in anhydrous tetrahydrofuran (766 µL) under a stream of nitrogen were added cesium carbonate (149 mg, 460 µmol) and 5,6,7,8-tetrahydronaphthalen-1-ol (CAS 529-35-1, 22.6 mg, 153 µmol). The resulting suspension was heated to 60° C. for 24 h and cooled to room temperature. Celite was added to the resulting mixture, volatiles were removed under reduced pressure, and the residue was purified by reverse-phase column chromatography on C18-silica gel (10-100% acetonitrile/water with 0.1% formic acid gradient) to give the title compound (48.6 mg).

LC-MS (Method 3): $R_t$=2.12 min; MS (ESIpos): m/z=667 [M+1]$^+$ $^1$H NMR (300 MHz, Chloroform-d) δ [ppm]: 7.64 (d, 1H), 7.28 (s, 1H), 7.05 (t, 1H), 6.71 (d, 1H), 6.60 (d, 1H), 4.52 (d, 1H), 4.47-4.09 (m, 6H), 4.01 (t, 2H), 3.91 (s, 3H), 3.40-3.14 (m, 1H), 2.91 (s, 3H), 2.77 (s, 6H), 2.56-2.42 (m, 1H), 2.36-2.02 (m, 4H), 1.90-1.69 (m, 6H), 1.39 (t, 3H), 0.89 (t, 3H).

Intermediate 57

(rac)-Ethyl 13-chloro-12-ethyl-1-(34(4-fluoronaphthalen-1-yl)oxy)propyl)-8,11-dimethyl-4,5,6,8,9,11-hexahydropyrazolo[3',4':4,5][1,2,8]thiadiazacycloundecino[6,7,8-hi]indole-2-carboxylate 7,7-dioxide

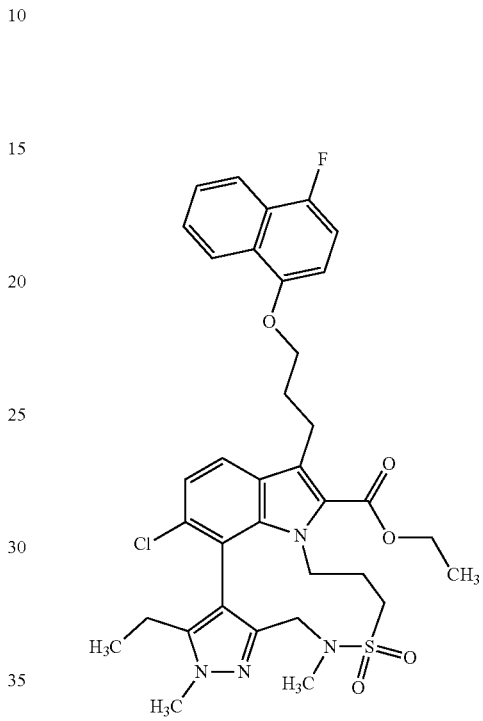

To a solution of (rac)-ethyl 1-(3-bromopropyl)-13-chloro-12-ethyl-8,11-dimethyl-4,5,6,8,9,11-hexahydropyrazolo[3',4':4,5][1,2,8]thiadiazacycloundecino[6,7,8-hi]indole-2-carboxylate 7,7-dioxide (see Intermediate 51, 45.0 mg, 75.0 µmol) in anhydrous tetrahydrofuran (766 µL) under a stream of nitrogen were added cesium carbonate (24.9 mg, 76.7 µmol) and 4-fluoronaphthalen-1-ol (CAS 315-53-7, 24.8 mg, 153 µmol). The resulting suspension was heated to 60° C. for 24 h and cooled to room temperature. Celite was added to the resulting mixture, volatiles were removed under reduced pressure, and the residue was purified by reverse-phase column chromatography on C18-silica gel (10-100% acetonitrile/water with 0.1% formic acid gradient) to give the title compound (42.4 mg).

LC-MS (Method 3): $R_t$=1.97 min; MS (ESIpos): m/z=682 [M+1]$^+$ $^1$H NMR (300 MHz, Chloroform-d) δ [ppm]: 8.35 (dd, 1H), 8.12-8.06 (m, 1H), 8.03 (d, 1H), 7.64 (d, 1H), 7.61-7.54 (m, 2H), 7.20 (d, 1H), 7.02 (dd, 1H), 6.63 (dd, 1H), 4.52 (m, 1H), 4.44-4.07 (m, 7H), 3.91 (s, 3H), 3.48-3.23 (m, 2H), 2.90 (s, 3H), 2.59-2.43 (m, 1H), 2.38-2.16 (m, 4H), 2.16-2.02 (m, 1H), 1.94-1.73 (m, 2H), 1.37 (t, 3H), 0.88 (t, 3H).

201

Intermediate 58

Ethyl 7-bromo-3-(3-ethoxy-3-oxo-propyl)-6-fluoro-1H-indole-2-carboxylate

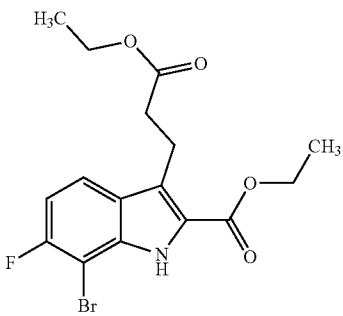 [SMILES: CCOC(=O)CCc1c(C(=O)OCC)[nH]c2c(Br)c(F)ccc12]

To a stirred suspension of 2-bromo-3-fluoroaniline (CAS 111721-75-6, 40.0 g, 210 mmol, 1.00 eq.) in an aqueous hydrochloric acid solution (53.0 mL concentrated hydrochloric acid in 339 mL water, 630 mmol, 3.00 eq.) was added a 2.5 M solution of sodium nitrite in water (83.9 mL, 210 mmol, 1.00 eq.) via dropping funnel at a temperature of 0° C. After complete addition, a 4.5 M sodium acetate solution (262 mL, 1.18 mol, 5.62 eq.) in water was added via dropping funnel, followed by addition of ethyl 2-oxocyclopentanecarboxylate (CAS 611-10-9, 31.0 mL, 210 mmol, 1.00 eq.). The resulting yellow suspension was maintained at 0° C. for 15 minutes and then warmed to room temperature and stirred for 2 hours. The reaction mixture was extracted four times with dichloromethane (200 mL each), and the combined organic extracts were dried (magnesium sulfate), filtered and concentrated under reduced pressure to give the crude corresponding intermediate hydrazone as an orange solid.

The residue was re-suspended in ethanol (210 mL, 1.00 M), cooled to 0° C., followed by slow addition of concentrated sulfuric acid (27.9 mL, 525 mmol, 2.50 eq.). The dark red solution was heated at 95° C. for 13 days, cooled to room temperature and partially concentrated under reduced pressure. The dark brown solution was poured onto ice/water (500 mL) and extracted thrice with dichloromethane (500 mL each). The combined organic extracts were washed with saturated aqueous sodium bicarbonate (500 mL), dried (magnesium sulfate), filtered and concentrated under reduced pressure to give a brown solid. The residue was purified by flash column chromatography (20% ethyl acetate/hexanes) and then recrystallised from hot 10% ethyl acetate/hexanes to give the title compound as a white fluffy solid (40.8 g).

LC-MS (Method 3): $R_t$=1.62 min; MS (ESIpos): m/z=388 [M+H]$^+$ $^1$H NMR (300 MHz, Chloroform-d) δ [ppm]: 8.81 (0.78), 7.63 (1.03), 6.98 (1.02), 4.44 (2.08), 4.08 (2.08), 3.36 (2.07), 2.66 (2.08), 1.44 (3.27), 1.20 (3.61).

202

Intermediate 59

Ethyl 7-bromo-6-fluoro-3-(3-hydroxypropyl)-1H-indole-2-carboxylate

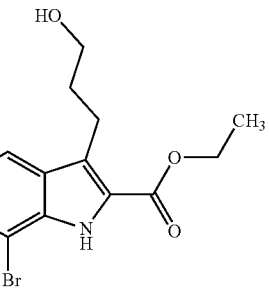

To a stirred solution of ethyl 7-bromo-3-(3-ethoxy-3-oxopropyl)-6-fluoro-1H-indole-2-carboxylate (see intermediate 58, 24.0 g, 62.1 mmol, 1.00 eq.) in anhydrous tetrahydrofuran (621 mL, 0.10 M) was added borane dimethyl sulfide complex (23.4 mL, 248 mmol, 4.00 eq.) at a temperature of 0° C. The resulting mixture was stirred at 0° C. for 30 minutes and then warmed to room temperature and stirred for 2 days. Methanol was added to the mixture to decompose any remaining borane and the mixture was concentrated three times from methanol. The residue was purified by flash column chromatography (30-100% ethyl acetate/hexanes gradient) to give the title compound as a white solid (19.1 g).

LC-MS (Method 3): $R_t$=1.33 min; MS (ESIpos): m/z=346 [M+H]$^+$ $^1$H NMR (300 MHz, Chloroform-d) δ [ppm]: 1.45 (3.12), 1.93 (2.05), 2.28 (0.95), 3.21 (2.02), 3.57 (2.08), 4.46 (2.04), 6.98 (0.99), 7.59 (1.03), 8.73 (0.72).

Intermediate 60

Ethyl 7-bromo-3-(3-((tert-butyldimethylsilyl)oxy)propyl)-6-fluoro-1H-indole-2-carboxylate

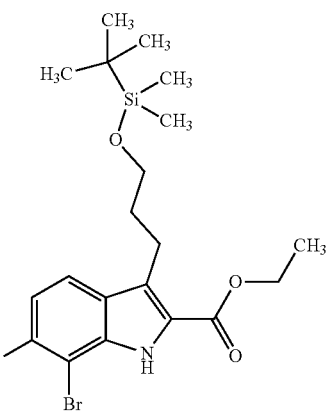

To a stirred solution of ethyl 7-bromo-6-fluoro-3-(3-hydroxypropyl)-1H-indole-2-carboxylate (see intermediate 59, 18.4 g, 53.1 mmol, 1.00 eq.) in anhydrous dichloromethane (265 mL, 0.20 M) was added imidazole (5.41 g, 79.6 mmol, 1.50 eq.) and tert-butylchlorodimethylsilane (CAS 18162-48-6, 9.60 g, 63.7 mmol, 1.20 eq.) at a temperature of 0° C. The resulting mixture was warmed to room temperature and stirred for 30 minutes. The mixture was diluted with water (200 mL) and extracted thrice with dichloromethane (100 mL each) The combined organic extracts were dried (magnesium sulfate), filtered and concentrated under reduced pressure. The residue was purified by flash column chromatography (0-20% ethyl acetate/hexanes gradient) to give the title compound as a white solid (23.2 g).

LC-MS (Method 3): $R_t$=2.21 min; MS (ESIpos): m/z=458 [M+H]$^+$.

$^1$H-NMR (300 MHz, CHLOROFORM-d) δ [ppm]: 8.77 (s, 1H), 7.61 (dd, 1H), 6.96 (t, 1H), 4.43 (q, 2H), 3.65 (t, 2H), 3.12 (m, 2H), 1.86 (m, 2H), 1.43 (t, 3H), 0.92 (s, 9H), 0.05 (s, 6H).

Intermediate 61

Ethyl 3-(3-((tert-butyldimethylsilyl)oxy)propyl)-6-fluoro-7-(4,4,5,5-tetramethyl-1,3,2-dioxaborolan-2-yl)-1H-indole-2-carboxylate

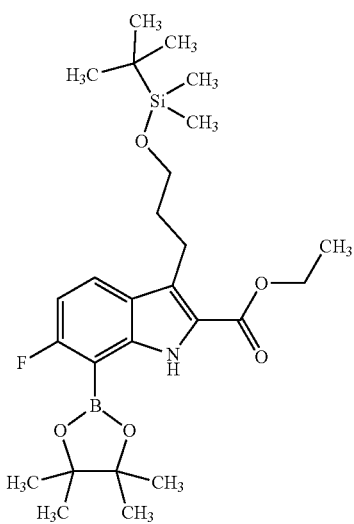 [SMILES: CCOC(=O)c1[nH]c2c(B3OC(C)(C)C(C)(C)O3)c(F)ccc2c1CCCO[Si](C)(C)C(C)(C)C]

To a mixture of ethyl 7-bromo-3-(3-((tert-butyldimethylsilyl)oxy)propyl)-6-fluoro-1H-indole-2-carboxylate (see intermediate 60, 11.0 g, 24.0 mmol, 1.00 eq.), bis(pinacolato)diboron (CAS 78183-34-3, 7.28 g, 28.7 mmol, 1.20 eq.), potassium acetate (4.71 g, 48.0 mmol, 2.00 eq.) and Pd(dppf)Cl2×CH$_2$Cl$_2$ (979 mg, 1.20 mmol, 5.00 mol-%) under a nitrogen atmosphere was added 1,4-dioxane sparged with nitrogen (48.0 mL, 0.50 M). The resulting red suspension was heated to 90° C. for 2 days, and then cooled to room temperature. Celite was added to the resulting mixture, volatiles were removed under reduced pressure, and the residue was purified by flash column chromatography (5-20% ethyl acetate/hexanes gradient) to give the title compound as yellow solid. (12.1 g, >90% pure). The crude title compound was used directly in the next step.

LC-MS (Method 3): $R_t$=2.35 min; MS (ESIpos): m/z=506 [M+H]$^+$.

$^1$H-NMR (300 MHz, CHLOROFORM-d) δ [ppm]: 9.67 (s, 1H), 7.76 (m, 1H), 6.86 (dd, 1H), 4.41 (q, 2H), 3.65 (t, 2H), 3.12 (m, 2H), 1.86 (m, 2H), 1.42 (d, 14H), 1.26 (s, 3H), 0.92 (s, 9H), 0.05 (s, 6H).

Intermediate 62

Ethyl 3-(3-((tert-butyldimethylsilyl)oxy)propyl)-6-fluoro-7-(3-(hydroxymethyl)-1,5-dimethyl-1H-pyrazol-4-yl)-1H-indole-2-carboxylate

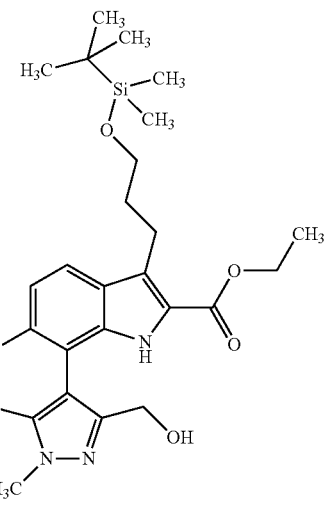

To a stirred suspension of (4-bromo-1,5-dimethyl-1H-pyrazol-3-yl)methanol (intermediate 6, 3.85 g, 18.8 mmol, 1.20 eq.), XPhos Pd G3 (922 mg, 1.09 mmol, 7.00 mol %) and potassium phosphate tribasic (6.64 g, 31.3 mmol, 2.00 eq.) in a 2:1 mixture of 1,4-dioxane/water degassed with argon (45 mL, 0.33 M) was slowly added dropwise (over a period of approximately 1h), a solution of ethyl-3-(3-((tert-butyldimethylsilyl)oxy)propyl)-6-fluoro-7-(4,4,5,5-tetramethyl-1,3,2-dioxaborolan-2-yl)-1H-indole-2-carboxylate (see intermediate 61, 7.96 g, 15.7 mmol, 1.00 eq.) in 1,4-dioxane degassed with argon (16 mL, 1.00 M) at a temperature of 50° C. The resulting dark mixture was heated to 50° C. for a further 30 min, cooled to room temperature and concentrated under reduced pressure. The residue was dissolved in water (50 mL) and extracted thrice with ethyl acetate (50 mL each). The combined organic extracts were washed with brine (50 mL), dried (magnesium sulfate), filtered and concentrated under reduced pressure. The residue was purified by flash column chromatography (0-100% acetone/dichloromethane gradient), followed by reverse phase column chromatography (10-100% acetonitrile/water gradient) to give the title compound as an off-white solid (5.67 g).

LC-MS (Method 3): $R_t$=1.94 min; MS (ESIpos): m/z=502 [M−H]$^-$.

$^1$H-NMR (300 MHz, CHLOROFORM-d) δ [ppm]: 10.12 (s, 1H), 7.65 (dd, 2H), 6.99 (m, 2H), 4.70 (dt, 2H), 4.36 (m, 6H), 3.89 (s, 6H), 3.70 (m, 4H), 3.58 (m, 1H), 3.15 (dd, 4H), 2.17 (d, 6H), 1.92 (m, 4H), 1.37 (m, 6H), 0.93 (d, 19H), 0.07 (d, 12H).

Intermediate 63

Ethyl 3-(3-((tert-butyldimethylsilyl)oxy)propyl)-7-(1,5-dimethyl-3-((methylamino)methyl)-1H-pyrazol-4-yl)-6-fluoro-1H-indole-2-carboxylate

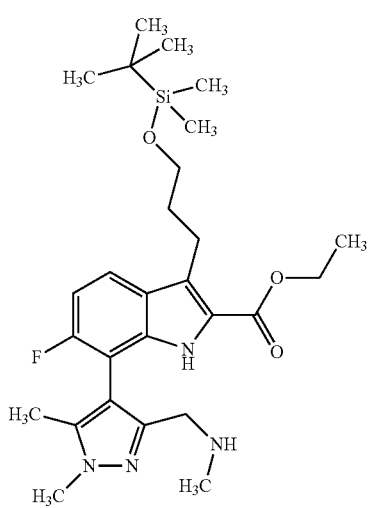 [SMILES: CCOC(=O)c1[nH]c2c(-c3c(CNC)nn(C)c3C)c(F)ccc2c1CCCO[Si](C)(C)C(C)(C)C]

To a stirred solution of ethyl 3-(3-((tert-butyldimethylsilyl)oxy)propyl)-7-(5-ethyl-3-(hydroxymethyl)-1-methyl-1H-pyrazol-4-yl)-6-fluoro-1H-indole-2-carboxylate (see intermediate 62, 1.51 g, 3.00 mmol, 1.00 eq.) in anhydrous dichloromethane (30.0 mL, 0.10 M) was added N,N-diisopropylethylamine (1.04 mL, 6.00 mmol, 2.00 eq.), followed by dropwise addition of methanesulfonyl chloride (301 µL, 3.90 mmol, 1.30 eq.), at a temperature of 0° C. The resulting mixture was stirred at 0° C. for 2 hours, at which point a 2.0 M solution of methylamine in tetrahydrofuran (15.0 mL, 30.0 mmol, 10.0 eq.) was added quickly. The yellow mixture was warmed to room temperature and was stirred for 4 hours. Celite was added to the resulting mixture, volatiles were removed under reduced pressure, and the residue was purified by flash column chromatography (0-70% acetone/dichloromethane gradient followed by 0-10% methanol/dichloromethane with 1% ammonia gradient) to give the title compound as a yellow solid (1.47 g).

LC-MS (Method 3): $R_t$=5.17 min; MS (ESIpos): m/z=517 [M+H]$^+$.

$^1$H-NMR (300 MHz, CHLOROFORM-d) δ [ppm]: 13.04 (s, 1H), 7.62 (dd, 1H), 6.96 (dd, 1H), 4.36 (m, 2H), 3.84 (s, 3H), 3.71 (m, 3H), 3.31 (d, 1H), 3.16 (m, 2H), 2.46 (s, 3H), 2.17 (d, 3H), 1.92 (m, 2H), 1.62 (s, 2H), 1.38 (t, 3H), 0.92 (s, 9H), 0.07 (s, 6H).

Intermediate 64

Ethyl 3-(3-((tert-butyldimethylsilyl)oxy)propyl)-7-(3-(((3-chloro-N-methylpropyl)sulfonamido)methyl)-1,5-dimethyl-1H-pyrazol-4-yl)-6-fluoro-1H-indole-2-carboxylate

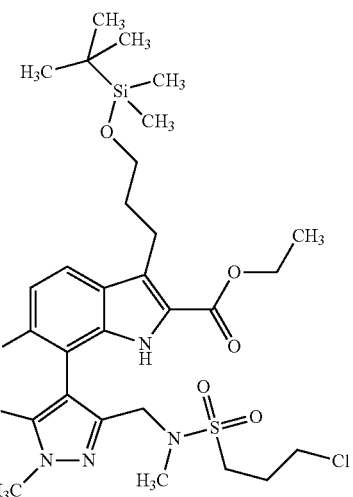

To a stirred solution of ethyl 3-(3-((tert-butyldimethylsilyl)oxy)propyl)-7-(1,5-dimethyl-3-((methylamino)methyl)-1H-pyrazol-4-yl)-6-fluoro-1H-indole-2-carboxylate (see intermediate 63, 1.46 g, 2.82 mmol, 1.00 eq.) in anhydrous dichloromethane (14.1 mL, 0.20 M) was added N,N-diisopropylethylamine (981 µL, 5.64 mmol, 2.00 eq.), followed by dropwise addition of 3-chloropropane-1-sulfonyl chloride (CAS 1633-82-5, 410 µL, 3.38 mmol, 1.20 eq.), at a temperature of 0° C. The resulting yellow mixture was warmed to room temperature and was stirred for 1 hour. Celite was added to the resulting mixture, volatiles were removed under reduced pressure, and the residue was purified by flash column chromatography (0-30% acetone/dichloromethane gradient) to give the title compound as a yellow oil (1.79 g).

LC-MS (Method 4): $R_t$=5.67 min; MS (ESIpos): m/z=557 [M+H]$^+$.

$^1$H-NMR (300 MHz, CHLOROFORM-d) δ [ppm]: 8.40 (s, 1H), 7.67 (m, 1H), 6.99 (dd, 1H), 4.38 (m, 3H), 4.15 (d, 1H), 3.89 (s, 3H), 3.69 (m, 2H), 3.56 (t, 2H), 3.13 (m, 2H), 2.97 (m, 2H), 2.72 (s, 3H), 2.12 (m, 5H), 1.90 (m, 2H), 1.40 (t, 3H), 0.93 (s, 9H), 0.07 (s, 6H).

207

Intermediate 65

(rac)-Ethyl 1-(3-(((tert-butyldimethylsilyl)oxy)propyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide

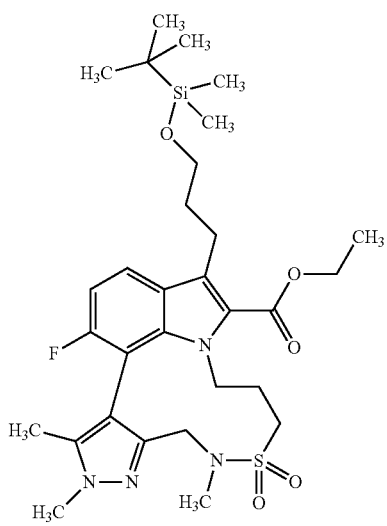 [SMILES: CCOC(=O)c1c(CCCO[Si](C)(C)C(C)(C)C)c2ccc(F)c3c2n1CCCS(=O)(=O)N(C)Cc1nn(C)c(C)c1-3]

To a stirred solution of ethyl 3-(3-((tert-butyldimethylsilyl)oxy)propyl)-7-(3-(((3-chloro-N-methylpropyl)sulfonamido)methyl)-1,5-dimethyl-1H-pyrazol-4-yl)-6-fluoro-1H-indole-2-carboxylate (see intermediate 64, 1.79 g, 1.56 mmol, 1.00 eq.) in anhydrous acetonitrile degassed with argon (31.2 mL, 0.05 M) were added sodium iodide (203 mg, 1.36 mmol, 0.50 eq.) and cesium carbonate (1.52 g, 4.68 mmol, 3.00 eq.). The resulting orange suspension was heated to 60° C. for 10 days, and then cooled to room temperature. Celite was added to the resulting mixture, volatiles were removed under reduced pressure, and the residue was purified by flash column chromatography (0-100% ethyl acetate/hexanes gradient) to give the title compound as a yellow oil (807 mg, >95% purity).

LC-MS (Method 4): $R_t$=5.51 min; MS (ESIpos): m/z=621 [M+H]$^+$.

$^1$H-NMR (300 MHz, CHLOROFORM-d) δ [ppm]: 7.71 (dd, 1H), 6.99 (t, 1H), 4.55 (dt, 1H), 4.33 (m, 5H), 3.87 (s, 3H), 3.67 (m, 2H), 3.10 (m, 2H), 2.93 (s, 3H), 2.50 (m, 1H), 2.14 (m, 1H), 1.88 (m, 7H), 1.41 (t, 3H), 0.94 (s, 9H), 0.08 (s, 6H).

208

Intermediate 66

(rac)-Ethyl 13-fluoro-1-(3-hydroxypropyl)-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide

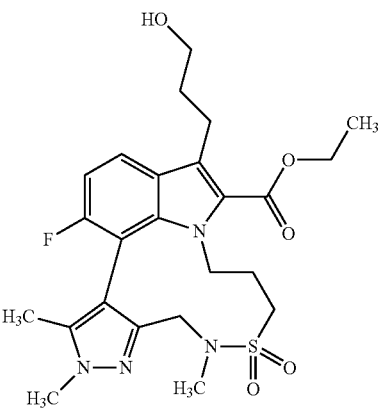 [SMILES: CCOC(=O)c1c(CCCO)c2ccc(F)c3c2n1CCCS(=O)(=O)N(C)Cc1nn(C)c(C)c1-3]

To a stirred solution of (rac)-ethyl 1-(3-((tert-butyldimethylsilyl)oxy)propyl)-13-fluoro-8,11,12-trimethyl-5,6,9,11-tetrahydro-4H,8H-pyrazolo[3',4':4,5][1]thia[2,8]diazacyclo-undecino[6,7,8-hi]indole-2-carboxylate 7,7-dioxide (see intermediate 65, 805 mg, 1.29 mmol, 1.00 eq.) in anhydrous tetrahydrofuran (25.8 mL, 0.05 M) was added a 1.0 M solution of tetrabutylammonium fluoride in tetrahydrofuran (1.54 mL, 1.54 mmol, 1.20 eq.) at a temperature of 0° C. The resulting yellow mixture was warmed to room temperature, stirred for 2 hours and then concentrated under reduced pressure. The residue was resuspended in 1.0 M aqueous hydrochloric acid (20 mL) and extracted thrice with ethyl acetate (20 mL each). The combined organic extracts were washed with brine (20 mL), dried (magnesium sulfate), filtered and concentrated under reduced pressure. The crude product was purified by flash column chromatography (0-40% acetone/dichloromethane gradient) to give the title compound as a white solid (483 mg, >95% purity).

LC-MS (Method 4): $R_t$=2.82 min; MS (ESIpos): m/z=507 [M+H]$^+$.

$^1$H-NMR (300 MHz, CHLOROFORM-d) δ [ppm]: 7.69 (dd, 1H), 7.01 (t, 1H), 4.39 (m, 5H), 4.07 (d, 1H), 3.88 (s, 3H), 3.59 (tdd, 2H), 3.18 (t, 2H), 2.95 (s, 3H), 2.53 (ddd, 1H), 2.11 (ddd, 1H), 1.88 (m, 7H), 1.59 (s, 3H), 1.41 (t, 3H).

Intermediate 67

(rac)-Ethyl 1-(3-bromopropyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide

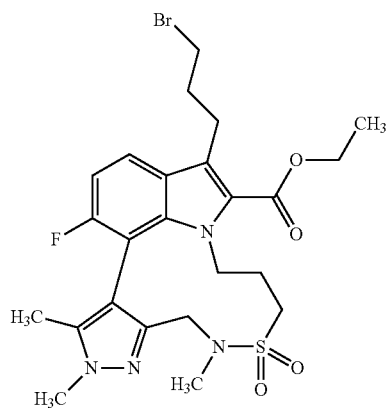 [SMILES: CCOC(=O)c1c(CCCBr)c2ccc(F)c3c2n1CCCS(=O)(=O)N(C)Cc1nn(C)c(C)c1-3]

To a stirred solution of (rac)-ethyl 13-fluoro-1-(3-hydroxpropyl)-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 66, 483 mg, 0.95 mmol, 1.00 eq.) and triphenylphosphine (272 mg, 1.04 mmol, 1.10 eq.) in anhydrous dichloromethane (9.53 mL, 0.10 M) was added carbon tetrabromide (CAS 558-13-4, 344 mg, 1.04 mmol, 1.10 eq.) in one portion at a temperature of 0° C. The resulting mixture was warmed to room temperature and was stirred for 30 minutes. Celite was added to the resulting mixture, volatiles were removed under reduced pressure, and the residue was purified by flash column chromatography (0-20% acetone/dichloromethane gradient) to give the title compound as a colourless oil (393 mg).

LC-MS (Method 4): $R_t$=4.13 min; MS (ESIpos): m/z=569 [M+H]$^+$.

$^1$H-NMR (300 MHz, CHLOROFORM-d) δ [ppm]: 7.72 (dd, 1H), 7.03 (t, 1H), 4.55 (dt, 1H), 4.39 (m, 4H), 4.09 (d, 1H), 3.88 (s, 3H), 3.46 (td, 2H), 3.23 (m, 2H), 2.93 (s, 3H), 2.51 (m, 1H), 2.19 (m, 3H), 1.91 (s, 6H), 1.42 (t, 3H).

Intermediate 68

(rac)-Ethyl 13-fluoro-1-(3-((6-fluoronaphthalen-1-yl)oxy)propyl)-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide

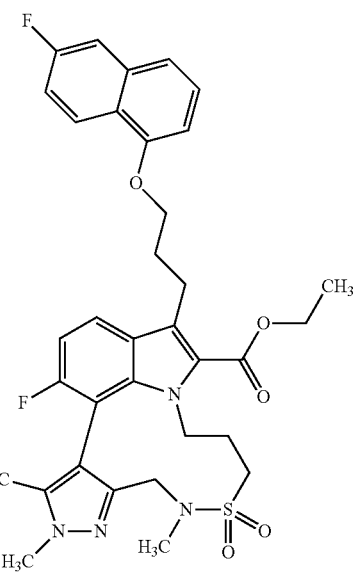

To a stirred solution of (rac)-ethyl 1-(3-bromopropyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 67, 170 mg, 0.30 mmol, 1.00 eq.) in anhydrous tetrahydrofuran (3.00 mL, 0.10 M) were added cesium carbonate (583 mg, 1.80 mmol, 6.00 eq.) and 6-fluoronaphthalen-1-ol (CAS 804498-72-4, 97.2 mg, 0.60 mmol, 2.00 eq.). The resulting suspension was heated to 55° C. for 16 hours, cooled to room temperature and then adsorbed onto Celite. The residue was purified by reverse phase column chromatography (10-100% acetonitrile/water with 0.1% formic acid gradient) to give the title compound as a mixture with the corresponding methyl ester, presumably as a result of using methanol during adsorption onto Celite. Full characterization was performed following ester hydrolysis to confirm structure (see Example 25).

LC-MS (Method 3): $R_t$=1.90 min; MS (ESIpos): m/z=651 [M+H]$^+$ (title compound), LC-MS (Method 3): $R_t$=1.86 min; MS (ESIpos): m/z=637 [M+H]$^+$ (corresponding methyl ester).

211

Intermediate 69

(rac)-Ethyl 13-fluoro-8,11,12-trimethyl-1-(3-(naph-thalen-1-yloxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide

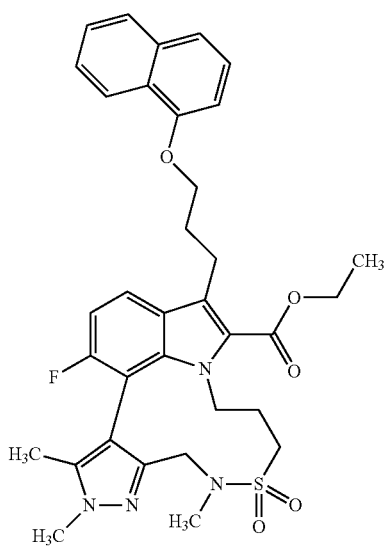 [SMILES: CCOC(=O)c1c(CCCOc2cccc3ccccc23)c2ccc(F)c3c2n1CCCS(=O)(=O)N(C)Cc1nn(C)c(C)c1-3]

To a stirred solution of (rac)-ethyl 1-(3-bromopropyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 67, 38.0 mg, 73.7 μmol, 1.00 eq.) in anhydrous tetrahydrofuran (737 μL, 0.10 M) were added cesium carbonate (144 mg, 443 μmol, 6.00 eq.) and naphthalen-1-ol (CAS 90-15-3, 21.2 mg, 148 μmol, 2.00 eq.). The resulting suspension was heated to 55° C. for 24 hours, cooled to room temperature and then adsorbed onto Celite. The residue was purified by reverse phase column chromatography (10-100% acetonitrile/water with 0.1% formic acid gradient) to give the title compound as a mixture with the corresponding methyl ester, presumably as a result of using methanol during adsorption onto Celite. Full characterization was performed following ester hydrolysis to confirm structure (see Example 26).

LC-MS (Method 3): $R_t$=1.89 min; MS (ESIpos): m/z=633 [M+H]$^+$ (title compound), LC-MS (Method 3): $R_t$=1.83 min; MS (ESIpos): m/z=619 [M+H]$^+$ (corresponding methyl ester).

212

Intermediate 70

(rac)-Ethyl 1-(3-((2,3-dihydro-1H-inden-4-yl)oxy)propyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide

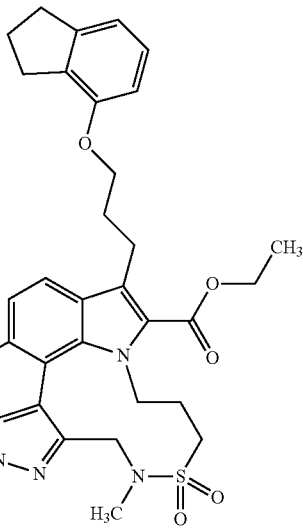

To a stirred solution of (rac)-ethyl 1-(3-bromopropyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 67, 42.0 mg, 73.8 μmol, 1.00 eq.) in anhydrous tetrahydrofuran (737 μL, 0.10 M) were added cesium carbonate (144 mg, 443 μmol, 6.00 eq.) and 4-indanol (CAS 1641-41-4, 19.7 mg, 148 mmol, 2.00 eq.). The resulting suspension was heated to 55° C. for 16 hours, cooled to room temperature and then adsorbed onto Celite. The residue was purified by reverse phase column chromatography (10-100% acetonitrile/water with 0.1% formic acid gradient) to give the title compound as a mixture with the corresponding methyl ester, presumably as a result of using methanol during adsorption onto Celite. Full characterization was performed following ester hydrolysis to confirm structure (see Example 27).

LC-MS (Method 3): $R_t$=1.92 min; MS (ESIpos): m/z=623 [M+H]$^+$ (title compound), LC-MS (Method 3): $R_t$=1.86 min; MS (ESIpos): m/z=609 [M+H]$^+$ (corresponding methyl ester).

213

Intermediate 71

(rac)-Ethyl 1-(3-(4-chloro-3,5-dimethylphenoxy)propyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide

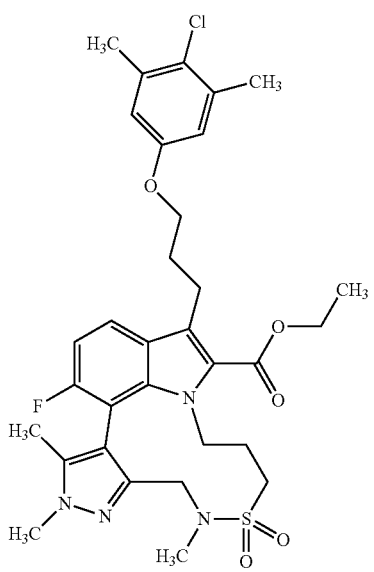 [SMILES: CCOC(=O)c1c(CCCOc2cc(C)c(Cl)c(C)c2)c2ccc(F)c3c2n1CCCS(=O)(=O)N(C)Cc1nn(C)c(C)c1-3]

To a stirred solution of (rac)-ethyl 1-(3-bromopropyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 67, 42.0 mg, 73.8 μmol, 1.00 eq.) in anhydrous tetrahydrofuran (737 μL, 0.10 M) were added cesium carbonate (144 mg, 443 μmol, 6.00 eq.) and 4-chloro-3,5-dimethylphenol (CAS 88-04-0, 23.0 mg, 148 μmol, 2.00 eq.). The resulting suspension was heated to 55° C. for 16 hours, cooled to room temperature and then adsorbed onto Celite. The residue was purified by reverse phase column chromatography (10-100% acetonitrile/water with 0.1% formic acid gradient) to give the title compound as a mixture with the corresponding methyl ester, presumably as a result of using methanol during adsorption onto Celite. Full characterization was performed following ester hydrolysis to confirm structure (see Example 28).

LC-MS (Method 3): $R_t$=1.98 min; MS (ESIpos): m/z=645 [M+H]$^+$ (title compound), LC-MS (Method 3): $R_t$=1.91 min; MS (ESIpos): m/z=631 [M+H]$^+$ (corresponding methyl ester).

214

Intermediate 72

(rac)-Ethyl 13-fluoro-8,11,12-trimethyl-1-(3-((5,6,7,8-tetrahydronaphthalen-1-yl)oxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide

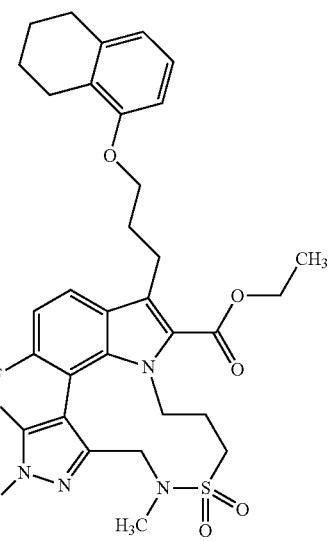

To a stirred solution of (rac)-ethyl 1-(3-bromopropyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 67, 42.0 mg, 73.8 μmol, 1.00 eq.) in anhydrous tetrahydrofuran (737 μL, 0.10 M) were added cesium carbonate (144 mg, 443 μmol, 6.00 eq.) and 5,6,7,8-tetrahydronaphthalen-1-ol (CAS 529-35-1, 21.8 mg, 148 μmol, 2.00 eq.). The resulting suspension was heated to 55° C. for 16 hours, cooled to room temperature and then adsorbed onto Celite. The residue was purified by reverse phase column chromatography (15.5 g HP C18, 10-100% acetonitrile/water with 0.1% formic acid gradient) to give the title compound as a mixture with the corresponding methyl ester, presumably as a result of using methanol during adsorption onto Celite. Full characterization was performed following ester hydrolysis to confirm structure (see Example 29).

LC-MS (Method 3): $R_t$=2.00 min; MS (ESIpos): m/z=637 [M+H]$^+$ (title compound), LC-MS (Method 3): $R_t$=1.94 min; MS (ESIpos): m/z=623 [M+H]$^+$ (corresponding methyl ester).

Intermediate 73

(rac)-Ethyl 13-fluoro-1-(3-((4-fluoronaphthalen-1-yl)oxy)propyl)-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide

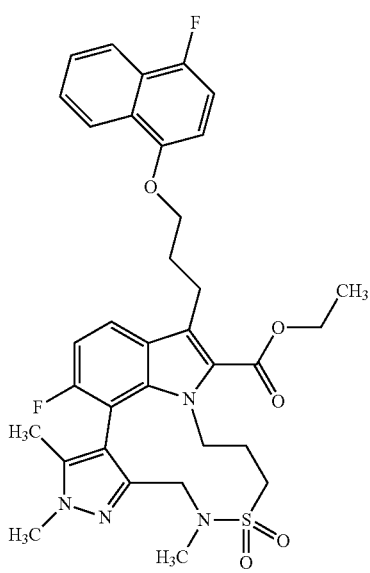 [SMILES: CCOC(=O)c1c(CCCOc2ccc(F)c3ccccc23)c2ccc(F)c3c2n1CCCS(=O)(=O)N(C)Cc1nn(C)c(C)c1-3]

To a stirred solution of (rac)-ethyl 1-(3-bromopropyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 67, 42.0 mg, 73.8 µmol, 1.00 eq.) in anhydrous tetrahydrofuran (737 µL, 0.10 M) were added cesium carbonate (144 mg, 443 µmol, 6.00 eq.) and 4-fluoronaphthalen-1-ol (CAS 315-53-7, 23.9 mg, 148 µmol, 2.00 eq.). The resulting suspension was heated to 55° C. for 16 hours, cooled to room temperature and then adsorbed onto Celite. The residue was purified by reverse phase column chromatography (10-100% acetonitrile/water with 0.1% formic acid gradient) to give the title compound as a mixture with the corresponding methyl ester, presumably as a result of using methanol during adsorption onto Celite. Full characterization was performed following ester hydrolysis to confirm structure (see Example 30).

LC-MS (Method 3): $R_t$=1.92 min; MS (ESIpos): m/z=651 [M+H]$^+$ (title compound), LC-MS (Method 3): $R_t$=1.86 min; MS (ESIpos): m/z=637 [M+H]$^+$ (corresponding methyl ester).

Intermediate 74

Ethyl 3-(3-((tert-butyldimethylsilyl)oxy)propyl)-7-(5-ethyl-3-(hydroxymethyl)-1-methyl-1H-pyrazol-4-yl)-6-fluoro-1H-indole-2-carboxylate

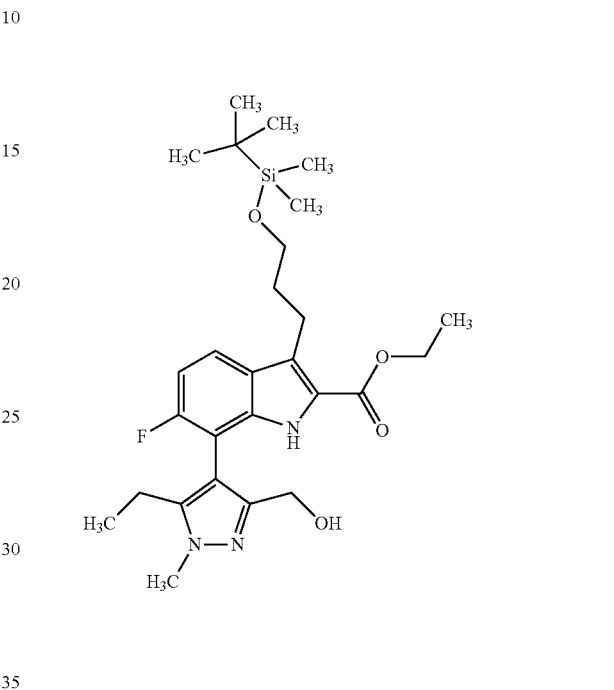

To a stirred suspension of (4-bromo-5-ethyl-1-methyl-1H-pyrazol-3-yl)methanol (see intermediate 9, 3.33 g, 15.2 mmol, 1.00 eq.), XPhos Pd G3 (752 mg, 0.89 mmol, 7.00 mol-%) and potassium phosphate tribasic (5.39 g, 25.4 mmol, 2.00 eq.) in a 2:1 mixture of 1,4-dioxane/water degassed with argon (38.1 mL) was slowly added dropwise (over a period of approximately 1h) a solution of ethyl 3-(3-((tert-butyldimethylsilyl)oxy)propyl)-6-fluoro-7-(4,4,5,5-tetramethyl-1,3,2-dioxaborolan-2-yl)-1H-indole-2-carboxylate (see intermediate 61, 6.42 g, 12.7 mmol, 1.00 eq.) in 1,4-dioxane degassed with argon (12.7 mL, 1.00 M) at a temperature of 50° C. The resulting dark mixture was heated to 50° C. for a further 30 minutes, cooled to room temperature and concentrated under reduced pressure. The residue was dissolved in water (50 mL) and extracted thrice with ethyl acetate (50 mL each). The combined organic extracts were washed with brine (50 mL), dried (magnesium sulfate), filtered and concentrated under reduced pressure. The residue was purified by flash column chromatography (0-100% acetone/dichloromethane gradient), followed by reverse phase column chromatography (10-100% acetonitrile/water gradient) to give the title compound as a light yellow solid (3.37 g LC-MS (Method 3): $R_t$=1.99 min; MS (ESIpos): m/z=518 [M+H]$^+$.

$^1$H-NMR (300 MHz, CHLOROFORM-d) δ [ppm]: 9.60 (s, 1H), 7.64 (dd, 1H), 6.97 (dd, 1H), 4.63 (d, 1H), 4.36 (m, 3H), 3.92 (s, 3H), 3.70 (t, 2H), 3.15 (m, 2H), 2.57 (ddt, 2H), 1.91 (m, 2H), 1.37 (t, 3H), 1.08 (t, 3H), 0.93 (s, 9H), 0.07 (s, 6H).

Intermediate 75

Ethyl 3-(3-((tert-butyldimethylsilyl)oxy)propyl)-7-(5-ethyl-1-methyl-3-((methylamino)methyl)-1H-pyrazol-4-yl)-6-fluoro-1H-indole-2-carboxylate

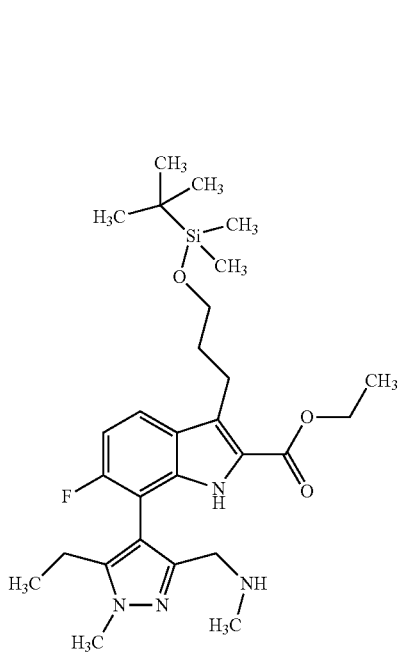 [SMILES: CCOC(=O)c1[nH]c2c(-c3c(CNC)nn(C)c3CC)c(F)ccc2c1CCCO[Si](C)(C)C(C)(C)C]

To a stirred solution of ethyl 3-(3-((tert-butyldimethylsilyl)oxy)propyl)-7-(5-ethyl-3-(hydroxymethyl)-1-methyl-1H-pyrazol-4-yl)-6-fluoro-1H-indole-2-carboxylate (see intermediate 74, 1.03 g, 2.00 mmol, 1.00 eq.) in anhydrous dichloromethane (20.0 mL, 0.10 M) was added N,N-diisopropylethylamine (696 μL, 4.00 mmol, 2.00 eq.), followed by dropwise addition of methanesulfonyl chloride (200 μL, 2.60 mmol, 1.30 eq.), at a temperature of 0° C. The resulting mixture was stirred at 0° C. for 2 hours, at which point a 2.0 M solution of methylamine in tetrahydrofuran (1.50 mL, 3.00 mmol, 10.0 eq.) was added quickly. The yellow mixture was warmed to room temperature and was stirred for 4 hours. Celite was added to the resulting mixture, volatiles were removed under reduced pressure, and the residue was purified by flash column chromatography (0-70% acetone/dichloromethane gradient followed by 0-10% methanol/dichloromethane with 1% ammonia gradient) to give the title compound as a yellow oil (859 mg).

LC-MS (Method 4): $R_t$=5.19 min; MS (ESIpos): m/z=531 [M+H]$^+$.

$^1$H-NMR (300 MHz, CHLOROFORM-d) δ [ppm]: 7.61 (dd, 1H), 6.95 (dd, 1H), 4.37 (m, 2H), 3.88 (s, 3H), 3.71 (m, 3H), 3.27 (d, 1H), 3.15 (m, 2H), 2.59 (m, 2H), 2.43 (s, 3H), 1.91 (m, 2H), 1.38 (t, 3H), 1.09 (m, 3H), 0.92 (s, 9H), 0.06 (s, 6H).

Intermediate 76

Ethyl 3-(3-((tert-butyldimethylsilyl)oxy)propyl)-7-(3-(((3-chloro-N-methylpropyl)sulfonamido)methyl)-5-ethyl-1-methyl-1H-pyrazol-4-yl)-6-fluoro-1H-indole-2-carboxylate

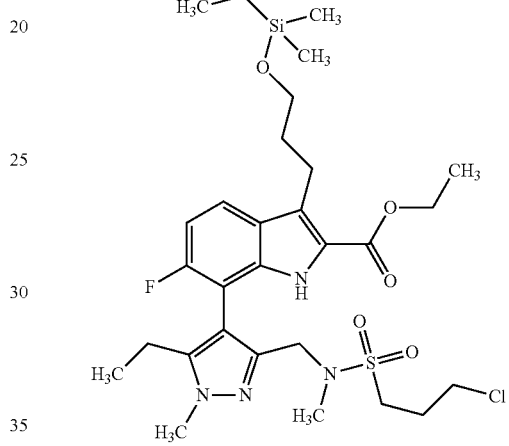

To a stirred solution of ethyl 3-(3-((tert-butyldimethylsilyl)oxy)propyl)-7-(5-ethyl-1-methyl-3-((methylamino)methyl)-1H-pyrazol-4-yl)-6-fluoro-1H-indole-2-carboxylate (see intermediate 75, 850 mg, 1.60 mmol, 1.00 eq.) in anhydrous dichloromethane (8.00 mL, 0.20 M) was added N,N-diisopropylethylamine (556 μL, 3.20 mmol, 2.00 eq.), followed by dropwise addition of 3-chloropropane-1-sulfonyl chloride (CAS 1633-82-5, 232 μL, 1.92 mmol, 1.20 eq.), at a temperature of 0° C. The resulting yellow mixture was warmed to room temperature and was stirred for 1 hour. Celite was added to the resulting mixture, volatiles were removed under reduced pressure, and the residue was purified by flash column chromatography (0-20% acetone/dichloromethane gradient) to give the title compound as a yellow oil (1.05 g).

LC-MS (Method 4): $R_t$=5.83 min; MS (ESIpos): m/z=571 [M+H]$^+$.

$^1$H-NMR (300 MHz, CHLOROFORM-d) δ [ppm]: 8.37 (s, 1H), 7.67 (m, 1H), 6.98 (dd, 1H), 4.36 (m, 3H), 4.09 (d, 1H), 3.92 (s, 3H), 3.69 (t, 2H), 3.57 (m, 1H), 3.13 (m, 2H), 2.95 (m, 2H), 2.72 (s, 3H), 2.51 (ddt, 2H), 2.13 (m, 2H), 1.90 (m, 2H), 1.40 (t, 3H), 1.05 (t, 3H), 0.93 (s, 9H), 0.07 (s, 6H).

Intermediate 77

(rac)-Ethyl 1-(3-((tert-butyldimethylsilyl)oxy)propyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

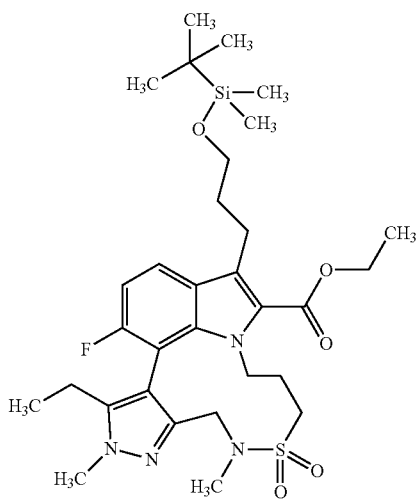 [SMILES: CCOC(=O)c1c(CCCO[Si](C)(C)C(C)(C)C)c2ccc(F)c3c2n1CCCS(=O)(=O)N(C)Cc1nn(C)c(CC)c1-3]

To a stirred solution of ethyl 3-(3-((tert-butyldimethylsilyl)oxy)propyl)-7-(3-(((3-chloro-N-methylpropyl)sulfonamido)methyl)-5-ethyl-1-methyl-1H-pyrazol-4-yl)-6-fluoro-1H-indole-2-carboxylate (see intermediate 76, 1.05 g, 1.56 mmol, 1.00 eq.) in anhydrous acetonitrile degassed with argon (31.2 mL, 0.05 M) was added cesium carbonate (1.52 g, 4.68 mmol, 3.00 eq.). The resulting orange suspension was heated to 60° C. for 3 days and then cooled to room temperature. Celite was added to the resulting mixture, volatiles were removed under reduced pressure, and the residue was purified by flash column chromatography (0-100% ethyl acetate/hexanes gradient) to give the title compound as a yellow oil (547 mg).

LC-MS (Method 4): $R_t$=5.71 min; MS (ESIpos): m/z=635 [M+H]$^+$.

$^1$H-NMR (300 MHz, CHLOROFORM-d) δ [ppm]: 7.71 (dd, 1H), 6.99 (t, 1H), 4.38 (m, 5H), 4.06 (d, 1H), 3.90 (s, 3H), 3.67 (t, 2H), 3.11 (m, 2H), 2.95 (s, 3H), 2.51 (dt, 1H), 2.27 (m, 2H), 2.09 (dt, 1H), 1.86 (m, 4H), 1.40 (t, 3H), 0.92 (m, 12H), 0.08 (d, 6H).

Intermediate 78

(rac)-Ethyl 12-ethyl-13-fluoro-1-(3-hydroxpropyl)-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

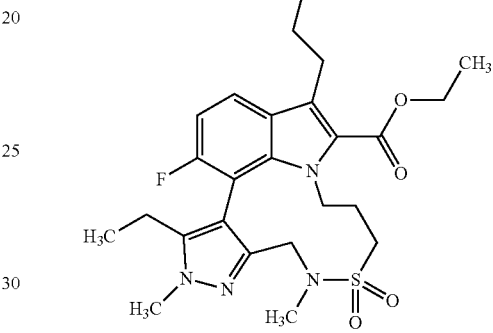

To a stirred solution of (rac)-ethyl 1-(3-((tert-butyldimethylsilyl)oxy)propyl)-12-ethyl-13-fluoro-8,11-dimethyl-5,6,9,11-tetrahydro-4H,8H-pyrazolo[3',4':4,5][1]thia[2,8]diazacyclo-undecino[6,7,8-hi]indole-2-carboxylate 7,7-dioxide (see intermediate 77, 540 mg, 0.85 mmol, 1.00 eq.) in anhydrous tetrahydrofuran (17.0 mL, 0.05 M) was added a 1.0 M solution of tetrabutylammonium fluoride in tetrahydrofuran (1.02 mL, 1.02 mmol, 1.20 eq.) at a temperature of 0° C. The resulting yellow mixture was warmed to room temperature, stirred for 2 hours and then concentrated under reduced pressure. The residue was resuspended in 1.0 M aqueous hydrochloric acid (20 mL) and extracted thrice with ethyl acetate (20 mL each). The combined organic extracts were washed with brine (20 mL), dried (magnesium sulfate), filtered and concentrated under reduced pressure. The residue was purified by flash column chromatography (0-30% acetone/dichloromethane gradient) to give the title compound as a white solid (322 mg).

LC-MS (Method 4): $R_t$=3.03 min; MS (ESIpos): m/z=521 [M+H]$^+$.

$^1$H-NMR (300 MHz, CHLOROFORM-d) δ [ppm]: 7.69 (dd, 1H), 7.01 (t, 1H), 4.37 (m, 5H), 4.05 (d, 1H), 3.90 (s, 3H), 3.60 (m, 2H), 3.18 (m, 2H), 2.97 (s, 3H), 2.52 (m, 1H), 2.27 (m, 3H), 1.98 (m, 5H), 1.40 (t, 3H), 0.92 (t, 3H).

221

Intermediate 79

(rac)-Ethyl 1-(3-bromopropyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

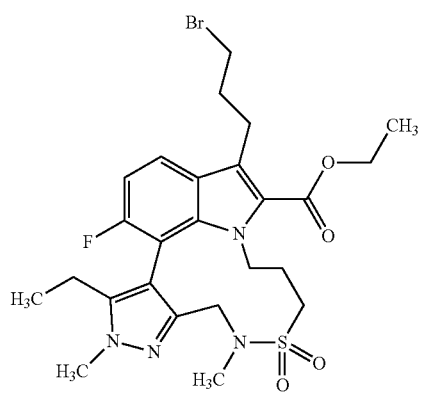 [SMILES: CCOC(=O)c1c(CCCBr)c2ccc(F)c3c2n1CCCS(=O)(=O)N(C)Cc1nn(C)c(CC)c1-3]

To a stirred solution of (rac)-ethyl 12-ethyl-13-fluoro-1-(3-hydroxypropyl)-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 78, 307 mg, 0.59 mmol, 1.00 eq.) and triphenylphosphine (170 mg, 0.65 mmol, 1.10 eq.) in anhydrous dichloromethane (5.89 mL, 0.10 M) was added carbon tetrabromide (CAS 558-13-4, 215 mg, 0.65 mmol, 1.10 eq.) in one portion at a temperature of 0° C. The resulting mixture was warmed to room temperature and was stirred for 30 minutes. Celite was added to the resulting mixture, volatiles were removed under reduced pressure, and the residue was purified by flash column chromatography (0-20% acetone/dichloromethane gradient) to give the title compound as a white solid (315 mg).

LC-MS (Method 4): $R_t$=4.30 min; MS (ESIpos): m/z=583 [M+H]$^+$.

$^1$H-NMR (300 MHz, CHLOROFORM-d) δ [ppm]: 7.72 (dd, 1H), 7.03 (t, 1H), 4.39 (m, 5H), 4.06 (d, 1H), 3.90 (s, 3H), 3.47 (m, 2H), 3.22 (m, 2H), 2.95 (s, 3H), 2.51 (dt, 1H), 2.24 (m, 4H), 2.09 (m, 1H), 1.86 (m, 2H), 1.42 (t, 3H), 0.92 (t, 3H).

222

Intermediate 80

(rac)-Ethyl 12-ethyl-13-fluoro-1-(3-((6-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

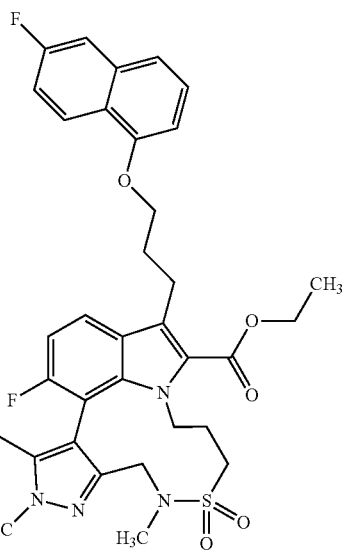

To a stirred solution of (rac)-ethyl 1-(3-bromopropyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 79, 116 mg, 0.20 mmol, 1.00 eq.) in anhydrous tetrahydrofuran (2.00 mL, 0.10 M) were added cesium carbonate (390 mg, 1.20 mmol, 6.00 eq.) and 6-fluoronaphthalen-1-ol (CAS 804498-72-4, 64.8 mg, 0.40 mmol, 2.00 eq.). The resulting suspension was heated to 55° C. for 16 hours and was then cooled to room temperature. Celite was added to the resulting mixture, volatiles were removed under reduced pressure, and the residue was purified by reverse phase column chromatography (10-100% acetonitrile/water with 0.1% formic acid gradient) to give the title compound as a tan solid (126 mg).

LC-MS (Method 4): $R_t$=5.21 min; MS (ESIpos): m/z=665 [M+H]$^+$.

$^1$H-NMR (300 MHz, CHLOROFORM-d) δ [ppm]: 8.37 (dd, 1H), 7.66 (dd, 1H), 7.40 (m, 3H), 7.26 (s, 5H), 6.91 (t, 1H), 6.71 (dd, 1H), 4.53 (dt, 1H), 4.33 (m, 4H), 4.18 (m, 2H), 4.07 (d, 1H), 3.90 (s, 3H), 3.35 (m, 2H), 2.95 (s, 3H), 2.53 (dt, 1H), 2.27 (m, 4H), 2.11 (dt, 1H), 1.87 (m, 2H), 1.36 (t, 3H), 0.91 (t, 3H).

223

Intermediate 81

(rac)-Ethyl 12-ethyl-13-fluoro-8,11-dimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide

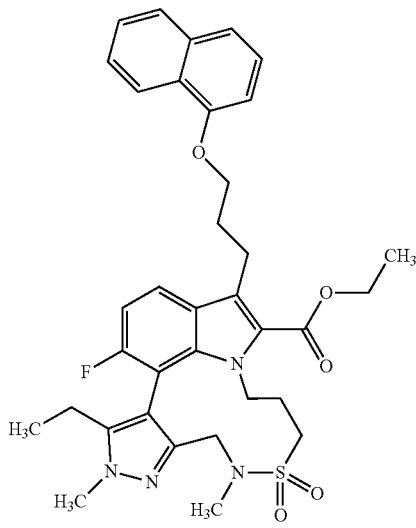 [SMILES: CCOC(=O)c1c(CCCOc2cccc3ccccc23)c2ccc(F)c3c2n1CCCS(=O)(=O)N(C)Cc1nn(C)c(CC)c1-3]

To a stirred solution of (rac)-ethyl 1-(3-bromopropyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 79, 38.0 mg, 65.1 μmol, 1.00 eq.) in anhydrous tetrahydrofuran (651 μL, 0.10 M) were added cesium carbonate (127 mg, 391 μmol, 6.00 eq.) and naphthalen-1-ol (CAS 90-15-3, 18.7 mg, 130 μmol, 2.00 eq.). The resulting suspension was heated to 55° C. for 16 hours and was then cooled to room temperature. Celite was added to the resulting mixture, volatiles were removed under reduced pressure, and the residue was purified by reverse phase column chromatography (10-100% acetonitrile/water with 0.1% formic acid gradient) to give the title compound as a tan solid (39.3 mg).

LC-MS (Method 4): $R_t$=5.16 min; MS (ESIpos): m/z=647 [M+H]$^+$.

$^1$H-NMR (300 MHz, CHLOROFORM-d) δ [ppm]: 8.38 (m, 1H), 7.82 (m, 1H), 7.68 (dd, 1H), 7.51 (m, 2H), 7.44 (d, 1H), 7.36 (dd, 1H), 6.90 (t, 1H), 6.77 (dd, 1H), 4.54 (dt, 1H), 4.34 (m, 4H), 4.19 (m, 2H), 4.07 (d, 1H), 3.90 (s, 3H), 3.37 (m, 2H), 2.95 (s, 3H), 2.53 (dt, 1H), 2.27 (m, 4H), 2.12 (dt, 1H), 1.87 (m, 2H), 1.37 (t, 3H), 0.91 (t, 3H).

224

Intermediate 82

(rac)-Ethyl 1-(3-((2,3-dihydro-1H-inden-4-yl)oxy)propyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

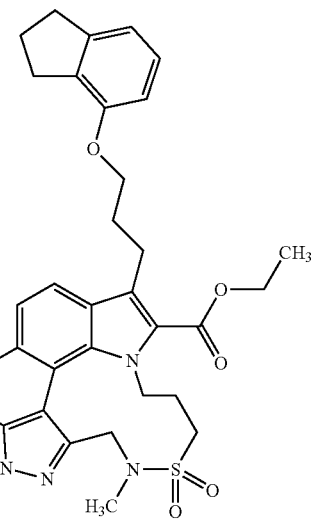

To a stirred solution of (rac)-ethyl 1-(3-bromopropyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 79, 38.0 mg, 65.1 μmol, 1.00 eq.) in anhydrous tetrahydrofuran (651 μL, 0.10 M) were added cesium carbonate (127 mg, 391 μmol, 6.00 eq.) and 4-indanol (CAS 1641-41-4, 17.4 mg, 130 μmol, 2.00 eq.). The resulting suspension was heated to 55° C. for 16 hours and was then cooled to room temperature. Celite was added to the resulting mixture, volatiles were removed under reduced pressure, and the residue was purified by reverse phase column chromatography (10-100% acetonitrile/water with 0.1% formic acid gradient) to give the title compound as a tan solid (38.7 mg).

LC-MS (Method 4): $R_t$=5.27 min; MS (ESIpos): m/z=637 [M+H]$^+$.

$^1$H-NMR (300 MHz, CHLOROFORM-d) δ [ppm]: 7.68 (dd, 1H), 7.10 (t, 1H), 6.97 (t, 1H), 6.86 (d, 1H), 6.62 (d, 1H), 4.53 (dt, 1H), 4.36 (m, 4H), 4.05 (m, 3H), 3.90 (s, 3H), 3.25 (m, 2H), 2.94 (m, 7H), 2.52 (dt, 1H), 2.28 (m, 2H), 2.10 (m, 5H), 1.89 (m, 2H), 1.39 (t, 3H), 0.91 (t, 3H).

Intermediate 83

(rac)-Ethyl 1-(3-(4-chloro-3,5-dimethylphenoxy) propyl)-12-ethyl-13-fluoro-8,11-dimethyl-5,6,9,11-tetrahydro-4H,8H-pyrazolo[3',4':4,5][1]thia[2,8] diazacycloundecino[6,7,8-hi]indole-2-carboxylate 7,7-dioxide

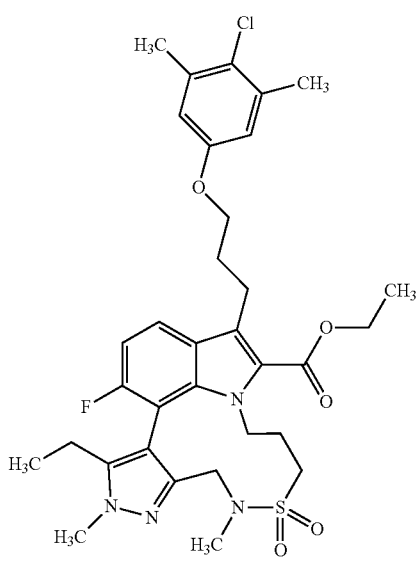 [SMILES: CCOC(=O)c1c(CCCOc2cc(C)c(Cl)c(C)c2)c2ccc(F)c3c2n1CCCS(=O)(=O)N(C)Cc1nn(C)c(CC)c1-3]

To a stirred solution of (rac)-ethyl 1-(3-bromopropyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 79, 38.0 mg, 65.1 μmol, 1.00 eq.) in anhydrous tetrahydrofuran (651 μL, 0.10 M) were added cesium carbonate (127 mg, 391 μmol, 6.00 eq.) and 4-chloro-3,5-dimethylphenol (CAS 88-04-0, 20.3 mg, 130 μmol, 2.00 eq.). The resulting suspension was heated to 55° C. for 16 hours and was then cooled to room temperature. Celite was added to the resulting mixture, volatiles were removed under reduced pressure, and the residue was purified by reverse phase column chromatography (10-100% acetonitrile/water with 0.1% formic acid gradient) to give the title compound as a tan solid (40.6 mg).

LC-MS (Method 4): $R_t$=5.43 min; MS (ESIpos): m/z=659 [M+H]$^+$.

$^1$H-NMR (300 MHz, CHLOROFORM-d) δ [ppm]: 7.66 (dd, 1H), 6.97 (t, 1H), 6.64 (s, 2H), 4.53 (dt, 1H), 4.35 (m, 4H), 4.07 (d, 1H), 3.95 (m, 2H), 3.90 (s, 3H), 3.23 (m, 2H), 2.95 (s, 3H), 2.52 (dt, 1H), 2.35 (s, 8H), 2.11 (m, 3H), 1.88 (m, 2H), 1.41 (t, 3H), 0.91 (t, 3H).

Intermediate 84

(rac)-Ethyl 12-ethyl-13-fluoro-8,11-dimethyl-1-(3-((5,6,7,8-tetrahydronaphthalen-1-yl)oxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide

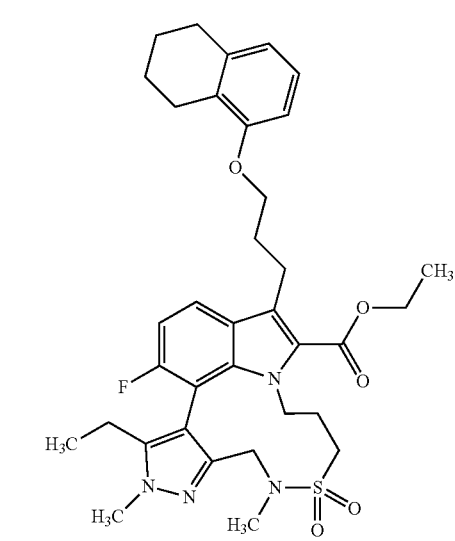 [SMILES: CCOC(=O)c1c(CCCOc2cccc3c2CCCC3)c2ccc(F)c3c2n1CCCS(=O)(=O)N(C)Cc1nn(C)c(CC)c1-3]

To a stirred solution of (rac)-ethyl 1-(3-bromopropyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 79, 38.0 mg, 65.1 μmol, 1.00 eq.) in anhydrous tetrahydrofuran (651 μL, 0.10 M) were added cesium carbonate (127 mg, 391 μmol, 6.00 eq.) and 5,6,7,8-tetrahydronaphthalen-1-ol (CAS 529-35-1, 19.2 mg, 130 μmol, 2.00 eq.). The resulting suspension was heated to 55° C. for 16 hours and was then cooled to room temperature. Celite was added to the resulting mixture, volatiles were removed under reduced pressure, and the residue was purified by reverse phase column chromatography (10-100% acetonitrile/water with 0.1% formic acid gradient) to give the title compound as a tan solid (38.6 mg).

LC-MS (Method 4): $R_t$=5.54 min; MS (ESIpos): m/z=651 [M+H]$^+$.

$^1$H-NMR (300 MHz, CHLOROFORM-d) δ [ppm]: 7.67 (dd, 1H), 7.00 (m, 2H), 6.71 (d, 1H), 6.61 (dd, 1H), 4.53 (dt, 1H), 4.35 (m, 4H), 4.04 (m, 3H), 3.90 (s, 3H), 3.24 (m, 2H), 2.95 (s, 3H), 2.77 (m, 4H), 2.52 (dt, 1H), 2.28 (m, 2H), 2.12 (m, 3H), 1.83 (m, 2H), 1.39 (t, 3H), 0.92 (t, 3H).

Intermediate 85

(rac)-Ethyl 12-ethyl-13-fluoro-1-(3(4-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

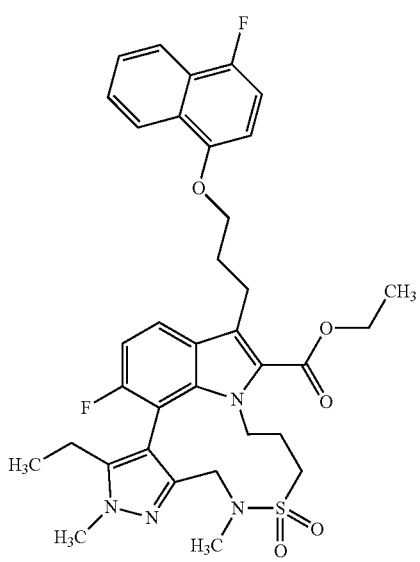 [SMILES: CCOC(=O)c1c(CCCOc2ccc(F)c3ccccc23)c2ccc(F)c3c2n1CCCS(=O)(=O)N(C)Cc1nn(C)c(CC)c1-3]

To a stirred solution of (rac)-ethyl 1-(3-bromopropyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 79, 38.0 mg, 65.1 μmol, 1.00 eq.) in anhydrous tetrahydrofuran (651 μL, 0.10 M) were added cesium carbonate (127 mg, 391 μmol, 6.00 eq.) and 4-fluoronaphthalen-1-ol (CAS 315-53-7, 21.1 mg, 130 μmol, 2.00 eq.). The resulting suspension was heated to 55° C. for 16 hours and was then cooled to room temperature Celite was added to the resulting mixture, volatiles were removed under reduced pressure, and the residue was purified by reverse phase column chromatography (10-100% acetonitrile/water with 0.1% formic acid gradient) to give the title compound as a tan solid (37.2 mg).

LC-MS (Method 4): R$_t$=5.26 min; MS (ESIpos): m/z=665 [M+H]$^+$.

$^1$H-NMR (300 MHz, CHLOROFORM-d) δ [ppm]: 8.36 (m, 1H), 8.07 (m, 1H), 7.67 (dd, 1H), 7.59 (m, 2H), 7.02 (dd, 1H), 6.91 (t, 1H), 6.63 (dd, 1H), 4.53 (dt, 1H), 4.34 (m, 4H), 4.13 (m, 3H), 3.90 (s, 3H), 3.36 (m, 2H), 2.95 (s, 3H), 2.53 (dt, 1H), 2.27 (m, 4H), 2.11 (dt, 1H), 1.87 (m, 2H), 1.37 (t, 3H), 0.91 (t, 3H).

Intermediate 86

4-bromo-1,5-dimethyl-1H-pyrazole-3-carboxylic acid

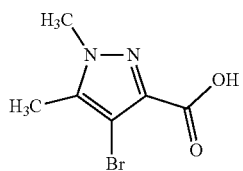

To a solution of ethyl 4-bromo-1,5-dimethyl-1H-pyrazole-3-carboxylate (see Intermediate 5, 600 g, 2.43 mol, 1 eq) in methanol (6 L) was added drop wise potassium hydroxide (272.48 g, 4.86 mol, 2 eq) in water (1.5 L) at 0° C. The resulting mixture was stirred at 10° C. for 2 h. The reaction mixture was filtered and washed with methanol (500 mL) to give a white solid. The solid was dissolved in water (10 L) and acified with 1 N hydrochloric acid to pH=3. Amounts of white solid were formed. The solid was separated by filteration and washed with water (500 mL), dried to give the desired compound (850 g, 3.88 mol, 79.91% yield, batches 2) as a white solid, which was directly used without further purification.

Intermediate 87

4-bromo-N-methoxy-N,1,5-trimethyl-1H-pyrazole-3-carboxamide

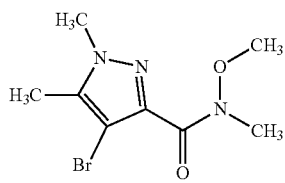

To a solution of 4-bromo-1,5-dimethyl-1H-pyrazole-3-carboxylic acid (Intermediate 86, 100 g, 456.55 mmol, 1 eq) in THF (1000 mL) was added oxalyl chloride (144.87 g, 1.14 mol, 99.91 mL, 2.5 eq) and DMF (1.00 g, 13.68 mmol, 1.05 mL, 0.03 eq). The mixture was stirred at 10° C. for 1 h. The reaction mixture was concentrated under reduced pressure to remove THF and oxalyl chloride to give 4-bromo-1,5-dimethyl-pyrazole-3-carbonyl chloride (108 g, 454.77 mmol, 99.61% yield) as a yellow solid.

To a solution of N,O-dimethylhydroxylamine hydrochloride (1:1) (66.54 g, 682.16 mmol, 1.5 eq) and triethylamine (138.06 g, 1.36 mol, 189.90 mL, 3 eq) in THF (1000 mL) was added drop wise 4-bromo-1,5-dimethyl-pyrazole-3-carbonyl chloride (108 g, 454.77 mmol, 1 eq) in THF (500 mL) at 0° C. After addition, the mixture was stirred at 10° C. for 12 h, and then heated to 40° C. for 12 h. The reaction mixture was quenched by addition water (2 L), and concentrated under reduced pressure to remove THF, and then extracted with ethyl acetate (2 L three times). The combined organic layers were washed with aqueous sodium carbonate solution (1 L), 1 N hydrochloric acid (1 L), brine (1 L) in return, dried over sodium sulfate, filtered and concentrated under reduced pressure to give the desired compound (100 g, 347.19 mmol, 76.34% yield) as a brown solid, which was directly used without further purification.

LC-MS (analytically method see below): $R_t$=0.577 min; MS (ESIpos): m/z=262 [M+H]$^+$.

Analytical HPLC Method:
Instrument: Agilent 1200 LC/G1956A MSD; Column: Chromolith Flash RP-18e 25*2 mm; Mobile Phase: A: 0.0375% TFA in Water (v/v); B: 0.01875% TFA in Acetonitrile (v/v); Gradient 0.01 min 5% B→0.8 min 95% B→1.2 min 95% B→1.21 min 5% B→1.5 min 5% B; flow rate: 1.5 mL/min; Column Temp: 50° C.; UV detection: 220 nm & 254 nm.

Intermediate 88

1-(4-bromo-1,5-dimethyl-1H-pyrazol-3-yl)prop-2-en-1-one

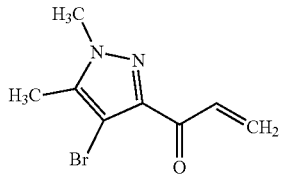

To a solution of 4-bromo-N-methoxy-N,1,5-trimethyl-1H-pyrazole-3-carboxamide (Intermediate 87, 100 g, 381.53 mmol, 1 eq) in THF (2 L) was added bromo(vinyl)magnesium (1 M, 763.44 mL, 2 eq) at 0° C. and the solution was stirred at 10° C. for 2 hr. The reaction mixture was directly used without further purification. 1-(4-bromo-1,5-dimethyl-1H-pyrazol-3-yl)prop-2-en-1-one (87.4 g, 381.54 mmol, 100.00% yield) was obtained in THF (2763 mL) as a yellow liquid.

Intermediate 89

1-(4-bromo-1,5-dimethyl-1H-pyrazol-3-yl)-3-(morpholin-4-yl)propan-1-one

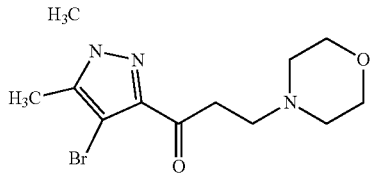

To a solution of morpholine (132.96 g, 1.53 mol, 134.30 mL, 4 eq) in THF (800 mL) was added 1-(4-bromo-1,5-dimethyl-1H-pyrazol-3-yl)prop-2-en-1-one (Intermediate 88, 87.4 g, 381.54 mmol, 1 eq) in THF (2763 mL). The mixture was stirred at 10° C. for 1 h. The reaction mixture was quenched by addition brine (2 L), filtered, and then extracted with ethyl acetate (1 L three times). The combined organic layers were washed with water (1 L), brine (1 L) in return, dried over sodium sulfate, filtered and concentrated under reduced pressure to give the desired compound (106 g, 271.54 mmol, 71.17% yield, 81% purity) as a yellow solid, which was directly used without further purification.

LC-MS (analytically method see below): $R_t$=0.794 min; MS (ESIpos): m/z=316 [M+H]$^+$.

Analytical HPLC Method:
Instrument: Agilent 1200 LC/G1956A MSD; Column: Chromolith Flash RP-18e 25*2 mm; Mobile Phase: A: 0.0375% TFA in Water (v/v); B: 0.01875% TFA in Acetonitrile (v/v); Gradient 0.01 min 5% B→0.8 min 95% B→1.2 min 95% B→1.21 min 5% B→1.5 min 5% B; flow rate: 1.5 mL/min; Column Temp: 50° C.; UV detection: 220 nm & 254 nm.

LC-MS (analytically method see below): $R_t$=0.763 min; 81% purity

Analytical HPLC Method:
HPLC Instrument: SHIMADZU LC-20AB; Column: Kinetex C18 LC Column 4.6×50 mm, 5 um; Mobile Phase: A: 0.0375% TFA in water (v/v); B: 0.01875% TFA in Acetonitrile (v/v); Gradient 0.00 min 10% B→2.4 min 80% B→3.7 min 80% B→3.71 min 10% B→4.00 min 10% B; flow rate: 1.5 mL/min; Column Temp: 50° C.; UV detection: 220 nm & 215 nm&254 nm.

Intermediate 90

1-(4-bromo-1,5-dimethyl-1H-pyrazol-3-yl)-3-(morpholin-4-yl)propan-1-ol

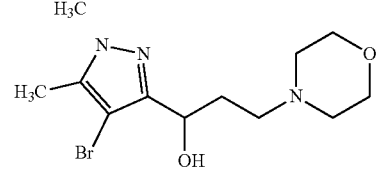

To a solution of 1-(4-bromo-1,5-dimethyl-1H-pyrazol-3-yl)-3-(morpholin-4-yl)propan-1-one (Intermediate 89, 106 g, 335.24 mmol, 1 eq) in methanol (1 L) at 0° C. was added sodium boronate (50.73 g, 1.34 mol, 4 eq), the mixture stirred at 20° C. for 1 h. Water (1.5 L) was added and the mixture extracted with ethyl acetate (1 L three times). The combined organic layers were dried over sodium sulfate, filtered and concentrated under reduced pressure to give a yellow gum. The light yellow solid was obtained by re-crystallized with propanol, which was combined with other batches. The re-crystallized mother liquor was purified by column chromatography (silica gel, ethyl acetate:methanol=1:0 to 15:1) and re-crystallized with ethanol to give another desired product. The two batches product were combined to give the desired compound (100.45 g, 312.52 mmol, 93.22% yield, 99% purity) as a light yellow solid.

$^1$H-NMR (400 MHz, CDCl3) δ [ppm]=6.21 (br s, 1H), 4.95 (dd, J=8, 4 Hz, 1H), 3.75 (s, 3H), 3.69 (t, J=8, 4 Hz, 4H), 2.60-2.72 (m, 4H), 2.32-2.51 (m, 2H), 2.20 (s, 3H), 2.07-2.16 (m, 1H), 1.78-1.84 (m, 1H).

LC-MS (analytically method see below): $R_t$=0.754 min; MS (ESIpos): m/z=318 [M+H]$^+$.

Analytical HPLC Method:
Instrument: SHIMADZU LCMS-2020; Column: Kinetex EVO C18 2.1×30 mm, 5 um; Mobile Phase: A: 0.025% NH3.H2O in water (v/v); B: Acetonitrile; Gradient 0.0 min 5% B→0.8 min 95% B→1.2 min 95% B→1.21 min 5% B→1.55 min 5% B; flow rate: 1.5 mL/min; Column Temp: 40° C.; UV detection: 220 nm & 254 nm.

Intermediate 91

4-bromo-5-ethyl-1-methyl-1H-pyrazole-3-carboxylic acid

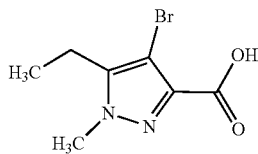

4-Bromo-5-ethyl-1-methyl-1H-pyrazole-3-carbaldehyde (see Intermediate 37, 25.6 g, 118 mmol) was dissolved in a mixture of 270 mL tert-butanol and of 70 mL water and cooled down to 0° C. Sodium dihydrogen phosphate (32.5 g, 236 mmol), sodium chlorite (42.7 g, 472 mmol) and 2-methyl-2.butene (37 mL, 350 mmol) were added and warmed up to room temperature. The suspension was stirred over night at rt. The reaction mixture was quenched with water and extracted with ethyl acetate The aqueous phase was extracted with tetrahydrofurane and then with dichloromethane. The combined organic layers were dried over sodium sulfate, filtered and concentrated under reduced pressure (8 g of yellow crude material). To the aqueous phase acetic acid was added to adjust the pH to 3-4, and extracted again with ethyl acetate thrice. The combined organic phases were dried over sodium sulfate, filtered and concentrated under reduced pressure (14 g of second crude material). The combined crude materials were crystallized with a mixture of methyl-tert-butylether and pentane. to give 18 g of the title compound (98% purity, 64% yield).

LC-MS (Method 1): $R_t$=0.79 min; MS (ESIneg): m/z=231 [M-H]$^-$ $^1$H-NMR (400 MHz, DMSO-d6) δ[ppm]: 1.077 (2.78), 1.085 (0.53), 1.096 (6.66), 1.102 (0.48), 1.115 (2.81), 2.518 (0.44), 2.663 (0.84), 2.681 (2.65), 2.700 (2.59), 2.719 (0.74), 3.759 (0.74), 3.877 (16.00).

Intermediate 92

4-bromo-5-ethyl-1-methyl-1H-pyrazole-3-carbonyl chloride

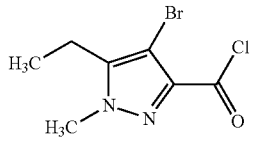

4-Bromo-5-ethyl-1-methyl-1H-pyrazole-3-carboxylic acid (see Intermediate 91, 23.2 g, 99.5 mmol) was dissolved in 200 mL of tetrahydrofuran, 200 μL of N,N-dimethyl formamide and oxalyl chloride (21.7 mL, 249 mmol) were added at 0° C. and the mixture was stirred for 2 h at 0° C. The reaction mixture was concentrated under reduced pressure to give 25.0 g of the title compound which was used without further purification.

Intermediate 93

4-bromo-5-ethyl-N-methoxy-N,1-dimethyl-1H-pyrazole-3-carboxamide

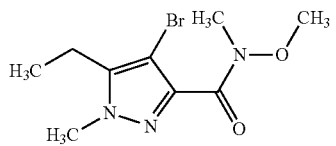

N-Methoxymethanamine hydrogen chloride (1/1) (9.10 g, 93.3 mmol) and triethylamine (26 mL, 187 mmol) were dissolved in 100 mL tetrahydrofuran and a solution of 4-bromo-5-ethyl-1-methyl-1H-pyrazole-3-carbonyl chloride (see Intermediate 92, 15.7 g) in 80 mL of tetrahydrofuran was added at 0° C. dropwise and the mixture was stirred for 1 h at 0° C. and for 72 h at room temperature. The mixture was filtered and concentrated under reduced pressure. The crude material was purified by flash chromatography using silica gel (aminophase, gradient hexane/ethyl acetate) to provide 10.1 g of the title compound.

LC-MS (Method 2): $R_t$=0.88 min; MS (ESIpos): m/z=276 [M+H]$^+$ $^1$H-NMR (400 MHz, DMSO-d6) δ[ppm]: 1.092 (3.05), 1.111 (7.13), 1.130 (3.12), 2.657 (0.90), 2.675 (2.92), 2.694 (2.85), 2.713 (0.83), 3.238 (10.88), 3.337 (13.44), 3.846 (16.00).

Intermediate 94

1-(4-bromo-5-ethyl-1-methyl-1H-pyrazol-3-yl)prop-2-en-1-one

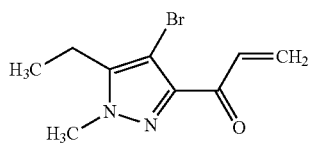

4-Bromo-5-ethyl-N-methoxy-N,1-dimethyl-1H-pyrazole-3-carboxamide (see Intermediate 93, 18.4 g, 66.5 mmol) was dissolved in 240 mL of tetrahydrofuran, a solution of bromo(vinyl)magnesium (133 mL, 1.0 M in THF, 133 mmol) was added at 0° C. dropwise and the mixture was stirred for 15 minutes at 0° C. The reaction mixture was used directly in the next step.

Intermediate 95

1-(4-bromo-5-ethyl-1-methyl-1H-pyrazol-3-yl)-3-(morpholin-4-yl)propan-1-one

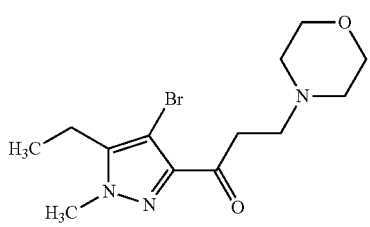 [SMILES: CCc1c(Br)c(C(=O)CCN2CCOCC2)nn1C]

Morpholine (23.2 mL, 266 mmol) was dissolved in 20 mL of tetrahydrofuran, a solution of 1-(4-bromo-5-ethyl-1-methyl-1H-pyrazol-3-yl)prop-2-en-1-one (see Intermediate 94) in tetrahydrofuran was added dropwise at 0° C. and the mixture was stirred for 30 minutes at 0 C. The reaction mixture was filtered, concentrated, diluted with water and extracted with dichloromethane. The combined organic layers were dried over sodium sulfate and concentrated. The crude material was purified by flash chromatography silica gel (aminophase, gradient dichloromethane/ethyl acetate) to give 16.5 g of the title compound.

LC-MS (Method 2): $R_t$=0.97 min; MS (ESIpos): m/z=330 [M+H]$^+$ $^1$H-NMR (400 MHz, DMSO-d6) δ[ppm]: 1.078 (2.81), 1.097 (6.63), 1.116 (2.81), 1.983 (9.02), 2.327 (0.43), 2.344 (1.63), 2.355 (2.26), 2.366 (1.72), 2.518 (1.13), 2.522 (0.72), 2.608 (1.59), 2.626 (3.35), 2.644 (1.85), 2.671 (1.00), 2.690 (2.68), 2.709 (2.57), 2.728 (0.89), 3.042 (1.79), 3.060 (3.29), 3.077 (1.55), 3.388 (0.78), 3.393 (1.08), 3.404 (1.70), 3.412 (1.36), 3.417 (1.23), 3.506 (1.39), 3.514 (3.10), 3.518 (2.56), 3.525 (3.68), 3.537 (2.64), 3.547 (1.32), 3.559 (1.23), 3.571 (0.83), 3.917 (16.00).

Intermediate 96

(rac)-1-(4-bromo-5-ethyl-1-methyl-1H-pyrazol-3-yl)-3-(morpholin-4-yl)propan-1-ol

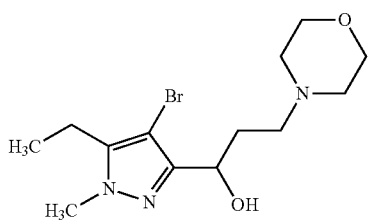 [SMILES: CCc1c(Br)c(C(O)CCN2CCOCC2)nn1C]

1-(4-Bromo-5-ethyl-1-methyl-1H-pyrazol-3-yl)-3-(morpholin-4-yl)propan-1-one (see Intermediate 95, 7.40 g, 22.4 mmol) was dissolved in 60 mL of methanol, sodium borohydride (3.39 g, 89.6 mmol) was added and the mixture was stirred for 22 h at room temperature. Water was added and the mixture was extracted with ethyl acetate. The combined organic layers were washed with brine, filtered using a water resistant filter and concentrated under reduced pressure to provide 5.68 g (74% yield) of the title compound.

LC-MS (Method 2): $R_t$=0.88 min; MS (ESIpos): m/z=332 [M+H]$^+$ $^1$H-NMR (400 MHz, DMSO-d6) δ[ppm]: 1.060 (2.63), 1.079 (6.44), 1.098 (2.75), 1.154 (0.73), 1.172 (1.55), 1.190 (0.77), 1.816 (0.42), 1.833 (0.50), 1.836 (0.44), 1.850 (0.47), 1.873 (0.42), 1.878 (0.47), 1.893 (0.59), 1.912 (0.42), 1.987 (2.56), 2.296 (1.09), 2.314 (2.81), 2.326 (2.49), 2.331 (2.41), 2.346 (0.79), 2.518 (0.63), 2.523 (0.42), 2.601 (0.78), 2.620 (2.58), 2.639 (2.46), 2.658 (0.72), 3.534 (2.22), 3.546 (3.34), 3.557 (2.20), 3.751 (16.00), 4.017 (0.58), 4.035 (0.57), 4.557 (0.47), 4.566 (0.47), 4.578 (0.48), 5.113 (0.77), 5.125 (0.84).

Intermediate 97

Ethyl 7-bromo-6-chloro-3-{3-[(6-fluoronaphthalen-1-yl)oxy]propyl}-1H-indole-2-carboxylate

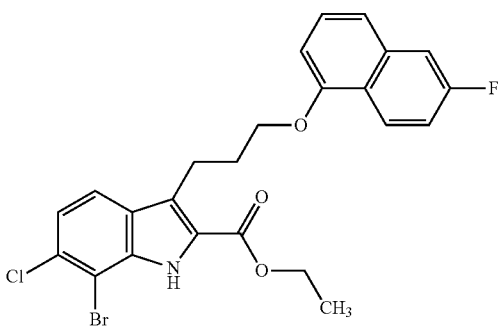 [SMILES: CCOC(=O)c1[nH]c2c(Br)c(Cl)ccc2c1CCCOc1cccc2cc(F)ccc12]

To a solution of triphenylphosphine (1.60 g, 6.10 mmol) in THF (20 mL), 6-fluoronaphthalen-1-(CAS 804498-72-4, 989 mg, 6.10 mmol) was added. The mixture was cooled to −10° C. and diisopropyl azodicarboxylate (1.2 mL, 6.1 mmol) was added dropwise. After complete addition, the mixture was stirred for 10 minutes, and ethyl 7-bromo-6-chloro-3-(3-hydroxypropyl)-1H-indole-2-carboxylate (see Intermediate 2, 2.00 g, 5.55 mmol), dissolved in THF (20 mL), was added dropwise. The mixture was allowed to warm to rt and was stirred overnight. The reaction mixture was concentrated under reduced pressure and the residue was triturated with methanol. The remaining solids were isolated by filtration.

In a second preparation, to a solution of triphenylphosphine (1.60 g, 6.10 mmol) in THF (20 mL), 6-fluoronaphthalen-1-ol (CAS 804498-72-4, 989 mg, 6.10 mmol) was added. The mixture was cooled to −10° C. and diisopropyl azodicarboxylate (1.2 mL, 6.1 mmol) was added dropwise. After complete addition, the mixture was stirred for 10 minutes and ethyl 7-bromo-6-chloro-3-(3-hydroxypropyl)-1H-indole-2-carboxylate (see Intermediate 2, 2.00 g, 5.55 mmol), dissolved in THF (20 mL), was added dropwise. The mixture was allowed to warm to rt and was stirred for 3 days. The reaction mixture was concentrated under reduced pressure and the residue was triturated with methanol. The remaining solids were isolated by filtration.

In a third preparation, to a solution of triphenylphosphine (1.60 g, 6.10 mmol) in THF (20 mL), 6-fluoronaphthalen-1-ol (CAS 804498-72-4, 989 mg, 6.10 mmol) was added. The mixture was cooled to −10° C. and diisopropyl azodicarboxylate (1.2 mL, 6.1 mmol) was added dropwise. After complete addition, the mixture was stirred for 10 minutes, and ethyl 7-bromo-6-chloro-3-(3-hydroxypropyl)-1H-indole-2-carboxylate (see Intermediate 2, 2.00 g, 5.55 mmol), dissolved in THF (20 mL), was added dropwise. The mixture was allowed to warm to rt and was stirred overnight. The reaction mixture was concentrated under reduced pressure and the residue was triturated with methanol. The remaining solids were isolated by filtration.

Combined with the products of the other preparations, the crude material was purified by flash chromatography using silica gel (hexane/ethyl acetate gradient). The obtained material was triturated with a mixture of tert.-butyl methyl ether and petroleum ether, and the remaining solids were isolated by filtration and dried to give the title compound (2.4 g). The filtrate was concentrated and triturated with methanol. The remaining solids were isolated by filtration and dried to give a second batch of the title compound (1.88 g).

LC-MS (Method 1): $R_t$=1.80 min; MS (ESIneg): m/z=502 [M−H]⁻

¹H-NMR (400 MHz, DMSO-d6) δ[ppm]: 1.191 (0.89), 1.208 (1.68), 1.226 (0.79), 1.275 (7.17), 1.286 (1.82), 1.293 (16.00), 1.303 (2.45), 1.310 (7.38), 1.321 (1.00), 2.177 (1.63), 2.194 (2.33), 2.211 (1.65), 2.227 (0.56), 2.518 (5.40), 2.523 (3.59), 3.280 (2.10), 3.299 (3.61), 3.317 (2.70), 4.147 (2.35), 4.162 (4.59), 4.176 (2.33), 4.190 (0.84), 4.269 (2.24), 4.286 (7.10), 4.304 (6.99), 4.322 (2.10), 5.759 (0.86), 6.834 (1.79), 6.842 (1.91), 6.848 (1.61), 6.856 (1.91), 7.168 (5.12), 7.189 (5.66), 7.240 (0.68), 7.249 (0.72), 7.261 (0.61), 7.271 (0.61), 7.316 (1.23), 7.322 (1.37), 7.333 (1.19), 7.339 (2.17), 7.345 (2.33), 7.360 (1.21), 7.367 (1.37), 7.391 (0.51), 7.412 (3.59), 7.418 (3.89), 7.426 (8.20), 7.438 (0.54), 7.579 (0.51), 7.600 (0.49), 7.624 (2.17), 7.630 (2.17), 7.650 (2.14), 7.656 (2.07), 7.721 (4.87), 7.743 (4.59), 7.757 (0.58), 7.778 (0.47), 8.046 (1.89), 8.061 (1.98), 8.069 (1.91), 8.084 (1.82), 11.517 (3.28).

On larger scale the title compound could be obtained in a similar manner with slightly modified reaction conditions in two batches: To a stirred solution of ethyl 7-bromo-6-chloro-3-(3-hydroxypropyl)-1H-indole-2-carboxylate (see Intermediate 2, 2000 g) and N,N-diethylethanamine (1.77 kg) in dichloromethane (20.0 L) was added methanesulfonyl chloride (1.30 kg) dropwise over 3 hrs at 0-5° C. under an atmosphere of nitrogen. After addition, the reaction mixture was stirred at 25° C. for 16 hrs. The mixture was washed with water (8 L) and concentrated to give a brown solid (3.99 kg, crude). This material (697 g) was added to a stirred solution of 6-fluoronaphthalen-1-ol (CAS 804498-72-4, 214 g) and potassium carbonate (428 g) in acetonitrile (5400 mL) under an atmosphere of nitrogen, and the reaction mixture was stirred at 85° C. for 16 hrs. The mixture was filtered, and the solution was concentrated. The residue was purified by silica gel chromatography (petrol ether/dichloromethane=3/1) to obtain a crude material, which was then slurried in petrol ether/dichloromethane (800/200 mL) at 20° C. for 16 hrs, and was filtered to obtain the title compound (262 g).

Intermediate 98 ethyl 6-chloro-3-{3-[(6-fluoronaphthalen-1-yl)oxy]propyl}-7-(4,4,5,5-tetramethyl-1,3,2-dioxa-borolan-2-yl)-1H-indole-2-carboxylate

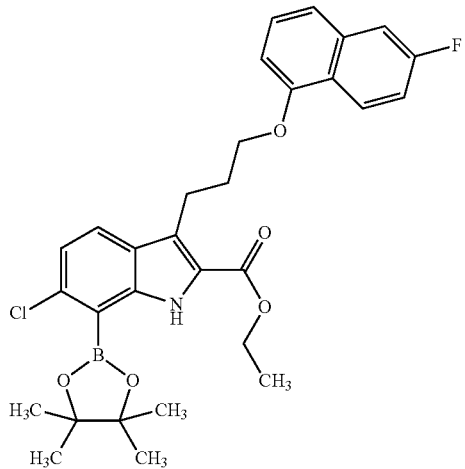 [SMILES: CCOC(=O)c1[nH]c2c(B3OC(C)(C)C(C)(C)O3)c(Cl)ccc2c1CCCOc1cccc2cc(F)ccc12]

To a solution of ethyl-7-bromo-6-chloro-3-{3-[(6-fluoronaphthalen-1-yl)oxy]propyl}-1H-indole-2-carboxylate (see Intermediate 97, 200 mg, 396 μmol) in DMF (3 mL), octamethyl-2,2'-bi-1,3,2-dioxaborolane (CAS 78183-34-3151 mg, 594 μmol), potassium acetate (117 mg, 1.19 mmol) and [1,1'-Bis(diphenylphosphino)ferrocene]dichloro-palladium(II) (32.4 mg, 39.6 μmol) were added. The mixture was purged with argon for 10 minutes. The tube was sealed and stirred at 95° C. for 12 hours. After cooling to rt the mixture was filtered and purified by preparative HPLC (Method P3) to give the title compound (34 mg, 12% yield).

LC-MS (Method 1): $R_t$=1.90 min; MS (ESIpos): m/z=552 [M+H]⁺

¹H-NMR (400 MHz, DMSO-d6) δ[ppm]: 1.257 (2.02), 1.275 (4.69), 1.292 (2.08), 1.324 (2.13), 1.373 (2.56), 1.383 (16.00), 2.202 (0.58), 2.219 (0.41), 2.518 (1.69), 2.522 (1.13), 3.301 (0.50), 3.320 (1.26), 4.144 (0.54), 4.159 (1.11), 4.173 (0.52), 4.235 (0.54), 4.252 (1.83), 4.270 (1.80), 4.288 (0.51), 5.758 (0.73), 6.824 (0.49), 6.832 (0.50), 6.838 (0.42), 6.846 (0.53), 7.045 (1.22), 7.067 (1.18), 7.319 (0.49), 7.326 (0.53), 7.408 (0.98), 7.414 (1.04), 7.422 (2.36), 7.622 (0.57), 7.629 (0.58), 7.648 (0.58), 7.655 (0.57), 7.839 (0.81), 7.861 (0.72), 8.010 (0.44), 8.024 (0.47), 8.033 (0.47), 8.047 (0.45), 9.978 (0.64).

On larger scale the title compound could be obtained in a similar manner with slightly modified reaction conditions: To a stirred solution of 4,4,4',4',5,5,5',5'-octamethyl-2,2'-bi-1,3,2-dioxaborolane (CAS 78183-34-3151 mg, 91.7 g), sodium carbonate (76.6 g) and [1,1'-Bis(diphenylphosphino)ferrocene]dichloro-palladium(II) (4.40 g) in 1,4-dioxane (700 mL) was added ethyl-7-bromo-6-chloro-3-{3-[(6-fluoronaphthalen-1-yl)oxy]propyl}-1H-indole-2-carboxylate (see Intermediate 97, 70 g) under an atmosphere of nitrogen, and the reaction mixture was stirred at 100° C. for 40 hrs. The residue was slurried in a mixture of ethanol and dichloromethane (300 and 50 mL) at 20° C. for 16 hrs, then recrystallized in dichloromethane (80 mL) from 50° C. to 0° C. for 3 hrs, and filtered to obtain the title compound (84.8 g). The filtrate was purified by silica gel column chromatography (petrol ether/ethyl acetate/dichloromethane=20/0/0-20/1/1) to obtain the title compound (21.2 g).

Intermediate 99 ethyl 3-{3-[(tert-butyldimethylsilyl)oxy]propyl}-6-chloro-7-[3-(hydroxymethyl)-1,5-dimethyl-1H-pyrazol-4-yl]-1H-indole-2-carboxylate

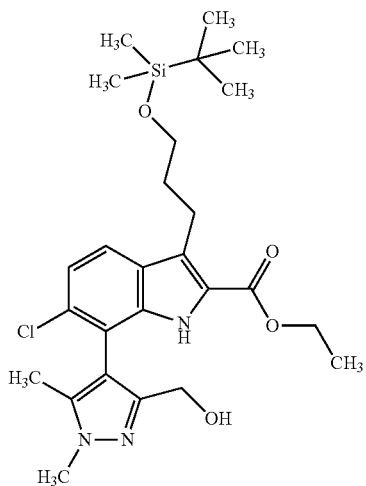 [SMILES: CCOC(=O)c1[nH]c2c(-c3c(CO)nn(C)c3C)c(Cl)ccc2c1CCCO[Si](C)(C)C(C)(C)C]

The reaction was split equally into four microwave vessels and combined for work up and purification. A microwave vessel equipped with a stir bar was charged with ethyl 3-{3-[(tert-butyldimethylsilyl)oxy]propyl}-6-chloro-7-(4,4,5,5-tetramethyl-1,3,2-dioxaborolan-2-yl)-1H-indole-2-carboxylate (see Intermediate 45, 2.0 g, 3.83 mmol), (4-bromo-1,5-dimethyl-1H-pyrazol-3-yl)methanol (see Intermediate 6, 863 mg, 4.21 mmol), potassium phosphate (1.62 g, 7.66 mmol), and SPhos Pd G3 (163 mg, 210 µmol). The vessel was purged with nitrogen and filled with degassed toluene (40 mL) and water (15 mL). The mixture was stirred in a microwave reactor at 110° C. for 20 min, then cooled to room temperature and diluted with ethyl acetate and water. The layers were separated and the aqueous phase was extracted twice more with ethyl acetate. The combined organic phases were washed with brine, dried over sodium sulfate, filtered, and concentrated. The crude residue was purified by flash chromatography on silica gel (0-100% acetone/dichloromethane) and fractions were re-purified by reverse-phase chromatography on C18-silica gel (10-100% acetonitrile/water) to obtain the title compound (0.677 g).

$^1$H NMR (Chloroform-d) δ: 9.12 (s, 1H), 7.63 (dd, 1H), 7.23 (d, 2H), 4.59 (dd, 1H), 4.43-4.28 (m, 3H), 3.90 (s, 3H), 3.69 (t, 2H), 3.13 (dd, 2H), 2.11 (s, 5H), 1.97-1.81 (m, 2H), 1.38 (t, 4H), 0.93 (s, 9H), 0.07 (s, 6H).

Intermediate 100 ethyl 3-(3-((tert-butyldimethylsilyl)oxy)propyl)-6-chloro-7-(3-((cyclopropylamino)methyl)-1,5-dimethyl-1H-pyrazol-4-yl)-1H-indole-2-carboxylate

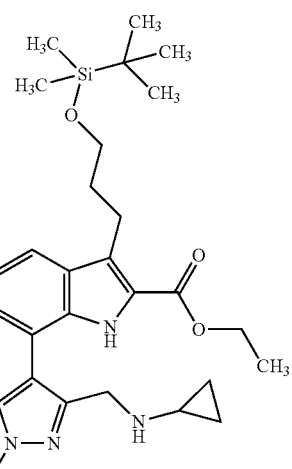

To a 0° C. stirred solution of ethyl 3-{3-[(tert-butyldimethylsilyl)oxy]propyl}-6-chloro-7-[3-(hydroxymethyl)-1,5-dimethyl-1H-pyrazol-4-yl]-1H-indole-2-carboxylate (Intermediate 99, 0.632 g, 1.21 mmol) in anhydrous dichloromethane (12 mL), under a stream of nitrogen, was added N,N-diisopropylethylamine (420 µL, 2.42 mmol) followed by dropwise addition of mesyl chloride (139 µL, 1.81 mmol). The resulting mixture was stirred at 0° C. for 2 h and then concentrated. The mixture was re-dissolved in acetonitrile (6 mL) and added to a solution of cyclopropylamine (837 µL, 12.1 mmol) in acetonitrile (6 mL) at 0° C. The mixture was warmed to room temperature, stirred overnight and then adsorbed onto Celite. The residue was purified by flash column chromatography on silica gel (0-10% methanol/dichloromethane) to give the title compound (0.534 g).

LC-MS (Method 3): $R_t$=1.55 min; MS (ESIpos): m/z=559 [M+H]$^+$ $^1$H NMR (300 MHz, Chloroform-d) δ 10.25 (s, 1H), 7.61 (d, 1H), 7.22 (d, 1H), 4.51-4.24 (m, 2H), 3.86 (s, 3H), 3.82-3.62 (m, 4H), 3.43 (d, 1H), 3.25-3.02 (m, 2H), 2.15 (dq, 1H), 2.10 (s, 3H), 1.90 (p, 2H), 1.56 (t, 0H), 1.39 (t, 5H), 0.92 (s, 11H), 0.52 (td, 1H), 0.43-0.16 (m, 2H), 0.06 (d, 7H), 0.00-0.14 (m, 1H).

239
Intermediate 101 ethyl 3-(3-((tert-butyldimethylsilyl)oxy)propyl)-6-chloro-7-(3-((3-chloro-N-cyclopropylpropylsulfonamido)methyl)-1,5-dimethyl-1H-pyrazol-4-yl)-1H-indole-2-carboxylate

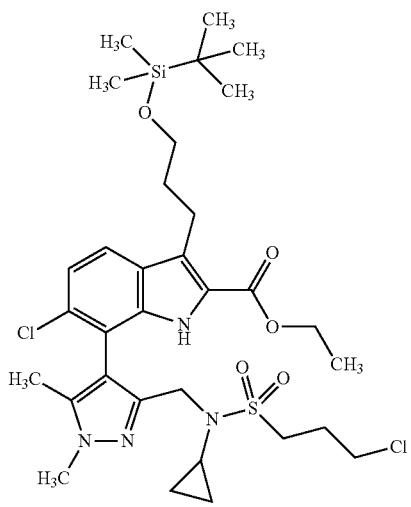 [SMILES: CCOC(=O)c1[nH]c2c(-c3c(CN(C4CC4)S(=O)(=O)CCCCl)nn(C)c3C)c(Cl)ccc2c1CCCO[Si](C)(C)C(C)(C)C]

To a solution of ethyl 3-(3-((tert-butyldimethylsilyl)oxy)propyl)-6-chloro-7-(3-((cyclopropylamino)methyl)-1,5-dimethyl-1H-pyrazol-4-yl)-1H-indole-2-carboxylate (Intermediate 100, 0.799 g, 1.42 mmol) in anhydrous dichloromethane (7 mL) at 0° C. was added N,N-diisopropylethylamine (494 μL, 2.84 mmol), followed by dropwise addition of 3-chloropropane-1-sulfonyl chloride (206 μL, 1.70 mmol) The resulting mixture was warmed to room temperature, stirred for 30 min and then adsorbed onto Celite. The residue was purified by flash column chromatography on silica gel (0-100% ethyl acetate/hexanes) to give the title compound (0.67 g).

LC-MS (Method 3): $R_t$=2.21 min; MS (ESIpos): m/z=699 [M+H]$^+$

1H NMR (300 MHz, Chloroform-d) δ 8.42 (s, 1H), 7.64 (d, 1H), 7.23 (d, 1H), 4.49-4.32 (m, 3H), 4.16 (d, 1H), 3.90 (s, 3H), 3.67 (q, 4H), 3.41-3.19 (m, 2H), 3.19-3.07 (m, 2H), 2.39-2.20 (m, 2H), 2.11 (s, 3H), 2.06 (d, 0H), 1.89 (p, 2H), 1.40 (t, 3H), 0.93 (s, 8H), 0.74-0.62 (m, 1H), 0.51-0.33 (m, 1H), 0.29-0.19 (m, 1H), 0.07 (s, 6H).

240
Intermediate 102

(rac)-ethyl 1-(3-((tert-butyldimethylsilyl)oxy)propyl)-13-chloro-8-cyclopropyl-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

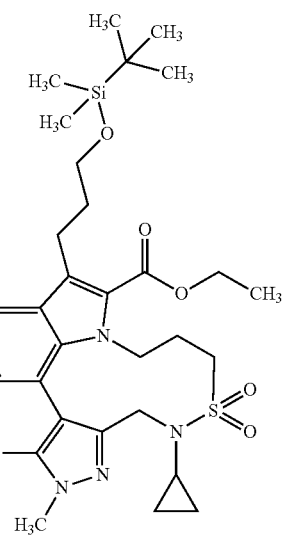

To a solution of ethyl 3-(3-((tert-butyldimethylsilyl)oxy)propyl)-6-chloro-7-(3-((3-chloro-N-cyclopropylpropylsulfonamido)methyl)-1,5-dimethyl-1H-pyrazol-4-yl)-1H-indole-2-carboxylate (Intermediate 101, 0.67 g, 957 μmol) in anhydrous acetonitrile (19 mL) was added cesium carbonate (1.24 g, 3.82 mmol). The resulting suspension was stirred at 60° C. for 2 days, cooled to room temperature and concentrated. Water was added and the aqueous phase was extracted three times with ethyl acetate. The combined organic phases were washed with brine, dried over sodium sulfate, filtered, and concentrated. The residue was purified by flash column chromatography on silica gel (20-100% ethyl acetate/hexanes) to give the title compound (0.381 g).

LC-MS (Method 3): $R_t$=2.16 min; MS (ESIpos): m/z=663 [M+H]$^+$ $^1$H NMR (300 MHz, Chloroform-d) δ 7.69 (d, 1H), 7.28 (d, 1H), 4.70-4.52 (m, 2H), 4.47-4.28 (m, 2H), 4.15 (d, 1H), 4.03-3.80 (m, 5H), 3.67 (t, 3H), 3.10 (qt, 3H), 2.68 (ddd, 1H), 2.51 (dt, 1H), 2.32 (dq, 1H), 2.18-1.99 (m, 1H), 1.94 (d, 3H), 1.86 (q, 2H), 1.68 (d, 1H), 1.47-1.33 (m, 4H), 0.94 (d, 9H), 0.56-0.35 (m, 3H), 0.08 (d, 7H), 0.05-0.07 (m, 3H), −0.07-0.22 (m, 1H).

241

Intermediate 103

(rac)-ethyl 13-chloro-8-cyclopropyl-1-(3-hydroxypropyl)-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

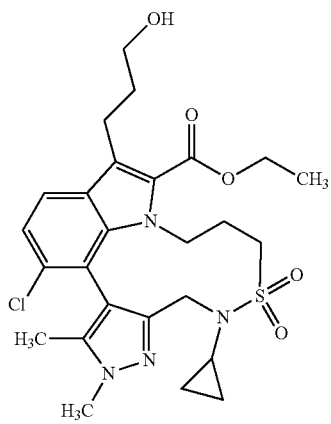 [SMILES: CCOC(=O)c1c(CCCO)c2ccc(Cl)c3c2n1CCCS(=O)(=O)N(C1CC1)Cc1nn(C)c(C)c1-3]

To a solution of (rac)-ethyl 1-(3-((tert-butyldimethylsilyl)oxy)propyl)-13-chloro-8-cyclopropyl-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 102, 0.418 g, 0.630 mmol) in anhydrous THF (12.5 mL) at 0° C. was added a solution of TBAF (755 µL, 0.755 mmol, 1 M in THF). The resulting mixture was warmed to room temperature, stirred for 3 h and then concentrated under reduced pressure. The residue was re-suspended in 1 M aqueous hydrochloric acid and extracted three times with ethyl acetate. The combined organic extracts were washed with brine, dried over sodium sulfate, filtered and concentrated under reduced pressure. The crude residue was purified by flash column chromatography on silica gel (0-50% acetone/dichloromethane) to give the title compound (0.156 g).

LC-MS (Method 3): $R_t$=1.40 min; MS (ESIpos): m/z=503 [M+H]$^+$ $^1$H NMR (300 MHz, Chloroform-d) δ 7.67 (d, 1H), 7.29 (d, 1H), 4.64 (d, 1H), 4.53 (dt, 1H), 4.46-4.32 (m, 2H), 4.15 (d, 1H), 4.02 (ddd, 1H), 3.89 (s, 3H), 3.63 (s, 2H), 3.16 (t, 2H), 2.74-2.48 (m, 2H), 2.40-2.23 (m, 1H), 2.17 (s, 6H), 2.14-2.00 (m, 1H), 1.94 (s, 4H), 1.74 1.63 (m, 0H), 1.42 (t, 3H), 0.58-0.37 (m, 1H), 0.09-0.17 (m, 2H).

242

Intermediate 104

(rac)-ethyl 1-(3-bromopropyl)-13-chloro-8-cyclopropyl-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

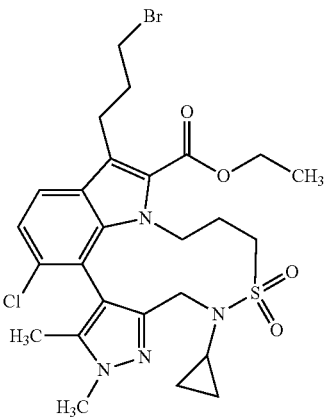 [SMILES: CCOC(=O)c1c(CCCBr)c2ccc(Cl)c3c2n1CCCS(=O)(=O)N(C1CC1)Cc1nn(C)c(C)c1-3]

To a 0° C. stirred solution of (rac)-ethyl 13-chloro-8-cyclopropyl-1-(3-hydroxypropyl)-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 103, 156 mg, 284 µmol) and triphenylphosphine (81.8 mg, 312 µmol) in anhydrous dichloromethane (3 mL) was added tetrabromomethane (103 mg, 312 µmol). The resulting mixture was warmed to room temperature, stirred for 4 h, and then adsorbed onto Celite. The residue was purified by reverse-phase flash column chromatography on C18-silica gel (10-100% acetonitrile/water with 0.1% formic acid) to give the title compound (0.115 g).

LC-MS (Method 3): $R_t$=1.76 min; MS (ESIpos): m/z=613 [M+H]$^+$

1H NMR (300 MHz, Chloroform-d) δ 7.70 (d, 1H), 7.30 (d, 1H), 4.63 (dd, 2H), 4.40 (qd, 2H), 4.14 (d, 1H), 4.07-3.92 (m, 1H), 3.89 (s, 3H), 3.53-3.41 (m, 2H), 3.38-3.06 (m, 2H), 2.78-2.67 (m, 1H), 2.52 (ddd, 1H), 2.34 (dt, 1H), 2.22 (p, 2H), 2.14-2.02 (m, 1H), 1.95 (s, 3H), 1.76-1.60 (m, 1H), 1.43 (t, 3H), 0.60-0.33 (m, 1H), 0.08-0.28 (m, 1H).

Intermediate 105

(rac)-ethyl 13-chloro-8-cyclopropyl-11,12-dimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide

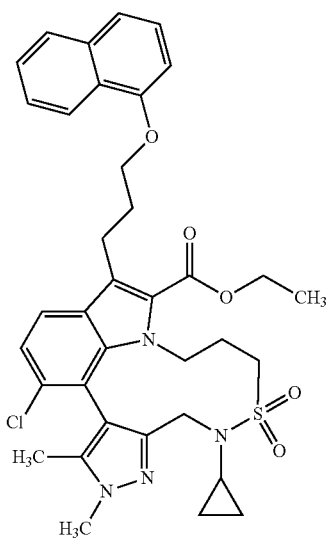 [SMILES: CCOC(=O)c1c(CCCOc2cccc3ccccc23)c2ccc(Cl)c3c2n1CCCS(=O)(=O)N(C1CC1)Cc1nn(C)c(C)c1-3]

A mixture of (rac)-ethyl 1-(3-bromopropyl)-13-chloro-8-cyclopropyl-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 104, 40 mg, 65.3 µmol), naphthalen-1-ol (11.2 mg, 78.3 µmol), and cesium carbonate (25.5 mg, 78.3 µmol) in dry tetrahydrofuran (1 mL) was stirred at 60° C. for 18 h. The mixture was cooled, adsorbed onto Celite, and purified by reverse-phase flash column chromatography on C18-silica gel (10-100% acetonitrile/water with 0.1% formic acid) to obtain the title compound (40 mg).

LC-MS (Method 3): $R_t$=2.0 min; MS (ESIpos): m/z=675 [M+H]$^+$ $^1$H NMR (300 MHz, Chloroform-d) δ 8.43-8.33 (m, 1H), 7.89-7.78 (m, 1H), 7.66 (d, 1H), 7.58-7.45 (m, 2H), 7.48-7.29 (m, 2H), 7.16 (d, 1H), 6.80-6.70 (m, 1H), 4.64 (dd, 2H), 4.35 (qd, 2H), 4.20-4.08 (m, 3H), 4.06-3.92 (m, 1H), 3.89 (s, 3H), 3.35 (tq, 2H), 2.72 (ddd, 1H), 2.52 (ddd, 1H), 2.37-2.20 (m, 3H), 2.08 (tt, 1H), 1.94 (s, 3H), 1.75-1.57 (m, 1H), 1.39 (t, 3H), 0.60-0.34 (m, 1H), 0.09-0.08 (m, 1H), −0.12--0.26 (m, 1H).

Intermediate 106

(rac)-ethyl 13-chloro-8-cyclopropyl-1-(3-((6-fluoronaphthalen-1-yl)oxy)propyl)-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

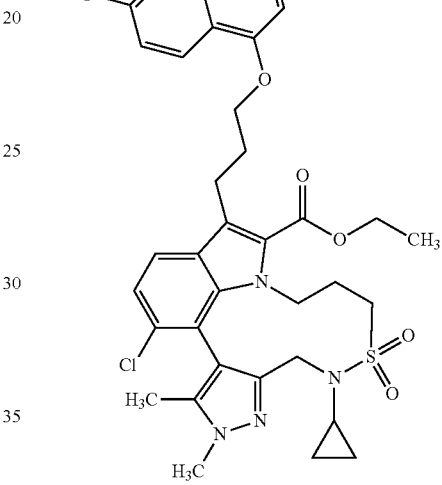

A mixture of (rac)-ethyl 1-(3-bromopropyl)-13-chloro-8-cyclopropyl-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 104, 0.11 g, 179 µmol), 6-fluoronaphthalen-1-ol (34.7 mg, 214 µmol), and cesium carbonate (69.7 mg, 214 µmol) in dry tetrahydrofuran (2 mL) was stirred at 60° C. for 2 days. The mixture was cooled, adsorbed onto Celite, and purified by reverse-phase flash column chromatography on C18-silica gel (10-100% acetonitrile/water with 0.1% formic acid) to obtain the title compound (0.12 g).

LC-MS (Method 3): $R_t$=2.0 min; MS (ESIpos): m/z=693 [M+H]$^+$ $^1$H NMR (Chloroform-d) δ: 8.37 (dd, 1H), 7.63 (d, 1H), 7.43 (dd, 1H), 7.39-7.33 (m, 2H), 7.29 (d, 1H), 7.17 (d, 1H), 6.79-6.64 (m, 1H), 4.63 (dd, 2H), 4.34 (qd, 2H), 4.25-4.10 (m, 4H), 3.99 (dd, 1H), 3.89 (s, 4H), 3.48-3.19 (m, 2H), 2.72 (ddd, 1H), 2.58-2.47 (m, 1H), 2.41-2.22 (m, 4H), 2.18-2.00 (m, 1H), 1.94 (s, 3H), 1.38 (t, 3H), 0.47 (dd, 2H), 0.02 (d, 1H), −0.18 (d, 1H).

Intermediate 107

(rac)-ethyl 7-(3-(1-(rac)-hydroxy-3-morpholinopropyl)-1,5-dimethyl-1H-pyrazol-4-yl)-3-(3-(naphthalen-1-yloxy)propyl)-1H-indole-2-carboxylate

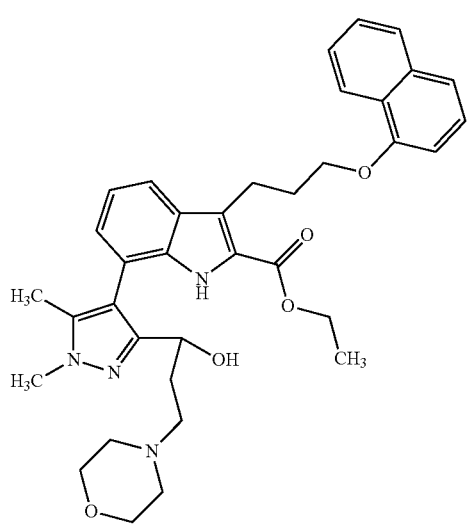 [SMILES: CCOC(=O)c1[nH]c2c(-c3c(C(O)CCN4CCOCC4)nn(C)c3C)cccc2c1CCCOc1cccc2ccccc12]

A microwave vial was charged with a magnetic stir bar, ethyl 3-(3-(naphthalen-1-yloxy)propyl)-7-(4,4,5,5-tetramethyl-1,3,2-dioxaborolan-2-yl)-1H-indole-2-carboxylate (Intermediate 1, 0.5 g, 1.00 mmol), (rac)-1-(4-bromo-1,5-dimethyl-1H-pyrazol-3-yl)-3-morpholinopropan-1-ol (see Intermediate 90, 381 mg, 1.20 mmol), SPhos Pd G3 (39.0 mg, 50.0 µmol) and potassium phosphate (424 mg, 2.00 mmol). The vial was sealed with a septum and purged with nitrogen. Degassed toluene (2 mL) and water (800 µL) were then added, the septum was replaced, and the vial was sealed. The mixture was heated in the microwave at 110° C. for 20 min. The resulting dark mixture was cooled to room temperature and extracted with ethyl acetate. The organic phase was separated, dried over sodium sulfate, filtered, and concentrated. The residue was purified by flash column chromatography on silica gel (0-10% methanol/dichloromethane) and re-purified by reverse-phase flash column chromatography on C18-silica gel (10-100% water/acetonitrile) to obtain the title compound (0.153 g) which was formed as a mixture of two diastereomers as a result of atropisomerism at the newly formed bi-heteroaryl bond.

LC-MS (Method 3): $R_t$=1.39 min; MS (ESIpos): m/z=611 [M+H]$^+$ $^1$H NMR (Chloroform-d) δ: 10.76 (s, 1H), 8.41-8.30 (m, 1H), 7.86-7.74 (m, 1H), 7.69 (dd, 1H), 7.55-7.43 (m, 2H), 7.44-7.30 (m, 2H), 7.19-7.04 (m, 2H), 6.77 (dd, 1H), 4.86 (s, 1H), 4.36 (qd, 2H), 4.23 (t, 2H), 3.87 (s, 3H), 3.63 (s, 3H), 3.45 (t, 2H), 2.56 (d, 3H), 2.36 (p, 3H), 2.19 (s, 4H), 1.97 (s, 1H), 1.38 (t, 3H).

Intermediate 108

(rac)-ethyl 7-(1,5-dimethyl-3-(1-(rac)-(methylamino)-3-morpholinopropyl)-1H-pyrazol-4-yl)-3-(3-(naphthalen-1-yloxy)propyl)-1H-indole-2-carboxylate

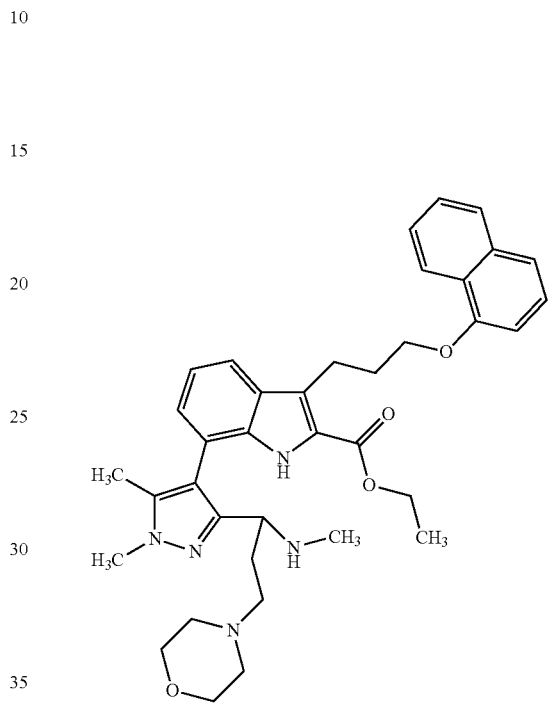

To a solution of (rac)-ethyl 7-(3-(1-(rac)-hydroxy-3-morpholinopropyl)-1,5-dimethyl-1H-pyrazol-4-yl)-3-(3-(naphthalen-1-yloxy)propyl)-1H-indole-2-carboxylate (Intermediate 107, 0.2 g, 327 µmol) in dichloromethane (3.5 mL) at 0° C. under a stream of nitrogen was added mesyl chloride (37.9 µL, 490 µmol), followed by N,N-diisopropylethylamine (113 µL, 654 µmol). The mixture was stirred at 0° C. for 90 min, concentrated, and re-suspended in acetonitrile (3.5 mL). A solution of methylamine (1.63 mL, 3.27 mmol, 2 M in THF) was added and the reaction was stirred at room temperature for 2 days and then concentrated. The residue was purified by flash chromatography on silica gel (0-20% (7 N ammonia in methanol)/dichloromethane) to obtain the title compound (0.141 g).

LC-MS (Method 3): $R_t$=1.24 min; MS (ESIpos): m/z=624 [M+H]$^+$ $^1$H NMR (Chloroform-d) δ: 8.44-8.32 (m, 1H), 7.89-7.75 (m, 1H), 7.68 (d, 1H), 7.55-7.47 (m, 2H), 7.38 (dt, 2H), 7.08 (dt, 2H), 6.78 (d, 1H), 4.38 (q, 2H), 4.22 (t, 2H), 3.85 (s, 3H), 3.49 (d, 7H), 2.54 (s, 3H), 2.36 (m, 4H), 2.23 (s, 3H), 2.08 (m, 5H), 1.40 (t, 3H), 1.26 (s, 2H).

247

Intermediate 109

(rac) ethyl 7-(3-(1-(((3-chloro-N-methylpropyl)sulfonamido)-3-(rac)-morpholinopropyl)-1,5-dimethyl-1H-pyrazol-4-yl)-3-(3-(naphthalen-1-yloxy)propyl)-1H-indole-2-carboxylate

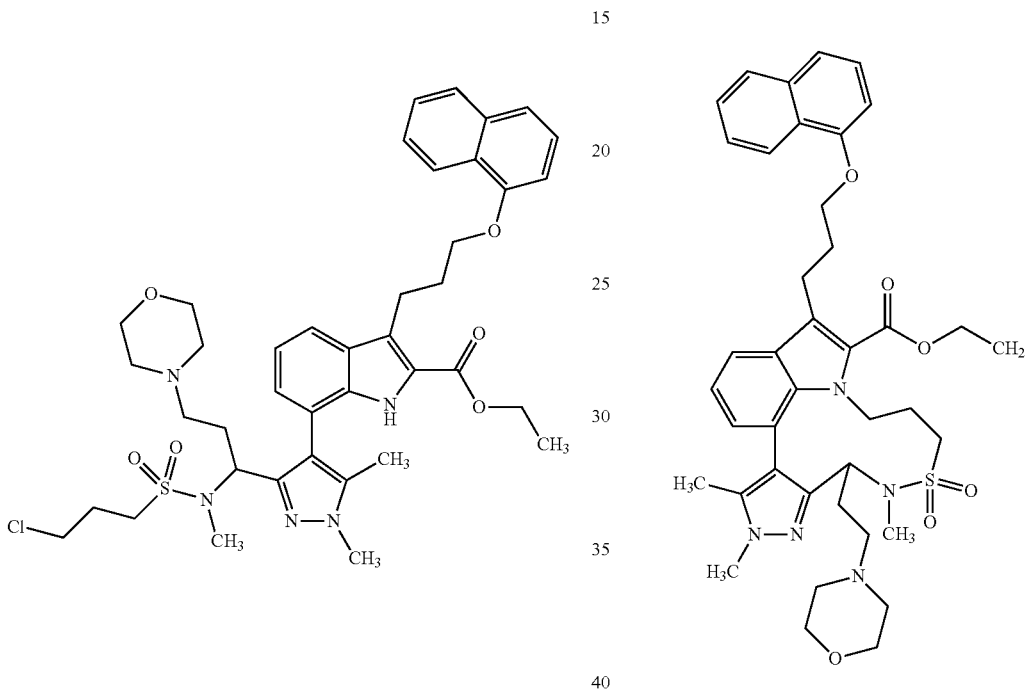

To a 0° C. stirred solution of (rac)-ethyl 7-(1,5-dimethyl-3-(1-(rac)-(methylamino)-3-morpholinopropyl)-1H-pyrazol-4-yl)-3-(3-(naphthalen-1-yloxy)propyl)-1H-indole-2-carboxylate (Intermediate 108, 0.208 g, 333 µmol) in dry dichloromethane (3.5 mL) under a stream of nitrogen was added 3-chloropropane-1-sulfonyl chloride (48.4 µL, 399 µmol) followed by N,N-diisopropylethylamine (115 µL, 666 µmol). After stirring for 30 min, the mixture was adsorbed directly onto Celite and purified by flash column chromatography on silica gel (20% acetone/dichloromethane) to obtain the title compound (0.195 g).

LC-MS (Method 3): $R_t$=1.61 min; MS (ESIpos): m/z=764 [M+H]$^+$ $^1$H NMR (Chloroform-d) δ: 8.59 (s, 1H), 8.46-8.32 (m, 2H), 7.81 (dd, 1H), 7.70 (t, 1H), 7.56 7.46 (m, 2H), 7.45-7.29 (m, 3H), 7.24-7.07 (m, 1H), 6.78 (t, 1H), 4.44-4.29 (m, 2H), 4.30-4.16 (m, 2H), 3.87 (d, 3H), 3.65 (s, 3H), 3.54-3.29 (m, 5H), 3.25-3.11 (m, 1H), 2.90 (s, 1H), 2.83 (s, 2H), 2.44 (s, 2H), 2.40-2.21 (m, 7H), 2.12 (d, 3H), 2.02 (s, 3H), 1.70-1.59 (m, 1H), 1.37 (td, 3H).

248

Intermediate 110 ethyl 8,11,12-trimethyl-9-(2-morpholinoethyl)-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide
(Mixture of Stereoisomers)

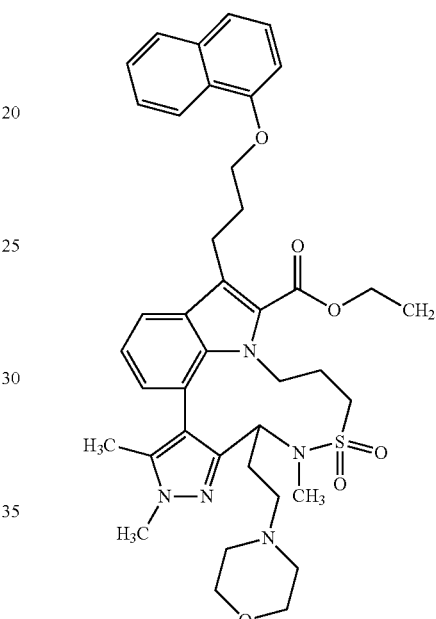

To a solution of ethyl 7-(3-(1-((3-chloro-N-methylpropyl)sulfonamido)-3-morpholinopropyl)-1,5-dimethyl-1H-pyrazol-4-yl)-3-(3-(naphthalen-1-yloxy)propyl)-1H-indole-2-carboxylate (Intermediate 109, 0.19 g, 248 µmol) in anhydrous acetonitrile (5 mL) was added cesium carbonate (323 mg, 992 µmol). The resulting suspension was stirred at 60° C. for 2 days, cooled to room temperature and adsorbed onto Celite. The residue was purified by flash column chromatography on silica gel (0-20% (7N ammonia in methanol)/dichloromethane) to give the title compound (0.18 g).

LC-MS (Method 3): $R_t$=1.38 min; MS (ESIpos): m/z=730 [M+H]$^+$

1H NMR (Chloroform-d) δ: 8.44-8.34 (m, 1H), 7.87-7.69 (m, 2H), 7.50 (dt, 3H), 7.39 (dt, 3H), 7.16-6.91 (m, 2H), 6.78 (d, 1H), 4.78 (dd, 1H), 4.53 (d, 1H), 4.33 (dd, 1H), 4.22 (t, 3H), 3.86 (s, 3H), 3.74-3.61 (m, 4H), 3.51-3.29 (m, 2H), 3.01 (s, 3H), 2.44 (dd, 6H), 2.32 (d, 7H), 2.11 (t, 1H), 1.96 (s, 4H), 1.86 (d, 6H), 1.43-1.28 (m, 12H), 1.12 (s, 8H).

Intermediate 111

(rac)-ethyl 6-chloro-3-(3-((6-fluoronaphthalen-1-yl)oxy)propyl)-7-(3-(1-(rac)-hydroxy-3-morpholinopropyl)-1,5-dimethyl-1H-pyrazol-4-yl)-1H-indole-2-carboxylate

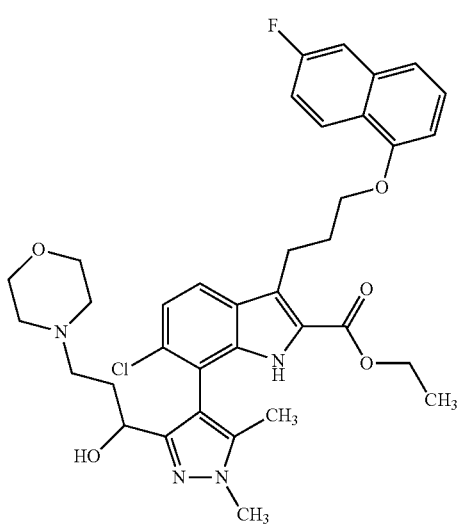 [SMILES: CCOC(=O)c1[nH]c2c(-c3c(C(O)CCN4CCOCC4)nn(C)c3C)c(Cl)ccc2c1CCCOc1cccc2cc(F)ccc12]

A round bottom flask equipped with a stir bar was charged with ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (see Intermediate 98, 1 g, 1.81 mmol), 1-(4-bromo-1,5-dimethyl-1H-pyrazol-3-yl)-3-(morpholin-4-yl)propan-1-ol (see Intermediate 90, 747 mg, 2.35 mmol), potassium phosphate (768 mg, 3.62 mmol), and RuPhos Pd G3 (83.2 mg, 99.5 μmol). The flask was purged with nitrogen and filled with degassed toluene (20 mL) and water (4 mL). The mixture was heated at 110° C. for 2h, cooled to room temperature, and filtered over a pad of Celite. The mixture was diluted with water and extracted three times with ethyl acetate. The combined organic phases were washed with brine, dried over sodium sulfate, filtered, and concentrated. The crude residue was purified by flash chromatography on silica gel (0-10% methanol/dichloromethane) to obtain the title compound (0.711 g), which was formed as a mixture of two diastereomers as a result of atropisomerism at the newly formed bi-heteroaryl bond.

LC-MS (Method 4): $R_t$=3.97 min; MS (ESIpos): m/z=663 [M+H]$^+$ $^1$H NMR (300 MHz, Chloroform-d) δ 9.80 (s, 1H), 8.33 (dd, 1H), 7.69-7.54 (m, 1H), 7.49-7.32 (m, 3H), 7.27-7.13 (m, 2H), 6.73 (dd, 1H), 5.01 (dd, 1H), 4.63 (dd, 1H), 4.36 (m, 2H), 4.22 (t, 2H), 3.89 (d, 3H), 3.80 (s, 5H), 3.42 (q, 2H), 2.71 (s, 5H), 2.44-2.29 (m, 2H), 2.25 (s, 2H), 2.10 (s, 2H), 1.92 (s, 1H), 1.37 (m, 3H), 1.26 (s, 8H).

Intermediate 112

(rac)-ethyl 6-chloro-7-(1,5-dimethyl-3-(1-(rac)-(methylamino)-3-morpholinopropyl)-1H-pyrazol-4-yl)-3-(3-((6-fluoronaphthalen-1-yl)oxy)propyl)-1H-indole-2-carboxylate

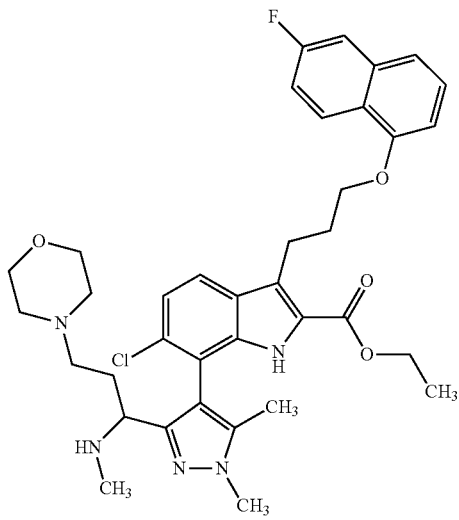 [SMILES: CCOC(=O)c1[nH]c2c(-c3c(C(CCN4CCOCC4)NC)nn(C)c3C)c(Cl)ccc2c1CCCOc1cccc2cc(F)ccc12]

Intermediate 113

(rac)-ethyl 6-chloro-7-(1,5-dimethyl-3-(rac)-(3-(methylamino)-1-morpholinopropyl)-1H-pyrazol-4-yl)-3-(3-((6-fluoronaphthalen-1-yl)oxy)propyl)-1H-indole-2-carboxylate

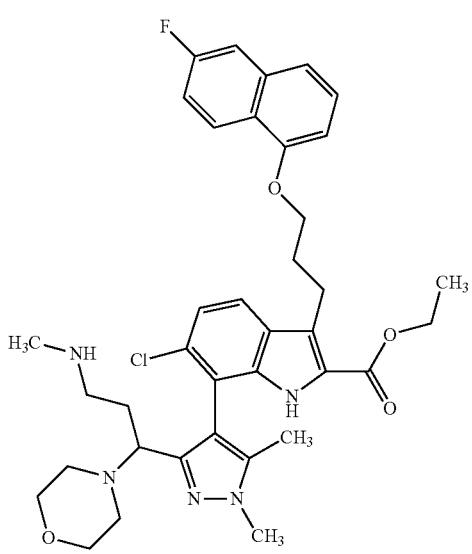 [SMILES: CCOC(=O)c1[nH]c2c(-c3c(C(CCNC)N4CCOCC4)nn(C)c3C)c(Cl)ccc2c1CCCOc1cccc2cc(F)ccc12]

To a solution of (rac)-ethyl 6-chloro-3-(3-((6-fluoronaphthalen-1-yl)oxy)propyl)-7-(3-(1-(rac)-hydroxy-3-morpholinopropyl)-1,5-dimethyl-1H-pyrazol-4-yl)-1H-indole-2-carboxylate (Intermediate 111, 0.35 g, 437 μmol) in dichloromethane (5.5 mL) at 0° C. under a stream of nitrogen was added N,N-diisopropylethylamine (180 µL, 1.04 mmol), followed by mesyl chloride (60.8 µL, 786 µmol). The mixture was stirred at 0° C. for 2 h, then concentrated, re-suspended in acetonitrile (5.5 mL), and treated with methylamine (2.62 mL, 5.24 mmol, 2 M in THF). The reaction mixture was heated at 60° C. and stirred for 24 h. After cooling to room temperature, the mixture was diluted with 1:1 brine/saturated aqueous sodium bicarbonate mixture. The aqueous phase was extracted three times with dichloromethane, dried over sodium sulfate, filtered, and concentrated. The residue was purified by flash chromatography on silica gel (0-10% methanol/dichloromethane) to obtain, in order of elution, Intermediate 112 (85.9 mg) and Intermediate 113 (96.2 mg).

Intermediate 112: LC-MS (Method 4): $R_t$=3.46 min; MS (ESIpos): m/z=677 [M+H]$^+$ $^1$H NMR (300 MHz, Chloroform-d) δ 8.34 (ddd, 1H), 7.61-7.53 (m, 1H), 7.45-7.30 (m, 4H), 7.22 (dd, 1H), 7.14 (dd, 1H), 6.70 (s, 1H), 4.35 (p, 2H), 4.19 (q, 2H), 3.85 (d, 3H), 3.54 (s, 5H), 3.40 (d, 1H), 2.52 (s, 1H), 2.32 (dd, 6H), 2.09 (d, 3H), 1.58 (s, 9H), 1.36 (q, 3H).

Intermediate 113: LC-MS (Method 4): $R_t$=3.55 min; MS (ESIpos): m/z=677 [M+H]$^+$ $^1$H NMR (300 MHz, Chloroform-d) δ 8.33 (dd, 1H), 7.55 (d, 1H), 7.46-7.30 (m, 3H), 7.25-7.20 (m, 1H), 7.13 (d, 1H), 6.71 (dd, 1H), 4.33 (q, 2H), 4.19 (t, 2H), 3.87 (s, 3H), 3.77 (s, 1H), 3.69 (t, 2H), 3.56 (s, 4H), 3.47-3.30 (m, 3H), 2.89 (d, 1H), 2.80-2.69 (m, 1H), 2.44 (m, 4H), 2.38 2.10 (m, 8H), 2.09 (s, 3H), 2.00-1.75 (m, 1H), 1.35 (t, 3H).

Intermediate 114

(rac)-ethyl 6-chloro-7-(3-(3-((3-chloro-N-methylpropyl)sulfonamido)-1-(rac)-morpholinopropyl)-1,5-dimethyl-1H-pyrazol-4-yl)-3-(3-((6-fluoronaphthalen-1-yl)oxy)propyl)-1H-indole-2-carboxylate

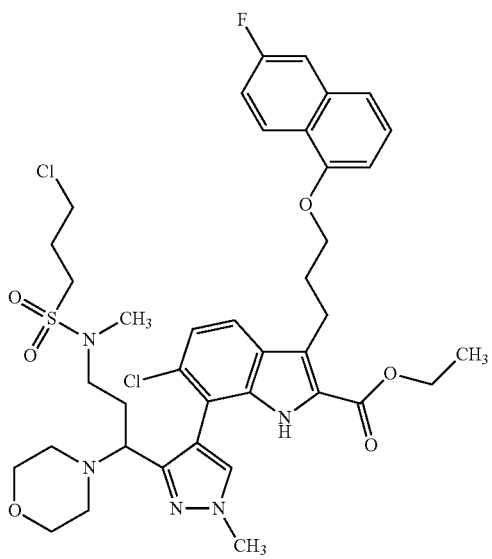 [SMILES: CCOC(=O)c1[nH]c2c(-c3cn(C)nc3C(CCN(C)S(=O)(=O)CCCCl)N3CCOCC3)c(Cl)ccc2c1CCCOc1cccc2cc(F)ccc12]

To a solution of (rac)-ethyl 6-chloro-7-(1,5-dimethyl-3-(3-(methylamino)-1-(rac)-morpholinopropyl)-1H-pyrazol-4-yl)-3-(3-((6-fluoronaphthalen-1-yl)oxy)propyl)-1H-indole-2-carboxylate (Intermediate 113, 0.16 g, 236 µmol) in dry dichloromethane (1.2 mL) at 0° C. was added N,N-diisopropylethylamine (82.2 µL, 472 µmol), followed by 3-chloropropane-1-sulfonyl chloride (37.1 µL, 306 µmol). After stirring for 2 h, the mixture was concentrated and purified by flash column chromatography on silica gel (0-10% methanol/dichloromethane) to obtain the title compound (0.151 g).

LC-MS (Method 4): $R_t$=4.34 min; MS (ESIpos): m/z=817 [M+H]$^+$ $^1$H NMR (300 MHz, Chloroform-d) δ 9.07 (s, 1H), 8.34 (dd, 1H), 7.62-7.55 (m, 1H), 7.47-7.32 (m, 4H), 7.25-7.20 (m, 1H), 7.14 (d, 1H), 6.70 (dd, 1H), 4.45-4.27 (m, 3H), 4.18 (t, 3H), 3.88 (s, 3H), 3.63 (t, 2H), 3.58 (t, 3H), 3.46-3.22 (m, 5H), 3.22-3.09 (m, 2H), 3.07-2.94 (m, 2H), 2.69 (s, 3H), 2.48-2.38 (m, 2H), 2.34 (t, 2H), 2.29-2.13 (m, 4H), 2.10 (s, 4H), 1.35 (t, 3H).

Intermediate 115 ethyl 15-chloro-1-(3-((6-fluoronaphthalen-1-yl)oxy)propyl)-8,13,14-trimethyl-11-morpholino-5,6,9,10,11,13-hexahydro-4H,8H-pyrazolo[3',4':6,7][1]thia[2,10]diazacyclotridecino[8,9,10-hi]indole-2-carboxylate 7,7-dioxide (Mixture of Stereoisomers)

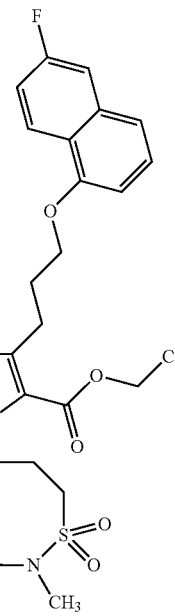

To a solution of (rac)-ethyl 6-chloro-7-(3-(3-((3-chloro-N-methylpropyl)sulfonamido)-1-(rac)-morpholinopropyl)-1,5-dimethyl-1H-pyrazol-4-yl)-3-(3-((6-fluoronaphthalen-1-yl)oxy)propyl)-1H-indole-2-carboxylate (Intermediate 114, 0.15 g, 183 µmol) in acetonitrile (4.5 mL) was added cesium carbonate (238 mg, 732 µmol) and the mixture was heated at 60° C. and stirred for 2 days. The mixture was cooled to room temperature and adsorbed onto Celite. The crude residue was purified by flash column chromatography on silica gel (0-10% methanol/dichloromethane) to obtain the title compound (90.9 mg).

LC-MS (Method 4): $R_t$=4.19 min; MS (ESIpos): m/z=781 [M+H]$^+$ $^1$H NMR (Chloroform-d) δ: 8.36 (dd, 1H), 7.66-7.57 (m, 1H), 7.48-7.33 (m, 3H), 7.19 (d, 1H), 6.72 (dd, 1H), 4.67-4.56 (m, 1H), 4.37 (q, 2H), 4.20 (t, 2H), 3.89 (s, 3H), 3.83 (d, 2H), 3.69-3.52 (m, 3H), 3.47-3.25 (m, 4H), 3.07 (d, 2H), 2.93-2.76 (m, 2H), 2.74 (s, 3H), 2.46 (d, 2H), 2.42-2.21 (m, 5H), 2.10 (d, 2H), 2.05 (s, 4H), 1.65 (d, 1H), 1.41 (t, 3H)

Intermediate 116

(rac)-ethyl 6-chloro-7-(3-(1-(rac)-((3-chloro-N-methylpropyl)sulfonamido)-3-morpholinopropyl)-1,5-dimethyl-1H-pyrazol-4-yl)-3-(3-((6-fluoronaphthalen-1-yl)oxy)propyl)-1H-indole-2-carboxylate (Mixture of Stereoisomers)

Intermediate 117 ethyl 13-chloro-1-(3-((6-fluoronaphthalen-1-yl)oxy)propyl)-8,11,12-trimethyl-9-(2-morpholinoethyl)-5,6,9,11-tetrahydro-4H,8H-pyrazolo[3',4':4,5][1]thia[2,8]diazacycloundecino[6,7,8-hi]indole-2-carboxylate 7,7-dioxide (Mixture of Stereoisomers)

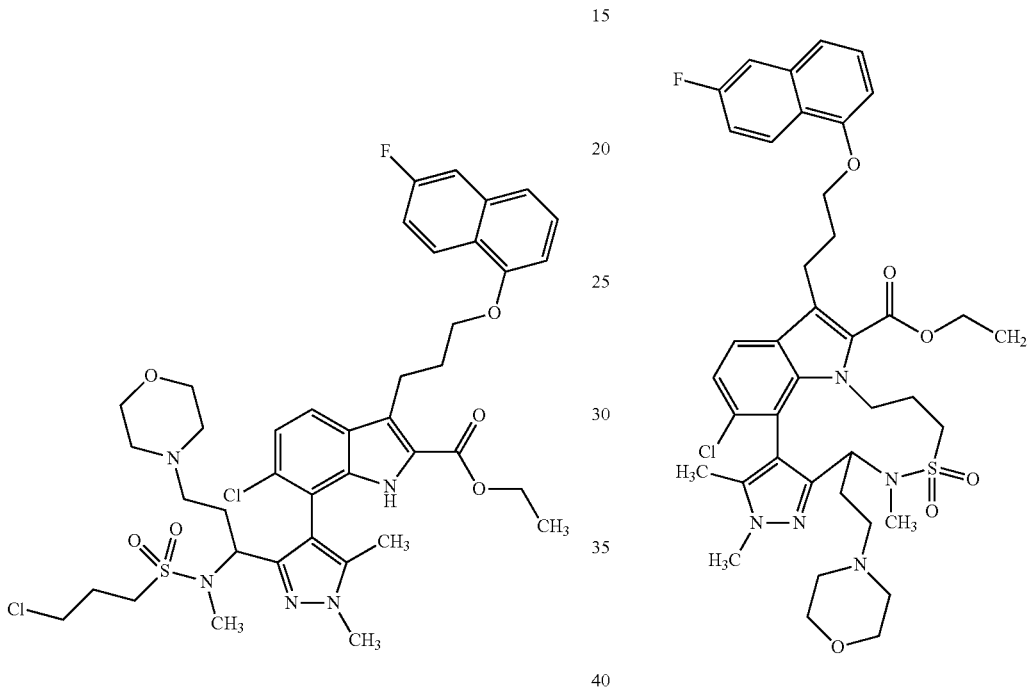

To a solution of (rac)-ethyl 6-chloro-7-(1,5-dimethyl-3-(1-(rac)-(methylamino)-3-morpholinopropyl)-1H-pyrazol-4-yl)-3-(3-((6-fluoronaphthalen-1-yl)oxy)propyl)-1H-indole-2-carboxylate (Intermediate 112, 0.178 g, 263 μmol) in dry dichloromethane (1.5 mL) at 0° C. was added N,N-diisopropylethylamine (45.6 μL, 263 μmol), followed by 3-chloropropane-1-sulfonyl chloride (31.9 μL, 263 μmol). After stirring for 2 h, the reaction mixture was concentrated and purified by flash column chromatography on silica gel (0-100% ethyl acetate/hexanes) to obtain the title compound (0.156 g) as a mixture of diastereomers.

peak 1: LC-MS (Method 4): $R_t$=3.96 min; MS (ESIpos): m/z=816 [M+H]$^+$ peak 2: LC-MS (Method 4): $R_t$=4.15 min; MS (ESIpos): m/z=816 [M+H]$^+$ $^1$H NMR (300 MHz, Chloroform-d) δ 8.65 (s, 1H), 8.34 (dd, 1H), 7.59 (d, 1H), 7.47-7.27 (m, 3H), 7.24-7.08 (m, 1H), 6.77-6.67 (m, 1H), 4.89-4.76 (m, 1H), 4.35 (dd, 2H), 4.19 (q, 2H), 3.88 (d, 3H), 3.56 (s, 2H), 3.48-3.32 (m, 1H), 2.93 (s, 2H), 2.78 (s, 1H), 2.33 (t, 3H), 2.06 (d, 9H), 1.57 (s, 5H), 1.36 (t, 3H).

To a solution of ethyl 6-chloro-7-(3-(1-((3-chloro-N-methylpropyl)sulfonamido)-3-morpholinopropyl)-1,5-dimethyl-1H-pyrazol-4-yl)-3-(3-((6-fluoronaphthalen-1-yl)oxy)propyl)-1H-indole-2-carboxylate (Intermediate 116, 0.153 g, 187 μmol) in acetonitrile (5 mL) was added cesium carbonate (243 mg, 748 μmol) and the mixture was heated at 60° C. and stirred for 2 days. The mixture was cooled to room temperature and adsorbed onto Celite. The crude residue was purified by flash column chromatography on silica gel (0-20% methanol/dichloromethane) to obtain the title compound (120 mg).

LC-MS (Method 4): $R_t$=4.19 min; MS (ESIpos): m/z=781 [M+H]$^+$ $^1$H NMR (300 MHz, Chloroform-d) δ 8.40-8.31 (m, 1H), 7.62 (dd, 1H), 7.47-7.33 (m, 3H), 7.18 (dd, 1H), 6.71 (ddd, 1H), 5.44-5.34 (m, 1H), 4.66-4.42 (m, 1H), 4.42-4.24 (m, 3H), 4.18 (t, 2H), 3.86 (d, 3H), 3.69 (s, 3H), 3.34 (m, 2H), 3.02 (s, 2H), 2.83-2.58 (m, 1H), 2.42 (d, 5H), 2.29 (t, 2H), 2.22-2.11 (m, 1H), 2.11-1.97 (m, 1H), 1.91 (s, 1H), 1.82 (d, 3H), 1.36 (td, 3H).

Intermediate 118 ethyl 6-chloro-3-(3-((6-fluoronaphthalen-1-yl)oxy)propyl)-7-(3-(hydroxymethyl)-1,5-dimethyl-1H-pyrazol-4-yl)-1H-indole-2-carboxylate

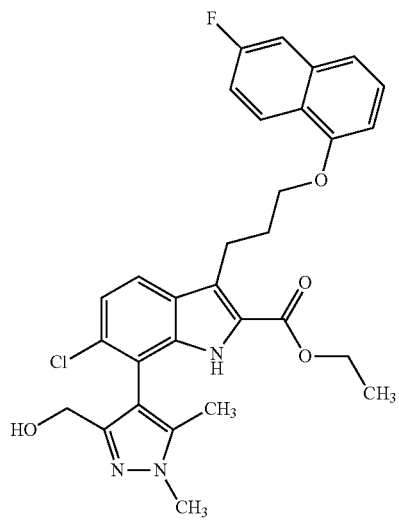 [SMILES: CCOC(=O)c1[nH]c2c(-c3c(CO)nn(C)c3C)c(Cl)ccc2c1CCCOc1cccc2cc(F)ccc12]

The reaction was split into four vessels and combined for workup and purification. A microwave vial equipped with a stir bar was charged with ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (Intermediate 98, 2.8 g, 5.07 mmol), (4-bromo-1,5-dimethyl-1H-pyrazol-3-yl)methanol (Intermediate 6, 1.14 g, 5.57 mmol), potassium phosphate (2.14 g, 10.1 mmol), and SPhos Pd G3 (216 mg, 278 µmol). The vial was purged with nitrogen and filled with degassed toluene (50 mL) and water (20 mL). The vial was sealed and the mixture was stirred in the microwave at 110° C. for 20 min. The mixture was cooled to room temperature, filtered over Celite, and diluted with water. The mixture was extracted three times with ethyl acetate and the combined organic phases were washed with brine, dried over sodium sulfate, filtered, and concentrated. The crude residue was purified by flash chromatography on silica gel (0-100% acetone/dichloromethane) and re-purified by reverse-phase flash column chromatography on C18-silica gel (10-100% acetonitrile/water) to obtain the title compound (1.87 g).

LC-MS (Method 3): $R_t$=1.79 min; MS (ESIpos): m/z=551 [M+H]$^+$ $^1$H NMR (300 MHz, Chloroform-d) δ 9.33 (s, 1H), 8.33 (dd, 1H), 7.58 (dd, 1H), 7.45-7.31 (m, 3H), 7.25-7.10 (m, 2H), 6.71 (dd, 1H), 4.61 (d, 1H), 4.41-4.26 (m, 3H), 4.19 (t, 2H), 3.90 (s, 3H), 3.39 (t, 2H), 2.34 (p, 2H), 2.12 (s, 3H), 1.34 (t, 3H).

Intermediate 119 ethyl 6-chloro-7-(3-(((2,4-dimethoxybenzyl)amino)methyl)-1,5-dimethyl-1H-pyrazol-4-yl)-3-(3-((6-fluoronaphthalen-1-yl)oxy)propyl)-1H-indole-2-carboxylate

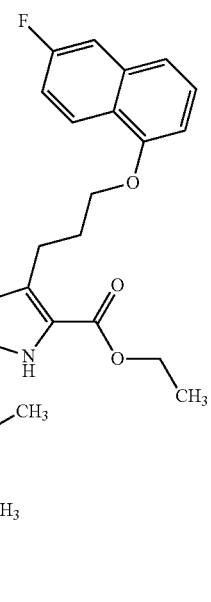

To a 0° C. stirred solution of ethyl 6-chloro-3-(3-((6-fluoronaphthalen-1-yl)oxy)propyl)-7-(3-(hydroxymethyl)-1,5-dimethyl-1H-pyrazol-4-yl)-1H-indole-2-carboxylate (Intermediate 118, 1 g, 1.81 mmol) in anhydrous dichloromethane (18 mL), under a stream of nitrogen, was added N,N-diisopropylethylamine (629 µL, 3.62 mmol), followed by dropwise addition of mesyl chloride (181 µL, 2.35 mmol). The resulting mixture was stirred at 0° C. for 2 h, then warmed to room temperature and stirred for 3 h. The mixture was concentrated, re-dissolved in acetonitrile (9 mL), and added to a solution of 1-(2,4-dimethoxyphenyl)methanamine (1.51 g, 9.05 mmol) in acetonitrile (9 mL) at 0° C. The mixture was warmed to room temperature, stirred overnight, and concentrated. Ethyl acetate was added and the solution was washed with 1:1 saturated sodium bicarbonate/brine mixture. The organic phase was separated and dried over sodium sulfate, filtered, and concentrated. The crude residue was purified by flash column chromatography on silica gel (0-100% acetone/dichloromethane) to give the title compound (1.2 g).

LC-MS (Method 4): $R_t$=4.79 min; MS (ESIpos): m/z=699 [M+H]$^+$

Intermediate 120 ethyl 6-chloro-7-(3-(((3-chloro-N-(2,4-dimethoxy-benzyl)propyl)sulfonamido)methyl)-1,5-dimethyl-1H-pyrazol-4-yl)-3-(3-((6-fluoronaphthalen-1-yl)oxy)propyl)-1H-indole-2-carboxylate

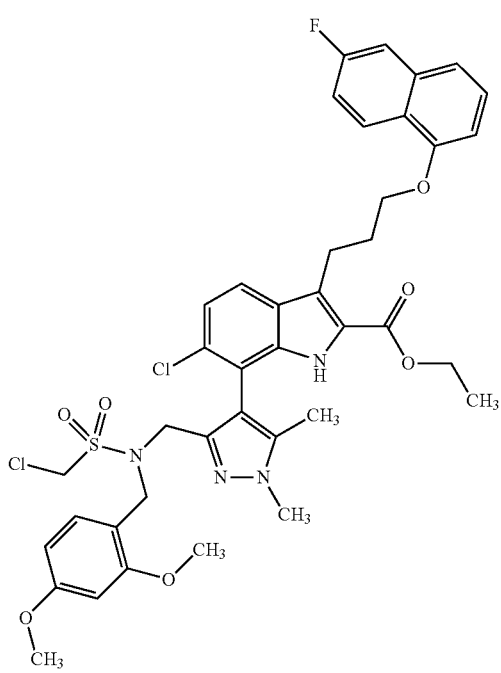 [SMILES: CCOC(=O)c1[nH]c2c(-c3c(CN(Cc4ccc(OC)cc4OC)S(=O)(=O)CCl)nn(C)c3C)c(Cl)ccc2c1CCCOc1cccc2cc(F)ccc12]

To a solution of ethyl 6-chloro-7-(3-(((2,4-dimethoxybenzyl)amino)methyl)-1,5-dimethyl-1H-pyrazol-4-yl)-3-(3-((6-fluoronaphthalen-1-yl)oxy)propyl)-1H-indole-2-carboxylate (Intermediate 119, 1.2 g, 1.71 mmol) in dry dichloromethane (17 mL) at 0° C. was added 3-chloropropane-1-sulfonyl chloride (248 μL, 2.05 mmol), followed by N,N-diisopropylethylamine (595 μL, 3.42 mmol). After stirring for 2 h, excess 3-chloropropane-1-sulfonyl chloride (248 μL, 2.05 mmol) and N,N-diisopropylethylamine (595 μL, 3.42 mmol) were added and the mixture continued to stir overnight. The mixture was adsorbed onto Celite and purified by flash column chromatography on silica gel (0-100% ethyl acetate/hexanes) to obtain the title compound (0.52 g).

LC-MS (Method 3): $R_t$=2.09 min; MS (ESIpos): m/z=839 [M+H]$^+$ $^1$H NMR (300 MHz, Chloroform-d) δ 8.52 (s, 1H), 8.34 (dd, 1H), 7.54 (d, 1H), 7.46-7.32 (m, 3H), 7.25-7.17 (m, 1H), 7.13-6.98 (m, 2H), 6.70 (dd, 1H), 6.46 (d, 1H), 6.32-6.24 (m, 2H), 4.40-4.23 (m, 5H), 4.18 (dd, 3H), 3.90 (s, 3H), 3.83 (d, 1H), 3.73 (s, 3H), 3.64 (s, 3H), 3.55 (td, 2H), 3.42-3.31 (m, 2H), 3.22-2.93 (m, 2H), 2.31 (p, 2H), 2.16 (p, 2H), 2.07 (s, 3H), 1.35 (t, 3H).

Intermediate 121

(rac)-ethyl 13-chloro-8-(2,4-dimethoxybenzyl)-1-(3-((6-fluoronaphthalen-1-yl)oxy)propyl)-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

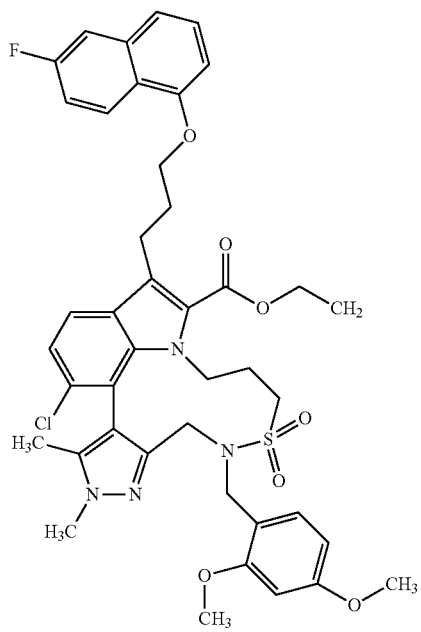 [SMILES: CCOC(=O)c1c(CCCOc2cccc3cc(F)ccc23)c2ccc(Cl)c3c2n1CCCS(=O)(=O)N(Cc1ccc(OC)cc1OC)Cc1nn(C)c(C)c1-3]

To a solution of ethyl 6-chloro-7-(3-(((3-chloro-N-(2,4-dimethoxybenzyl) propyl)sulfonamido)methyl)-1,5-dimethyl-1H-pyrazol-4-yl)-3-(3-((6-fluoronaphthalen-1-yl)oxy)propyl)-1H-indole-2-carboxylate (Intermediate 120, 0.519 g, 618 μmol) in acetonitrile (12 mL) was added cesium carbonate (1.0 g, 3.09 mmol) and the mixture was stirred at 60° C. overnight. The mixture was cooled to room temperature and concentrated. The crude residue was purified by flash chromatography on silica gel (0-10% methanol/dichloromethane) to obtain the title compound (0.239 g).

LC-MS (Method 4): $R_t$=5.65 min; MS (ESIpos): m/z=803 [M+H]$^+$ $^1$H NMR (300 MHz, Chloroform-d) δ 8.36 (dd, 1H), 7.68-7.58 (m, 1H), 7.45-7.28 (m, 4H), 7.20 (t, 1H), 6.70 (q, 1H), 6.51-6.29 (m, 2H), 4.77-4.61 (m, 1H), 4.61-3.99 (m, 8H), 3.88 (s, 3H), 3.79 (d, 7H), 3.74 (s, 3H), 3.63-3.20 (m, 2H), 2.59-2.40 (m, 1H), 2.40-2.26 (m, 2H), 2.15-1.91 (m, 1H), 1.88 (s, 2H), 1.39 (d, 2H), 1.32 (d, 1H).

Intermediate 122

(rac)-ethyl 13-chloro-1-(3-((6-fluoronaphthalen-1-yl)oxy)propyl)-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide

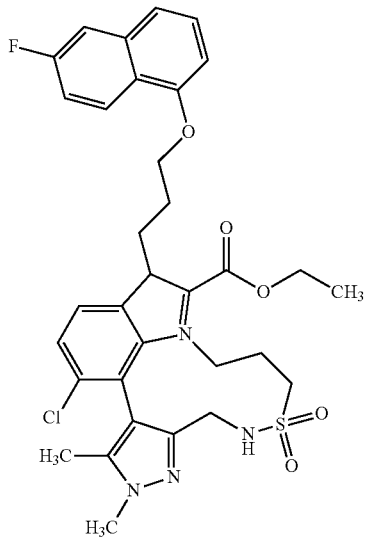

A mixture of (rac)-ethyl 13-chloro-8-(2,4-dimethoxybenzyl)-1-(3-((6-fluoronaphthalen-1-yl)oxy)propyl)-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 121, 0.198 g, 246 μmol) in dichloromethane (2.5 mL) and trifluoroacetic acid (564 μL, 7.37 mmol) was stirred at room temperature for 2 h before concentrating. The crude residue was purified by reverse-phase flash chromatography on C18-silica gel (10-100% acetonitrile/water with 0.1% formic acid) to obtain the title compound (64.7 mg).

LC-MS (Method 4): $R_t$=4.91 min; MS (ESIpos): m/z=653 [M+H]$^+$ $^1$H NMR (300 MHz, Chloroform-d) δ 8.36 (dd, 1H), 7.64 (d, 1H), 7.46-7.34 (m, 3H), 7.22 (d, 1H), 6.73 (dd, 1H), 4.58 (s, 1H), 4.47-4.25 (m, 2H), 4.25-4.01 (m, 3H), 3.97 (s, 1H), 3.88 (s, 3H), 3.36 (ddt, 2H), 2.43 (s, 2H), 2.38-2.19 (m, 2H), 1.97 (d, 1H), 1.75 (s, 1H), 1.58 (s, 5H), 1.37 (t, 3H).

Intermediate 123 ethyl 6-chloro-7-(5-ethyl-3-(hydroxymethyl)-1-methyl-1H-pyrazol-4-yl)-3-(3-((6-fluoronaphthalen-1-yl)oxy)propyl)-1H-indole-2-carboxylate

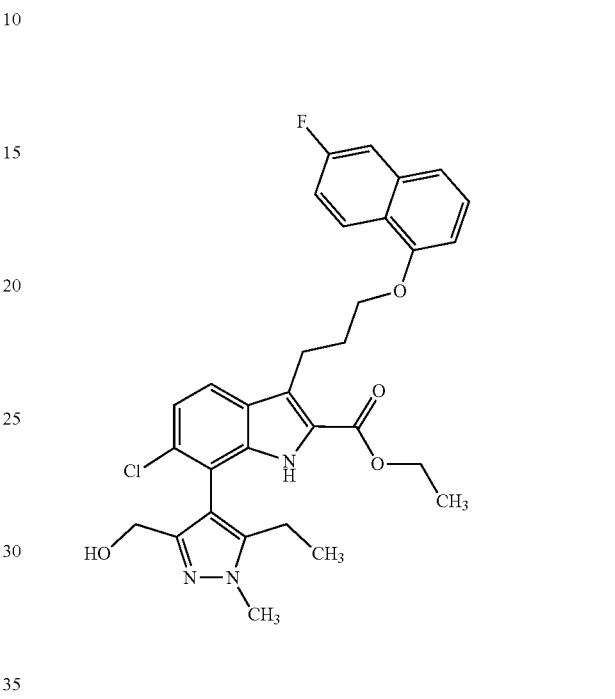

A round bottom flask equipped with a stir bar and a condenser was charged with ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (Intermediate 98, 3 g, 5.43 mmol), (4-bromo-5-ethyl-1-methyl-1H-pyrazol-3-yl)methanol (Intermediate 9, 1.66 g, 7.60 mmol), potassium phosphate (2.29 g, 10.8 mmol) and RuPhos Pd G3 (249 mg, 298 μmol). The flask was purged with nitrogen and filled with degassed toluene (60 mL) and water (12 mL). The mixture was heated at 110° C. for 3.5 h, cooled to room temperature, and filtered over a pad of Celite. The mixture was diluted with water and extracted three times with ethyl acetate. The combined organic phases were washed with brine, dried over sodium sulfate, filtered, and concentrated. The crude residue was purified by flash chromatography on silica gel (0-10% methanol/dichloromethane) and re-purified by reverse phase column chromatography on C18-silica gel (20-100% acetonitrile/water with 0.1% formic acid) to obtain the title compound (1.27 g).

LC-MS (Method 4): $R_t$=4.99 min; MS (ESIeg): m/z=562 [M−H]$^−$ $^1$H NMR (300 MHz, Chloroform-d) δ 8.85 (s, 1H), 8.34 (dd, 1H), 7.59 (dd, 1H), 7.45-7.33 (m, 3H), 7.25 (ddd, 5H), 7.17 (d, 1H), 6.72 (dd, 1H), 4.53 (d, 1H), 4.39-4.29 (m, 3H), 4.20 (t, 2H), 3.94 (s, 3H), 3.38 (t, 2H), 2.51 (ddt, 2H), 2.34 (p, 2H), 1.35 (t, 3H), 1.01 (t, 3H).

Intermediate 124 ethyl 6-chloro-7-(3-((cyclopropylamino)methyl)-5-ethyl-1-methyl-1H-pyrazol-4-yl)-3-(3-((6-fluoronaphthalen-1-yl)oxy)propyl)-1H-indole-2-carboxylate

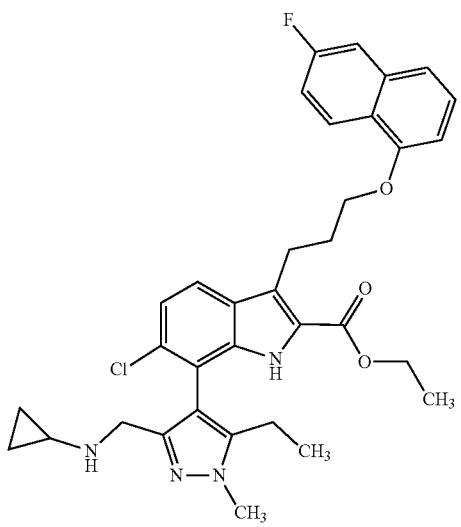

To a 0° C. stirred solution of ethyl 6-chloro-7-(5-ethyl-3-(hydroxymethyl)-1-methyl-1H-pyrazol-4-yl)-3-(3-((6-fluoronaphthalen-1-yl)oxy)propyl)-1H-indole-2-carboxylate (Intermediate 123, 1.23 g, 2.18 mmol) in anhydrous dichloromethane (22 mL), under a stream of nitrogen, was added N,N-diisopropylethylamine (758 μL, 4.36 mmol), followed by dropwise addition of methanesulfonyl chloride (218 μL, 2.83 mmol). The resulting mixture was stirred at 0° C. for 2 h, then warmed to room temperature and stirred overnight. The mixture was diluted with dichloromethane and washed with 1:1 saturated sodium bicarbonate/brine mixture. The organic phase was dried over sodium sulfate, filtered, and concentrated. The crude residue was re-dissolved in acetonitrile (11 mL) and added to a solution of cyclopropanamine (1.50 mL, 21.8 mmol) in acetonitrile (11 mL) at 0° C. The mixture was stirred for 2h at room temperature then for 1h at 40° C. The mixture was adsorbed onto Celite and purified by flash column chromatography on silica gel (0-10% methanol/dichloromethane) to give the title compound (1.02 g).

LC-MS (Method 4): $R_f$=3.36 min; MS (ESIneg): m/z=601 [M−H]⁻

$^1$H NMR (400 MHz, Chloroform-d) δ 9.77 (s, 1H), 8.33 (dd, 1H), 7.58 (d, 1H), 7.43-7.33 (m, 3H), 7.25-7.20 (m, 1H), 7.17 (d, 1H), 6.73-6.69 (m, 1H), 4.41-4.29 (m, 2H), 4.20 (t, 2H), 3.90 (d, 3H), 3.72 (d, 1H), 3.42-3.35 (m, 3H), 2.53 (dp, 3H), 2.34 (p, 2H), 2.09 (dt, 1H), 1.36 (dd, 3H), 0.98 (t, 3H), 0.43-0.36 (m, 1H), 0.34-0.27 (m, 1H), 0.23-0.16 (m, 1H), −0.10-−0.17 (m, 1H).

Intermediate 125 ethyl 6-chloro-7-(3-(((3-chloro-N-cyclopropylpropyl)sulfonamido)methyl)-5-ethyl-1-methyl-1H-pyrazol-4-yl)-3-(3-((6-fluoronaphthalen-1-yl)oxy)propyl)-1H-indole-2-carboxylate

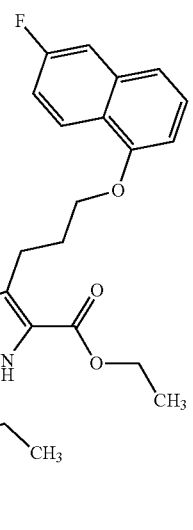

To a solution of ethyl 6-chloro-7-(3-((cyclopropylamino)methyl)-5-ethyl-1-methyl-1H-pyrazol-4-yl)-3-(3-((6-fluoronaphthalen-1-yl)oxy)propyl)-1H-indole-2-carboxylate (Intermediate 124, 1.022 g, 1.69 mmol) in dry dichloromethane (8.5 mL) at 0° C. under nitrogen was added N,N-diisopropylethylamine (436 mg, 3.38 mmol), followed by a solution of 3-chloropropane-1-sulfonyl chloride (357 mg, 2.02 mmol) in dichloromethane (0.5 mL). The mixture was stirred at 0° C. for 30 min before concentrating to give an oil. The residue was purified by flash column chromatography on silica gel (0-100% ethyl acetate/hexanes) to obtain the title compound (0.981 g) as a white solid.

LC-MS (Method 4): $R_f$=5.92 min; MS (ESIpos): m/z=747 [M+H]⁺

$^1$H NMR (400 MHz, Chloroform-d) δ 8.45 (s, 1H), 8.35 (dd, 1H), 7.59 (d, 1H), 7.44-7.32 (m, 3H), 7.15 (d, 1H), 6.70 (dd, 1H), 4.34 (dd, 3H), 4.19 (d, 2H), 3.93 (s, 3H), 3.67 (m, 2H), 3.42-3.23 (m, 4H), 2.49 (m, 3H), 2.31 (m, 4H), 1.36 (t, 3H), 1.21 (d, 2H), 1.01 (t, 3H), 0.71-0.61 (m, 1H), 0.44 (t, 2H), 0.39-0.30 (m, 1H).

Intermediate 126

(rac)-ethyl 13-chloro-8-cyclopropyl-12-ethyl-1-(3-((6-fluoronaphthalen-1-yl)oxy)propyl)-11-methyl-5,6,9,11-tetrahydro-4H,8H-pyrazolo[3',4':4,5][1]thia[2,8]diazacycloundecino[6,7,8-hi]indole-2-carboxylate 7,7-dioxide

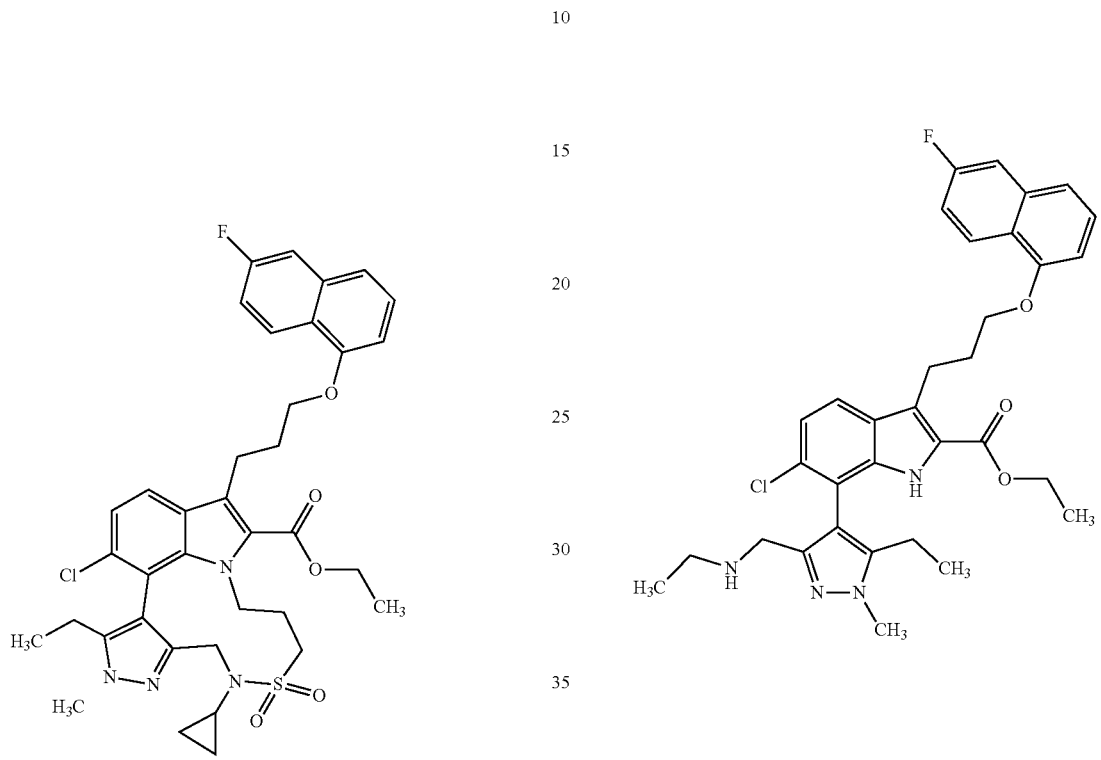

A mixture of ethyl 6-chloro-7-(3-(((3-chloro-N-cyclopropylpropyl)sulfonamido)methyl)-5-ethyl-1-methyl-1H-pyrazol-4-yl)-3-(3-((6-fluoronaphthalen-1-yl)oxy)propyl)-1H-indole-2-carboxylate (Intermediate 125, 882 mg, 1.18 mmol) and cesium carbonate (1.53 g, 4.72 mmol) in dry acetonitrile (25 mL) was stirred at 60° C. overnight. The mixture was cooled, concentrated, and purified by flash column chromatography on silica gel (0-100% ethyl acetate/hexanes) to obtain the title compound (763 mg) as a white solid.

LC-MS (Method 4): $R_t$=5.66 min; MS (ESIpos): m/z=708 [M+H]$^+$ $^1$H NMR (300 MHz, Chloroform-d) δ 8.38 (dd, 1H), 7.63 (d, 1H), 7.43 (dd, 1H), 7.39-7.32 (m, 2H), 7.31-7.23 (m, 6H), 7.17 (d, 1H), 6.73-6.66 (m, 1H), 4.68-4.51 (m, 2H), 4.34 (qd, 2H), 4.20-4.12 (m, 3H), 3.91 (s, 3H), 3.42-3.27 (m, 2H), 2.73-2.50 (m, 2H), 2.37-2.26 (m, 4H), 2.13 (m, 1H), 1.69 (s, 1H), 1.38 (t, 3H), 1.27 (d, 2H), 0.94 (t, 3H), 0.56-0.37 (m, 2H), 0.08-0.03 (m, 1H), −0.14 (dd, 1H).

Intermediate 127 ethyl 6-chloro-7-(5-ethyl-3-((ethylamino)methyl)-1-methyl-1H-pyrazol-4-yl)-3-(3-((6-fluoronaphthalen-1-yl)oxy)propyl)-1H-indole-2-carboxylate

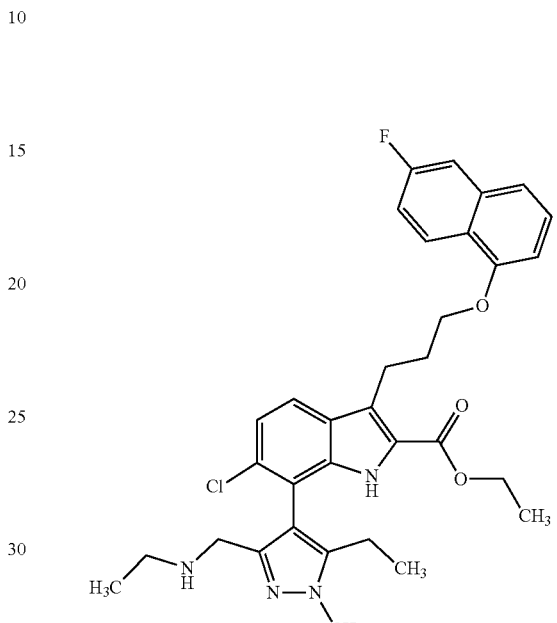

To a 0° C. stirred solution of ethyl 6-chloro-7-(5-ethyl-3-(hydroxymethyl)-1-methyl-1H-pyrazol-4-yl)-3-(3-((6-fluoronaphthalen-1-yl)oxy)propyl)-1H-indole-2-carboxylate (Intermediate 122, 1.0 g, 1.77 mmol) in anhydrous dichloromethane (18 mL), under a stream of nitrogen, was added N,N-diisopropylethylamine (615 μL, 3.54 mmol), followed by dropwise addition of methanesulfonyl chloride (177 μL, 2.30 mmol). The resulting mixture was stirred at 0° C. for 2 h, at which point a solution of ethylamine (2 M in THF, 8.85 mL, 17.7 mmol) was added quickly. The mixture was warmed to room temperature, stirred for 3.5 h, diluted with dichloromethane, and then washed with a 1:1 mixture of brine and saturated aqueous sodium bicarbonate solution. The organic phase was dried over sodium sulfate, filtered, and concentrated. The residue was purified by flash column chromatography on silica gel (0-20% 7N ammonia in methanol/dichloromethane) to give the title compound (727 mg) as a white solid.

LC-MS (Method 4): $R_t$=3.81 min; MS (ESIneg): m/z=590 [M−H]$^−$ $^1$H NMR (300 MHz, Chloroform-d) δ 10.92 (s, 1H), 8.32 (dd, 1H), 7.57 (d, 1H), 7.43-7.32 (m, 3H), 7.25-7.19 (m, 1H), 7.16 (d, 1H), 6.70 (dd, 1H), 4.34 (p, 2H), 4.19 (t, 2H), 3.90 (s, 3H), 3.67 (d, 1H), 3.39 (t, 2H), 3.27 (d, 1H), 2.66-2.46 (m, 4H), 2.34 (p, 2H), 1.35 (t, 3H), 1.00 (q, 6H).

265
Intermediate 128 ethyl 6-chloro-7-(3-(((3-chloro-N-ethylpropyl)sulfonamido)methyl)-5-ethyl-1-methyl-1H-pyrazol-4-yl)-3-(3-((6-fluoronaphthalen-1-yl)oxy)propyl)-1H-indole-2-carboxylate

266
Intermediate 129

(rac)-ethyl 13-chloro-8,12-diethyl-1-(3-((6-fluoronaphthalen-1-yl)oxy)propyl)-11-methyl-5,6,9,11-tetrahydro-4H,8H-pyrazolo[3',4':4,5][1]thia[2,8]diazacycloundecino[6,7,8-hi]indole-2-carboxylate 7,7-dioxide

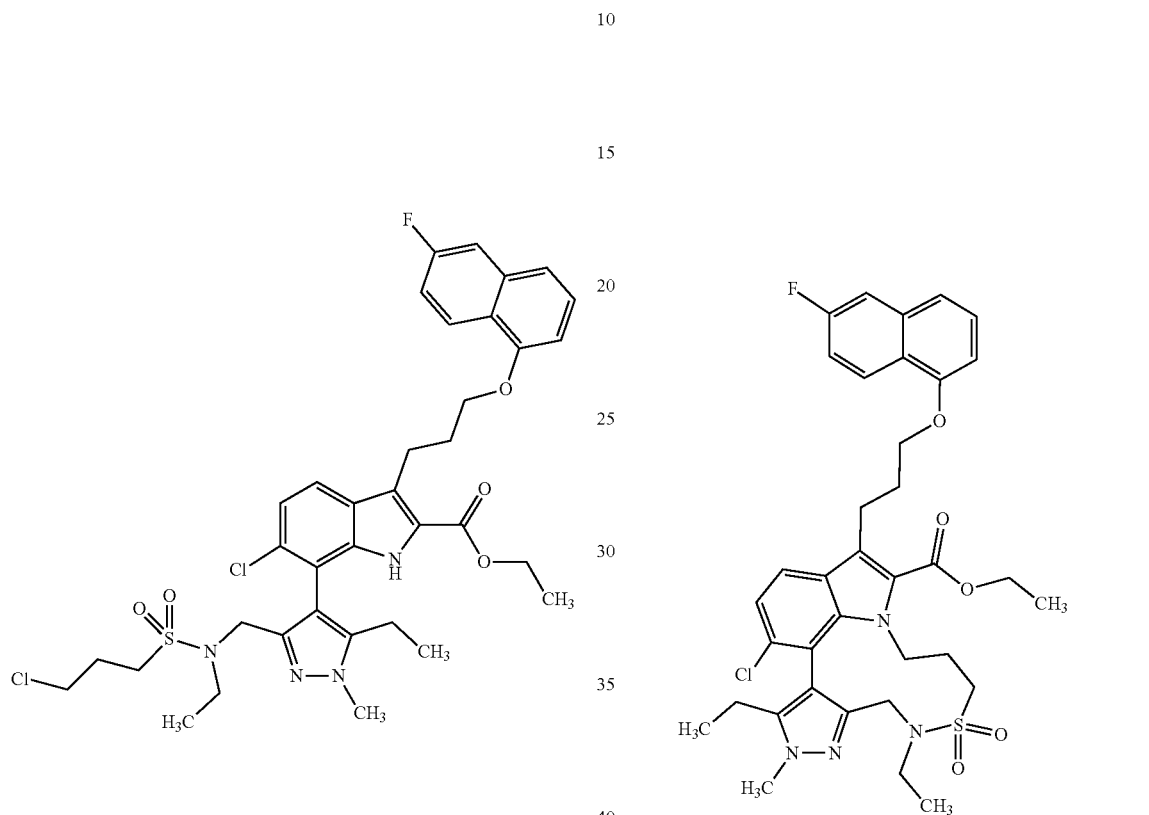

To a solution of ethyl 6-chloro-7-(5-ethyl-3-((ethylamino)methyl)-1-methyl-1H-pyrazol-4-yl)-3-(3-((6-fluoronaphthalen-1-yl)oxy)propyl)-1H-indole-2-carboxylate (Intermediate 127, 727 mg, 1.22 mmol) in dry dichloromethane (6 mL) at 0° C. under nitrogen was added N,N-diisopropylethylamine (424 µL, 2.44 mmol), followed by a solution of 3-chloropropane-1-sulfonyl chloride (258 mg, 1.46 mmol) in 1 mL of dichloromethane. Stirred at 0° C. for 1h before concentrating to give an oil. The residue was purified by flash column chromatography on silica gel (0-100% ethyl acetate/hexanes) to obtain the title compound (825 mg) as a white foam.

LC-MS (Method 4): $R_f$=5.86 min; MS (ESIneg): m/z=730 [M−H]−

$^1$H NMR (300 MHz, Chloroform-d) δ 8.40-8.31 (m, 2H), 7.62-7.57 (m, 1H), 7.45-7.34 (m, 3H), 7.17 (d, 1H), 6.70 (dd, 1H), 4.40-4.26 (m, 3H), 4.21-4.07 (m, 3H), 3.92 (s, 3H), 3.61-3.53 (m, 2H), 3.38 (t, 2H), 3.20-3.11 (m, 2H), 3.08-2.88 (m, 2H), 2.49 (m, 2H), 2.34 (q, 2H), 2.15 (p, 2H), 1.36 (t, 3H), 1.01 (t, 3H), 0.88 (t, 3H).

A mixture of ethyl 6-chloro-7-(3-(((3-chloro-N-ethylpropyl)sulfonamido)methyl)-5-ethyl-1-methyl-1H-pyrazol-4-yl)-3-(3-((6-fluoronaphthalen-1-yl)oxy)propyl)-1H-indole-2-carboxylate (Intermediate 128, 825 mg, 1.12 mmol) and cesium carbonate (1.45 g, 4.48 mmol) in dry acetonitrile (22 mL) were stirred at 60° C. for 2 days. The mixture was cooled, concentrated, and purified by flash column chromatography on silica gel (20-100% ethyl acetate/hexanes) to obtain the title compound (567 mg) as a white solid.

LC-MS (Method 4): $R_f$=5.73 min; MS (ESIpos): m/z=695 [M+H]+

$^1$H NMR (300 MHz, Chloroform-d) δ 8.37 (dd, 1H), 7.62 (d, 1H), 7.47-7.33 (m, 3H), 7.30-7.22 (m, 5H), 7.20 (d, 1H), 6.71 (dd, 1H), 4.54 (dt, 1H), 4.39-4.13 (m, 7H), 3.90 (s, 3H), 3.38 (m, 4H), 2.46 (dd, 1H), 2.35-2.08 (m, 5H), 1.81 (d, 2H), 1.36 (t, 3H), 1.23 (t, 3H), 0.88 (t, 3H).

Intermediate 130

(rac)-ethyl 6-chloro-7-(5-ethyl-3-(1-(rac)-hydroxy-3-(tetrahydro-2H-pyran-4-yl)propyl)-1-methyl-1H-pyrazol-4-yl)-3-(3-((6-fluoronaphthalen-1-yl)oxy)propyl)-1H-indole-2-carboxylate

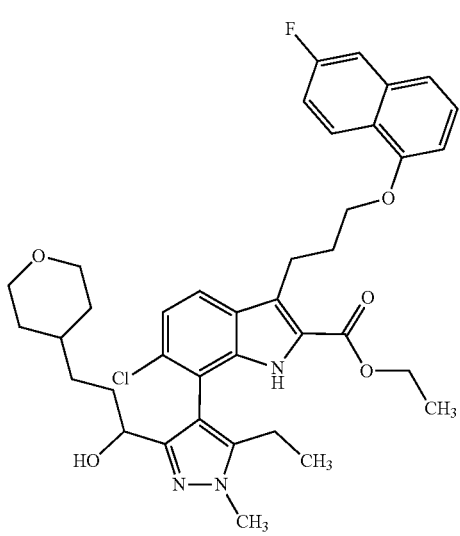

To a solution of (rac)-1-(4-bromo-5-ethyl-1-methyl-1H-pyrazol-3-yl)-3-(oxan-4-yl)propan-1-ol (see Intermediate 150, 1.79 g, 5.43 mmol) in toluene (45 mL) was added ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (Intermediate 98, 2.5 g, 4.53 mmol), potassium phosphate (1.92 g, 9.06 mmol), RuPhos Pd G3 (189 mg, 226 µmol), and water (18 mL). The solution was sparged with nitrogen for 10 min then stirred at 90° C. for 2 h. The mixture was cooled to room temperature, filtered over Celite, and diluted with water. The aqueous phase was extracted three times with ethyl acetate. The combined organic phases were washed with brine, dried over sodium sulfate, filtered, and concentrated. The crude residue was purified by flash chromatography on silica gel (0-20% methanol/dichloromethane) and then re-purified by reverse-phase flash chromatography on C18-silica gel (10-100% acetonitrile/water with 0.1% formic acid) to obtain the title compound (0.976 g) as a 3.7:1 mixture of diastereomers, which was formed as a mixture of two diastereomers as a result of atropisomerism at the newly formed bi-heteroaryl bond.

Diastereomer 1: LC-MS (Method 4): R$_t$=5.34 min; MS (ESIneg): m/z=674 [M−H]$^-$ Diastereomer 2: LC-MS (Method 4): R$_t$=5.43 min; MS (ESIneg): m/z=674 [M−H]$^-$ $^1$H NMR (300 MHz, Chloroform-d) δ 8.75 (d, 1H), 8.34 (dd, 1H), 8.01 (s, 1H), 7.59 (d, 1H), 7.52-7.29 (m, 4H), 7.22-7.10 (m, 2H), 6.72 (dd, 1H), 4.34 (q, 3H), 4.20 (t, 2H), 3.92 (d, 4H), 3.84 (d, 3H), 3.38 (t, 3H), 3.30-3.12 (m, 1H), 2.59-2.40 (m, 2H), 2.33 (t, 2H), 1.79-1.49 (m, 2H), 1.44 (d, 1H), 1.35 (t, 4H), 1.31-1.05 (m, 1H), 1.00 (m, 4H).

Intermediate 131

(rac)-ethyl 6-chloro-7-(5-ethyl-1-methyl-3-(1-(rac)-(methylamino)-3-(tetrahydro-2H-pyran-4-yl)propyl)-1H-pyrazol-4-yl)-3-(3-((6-fluoronaphthalen-1-yl)oxy)propyl)-1H-indole-2-carboxylate (Mixture of Stereoisomers)

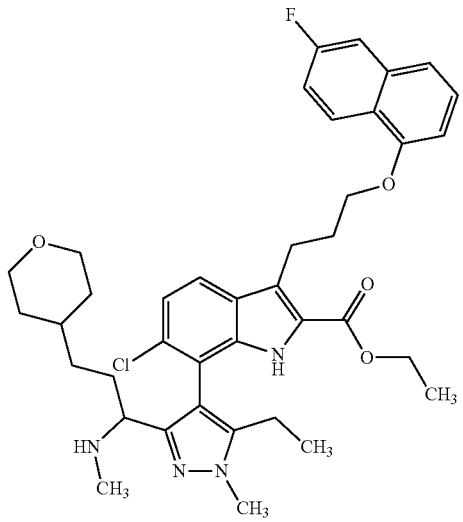

To a solution of (rac)-ethyl 6-chloro-7-(5-ethyl-3-(1-(rac)-hydroxy-3-(tetrahydro-2H-pyran-4-yl)propyl)-1-methyl-1H-pyrazol-4-yl)-3-(3-((6-fluoronaphthalen-1-yl)oxy)propyl)-1H-indole-2-carboxylate (Intermediate 130, 0.5 g, 613 µmol) in dichloromethane (8 mL) at 0° C. under a stream of nitrogen was added N,N-diisopropylethylamine (254 µL, 1.47 mmol), followed by mesyl chloride (84.4 µL, 1.10 mmol). After stirring at 0° C. for 2 h, the mixture was concentrated and the crude oil was dissolved in acetonitrile (2 mL) and added to a solution of methylamine (3.67 mL, 7.35 mmol, 2 M in THF) in acetonitrile (3 mL). The reaction mixture was heated at 60° C. and stirred for 24 h before cooling to room temperature. A solution of 1:1 brine/saturated aqueous sodium bicarbonate was added and the mixture was extracted three times with dichloromethane, dried over sodium sulfate, filtered, and concentrated. The residue was purified by flash chromatography on silica gel (0-20% methanol/dichloromethane) to obtain the title compound (175 mg) as a 1.5:1 mixture of diastereomers.

Diastereomer 1: LC-MS (Method 5): R$_t$=1.46 min; MS (ESIpos): m/z=689 [M+H]$^+$ Diastereomer 2: LC-MS (Method 5): R$_t$=1.48 min; MS (ESIpos): m/z=689 [M+H]$^+$ $^1$H NMR (300 MHz, Chloroform-d) δ 8.35 (dt, 1H), 7.61-7.54 (m, 1H), 7.45-7.29 (m, 3H), 7.25-7.11 (m, 1H), 6.79-6.63 (m, 1H), 4.42-4.29 (m, 1H), 4.20 (q, 2H), 3.90 (d, 4H), 3.78 (d, 1H), 3.58 (s, 1H), 3.38 (q, 2H), 3.28-3.09 (m, 3H), 2.62-2.43 (m, 3H), 2.34 (d, 3H), 1.54 (s, 9H), 1.35 (m, 3H), 1.29-1.04 (m, 1H), 0.98 (q, 3H).

Intermediate 132

(rac)-ethyl 6-chloro-7-(3-(1-(rac)-((3-chloro-N-methylpropyl)sulfonamido)-3-(tetrahydro-2H-pyran-4-yl)propyl)-5-ethyl-1-methyl-1H-pyrazol-4-yl)-3-(3-((6-fluoronaphthalen-1-yl)oxy)propyl)-1H-indole-2-carboxylate (Mixture of Stereoisomers)

To a solution of ethyl 6-chloro-7-(5-ethyl-1-methyl-3-(1-(methylamino)-3-(tetrahydro-2H-pyran-4-yl)propyl)-1H-pyrazol-4-yl)-3-(3-((6-fluoronaphthalen-1-yl)oxy)propyl)-1H-indole-2-carboxylate (Intermediate 131, 0.33 g, 478 μmol) in dry dichloromethane (2.5 mL) at 0° C. was added N,N-diisopropylethylamine (165 μL, 956 μmol), followed by 3-chloropropane-1-sulfonyl chloride (86.5 μL, 717 μmol). After stirring for 2 h, the reaction mixture was concentrated and purified by flash column chromatography on silica gel (0-100% ethyl acetate/hexanes) to obtain the title compound (0.286 g) as a 1.5:1 mixture of diastereoisomers.

Diastereomer 1: LC-MS (Method 4): R$_t$=5.92 min; MS (ESIneg): m/z=828 [M–H]$^-$ Diastereomer 2: LC-MS (Method 4): R$_t$=5.99 min; MS (ESIneg): m/z=828 [M–H]$^-$ $^1$H NMR (300 MHz, Chloroform-d) δ 8.43 (s, 1H), 8.40-8.28 (m, 3H), 7.60 (dd, 2H), 7.47-7.30 (m, 7H), 7.25-7.07 (m, 3H), 6.72 (dd, 2H), 4.66 (dd, 1H), 4.61-4.52 (m, 1H), 4.35 (m, 5H), 4.20 (m, 5H), 3.91 (d, 7H), 3.83 (t, 6H), 3.63-3.13 (m, 8H), 2.92-2.87 (m, 1H), 2.85 (d, 7H), 2.78-2.58 (m, 1H), 2.58-2.40 (m, 4H), 2.40-2.23 (m, 6H), 2.06 (m, 2H), 1.92 (dt, 2H), 1.81 (dd, 3H), 1.43 (d, 1H), 1.40-1.30 (m, 7H), 1.30-1.05 (m, 6H), 1.01 (m, 7H).

Intermediate 133

(rac)-ethyl 13-chloro-12-ethyl-1-(3-((6-fluoronaphthalen-1-yl)oxy)propyl)-8,11-dimethyl-9-(2-(tetrahydro-2H-pyran-4-yl)ethyl)-5,6,9,11-tetrahydro-4H,8H-pyrazolo[3',4':4,5][1]thia[2,8]diazacycloundecino[6,7,8-hi]indole-2-carboxylate 7,7-dioxide-(Racemic Mixture)

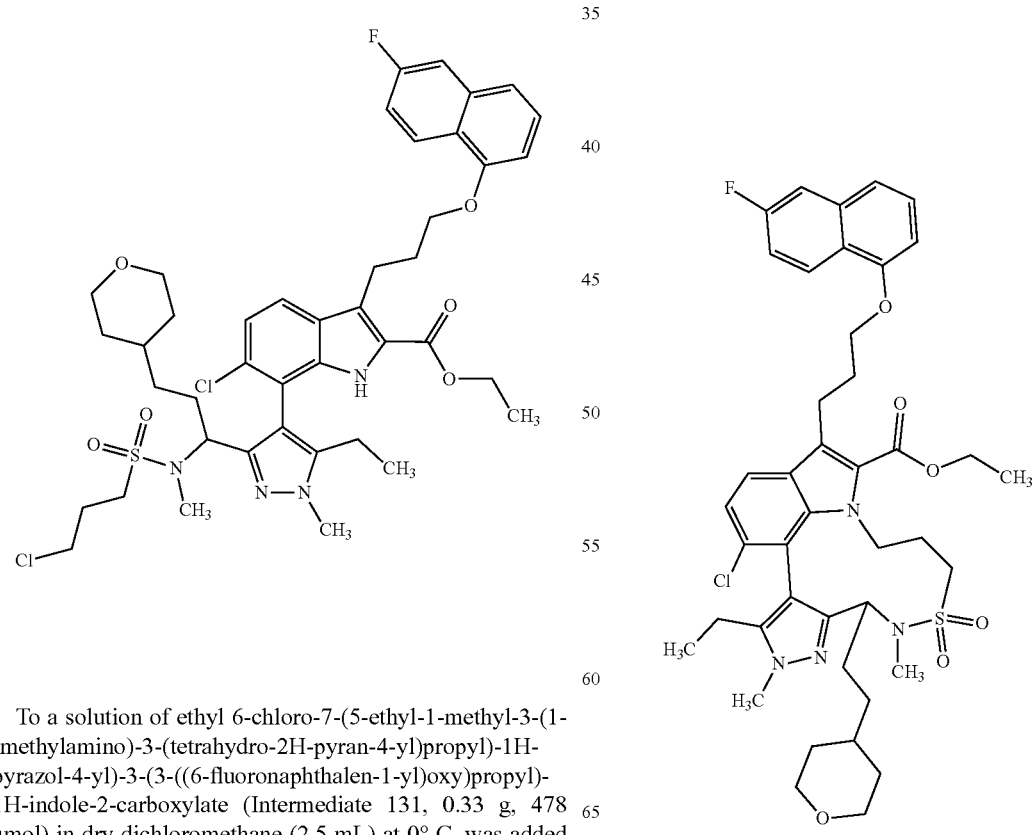

Intermediate 134

(rac)-ethyl 13-chloro-12-ethyl-1-(3-((6-fluoronaphthalen-1-yl)oxy)propyl)-8,11-dimethyl-9-(2-(tetrahydro-2H-pyran-4-yl)ethyl)-5,6,9,11-tetrahydro-4H,8H-pyrazolo[3',4':4,5][1]thia[2,8]diazacycloundecino[6,7,8-hi]indole-2-carboxylate 7,7-dioxide-(Racemic Mixture)

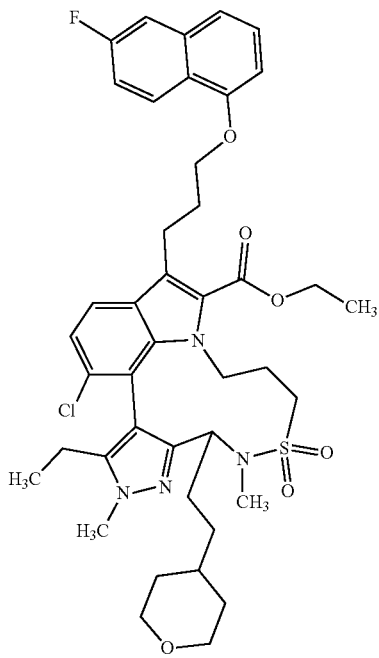 [SMILES: CCOC(=O)c1c(CCCOc2cccc3cc(F)ccc23)c2ccc(Cl)c3c2n1CCCS(=O)(=O)N(C)C(CCC1CCOCC1)c1nn(C)c(CC)c1-3]

To a solution of ethyl 6-chloro-7-(3-(14(3-chloro-N-methylpropyl)sulfonamido)-3-(tetrahydro-2H-pyran-4-yl)propyl)-5-ethyl-1-methyl-1H-pyrazol-4-yl)-3-(3-((6-fluoronaphthalen-1-yl)oxy)propyl)-1H-indole-2-carboxylate (Intermediate 132, 0.4 g, 482 µmol) in acetonitrile (14 mL) was added cesium carbonate (625 mg, 1.92 mmol) and the mixture was heated at 60° C. and stirred for 2 days. The mixture was cooled to room temperature and adsorbed onto Celite. The crude residue was purified by flash column chromatography on silica gel (0-10% methanol/dichloromethane) to obtain, in order of elution, Intermediate 133 (123 mg) and Intermediate 134 (173 mg).

Intermediate 133: LC-MS (Method 4): $R_t$=5.89 min; MS (ESIpos): m/z=794 [M+H]$^+$ $^1$H NMR (300 MHz, Chloroform-d) δ 8.36 (dd, 1H), 7.62 (d, 1H), 7.52-7.35 (m, 2H), 7.26 (s, 9H), 6.72 (dd, 1H), 4.56-4.44 (m, 2H), 4.33 (m, 2H), 4.26-4.06 (m, 2H), 3.91 (s, 4H), 3.46-3.22 (m, 3H), 3.01 (s, 3H), 2.61-2.46 (m, 1H), 2.27 (d, 2H), 2.25-2.11 (m, 2H), 2.00 (dd, 2H), 1.84 (d, 2H), 1.62 (d, 2H), 1.54 (s, 4H), 1.41-1.18 (m, 7H), 0.86 (t, 3H).

Intermediate 134: LC-MS (Method 4): $R_t$=5.89 min; MS (ESIpos): m/z=794 [M+H]$^+$ $^1$H NMR (300 MHz, Chloroform-d) δ 8.37 (dd, 1H), 7.62 (d, 1H), 7.46-7.32 (m, 3H), 7.26 (s, 10H), 7.16 (d, 1H), 6.72-6.62 (m, 1H), 5.28 (dd, 1H), 4.40-4.25 (m, 3H), 4.25-4.09 (m, 3H), 3.93 (d, 3H), 3.87 (s, 4H), 3.46-3.21 (m, 4H), 2.76-2.60 (m, 1H), 2.25 (dd, 5H), 1.87 (s, 3H), 1.59 (d, 2H), 1.36 (t, 3H), 1.28 (d, 6H), 0.91 (t, 3H).

Intermediate 135 ethyl 6-chloro-7-(5-ethyl-3-(((4-methoxybenzyl)amino)methyl)-1-methyl-1H-pyrazol-4-yl)-3-(3-((6-fluoronaphthalen-1-yl)oxy)propyl)-1H-indole-2-carboxylate

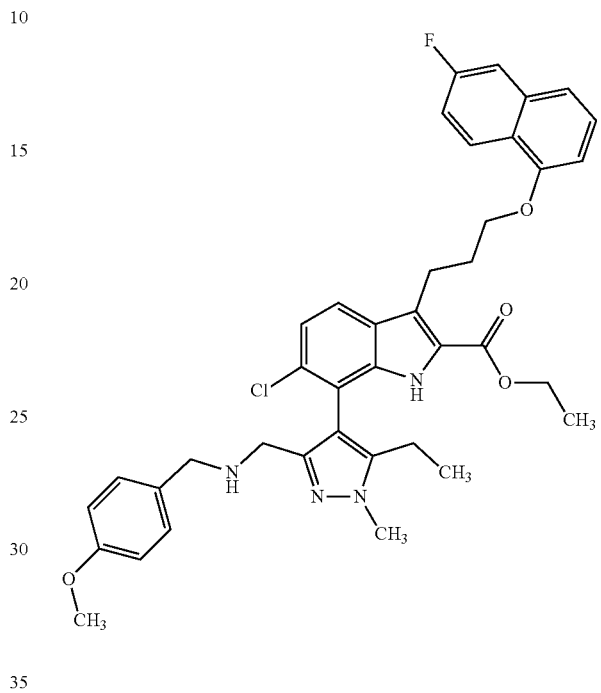

To a 0° C. stirred solution of ethyl 6-chloro-7-(5-ethyl-3-(hydroxymethyl)-1-methyl-1H-pyrazol-4-yl)-3-(3-((6-fluoronaphthalen-1-yl)oxy)propyl)-1H-indole-2-carboxylate (Intermediate 122, 1.75 g, 3.10 mmol) in anhydrous dichloromethane (30 mL), under a stream of nitrogen, was added N,N-diisopropylethylamine (1.07 mL, 6.20 mmol), followed by dropwise addition of mesyl chloride (311 µL, 4.03 mmol). The resulting mixture was stirred at 0° C. for 2 h, then warmed to room temperature, stirred overnight, and concentrated. The crude residue was re-dissolved in acetonitrile (15 mL), and added dropwise to a solution of 1-(4-methoxyphenyl)methanamine (4.12 mL, 31.0 mmol) in acetonitrile (15 mL) at 0° C. The resulting mixture was warmed to 50° C. and stirred for 2h. The mixture was concentrated, then diluted with ethyl acetate and washed with 1:1 saturated sodium bicarbonate/brine mixture. The organic phase was dried over sodium sulfate, filtered, and concentrated. The crude residue was purified by flash column chromatography on silica gel (0-20% 7 N ammonia in methanol/dichloromethane) to give the title compound (2.0 g) as a foam.

LC-MS (Method 4): $R_t$=4.14 min; MS (ESIneg): m/z=681 [M−H]$^−$ $^1$H NMR (300 MHz, Chloroform-d) δ 10.25 (s, 1H), 8.33 (dd, 1H), 7.57 (d, 1H), 7.41 (dd, 1H), 7.38-7.30 (m, 2H), 7.29-7.19 (m, 4H), 7.16 (d, 1H), 7.04 (d, 2H), 6.78-6.66 (m, 3H), 4.38-4.24 (m, 2H), 4.20 (t, 2H), 3.89 (s, 2H), 3.74 (s, 3H), 3.71-3.50 (m, 3H), 3.49 (s, 3H), 3.40 (t, 2H), 3.29 (d, 1H), 2.52 (ddq, 2H), 2.35 (p, 2H), 1.33 (t, 3H), 0.99 (t, 3H).

Intermediate 136 ethyl 6-chloro-7-(3-(((3-chloro-N-(4-methoxybenzyl)propyl)sulfonamido)methyl)-5-ethyl-1-methyl-1H-pyrazol-4-yl)-3-(3-((6-fluoronaphthalen-1-yl)oxy)propyl)-1H-indole-2-carboxylate

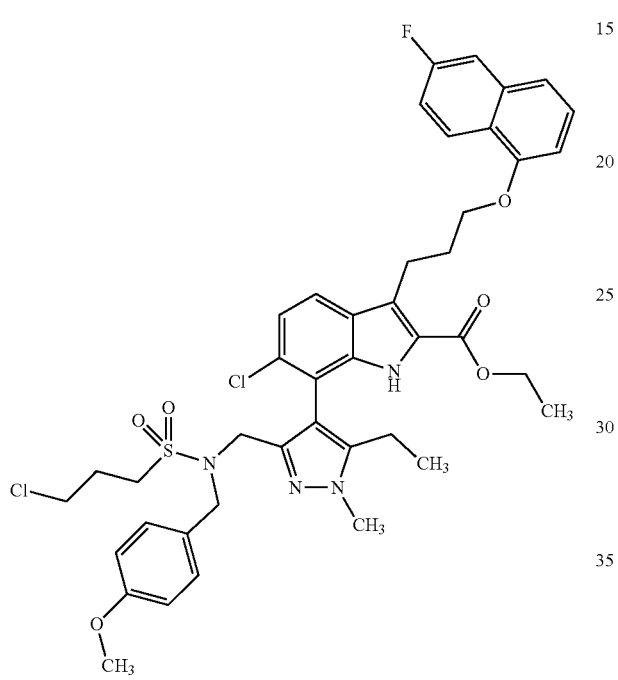

To a solution of ethyl 6-chloro-7-(5-ethyl-3-(((4-methoxybenzyl)amino)methyl)-1-methyl-1H-pyrazol-4-yl)-3-(3-((6-fluoronaphthalen-1-yl)oxy)propyl)-1H-indole-2-carboxylate (Intermediate 135, 1.9 g, 2.78 mmol) in dry dichloromethane (30 mL) at 0° C. was added 3-chloropropane-1-sulfonyl chloride (472 µL, 3.89 mmol), followed by N,N-diisopropylethylamine (967 µL, 5.56 mmol). The mixture was stirred for 1h at 0° C., then adsorbed onto Celite and purified by flash column chromatography on silica gel (20-70% ethyl acetate/hexanes) to obtain the title compound (1.58 g).

LC-MS (Method 4): $R_t$=6.16 min; MS (ESIneg): m/z=821 [M−H]⁻

¹H NMR (300 MHz, Chloroform-d) δ 8.42-8.31 (m, 2H), 7.60 (dd, 1H), 7.42 (dd, 1H), 7.38-7.33 (m, 2H), 7.25 (ddd, 6H), 7.17 (d, 1H), 6.94-6.87 (m, 2H), 6.71 (dd, 1H), 6.67-6.61 (m, 2H), 4.35 (q, 2H), 4.23-4.02 (m, 6H), 3.95 (s, 3H), 3.70 (s, 3H), 3.61 (td, 2H), 3.37 (t, 2H), 3.26-3.08 (m, 2H), 2.50 (ddt, 2H), 2.33 (p, 2H), 2.21 (p, 2H), 1.35 (t, 3H), 1.01 (t, 3H).

Intermediate 137

(rac)-methyl 13-chloro-12-ethyl-1-(3-((6-fluoronaphthalen-1-yl)oxy)propyl)-8-(4-methoxybenzyl)-11-methyl-5,6,9,11-tetrahydro-4H,8H-pyrazolo[3',4':4,5][1]thia[2,8]diazacycloundecino[6,7,8-hi]indole-2-carboxylate 7,7-dioxide

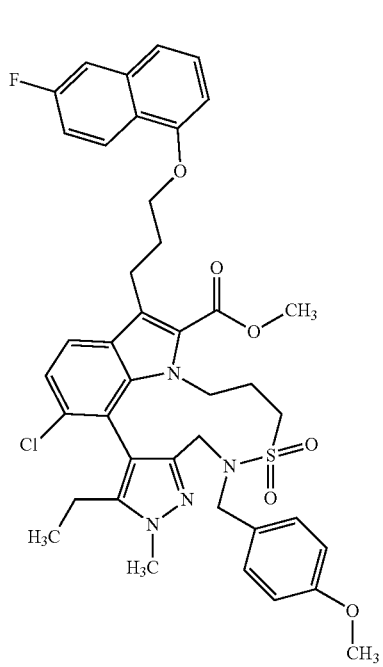 [SMILES: CCc1c2c(nn1C)CN(Cc1ccc(OC)cc1)S(=O)(=O)CCCn1c(C(=O)OC)c(CCCOc3cccc4cc(F)ccc34)c3ccc(Cl)c-2c31]

A mixture of ethyl 6-chloro-7-(3-(((3-chloro-N-(4-methoxybenzyl)propyl)sulfonamido)methyl)-5-ethyl-1-methyl-1H-pyrazol-4-yl)-3-(3-((6-fluoronaphthalen-1-yl)oxy)propyl)-1H-indole-2-carboxylate (Intermediate 136, 1.53 g, 1.85 mmol) and cesium carbonate (2.41 g, 7.40 mmol) in dry acetonitrile (37 mL) was stirred at 50° C. for 3 days. After cooling to room temperature, the mixture was concentrated, re-dissolved in methanol, and adsorbed onto Celite. The residue was purified by flash column chromatography on silica gel (0-100% ethyl acetate/hexanes) to obtain the title compound (800 mg), predominantly as the methyl ester (94%).

LC-MS (Method 4): $R_t$=5.93 min; MS (ESIpos): m/z=773 [M+H]⁺

¹H NMR (300 MHz, Chloroform-d) δ 8.37 (dd, 1H), 7.64 (d, 1H), 7.50-7.34 (m, 5H), 7.30-7.24 (m, 8H), 7.22 (d, 1H), 6.89 (d, 2H), 6.70 (dd, 1H), 4.58 (d, 1H), 4.47-4.33 (m, 2H), 4.18 (t, 2H), 4.08 (s, 2H), 3.95 (s, 3H), 3.81 (d, 6H), 3.43-3.26 (m, 2H), 2.52 (dd, 1H), 2.35-2.18 (m, 5H), 1.81 (d, 2H), 0.90 (t, 3H).

Intermediate 138

(rac)-methyl 13-chloro-12-ethyl-1-(3-((6-fluoronaphthalen-1-yl)oxy)propyl)-11-methyl-5,6,9,11-tetrahydro-4H,8H-pyrazolo[3',4':4,5][1]thia[2,8]diazacycloundecino[6,7,8-hi]indole-2-carboxylate 7,7-dioxide

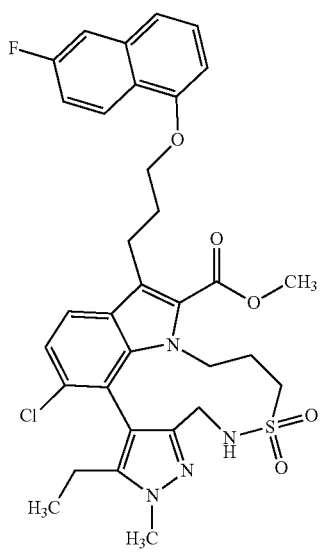 [SMILES: CCc1c2c(nn1C)CNS(=O)(=O)CCCn1c(C(=O)OC)c(CCCOc3cccc4cc(F)ccc34)c3ccc(Cl)c-2c31]

To a solution of (rac)-methyl 13-chloro-12-ethyl-1-(3-((6-fluoronaphthalen-1-yl)oxy)propyl)-8-(4-methoxybenzyl)-11-methyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 137, 800 mg, 1.03 mmol) in 5:1 dichloromethane/trifluoroacetic acid (20 mL) was added anisole (668 mg, 6.18 mmol) under a stream of nitrogen. The mixture was stirred for 3 days at reflux then concentrated. The crude residue was purified by flash column chromatography (0-100% ethyl acetate/hexanes) and re-purified by reverse phase column chromatography on C18-silica gel (50-100% acetonitril/water with 0.1% formic acid) to obtain the title compound (270 mg) as a white solid.

LC-MS (Method 4): $R_t$=4.72 min; MS (ESIpos): m/z=655 [M+H]$^+$ $^1$H NMR (300 MHz, Chloroform-d) δ 8.37 (dd, 1H), 7.65 (d, 1H), 7.46-7.34 (m, 3H), 7.30-7.19 (m, 7H), 6.73 (dd, 1H), 4.67-4.52 (m, 2H), 4.39 (dd, 1H), 4.19 (t, 2H), 4.07 (dd, 2H), 3.90 (s, 3H), 3.81 (s, 3H), 3.33 (hept, 2H), 2.47 (ddd, 1H), 2.28 (dq, 5H), 1.94 (s, 1H), 1.77 (s, 1H), 0.90 (t, 3H).

Intermediate 139

(rac)-ethyl 6-chloro-7-(5-ethyl-3-(1-(rac)-hydroxy-3-morpholinopropyl)-1-methyl-1H-pyrazol-4-yl)-3-(3-((6-fluoronaphthalen-1-yl)oxy)propyl)-1H-indole-2-carboxylate (Mixture of Isomers)

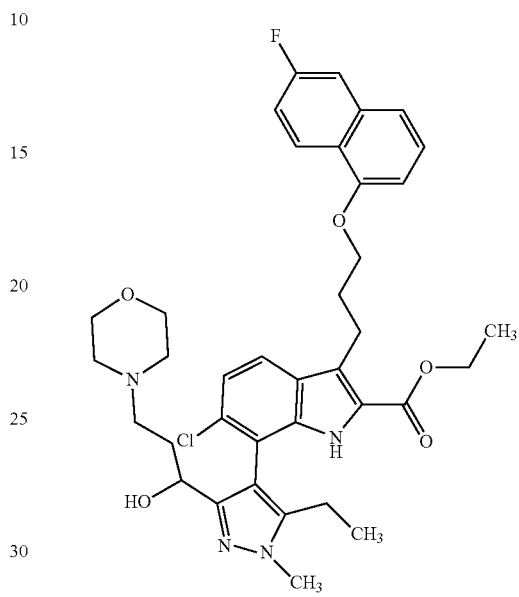

A 150-mL pressure vessel equipped with a stir bar was charged with ethyl 6-chloro-3-{3-[(6-fluoronaphthalen-1-yl)oxy]propyl}-7-(4,4,5,5-tetramethyl-1,3,2-dioxaborolan-2-yl)-1H-indole-2-carboxylate (Intermediate 98, 1.6 g, 2.89 mmol), 1-(4-bromo-5-ethyl-1-methyl-1H-pyrazol-3-yl)-3-(morpholin-4-yl)propan-1-ol (see Intermediate 96, 1.24 g, 3.75 mmol), potassium phosphate (1.22 g, 5.78 mmol), dioxane (40 mL) and water (8 mL). The mixture was degassed via argon sparging for 10 min before adding RuPhos Pd G3 (120 mg, 144 µmol). The vessel was sealed and placed into a pre-heated aluminum block at 180° C. and the reaction was gradually cooled to 110° C. After stirring for 2 h, the mixture was cooled to room temperature and filtered over a pad of Celite. The mixture was diluted with water and extracted three times with ethyl acetate. The combined organic phases were washed with brine, dried over sodium sulfate, filtered, and concentrated. The crude residue was purified by flash chromatography on silica gel (0-10% methanol/dichloromethane) and re-purified by reverse-phase chromatography on C18-silica (10-100% acetonitrile/water with 0.1% formic acid) to obtain the title compound (0.608 g) as a 1:3 mixture of isomers, which was formed as a mixture of two diastereomers as a result of atropisomerism at the newly formed bi-heteroaryl bond.

LC-MS (Method 5): Rt=1.47 min; MS (ESIpos): m/z=678 [M+H]$^+$ $^1$H NMR (Chloroform-d) δ: 9.38 (s, 1H), 9.16 (s, 3H), 8.35 (ddd, 3H), 7.58 (dd, 3H), 7.44-7.32 (m, 2H), 7.25-7.21 (m, 3H), 7.16 (dd, 3H), 6.72 (dt, 3H), 4.88 (dd, 1H), 4.56 (dd, 3H), 4.34 (m, 5H), 4.21 (t, 5H), 3.92 (d, 8H), 3.69 (t, 10H), 3.57-3.44 (m, 3H), 3.39 (m, 5H), 2.80-2.68 (m, 5H), 2.69-2.58 (m, 3H), 2.47 (m, 10H), 2.34 (p, 5H), 2.24 (m, 4H), 1.89-1.78 (m, 3H), 1.35 (m, 7H), 0.97 (m, 7H).

Intermediate 140

(rac)-ethyl 6-chloro-7-(5-ethyl-1-methyl-3-(1-(rac)-(methylamino)-3-morpholinopropyl)-1H-pyrazol-4-yl)-3-(3-((6-fluoronaphthalen-1-yl)oxy)propyl)-1H-indole-2-carboxylate

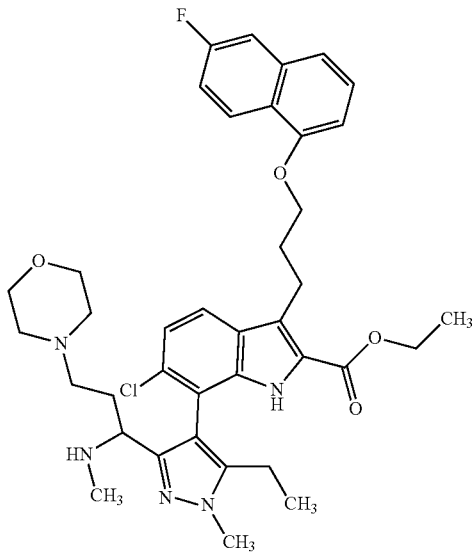 [SMILES: CCOC(=O)c1[nH]c2c(-c3c(C(CCN4CCOCC4)NC)nn(C)c3CC)c(Cl)ccc2c1CCCOc1cccc2cc(F)ccc12]

For the preparation of the title compound see Intermediate 141.

Intermediate 141

(rac)-ethyl 6-chloro-7-(5-ethyl-1-methyl-3-(3-(methylamino)-1-(rac)-morpholinopropyl)-1H-pyrazol-4-yl)-3-(3-((6-fluoronaphthalen-1-yl)oxy)propyl)-1H-indole-2-carboxylate

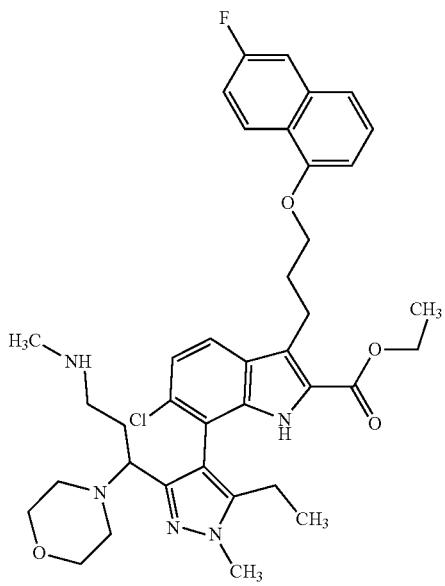 [SMILES: CCOC(=O)c1[nH]c2c(-c3c(C(CCNC)N4CCOCC4)nn(C)c3CC)c(Cl)ccc2c1CCCOc1cccc2cc(F)ccc12]

To a solution of ethyl 6-chloro-7-(5-ethyl-3-(1-hydroxy-3-morpholinopropyl)-1-methyl-1H-pyrazol-4-yl)-3-(3-((6-fluoronaphthalen-1-yl)oxy)propyl)-1H-indole-2-carboxylate (Intermediate 139, 0.72 g, 1.06 mmol) in dichloromethane (13 mL) at 0° C. under a stream of nitrogen was added N,N-diisopropylethylamine (553 μL, 3.18 mmol), followed by mesyl chloride (100 μL, 1.27 mmol). After stirring at 0° C. for 2 h, the mixture was washed with 1:1 saturated aqueous sodium bicarbonate/brine solution. The organic phase was separated, dried over sodium sulfate, filtered, and concentrated. The crude residue was suspended in acetonitrile (13 mL) and treated with methylamine (6.35 mL, 12.7 mmol, 2 M in THF). The reaction mixture was heated at 50° C. and stirred for 24 h. The mixture was cooled, concentrated, and purified by flash chromatography on silica gel (0-10% basic methanol/dichloromethane) to obtain, Intermediate 140 (0.316 g) and Intermediate 141 (0.248 g).

Intermediate 140: LC-MS (Method 3): $R_t$=1.33 min; MS (ESIpos): m/z=690 [M+H]$^+$ $^1$H NMR (Chloroform-d) δ: 8.35 (dt, 1H), 7.61-7.50 (m, 1H), 7.46-7.32 (m, 3H), 7.15 (dd, 1H), 6.71 (d, 1H), 4.35 (p, 2H), 4.20 (q, 2H), 3.89 (d, 3H), 3.65 (t, 1H), 3.52 (dt, 4H), 3.43-3.32 (m, 2H), 2.64-2.41 (m, 3H), 2.41-2.15 (m, 5H), 2.06 (m, 2H), 1.54 (s, 32H), 1.41-1.31 (m, 3H), 1.05-0.86 (m, 4H).

Intermediate 141: LC-MS (Method 3): $R_t$=1.40 min; MS (ESIpos): m/z=690 [M+H]$^+$ $^1$H NMR (Chloroform-d) δ: 8.34 (td, 5H), 7.57 (dd, 4H), 7.45-7.31 (m, 14H), 7.25-7.20 (m, 3H), 7.15 (dd, 4H), 6.70 (td, 5H), 4.40-4.29 (m, 9H), 4.25-4.14 (m, 9H), 3.91 (s, 13H), 3.63-3.49 (m, 13H), 3.43-3.30 (m, 11H), 3.22 (dd, 1H), 2.91-2.77 (m, 4H), 2.68 (tt, 5H), 2.61-2.37 (m, 8H), 2.37-2.27 (m, 10H), 2.21 (s, 20H), 2.09-1.99 (m, 1H), 1.88-1.78 (m, 4H), 1.36 (td, 13H), 0.98 (td, 14H).

Intermediate 142

(rac)-ethyl 6-chloro-7-(3-(1-(rac)-((3-chloro-N-methylpropyl)sulfonamido)-3-morpholinopropyl)-5-ethyl-1-methyl-1H-pyrazol-4-yl)-3-(3-((6-fluoronaphthalen-1-yl)oxy)propyl)-1H-indole-2-carboxylate (Mixture of Stereoisomers)

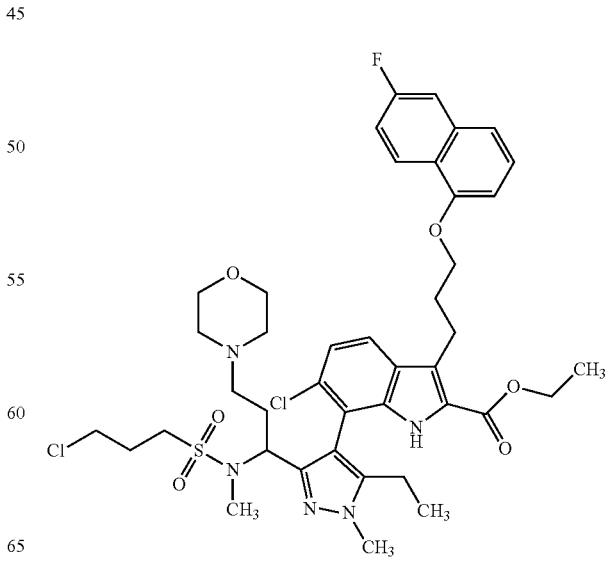

To a solution of ethyl 6-chloro-7-(5-ethyl-1-methyl-3-(1-(methylamino)-3-morpholinopropyl)-1H-pyrazol-4-yl)-3-(3-((6-fluoronaphthalen-1-yl)oxy)propyl)-1H-indole-2-carboxylate (Intermediate 140, 0.66 g, 956 µmol) in dry dichloromethane (5 mL) at 0° C. was added N,N-diisopropylethylamine (330 µL, 1.91 mmol), followed by 3-chloropropane-1-sulfonyl chloride (140 µL, 1.14 mmol). After stirring for 2 h, the reaction mixture was concentrated and purified by flash column chromatography on silica gel (60-100% ethyl acetate/hexanes) to obtain the title compound (0.736 g) as a 1.3:1 mixture of diastereomers.

Diastereomer 1: LC-MS (Method 7): $R_t$=3.07 min; MS (ESIpos): m/z=832 [M+H]$^+$ Diastereomer 2: LC-MS (Method 7): $R_t$=3.15 min; MS (ESIpos): m/z=832 [M+H]$^+$ $^1$H NMR (400 MHz, Chloroform-d) δ 8.55 (s, 1H), 8.35 (ddd, 1H), 7.64-7.56 (m, 1H), 7.46-7.30 (m, 3H), 7.23 (s, 1H), 7.23-7.13 (m, 1H), 6.76-6.67 (m, 1H), 4.77 (d, 1H), 4.41-4.29 (m, 2H), 4.20 (q, 2H), 3.91 (d, 3H), 3.63-3.21 (m, 7H), 2.86 (d, 4H), 2.60-2.39 (m, 3H), 2.39-2.23 (m, 4H), 2.20-1.78 (m, 5H), 1.36 (td, 3H), 1.00 (q, 3H).

Intermediate 143

(rac)-ethyl 13-chloro-12-ethyl-1-(3-((6-fluoronaphthalen-1-yl)oxy)propyl)-8,11-dimethyl-9-(rac)-(2-morpholinoethyl)-5,6,9,11-tetrahydro-4H,8H-pyrazolo[3',4':4,5][1]thia[2,8]diazacycloundecino[6,7,8-hi]indole-2-carboxylate 7,7-dioxide (Mixture of Stereoisomers)

To a solution of ethyl 6-chloro-7-(3-(1-((3-chloro-N-methylpropyl)sulfonamido)-3-morpholinopropyl)-5-ethyl-1-methyl-1H-pyrazol-4-yl)-3-(3-((6-fluoronaphthalen-1-yl)oxy)propyl)-1H-indole-2-carboxylate (Intermediate 142, 0.7 g, 841 µmol) in acetonitrile (17 mL) was added cesium carbonate (1.09 g, 3.36 mmol) and the mixture was heated at 60° C. and stirred for 2 days. The mixture was cooled to room temperature and adsorbed onto Celite. The crude residue was purified by flash column chromatography on silica gel (0-10% methanol/dichloromethane) to obtain the title compound (0.3 g) as a mixture of diastereomers.

LC-MS (Method 3): $R_t$=1.51 min; MS (ESIpos): m/z=794 [M+H]$^+$ $^1$H NMR (400 MHz, Chloroform-d) δ 8.37 (ddd, 3H), 7.62 (dd, 3H), 7.45-7.32 (m, 9H), 7.26 (s, 21H), 7.18 (dd, 3H), 6.76-6.67 (m, 3H), 5.42 (dd, 1H), 4.85-4.75 (m, 1H), 4.61 (t, 2H), 4.49 (d, 1H), 4.44-4.24 (m, 6H), 4.18 (t, 5H), 4.03-3.79 (m, 10H), 3.70 (dd, 7H), 3.67-3.22 (m, 10H), 3.02 (s, 5H), 2.59-2.37 (m, 19H), 2.32 (dd, 3H), 2.25-2.12 (m, 5H), 2.08-1.97 (m, 2H), 1.91 (s, 3H), 1.81 (s, 3H), 1.36 (td, 10H), 1.03 (t, 2H), 0.88 (dt, 7H).

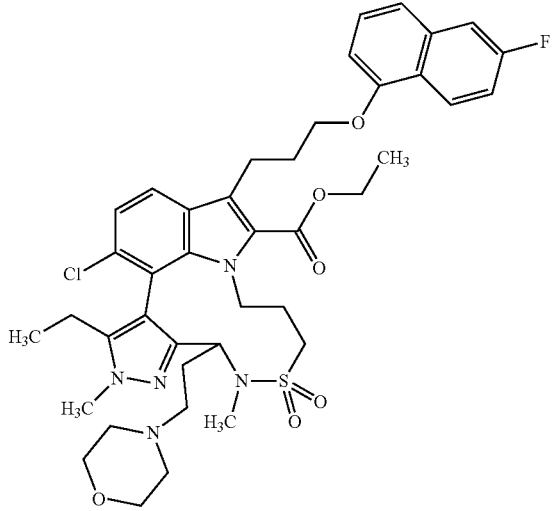 [SMILES: CCOC(=O)c1c(CCCOc2cccc3cc(F)ccc23)c2ccc(Cl)c3c2n1CCCS(=O)(=O)N(C)C(CCN1CCOCC1)c1nn(C)c(CC)c1-3]

Intermediate 144

(rac)-ethyl 6-chloro-7-(3-(3-((3-chloro-N-methylpropyl)sulfonamido)-1-(rac)morpholinopropyl)-5-ethyl-1-methyl-1H-pyrazol-4-yl)-3-(3-((6-fluoronaphthalen-1-yl)oxy)propyl)-1H-indole-2-carboxylate (Mixture of Stereoisomers)

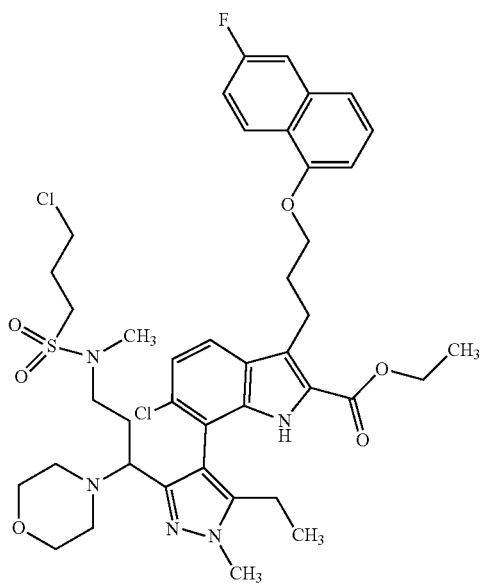 [SMILES: CCOC(=O)c1[nH]c2c(-c3c(C(CCN(C)S(=O)(=O)CCCCl)N4CCOCC4)nn(C)c3CC)c(Cl)ccc2c1CCCOc1cccc2cc(F)ccc12]

To a solution of ethyl 6-chloro-7-(5-ethyl-1-methyl-3-(3-(methylamino)-1-morpholinopropyl)-1H-pyrazol-4-yl)-3-(3-((6-fluoronaphthalen-1-yl)oxy)propyl)-1H-indole-2-carboxylate (Intermediate 141, 0.64 g, 927 μmol) in dry dichloromethane (5 mL) at 0° C. was added N,N-diisopropylethylamine (322 μL, 1.85 mmol), followed by 3-chloropropane-1-sulfonyl chloride (134 μL, 1.11 mmol). After stirring for 30 min, the reaction mixture was concentrated and purified by flash column chromatography on silica gel (0-100% acetone/dichloromethane) to obtain the title compound (0.57 g) as a mixture of diastereomers.

LC-MS (Method 5): $R_t$=1.56 min; MS (ESIpos): m/z=832 [M+H]$^+$ $^1$H NMR (400 MHz, Chloroform-d) δ 8.89 (s, 1H), 8.68 (s, 4H), 8.35 (dd, 5H), 7.58 (dd, 5H), 7.45-7.32 (m, 16H), 7.24-7.20 (m, 1H), 7.16 (dd, 5H), 6.71 (dd, 5H), 4.34 (qq, 9H), 4.19 (t, 10H), 3.91 (d, 15H), 3.63 (t, 10H), 3.61-3.46 (m, 15H), 3.37 (m, 8H), 3.33-3.15 (m, 8H), 3.15-2.94 (m, 12H), 2.82 (s, 3H), 2.73 (s, 12H), 2.63-2.46 (m, 8H), 2.46-2.39 (m, 4H), 2.35 (q, 8H), 2.29-2.13 (m, 19H), 2.04 (s, 8H), 1.36 (td, 15H), 1.00 (q, 15H).

Intermediate 145

(rac)-ethyl 15-chloro-14-ethyl-1-(3-((6-fluoronaphthalen-1-yl)oxy)propyl)-8,13-dimethyl-11-(rac)-morpholino-5,6,9,10,11,13-hexahydro-4H,8H-pyrazolo[3',4':6,7][1]thia[2,10]diazacyclotridecino[8,9,10-hi]indole-2-carboxylate 7,7-dioxide (Mixture of Stereoisomers)

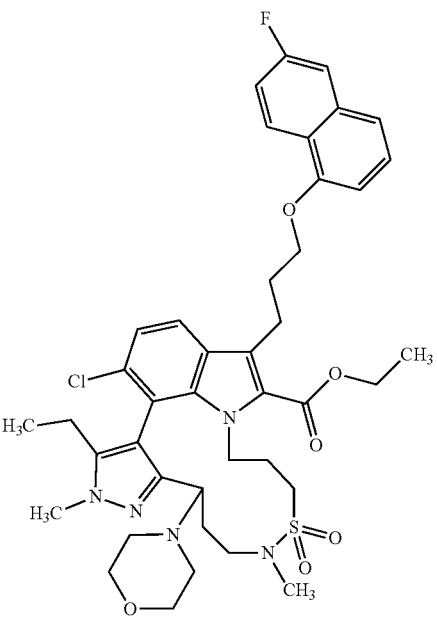 [SMILES: CCOC(=O)c1c(CCCOc2cccc3cc(F)ccc23)c2ccc(Cl)c3c2n1CCCS(=O)(=O)N(C)CCC(N1CCOCC1)c1nn(C)c(CC)c1-3]

To a solution of ethyl 6-chloro-7-(3-(3-((3-chloro-N-methylpropyl)sulfonamido)-1-morpholinopropyl)-5-ethyl-1-methyl-1H-pyrazol-4-yl)-3-(3-((6-fluoronaphthalen-1-yl)oxy)propyl)-1H-indole-2-carboxylate (Intermediate 144, 0.57 g, 684 μmol) in acetonitrile (14 mL) was added cesium carbonate (889 mg, 2.73 mmol) and the mixture was heated at 60° C. and stirred for 2 days. The mixture was cooled to room temperature and adsorbed onto Celite. The crude residue was purified by flash column chromatography on silica gel (0-10% methanol/dichloromethane) to obtain the title compound (0.547 g) as a mixture of diastereomers.

LC-MS (Method 5): $R_t$=1.68 min; MS (ESIpos): m/z=796 [M+H]$^+$ $^1$H NMR (Chloroform-d) δ: 8.35 (dd, 2H), 7.59 (dd, 2H), 7.48-7.32 (m, 5H), 7.26 (s, 12H), 7.18 (d, 1H), 6.71 (dd, 2H), 4.64-4.52 (m, 1H), 4.36 (qd, 3H), 4.19 (t, 4H), 4.01-3.87 (m, 6H), 3.87-3.74 (m, 1H), 3.70-3.55 (m, 5H), 3.49 (s, 4H), 3.35 (dq, 9H), 3.20-3.01 (m, 3H), 2.90-2.77 (m, 2H), 2.72 (s, 4H), 2.58-2.39 (m, 5H), 2.39-2.15 (m, 5H), 2.11 (s, 2H), 2.04-1.88 (m, 1H), 1.69-1.59 (m, 2H), 1.49-1.32 (m, 5H), 1.19 (td, 1H), 1.05 (t, 4H), 0.99 (q, 1H).

Intermediate 146 ethyl 6-chloro-7-(5-ethyl-1-methyl-3-(((2-morpholinoethyl)amino)methyl)-1H-pyrazol-4-yl)-3-(3-((6-fluoronaphthalen-1-yl)oxy)propyl)-1H-indole-2-carboxylate

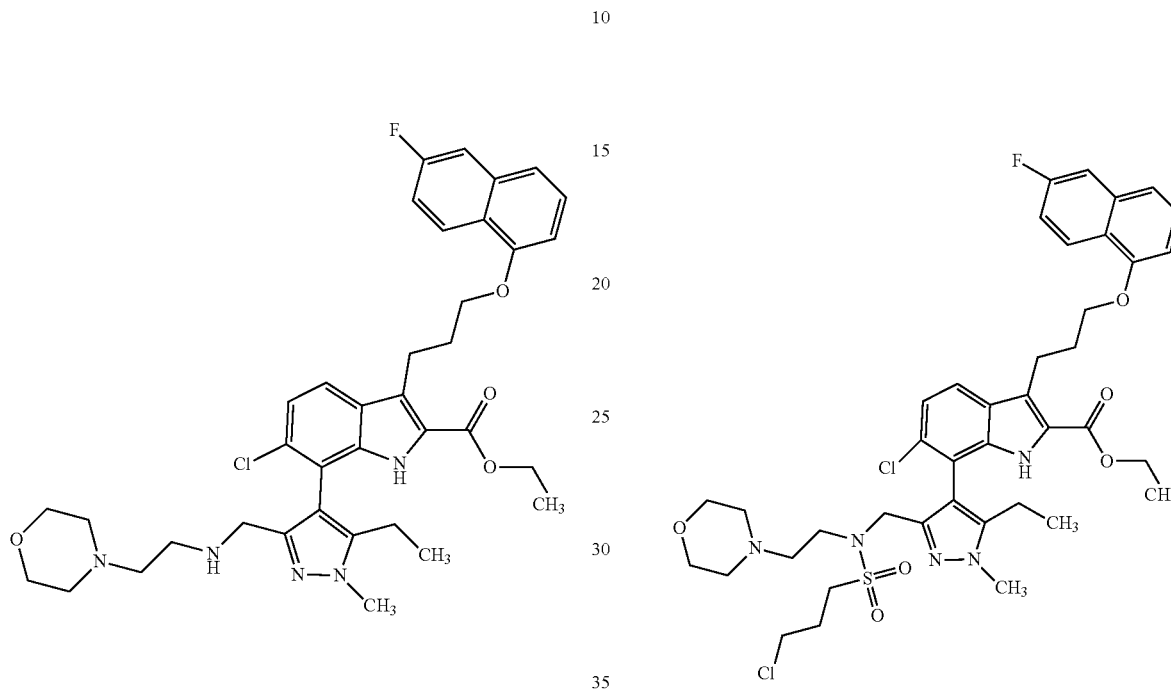

To a solution of ethyl 6-chloro-7-[5-ethyl-3-(hydroxymethyl)-1-methyl-1H-pyrazol-4-yl]-3-{3-[(6-fluoronaphthalen-1-yl)oxy]propyl}-1H-indole-2-carboxylate (Intermediate 123, 1.3 g, 2.30 mmol) in dichloromethane (46 mL) at 0° C. was added N,N-diisopropylethylamine (598 μL, 3.44 mmol), followed by mesyl chloride (355 μL, 4.60 mmol). The resulting mixture was stirred at 0° C. for 1 h and then at room temperature for 2 h. The mixture was re-cooled to 0° C. and a solution of 4-(2-aminoethyl)morpholine (5.75 mL, 11.5 mmol, 2 M in THF) was subsequently added. The mixture was warmed to room temperature and stirred overnight. A 1:1 mixture of brine and saturated aqueous sodium bicarbonate was added and the mixture was extracted three times with dichloromethane. The combined organic phases were dried over sodium sulfate, filtered and concentrated. The crude residue was purified by flash column chromatography on silica gel (0-20% methanol/dichloromethane then 20% (7 N ammonia in methanol)/dichloromethane) to obtain the title compound (0.926 g) as a foam.

LC-MS (Method 7): $R_f$=2.63 min; MS (ESIpos): m/z=677 [M+H]$^+$ $^1$H NMR (400 MHz, Chloroform-d) δ 8.43-8.30 (m, 1H), 7.60 (d, 1H), 7.47-7.34 (m, 3H), 7.25 (dd, 1H), 7.19 (d, 1H), 6.74 (dd, 1H), 4.45-4.29 (m, 2H), 4.22 (q, J=6.2 Hz, 2H), 3.92 (s, 2H), 3.77-3.65 (m, 5H), 3.50-3.31 (m, 3H), 2.69 (dd, 1H), 2.64-2.45 (m, 4H), 2.45-2.31 (m, 5H), 1.76 (s, 11H), 1.35 (dt, 3H), 1.00 (q, 3H).

Intermediate 147 ethyl 6-chloro-7-(3-(((3-chloro-N-(2-morpholinoethyl)propyl)sulfonamido)methyl)-5-ethyl-1-methyl-1H-pyrazol-4-yl)-3-(3-((6-fluoronaphthalen-1-yl)oxy)propyl)-1H-indole-2-carboxylate

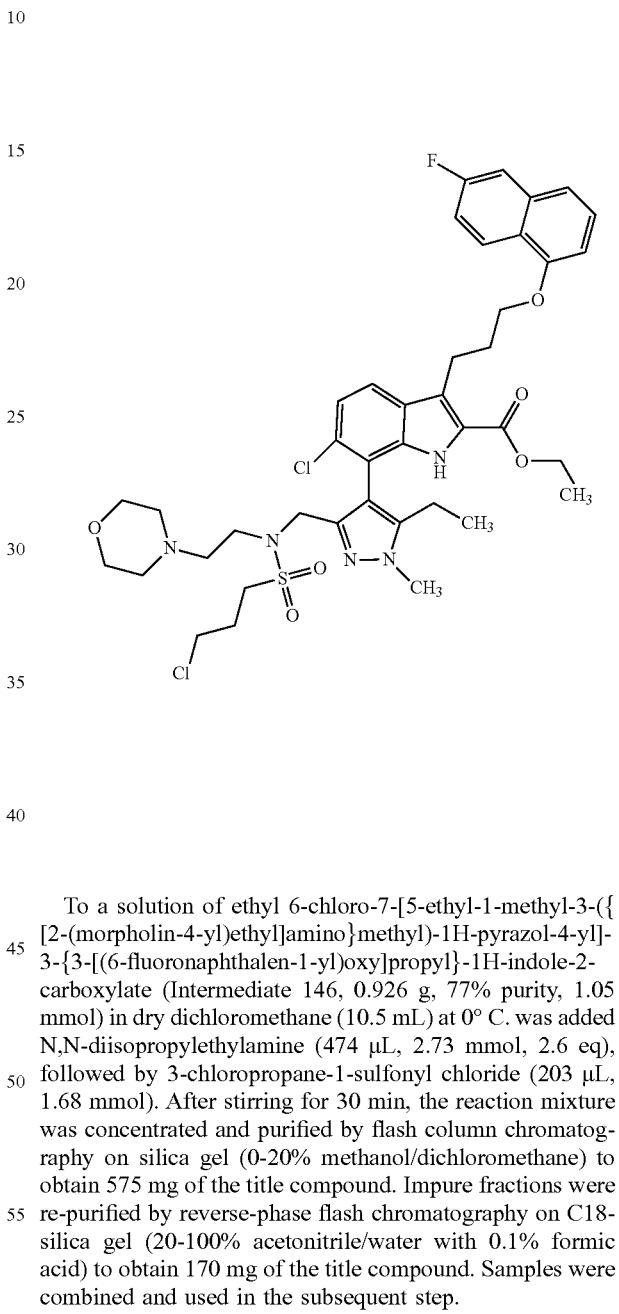

To a solution of ethyl 6-chloro-7-[5-ethyl-1-methyl-3-({[2-(morpholin-4-yl)ethyl]amino}methyl)-1H-pyrazol-4-yl]-3-{3-[(6-fluoronaphthalen-1-yl)oxy]propyl}-1H-indole-2-carboxylate (Intermediate 146, 0.926 g, 77% purity, 1.05 mmol) in dry dichloromethane (10.5 mL) at 0° C. was added N,N-diisopropylethylamine (474 μL, 2.73 mmol, 2.6 eq), followed by 3-chloropropane-1-sulfonyl chloride (203 μL, 1.68 mmol). After stirring for 30 min, the reaction mixture was concentrated and purified by flash column chromatography on silica gel (0-20% methanol/dichloromethane) to obtain 575 mg of the title compound. Impure fractions were re-purified by reverse-phase flash chromatography on C18-silica gel (20-100% acetonitrile/water with 0.1% formic acid) to obtain 170 mg of the title compound. Samples were combined and used in the subsequent step.

LC-MS (Method 7): $R_f$=2.90 min; MS (ESIneg): m/z=815 [M−H]$^−$ $^1$H NMR (400 MHz, Chloroform-d) δ 8.58 (s, 1H), 8.34 (dd, 1H), 7.60 (d, 1H), 7.45-7.31 (m, 3H), 7.26 (s, 8H), 7.18 (d, 1H), 6.72 (dd, 1H), 4.42-4.28 (m, 3H), 4.20 (dd, 3H), 3.91 (s, 3H), 3.69-3.45 (m, 6H), 3.37 (m, 2H), 3.25 (s, 1H), 3.09 (d, 2H), 2.61-2.41 (m, 2H), 2.33 (p, 5H), 2.16 (q, 2H), 1.71 (d, 18H), 1.36 (t, 3H), 1.01 (t, 3H).

Intermediate 148

(rac)-ethyl 13-chloro-12-ethyl-1-(3-((6-fluoronaphthalen-1-yl)oxy)propyl)-11-methyl-8-(2-morpholinoethyl)-5,6,9,11-tetrahydro-4H,8H-pyrazolo[3',4':4,5][1]thia[2,8]diazacycloundecino[6,7,8-hi]indole-2-carboxylate 7,7-dioxide

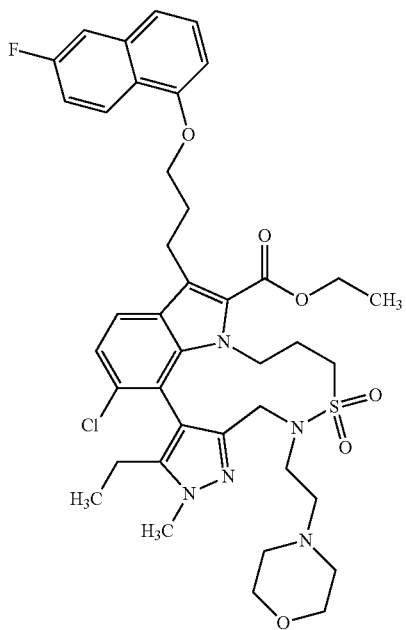 [SMILES: CCOC(=O)c1c(CCCOc2cccc3cc(F)ccc23)c2ccc(Cl)c3c2n1CCCS(=O)(=O)N(CCN1CCOCC1)Cc1nn(C)c(CC)c1-3]

To a solution of ethyl 6-chloro-7-[5-ethyl-1-methyl-3-({N-[2-(morpholin-4-yl)ethyl]3-chloropropanesulfonamido}methyl)-1H-pyrazol-4-yl]-3-{3-[(6-fluoronaphthalen-1-yl)oxy]propyl}-1H-indole-2-carboxylate (Intermediate 147, 0.74 g, 905 µmol) in acetonitrile (18.0 mL) was added cesium carbonate (1.17 g, 3.61 mmol) and the mixture was heated at 40° C. and stirred for 2 days. The mixture was cooled to room temperature and adsorbed onto Celite. The crude residue was purified by flash chromatography on silica gel (20% methanol/dichloromethane) to obtain the title compound (638 mg) as a foam.

LC-MS (Method 7): $R_t$=2.81 min; MS (ESIpos): m/z=784 [M+H]$^+$ $^1$H NMR (400 MHz, Chloroform-d) δ 8.36 (dd, 1H), 7.63 (d, 1H), 7.46-7.34 (m, 3H), 7.26 (s, 5H), 7.20 (d, 1H), 6.72 (dd, 1H), 4.55 (dt, 1H), 4.42-4.23 (m, 4H), 4.19 (q, 3H), 3.89 (s, 3H), 3.71 (t, 4H), 3.51 (s, 1H), 3.34 (m, 3H), 2.63 (d, 2H), 2.54 (s, 3H), 2.51 (s, 1H), 2.23 (m, 5H), 1.86 (s, 1H), 1.75 (d, 1H), 1.36 (t, 3H), 0.88 (t, 3H).

Intermediate 149 bromido[2-(oxan-4-yl)ethyl]magnesium

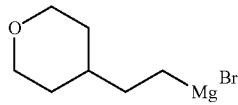

Magnesium (1.68 g, 69.1 mmol) was stirred under argon for 40 h, 50 mL THF was added. Than dropwise addition of $^\#$-(2-bromoethyl)oxane (10 ml, 69 mmol) in 15 mL THF. The reaction mixture was heated up to 55° C., gas evolution was observed. The reaction mixture was stirred for 1 h at 50° C., than cooled down to rt. The solution was used in the following reaction without any workup.

Intermediate 150

(rac)-1-(4-bromo-5-ethyl-1-methyl-1H-pyrazol-3-yl)-3-(oxan-4-yl)propan-1-ol

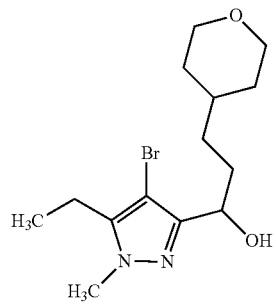 [SMILES: CCc1c(Br)c(C(O)CCC2CCOCC2)nn1C]

4-Bromo-5-ethyl-1-methyl-1H-pyrazole-3-carbaldehyde (see Intermediate 37, 6.00 g, 27.6 mmol) in 50 mL THF was vigorously stirred at −78° C. Then bromido[2-(oxan-4-yl)ethyl]magnesium (see Intermediate 149, 15.0 g, 69.1 mmol in 90 mL THF) was added dropwise via transfer cannula. The reaction mixture was stirred for 1 h at −78° C. and then warmed up over night. The reaction was carefully diluted with saturated aqueous ammonium chloride and extracted with dichloromethane three times. The combined organic layers were washed with saturated aqueous ammonium chloride solution, dried over magnesium sulfate and concentrated under reduced pressure. The crude product was purified by column chromatography twice (330 g column, hexane/ethyl acetate 15-100%, 254+280 nm and C18, 275 g, 10-100% acetonitrile in water) to provide the target compound: 2 g 1H-NMR (300 MHz, CHLOROFORM-d) delta [ppm]: 1.153 (3.16), 1.178 (7.18), 1.203 (3.44), 1.240 (1.33), 1.252 (0.74), 1.264 (2.54), 1.272 (0.62), 1.277 (0.60), 1.288 (1.73), 1.294 (1.01), 1.306 (0.70), 1.318 (0.75), 1.330 (0.67), 1.337 (0.55), 1.350 (0.63), 1.406 (0.40), 1.426 (0.41), 1.440 (0.51), 1.451 (0.36), 1.459 (0.54), 1.473 (0.40), 1.485 (0.51), 1.499 (0.49), 1.508 (0.34), 1.519 (0.36), 1.531 (0.33), 1.598 (0.99), 1.605 (0.86), 1.641 (0.77), 1.648 (0.71), 1.831 (0.45), 1.848 (0.45), 1.859 (0.59), 1.864 (0.66), 1.874 (0.57), 1.881 (0.84), 1.889 (0.60), 1.900 (0.55), 1.909 (0.55), 1.911 (0.53), 1.933 (0.37), 2.051 (3.80), 2.631 (1.08), 2.655 (3.21), 2.681 (3.02), 2.706 (0.88), 3.320 (0.80), 3.327 (0.88), 3.359 (1.56), 3.366 (1.57), 3.399 (0.90), 3.405 (0.86), 3.804 (16.00), 3.922 (0.95), 3.933 (0.92), 3.958 (0.82), 3.971 (0.74), 4.114 (0.85), 4.138 (0.83), 4.693 (0.80), 4.711 (0.94), 4.718 (0.81), 4.737 (0.74), 8.054 (0.43).

EXAMPLES

Example 1

(rac)-2,3-Dimethyl-14-[2-(morpholin-4-yl)ethyl]-7-{3-[(naphthalen-1-yl)oxy]propyl}-13,13-dioxo-10,11,12,13,14,15-hexahydro-2H-13λ⁶-pyrazolo[3',4':4,5][1,2,8]thiadiazacycloundecino-[6,7,8-hi]indole-8-carboxylic acid

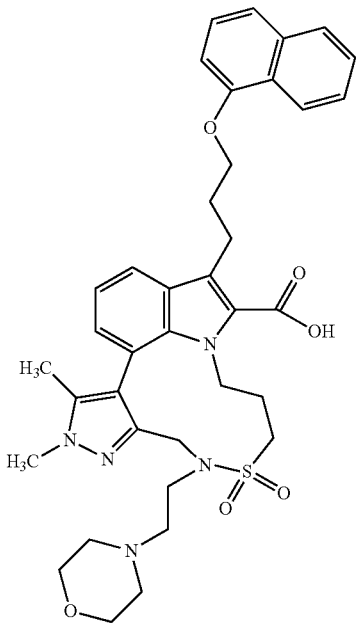 [SMILES: Cc1c2c(nn1C)CN(CCN1CCOCC1)S(=O)(=O)CCCn1c(C(=O)O)c(CCCOc3cccc4ccccc34)c3cccc-2c31]

To a solution of crude (rac)-ethyl-2,3-dimethyl-14-[2-(morpholin-4-yl)ethyl]-7-{3-[(naphthalen-1-yl)oxy]propyl}-13,13-dioxo-10,11,12,13,14,15-hexahydro-2H-13λ⁶-pyrazolo[3',4':4,5]-[1,2,8]thiadiazacycloundecino[6,7,8-hi]indole-8-carboxylate (see intermediate 14, 60.7 mg, 85.0 μmol) in a mixture of 3.5 mL of THF and 2 mL of ethanol under a stream of nitrogen was added an aqueous solution of lithium hydroxide (850 μL, 2.0 M, 1.7 mmol). The mixture was heated to 50° C. and stirred overnight. After cooling to rt and removal of solvents by rotary evaporation the residue was diluted with water (20 mL) and adjusted to pH 2 with 1-molar aqueous hydrochloric acid. The product was extracted from aqueous phase with ethyl acetate (three times; 20 mL each) and the combined organic layers were passed through a water resistant filter and concentrated under reduced pressure. The crude material was purified by flash chromatography on silica gel (0-20% dichloromethane/ethanol) to obtain, after lyophilization, the title compound (23.7 mg) as a solid.

LC-MS (Method 1): R$_t$=1.42 min; MS (ESIpos): m/z=686 [M+H]$^+$ $^1$H-NMR (400 MHz, DMSO-d6) δ[ppm]: 0.798 (2.14), 0.803 (1.02), 0.814 (2.30), 0.821 (2.37), 0.840 (1.25), 0.851 (0.58), 0.886 (1.18), 0.904 (2.46), 0.923 (1.22), 1.233 (1.57), 1.255 (0.77), 1.645 (0.45), 1.733 (0.54), 1.751 (0.58), 1.837 (13.63), 1.907 (0.96), 2.171 (0.90), 2.190 (1.76), 2.210 (2.43), 2.226 (1.60), 2.323 (4.80), 2.327 (5.02), 2.331 (4.13), 2.358 (1.15), 2.373 (0.90), 2.388 (1.06), 2.394 (1.18), 2.407 (1.15), 2.413 (1.41), 2.430 (0.99), 2.522 (12.51), 2.596 (0.67), 2.665 (1.38), 2.669 (1.95), 2.673 (1.47), 3.252 (0.74), 3.270 (0.96), 3.285 (1.06), 3.304 (1.89), 3.361 (1.98), 3.395 (0.86), 3.414 (0.45), 3.499 (3.33), 3.511 (5.31), 3.521 (3.58), 3.802 (16.00), 3.840 (0.64), 3.911 (0.51), 4.170 (1.70), 4.180 (2.62), 4.196 (1.70), 4.208 (2.69), 4.224 (2.59), 4.262 (0.64), 4.606 (0.48), 6.869 (2.05), 6.887 (2.24), 6.946 (0.96), 6.964 (1.18), 7.067 (1.09), 7.086 (1.66), 7.104 (0.90), 7.359 (1.44), 7.379 (2.75), 7.399 (2.14), 7.443 (3.04), 7.464 (1.76), 7.500 (0.67), 7.512 (1.95), 7.517 (3.26), 7.526 (3.58), 7.536 (3.20), 7.540 (2.27), 7.552 (0.70), 7.761 (1.18), 7.780 (1.12), 7.857 (1.70), 7.868 (1.06), 7.871 (1.15), 7.874 (1.22), 7.880 (1.50), 8.256 (1.47), 8.263 (1.09), 8.280 (1.47).

The title compound (87 mg) was separated into enantiomers by preparative chiral HPLC to give enantiomer 1 (36 mg, see Example 2) and enantiomer 2 (37 mg, see Example 3).

Preparative Chiral HPLC Method:
Instrument: Labomatic HD5000, Labocord-5000; Gilson GX-241, Labcol Vario 4000, column: Chiralpak IG 5μ 250×30 mm; Eluent A: hexane+0.1 Vol-% N-ethylethanamine (99%); Eluent B: ethanol; Gradient: 20-50% B in 12 min; Flow 40.0 mL/min; UV 254 nm Analytical Chiral HPLC Method:
Instrument: Agilent HPLC 1260; column: Chiralpak IG 3μ 100×4.6 mm; Eluent A: hexane+0.1 Vol-% N-ethylethanamine (99%); Eluent B: ethanol; Gradient: 20-50% B in 7 min; Flow 1.4 mL/min; Temperature: 25° C.; DAD 254 nm

Example 2

2,3-Dimethyl-14-[2-(morpholin-4-yl)ethyl]-7-{3-[(naphthalen-1-yl)oxy]propyl}-13,13-dioxo-10,11,12,13,14,15-hexahydro-2H-13λ⁶-pyrazolo[3',4':4,5][1,2,8]thiadiazacycloundecino-[6,7,8-hi]indole-8-carboxylic acid-N-ethylethanamine salt (Enantiomer 1)

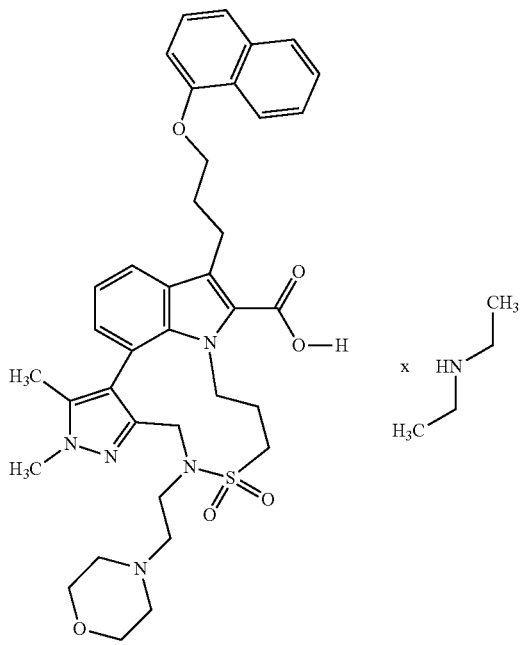

For the preparation of the racemic title compound see Example 1. Separation of enantiomers by preparative chiral HPLC (method see Example 1) gave the title compound (41 mg).

Analytical Chiral HPLC (method see Example 1): $R_t$=4.56 min.

LC-MS (Method 1): $R_t$=1.33 min; MS (ESIpos): m/z=686 [M+H]$^+$ $^1$H-NMR (400 MHz, DMSO-d6) δ[ppm]: 0.967 (0.58), 1.107 (16.00), 1.132 (3.67), 1.150 (7.80), 1.168 (3.85), 1.234 (0.62), 1.668 (0.42), 1.853 (5.84), 2.178 (0.59), 2.195 (0.93), 2.212 (0.70), 2.296 (1.38), 2.318 (0.98), 2.322 (1.17), 2.326 (1.22), 2.331 (0.91), 2.336 (0.63), 2.371 (0.47), 2.518 (3.24), 2.522 (1.99), 2.664 (0.54), 2.669 (0.75), 2.673 (0.57), 2.838 (1.01), 2.855 (3.12), 2.874 (3.07), 2.891 (1.00), 3.192 (0.42), 3.207 (0.41), 3.224 (0.51), 3.490 (1.43), 3.500 (2.28), 3.511 (1.43), 3.797 (7.33), 4.135 (0.63), 4.153 (0.88), 4.171 (1.43), 4.184 (0.53), 4.192 (0.62), 4.209 (0.95), 6.794 (0.46), 6.811 (0.53), 6.849 (0.88), 6.868 (0.95), 6.973 (0.51), 6.992 (0.79), 7.011 (0.43), 7.346 (0.66), 7.366 (1.22), 7.385 (0.95), 7.429 (1.27), 7.450 (0.74), 7.502 (0.79), 7.507 (1.40), 7.516 (1.62), 7.526 (1.47), 7.531 (0.88), 7.627 (0.57), 7.646 (0.53), 7.848 (0.73), 7.866 (0.48), 7.871 (0.61), 8.250 (0.66), 8.258 (0.49), 8.274 (0.59).

Example 3

2,3-Dimethyl-14-[2-(morpholin-4-yl)ethyl]-7-{3-[(naphthalen-1-yl)oxy]propyl}-13,13-dioxo-10,11,12,13,14,15-hexahydro-2H-13λ$^6$-pyrazolo[3',4':4,5][1,2,8]thiadiazacycloundecino-[6,7,8-hi]indole-8-carboxylic acid-N-ethylethanamine salt (Enantiomer 2)

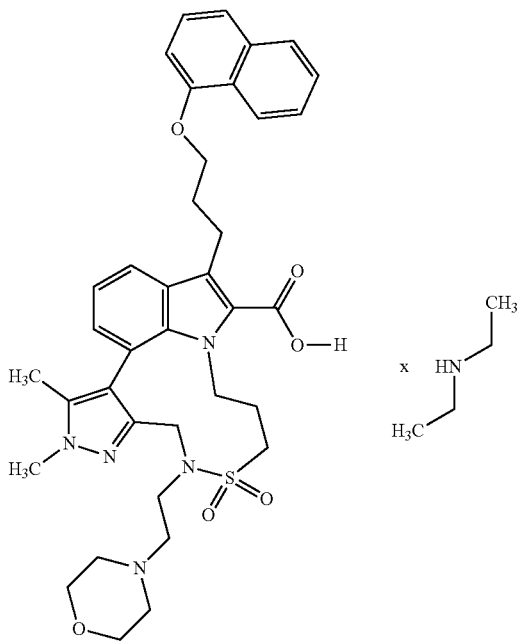

For the preparation of the racemic title compound see Example 1. Separation of enantiomers by preparative chiral HPLC (method see Example 1) gave the title compound (43 mg).

Analytical Chiral HPLC (method see Example 1): $R_t$=6.01 min.

LC-MS (Method 1): $R_t$=1.29 min; MS (ESIpos): m/z=686 [M+H]$^+$ $^1$H-NMR (400 MHz, DMSO-d6) δ[ppm]: 0.967 (0.63), 1.107 (16.00), 1.125 (3.35), 1.144 (7.71), 1.161 (3.41), 1.234 (0.63), 1.854 (5.60), 2.176 (0.58), 2.193 (0.92), 2.210 (0.70), 2.294 (1.35), 2.318 (1.06), 2.322 (1.39), 2.326 (1.53), 2.331 (1.17), 2.336 (0.74), 2.373 (0.47), 2.518 (4.77), 2.522 (2.92), 2.664 (0.77), 2.669 (1.08), 2.673 (0.79), 2.831 (0.90), 2.849 (2.68), 2.867 (2.68), 2.886 (0.90), 3.221 (0.47), 3.489 (1.39), 3.500 (2.20), 3.511 (1.41), 3.797 (7.08), 4.133 (0.59), 4.153 (0.86), 4.169 (1.48), 4.191 (0.81), 4.208 (0.92), 6.808 (0.43), 6.851 (0.85), 6.868 (0.92), 6.971 (0.43), 6.990 (0.68), 7.346 (0.61), 7.367 (1.19), 7.386 (0.94), 7.429 (1.23), 7.450 (0.72), 7.502 (0.77), 7.507 (1.39), 7.516 (1.55), 7.526 (1.48), 7.531 (0.88), 7.623 (0.47), 7.643 (0.45), 7.848 (0.70), 7.865 (0.49), 7.871 (0.61), 8.250 (0.65), 8.258 (0.49), 8.275 (0.59).

Example 4

(rac)-4-Chloro-2,3,14-trimethyl-7-{3-[(naphthalen-1-yl)oxy]propyl}-13,13-dioxo-10,11,12,13,14,15-hexahydro-2H-13λ$^6$-pyrazolo[3',4':4,5][1,2,8]thiadiazacycloundecino-[6,7,8-hi]indole-8-carboxylic acid

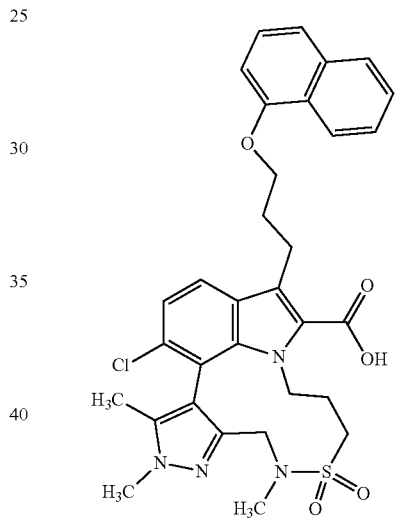

To a solution of (rac)-ethyl-4-chloro-2,3,14-trimethyl-7-{3-[(naphthalen-1-yl)oxy]propyl}-13,13-dioxo-10,11,12, 13,14,15-hexahydro-2H-13λ$^6$-pyrazolo[3',4':4,5][1,2,8] thiadiazacyclo-undecino[6,7,8-hi]indole-8-carboxylate (see intermediate 17, 171 mg, 264 µmol) in a mixture of 11 mL of THF and 6 mL of ethanol under a stream of nitrogen was added an aqueous solution of lithium hydroxide (2.6 mL, 2.0 M, 5.3 mmol). The mixture was heated to 50° C. and stirred for 3 hours. After cooling to rt and removal of solvents by rotary evaporation the residue was diluted with water (20 mL) and adjusted to pH 2 with 1-molar aqueous hydrochloric acid. The product was extracted from aqueous phase with ethyl acetate (three times; 20 mL each) and the combined organic layers were washed with brine, passed through a water resistant filter and concentrated under reduced pressure. The crude material was purified by flash chromatography on silica gel (0-20% dichloromethane/ethanol) to obtain, after lyophilization, the title compound (160 mg, 96%, purity, 94%, yield) as a solid.

LC-MS (Method 1): $R_t$=1.48 min; MS (ESIneg): m/z=620 [M−H]$^-$

¹H-NMR (400 MHz, DMSO-d6) δ[ppm]: 1.232 (0.76), 1.258 (0.42), 1.275 (0.55), 1.619 (0.47), 1.638 (0.51), 1.739 (0.60), 1.782 (15.67), 1.959 (0.54), 1.988 (0.62), 2.005 (0.68), 2.025 (0.54), 2.168 (0.41), 2.185 (1.17), 2.201 (1.85), 2.218 (1.33), 2.323 (0.55), 2.327 (0.78), 2.331 (0.58), 2.518 (8.04), 2.523 (6.34), 2.540 (2.97), 2.660 (0.97), 2.665 (1.04), 2.669 (1.28), 2.674 (1.47), 2.692 (8.92), 3.263 (0.63), 3.278 (0.71), 3.297 (1.22), 3.358 (1.61), 3.377 (0.90), 3.391 (0.85), 3.830 (16.00), 3.936 (0.44), 3.948 (0.44), 3.959 (0.74), 3.971 (0.55), 3.983 (0.51), 3.996 (0.44), 4.115 (4.49), 4.155 (1.44), 4.171 (2.61), 4.187 (1.47), 4.476 (0.41), 4.486 (0.71), 4.498 (0.55), 4.510 (0.51), 4.521 (0.67), 4.533 (0.42), 6.868 (1.95), 6.886 (2.23), 7.247 (3.62), 7.269 (3.91), 7.361 (1.41), 7.381 (2.66), 7.401 (2.14), 7.446 (2.86), 7.467 (1.71), 7.501 (0.60), 7.514 (1.79), 7.519 (3.13), 7.528 (3.66), 7.538 (3.37), 7.543 (2.13), 7.555 (0.75), 7.560 (0.42), 7.818 (3.24), 7.839 (3.09), 7.850 (0.53), 7.858 (1.70), 7.861 (1.31), 7.868 (1.00), 7.873 (1.20), 7.875 (1.22), 7.881 (1.53), 8.246 (1.39), 8.253 (1.16), 8.258 (0.74), 8.270 (1.37), 13.420 (0.49).

The title compound (107 mg) was separated into enantiomers by preparative chiral HPLC to give enantiomer 1 (56 mg, see Example 5) and enantiomer 2 (55 mg, see Example 6).

Preparative Chiral HPLC Method:

Instrument: Labomatic HD5000, Labocord-5000; Gilson GX-241, Labcol Vario 4000, column: YMC Amylose SA 5μ 250×30 mm; Eluent: hexane+0.1 Vol-% N-ethylethanamine (99%)/ethanol 80:20; Flow 40.0 mL/min; UV 254 nm Analytical Chiral HPLC Method:

Instrument: Agilent HPLC 1260; column: YMC Amylose SA 3μ 100×4.6 mm; Eluent: hexane+0.1 Vol-% N-ethylethanamine (99%)/ethanol 80:20; Flow 1.4 mL/min; Temperature: 25° C.; DAD 254 nm Example 5

4-Chloro-2,3,14-trimethyl-7-{3-[(naphthalen-1-yl)oxy]propyl}-13,13-dioxo-10,11,12,13,14,15-hexahydro-2H-13λ⁶-pyrazolo[3',4':4,5][1,2,8]thiadiazacycloundecino[6,7,8-hi]indole-8-carboxylic acid-N-ethylethanamine salt (Enantiomer 1)

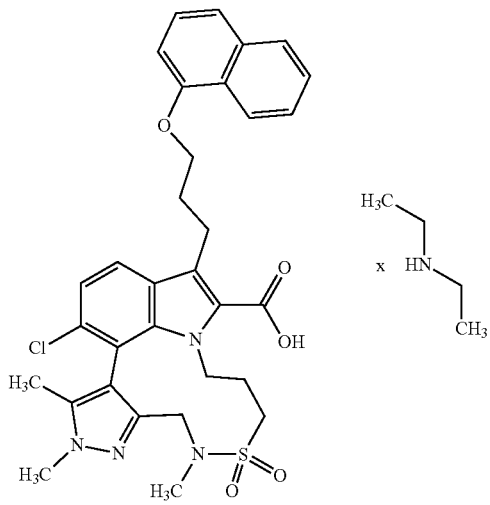

For the preparation of the racemic title compound see Example 4. Separation of enantiomers by preparative chiral HPLC (method see Example 4) gave the title compound (56 mg).

Analytical Chiral HPLC (method see Example 4): $R_t$=1.96 min.

LC-MS (Method 1): $R_t$=1.46 min; MS (ESIpos): m/z=621 [M+H]⁺

¹H-NMR (400 MHz, DMSO-d6) δ[ppm]: 0.967 (0.66), 1.107 (16.00), 1.128 (3.77), 1.146 (8.23), 1.164 (3.88), 1.234 (0.53), 1.802 (5.94), 2.166 (0.48), 2.183 (0.74), 2.201 (0.52), 2.331 (0.57), 2.518 (3.60), 2.522 (2.29), 2.619 (2.12), 2.673 (0.61), 2.840 (1.04), 2.858 (3.13), 2.876 (3.13), 2.895 (0.96), 3.281 (0.48), 3.821 (6.27), 4.070 (0.82), 4.097 (0.77), 4.130 (0.83), 4.147 (0.78), 4.191 (0.62), 6.835 (0.75), 6.853 (0.81), 7.095 (0.83), 7.116 (0.88), 7.343 (0.56), 7.363 (1.04), 7.382 (0.81), 7.429 (1.09), 7.450 (0.62), 7.503 (0.70), 7.508 (1.24), 7.517 (1.35), 7.527 (1.27), 7.532 (0.75), 7.604 (0.59), 7.625 (0.55), 7.847 (0.62), 7.865 (0.40), 7.871 (0.52), 8.243 (0.56), 8.250 (0.42), 8.267 (0.52).

Example 6

4-Chloro-2,3,14-trimethyl-7-{3-[(naphthalen-1-yl)oxy]propyl}-13,13-dioxo-10,11,12,13,14,15-hexahydro-2H-13λ⁶-pyrazolo[3',4':4,5][1,2,8]thiadiazacycloundecino[6,7,8-hi]indole-8-carboxylic acid-N-ethylethanamine salt (Enantiomer 2)

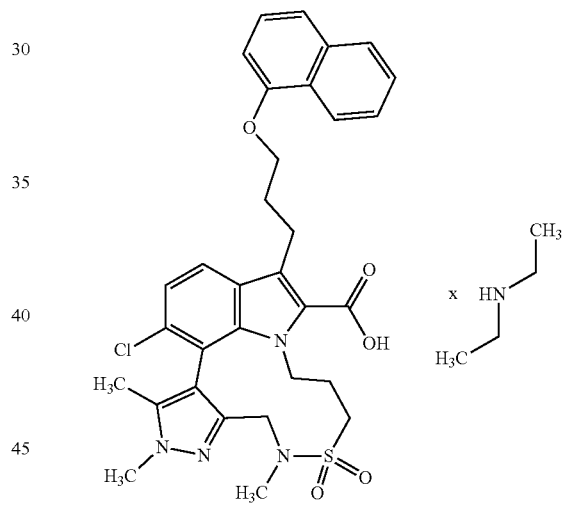

For the preparation of the racemic title compound see Example 4. Separation of enantiomers by preparative chiral HPLC (method see Example 4) gave the title compound (55 mg).

Analytical Chiral HPLC (method see Example 4): $R_t$=4.77 min.

LC-MS (Method 1): $R_t$=1.46 min; MS (ESIpos): m/z=621 [M+H]⁺

¹H-NMR (400 MHz, DMSO-d6) δ[ppm]: 0.967 (0.73), 1.107 (16.00), 1.130 (4.44), 1.148 (10.00), 1.167 (4.67), 1.234 (0.67), 1.259 (0.49), 1.802 (7.62), 2.167 (0.64), 2.184 (0.97), 2.202 (0.73), 2.331 (0.64), 2.518 (3.68), 2.523 (2.42), 2.620 (2.82), 2.673 (0.66), 2.843 (1.27), 2.860 (3.98), 2.879 (3.87), 2.896 (1.19), 3.181 (0.47), 3.283 (0.69), 3.821 (7.99), 4.071 (1.09), 4.097 (1.02), 4.114 (0.44), 4.130 (1.12), 4.147 (1.02), 4.192 (0.59), 6.835 (0.99), 6.853 (1.06), 7.097 (1.13), 7.118 (1.19), 7.343 (0.70), 7.363 (1.32), 7.382 (1.00), 7.429 (1.40), 7.450 (0.83), 7.503 (0.90), 7.508 (1.53), 7.517 (1.69), 7.527 (1.59), 7.532 (0.93), 7.606 (0.83), 7.627 (0.74), 7.847 (0.82), 7.858 (0.42), 7.866 (0.52), 7.871 (0.66), 8.243 (0.73), 8.250 (0.54), 8.267 (0.66).

Example 7

(rac)-12-Ethyl-13-fluoro-1-(3-((6-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide

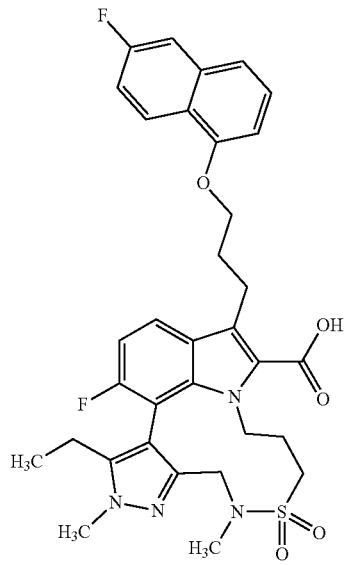 [SMILES: CCc1c2c(nn1C)CN(C)S(=O)(=O)CCCn1c(C(=O)O)c(CCCOc3cccc4cc(F)ccc34)c3ccc(F)c-2c31]

To a stirred solution of (rac)-ethyl 12-ethyl-13-fluoro-1-(3-((6-fluoronaphthalen-1-yl)oxy)propyl)-8,11-dimethyl-5,6,9,11-tetrahydro-4H,8H-pyrazolo[3',4':4,5][1]thia[2,8]diazacycloundecino-[6,7,8-hi]indole-2-carboxylate 7,7-dioxide (see intermediate 80, 123 mg, 185 μmol, 1.00 eq.) in ethanol (0.74 mL, 0.25 M) was added a 2.0 M solution of sodium hydroxide in water (231 μL, 463 μmol, 2.50 eq.). The resulting yellow solution was heated to 70° C. for 3 days, cooled to room temperature and then acidified with 1.0 M aqueous hydrochloric acid. Celite was added to the resulting mixture, volatiles were removed under reduced pressure, and the residue was subjected to reverse phase column chromatography (10-100% acetonitrile/water with 0.1% formic acid gradient) to give the title compound as a white solid (88.2 mg).

LC-MS (Method 4): $R_t$=4.40 min; MS (ESIpos): m/z=637 [M+H]$^+$.

$^1$H-NMR (300 MHz, DMSO-d) δ [ppm]: 13.30 (s, 1H), 8.32 (m, 1H), 7.85 (dd, 1H), 7.66 (dd, 1H), 7.42 (m, 3H), 7.04 (t, 1H), 6.85 (dd, 1H), 4.46 (m, 1H), 4.12 (m, 5H), 3.86 (s, 3H), 3.32 (m, 4H), 2.74 (m, 3H), 2.22 (m, 4H), 1.91 (m, 1H), 1.74 (m, 2H), 0.81 (t, 3H).

The title compound (77 mg) was separated into enantiomers by preparative chiral HPLC to give enantiomer 1 (32 mg, see Example 8) and enantiomer 2 (35 mg, see Example 9).
Preparative Chiral HPLC Method:
Instrument: Labomatic HD5000, Labocord-5000; Gilson GX-241, Labcol Vario 4000, column: Chiralpak IA 5μ 250×30 mm; Eluent A: hexane+0.1 Vol-% trifluoroacetic acid; Eluent B: 2-propanol; isocratic: 60% A+40% B; Flow 40.0 mL/min; UV 254 nm Analytical Chiral HPLC Method:
Instrument: Agilent HPLC 1260; column: Chiralpak IA 3μ 100×4.6 mm; Eluent A: hexane+0.1 Vol-% trifluoroacetic acid; Eluent B: 2-propanol; isocratic: 60% A+40% B; Flow 1.4 mL/min; Temperature: 25° C.; DAD 254 nm

Example 8

(+)-3-Ethyl-4-fluoro-7-{3-[(6-fluoronaphthalen-1-yl)oxy]propyl}-2,14-dimethyl-13,13-dioxo-10,11,12,13,14,15-hexahydro-2H-13λ$^6$-pyrazolo[3',4':4,5][1,2,8]thiadiazacycloundecino-[6,7,8-hi]indole-8-carboxylic acid (Enantiomer 1)

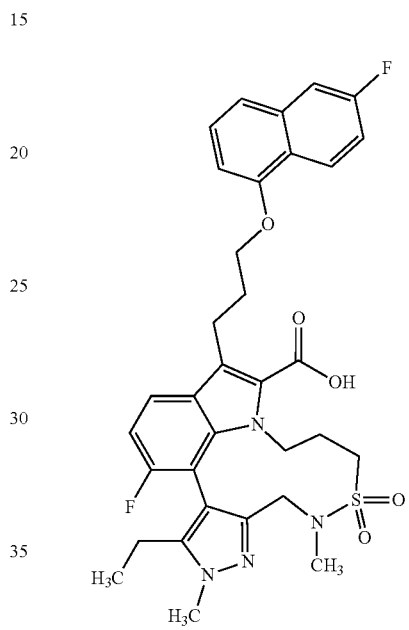

For the preparation of the racemic title compound see Example 7. Separation of enantiomers by preparative chiral HPLC (method see Example 7) gave the title compound (32 mg).
Analytical Chiral HPLC (method see Example 7): $R_t$=4.93 min.
LC-MS (Method 1): $R_t$=1.47 min; MS (ESIpos): m/z=637 [M+H]$^+$
Specific Optical Rotation (Method O1): +79.3° (c=10 mg/mL, DMSO)

$^1$H-NMR (400 MHz, DMSO-d6) δ[ppm]: 0.787 (5.69), 0.806 (13.30), 0.824 (6.08), 1.027 (3.44), 1.035 (0.76), 1.042 (3.56), 1.053 (1.21), 1.070 (0.70), 1.136 (5.03), 1.154 (11.01), 1.173 (5.06), 1.230 (0.41), 1.315 (0.57), 1.331 (0.54), 1.743 (1.65), 1.887 (0.70), 1.907 (0.64), 1.917 (0.86), 1.939 (0.67), 2.162 (0.92), 2.181 (2.51), 2.199 (4.45), 2.218 (3.91), 2.224 (3.18), 2.236 (1.46), 2.243 (2.39), 2.262 (1.30), 2.281 (0.70), 2.318 (0.54), 2.518 (7.63), 2.523 (5.09), 2.706 (1.02), 2.725 (1.34), 2.744 (16.00), 2.902 (1.37), 2.920 (1.72), 2.933 (1.69), 2.951 (1.30), 3.166 (0.89), 3.257 (0.45), 3.276 (0.83), 3.290 (1.18), 3.309 (2.04), 3.321 (1.30), 3.340 (2.04), 3.359 (1.15), 3.374 (0.95), 3.392 (0.48), 3.429 (0.86), 3.446 (0.83), 3.463 (0.41), 3.739 (3.79), 3.754 (3.75), 3.769 (3.40), 3.784 (2.80), 3.821 (1.88), 3.961 (0.54), 4.002 (2.42), 4.015 (0.95), 4.040 (3.82), 4.050 (1.56), 4.064 (1.05), 4.076 (0.89), 4.090 (0.83), 4.150 (5.47), 4.165 (4.77), 4.181 (2.54), 4.189 (2.83), 4.450 (1.37), 4.461 (0.92), 4.475 (0.83), 4.485 (1.15), 6.838 (2.39), 6.843 (2.51), 6.854 (2.29), 6.860 (2.61), 7.022 (2.74), 7.045 (4.49), 7.067 (2.67), 7.371 (1.56), 7.378 (1.75), 7.393 (2.42), 7.401 (3.34), 7.416 (1.81), 7.423 (5.57), 7.440 (9.26), 7.456 (1.02), 7.646 (2.83), 7.653 (2.96), 7.672 (2.86), 7.679 (2.89), 7.835 (2.42), 7.848 (2.54), 7.856 (2.67), 7.870 (2.51), 8.295 (2.45), 8.310 (2.61), 8.318 (2.58), 8.333 (2.42).

Example 9

(−)-3-Ethyl-4-fluoro-7-{3-[(6-fluoronaphthalen-1-yl)oxy]propyl}-2,14-dimethyl-13,13-dioxo-10,11,12,13,14,15-hexahydro-2H-13λ⁶-pyrazolo[3',4':4,5][1,2,8]thiadiazacycloundecino-[6,7,8-hi]indole-8-carboxylic acid (Enantiomer 2)

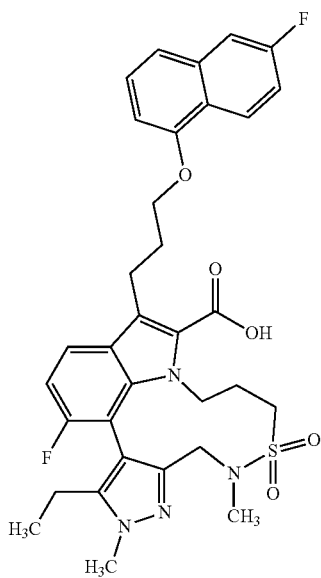 [SMILES: CCc1c2c(nn1C)CN(C)S(=O)(=O)CCCn1c(C(=O)O)c(CCCOc3cccc4cc(F)ccc34)c3ccc(F)c-2c31]

For the preparation of the racemic title compound see Example 7. Separation of enantiomers by preparative chiral HPLC (method see Example 7) gave the title compound (35 mg).

Analytical Chiral HPLC (method see Example 7): $R_t$=6.62 min.

LC-MS (Method 1): $R_t$=1.47 min; MS (ESIpos): m/z=637 [M+H]⁺

Specific Optical Rotation (Method O1): −67.8° (c=10 mg/mL, DMSO)

¹H-NMR (400 MHz, DMSO-d6) δ[ppm]: 0.787 (2.86), 0.806 (6.72), 0.824 (3.02), 1.136 (2.94), 1.154 (6.26), 1.172 (2.94), 1.744 (0.84), 1.918 (0.43), 2.162 (0.46), 2.181 (1.27), 2.199 (2.24), 2.218 (1.94), 2.243 (1.19), 2.262 (0.65), 2.336 (0.49), 2.518 (5.94), 2.523 (4.13), 2.705 (0.51), 2.725 (0.67), 2.744 (7.96), 2.902 (0.78), 2.921 (0.97), 2.933 (0.97), 2.951 (0.76), 3.275 (0.46), 3.290 (0.65), 3.309 (1.11), 3.328 (0.73), 3.340 (1.11), 3.359 (0.70), 3.373 (0.62), 3.392 (0.46), 3.860 (16.00), 4.002 (1.11), 4.015 (0.40), 4.040 (1.86), 4.050 (0.70), 4.064 (0.46), 4.150 (2.73), 4.165 (2.35), 4.181 (1.24), 4.188 (1.38), 4.449 (0.67), 4.461 (0.46), 4.484 (0.57), 6.838 (1.21), 6.844 (1.27), 6.855 (1.16), 6.860 (1.30), 7.022 (1.35), 7.045 (2.27), 7.067 (1.40), 7.371 (0.76), 7.378 (0.92), 7.394 (1.19), 7.401 (1.65), 7.416 (0.92), 7.423 (2.81), 7.440 (4.64), 7.456 (0.51), 7.646 (1.38), 7.653 (1.46), 7.672 (1.40), 7.679 (1.43), 7.835 (1.24), 7.849 (1.27), 7.857 (1.32), 7.870 (1.21), 8.295 (1.24), 8.310 (1.30), 8.318 (1.27), 8.333 (1.21).

Example 10

(rac)-2,3,14-Trimethyl-7-[3-(1-naphthyloxy)propyl]-11,12,14,15-tetrahydro-2H,10H-pyrazolo[3',4':4,5][1,2,8]thiadiazacycloundecino[6,7,8-hi]indole-8-carboxylic acid 13,13-dioxide

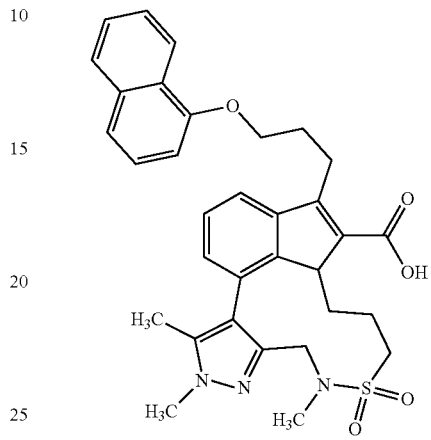

To a solution of ethyl 7-(3-((3-chloro-N-methylpropylsulfonamido)methyl)-1,5-dimethyl-1H-pyrazol-4-yl)-3-(3-(naphthalen-1-yloxy)propyl)-1H-indole-2-carboxylate (see Intermediate 19, 0.31 g, 476 µmol) in dry dimethylformamide (19.0 mL) was added 60% sodium hydride (56.6 mg, 1.42 mmol) as a dispersion in oil at room temperature, and the mixture was stirred at 60° C. overnight. Excess sodium hydride (56.6 mg, 1.42 mmol) was added and the mixture was stirred an additional 24 h. The mixture was cooled to room temperature and concentrated three times from benzene to remove solvent.

The crude residue was suspended in a 2:1 mixture of tetrahydrofuran and ethanol (18 mL), treated with 2 M aqueous lithium hydroxide (2.83 mL, 5.67 mmol), and stirred overnight at 50° C. The mixture was cooled to 0° C. and treated with 1 N aqueous hydrochloric acid (993 µL, 5.96 mmol). The mixture was then extracted three times with ethyl acetate and the combined organic phases were washed with brine, dried over sodium sulfate, filtered, and concentrated. The crude residue was purified by flash column chromatography on silica gel (0-100% ethyl acetate/hexanes) to obtain the title compound (150 mg) as a beige solid after lyophilization.

LC-MS (Method 4): $R_t$=4.13 min; MS (ESIpos): m/z=587 [M+H]⁺

¹H NMR (Chloroform-d) δ [ppm]: 8.47-8.32 (m, 1H), 7.87-7.74 (m, 2H), 7.51 (ddd, 2H), 7.48-7.30 (m, 2H), 7.14 (dd, 1H), 7.02 (dd, 1H), 6.78 (dd, 1H), 4.64-4.53 (m, 1H), 4.47 (d, 1H), 4.34-4.16 (m, 3H), 4.08 (d, 1H), 3.89 (s, 3H), 3.50 (ddt, 2H), 2.95 (s, 3H), 2.52 (dd, 1H), 2.36 (q, 2H), 2.21-2.07 (m, 1H), 1.89 (s, 6H)

The title compound (109 mg) was separated into enantiomers by preparative chiral HPLC to give enantiomer 1 (50 mg, see Example 11) and enantiomer 2 (52 mg, see Example 12).

Preparative Chiral HPLC Method:

Instrument: Labomatic HD5000, Labocord-5000; Gilson GX-241, Labcol Vario 4000, column: Chiralpak IG 5µ 250×30 mm; Eluent A: hexane+0.1 Vol-% N-ethylethanamine (99%); Eluent B: ethanol; Gradient: 20→50% B in 20 min; Flow 40.0 mL/min; UV 254 nm Analytical Chiral HPLC Method:

Instrument: Agilent HPLC 1260; column: Chiralpak IG 3µ 100×4.6 mm; Eluent A: hexane+0.1 Vol-% N-ethyl-ethanamine (99%); Eluent B: ethanol; Gradient: 20-50% B in 7 min; Flow 1.4 mL/min; Temperature: 25° C.; DAD 254 nm Example 11

(+)-2,3,14-Trimethyl-7-[3-(1-naphthyloxy)propyl]-11,12,14,15-tetrahydro-2H,10H-pyrazolo[3',4':4,5][1,2,8]thiadiazacycloundecino[6,7,8-hi]indole-8-carboxylic acid 13,13-dioxide-N-ethylethanamine Salt (Enantiomer 1)

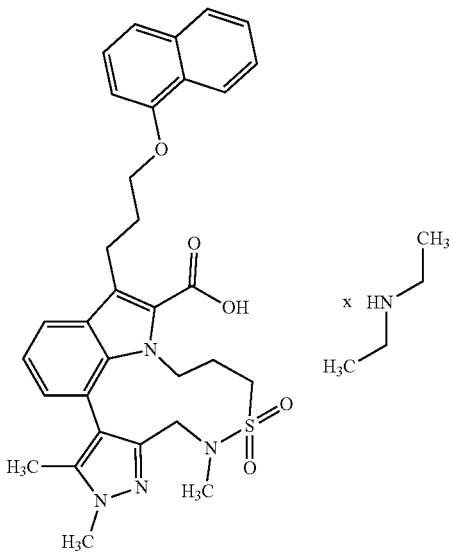

For the preparation of the racemic title compound see Example 10. Separation of enantiomers by preparative chiral HPLC (method see Example 10) gave the title compound (50 mg).

Analytical Chiral HPLC (method see Example 10): R$_t$=4.19 min.

LC-MS (Method 1): R$_t$=1.43 min; MS (ESIpos): m/z=587 [M+H]$^+$

Specific Optical Rotation (Method O1): +114.9° (c=10 mg/mL, DMSO)

$^1$H-NMR (400 MHz, DMSO-d6) δ[ppm]: 1.132 (7.25), 1.151 (16.00), 1.168 (7.50), 1.836 (13.36), 1.903 (0.86), 2.182 (1.04), 2.199 (1.57), 2.216 (1.08), 2.323 (0.64), 2.327 (0.93), 2.331 (0.69), 2.518 (4.14), 2.523 (2.67), 2.537 (0.44), 2.657 (4.61), 2.669 (1.69), 2.673 (1.11), 2.827 (1.82), 2.845 (5.44), 2.863 (5.33), 2.882 (1.65), 3.186 (0.67), 3.200 (0.69), 3.219 (1.02), 3.237 (0.67), 3.801 (14.24), 3.874 (0.52), 3.977 (0.96), 4.015 (1.27), 4.121 (0.47), 4.128 (0.64), 4.145 (1.62), 4.162 (1.98), 4.167 (2.07), 4.178 (0.75), 4.186 (0.53), 4.205 (1.18), 4.641 (0.50), 4.676 (0.47), 6.762 (1.19), 6.779 (1.35), 6.837 (1.63), 6.855 (1.69), 6.955 (1.27), 6.974 (1.77), 6.992 (1.10), 7.340 (1.22), 7.360 (2.26), 7.379 (1.71), 7.427 (2.32), 7.448 (1.36), 7.492 (0.44), 7.504 (1.51), 7.508 (2.32), 7.518 (2.75), 7.528 (2.29), 7.531 (1.79), 7.543 (0.50), 7.615 (1.33), 7.635 (1.22), 7.847 (1.32), 7.851 (0.96), 7.861 (0.86), 7.865 (0.86), 7.871 (1.15), 8.255 (1.18), 8.266 (0.83), 8.280 (1.10).

Example 12

(−)-2,3,14-Trimethyl-7-[3-(1-naphthyloxy)propyl]-11,12,14,15-tetrahydro-2H,10H-pyrazolo[3',4':4,5][1,2,8]thiadiazacycloundecino[6,7,8-hi]indole-8-carboxylic acid 13,13-dioxide-N-ethylethanamine Salt (Enantiomer 2)

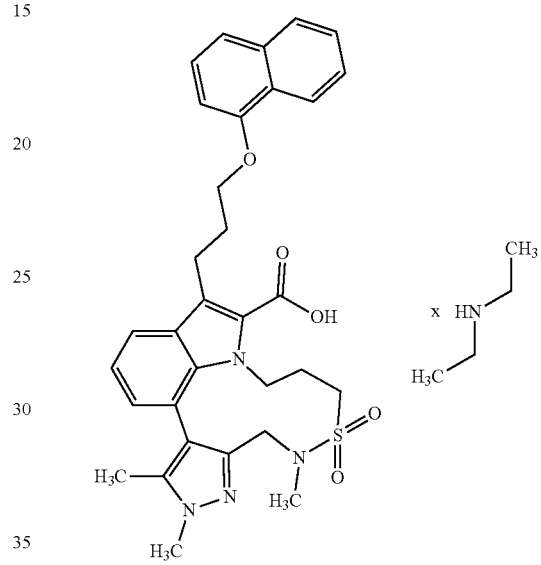

For the preparation of the racemic title compound see Example 10. Separation of enantiomers by preparative chiral HPLC (method see Example 10) gave the title compound (52 mg).

Analytical Chiral HPLC (method see Example 10): R$_t$=5.98 min.

LC-MS (Method 1): R$_t$=1.43 min; MS (ESIpos): m/z=587 [M+H]$^+$

Specific Optical Rotation (Method O1): −106.1° (c=10 mg/mL, DMSO)

$^1$H-NMR (400 MHz, DMSO-d6) δ[ppm]: 0.795 (0.52), 0.798 (0.72), 0.814 (0.91), 0.821 (0.81), 0.840 (0.46), 0.886 (0.42), 0.904 (0.83), 1.006 (0.48), 1.084 (0.64), 1.132 (7.04), 1.151 (16.00), 1.169 (7.39), 1.259 (0.74), 1.837 (13.30), 1.902 (0.81), 2.050 (0.64), 2.182 (1.04), 2.199 (1.58), 2.216 (1.09), 2.323 (0.60), 2.327 (0.83), 2.331 (0.59), 2.518 (3.40), 2.523 (2.36), 2.542 (0.45), 2.657 (4.57), 2.669 (1.54), 2.673 (1.01), 2.824 (1.71), 2.843 (4.94), 2.860 (4.89), 2.879 (1.56), 3.185 (0.68), 3.200 (0.67), 3.218 (1.00), 3.236 (0.64), 3.801 (14.21), 3.873 (0.52), 3.977 (0.97), 4.015 (1.27), 4.120 (0.48), 4.128 (0.64), 4.144 (1.61), 4.166 (2.16), 4.177 (0.76), 4.186 (0.56), 4.204 (1.22), 4.648 (0.52), 4.681 (0.48), 6.758 (1.26), 6.775 (1.45), 6.836 (1.60), 6.854 (1.69), 6.953 (1.32), 6.972 (1.87), 6.991 (1.19), 7.339 (1.17), 7.360 (2.23), 7.379 (1.76), 7.427 (2.31), 7.448 (1.38), 7.491 (0.45), 7.504 (1.57), 7.508 (2.42), 7.517 (2.73), 7.527 (2.33), 7.531 (1.79), 7.543 (0.51), 7.612 (1.39), 7.630 (1.27), 7.847 (1.34), 7.851 (0.97), 7.861 (0.85), 7.865 (0.86), 7.871 (1.15), 8.255 (1.16), 8.266 (0.81), 8.280 (1.08).

Example 13

(rac)-12-Ethyl-11-methyl-1-(3-(naphthalen-1-yloxy)propyl)-8-(3-(2-oxopyrrolidin-1-yl)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide

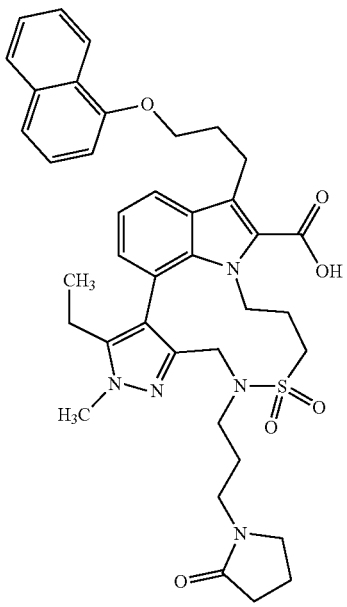 [SMILES: CCc1c2c(nn1C)CN(CCCN1CCCC1=O)S(=O)(=O)CCCn1c(C(=O)O)c(CCCOc3cccc4ccccc34)c3cccc-2c31]

A mixture of (rac)-ethyl 12-ethyl-11-methyl-1-(3-(naphthalen-1-yloxy)propyl)-8-(3-(2-oxopyrrolidin-1-yl)propyl)-4,5,6,8,9,11-hexahydropyrazolo[3',4':4,5][1,2,8]thiadiazacyclo-undecino[6,7,8-hi]indole-2-carboxylate 7,7-dioxide (see Intermediate 23, 0.206 g, 277 μmol) in tetrahydrofuran (11.0 mL) and ethanol (6.15 mL) was treated with 2 M aqueous lithium hydroxide (2.77 mL, 5.54 mmol). The mixture was heated to 60° C. and stirred overnight. The mixture was cooled to room temperature, concentrated, and re-suspended in tetrahydrofuran. The resulting mixture was then treated with 6 N aqueous hydrochloric acid (940 μL, 5.64 mmol). Celite was added to the resulting mixture, and volatiles were removed under reduced pressure. The residue was purified by reverse-phase flash column chromatography on C18-silica gel (10-100% acetonitrile/water with 0.1% TFA) to obtain, after lyophilization, the title compound (0.117 g) as a solid.

LC-MS (Method 4): $R_t$=4.16 min; MS (ESIneg): m/z=710 [M−H]⁻

¹H NMR (400 MHz, DMSO-d6) δ[ppm]: 13.24 (s, 1H), 8.38-8.07 (m, 1H), 7.96-7.78 (m, 2H), 7.53 (m, 2H), 7.45 (d, 1H), 7.38 (t, 1H), 7.11 (t, 1H), 6.98 (dd, 1H), 6.88 (d, 1H), 4.51 (m, 1H), 4.25-3.97 (m, 5H), 3.84 (s, 3H), 3.41 (s, 20H), 3.19-3.04 (m, 2H), 2.70-2.54 (m, 1H), 2.31-2.10 (m, 6H), 1.94 (p, 2H), 1.62 (m, 1H), 0.80 (t, 3H).

Example 14

(rac)-12-Ethyl-11-methyl-1-(3-(naphthalen-1-yloxy)propyl)-8-(2-(piperidin-1-yl)ethyl)-4,5,6,8,9,11-hexahydropyrazolo[3',4':4,5][1,2,8]thiadiazacycloundecino[6,7,8-hi]indole-2-carboxylic acid 7,7-dioxide 2,2,2-trifluoroacetic acid salt

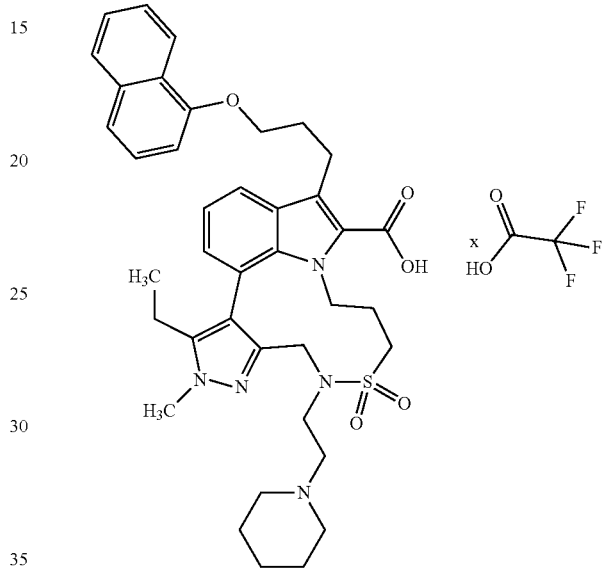

A mixture of (rac)-ethyl 12-ethyl-11-methyl-1-(3-(naphthalen-1-yloxy)propyl)-8-(2-(piperidin-1-yl)ethyl)-4,5,6,8,9,11-hexahydropyrazolo[3',4':4,5][1,2,8]thiadiazacycloundecino[6,7,8-hi]indole-2-carboxylate 7,7-dioxide (see Intermediate 26, 196 mg, 269 μmol) in tetrahydrofuran (10.7 mL) and ethanol (5.97 mL) was treated with 2 M aqueous lithium hydroxide (2.68 mL, 5.37 mmol). The mixture was heated to 60° C. and stirred overnight. The mixture was cooled to room temperature, concentrated, and re-suspended in tetrahydrofuran. The resulting mixture was then treated with 6 N aqueous hydrochloric acid (940 μL, 5.64 mmol). Celite was added to the resulting mixture, and volatiles were removed under reduced pressure. The residue was purified by reverse-phase flash column chromatography on C18-silica gel (10-100% acetonitrile/water with 0.1% TFA) to obtain, after lyophilization, the title compound (84.5 mg) as a solid.

LC-MS (Method 4): $R_t$=4.57 min; MS (ESIpos): m/z=698 [M+H]⁺

¹H NMR (400 MHz, DMSO-d6) δ[ppm]: 13.31 (s, 1H), 9.25 (s, 1H), 8.33-8.23 (m, 1H), 7.93-7.79 (m, 2H), 7.64-7.33 (m, 4H), 7.14 (t, 1H), 7.01 (dd, 1H), 6.89 (d, 1H), 4.59-4.51 (m, 1H), 4.26-4.17 (m, 4H), 4.11-3.93 (m, 1H), 3.87 (s, 3H), 3.51 (dd, 3H), 3.36 (m, 3H), 3.16 (s, 1H), 2.96 (t, 2H), 2.75 (dd, 1H), 2.33-2.12 (m, 4H), 2.02 (dd, 1H), 1.91-1.58 (m, 7H), 1.42 (t, 1H), 0.82 (t, 3H).

Example 15

(rac)-12-Ethyl-11-methyl-8-(3-morpholinopropyl)-1-(3-(naphthalen-1-yloxy)propyl)-4,5,6,8,9,11-hexahydropyrazolo[3',4':4,5][1,2,8]thiadiazacycloundecino[6,7,8-hi]indole-2-carboxylic acid 7,7-dioxide 2,2,2-trifluoroacetic acid salt

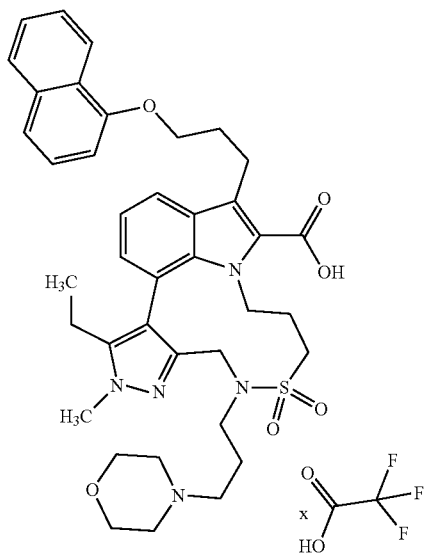

To a solution of ethyl 7-(3-((3-chloro-N-(3-morpholinopropyl)propylsulfonamido)methyl)-5-ethyl-1-methyl-1H-pyrazol-4-yl)-3-(3-(naphthalen-1-yloxy)propyl)-1H-indole-2-carboxylate (see Intermediate 28, 0.24 g, 308 µmol) in dry dimethylformamide (12.3 mL) was added 60% sodium hydride (36.8 mg, 924 µmol) as a dispersion in oil at room temperature, and the mixture was stirred at 60° C. for 6 h. The resulting mixture was cooled to room temperature, concentrated, and re-suspended in tetrahydrofuran. The mixture was then treated with 1 N aqueous hydrochloric acid. Celite was added to the resulting mixture, and volatiles were removed under reduced pressure. The residue was purified by reverse-phase flash column chromatography on C18-silica gel (10-100% acetonitrile/water with 0.1% TFA) to obtain, after lyophilization, the title compound (123 mg) as a solid.

LC-MS (Method 4): $R_t$=4.44 min; MS (ESIpos): m/z=714 [M+H]$^+$ $^1$H NMR (400 MHz, DMSO-d6) δ[ppm]: 13.27 (s, 1H), 9.62 (s, 1H), 8.32-8.24 (m, 1H), 7.91-7.79 (m, 2H), 7.59-7.47 (m, 2H), 7.49-7.34 (m, 2H), 7.17-7.05 (m, 1H), 7.00 (dd, 1H), 6.91-6.84 (m, 1H), 4.58-4.49 (m, 1H), 4.31-4.10 (m, 4H), 4.00 (d, 3H), 3.85 (s, 3H), 3.65 (t, 2H), 3.53-3.21 (m, 3H), 3.08 (s, 4H), 2.86 (s, 1H), 2.72-2.60 (m, 1H), 2.20 (dh, 4H), 2.06 (d, 1H), 2.01-1.87 (m, 3H), 1.73 (s, 2H), 0.80 (t, 3H)

Example 16

(rac)-12-Ethyl-11-methyl-1-(3-(naphthalen-1-yloxy)propyl)-8-(3-(pyrrolidin-1-yl)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide

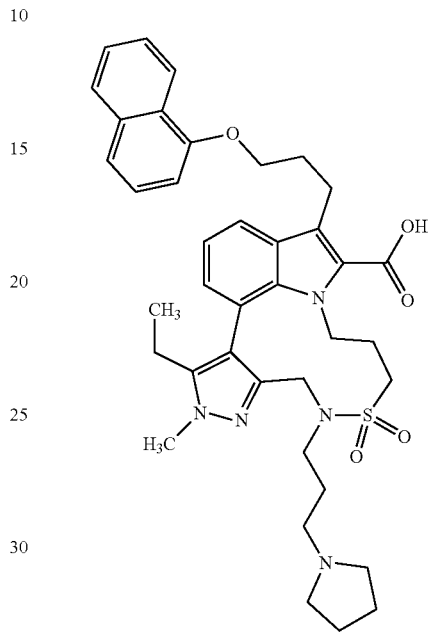

To a solution of ethyl 7-(3-((3-chloro-N-(3-(pyrrolidin-1-yl)propyl)propylsulfonamido)methyl)-5-ethyl-1-methyl-1H-pyrazol-4-yl)-3-(3-(naphthalen-1-yloxy)propyl)-1H-indole-2-carboxylate (see Intermediate 30, 88 mg, 115 µmol) in dry dimethylformamide (4.59 mL) was added 60% sodium hydride (11.4 mg, 287 µmol) as a dispersion in oil at room temperature, and the mixture was stirred at 60° C. After 2 days, an additional portion of sodium hydride (11.4 mg, 287 µmol) was added and the mixture was stirred for further 7 days. The mixture was cooled, and the reaction was stopped by the addition of water (1 mL). The mixture was subsequently concentrated by co-evaporation with toluene for three times.

The crude residue was dissolved in ethanol (2.29 mL) and treated with 2 M aqueous sodium hydroxide (287 µL, 287 µmol). The mixture was heated to 60° C. and stirred overnight. The mixture was then cooled to room temperature, concentrated, and re-suspended in tetrahydrofuran. The mixture was subsequently treated with 1 N aqueous hydrochloric acid (940 µL, 5.64 mmol). Celite was added to the resulting mixture, and volatiles were removed under reduced pressure. The residue was purified by reverse-phase flash column chromatography on C18-silica gel (10-100% acetonitrile/water with 0.1% formic acid) to obtain, after lyophilization, the title compound (13.2 mg) as a white solid.

LC-MS (Method 4): $R_t$=3.23 min; MS (ESIpos): m/z=699 [M+H]$^+$ $^1$H NMR (DMSO-d6) δ[ppm]: 8.32-8.23 (m, 1H), 8.19 (s, 0H), 7.86 (dt, 1H), 7.72 (dd, 1H), 7.59-7.31 (m, 5H), 7.11-6.99 (m, 1H), 6.93-6.81 (m, 2H), 4.59 (d, 1H), 4.16 (d, 5H), 3.96 (d, 1H), 3.82 (s, 3H), 3.31 (m, 20H), 2.73 (d, 4H), 2.57 (s, 1H), 2.21 (q, 4H), 1.76 (s, 5H), 0.80 (t, 3H)

303

Example 17

(rac)-12-Ethyl-11-methyl-1-(3-(naphthalen-1-yloxy)propyl)-4,5,6,8,9,11-hexahydropyrazolo[3',4':4,5][1,2,8]thiadiazacycloundecino[6,7,8-hi]indole-2-carboxylic acid 7,7-dioxide

304

Example 18

12-Ethyl-8,9,11-trimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide (Mixture of Stereoisomers)

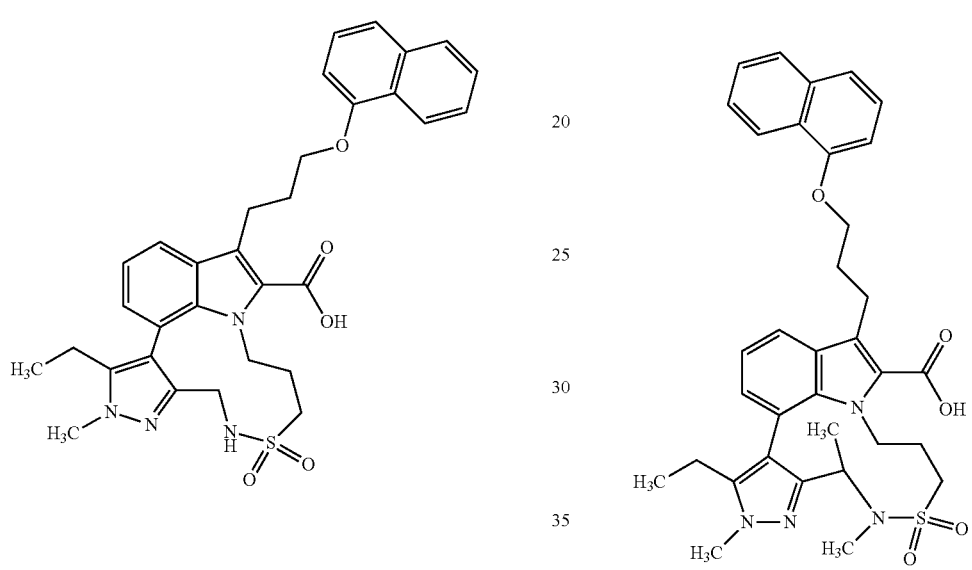

A mixture of crude (rac)-ethyl 12-ethyl-11-methyl-1-(3-(naphthalen-1-yloxy)propyl)-4,5,6,8,9,11-hexahydropyrazolo[3',4':4,5][1,2,8]thiadiazacycloundecino[6,7,8-hi]indole-2-carboxylate 7,7-dioxide (see Intermediate 36, 23 mg, 28.7 μmol) in tetrahydrofuran (1.14 mL) and ethanol (637 μL) was treated with 2 M aqueous lithium hydroxide (143 μL, 287 μmol). The mixture was heated to 60° C. and stirred overnight. The mixture was cooled to 0° C. and was then treated with 1 N aqueous hydrochloric acid (100 μL, 602 μmol). Celite was added to the resulting mixture, volatiles were removed under reduced pressure, and the residue was subjected to reverse-phase flash column chromatography on C18-silica gel (10-100% acetonitrile/water with 0.1% TFA) to obtain, after lyophilization, the title compound (9.7 mg) as a solid.

LC-MS (Method 4): $R_t$=4.10 min; MS (ESIpos): m/z=587 [M+H]$^+$ $^1$H NMR (400 MHz, DMSO-d6) δ[ppm]: 13.23 (s, 1H), 8.34-8.22 (m, 1H), 7.87 (dt, 2.6 Hz, 1H), 7.79 (dd, 1H), 7.57-7.42 (m, 3H), 7.39 (t, 1H), 7.16-7.06 (m, 1H), 7.01-6.95 (m, 1H), 6.90 (d, 1H), 4.58 (d, 1H), 4.21 (t, 2H), 4.10 (dd, 1H), 4.02 (s, 2H), 3.93 (dd, 1H), 3.83 (s, 3H), 3.40-3.26 (m, 1H), 2.29-2.15 (m, 5H), 2.00 (s, 1H), 1.85 (s, 1H), 1.61 (s, 1H), 0.80 (t, 3H).

To a stirred solution of ethyl 12-ethyl-8,9,11-trimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide (mixture of stereoisomers; see Intermediate 43; 111 mg, 172 μmol) in ethanol (688 μL) was added a 2 M solution of lithium hydroxide (855 μL, 1.71 mmol). The resulting solution was heated to 60° C. for 2 days. The mixture was cooled and acidified with 1 N aqueous hydrochloric acid. Celite was added to the resulting mixture, and volatiles were removed under reduced pressure. The residue was purified by reverse-phase flash column chromatography on C18-silica gel (10-100% acetonitrile/water with 0.1% formic acid) to obtain the title compound (68.3 mg) as a 3:1 mixture of diastereomers.

LC-MS (Method 4): $R_t$=4.55 min; MS (ESIpos): m/z=615 [M+H]$^+$ $^1$H NMR (300 MHz, DMSO-d6) δ[ppm]: 13.27 (s, 1H), 8.33-8.23 (m, 2H), 7.92-7.71 (m, 2H), 7.60-7.46 (m, 2H), 7.50-7.30 (m, 3H), 7.17-6.79 (m, 3H), 4.63 (q, 1H), 4.45 (d, 1H), 4.23-4.03 (m, 4H), 3.85 (s, 3H), 3.81 (d, 1H), 2.86 (s, 3H), 2.20 (s, 3H), 2.30-1.98 (m, 3H), 1.72 (s, 3H), 1.46 (dd, 3H), 0.81 (dt, 3H).

Example 19

(rac)-13-Chloro-12-ethyl-1-(3-((6-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide

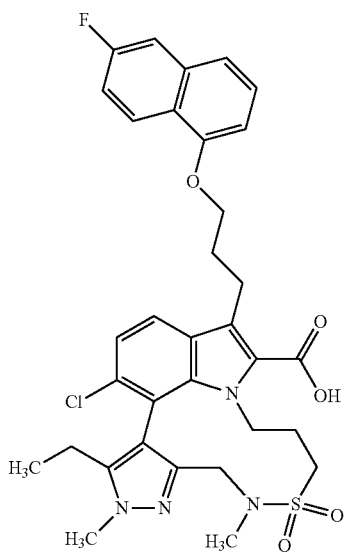 [SMILES: CCc1c2c(nn1C)CN(C)S(=O)(=O)CCCn1c(C(=O)O)c(CCCOc3cccc4cc(F)ccc34)c3ccc(Cl)c-2c31]

To a stirred solution of (rac)-ethyl 13-chloro-12-ethyl-1-(3-((6-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (see Intermediate 52, 168 mg, 246 μmol) in ethanol (980 μL) was added a 2 M solution of aqueous sodium hydroxide (307 μL, 614 μmol). The resulting solution was heated to 60° C. for 18 h, cooled to room temperature and then acidified with 1 N aqueous hydrochloric acid. Celite was added to the resulting mixture, and volatiles were removed under reduced pressure. The residue was purified by reverse phase column chromatography on C18-silica gel (10-100% acetonitrile/water with 0.1% formic acid gradient) to give, after lyophilization, the title compound (145 mg) as a white solid.

LC-MS (Method 4): $R_t$=4.54 min; MS (ESIneg): m/z=652 [M–H]⁻

$^1$H NMR (300 MHz, DMSO-d6) δ[ppm]: 13.41 (s, 1H), 8.31 (dd, 1H), 7.83 (d, 1H), 7.66 (dd, 1H), 7.54-7.34 (m, 3H), 7.27 (d, 1H), 6.85 (dd, 1H), 4.46 (d, 1H), 4.25-3.93 (m, 5H), 3.86 (s, 3H), 2.72 (s, 4H), 2.29-2.09 (m, 3H), 1.97-1.56 (m, 3H), 0.78 (t, 3H).

The title compound (135 mg) was separated into enantiomers by preparative chiral HPLC to give enantiomer 1 (64 mg, see Example 36) and enantiomer 2 (66 mg, see Example 37).

Preparative Chiral HPLC Method:
Instrument: Labomatic HD5000, Labocord-5000; Gilson GX-241, Labcol Vario 4000, Column: Chiralpak IG 5μ 250×30 mm; Eluent A: Hexane+0.1 Vol-% Trifluoroacetic acid (99%); Eluent B: Acetonitrile; Gradient: 40-80% B in 20 min; Flow 40.0 mL/min; UV 254 nm Analytical Chiral HPLC Method:
Instrument: Waters Alliance 2695 Agilent HPLC 1260; Column: Chiralpak IG 3μ 100×4.6 mm; Eluent A: Hexane+0.1 Vol-% Trifluoroacetic acid (99%); Eluent B: Acetonitrile; Gradient: 20-90% B in 7 min; Flow 1.4 mL/min; Temperature: 25° C.; DAD 254 nm

Example 20

(rac)-13-Chloro-12-ethyl-8,11-dimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide

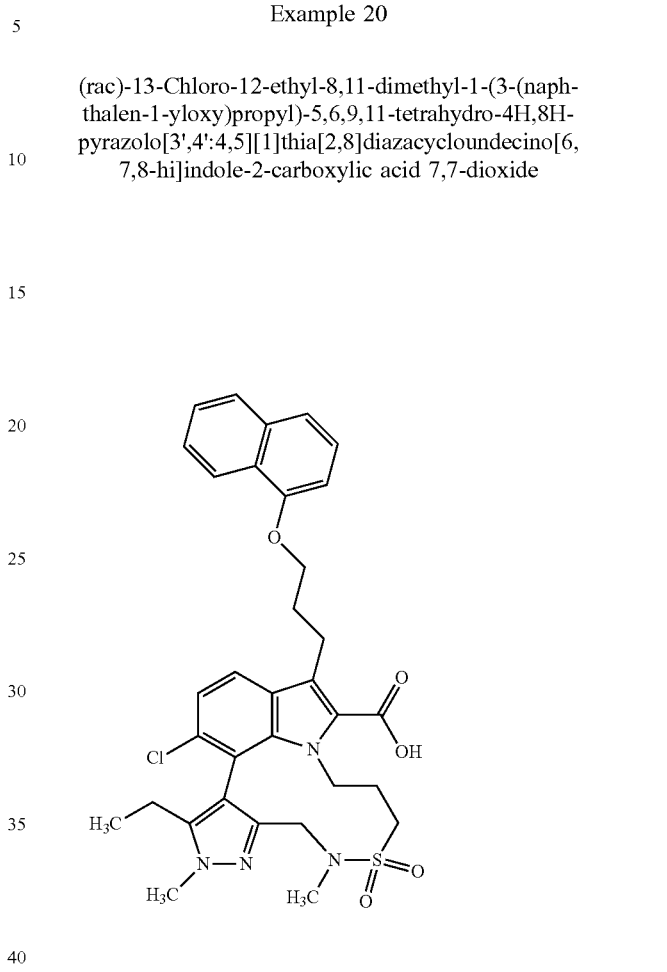

To a stirred solution of (rac)-ethyl 13-chloro-12-ethyl-8,11-dimethyl-1-(3-(naphthalen-1-yloxy)propyl)-4,5,6,8,9,11-hexahydropyrazolo[3',4':4,5][1,2,8]thiadiazacycloundecino[6,7,8-hi]indole-2-carboxylate 7,7-dioxide (see Intermediate 53, 47 mg, 70.8 μmol) in ethanol (283 μL) was added a solution of 2 M aqueous sodium hydroxide (88.5 μL, 177 μmol). The resulting solution was heated to 60° C. for 18 h, cooled to room temperature, and then acidified with 1 N aqueous hydrochloric acid. Celite was added to the resulting mixture, and volatiles were removed under reduced pressure. The residue was purified by reverse phase column chromatography on C18-silica gel (10-100% acetonitrile/water with 0.1% formic acid gradient) to give, after lyophilization, the title compound (39.1 mg) as a white solid.

LC-MS (Method 4): $R_t$=4.46 min; MS (ESIneg): m/z=634 [M–H]⁻

$^1$H NMR (300 MHz, DMSO-d6) δ[ppm]: 13.41 (s, 1H), 8.31-8.22 (m, 1H), 7.92-7.78 (m, 2H), 7.58-7.48 (m, 2H), 7.50-7.31 (m, 2H), 7.25 (d, 1H), 6.86 (d, 1H), 4.47 (d, 1H), 4.22-4.06 (m, 4H), 4.02 (d, 1H), 3.86 (s, 3H), 2.72 (s, 4H), 2.17 (m, 3H), 1.96-1.81 (m, 1H), 1.72 (s, 3H), 0.78 (t, 3H).

Example 21

(rac)-13-Chloro-1-(3-((2,3-dihydro-1H-inden-4-yl)oxy)propyl)-12-ethyl-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide

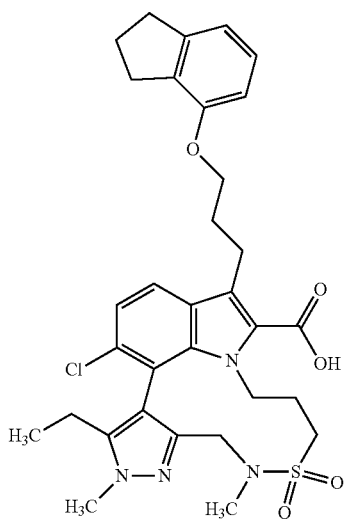 [SMILES: CCc1c2c(nn1C)CN(C)S(=O)(=O)CCCn1c(C(=O)O)c(CCCOc3cccc4c3CCC4)c3ccc(Cl)c-2c31]

To a stirred solution of (rac)-ethyl 13-chloro-1-(3-((2,3-dihydro-1H-inden-4-yl)oxy)propyl)-12-ethyl-8,11-dimethyl-4,5,6,8,9,11-hexahydropyrazolo[3',4':4,5][1,2,8]thiadiazacycloundecino-[6,7,8-hi]indole-2-carboxylate 7,7-dioxide (see Intermediate 54, 45.1 mg, 69.0 µmol) in ethanol (276 µL) was added a solution of 2 M aqueous sodium hydroxide (86.0 µL, 172 µmol). The resulting yellow solution was heated to 60° C. for 18 h, cooled to room temperature, and then acidified with 1 N aqueous hydrochloric acid. Celite was added to the resulting mixture, and volatiles were removed under reduced pressure. The residue was purified by reverse phase column chromatography on C18-silica gel (10-100% acetonitrile/water with 0.1% formic acid gradient) to give, after lyophilization, the title compound (33.4 mg).

LC-MS (Method 4): $R_t$=4.54 min; MS (ESIneg): m/z=624 [M−H]−

$^1$H NMR (300 MHz, DMSO-d6) δ[ppm]: 7.79 (d, 1H), 7.31 (d, 1H), 7.03 (t, 1H), 6.80 (d, 1H), 6.61 (d, 1H), 4.45 (d, 1H), 4.19-3.90 (m, 5H), 3.86 (s, 3H), 3.29-3.08 (m, 1H), 2.83 (dt, 4H), 2.72 (s, 4H), 2.31-1.55 (m, 8H), 0.79 (t, 3H).

Example 22

(rac)-13-Chloro-1-(3-(4-chloro-3,5-dimethylphenoxy)propyl)-12-ethyl-8,11-dimethyl-4,5,6,8,9,11-hexahydropyrazolo[3',4':4,5][1,2,8]thiadiazacycloundecino[6,7,8-hi]indole-2-carboxylic acid 7,7-dioxide

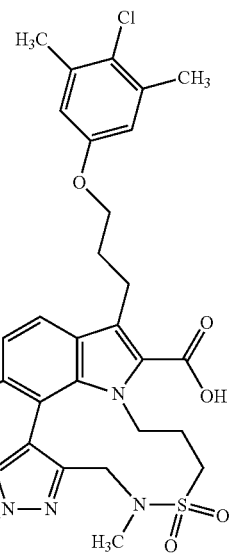

To a stirred solution of (rac)-ethyl 13-chloro-1-(3-(4-chloro-3,5-dimethylphenoxy)propyl)-12-ethyl-8,11-dimethyl-4,5,6,8,9,11-hexahydropyrazolo[3',4':4,5][1,2,8]thiadiazacycloundecino-[6,7,8-hi]indole-2-carboxylate 7,7-dioxide (see Intermediate 55, 47.7 mg, 70.5 µmol) in ethanol (282 µL) was added a solution of 2 M aqueous sodium hydroxide (88.0 µL, 176 µmol). The resulting yellow solution was heated to 60° C. for 18 h, cooled to room temperature, and then acidified with 1 N aqueous hydrochloric acid. Celite was added to the resulting mixture, and volatiles were removed under reduced pressure. The residue was purified by reverse phase column chromatography on C18-silica gel (10-100% acetonitrile/water with 0.1% formic acid gradient) to give, after lyophilization, the title compound (39.3 mg) as a white solid.

LC-MS (Method 4): $R_t$=4.73 min; MS (ESIneg): m/z=646 [M−H]−

$^1$H NMR (300 MHz, DMSO-d6) δ[ppm]: 13.32 (s, 1H), 7.80 (d, 1H), 7.31 (d, 1H), 6.72 (s, 2H), 4.44 (d, 1H), 4.20-3.88 (m, 4H), 3.86 (s, 3H), 3.17 (m, 2H), 2.71 (s, 4H), 2.26 (s, 7H), 2.24-1.95 (m, 3H), 1.93-1.54 (m, 3H), 0.78 (t, 3H).

Example 23

(rac)-13-Chloro-12-ethyl-8,11-dimethyl-1-(3-((5,6,7,8-tetrahydronaphthalen-1-yl)oxy)propyl)-4,5,6,8,9,11-hexahydropyrazolo[3',4':4,5][1,2,8]thiadiazacycloundecino[6,7,8-hi]indole-2-carboxylic acid 7,7-dioxide

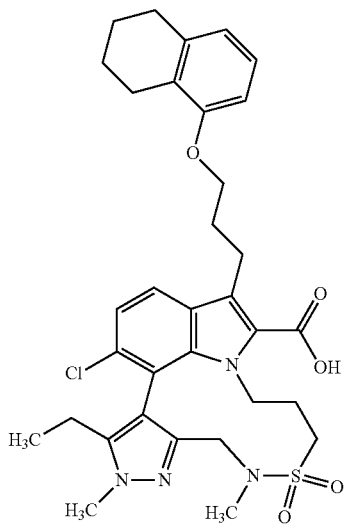 [SMILES: CCc1c2c(nn1C)CN(C)S(=O)(=O)CCCn1c(C(=O)O)c(CCCOc3cccc4c3CCCC4)c3ccc(Cl)c-2c31]

To a stirred solution of (rac)-ethyl 13-chloro-12-ethyl-8,11-dimethyl-1-(3-((5,6,7,8-tetrahydronaphthalen-1-yl)oxy)propyl)-4,5,6,8,9,11-hexahydropyrazolo[3',4':4,5][1,2,8]thiadiazacycloundecino[6,7,8-hi]indole-2-carboxylate 7,7-dioxide (see Intermediate 56, 48 mg, 71.9 μmol) in ethanol (287 μL) was added a solution of 2 M aqueous sodium hydroxide (89.5 μL, 179 μmol). The resulting solution was heated to 60° C. for 18 h, cooled to room temperature, and then acidified with 1 N aqueous hydrochloric acid. Celite was added to the resulting mixture, and volatiles were removed under reduced pressure. The residue was purified by reverse phase column chromatography on C18-silica gel (10-100% acetonitrile/water with 0.1% formic acid gradient) to give, after lyophilization, the title compound (35.3 mg) as a white solid.

LC-MS (Method 4): $R_t$=4.81 min; MS (ESIneg): m/z=638 [M-H]$^-$ $^1$H NMR (300 MHz, DMSO-d6) δ[ppm]: 13.34 (s, 1H), 7.79 (d, 1H), 7.32 (d, 1H), 6.98 (t, 1H), 6.67-6.55 (m, 2H), 4.45 (d, 1H), 4.20-4.01 (m, 2H), 3.94 (t, 2H), 3.86 (s, 3H), 3.28-3.11 (m, 1H), 2.75-2.57 (m, 9H), 2.28-1.97 (m, 5H), 1.87 (dd, 1H), 1.72 (s, 6H), 0.79 (t, H).

Example 24

(rac)-13-Chloro-12-ethyl-1-(34(4-fluoronaphthalen-1-yl)oxy)propyl)-8,11-dimethyl-4,5,6,8,9,11-hexahydropyrazolo[3',4':4,5][1,2,8]thiadiazacycloundecino[6,7,8-hi]indole-2-carboxylic acid 7,7-dioxide

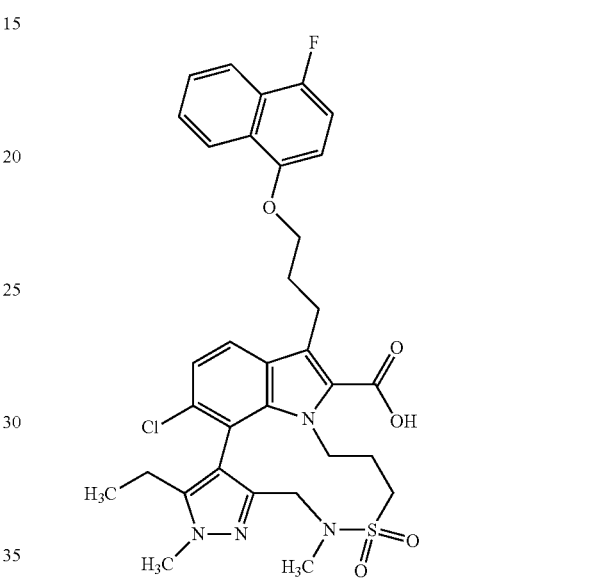

To a stirred solution of (rac)-ethyl 13-chloro-12-ethyl-1-(34(4-fluoronaphthalen-1-yl)oxy)propyl)-8,11-dimethyl-4,5,6,8,9,11-hexahydropyrazolo[3',4':4,5][1,2,8]thiadiazacyclo-undecino[6,7,8-hi]indole-2-carboxylate 7,7-dioxide (see Intermediate 57, 40.3 mg, 59.1 μmol) in ethanol (236 μL) was added a solution of 2 M aqueous sodium hydroxide (73.5 μL, 147 μmol). The resulting solution was heated to 60° C. for 18 h, cooled to room temperature, and then acidified with 1 N aqueous hydrochloric acid. Celite was added to the resulting mixture, and volatiles were removed under reduced pressure. The residue was purified by reverse phase column chromatography on C18-silica gel (10-100% acetonitrile/water with 0.1% formic acid gradient) to give, after lyophilization, the title compound (28.6 mg) as a white solid.

LC-MS (Method 4): $R_t$=4.57 min; MS (ESIneg): m/z=652 [M-H]$^-$ $^1$H NMR (300 MHz, DMSO-d6) δ[ppm]: 13.43 (s, 1H), 8.30 (dt, 1H), 8.06-7.95 (m, 1H), 7.82 (d, 1H), 7.73-7.58 (m, 2H), 7.30-7.13 (m, 2H), 6.80 (dd, 1H), 4.47 (d, 1H), 4.20-3.92 (m, 5H), 3.86 (s, 3H), 3.33-3.20 (m, 1H), 2.72 (s, 4H), 2.25-2.07 (m, 3H), 1.88 (dd, 1H), 1.71 (s, 3H), 0.78 (t, 3H).

Example 25

(rac)-13-Fluoro-1-(3-((6-fluoronaphthalen-1-yl)oxy)propyl)-8,11,12-trimethyl-5,6,9,11-tetrahydro-4H,8H-pyrazolo[3',4':4,5][1]thia[2,8]diazacycloundecino[6,7,8-hi]indole-2-carboxylic acid 7,7-dioxide

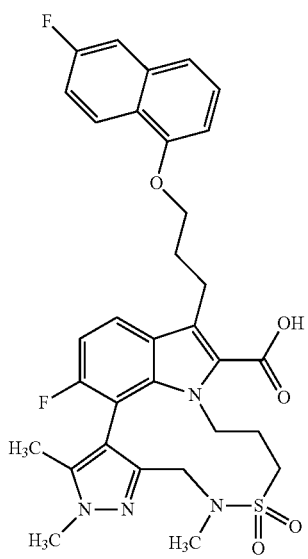 [SMILES: Cc1c2c(nn1C)CN(C)S(=O)(=O)CCCn1c(C(=O)O)c(CCCOc3cccc4cc(F)ccc34)c3ccc(F)c-2c31]

To a stirred solution of (rac)-ethyl 13-fluoro-1-(3-((6-fluoronaphthalen-1-yl)oxy)propyl)-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 68, 195 mg, 300 μmol, 1.00 eq.) in ethanol (1.20 mL, 0.25 M) was added a 2.0 M solution of sodium hydroxide in water (374 μL, 750 μmol, 2.50 eq.). The resulting yellow solution was heated to 70° C. for 3 days, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as an off-white solid (120 mg).

LC-MS (Method 4): $R_t$=4.15 min; MS (ESIpos): m/z=623 [M+H]$^+$.

$^1$H-NMR (300 MHz, DMSO-d) δ [ppm]: 13.30 (s, 1H), 8.31 (dd, 1H), 7.85 (dd, 1H), 7.66 (dd, 1H), 7.42 (m, 3H), 7.05 (t, 1H), 6.86 (dd, 1H), 4.52 (m, 1H), 4.11 (m, 5H), 3.83 (s, 3H), 3.33 (m, 4H), 2.71 (m, 3H), 2.20 (t, 2H), 2.07 (m, 1H), 1.85 (s, 3H), 1.71 (m, 2H).

The title compound (118 mg) was separated into enantiomers by preparative chiral HPLC to give enantiomer 1 (54 mg, see Example 38) and enantiomer 2 (54 mg, see Example 39).

Preparative Chiral HPLC Method:
Instrument: Labomatic HD5000, Labocord-5000; Gilson GX-241, Labcol Vario 4000, Column: YMC Cellulose SC 5μ 250×30 mm; Eluent A: Hexane+0.1 Vol-% Trifluoroacetic acid (99%); Eluent B: 2-Propanol; Gradient: 20-50% B in 20 min; Flow 40.0 mL/min; UV 254 nm Analytical Chiral HPLC Method:
Instrument: Waters Alliance 2695 Agilent HPLC 1260; Column: YMC Cellulose SC 3μ 100×4.6 mm; Eluent A: Hexane+0.1 Vol-% Trifluoroacetic acid (99%); Eluent B: 2-Propanol; Gradient: 20-50% B in 7 min; Flow 1.4 mL/min; Temperature: 25° C.; DAD 254 nm

Example 26

(rac)-13-Fluoro-8,11,12-trimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide

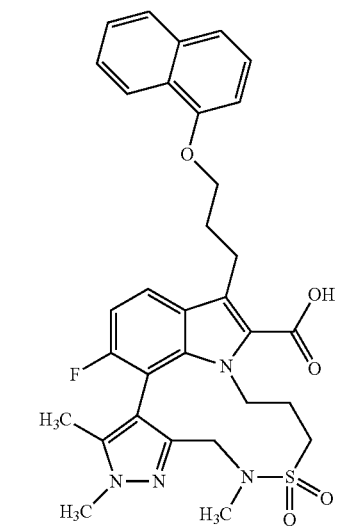 [SMILES: Cc1c2c(nn1C)CN(C)S(=O)(=O)CCCn1c(C(=O)O)c(CCCOc3cccc4ccccc34)c3ccc(F)c-2c31]

To a stirred solution of (rac)-ethyl 13-fluoro-8,11,12-trimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 69, 46.6 mg, 73.7 μmol, 1.00 eq.) in ethanol (0.30 mL, 0.25 M) was added a 2.0 M solution of sodium hydroxide in water (92.1 μL, 184 μmol, 2.50 eq.). The resulting yellow solution was heated to 70° C. for 20 hours, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as an off-white solid (27.8 mg).

LC-MS (Method 4): $R_t$=4.06 min; MS (ESIpos): m/z=605 [M+H]$^+$.

$^1$H-NMR (300 MHz, DMSO-d) 13.31 (s, 1H), 8.26 (m, 1H), 7.85 (m, 2H), 7.53 (m, 2H), 7.46 (d, 1H), 7.38 (m, 1H), 7.03 (t, 1H), 6.88 (m, 1H), 4.52 (d, 1H), 4.16 (m, 3H), 4.03 (m, 2H), 3.83 (s, 3H), 3.32 (s, 7H), 2.71 (s, 4H), 2.20 (m, 2H), 2.05 (m, 1H), 1.85 (s, 3H), 1.71 (m, 2H).

Example 27

(rac)-1-(3-((2,3-Dihydro-1H-inden-4-yl)oxy)propyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylic acid 7,7-dioxide

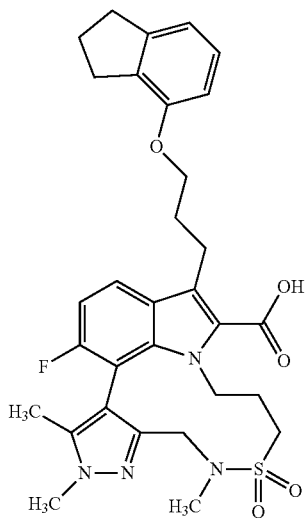 [SMILES: Cc1c2c(nn1C)CN(C)S(=O)(=O)CCCn1c(C(=O)O)c(CCCOc3cccc4c3CCC4)c3ccc(F)c-2c31]

To a stirred solution of (rac)-ethyl 1-(3-((2,3-dihydro-1H-inden-4-yl)oxy)propyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 70, 45.9 mg, 73.7 μmol, 1.00 eq.) in ethanol (0.30 mL, 0.25 M) was added a 2.0 M solution of sodium hydroxide in water (92.1 μL, 184 μmol, 2.50 eq.). The resulting yellow solution was heated to 70° C. for 20 hours, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as a white solid (23.5 mg).

LC-MS (Method 4): $R_t$=4.12 min; MS (ESIpos): m/z=595 [M+H]$^+$.

$^1$H-NMR (300 MHz, DMSO-d) δ [ppm]: 13.24 (s, 1H), 7.80 (dd, 1H), 7.06 (m, 2H), 6.79 (d, 1H), 6.62 (d, 1H), 4.50 (m, 1H), 4.05 (m, 5H), 3.83 (s, 3H), 3.20 (m, 2H), 2.83 (m, 4H), 2.71 (m, 4H), 2.03 (m, 5H), 1.86 (s, 3H), 1.70 (m, 3H).

Example 28

(rac)-1-(3-(4-Chloro-3,5-dimethylphenoxy)propyl)-13-fluoro-8,11,12-trimethyl-5,6,9,11-tetrahydro-4H,8H-pyrazolo[3',4':4,5][1]thia[2,8]diazacycloundecino[6,7,8-hi]indole-2-carboxylic acid 7,7-dioxide

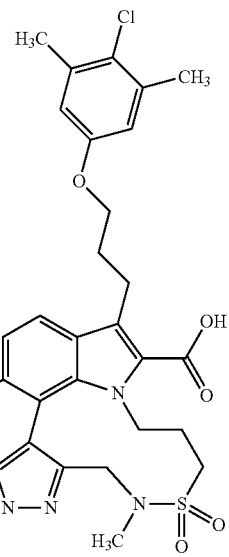

To a stirred solution of (rac)-ethyl 1-(3-(4-chloro-3,5-dimethylphenoxy)propyl)-13-fluoro-8,11,12-trimethyl-5,6,9,11-tetrahydro-4H,8H-pyrazolo[3',4':4,5][1]thia[2,8]diazacycloundecino-[6,7,8-hi]indole-2-carboxylate 7,7-dioxide (see intermediate 71, 47.5 mg, 73.7 μmol, 1.00 eq.) in ethanol (0.30 mL, 0.25 M) was added a 2.0 M solution of sodium hydroxide in water (92.1 μL, 184 μmol, 2.50 eq.). The resulting yellow solution was heated to 70° C. for 20 hours, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as a white solid (24.8 mg).

LC-MS (Method 4): $R_t$=4.32 min; MS (ESIpos): m/z=617 [M+H]$^+$.

$^1$H-NMR (300 MHz, DMSO-d) δ [ppm]: 13.24 (s, 1H), 7.81 (dd, 1H), 7.09 (t, 1H), 6.73 (s, 2H), 4.50 (m, 1H), 4.02 (m, 5H), 3.83 (s, 3H), 3.18 (m, 2H), 2.70 (m, 4H), 2.27 (s, 6H), 2.03 (m, 3H), 1.86 (s, 3H), 1.67 (m, 3H).

Example 29

(rac)-13-Fluoro-8,11,12-trimethyl-1-(3-((5,6,7,8-tetrahydronaphthalen-1-yl)oxy)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide

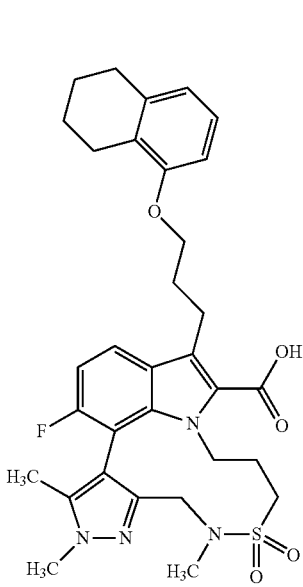 [SMILES: Cc1c2c(nn1C)CN(C)S(=O)(=O)CCCn1c(C(=O)O)c(CCCOc3cccc4c3CCCC4)c3ccc(F)c-2c31]

To a stirred solution of (rac)-ethyl 13-fluoro-8,11,12-trimethyl-1-(3-((5,6,7,8-tetrahydronaphthalen-1-yl)oxy)propyl)-5,6,9,11-tetrahydro-4H,8H-pyrazolo[3',4':4,5][1]thia-[2,8]diazacycloundecino[6,7,8-hi]indole-2-carboxylate 7,7-dioxide (see intermediate 72, 46.9 mg, 73.7 µmol, 1.00 eq.) in ethanol (0.30 mL, 0.25 M) was added a 2.0 M solution of sodium hydroxide in water (92.1 µL, 184 µmol, 2.50 eq.). The resulting yellow solution was heated to 70° C. for 20 hours, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as a white solid (20.0 mg).

LC-MS (Method 4): $R_t$=4.39 min; MS (ESIpos): m/z=609 [M+H]$^+$.

$^1$H-NMR (300 MHz, DMSO-d) δ [ppm]: 13.24 (s, 1H), 7.80 (dd, 1H), 7.10 (t, 1H), 6.98 (t, 1H), 6.62 (m, 2H), 4.51 (m, 1H), 4.04 (m, 5H), 3.83 (s, 3H), 3.21 (2, 1H), 2.67 (m, 8H), 2.03 (m, 3H), 1.86 (s, 3H), 1.71 (m, 7H).

Example 30

(rac)-13-Fluoro-1-(34(4-fluoronaphthalen-1-yl)oxy)propyl)-8,11,12-trimethyl-5,6,9,11-tetrahydro-4H,8H-pyrazolo[3',4':4,5][1]thia[2,8]diazacycloundecino[6,7,8-hi]indole-2-carboxylic acid 7,7-dioxide

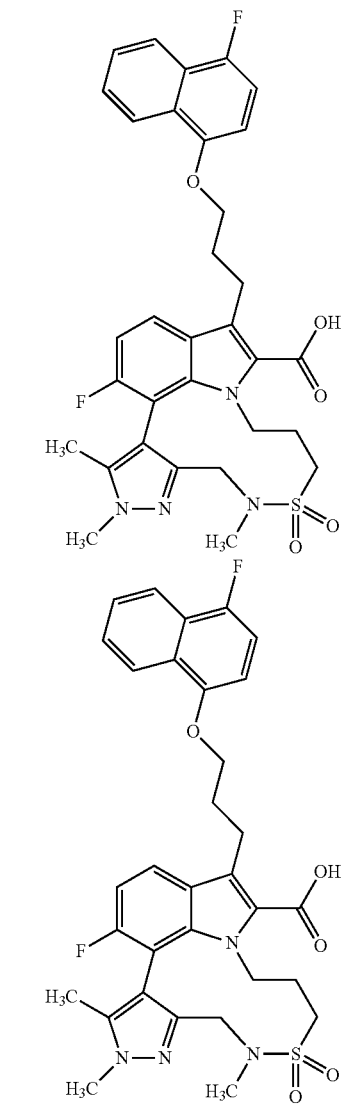

To a stirred solution of (rac)-ethyl 13-fluoro-1-(3-((4-fluoronaphthalen-1-yl)oxy)propyl)-8,11,12-trimethyl-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 73, 47.9 mg, 73.7 µmol, 1.00 eq.) in ethanol (0.30 mL, 0.25 M) was added a 2.0 M solution of sodium hydroxide in water (92.1 µL, 184 µmol, 2.50 eq.). The resulting yellow solution was heated to 70° C. for 20 hours, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as a white solid (23.1 mg).

Example 31

(rac)-12-Ethyl-13-fluoro-8,11-dimethyl-1-(3-(naph-thalen-1-yloxy)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide

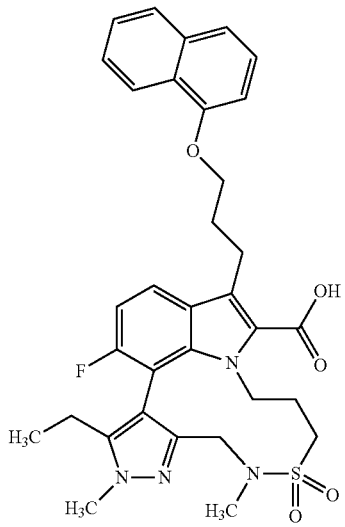 [SMILES: CCc1c2c(nn1C)CN(C)S(=O)(=O)CCCn1c(C(=O)O)c(CCCOc3cccc4ccccc34)c3ccc(F)c-2c31]

To a stirred solution of (rac)-ethyl 12-ethyl-13-fluoro-8,11-dimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide (see intermediate 81, 38.1 mg, 58.9 µmol, 1.00 eq.) in ethanol (0.24 mL, 0.25 M) was added a 2.0 M solution of sodium hydroxide in water (73.6 µL, 147 µmol, 2.50 eq.). The resulting yellow solution was heated to 70° C. for 20 hours, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as a white solid (17.1 mg).

LC-MS (Method 4): R$_t$=4.33 min; MS (ESIpos): m/z=619 [M+H]$^+$.

$^1$H-NMR (300 MHz, DMSO-d) δ [ppm]: 13.30 (s, 1H), 8.27 (m, 1H), 7.86 (m, 2H), 7.53 (m, 2H), 7.46 (d, 1H), 7.38 (t, 1H), 7.03 (t, 1H), 6.87 (m, 1H), 4.47 (m, 1H), 4.12 (m, 6H), 3.32 (m, 2H), 2.74 (m, 4H), 2.21 (m, 4H), 1.93 (m, 1H), 1.75 (m, 0H), 0.81 (t, 3H).

Example 32

(rac)-1-(3-((2,3-Dihydro-1H-inden-4-yl)oxy)propyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide

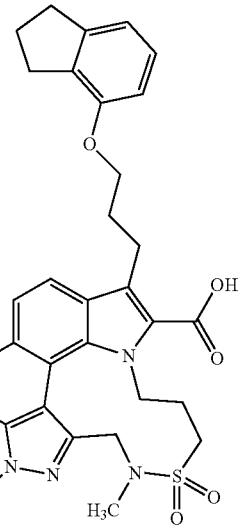

To a stirred solution of (rac)-ethyl 1-(34(2,3-dihydro-1H-inden-4-yl)oxy)propyl)-12-ethyl-13-fluoro-8,11-dimethyl-5,6,9,11-tetrahydro-4H,8H-pyrazolo[3',4':4,5][1]thia[2,8]diazacyclo-undecino[6,7,8-hi]indole-2-carboxylate 7,7-dioxide (see intermediate 82, 37.9 mg, 59.5 µmol, 1.00 eq.) in ethanol (0.24 mL, 0.25 M) was added a 2.0 M solution of sodium hydroxide in water (74.3 µL, 149 µmol, 2.50 eq.). The resulting yellow solution was heated to 70° C. for 20 hours, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as a white solid (28.0 mg).

LC-MS (Method 4): R$_t$=4.39 min; MS (ESIpos): m/z=609 [M+H]$^+$.

$^1$H-NMR (300 MHz, DMSO-d) δ [ppm]: 13.21 (s, 1H), 7.81 (dd, 1H), 7.06 (m, 2H), 6.80 (d, 1H), 6.62 (d, 1H), 4.45 (d, 1H), 4.17 (d, 1H), 3.99 (m, 4H), 3.86 (s, 3H), 3.20 (tt, 2H), 2.81 (m, 8H), 2.23 (hept, 2H), 2.00 (m, 5H), 1.73 (s, 2H), 0.81 (t, 3H).

---

LC-MS (Method 4): R$_t$=4.18 min; MS (ESIpos): m/z=623 [M+H]$^+$.

$^1$H-NMR (300 MHz, DMSO-d) δ [ppm]: $^1$H NMR (DMSO-d$_6$) δ: 13.31 (s, 1H), 8.29 (dt, 1H), 7.99 (m, 1H), 7.84 (dd, 1H), 7.66 (m, 2H), 7.20 (dd, 1H), 7.03 (t, 1H), 6.81 (dd, 1H), 4.52 (m, 1H), 4.13 (m, 5H), 3.83 (s, 3H), 3.31 (m, 5H), 2.71 (s, 4H), 2.21 (m, 2H), 2.04 (m, 1H), 1.84 (s, 3H), 1.71 (m, 3H).

Example 33

(rac)-1-(3-(4-Chloro-3,5-dimethylphenoxy)propyl)-12-ethyl-13-fluoro-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide

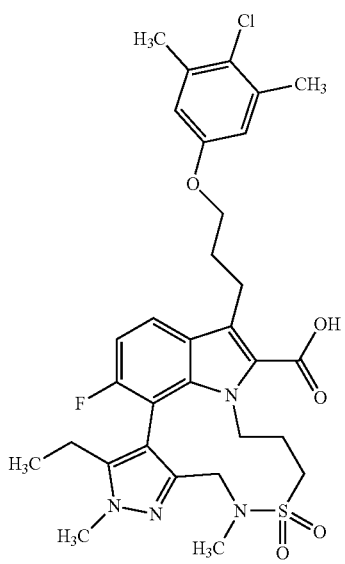 [SMILES: CCc1c2c(nn1C)CN(C)S(=O)(=O)CCCn1c(C(=O)O)c(CCCOc3cc(C)c(Cl)c(C)c3)c3ccc(F)c-2c31]

To a stirred solution of (rac)-ethyl 1-(3-(4-chloro-3,5-dimethylphenoxy)propyl)-12-ethyl-13-fluoro-8,11-dimethyl-5,6,9,11-tetrahydro-4H,8H-pyrazolo[3',4':4,5][1]thia[2,8]diazacyclo-undecino[6,7,8-hi]indole-2-carboxylate 7,7-dioxide (see intermediate 83, 39.7 mg, 60.0 μmol, 1.00 eq.) in ethanol (0.24 mL, 0.25 M) was added a 2.0 M solution of sodium hydroxide in water (75.2 μL, 151 μmol, 2.50 eq.). The resulting yellow solution was heated to 70° C. for 20 hours, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as a white solid (26.8 mg).

LC-MS (Method 4): $R_t$=4.58 min; MS (ESIpos): m/z=631 [M+H]$^+$.

$^1$H-NMR (300 MHz, DMSO-d) δ [ppm]: 13.22 (s, 1H), 7.82 (dd, 1H), 7.09 (t, 1H), 6.72 (s, 2H), 4.44 (m, 1H), 4.17 (d, 1H), 3.95 (m, 7H), 3.18 (m, 2H), 2.73 (m, 4H), 2.27 (s, 8H), 2.05 (m, 2H), 1.90 (m, 1H), 1.72 (m, 2H), 0.81 (t, 3H).

Example 34

(rac)-12-Ethyl-13-fluoro-8,11-dimethyl-1-(3-((5,6,7,8-tetrahydronaphthalen-1-yl)oxy)propyl)-5,6,9,11-tetrahydro-4H,8H-pyrazolo[3',4':4,5][1]thia[2,8]diazacycloundecino[6,7,8-hi]indole-2-carboxylic acid 7,7-dioxide

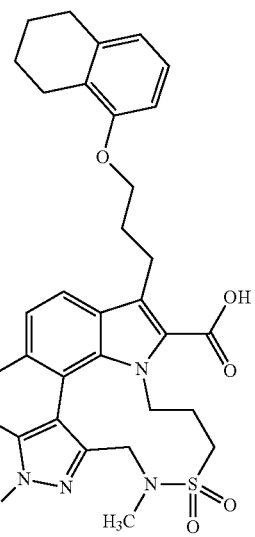

To a stirred solution of (rac)-ethyl 12-ethyl-13-fluoro-8,11-dimethyl-1-(3-((5,6,7,8-tetrahydronaphthalen-1-yl)oxy)propyl)-5,6,9,11-tetrahydro-4H,8H-pyrazolo[3',4':4,5][1]thia[2,8]-diazacycloundecino[6,7,8-hi]indole-2-carboxylate 7,7-dioxide (see intermediate 84, 37.8 mg, 58.1 μmol, 1.00 eq.) in ethanol (0.23 mL, 0.25 M) was added a 2.0 M solution of sodium hydroxide in water (72.6 μL, 145 μmol, 2.50 eq.). The resulting yellow solution was heated to 70° C. for 20 hours, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as a white solid (28.2 mg).

LC-MS (Method 4): $R_t$=4.65 min; MS (ESIpos): m/z=623 [M+H]$^+$.

$^1$H-NMR (300 MHz, DMSO-d) δ [ppm]: 13.24 (s, 1H), 7.81 (dd, 1H), 7.10 (t, 1H), 6.98 (t, 1H), 6.61 (t, 2H), 4.45 (m, 1H), 4.18 (d, 1H), 3.97 (m, 4H), 3.86 (s, 3H), 3.21 (m, 2H), 2.68 (m, 8H), 2.23 (m, 2H), 2.06 (m, 3H), 1.91 (m, 1H), 1.71 (m, 6H), 0.81 (t, 3H).

Example 35

(rac)-12-Ethyl-13-fluoro-1-(34(4-fluoronaphthalen-1-yl)oxy)propyl)-8,11-dimethyl-5,6,9,11-tetrahydro-4H,8H-pyrazolo[3',4':4,5][1]thia[2,8]diazacycloundecino[6,7,8-hi]indole-2-carboxylic acid 7,7-dioxide

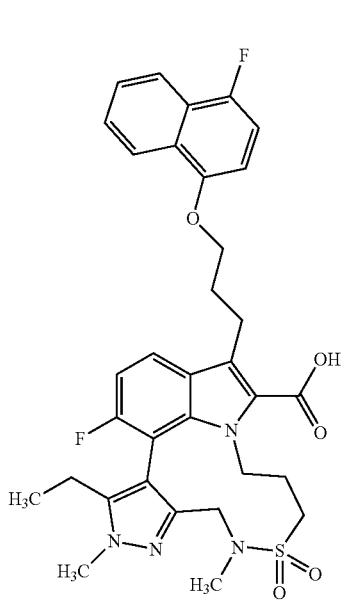 [SMILES: CCc1c2c(nn1C)CN(C)S(=O)(=O)CCCn1c(C(=O)O)c(CCCOc3ccc(F)c4ccccc34)c3ccc(F)c-2c31]

To a stirred solution of (rac)-ethyl 12-ethyl-13-fluoro-1-(34(4-fluoronaphthalen-1-yl)oxy)propyl)-8,11-dimethyl-5,6,9,11-tetrahydro-4H,8H-pyrazolo[3',4':4,5][1]thia[2,8]diazacycloundecino-[6,7,8-hi]indole-2-carboxylate 7,7-dioxide (see intermediate 85, 36.4 mg, 54.8 μmol, 1.00 eq.) in ethanol (0.22 mL, 0.25 M) was added a 2.0 M solution of sodium hydroxide in water (68.4 μL, 137 μmol, 2.50 eq.). The resulting yellow solution was heated to 70° C. for 20 hours, cooled to room temperature and then acidified with 1.0 M aqueous hydrochloric acid. Celite was added to the resulting mixture, and volatiles were removed under reduced pressure. The residue was purified by reverse phase column chromatography (10-100% acetonitrile/water with 0.1% formic acid gradient) to give the title compound as a white solid (22.6 mg).

LC-MS (Method 4): $R_t$=4.43 min; MS (ESIpos): m/z=637 [M+H]$^+$.

$^1$H-NMR (300 MHz, DMSO-d) δ [ppm]: 13.29 (s, 1H), 8.30 (dt, 1H), 7.99 (m, 1H), 7.85 (dd, 1H), 7.66 (m, 2H), 7.20 (dd, 1H), 7.03 (t, 1H), 6.81 (dd, 1H), 4.47 (d, 1H), 4.10 (m, 5H), 3.86 (s, 3H), 3.32 (m, 5H), 2.74 (m, 4H), 2.22 (m, 4H), 1.91 (m, 1H), 1.74 (m, 2H), 0.80 (t, 3H).

Example 36

(+)-4-chloro-3-ethyl-7-{3-[(6-fluoronaphthalen-1-yl)oxy]propyl}-2,14-dimethyl-13,13-dioxo-10,11,12,13,14,15-hexahydro-2H-13lambda$^6$-pyrazolo[3',4':4,5][1,2,8]thiadiazacycloundecino-[6,7,8-hi]indole-8-carboxylic acid (Enantiomer 1)

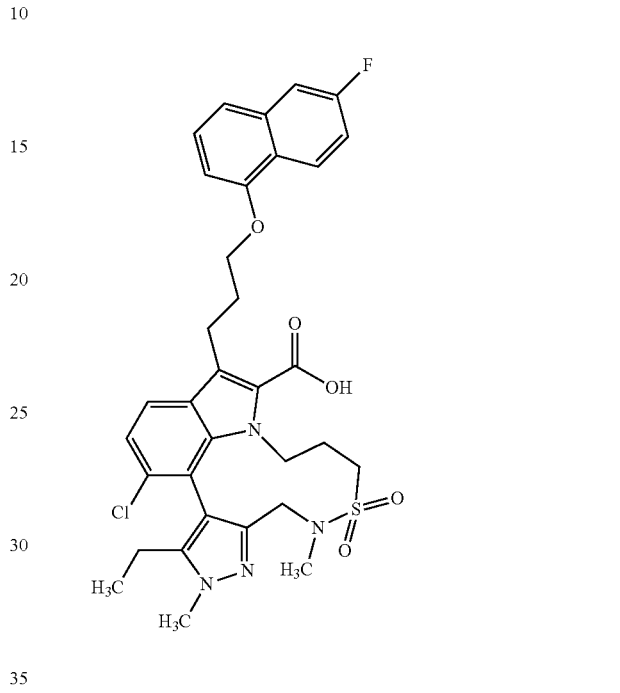

For the preparation of the racemic title compound see example 19. Separation of enantiomers by preparative chiral HPLC (method see example 19) gave the title compound (64 mg). The material was dried by lyophilisation to give 53.1 mg of the title compound.

Analytical Chiral HPLC (method see example 19): $R_t$=5.15 min.

LC-MS (Method 2): $R_t$=0.93 min; MS (ESIpos): m/z=653 [M+H]$^+$

Specific Optical Rotation (Method O1): 65.8° (c=10 mg/mL, DMSO)

$^1$H-NMR (400 MHz, DMSO-d6) δ[ppm]: 0.758 (3.26), 0.777 (7.43), 0.797 (3.43), 1.154 (0.79), 1.228 (0.53), 1.667 (0.47), 1.745 (0.56), 1.850 (0.50), 1.886 (0.59), 1.906 (0.47), 2.095 (0.41), 2.114 (0.76), 2.133 (1.26), 2.151 (1.20), 2.164 (1.53), 2.183 (2.29), 2.200 (2.32), 2.219 (1.35), 2.233 (0.47), 2.322 (0.82), 2.326 (1.14), 2.332 (0.82), 2.518 (6.34), 2.522 (4.08), 2.664 (0.91), 2.669 (1.35), 2.673 (1.29), 2.678 (1.00), 2.715 (7.93), 3.266 (1.23), 3.299 (3.29), 3.856 (16.00), 4.001 (0.68), 4.012 (0.50), 4.027 (0.50), 4.039 (0.44), 4.050 (0.73), 4.088 (2.06), 4.112 (2.32), 4.150 (1.67), 4.159 (2.41), 4.173 (1.20), 4.449 (0.65), 4.473 (0.44), 4.483 (0.59), 6.833 (1.26), 6.838 (1.29), 6.850 (1.29), 6.855 (1.32), 7.250 (3.11), 7.271 (3.20), 7.370 (0.79), 7.376 (0.88), 7.392 (1.35), 7.399 (1.97), 7.415 (1.17), 7.421 (2.73), 7.437 (4.37), 7.455 (0.59), 7.644 (1.53), 7.651 (1.61), 7.670 (1.56), 7.677 (1.56), 7.811 (2.58), 7.832 (2.35), 8.290 (1.29), 8.305 (1.38), 8.313 (1.32), 8.328 (1.26).

Example 37

(−)-4-chloro-3-ethyl-7-{3-[(6-fluoronaphthalen-1-yl)oxy]propyl}-2,14-dimethyl-13,13-dioxo-10,11,12,13,14,15-hexahydro-2H-13lambda⁶-pyrazolo[3',4':4,5][1,2,8]thiadiazacycloundecino-[6,7,8-hi]indole-8-carboxylic acid (Enantiomer 2)

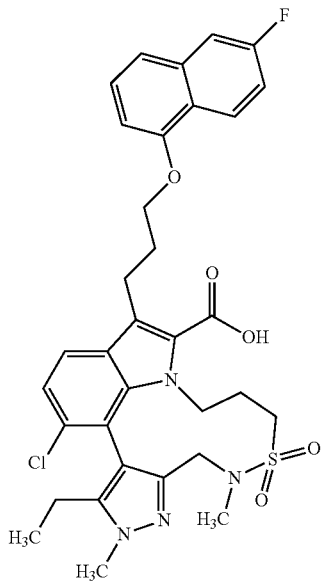 [SMILES: CCc1c2c(nn1C)CN(C)S(=O)(=O)CCCn1c(C(=O)O)c(CCCOc3cccc4cc(F)ccc34)c3ccc(Cl)c-2c31]

For the preparation of the racemic title compound see example 19. Separation of enantiomers by preparative chiral HPLC (method see example 19) gave the title compound (66 mg)). The material was dried by lyophilisation to give 51.1 mg of the title compound.

Analytical Chiral HPLC (method see example 19): $R_t$=5.55 min.

LC-MS (Method 2): $R_t$=0.93 min; MS (ESIpos): m/z=653 [M+H]⁺

Specific Optical Rotation (Method O1): −69.5° (c=10 mg/mL, DMSO)

¹H-NMR (400 MHz, DMSO-d6) δ[ppm]: 0.760 (3.05), 0.779 (6.98), 0.798 (3.27), 1.231 (0.43), 1.666 (0.43), 1.747 (0.50), 1.848 (0.47), 1.885 (0.53), 2.097 (0.41), 2.116 (0.71), 2.133 (1.17), 2.152 (1.12), 2.166 (1.43), 2.185 (2.08), 2.203 (2.05), 2.221 (1.15), 2.332 (0.71), 2.518 (5.84), 2.522 (3.82), 2.673 (0.88), 2.679 (0.71), 2.718 (7.53), 2.739 (0.69), 3.269 (0.55), 3.283 (0.86), 3.302 (1.74), 3.858 (16.00), 4.006 (0.64), 4.017 (0.47), 4.032 (0.47), 4.051 (0.74), 4.089 (1.86), 4.114 (2.12), 4.153 (1.52), 4.161 (2.31), 4.176 (1.15), 4.447 (0.62), 4.458 (0.47), 4.472 (0.41), 4.482 (0.55), 6.836 (1.22), 6.841 (1.29), 6.853 (1.24), 6.858 (1.33), 7.255 (3.44), 7.276 (3.39), 7.371 (0.79), 7.378 (0.88), 7.393 (1.29), 7.400 (1.84), 7.416 (1.03), 7.423 (2.88), 7.440 (4.34), 7.456 (0.55), 7.646 (1.45), 7.653 (1.50), 7.672 (1.48), 7.679 (1.45), 7.816 (2.82), 7.837 (2.60), 8.292 (1.26), 8.307 (1.34), 8.315 (1.29), 8.330 (1.22).

Example 38

(−)-4-fluoro-7-{3-[(6-fluoronaphthalen-1-yl)oxy]propyl}-2,3,14-trimethyl-13,13-dioxo-10,11,12,13,14,15-hexahydro-2H-13lambda⁶-pyrazolo[3',4':4,5][1,2,8]thiadiazacycloundecino-[6,7,8-hi]indole-8-carboxylic acid (Enantiomer 1)

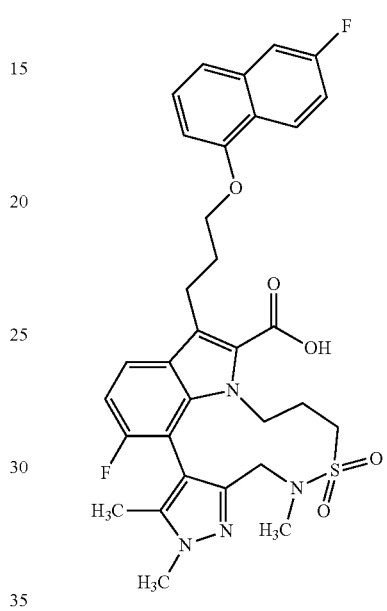

For the preparation of the racemic title compound see Example 25. Separation of enantiomers by preparative chiral HPLC (method see Example 25) gave the title compound (54 mg).

Analytical Chiral HPLC (method see Example 25): $R_t$=3.74 min.

LC-MS (Method 2): $R_t$=0.88 min; MS (ESIpos): m/z=623 [M+H]⁺

Specific Optical Rotation (Method O1): −95.0° (c=10 mg/mL, DMSO)

1H-NMR (400 MHz, DMSO-d6) delta [ppm]: 0.967 (0.27), 1.107 (16.00), 1.144 (0.18), 1.231 (0.19), 1.845 (4.47), 2.179 (0.30), 2.196 (0.47), 2.213 (0.31), 2.322 (0.25), 2.326 (0.34), 2.332 (0.24), 2.518 (1.24), 2.522 (0.80), 2.664 (0.39), 2.668 (0.48), 2.673 (0.33), 2.678 (0.24), 2.687 (0.18), 2.710 (2.51), 3.266 (0.18), 3.280 (0.19), 3.299 (0.31), 3.337 (0.16), 3.356 (0.32), 3.375 (0.22), 3.389 (0.24), 3.408 (0.17), 3.516 (0.72), 3.986 (0.21), 4.039 (0.30), 4.077 (0.52), 4.140 (0.61), 4.156 (0.35), 4.172 (0.73), 4.187 (0.37), 4.498 (0.20), 4.534 (0.18), 6.846 (0.38), 6.853 (0.39), 6.862 (0.35), 6.868 (0.40), 7.025 (0.42), 7.047 (0.70), 7.070 (0.43), 7.369 (0.24), 7.376 (0.29), 7.392 (0.38), 7.399 (0.42), 7.405 (0.17), 7.414 (0.28), 7.421 (0.35), 7.426 (0.68), 7.436 (0.78), 7.442 (1.67), 7.646 (0.44), 7.653 (0.46), 7.672 (0.44), 7.679 (0.45), 7.832 (0.38), 7.846 (0.41), 7.854 (0.42), 7.868 (0.38), 8.286 (0.39), 8.301 (0.41), 8.309 (0.40), 8.324 (0.38).

325

Example 39

(+)-4-fluoro-7-{3-[(6-fluoronaphthalen-1-yl)oxy]propyl}-2,3,14-trimethyl-13,13-dioxo-10,11,12,13,14,15-hexahydro-2H-13lambda⁶-pyrazolo[3',4':4,5][1,2,8]thiadiazacycloundecino-[6,7,8-hi]indole-8-carboxylic acid (Enantiomer 2)

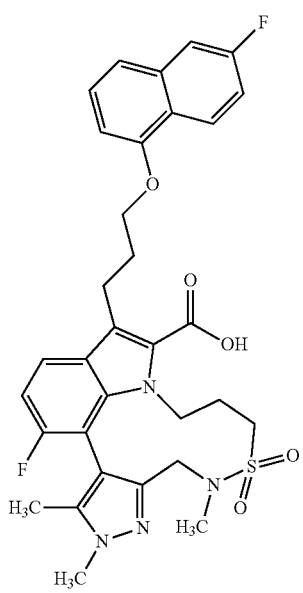 [SMILES: Cc1c2c(nn1C)CN(C)S(=O)(=O)CCCn1c(C(=O)O)c(CCCOc3cccc4cc(F)ccc34)c3ccc(F)c-2c31]

For the preparation of the racemic title compound see Example 25. Separation of enantiomers by preparative chiral HPLC (method see Example 25) gave the title compound (54 mg).

Analytical Chiral HPLC (method see Example 25): $R_t$=4.38 min.

LC-MS (Method 2): $R_t$=0.88 min; MS (ESIpos): m/z=623 [M+H]⁺

Specific Optical Rotation (Method O1): 86.4° (c=10 mg/mL, DMSO)

1H-NMR (400 MHz, DMSO-d6) delta [ppm]: 0.967 (0.16), 1.107 (16.00), 1.232 (0.21), 1.845 (4.17), 2.179 (0.27), 2.196 (0.42), 2.212 (0.28), 2.322 (0.32), 2.326 (0.44), 2.332 (0.32), 2.518 (1.67), 2.522 (1.07), 2.664 (0.46), 2.669 (0.58), 2.673 (0.40), 2.678 (0.26), 2.709 (2.30), 3.266 (0.17), 3.280 (0.19), 3.299 (0.31), 3.318 (0.17), 3.337 (0.20), 3.356 (0.38), 3.375 (0.34), 3.389 (0.45), 3.828 (4.45), 3.986 (0.19), 4.039 (0.27), 4.077 (0.48), 4.140 (0.56), 4.156 (0.32), 4.173 (0.67), 4.187 (0.33), 4.499 (0.18), 4.534 (0.16), 6.846 (0.34), 6.853 (0.36), 6.862 (0.32), 6.868 (0.37), 7.025 (0.41), 7.047 (0.64), 7.070 (0.40), 7.370 (0.23), 7.376 (0.27), 7.392 (0.35), 7.399 (0.39), 7.414 (0.26), 7.421 (0.32), 7.426 (0.62), 7.436 (0.70), 7.442 (1.55), 7.646 (0.42), 7.653 (0.43), 7.672 (0.42), 7.679 (0.42), 7.832 (0.36), 7.846 (0.38), 7.854 (0.40), 7.868 (0.36), 8.286 (0.36), 8.301 (0.38), 8.309 (0.37), 8.324 (0.35).

326

Example 40

(rac)-4-chloro-14-cyclopropyl-2,3-dimethyl-7-[3-(1-naphthyloxy)propyl]-11,12,14,15-tetrahydro-2H,10H-pyrazolo[3',4':4,5][1,2,8]thiadiazacycloundecino[6,7,8-hi]indole-8-carboxylic acid 13,13-dioxide

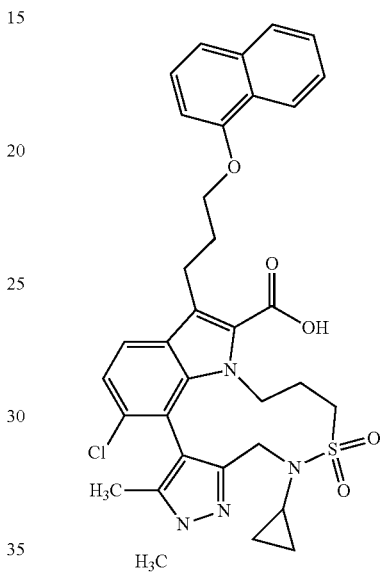

To a solution of ethyl 13-chloro-8-cyclopropyl-11,12-dimethyl-1-(3-(naphthalen-1-yloxy)propyl)-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 105, 40 mg, 59.2 μmol) in ethanol (236 μL) was added a 2 M aqueous solution of sodium hydroxide (74.0 μL, 148 μmol). The resulting mixture was heated at 60° C. for 18 h, cooled to room temperature, and then acidified with 1 N aqueous hydrochloric acid. The mixture was adsorbed onto Celite and purified by reverse phase column chromatography on C18-silica gel (10-100% acetonitrile/water with 0.1% formic acid) to give the title compound (31.9 mg) as a white solid.

LC-MS (Method 4): $R_t$=4.56 min; MS (ESIneg): m/z=645 [M−H]⁻

¹H NMR (300 MHz, DMSO-d6) δ 13.43 (s, 1H), 8.30-8.22 (m, 1H), 7.92-7.82 (m, 1H), 7.80 (d, 1H), 7.57-7.49 (m, 2H), 7.49-7.33 (m, 2H), 7.20 (d, 1H), 6.86 (dd, 1H), 4.64 (dt, 1H), 4.43 (d, 1H), 4.16 (t, 2H), 3.97 (d, 1H), 3.82 (s, 3H), 3.76-3.58 (m, 1H), 3.33 (s, 5H), 2.83 (ddd, 1H), 2.37 (dt, 1H), 2.30-2.14 (m, 3H), 1.90 (s, 4H), 1.41 (dt, 1H), 0.53-0.19 (m, 2H), −0.15 (d, 1H), −0.46 (d, 1H).

Example 41

(rac)-4-chloro-14-cyclopropyl-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide

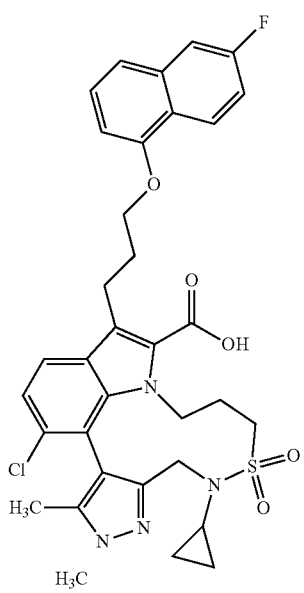

To a stirred solution of ethyl 13-chloro-8-cyclopropyl-1-(3-((6-fluoronaphthalen-1-yl)oxy)propyl)-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 106, 120 mg, 173 µmol) in ethanol (0.7 mL) was added a 2 M aqueous solution of sodium hydroxide (216 µL, 432 µmol). The resulting solution was heated at 60° C. for 18 h, cooled to room temperature, and then acidified with 1.0 M aqueous hydrochloric acid. The mixture was adsorbed onto Celite and then purified by reverse phase column chromatography on C18-silica gel (10-100% acetonitrile/water with 0.1% formic acid gradient) to afford the title compound (93.9 mg) as a white solid.

LC-MS (Method 4): $R_t$=4.63 min; MS (ESIneg): m/z=663 [M−H]⁻

¹H NMR (300 MHz, DMSO-d6) δ 13.41 (s, 1H), 8.31 (dd, 1H), 7.80 (d, 1H), 7.67 (dd, 1H), 7.49-7.35 (m, 3H), 7.22 (d, 1H), 6.84 (dd, 1H), 4.64 (dt, 1H), 4.43 (d, 1H), 4.16 (t, 2H), 3.97 (d, 1H), 3.82 (s, 3H), 3.74-3.63 (m, 1H), 3.33 (s, 5H), 2.93-2.72 (m, 1H), 2.43-2.31 (m, 1H), 2.28-2.11 (m, 1H), 1.90 (s, 4H), 1.47-1.34 (m, 1H), 0.35 (t, 2H), −0.07-0.22 (m, 1H), −0.38-0.53 (m, 1H).

The title compound (89 mg) was separated into enantiomers by preparative chiral HPLC to give enantiomer 1 (31 mg, see Example 42) and enantiomer 2 (27 mg, see Example 43).

Preparative Chiral HPLC Method:
Instrument: Labomatic HD5000, Labocord-5000; Gilson GX-241, Labcol Vario 4000, Column: Chiralpak IG 5µ 250×30 mm; Eluent A: Hexane+0.1 Vol-% Diethylamin (99%); Eluent B: Ethanol; Gradient: 40-50% B in 8 min; Flow 40.0 mL/min; UV 254 nm Analytical Chiral HPLC Method:
Instrument: Waters Alliance 2695 Agilent HPLC 1260; Column: Chiralpak IG 3µ 100×4.6 mm; Eluent A: Hexane+0.1 Vol-% Diethylamin (99%); Eluent B: Ethanol; Gradient: 20-50% B in 7 min; Flow 1.4 mL/min; Temperature: 25° C.; DAD 254 nm

Example 42

(−)-4-chloro-14-cyclopropyl-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide N-diethylamine salt (Enantiomer 1)

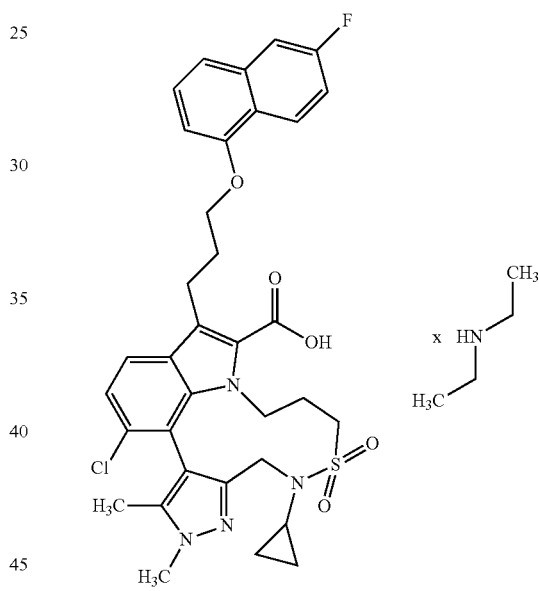

For the preparation of the racemic title compound see Example 41. Separation of enantiomers by preparative chiral HPLC (method see Example 41) gave the title compound (31 mg).

Analytical Chiral HPLC (method see Example 41): $R_t$=3.72 min.

LC-MS (Method 1): $R_t$=1.54 min; MS (ESIpos): m/z=665 [M+H]⁺

Specific Optical Rotation (Method O1): −31.3° C. (c=10 mg/mL, DMSO)

¹H-NMR (400 MHz, DMSO-d6) δ[ppm]: −0.525 (0.64), −0.515 (0.73), −0.218 (0.70), −0.208 (0.62), 0.228 (0.48), 0.244 (0.75), 0.261 (0.79), 0.272 (0.83), 0.290 (0.79), 0.967 (0.88), 0.994 (0.40), 1.009 (0.44), 1.109 (2.42), 1.144 (7.42), 1.161 (16.00), 1.180 (7.44), 1.209 (0.77), 1.230 (0.59), 1.259 (0.77), 1.486 (0.48), 1.511 (0.51), 1.525 (0.61), 1.539 (0.42), 1.770 (0.46), 1.785 (0.50), 1.801 (0.40), 1.893 (15.17), 2.121 (0.61), 2.129 (0.85), 2.137 (1.10), 2.146 (0.85), 2.155 (0.83), 2.174 (1.21), 2.192 (1.75), 2.209 (1.25), 2.226 (0.42), 2.323 (1.01), 2.327 (1.43), 2.332 (1.05), 2.337

(0.92), 2.351 (0.46), 2.364 (0.53), 2.377 (0.85), 2.390 (0.40), 2.518 (4.24), 2.523 (2.85), 2.665 (0.79), 2.669 (1.08), 2.673 (0.79), 2.841 (0.42), 2.853 (0.51), 2.868 (2.35), 2.886 (6.48), 2.904 (6.52), 2.922 (1.93), 3.180 (1.19), 3.198 (1.95), 3.215 (1.16), 3.508 (0.42), 3.523 (0.70), 3.542 (0.57), 3.558 (0.72), 3.807 (15.76), 3.915 (1.78), 3.952 (1.98), 4.127 (1.07), 4.139 (2.06), 4.157 (1.08), 4.418 (2.26), 4.455 (2.02), 4.696 (0.70), 4.712 (0.73), 4.731 (0.68), 6.810 (1.32), 6.816 (1.36), 6.826 (1.29), 6.832 (1.38), 7.073 (2.19), 7.094 (2.24), 7.372 (0.88), 7.378 (1.01), 7.394 (1.51), 7.401 (1.65), 7.409 (2.35), 7.426 (5.46), 7.442 (0.51), 7.599 (1.52), 7.620 (1.40), 7.637 (1.65), 7.644 (1.65), 7.663 (1.62), 7.670 (1.58), 8.293 (1.36), 8.308 (1.43), 8.316 (1.38), 8.331 (1.29).

Example 43

(+)-4-chloro-14-cyclopropyl-7-{3-[(6-fluoro-1-naph-thyl)oxy]propyl}-2,3-dimethyl-11,12,14,15-tetra-hydro-2H,10H-pyrazolo[3',4':4,5][1,2,8]thiadiazacy-cloundecino[6,7,8-hi]indole-8-carboxylic acid 13,13-dioxide N-diethylamine salt (Enantiomer 2)

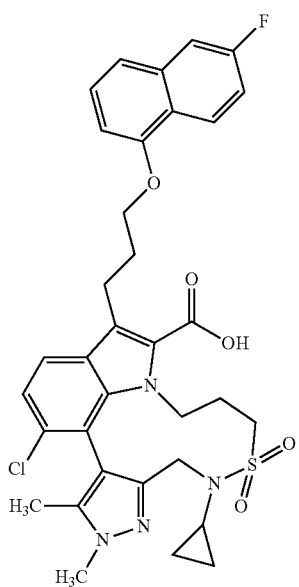

For the preparation of the racemic title compound see Example 41. Separation of enantiomers by preparative chiral HPLC (method see Example 41) gave the title compound (27 mg).

Analytical Chiral HPLC (method see Example 41): $R_t$=6.07 min.

LC-MS (Method 1): $R_t$=1.54 min; MS (ESIpos): m/z=665 [M+H]$^+$

Specific Optical Rotation (Method O1): 34.3° C. (c=10 mg/mL, DMSO)

$^1$H-NMR (400 MHz, DMSO-d6) δ[ppm]: −0.529 (0.55), −0.519 (0.63), −0.223 (0.60), −0.212 (0.53), 0.240 (0.64), 0.256 (0.73), 0.266 (0.76), 0.283 (0.69), 0.795 (0.55), 0.967 (0.56), 1.005 (0.49), 1.084 (0.73), 1.107 (2.58), 1.142 (7.63), 1.160 (16.00), 1.178 (7.82), 1.230 (0.55), 1.259 (1.40), 1.492 (0.41), 1.506 (0.61), 1.518 (0.47), 1.531 (0.55), 1.762 (0.40), 1.777 (0.44), 1.894 (13.95), 2.116 (0.52), 2.125 (0.73), 2.133 (0.96), 2.141 (0.76), 2.150 (0.56), 2.159 (0.53), 2.174 (1.02), 2.192 (1.48), 2.209 (1.04), 2.323 (0.82), 2.327 (1.18), 2.332 (0.85), 2.337 (0.78), 2.363 (0.43), 2.377 (0.70), 2.518 (3.08), 2.523 (2.26), 2.665 (0.64), 2.669 (0.93), 2.673 (0.66), 2.863 (2.18), 2.881 (6.85), 2.899 (6.12), 2.917 (2.08), 3.174 (1.01), 3.192 (1.66), 3.210 (0.98), 3.514 (0.63), 3.534 (0.49), 3.550 (0.66), 3.806 (14.60), 3.913 (1.57), 3.950 (1.74), 4.126 (0.87), 4.138 (1.68), 4.154 (0.89), 4.419 (1.98), 4.456 (1.79), 4.703 (0.58), 4.720 (0.63), 4.738 (0.58), 6.809 (1.13), 6.814 (1.16), 6.825 (1.08), 6.831 (1.19), 7.064 (2.17), 7.086 (2.26), 7.372 (0.76), 7.378 (0.89), 7.388 (0.60), 7.394 (1.25), 7.401 (1.42), 7.409 (2.03), 7.425 (4.85), 7.441 (0.46), 7.586 (1.51), 7.608 (1.37), 7.637 (1.40), 7.643 (1.44), 7.663 (1.42), 7.669 (1.37), 8.293 (1.16), 8.308 (1.24), 8.316 (1.21), 8.331 (1.13).

Example 44

(rac)-2,3,14-trimethyl-15-[2-(rac)-(morpholin-4-yl)ethyl]-7-[3-(1-naphthyloxy)propyl]-11,12,14,15-tetrahydro-2H,10H-pyrazolo[3',4':4,5][1,2,8]thiadi-azacycloundecino[6,7,8-hi]indole-8-carboxylic acid 13,13-dioxide (Mixture of Stereoisomers)

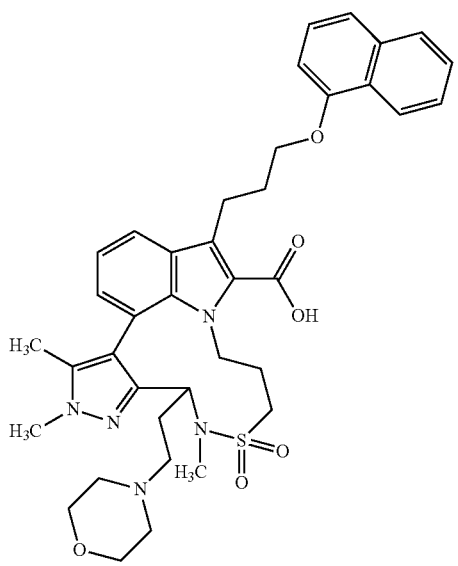 [SMILES: Cc1c2c(nn1C)C(CCN1CCOCC1)N(C)S(=O)(=O)CCCn1c(C(=O)O)c(CCCOc3cccc4ccccc34)c3cccc-2c31]

A suspension of ethyl 8,11,12-trimethyl-9-(2-morpholi-noethyl)-1-(3-(naphthalen-1-yloxy)propyl)-5,6,9,11-tetra-hydro-4H,8H-pyrazolo[3',4':4,5][1]thia[2,8]diazacycloun-decino[6,7,8-hi]indole-2-carboxylate 7,7-dioxide (Intermediate 110, 0.18 g, 247 μmol) in ethanol (988 μL) was treated with a 2 M aqueous solution of sodium hydroxide (308 μL, 617 μmol) and the mixture was stirred at 60° C. for 24 h. The solution was cooled to room temperature, acidified with aqueous 1 N HCl, and adsorbed directly onto Celite. The residue was purified by reverse-phase flash column chromatography on C18-silica gel (10-100% acetonitrile/water with 0.1% formic acid) to obtain the title compound (0.123 g) as a white solid.

LC-MS (Method 4): $R_t$=3.07 min; MS (ESIpos): m/z=700 [M+H]$^+$

1H NMR (400 MHz, DMSO-d6) δ 8.31-8.24 (m, 1H), 7.90-7.83 (m, 2H), 7.81 (d, 1H), 7.52 (q, 3H), 7.45 (d, 2H), 7.38 (t, 1H), 7.19-6.98 (m, 1H), 6.95 (d, 1H), 6.86 (dd, 1H), 4.70 (dd, 1H), 4.47 (d, 1H), 4.19 (t, 2H), 4.04 (s, 2H), 3.82 (s, 3H), 3.90-3.75 (m, 1H), 3.60-3.42 (m, 5H), 3.34 (s, 1H), 2.87 (s, 3H), 2.66 (dd, 1H), 2.44-2.29 (m, 4H), 2.28-2.18 (m, 8H), 1.97-1.83 (m, 2H), 1.76 (d, 5H).

The title compound (699 mg) was separated into enantiomers by preparative achiral and chiral HPLC to give enantiomer 1 (16 mg, see Example 45) and enantiomer 2 (14 mg, see Example 46).

Preparative Achiral HPLC Method:

Instrument: Waters Autopurification system; Column: YMC Triart C18 5μ 150×50 mm; Eluent A: water+0.1 Vol-% formic acid (99%), Eluent B: acetonitrile; Gradient: 0.00-0.50 min 40% B (40→100 mL/min), 0.51-7.50 min 40-70%, B (100 mL/min), DAD scan: 210-400 nm Preparative Chiral HPLC Method:

Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine (99%); Gradient B: Ethanol; Gradient: 20-50%, B; Flow 40.0 mL/min; UV 220 nm Analytical Chiral HPLC Method:

Instrument: Agilent HPLC 1260; Column: Chiralpak IG 3μ 100×4.6 mm; Eluent A: Hexane+0.1 Vol-% Diethylamine (99%); Eluent B: Ethanol; Gradient: 20-50%, B; Flow 1.4 mL/min; Temperature: 25° C.; DAD 220 nm Example 45

2,3,14-trimethyl-15-[2-(morpholin-4-yl)ethyl]-7-{3-[(naphthalen-1-yl)oxy]propyl}-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine Salt (Enantiomer 1)

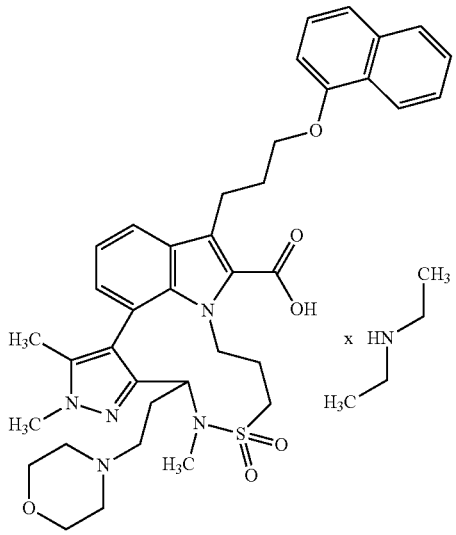

For the preparation of the racemic title compound see Example 44. Separation of enantiomers by preparative chiral HPLC (method see Example 44) gave the title compound (16 mg).

Analytical Chiral HPLC (method see Example 44): $R_t$=3.19 min.

LC-MS (Method 2): $R_t$=0.87 min; MS (ESIpos): m/z=700 [M+H]$^+$ $^1$H-NMR (400 MHz, DMSO-d6) δ[ppm]: 0.967 (0.71), 1.109 (1.44), 1.137 (1.93), 1.144 (0.71), 1.155 (4.29), 1.173 (1.95), 1.209 (0.46), 1.230 (0.62), 1.259 (0.82), 1.608 (0.49), 1.632 (0.49), 1.735 (0.53), 1.750 (0.60), 1.774 (0.66), 1.794 (15.03), 1.856 (0.71), 1.869 (0.89), 1.888 (0.86), 1.905 (0.66), 2.132 (0.64), 2.170 (2.21), 2.185 (2.90), 2.198 (2.92), 2.215 (2.06), 2.286 (0.40), 2.318 (1.02), 2.323 (1.55), 2.327 (2.10), 2.332 (1.81), 2.336 (1.35), 2.451 (0.49), 2.518 (4.54), 2.523 (3.43), 2.544 (0.69), 2.568 (0.44), 2.660 (0.44), 2.665 (0.97), 2.669 (1.35), 2.673 (0.97), 2.678 (0.44), 2.841 (0.58), 2.865 (13.85), 2.876 (1.93), 2.895 (0.55), 3.192 (0.73), 3.210 (1.17), 3.228 (1.28), 3.242 (1.84), 3.456 (2.12), 3.472 (2.06), 3.490 (1.90), 3.498 (2.01), 3.506 (1.90), 3.513 (1.90), 3.533 (1.06), 3.760 (0.95), 3.817 (16.00), 3.912 (0.62), 4.149 (0.84), 4.165 (1.59), 4.174 (1.59), 4.190 (0.77), 4.564 (0.55), 4.596 (0.51), 4.639 (0.89), 4.651 (0.91), 4.664 (0.93), 4.676 (0.80), 6.784 (1.08), 6.802 (1.24), 6.850 (1.81), 6.867 (1.95), 6.994 (1.08), 7.013 (1.64), 7.033 (0.93), 7.343 (1.37), 7.363 (2.54), 7.383 (2.01), 7.429 (2.66), 7.450 (1.57), 7.493 (0.55), 7.505 (1.99), 7.508 (2.37), 7.518 (2.72), 7.526 (2.08), 7.529 (2.32), 7.532 (2.26), 7.543 (0.62), 7.656 (1.24), 7.675 (1.15), 7.848 (1.59), 7.851 (1.11), 7.860 (1.33), 7.865 (1.04), 7.871 (1.33), 8.257 (1.35), 8.268 (1.13), 8.281 (1.22).

Example 46

2,3,14-trimethyl-15-[2-(morpholin-4-yl)ethyl]-7-{3-[(naphthalen-1-yl)oxy]propyl}-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine Salt (Enantiomer 2)

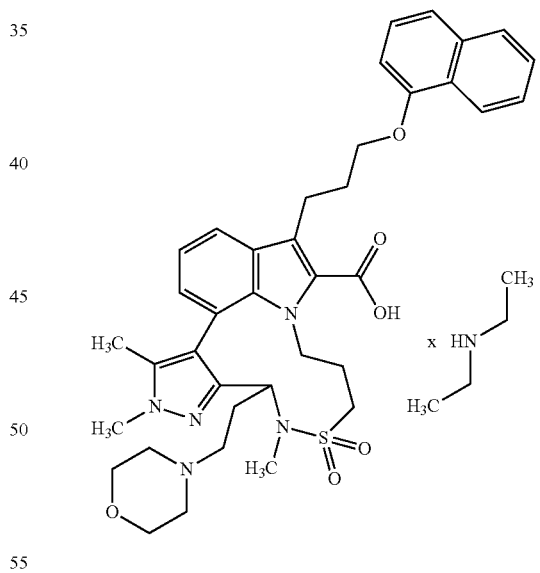

For the preparation of the racemic title compound see Example 44. Separation of enantiomers by preparative chiral HPLC (method see Example 44) gave the title compound (14 mg).

Analytical Chiral HPLC (method see Example 44): $R_t$=3.75 min.

LC-MS (Method 2): $R_t$=0.87 min; MS (ESIpos): m/z=700 [M+H]$^+$

Specific Optical Rotation (Method O1): was not determined $^1$H-NMR (400 MHz, DMSO-d6) δ[ppm]: 0.967 (0.62), 1.109 (1.24), 1.136 (1.81), 1.144 (0.71), 1.154 (3.89), 1.172

(1.89), 1.209 (0.54), 1.231 (0.85), 1.259 (0.87), 1.612 (0.48), 1.734 (0.82), 1.749 (0.62), 1.794 (15.18), 1.858 (0.73), 1.870 (0.90), 1.889 (0.79), 1.905 (0.76), 2.188 (2.96), 2.198 (3.16), 2.210 (2.26), 2.287 (0.42), 2.323 (1.86), 2.327 (2.46), 2.332 (2.12), 2.336 (1.50), 2.518 (5.53), 2.523 (4.20), 2.551 (0.68), 2.575 (0.45), 2.660 (0.59), 2.665 (1.21), 2.669 (1.72), 2.673 (1.21), 2.678 (0.56), 2.843 (0.62), 2.864 (14.73), 2.879 (1.58), 2.898 (0.51), 3.214 (0.99), 3.230 (1.10), 3.247 (1.58), 3.456 (1.72), 3.471 (1.75), 3.492 (1.66), 3.499 (1.83), 3.506 (1.75), 3.514 (1.72), 3.534 (0.90), 3.636 (0.42), 3.758 (0.79), 3.817 (16.00), 3.921 (0.59), 4.150 (0.90), 4.166 (1.69), 4.174 (1.69), 4.190 (0.87), 4.557 (0.59), 4.587 (0.54), 4.642 (0.87), 4.654 (0.90), 4.667 (0.96), 4.679 (0.82), 6.794 (0.96), 6.812 (1.10), 6.850 (1.95), 6.869 (2.03), 7.001 (0.99), 7.020 (1.50), 7.038 (0.85), 7.344 (1.50), 7.364 (2.71), 7.383 (2.12), 7.430 (2.79), 7.450 (1.64), 7.494 (0.62), 7.506 (2.03), 7.509 (2.60), 7.519 (2.96), 7.527 (2.20), 7.529 (2.43), 7.532 (2.31), 7.544 (0.65), 7.665 (1.10), 7.685 (1.02), 7.848 (1.69), 7.852 (1.19), 7.861 (1.35), 7.865 (1.10), 7.872 (1.41), 8.257 (1.41), 8.268 (1.21), 8.282 (1.33).

Example 47

(rac)-15-chloro-1-(3-((6-fluoronaphthalen-1-yl)oxy)propyl)-8,13,14-trimethyl-11-(rac)-morpholino-5,6,9,10,11,13-hexahydro-4H,8H-pyrazolo[3',4':6,7][1]thia[2,10]diazacyclotridecino[8,9,10-hi]indole-2-carboxylic acid 7,7-dioxide (Mixture of Stereoisomers)

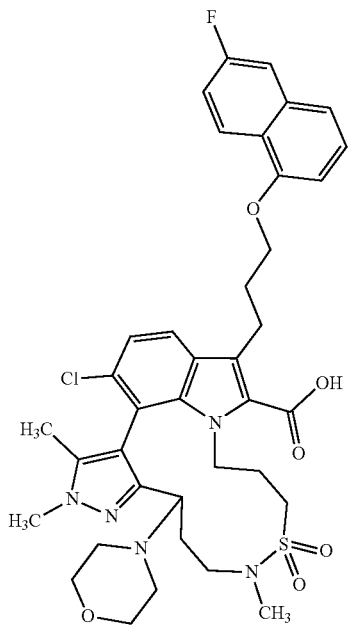 [SMILES: Cc1c2c(nn1C)C(N1CCOCC1)CCN(C)S(=O)(=O)CCCn1c(C(=O)O)c(CCCOc3cccc4cc(F)ccc34)c3ccc(Cl)c-2c31]

A solution of ethyl 15-chloro-1-(3-((6-fluoronaphthalen-1-yl)oxy)propyl)-8,13,14-trimethyl-11-morpholino-5,6,9,10,11,13-hexahydro-4H,8H-pyrazolo[3',4':6,7][1]thia[2,10]diazacyclotridecino[8,9,10-hi]indole-2-carboxylate 7,7-dioxide (Intermediate 115, 90 mg, 115 μmol) in ethanol (1 mL) was treated with a 2 M aqueous solution of sodium hydroxide (172 μL, 345 μmol) and stirred at 60° C. for 20 h. After cooling to room temperature, the mixture was acidified with 1 N aqueous HCl and adsorbed onto Celite. The crude mixture was purified by reverse-phase flash chromatography on C18-silica gel (10-100% acetonitrile/water with 0.1% formic acid) to obtain the title compound (48.4 mg).

LC-MS (Method 4): $R_t$=3.99 min; MS (ESIpos): m/z=752 [M+H]$^+$ $^1$H NMR (400 MHz, DMSO-d$_6$) δ 8.28 (dd, 1H), 7.71-7.59 (m, 2H), 7.46-7.35 (m, 3H), 7.15 (d, 1H), 6.85 (dd, 1H), 4.54 (d, 1H), 4.17 (t, 2H), 3.84 (s, 3H), 3.70 (t, 2H), 3.55-3.47 (m, 1H), 3.45-3.12 (m, 4H), 2.91 (dd, 2H), 2.60 (s, 3H), 2.40-2.32 (m, 2H), 2.32-2.10 (m, 5H), 1.97 (s, 3H), 1.55-1.42 (m, 1H).

Example 48

(rac)-4-chloro-7-{3-[(6-fluoro-1-naphthyl)oxy]propyl}-2,3,14-trimethyl-15-(rac)-[2-(morpholin-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide (Mixture of Stereoisomers)

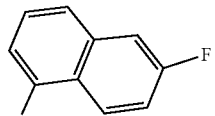

A solution of ethyl 13-chloro-1-(3-((6-fluoronaphthalen-1-yl)oxy)propyl)-8,11,12-trimethyl-9-(2-morpholinoethyl)-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 117, 0.118 g, 149 μmol) in ethanol (1 mL) was treated with a 2 M aqueous solution of sodium hydroxide (223 μL, 447 μmol) and stirred at 60° C. for 20 h. After cooling to room temperature, the mixture was acidified with 1 N aqueous HCl and adsorbed onto Celite. The crude mixture was purified by reverse-phase flash chromatography on C18-silica gel (10-100% acetonitrile/water with 0.1% formic acid) to obtain the title compound (0.104 g) as a white solid.

LC-MS (Method 4): $R_t$=3.45 min; MS (ESIpos): m/z=752 [M+H]$^+$ $^1$H NMR (400 MHz, DMSO-d$_6$) δ 8.30 (dt, 3H), 7.80 (dd, 2H), 7.65 (dd, 3H), 7.49-7.34 (m, 8H), 7.24 (dd, 2H), 6.84 (ddd, 2H), 5.23-5.14 (m, 1H), 4.55-4.39 (m, 3H), 4.28 (dt, 1H), 4.16 (dt, 5H), 4.07-3.93 (m, 3H), 3.84 (s, 4H), 3.78 (s, 3H), 3.54 (dt, 10H), 3.42-3.21 (m, 28H), 2.86 (s, 4H), 2.82-2.74 (m, 3H), 2.70-2.64 (m, 1H), 2.34 (d, 9H), 2.31-2.14 (m, 7H), 2.09-1.83 (m, 7H), 1.80 (s, 3H), 1.72 (d, 7H).

The mixture of stereoisomers (96 mg) were separated into enantiomers by preparative chiral HPLC to give enantiomer 1 (10 mg, see Example 66), enantiomer 2 (5 mg, see Example 67) and a mixture two further isomers of the product (16 mg see Example 65).
Preparative Chiral HPLC Method:
Instrument: Labomatic HD5000, Labocord-5000; Gilson GX-241, Labcol Vario 4000, Column: Cellulose SC 5µ 250×30 mm; Eluent A: Hexane+0.1 Vol-% Diethylamine (99%); Eluent B: 2-Propanol; Isocratic 60% A+40% B; Flow 50.0 ml/min; UV 254 nm
Analytical Chiral HPLC Method:
Instrument: Agilent HPLC 1260; Column: Cellulose SC 3µ 100×4.6 mm;
Eluent A: Hexane+0.1 Vol-% Diethylamine (99%); Eluent B: 2-Propanol; Gradient: 20 50% B in 7 min; Flow 1.4 ml/min; Temperature: 25° C.; DAD 254 nm Example 49

(rac)-4-chloro-14-(2,4-dimethoxybenzyl)-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide

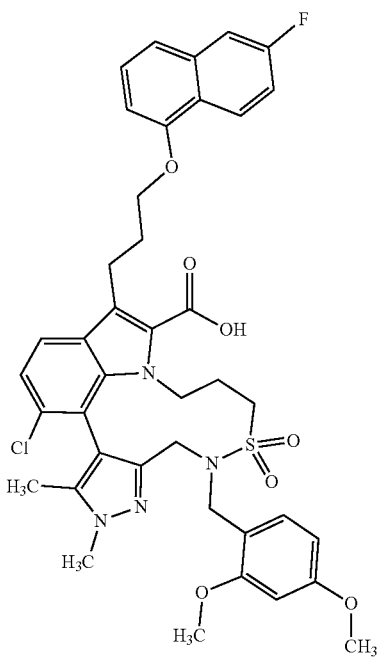 [SMILES: COc1ccc(CN2Cc3nn(C)c(C)c3-c3c(Cl)ccc4c(CCCOc5cccc6cc(F)ccc56)c(C(=O)O)n(c34)CCCS2(=O)=O)c(OC)c1]

A solution of (rac)-ethyl 13-chloro-8-(2,4-dimethoxybenzyl)-1-(3-((6-fluoronaphthalen-1-yl)oxy)propyl)-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 121, 46 mg, 57.2 µmol) in ethanol (572 µL) was treated with a solution of sodium hydroxide (1 M in water, 143 µL, 143 µmol) and stirred at 50° C. for 30 h. After cooling to room temperature, the mixture was acidified with 1 N aqueous HCl, adsorbed onto Celite, and purified by reverse-phase flash chromatography on C18-silica gel (10-100% acetonitrile/water with 0.1% formic acid) to obtain the title compound (18 mg).
LC-MS (Method 4): $R_t$=4.94 min; MS (ESIpos): m/z=775 [M+H]$^+$ $^1$H NMR (300 MHz, DMSO-d$_6$) δ 13.42 (s, 1H), 8.30 (dd, 1H), 7.84 (d, 1H), 7.66 (dd, 1H), 7.49-7.34 (m, 3H), 7.26 (d, 1H), 7.06 (d, 1H), 6.84 (dd, 1H), 6.53-6.41 (m, 2H), 4.82-4.65 (m, 1H), 4.29-3.96 (m, 4H), 3.82 (s, 3H), 3.74 (s, 3H), 3.68 (s, 3H), 3.33 (s, 16H), 2.49 (s, 7H), 2.28-2.14 (m, 2H), 1.83 (s, 3H).

Example 50

(rac)-4-chloro-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide

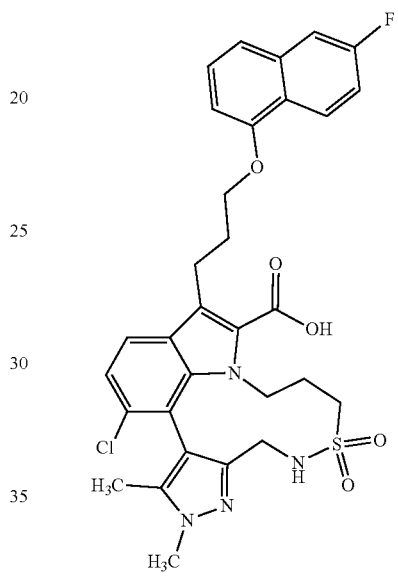

A solution of (rac)-ethyl 13-chloro-1-(3-((6-fluoronaphthalen-1-yl)oxy)propyl)-11,12-dimethyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 122, 84.5 mg, 129 µmol) in ethanol (665 µL) was treated with a solution of sodium hydroxide (1 M in water, 322 µL, 322 µmol) and the mixture was stirred at 50° C. for 30 h. More sodium hydroxide (1 M in, 322 µL, 322 µmol) was added and the mixture continued to stir for 20 h. After cooling to room temperature, the mixture was acidified with 1 N aqueous HCl, adsorbed onto Celite, and purified by reverse-phase flash chromatography on C18-silica gel (10-100% acetonitrile/water with 0.1% formic acid) to obtain, the title compound (49.5 mg).
LC-MS (Method 4): $R_t$=4.20 min; MS (ESIpos): m/z=625 [M+H]$^+$ $^1$H NMR (300 MHz, DMSO-d$_6$) δ 13.39 (s, 1H), 8.30 (dd, 1H), 7.81 (d, 1H), 7.67 (dd, 1H), 7.57 (dd, 1H), 7.50-7.36 (m, 3H), 7.28 (d, 1H), 6.89 (dd, 1H), 4.84-4.58 (m, 1H), 4.24-4.11 (m, 3H), 3.90 (dd, 1H), 3.81 (s, 3H), 3.73-3.52 (m, 1H), 3.33 (s, 7H), 2.31 (d, 2H), 2.27-2.03 (m, 2H), 1.92-1.81 (m, 1H), 1.79 (s, 3H), 1.40 (s, 1H).

The title compound (43 mg) was separated into enantiomers by preparative chiral HPLC to give enantiomer 1 (15 mg, see Example 51) and enantiomer 2 (14 mg, see Example 52).
Preparative Chiral HPLC Method:
Instrument: Labomatic HD5000, Labocord-5000; Gilson GX-241, Labcol Vario 4000, Column: Chiralpak IE 5µ

250×30 mm; Eluent A: Hexane+0.1 Vol-% Trifluoroacetic acid (99%); Eluent B: Isopropanol; Isocratic: 50% A+50% B; Flow 40.0 mL/min; UV 254 nm
Analytical Chiral HPLC Method:
Instrument: Waters Alliance 2695 Agilent HPLC 1260; Column: Chiralpak IE 3μ 100×4.6 mm; Eluent A: Hexane+0.1 Vol-% Trifluoroacetic acid (99%); Eluent B: Isopropanol; Gradient: 20-50%6 in 7 min; Flow 1.4 ml/min; Temperature: 25° C.; DAD 254 nm Example 51

4-chloro-7-{3-[(6-fluoronaphthalen-1-yl)oxy]propyl}-2,3-dimethyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (Enantiomer 1)

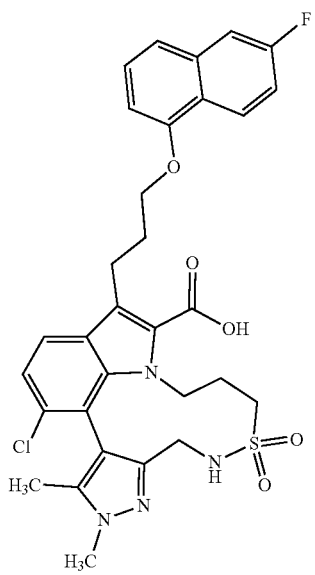 [SMILES: Cc1c2c(nn1C)CNS(=O)(=O)CCCn1c(C(=O)O)c(CCCOc3cccc4cc(F)ccc34)c3ccc(Cl)c-2c31]

For the preparation of the racemic title compound see Example 50. Separation of enantiomers by preparative chiral HPLC (method see Example 50) gave the title compound (15 mg).

Analytical Chiral HPLC (method see Example 50): R$_t$=4.44 min.

LC-MS (Method 1): R$_t$=1.43 min; MS (ESIpos): m/z=625 [M+H]$^+$

1H-NMR (400 MHz, DMSO-d6) delta [ppm]: 0.967 (0.23), 1.107 (16.00), 1.144 (0.19), 1.154 (0.26), 1.222 (0.26), 1.232 (0.39), 1.352 (0.18), 1.388 (0.26), 1.791 (8.04), 1.840 (0.23), 1.856 (0.26), 1.872 (0.21), 2.084 (0.20), 2.115 (0.23), 2.157 (0.20), 2.175 (0.56), 2.192 (0.86), 2.208 (0.58), 2.323 (0.43), 2.327 (0.58), 2.332 (0.45), 2.518 (1.88), 2.523 (1.27), 2.539 (0.24), 2.665 (0.35), 2.669 (0.49), 2.673 (0.35), 3.238 (0.16), 3.257 (0.34), 3.271 (0.42), 3.290 (0.71), 3.311 (0.78), 3.637 (0.21), 3.814 (8.51), 3.867 (0.34), 3.886 (0.39), 3.905 (0.47), 3.924 (0.42), 4.147 (0.58), 4.157 (0.64), 4.185 (1.21), 4.201 (1.59), 4.216 (0.74), 4.696 (0.26), 4.714 (0.26), 4.732 (0.25), 6.876 (0.67), 6.884 (0.73), 6.889 (0.61), 6.898 (0.71), 7.268 (2.02), 7.289 (2.13), 7.373 (0.44), 7.379 (0.52), 7.395 (0.72), 7.402 (0.78), 7.417 (0.52), 7.423 (0.54), 7.440 (1.49), 7.445 (1.58), 7.454 (3.11), 7.466 (0.19), 7.564 (0.45), 7.574 (0.54), 7.583 (0.51), 7.592 (0.45), 7.651 (0.83), 7.657 (0.84), 7.677 (0.84), 7.683 (0.82), 7.801 (1.86), 7.822 (1.65), 8.283 (0.73), 8.297 (0.75), 8.306 (0.73), 8.321 (0.71).

Example 52

4-chloro-7-{3-[(6-fluoronaphthalen-1-yl)oxy]propyl}-2,3-dimethyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (Enantiomer 2)

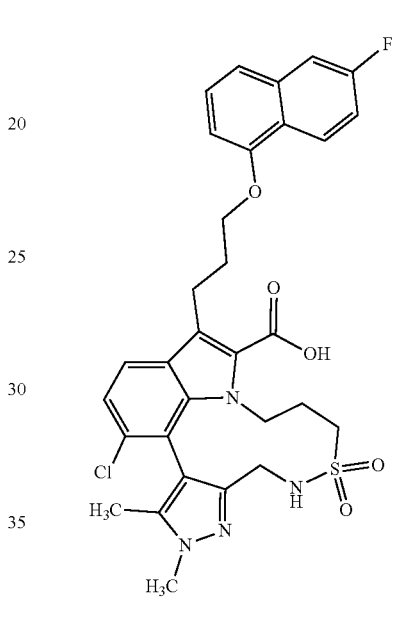

For the preparation of the racemic title compound see Example 50. Separation of enantiomers by preparative chiral HPLC (method see Example 50) gave the title compound (14 mg).

Analytical Chiral HPLC (method see Example 50): R$_t$=6.29 min.

LC-MS (Method 1): R$_t$=1.43 min; MS (ESIpos): m/z=625 [M+H]$^+$

1H-NMR (400 MHz, DMSO-d6) delta [ppm]: 1.107 (16.00), 1.135 (0.17), 1.154 (0.34), 1.172 (0.22), 1.222 (0.29), 1.231 (0.31), 1.334 (0.16), 1.791 (3.98), 2.175 (0.28), 2.192 (0.43), 2.209 (0.29), 2.322 (0.25), 2.327 (0.32), 2.331 (0.26), 2.518 (1.29), 2.523 (0.80), 2.664 (0.21), 2.669 (0.29), 2.673 (0.21), 3.271 (0.18), 3.290 (0.29), 3.311 (0.23), 3.331 (0.28), 3.350 (0.19), 3.364 (0.18), 3.589 (0.79), 3.867 (0.20), 3.886 (0.22), 3.905 (0.25), 3.924 (0.22), 4.147 (0.29), 4.156 (0.32), 4.185 (0.61), 4.201 (0.79), 4.216 (0.37), 6.876 (0.33), 6.884 (0.36), 6.889 (0.31), 6.898 (0.36), 7.267 (1.09), 7.289 (1.08), 7.372 (0.23), 7.379 (0.25), 7.395 (0.35), 7.402 (0.38), 7.417 (0.26), 7.424 (0.28), 7.441 (0.74), 7.445 (0.80), 7.453 (1.55), 7.566 (0.22), 7.576 (0.27), 7.585 (0.25), 7.594 (0.23), 7.651 (0.41), 7.657 (0.42), 7.677 (0.42), 7.683 (0.41), 7.801 (0.91), 7.822 (0.81), 8.283 (0.36), 8.297 (0.38), 8.306 (0.37), 8.321 (0.34).

Example 53

(rac)-4-chloro-14-cyclopropyl-3-ethyl-7-{3-[(6-fluoro-1-naphthyl)oxy]propyl}-2-methyl-11,12,14,15-tetrahydro-2H,10H-pyrazolo[3',4':4,5][1,2,8]thiadiazacycloundecino[6,7,8-hi]indole-8-carboxylic acid 13,13-dioxide

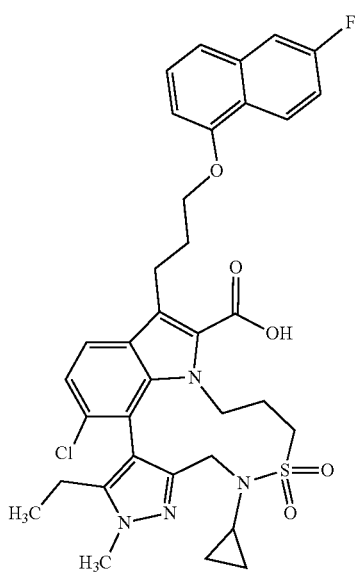 [SMILES: CCc1c2c(nn1C)CN(C1CC1)S(=O)(=O)CCCn1c(C(=O)O)c(CCCOc3cccc4cc(F)ccc34)c3ccc(Cl)c-2c31]

A solution of (rac)-ethyl 13-chloro-8-cyclopropyl-12-ethyl-1-(3-((6-fluoronaphthalen-1-yl)oxy)propyl)-11-methyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 126, 750 mg, 1.06 mmol) in ethanol (5.30 mL) was treated with a 2 M aqueous solution of sodium hydroxide (1.06 mL, 2.12 mmol) and stirred at 60° C. overnight. After cooling to room temperature, the mixture was acidified with 1 N aqueous hydrogen chloride, adsorbed onto Celite, and purified by reverse-phase flash chromatography on C18-silica gel (10-100% acetonitrile/water with 0.1% formic acid) to obtain, the title compound (539 mg) as a white solid.

LC-MS (Method 4): $R_t$=4.83 min; MS (ESIpos): m/z=680 $[M+H]^+$ $^1$H NMR (300 MHz, Chloroform-d) δ 8.38 (dd, 1H), 7.68 (d, 1H), 7.44-7.32 (m, 3H), 7.26 (s, 7H), 7.20 (d, 1H), 6.69 (dd, 1H), 4.62 (t, 2H), 4.20-4.01 (m, 4H), 3.92 (s, 3H), 3.49-3.36 (m, 2H), 2.72-2.48 (m, 2H), 2.39-2.28 (m, 4H), 2.10 (s, 1H), 1.72 (s, 1H), 0.95 (t, 3H), 0.58-0.39 (m, 2H), 0.10-0.01 (m, 1H), −0.11-0.21 (m, 1H).

The title compound (509 mg) was separated into enantiomers by preparative chiral HPLC to give enantiomer 1 (213 mg, see Example 54) and enantiomer 2 (207 mg, see Example 55).

Preparative Chiral HPLC Method:
Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine (99%); Eluent B: Ethanol; isocratic 65:35; Flow 40.0 mL/min; UV 236 nm Analytical Chiral HPLC Method:
Instrument: Agilent HPLC 1260; Column: Chiralpak IG 3μ 100×4.6 mm; Eluent A: Hexane+0.1 Vol-% Diethylamine (99%); Eluent B: Ethanol; Gradient: 20-50% B in 7 min; Flow 1.4 ml/min; Temperature: 25° C.; DAD 254 nm

Example 54

(−)-4-chloro-14-cyclopropyl-3-ethyl-7-{3-[(6-fluoronaphthalen-1-yl)oxy]propyl}-2-methyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine Salt (Enantiomer 1)

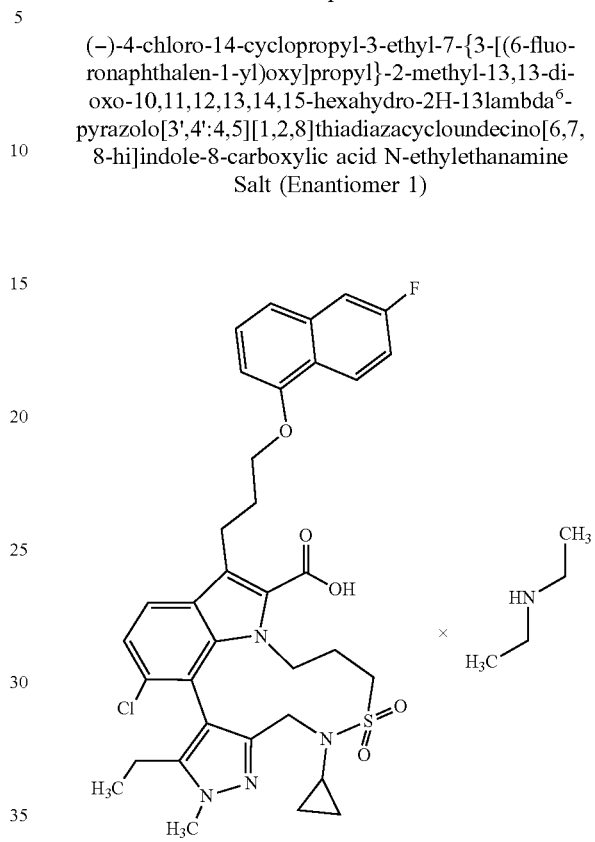

For the preparation of the racemic title compound see Example 53. Separation of enantiomers by preparative chiral HPLC (method see Example 53) gave the title compound (64 mg).

Analytical Chiral HPLC (method see Example 53): $R_t$=3.41 min.

LC-MS (Method 1): $R_t$=1.57 min; MS (ESIpos): m/z=679 $[M+H]^+$

Specific Optical Rotation (Method O1): −17.2° (c=10 mg/mL, DMSO)

1H-NMR (400 MHz, DMSO-d6) delta [ppm]: −0.509 (0.18), −0.499 (0.21), −0.245 (0.20), −0.235 (0.17), 0.238 (0.22), 0.254 (0.26), 0.263 (0.26), 0.280 (0.24), 0.839 (1.07), 0.858 (2.42), 0.876 (1.10), 0.904 (0.18), 1.107 (16.00), 1.138 (3.13), 1.157 (7.23), 1.175 (3.17), 2.116 (0.17), 2.124 (0.23), 2.132 (0.32), 2.141 (0.24), 2.149 (0.18), 2.184 (0.33), 2.202 (0.52), 2.219 (0.40), 2.242 (0.30), 2.260 (0.37), 2.279 (0.30), 2.314 (0.31), 2.322 (0.25), 2.327 (0.35), 2.332 (0.49), 2.351 (0.27), 2.370 (0.18), 2.416 (0.18), 2.442 (0.16), 2.454 (0.24), 2.467 (0.21), 2.518 (1.15), 2.523 (0.76), 2.664 (0.21), 2.669 (0.30), 2.673 (0.22), 2.805 (0.22), 2.852 (0.86), 2.871 (2.67), 2.888 (2.64), 2.907 (0.80), 3.162 (0.37), 3.180 (0.64), 3.198 (0.36), 3.632 (0.19), 3.649 (0.18), 3.667 (0.20), 3.831 (5.27), 3.887 (0.54), 3.924 (0.58), 4.120 (0.25), 4.136 (0.52), 4.144 (0.51), 4.153 (0.30), 4.160 (0.26), 4.192 (0.18), 4.421 (0.68), 4.459 (0.61), 4.648 (0.23), 4.665 (0.19), 4.682 (0.23), 6.801 (0.41), 6.807 (0.43), 6.818 (0.40), 6.823 (0.44), 7.056 (0.87), 7.077 (0.92), 7.372 (0.29), 7.379 (0.32), 7.384 (0.21), 7.394 (0.45), 7.402 (0.62), 7.404 (0.71), 7.423 (1.58), 7.439

(0.17), 7.573 (0.64), 7.594 (0.58), 7.636 (0.50), 7.642 (0.51), 7.662 (0.50), 7.668 (0.48), 8.297 (0.43), 8.312 (0.46), 8.321 (0.43), 8.335 (0.41).

Example 55

(+)-4-chloro-14-cyclopropyl-3-ethyl-7-{3-[(6-fluoronaphthalen-1-yl)oxy]propyl}-2-methyl-13,13-dioxo-10,11,12,13,14,15-hexahydro-2H-13lambda⁶-pyrazolo[3',4':4,5][1,2,8]thiadiazacycloundecino[6,7,8-hi]indole-8-carboxylic acid N-ethylethanamine Salt (Enantiomer 2)

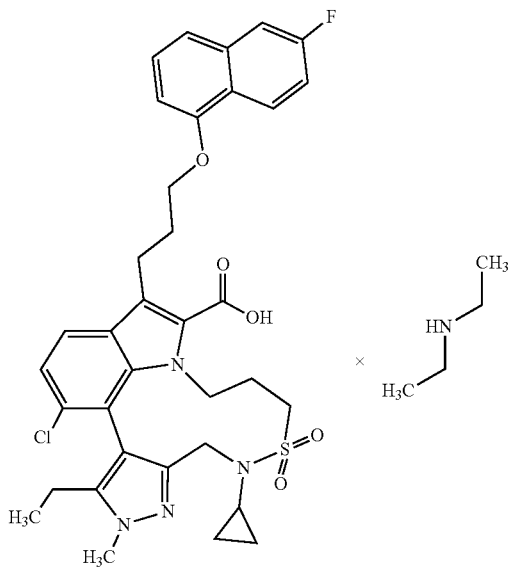

For the preparation of the racemic titled compound see Example 53. Separation of enantiomers by preparative chiral HPLC (method see Example 53) gave the titled compound (64 mg).

Analytical Chiral HPLC (method see Example 53): $R_t$=5.59 min.

LC-MS (Method 1): $R_t$=1.57 min; MS (ESIpos): m/z=679 [M+H]⁺

Specific Optical Rotation (Method O1): 20.2° (c=10 mg/mL, DMSO)

1H-NMR (400 MHz, DMSO-d6) delta [ppm]: −0.507 (0.28), −0.497 (0.32), −0.484 (0.24), −0.244 (0.30), −0.233 (0.27), 0.223 (0.20), 0.240 (0.34), 0.256 (0.40), 0.266 (0.41), 0.282 (0.37), 0.297 (0.21), 0.798 (0.36), 0.814 (0.41), 0.821 (0.41), 0.838 (1.73), 0.857 (3.83), 0.876 (1.73), 0.886 (0.29), 0.904 (0.49), 0.922 (0.23), 1.027 (0.17), 1.042 (0.19), 1.107 (16.00), 1.142 (4.66), 1.160 (10.03), 1.178 (4.87), 1.259 (0.20), 1.579 (0.17), 1.603 (0.19), 1.619 (0.23), 1.631 (0.16), 1.799 (0.19), 1.814 (0.22), 1.826 (0.21), 1.839 (0.19), 2.117 (0.26), 2.125 (0.35), 2.133 (0.49), 2.142 (0.36), 2.151 (0.27), 2.169 (0.19), 2.185 (0.50), 2.203 (0.79), 2.222 (0.67), 2.241 (0.47), 2.259 (0.58), 2.278 (0.47), 2.295 (0.22), 2.314 (0.48), 2.322 (0.31), 2.327 (0.44), 2.332 (0.73), 2.351 (0.40), 2.370 (0.29), 2.406 (0.20), 2.415 (0.28), 2.428 (0.19), 2.442 (0.23), 2.455 (0.33), 2.467 (0.22), 2.518 (1.29), 2.523 (0.90), 2.665 (0.25), 2.669 (0.35), 2.673 (0.25), 2.766 (0.18), 2.777 (0.20), 2.791 (0.22), 2.803 (0.33), 2.815 (0.19), 2.829 (0.19), 2.841 (0.17), 2.855 (1.29), 2.874 (3.93), 2.891 (4.02), 2.910 (1.19), 3.166 (0.58), 3.185 (1.00), 3.202 (0.55), 3.635 (0.29), 3.653 (0.30), 3.670 (0.31), 3.686 (0.16), 3.831 (8.22), 3.888 (0.85), 3.925 (0.89), 4.121 (0.37), 4.136 (0.77), 4.144 (0.78), 4.152 (0.45), 4.160 (0.39), 4.421 (1.05), 4.459 (0.93), 4.650 (0.35), 4.669 (0.29), 4.685 (0.35), 6.801 (0.62), 6.805 (0.64), 6.817 (0.61), 6.822 (0.65), 7.059 (1.48), 7.080 (1.54), 7.372 (0.42), 7.378 (0.51), 7.383 (0.32), 7.393 (0.68), 7.402 (0.97), 7.404 (1.10), 7.423 (2.30), 7.439 (0.27), 7.577 (1.09), 7.598 (0.97), 7.636 (0.74), 7.642 (0.74), 7.662 (0.74), 7.669 (0.72), 8.297 (0.64), 8.312 (0.66), 8.320 (0.66), 8.335 (0.61).

Example 56

(rac)-4-chloro-3,14-diethyl-7-{3-[(6-fluoro-1-naphthyl)oxy]propyl}-2-methyl-11,12,14,15-tetrahydro-2H,10H-pyrazolo[3',4':4,5][1,2,8]thiadiazacycloundecino[6,7,8-hi]indole-8-carboxylic acid 13,13-dioxide

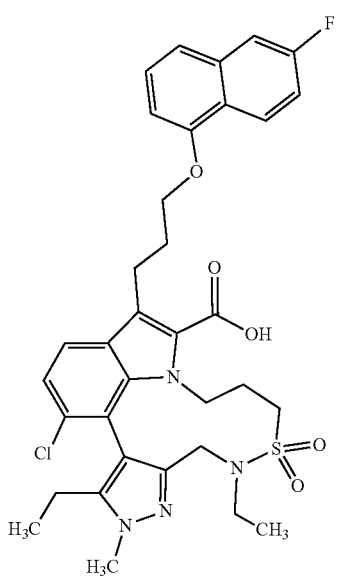 [SMILES: CCc1c2c(nn1C)CN(CC)S(=O)(=O)CCCn1c(C(=O)O)c(CCCOc3cccc4cc(F)ccc34)c3ccc(Cl)c-2c31]

A solution of (rac)-ethyl 13-chloro-8,12-diethyl-1-(3-((6-fluoronaphthalen-1-yl)oxy)propyl)-11-methyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 129, 550 mg, 791 µmol) in ethanol (4 mL) was treated with a 2 M aqueous solution of sodium hydroxide (1.58 mL, 3.16 mmol) and stirred at 60° C. overnight. After cooling to room temperature, the mixture was acidified with 1 N aqueous hydrogen chloride, adsorbed onto Celite, and purified by reverse-phase flash chromatography on C18-silica gel (10-100% acetonitrile/water with 0.1% formic acid) to obtain, the title compound (382 mg) as a white solid.

LC-MS (Method 4): $R_t$=4.85 min; MS (ESIpos): m/z=667 [M+H]⁺

¹H NMR (300 MHz, Chloroform-d) δ 8.37 (dd, 1H), 7.66 (d, 1H), 7.43-7.31 (m, 3H), 7.25-7.19 (m, 2H), 6.70 (dd, 1H), 4.59-4.47 (m, 1H), 4.35-4.11 (m, 5H), 3.91 (s, 3H), 3.36 (dq, 4H), 2.53-2.40 (m, 1H), 2.35-2.07 (m, 5H), 1.85 (s, 2H), 1.23 (t, 3H), 0.89 (t, 3H).

The title compound (368 mg) was separated into enantiomers by preparative chiral HPLC to give enantiomer 1 (153 mg, see Example 57) and enantiomer 2 (142 mg, see Example 58).

Preparative Chiral HPLC Method:
Instrument: Labomatic HD5000, Labocord-5000; Gilson GX-241, Labcol Vario 4000, Column: Chiralpak IG 5μ 250×30 mm; Eluent A: Hexane+0.1 Vol-% Diethylamine (99%); Eluent B: Ethanol; isocratic 7:3; Flow 40.0 mL/min; UV 298 nm Analytical Chiral HPLC Method:
Instrument: Agilent HPLC 1260; Column: Chiralpak IG 3μ 100×4.6 mm; Eluent A: Hexane+0.1 Vol-% Diethylamine (99%); Eluent B: Ethanol; Gradient: 20-50% B in 7 min; Flow 1.4 mL/min; Temperature: 25° C.; DAD 325 nm Example 57

(+)-4-chloro-3,14-diethyl-7-{3-[(6-fluoronaphthalen-1-yl)oxy]propyl}-2-methyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine Salt (Enantiomer 1)

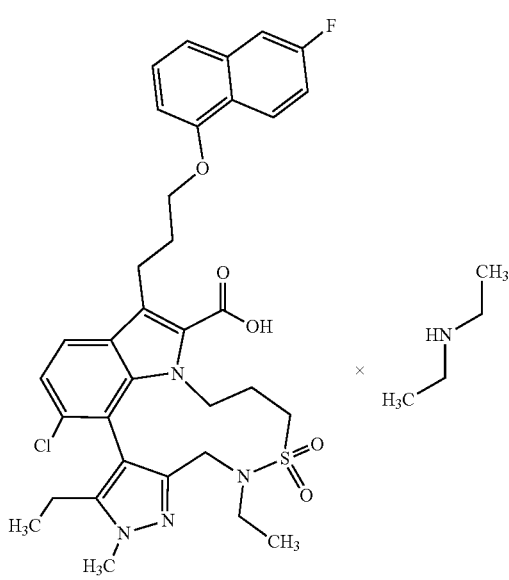

For the preparation of the racemic title compound see Example 56. Separation of enantiomers by preparative chiral HPLC (method see Example 56) gave the title compound (153 mg).

Analytical Chiral HPLC (method see Example 56): $R_t$=2.16 min.

LC-MS (Method 1): $R_t$=1.57 min; MS (ESIpos): m/z=667 [M+H]$^+$

Specific Optical Rotation (Method O1): 72.3° (c=10 mg/mL, DMSO)

1H-NMR (400 MHz, DMSO-d6) delta [ppm]: 0.770 (1.07), 0.790 (2.55), 0.808 (1.15), 1.032 (0.70), 1.049 (1.46), 1.066 (0.73), 1.107 (16.00), 1.134 (3.00), 1.152 (6.58), 1.170 (3.09), 1.663 (0.16), 2.144 (0.28), 2.163 (0.83), 2.182 (0.97), 2.204 (0.53), 2.444 (0.17), 2.518 (1.55), 2.522 (0.95), 2.846 (0.81), 2.865 (2.56), 2.883 (2.44), 2.901 (0.76), 3.171 (0.33), 3.185 (0.36), 3.204 (0.50), 3.221 (0.32), 3.247 (0.36), 3.265 (0.60), 3.768 (0.19), 3.849 (5.89), 3.973 (0.46), 4.011 (0.59), 4.098 (0.18), 4.105 (0.24), 4.121 (0.62), 4.137 (0.62), 4.153 (0.28), 4.167 (0.64), 4.205 (0.50), 4.673 (0.20), 4.707 (0.19), 6.797 (0.46), 6.801 (0.48), 6.814 (0.47), 6.818 (0.48), 7.107 (0.90), 7.128 (0.92), 7.365 (0.30), 7.371 (0.34), 7.379 (0.24), 7.387 (0.49), 7.394 (0.58), 7.400 (0.72), 7.409 (0.41), 7.417 (1.83), 7.421 (1.09), 7.438 (0.22), 7.610 (0.66), 7.632 (1.02), 7.639 (0.59), 7.659 (0.53), 7.666 (0.53), 8.287 (0.45), 8.302 (0.47), 8.310 (0.50), 8.325 (0.43).

Example 58

(−)-4-chloro-3,14-diethyl-7-{3-[(6-fluoronaphthalen-1-yl)oxy]propyl}-2-methyl-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid N-ethylethanamine Salt (Enantiomer 2)

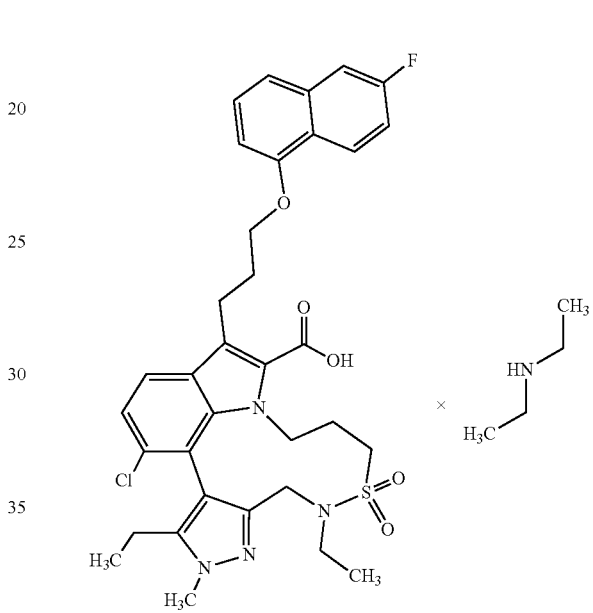

For the preparation of the racemic titled compound see Example 56. Separation of enantiomers by preparative chiral HPLC (method see Example 56) gave the titled compound (142 mg).

Analytical Chiral HPLC (method see Example 56): $R_t$=3.94 min.

LC-MS (Method 1): $R_t$=1.57 min; MS (ESIpos): m/z=667 [M+H]$^+$

Specific Optical Rotation (Method O1): −71.5° (c=10 mg/mL, DMSO)

1H-NMR (400 MHz, DMSO-d6) delta [ppm]: 0.770 (2.32), 0.789 (5.56), 0.808 (2.48), 0.967 (0.38), 1.033 (1.46), 1.050 (3.10), 1.067 (1.61), 1.083 (0.21), 1.107 (16.00), 1.137 (6.26), 1.156 (14.06), 1.173 (6.43), 1.208 (0.24), 1.232 (0.18), 1.259 (0.23), 1.667 (0.36), 1.716 (0.30), 2.019 (0.27), 2.144 (0.54), 2.162 (1.61), 2.172 (1.16), 2.182 (1.88), 2.189 (1.61), 2.205 (1.04), 2.451 (0.33), 2.518 (3.76), 2.522 (2.34), 2.660 (0.23), 2.852 (1.66), 2.871 (5.49), 2.889 (5.29), 2.907 (1.60), 3.062 (0.28), 3.158 (0.33), 3.177 (0.71), 3.194 (0.79), 3.209 (0.99), 3.228 (0.59), 3.250 (0.62), 3.269 (1.03), 3.288 (1.10), 3.777 (0.39), 3.850 (11.97), 3.975 (0.97), 4.013 (1.25), 4.099 (0.35), 4.107 (0.52), 4.123 (1.30), 4.138 (1.31), 4.154 (0.58), 4.168 (1.34), 4.206 (0.97), 4.668 (0.41), 4.690 (0.29), 4.702 (0.40), 6.798 (0.97), 6.802 (1.02), 6.815 (1.00), 6.819 (1.03), 7.114 (1.85), 7.135 (1.90), 7.364 (0.62), 7.371 (0.75), 7.379 (0.52), 7.386 (1.02), 7.393 (1.20), 7.400 (1.50), 7.409 (0.85), 7.417 (3.61), 7.421 (2.28), 7.438 (0.46), 7.620

(1.36), 7.633 (1.30), 7.640 (2.25), 7.659 (1.15), 7.665 (1.11), 8.287 (0.97), 8.302 (1.09), 8.310 (0.99), 8.325 (0.93).

Example 59

(rac)-4-chloro-3-ethyl-7-{3-[(6-fluoro-1-naphthyl)oxy]propyl}-2,14-dimethyl-15-[2-(tetrahydro-2H-pyran-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide (Racemate 2)

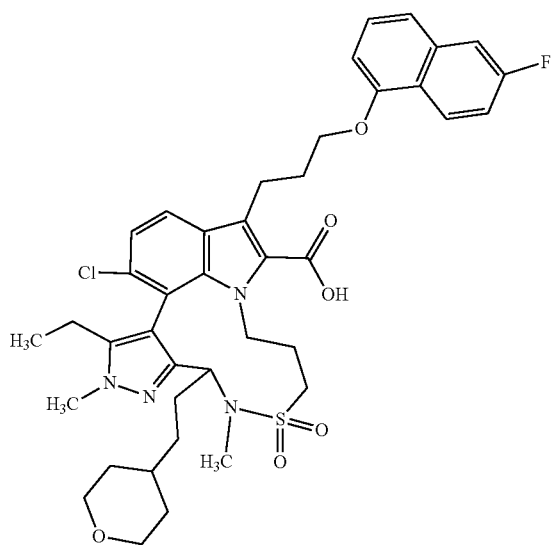 [SMILES: CCc1c2c(nn1C)C(CCC1CCOCC1)N(C)S(=O)(=O)CCCn1c(C(=O)O)c(CCCOc3cccc4cc(F)ccc34)c3ccc(Cl)c-2c31]

A solution of (rac)-ethyl 13-chloro-12-ethyl-1-(3-((6-fluoronaphthalen-1-yl)oxy)propyl)-8,11-dimethyl-9-(2-(tetrahydro-2H-pyran-4-yl)ethyl)-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 134, 173 mg, 218 μmol) in ethanol (1 mL) was treated with a 2 M aqueous solution of sodium hydroxide (327 μL, 654 μmol) and stirred at 60° C. for 24 h. After cooling to room temperature, the mixture was acidified with 1 N aqueous HCl and adsorbed onto Celite. The crude mixture was purified by reverse-phase flash chromatography on C18-silica gel (10-100% acetonitrile/water with 0.1% formic acid) to obtain the title compound (162 mg).

LC-MS (Method 4): $R_t$=5.05 min; MS (ESIpos): m/z=765 [M+H]$^+$ $^1$H NMR (300 MHz, DMSO-d$_6$) δ 13.35 (s, 1H), 8.32 (dd, 1H), 7.79 (d, 1H), 7.66 (dd, 1H), 7.49-7.35 (m, 3H), 7.21 (d, 1H), 6.82 (dd, 1H), 5.06 (t, 1H), 4.31-4.08 (m, 2H), 4.08-3.94 (m, 1H), 3.81 (s, 4H), 3.30-3.13 (m, 3H), 2.89-2.69 (m, 1H), 2.18 (dt, 4H), 1.98 (s, 1H), 1.75 (d, 2H), 1.71 (s, 3H), 1.50 (d, 3H), 1.31-1.02 (m, 4H), 0.82 (t, 3H).

The title compound (149 mg) was separated into enantiomers by preparative chiral HPLC to give enantiomer 3 (66 mg, see Example 63) and enantiomer 4 (58 mg, see Example 64).

Preparative Chiral HPLC Method:
Instrument: Labomatic HD5000, Labocord-5000; Gilson GX-241, Labcol Vario 4000, Column: Chiralpak IA 5μ 250×30 mm; Eluent A: Hexane+0.1 Vol-% Trifluoroacetic acid; Eluent B: 2-Propanol; Isocratic: 80% A+20% B; Flow 50.0 mL/min; UV 254 nm Analytical Chiral HPLC Method:
Instrument: Agilent HPLC 1260; Column: Chiralpak IA 3μ 100×4.6 mm; Eluent A: Hexane+0.1 Vol-% Trifluoroacetic acid; Eluent B: 2-Propanol; Isocratic: 80% A+20% B; Flow 1.4 mL/min; Temperature: 25° C.; DAD 254 nm

Example 60

(rac)-4-chloro-3-ethyl-7-{3-[(6-fluoro-1-naphthyl)oxy]propyl}-2,14-dimethyl-15-[2-(tetrahydro-2H-pyran-4-yl)ethyl]-11,12,14,15-tetrahydro-2H,10H-pyrazolo[3',4':4,5][1,2,8]thiadiazacycloundecino[6,7,8-hi]indole-8-carboxylic acid 13,13-dioxide (Racemate 1)

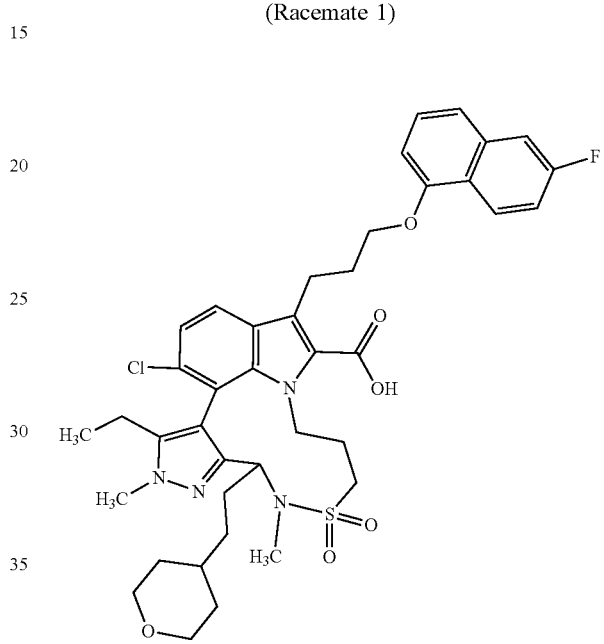

A solution of ethyl 13-chloro-12-ethyl-1-(3-((6-fluoronaphthalen-1-yl)oxy)propyl)-8,11-dimethyl-9-(2-(tetrahydro-2H-pyran-4-yl)ethyl)-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 133, 125 mg, 157 μmol) in ethanol (784 μL) was treated with a 2 M aqueous solution of sodium hydroxide (235 μL, 471 μmol) and stirred at 60° C. for 20 h. After cooling to room temperature, the mixture was acidified with 1 N aqueous HCl and adsorbed onto Celite. The crude mixture was purified by reverse-phase flash chromatography on C18-silica gel (10-100% acetonitrile/water with 0.1% formic acid) to obtain the title compound (110 mg).

LC-MS (Method 4): $R_t$=5.03 min; MS (ESIpos): m/z=765 [M+H]$^+$ $^1$H NMR (300 MHz, DMSO-d$_6$) δ 13.33 (s, 1H), 8.30 (dd, 1H), 7.83 (d, 1H), 7.66 (dd, 1H), 7.49-7.33 (m, 3H), 7.28 (d, 1H), 6.85 (dd, 1H), 4.50-4.33 (m, 2H), 4.17 (t, 2H), 3.98 (m, 1H), 3.87 (s, 3H), 3.85-3.71 (m, 2H), 3.20 (dd, 3H), 2.86 (s, 3H), 2.77 (d, 1H), 2.29-1.99 (m, 5H), 1.99-1.61 (m, 4H), 1.54 (m, 3H), 1.27-0.98 (m, 5H), 0.75 (t, 3H).

The title compound (101 mg) was separated into enantiomers by preparative chiral HPLC to give enantiomer 1 (37 mg, see Example 61) and enantiomer 2 (42 mg, see Example 62).

Preparative Chiral HPLC Method:
Instrument: Labomatic HD5000, Labocord-5000; Gilson GX-241, Labcol Vario 4000, Column: Cellulose SB 5μ

250×30 mm; Eluent A: Hexane+0.1 Vol-% Trifluoroacetic acid; Eluent B: 2-Propanol; Isocratic: 82% A+18% B; Flows 50.0 mL/min; UV 254 nm
Analytical Chiral HPLC Method:
Instrument: Agilent HPLC 1260; Column: Cellulose SB 3µ 100×4.6 mm; Eluent A: Hexane+0.1 Vol-% Trifluoroacetic acid; Eluent B: 2-Propanol; Isocratic: 82% A+18% B; Flow 1.4 mL/min; Temperature: 25° C.; DAD 254 nm Example 61

(+)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (Enantiomer 1)

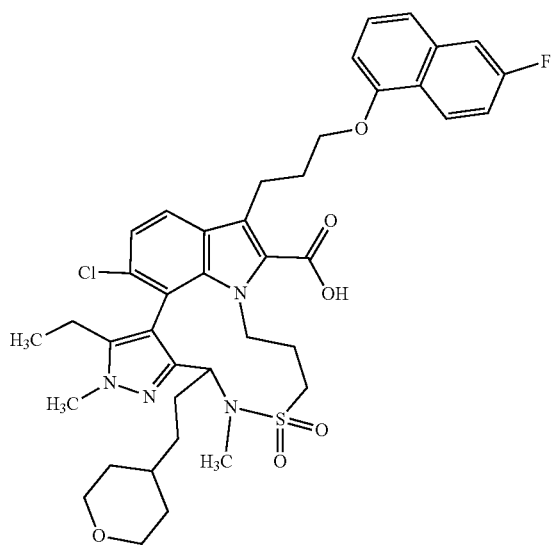 [SMILES: CCc1c2c(nn1C)C(CCC1CCOCC1)N(C)S(=O)(=O)CCCn1c(C(=O)O)c(CCCOc3cccc4cc(F)ccc34)c3ccc(Cl)c-2c31]

For the preparation of the racemic title compound see Example 60. Separation of enantiomers by preparative chiral HPLC (method see Example 60) gave the title compound (37 mg).
Analytical Chiral HPLC (method see Example 60): $R_t$=2.86 min.
LC-MS (Method 2): $R_t$=1.00 min; MS (ESIpos): m/z=765 [M+H]$^+$
Specific Optical Rotation (Method O1): 102.2° (c=10 mg/mL, DMSO)
$^1$H-NMR (400 MHz, DMSO-d6) δ[ppm]: 0.731 (3.67), 0.750 (8.17), 0.769 (3.83), 1.027 (1.30), 1.035 (0.77), 1.042 (1.47), 1.052 (1.37), 1.063 (1.33), 1.070 (1.17), 1.084 (1.10), 1.093 (1.47), 1.123 (0.73), 1.136 (2.87), 1.154 (5.53), 1.172 (3.27), 1.187 (1.57), 1.203 (1.73), 1.230 (1.07), 1.315 (0.80), 1.331 (0.77), 1.446 (0.77), 1.527 (1.97), 1.560 (1.73), 1.635 (0.60), 1.737 (1.13), 1.765 (1.30), 1.787 (0.47), 1.857 (0.50), 1.876 (0.63), 1.892 (0.70), 1.910 (0.57), 2.028 (0.87), 2.046 (1.50), 2.064 (2.07), 2.083 (1.70), 2.102 (0.97), 2.123 (1.23), 2.141 (1.30), 2.159 (1.20), 2.180 (1.60), 2.200 (2.17), 2.216 (1.43), 2.323 (1.33), 2.327 (1.87), 2.332 (1.43), 2.523 (5.40), 2.665 (1.30), 2.669 (1.87), 2.673 (1.43), 2.774 (0.53), 2.796 (1.07), 2.831 (0.87), 2.854 (16.00), 2.902 (0.77), 2.920 (1.00), 2.933 (0.97), 2.951 (0.73), 3.165 (0.63), 3.185 (0.90), 3.200 (1.00), 3.214 (1.67), 3.226 (1.67), 3.240 (1.07), 3.254 (1.07), 3.276 (0.57), 3.291 (0.93), 3.309 (1.97), 3.327 (1.93), 3.346 (0.90), 3.360 (0.57), 3.429 (0.50), 3.446 (0.50), 3.771 (6.13), 3.783 (6.30), 3.796 (5.43), 3.810 (4.80), 3.952 (1.00), 3.961 (1.97), 3.978 (1.23), 4.003 (0.83), 4.151 (1.80), 4.167 (3.50), 4.181 (1.77), 4.362 (1.20), 4.382 (2.40), 4.401 (1.57), 4.442 (0.70), 6.843 (1.53), 6.849 (1.63), 6.860 (1.53), 6.865 (1.67), 7.275 (4.07), 7.296 (4.07), 7.369 (0.93), 7.375 (1.10), 7.391 (1.57), 7.398 (1.77), 7.405 (0.77), 7.413 (1.10), 7.420 (1.37), 7.426 (2.63), 7.443 (6.23), 7.459 (0.63), 7.648 (1.77), 7.655 (1.83), 7.674 (1.80), 7.681 (1.83), 7.826 (3.67), 7.848 (3.27), 8.283 (1.53), 8.297 (1.63), 8.306 (1.63), 8.321 (1.53).

Example 62

(−)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (Enantiomer 2)

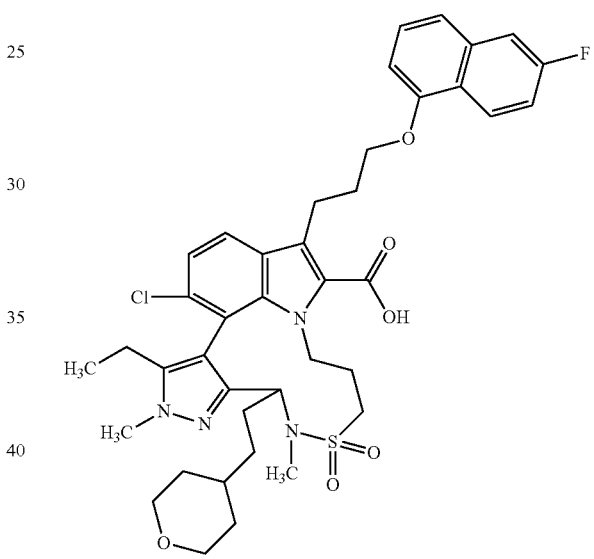

For the preparation of the racemic title compound see Example 60. Separation of enantiomers by preparative chiral HPLC (method see Example 60) gave the title compound (42 mg).
Analytical Chiral HPLC (method see Example 60): $R_t$=4.12 min.
LC-MS (Method 2): $R_t$=1.00 min; MS (ESIpos): m/z=765 [M+H]$^+$
Specific Optical Rotation (Method O1): −90.7° (c=10 mg/mL, DMSO)
$^1$H-NMR (400 MHz, DMSO-d6) δ[ppm]: 0.731 (3.18), 0.750 (7.09), 0.769 (3.33), 1.026 (1.26), 1.035 (1.05), 1.041 (1.40), 1.052 (2.01), 1.062 (1.17), 1.070 (1.34), 1.083 (0.93), 1.092 (1.26), 1.123 (0.70), 1.136 (4.00), 1.154 (8.06), 1.172 (4.53), 1.187 (1.37), 1.203 (1.49), 1.231 (1.28), 1.305 (0.50), 1.315 (0.79), 1.330 (0.82), 1.445 (0.64), 1.527 (1.64), 1.558 (1.43), 1.634 (0.50), 1.729 (0.93), 1.737 (0.93), 1.764 (1.05), 1.855 (0.44), 1.875 (0.53), 1.892 (0.61), 1.907 (0.53), 2.027 (0.76), 2.045 (1.28), 2.064 (1.75), 2.083 (1.40), 2.102 (0.79), 2.121 (1.02), 2.141 (1.11), 2.159 (1.02), 2.178 (1.37), 2.199 (1.78), 2.216 (1.20), 2.326 (1.66), 2.331 (1.20), 2.517 (10.86), 2.522 (6.69), 2.668 (1.69), 2.673 (1.23), 2.772

(0.44), 2.794 (0.91), 2.807 (0.55), 2.831 (0.76), 2.853 (13.58), 2.884 (0.41), 2.902 (1.11), 2.920 (1.43), 2.933 (1.40), 2.950 (1.05), 3.165 (1.87), 3.185 (0.79), 3.200 (0.91), 3.214 (1.43), 3.224 (1.37), 3.238 (0.93), 3.254 (0.93), 3.276 (0.50), 3.290 (0.82), 3.308 (1.69), 3.327 (1.66), 3.345 (0.79), 3.359 (0.55), 3.411 (0.44), 3.428 (0.85), 3.445 (0.93), 3.463 (0.53), 3.770 (2.72), 3.784 (3.04), 3.796 (2.66), 3.810 (2.39), 3.870 (16.00), 3.951 (0.70), 3.960 (1.66), 3.976 (0.93), 4.003 (0.61), 4.150 (1.49), 4.166 (2.89), 4.181 (1.46), 4.362 (0.99), 4.381 (1.99), 4.401 (1.31), 4.442 (0.58), 6.843 (1.34), 6.849 (1.37), 6.859 (1.31), 6.865 (1.40), 7.275 (3.71), 7.296 (3.80), 7.368 (0.85), 7.375 (0.93), 7.391 (1.37), 7.397 (1.52), 7.405 (0.67), 7.413 (0.96), 7.419 (1.20), 7.426 (2.28), 7.438 (2.89), 7.442 (5.28), 7.458 (0.61), 7.648 (1.52), 7.654 (1.61), 7.674 (1.55), 7.680 (1.58), 7.825 (3.33), 7.847 (3.01), 8.283 (1.37), 8.297 (1.46), 8.305 (1.43), 8.321 (1.34).

Example 63

(+)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (Enantiomer 3)

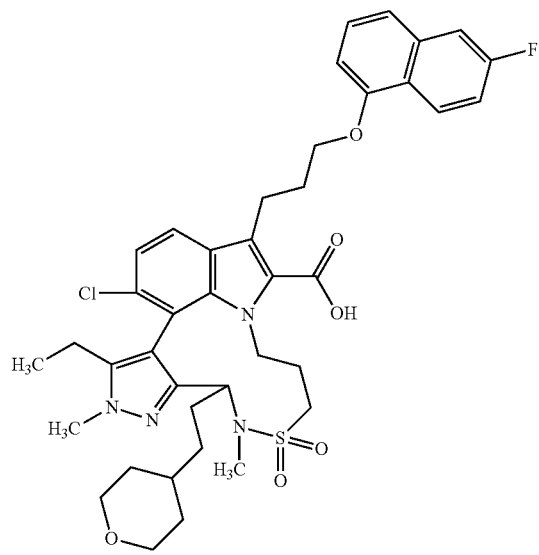 [SMILES: CCc1c2c(nn1C)C(CCC1CCOCC1)N(C)S(=O)(=O)CCCn1c(C(=O)O)c(CCCOc3cccc4cc(F)ccc34)c3ccc(Cl)c-2c31]

For the preparation of the racemic title compound see Example 59. Separation of enantiomers by preparative chiral HPLC (method see Example 59) gave the title compound (66 mg).

Analytical Chiral HPLC (method see Example 59): $R_t$=2.15 min.

LC-MS (Method 2): $R_t$=1.00 min; MS (ESIpos): m/z=765 [M+H]$^+$

Specific Optical Rotation (Method O1): 15.2° (c=10 mg/mL, DMSO)

$^1$H-NMR (400 MHz, DMSO-d6) δ[ppm]: 0.795 (2.94), 0.814 (6.63), 0.833 (3.10), 1.027 (0.43), 1.042 (0.48), 1.084 (0.81), 1.111 (1.27), 1.136 (2.65), 1.154 (4.39), 1.173 (2.38), 1.201 (0.61), 1.218 (0.48), 1.232 (0.88), 1.315 (1.24), 1.331 (1.27), 1.447 (0.41), 1.489 (1.13), 1.515 (1.43), 1.547 (0.66), 1.703 (12.67), 1.741 (0.91), 1.749 (0.97), 1.760 (0.91), 1.786 (0.59), 1.807 (0.45), 1.829 (0.45), 1.983 (0.45), 2.113 (0.43), 2.132 (0.72), 2.150 (1.20), 2.169 (1.56), 2.188 (2.04), 2.207 (2.17), 2.225 (1.70), 2.244 (0.72), 2.337 (0.43), 2.518 (5.18), 2.523 (3.53), 2.540 (0.41), 2.674 (0.93), 2.749 (0.50), 2.766 (0.50), 2.783 (0.45), 2.802 (0.43), 2.902 (0.48), 2.921 (0.61), 2.933 (0.59), 2.951 (0.45), 3.209 (1.09), 3.238 (2.20), 3.267 (1.45), 3.288 (0.91), 3.317 (0.95), 3.335 (0.57), 3.791 (1.67), 3.811 (16.00), 3.838 (0.81), 3.870 (0.52), 3.988 (1.11), 4.011 (1.54), 4.023 (1.45), 4.035 (1.54), 4.048 (1.58), 4.107 (1.95), 4.124 (2.24), 4.131 (2.38), 4.147 (2.87), 4.167 (2.83), 4.182 (2.10), 4.192 (1.88), 4.204 (1.74), 4.214 (1.81), 4.227 (1.47), 4.238 (1.31), 4.251 (1.31), 4.362 (0.48), 5.037 (0.81), 5.059 (1.13), 5.076 (0.79), 6.814 (1.22), 6.818 (1.24), 6.831 (1.24), 6.835 (1.29), 7.200 (3.49), 7.221 (3.49), 7.376 (0.81), 7.383 (0.91), 7.398 (1.54), 7.405 (1.40), 7.417 (1.97), 7.428 (1.40), 7.433 (4.25), 7.453 (0.59), 7.649 (1.43), 7.655 (1.47), 7.675 (1.45), 7.681 (1.47), 7.787 (3.12), 7.808 (2.81), 8.304 (1.22), 8.319 (1.29), 8.327 (1.22), 8.342 (1.18).

Example 64

(−)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (Enantiomer 4)

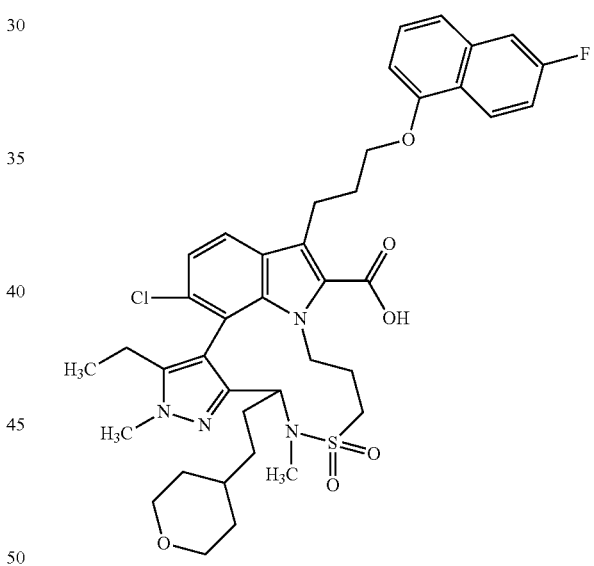

For the preparation of the racemic title compound see Example 59. Separation of enantiomers by preparative chiral HPLC (method see Example 59) gave the title compound (58 mg).

Analytical Chiral HPLC (method see Example 59): $R_t$=3.13 min.

LC-MS (Method 2): $R_t$=1.00 min; MS (ESIpos): m/z=765 [M+H]$^+$

Specific Optical Rotation (Method O1): −14.5° (c=10 mg/mL, DMSO)

$^1$H-NMR (400 MHz, DMSO-d6) δ[ppm]: 0.795 (2.86), 0.814 (6.60), 0.833 (3.05), 1.111 (1.28), 1.136 (2.80), 1.154 (4.77), 1.173 (2.54), 1.200 (0.57), 1.218 (0.48), 1.232 (0.82), 1.489 (1.14), 1.515 (1.43), 1.548 (0.65), 1.703 (12.59), 1.740 (0.88), 1.749 (0.99), 1.762 (0.88), 1.787 (0.57), 1.808 (0.44), 1.827 (0.42), 1.981 (0.46), 2.069 (0.55), 2.113 (0.44), 2.132 (0.74), 2.150 (1.20), 2.169 (1.56), 2.188 (2.02), 2.207 (2.14), 2.225 (1.70), 2.245 (0.69), 2.337 (0.40), 2.518 (5.11), 2.523 (3.53), 2.674 (0.86), 2.749 (0.48), 2.765 (0.50), 2.783 (0.46), 2.802 (0.42), 2.902 (0.53), 2.921 (0.67), 2.933 (0.65), 2.951 (0.50), 3.209 (1.07), 3.238 (2.19), 3.267 (1.41), 3.288 (0.84), 3.316 (0.90), 3.335 (0.55), 3.791 (1.68), 3.811 (16.00), 3.887 (0.55), 3.987 (1.18), 4.011 (1.60), 4.024 (1.47), 4.036 (1.53), 4.048 (1.51), 4.108 (1.41), 4.124 (1.62), 4.131 (1.72), 4.147 (2.19), 4.168 (2.12), 4.182 (1.45), 4.192 (1.26), 4.216 (1.30), 4.227 (1.03), 4.238 (0.90), 4.250 (0.99), 5.036 (0.82), 5.059 (1.16), 5.076 (0.80), 6.814 (1.24), 6.818 (1.28), 6.831 (1.24), 6.835 (1.30), 7.200 (3.51), 7.221 (3.49), 7.376 (0.80), 7.383 (0.88), 7.398 (1.53), 7.405 (1.41), 7.417 (1.98), 7.428 (1.39), 7.433 (4.27), 7.454 (0.57), 7.649 (1.41), 7.655 (1.45), 7.675 (1.43), 7.681 (1.41), 7.787 (3.13), 7.808 (2.80), 8.304 (1.22), 8.319 (1.28), 8.327 (1.24), 8.342 (1.18).

Example 65

(rac)-4-chloro-7-{3-[(6-fluoronaphthalen-1-yl)oxy]propyl}-2,3,14-trimethyl-15-(rac)-[2-(morpholin-4-yl)ethyl]-13,13-dioxo-10,11,12,13,14,15-hexahydro-2H-13lambda⁶-pyrazolo[3',4':4,5][1,2,8]thiadiazacycloundecino[6,7,8-hi]indole-8-carboxylic acid (Mixture of Stereoisomers)

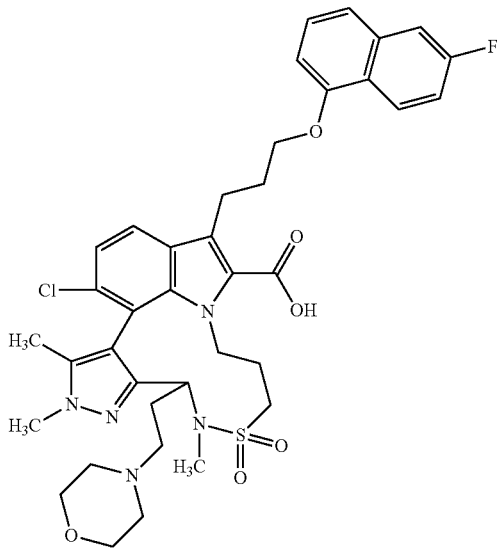 [SMILES: Cc1c2c(nn1C)C(CCN1CCOCC1)N(C)S(=O)(=O)CCCn1c(C(=O)O)c(CCCOc3cccc4cc(F)ccc34)c3ccc(Cl)c-2c31]

For the preparation of the title compound see Example 48. Separation of the mixture of stereoisomers by preparative chiral HPLC (method see Example 48) gave the titled compound (16 mg).

Analytical Chiral HPLC (method see Example 48): $R_t$=6.70-7.28 min.

LC-MS (Method 2): $R_t$=0.90 min; MS (ESIpos): m/z=752 [M+H]⁺

¹H-NMR (400 MHz, DMSO-d6) δ[ppm]: 0.830 (0.41), 0.848 (0.62), 1.140 (6.90), 1.159 (15.24), 1.177 (7.03), 1.228 (3.12), 1.254 (0.79), 1.294 (0.49), 1.667 (11.79), 1.710 (0.78), 1.731 (4.43), 1.762 (0.63), 1.809 (14.97), 1.839 (2.12), 1.857 (2.60), 1.871 (2.17), 1.906 (1.08), 2.177 (1.90), 2.195 (2.48), 2.211 (3.42), 2.230 (3.99), 2.247 (2.64), 2.327 (4.21), 2.332 (4.46), 2.336 (4.34), 2.518 (4.72), 2.522 (3.07), 2.539 (1.65), 2.664 (0.79), 2.668 (1.03), 2.673 (0.79), 2.736 (0.87), 2.748 (0.79), 2.762 (0.76), 2.774 (0.93), 2.787 (0.60), 2.861 (3.73), 2.886 (2.07), 2.905 (5.54), 2.923 (5.36), 2.941 (1.80), 2.993 (0.52), 3.255 (3.56), 3.508 (3.01), 3.520 (2.42), 3.535 (4.95), 3.546 (7.03), 3.557 (4.70), 3.743 (1.00), 3.779 (16.00), 3.840 (4.94), 3.856 (0.65), 3.913 (0.47), 3.930 (0.76), 3.948 (0.97), 3.965 (0.93), 3.983 (0.66), 4.115 (0.74), 4.123 (0.97), 4.140 (1.80), 4.159 (2.04), 4.166 (1.63), 4.182 (1.16), 4.287 (0.87), 4.300 (0.62), 4.307 (0.59), 4.322 (0.79), 4.501 (0.68), 5.163 (1.03), 5.181 (1.60), 5.202 (0.98), 6.808 (1.44), 6.812 (1.50), 6.824 (1.47), 6.829 (1.54), 6.840 (0.54), 6.846 (0.55), 6.856 (0.49), 6.862 (0.47), 7.161 (2.88), 7.181 (2.98), 7.239 (0.97), 7.261 (0.95), 7.361 (0.43), 7.367 (1.23), 7.374 (1.19), 7.390 (2.61), 7.397 (1.96), 7.411 (3.09), 7.419 (2.48), 7.428 (5.38), 7.435 (2.34), 7.444 (0.97), 7.639 (2.22), 7.646 (2.29), 7.665 (2.29), 7.672 (2.25), 7.722 (2.20), 7.744 (2.01), 7.778 (0.76), 7.799 (0.65), 8.276 (0.46), 8.291 (1.69), 8.298 (0.74), 8.307 (1.63), 8.315 (1.71), 8.330 (1.36).

Example 66

4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda⁶-pyrazolo[3',4':4,5][1,2,8]thiadiazacycloundecino[6,7,8-hi]indole-8-carboxylic acid (Enantiomer 1)

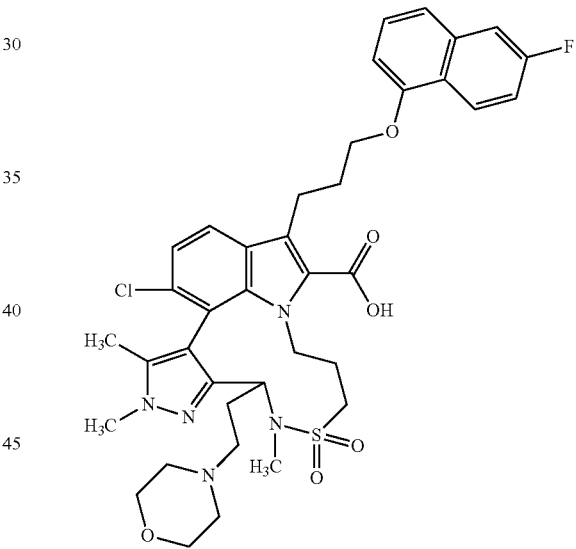

For the preparation of the title compound see Example 48. Separation of enantiomers by preparative chiral HPLC (method see Example 48) gave the title compound (10 mg).

Analytical Chiral HPLC (method see Example 48): $R_t$=4.49 min.

LC-MS (Method 2): $R_t$=0.91 min; MS (ESIpos): m/z=752 [M+H]⁺

Specific Optical Rotation (Method O1): was not measured

¹H-NMR (400 MHz, DMSO-d6) δ[ppm]: 1.139 (1.23), 1.158 (2.74), 1.175 (1.49), 1.696 (1.21), 1.733 (15.26), 1.784 (0.47), 1.820 (0.51), 1.833 (0.58), 1.907 (0.43), 1.991 (0.67), 2.007 (0.63), 2.028 (0.42), 2.172 (1.14), 2.189 (1.79), 2.207 (1.76), 2.230 (3.66), 2.259 (1.16), 2.299 (1.69), 2.318 (1.67), 2.322 (1.98), 2.326 (2.03), 2.331 (1.52), 2.518 (4.53), 2.522 (2.90), 2.539 (0.80), 2.664 (0.91), 2.668 (1.16), 2.673 (0.87), 2.678 (0.51), 2.737 (0.58), 2.749 (0.45), 2.761 (0.45), 2.777 (0.45), 2.863 (11.87), 2.886 (0.51), 2.904 (0.92), 2.922 (0.87), 3.222 (0.54), 3.240 (0.96), 3.255 (1.18), 3.273 (1.83), 3.422 (0.63), 3.440 (0.51), 3.495 (3.06), 3.506 (4.91), 3.517 (3.04), 3.842 (16.00), 3.944 (0.47), 3.959 (0.53), 3.978 (0.54), 4.153 (1.21), 4.168 (2.41), 4.184 (1.23), 4.465 (0.71), 4.483 (1.03), 4.501 (2.03), 6.844 (1.30), 6.850 (1.34), 6.860 (1.21), 6.865 (1.36), 7.237 (2.39), 7.259 (2.50), 7.363 (0.89), 7.370 (1.05), 7.386 (1.45), 7.393 (1.54), 7.400 (0.62), 7.408 (1.01), 7.414 (1.20), 7.422 (2.36), 7.431 (2.81), 7.437 (5.82), 7.452 (0.49), 7.641 (1.61), 7.648 (1.65), 7.667 (1.63), 7.674 (1.61), 7.774 (1.79), 7.796 (1.59), 8.277 (1.40), 8.292 (1.47), 8.301 (1.41), 8.315 (1.34).

Example 67

4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (Enantiomer 2)

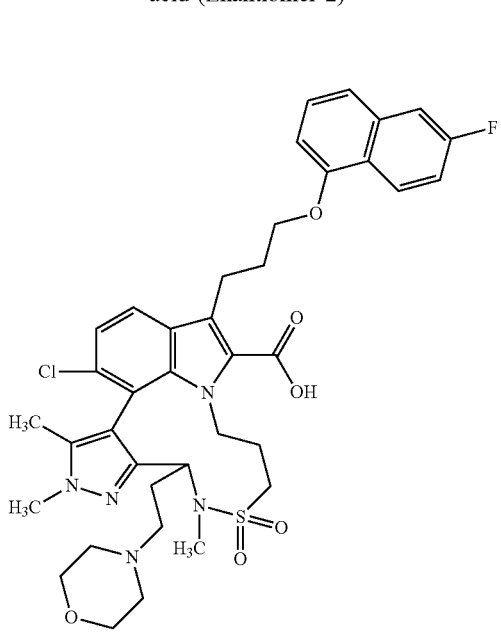

For the preparation of the title compound see Example 48. Separation of enantiomers by preparative chiral HPLC (method see Example 48) gave the title compound (5 mg).

Analytical Chiral HPLC (method see Example 48): $R_t$=5.91 min.

LC-MS (Method 2): $R_t$=0.92 min; MS (ESIpos): m/z=752 [M+H]$^+$

Specific Optical Rotation (Method O1): was not measured $^1$H-NMR (400 MHz, DMSO-d6) δ[ppm]: 1.155 (0.44), 1.699 (1.02), 1.732 (14.72), 1.782 (0.44), 1.807 (0.42), 1.819 (0.50), 1.907 (0.52), 1.997 (0.68), 2.012 (0.60), 2.030 (0.42), 2.174 (1.00), 2.191 (1.61), 2.209 (1.41), 2.237 (3.27), 2.265 (1.04), 2.318 (1.79), 2.322 (2.15), 2.326 (2.29), 2.331 (1.83), 2.518 (4.90), 2.522 (3.13), 2.539 (1.14), 2.659 (0.44), 2.664 (0.88), 2.669 (1.22), 2.673 (0.92), 2.678 (0.42), 2.754 (0.48), 2.772 (0.56), 2.786 (0.44), 2.794 (0.46), 2.862 (11.58), 3.255 (1.37), 3.288 (3.21), 3.498 (2.91), 3.509 (4.62), 3.519 (2.91), 3.842 (16.00), 3.981 (0.54), 3.995 (0.44), 4.158 (1.22), 4.173 (2.47), 4.189 (1.24), 4.443 (0.66), 4.453 (0.46), 4.467 (0.44), 4.478 (0.60), 4.490 (0.94), 4.507 (1.35), 4.523 (0.60), 6.849 (1.22), 6.856 (1.28), 6.865 (1.14), 6.871 (1.32), 7.259 (3.09), 7.279 (3.03), 7.365 (0.88), 7.372 (1.02), 7.388 (1.30), 7.395 (1.45), 7.405 (0.58), 7.410 (0.94), 7.416 (1.08), 7.426 (2.25), 7.435 (2.61), 7.441 (5.68), 7.455 (0.46), 7.644 (1.53), 7.650 (1.57), 7.670 (1.53), 7.676 (1.53), 7.803 (2.33), 7.825 (2.13), 8.276 (1.32), 8.291 (1.41), 8.299 (1.35), 8.315 (1.30).

Example 68

(rac)-4-chloro-3-ethyl-7-{3-[(6-fluoro-1-naphthyl)oxy]propyl}-2,14-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide

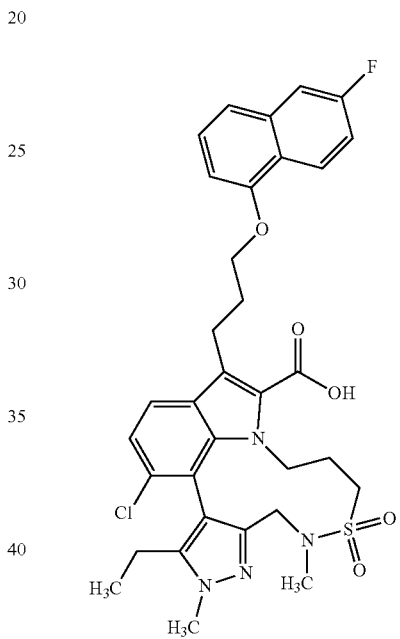

A solution of (rac)-methyl 13-chloro-12-ethyl-1-(3-((6-fluoronaphthalen-1-yl)oxy)propyl)-11-methyl-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 138, 270 mg, 413 μmol) in methanol (2 mL) was treated with a 2 M aqueous solution of sodium hydroxide (825 μL, 1.65 mmol) and stirred overnight at 60° C. After cooling to room temperature, the mixture was acidified with 1 N aqueous hydrogen chloride, adsorbed onto Celite, and purified by reverse-phase flash chromatography on C18-silica gel (10-100% acetonitrile/water with 0.1% formic acid) to obtain, the title compound (255 mg).

LC-MS (Method 4): $R_t$=4.17 min; MS (ESIpos): m/z=639 [M+H]$^+$ $^1$H NMR (300 MHz, Chloroform-d) δ 8.41 (dd, 1H), 7.73 (d, 1H), 7.45-7.21 (m, 6H), 7.06 (td, 1H), 6.76 (d, 1H), 4.71 (d, 1H), 4.40-4.14 (m, 4H), 4.05 (dd, 1H), 3.78 (s, 3H), 3.53 (d, 2H), 2.62-1.94 (m, 8H), 0.87 (t, 3H).

Example 69

(rac)-15-chloro-14-ethyl-1-(3-((6-fluoronaphthalen-1-yl)oxy)propyl)-8,13-dimethyl-11-(rac)-morpholino-5,6,9,10,11,13-hexahydro-4H,8H-pyrazolo[3',4':6,7][1]thia[2,10]diazacyclotridecino[8,9,10-hi]indole-2-carboxylic acid 7,7-dioxide (Mixture of Stereoisomers)

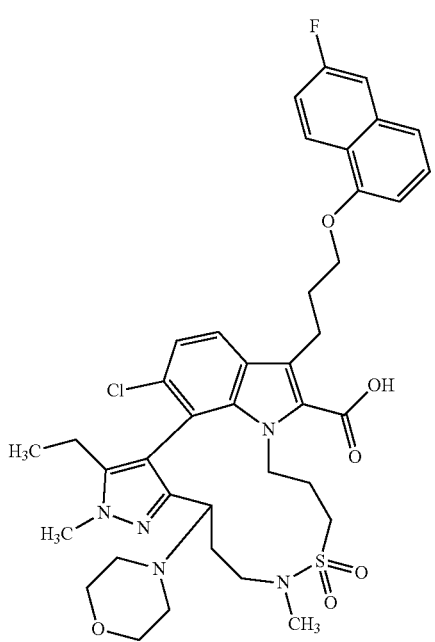 [SMILES: CCc1c2c(nn1C)C(N1CCOCC1)CCN(C)S(=O)(=O)CCCn1c(C(=O)O)c(CCCOc3cccc4cc(F)ccc34)c3ccc(Cl)c-2c31]

A solution of ethyl 15-chloro-14-ethyl-1-(3-((6-fluoronaphthalen-1-yl)oxy)propyl)-8,13-dimethyl-11-morpholino-5,6,9,10,11,13-hexahydro-4H,8H-pyrazolo[3',4':6,7][1]thia[2,10]diazacyclotridecino[8,9,10-hi]indole-2-carboxylate 7,7-dioxide (Intermediate 145, 0.547 g, 494 µmol) in ethanol (2.5 mL) was treated with a solution of 2 M aqueous sodium hydroxide (740 µL, 1.48 mmol) and stirred at 60° C. for 24 h. After cooling to room temperature, the mixture was acidified with 1 N aqueous HCl and concentrated. The crude mixture was purified by reverse-phase flash chromatography on C18-silica gel (10-100% acetonitrile/water with 0.1% formic acid) to obtain the title compound (0.23 g) as a mixture of diastereomers.

LC-MS (Method 5): $R_t$=1.46 min; MS (ESIneg): m/z=764 [M−H]⁻

¹H NMR (400 MHz, DMSO-$d_6$) δ 13.20 (s, 1H), 8.29 (dd, 1H), 7.74 (d, 1H), 7.66 (dd, 1H), 7.47-7.35 (m, 2H), 7.20 (d, 1H), 6.85 (dd, 1H), 4.52 (ddd, 1H), 4.18 (t, 2H), 3.89-3.76 (m, 1H), 3.68 (m, 1H), 3.56-3.40 (m, 3H), 3.44-3.31 (m, 6H), 3.34-3.17 (m, 7H), 2.97 (ddd, 2H), 2.61 (s, 3H), 2.47-2.32 (m, 2H), 2.37 (s, 2H), 2.34-2.05 (m, 4H), 1.95 (dt, 3H), 1.49 (q, 1H), 0.95 (t, 3H).

The mixture of stereoisomers (202 mg) were separated into enantiomers by preparative chiral HPLC to give enantiomer 1 (84 mg, see Example 70), enantiomer 2 (97.5 mg, see Example 71).

Preparative Chiral HPLC Method:
Instrument: Labomatic HD5000, Labocord-5000; Gilson GX-241, Labcol Vario 4000, Column: Cellulose SC 5µ 250×30 mm; Eluent A: Hexane+0.1 Vol-% trifluoroacetic acid (99%); Eluent B: 2-Propanol; Isocratic 60% A+40% B; Flow 50.0 mL/min; UV 254 nm Analytical Chiral HPLC Method:
Instrument: Agilent HPLC 1260; Column: Cellulose SC 3µ 100×4.6 mm; Eluent A: Hexane+0.1 Vol-% Trifluoroacetic acid (99%); Eluent B: 2-Propanol; Gradient: isocratic, 20 50% B in 7 min; Flow 1.4 mL/min; Temperature: 25° C.; DAD 254 nm

Example 70

(+)-4-chloro-3-ethyl-7-{3-[(6-fluoro-1-naphthyl)oxy]propyl}-2,14-dimethyl-17-(morpholin-4-yl)-11,12,14,15,16,17-hexahydro-2H,10H-pyrazolo[3',4':6,7][1,2,10]thiadiazacyclotridecino[8,9,10-hi]indole-8-carboxylic acid 13,13-dioxide trifluoroacetate salt (Enantiomer 1)

For the preparation of the racemic title compound see Example 69. Separation of enantiomers by preparative chiral HPLC (method see Example 69) gave the title compound (84 mg, 97% purity, 34% yield).

Analytical Chiral HPLC (method see Example 69): $R_t$=3.75 min.

LC-MS (Method 1): $R_t$=1.39 min; MS (ESIpos): m/z=766 [M+H]⁺

Specific Optical Rotation (Method O1): 34.7° (c=10 mg/mL, DMSO)

¹H-NMR (400 MHz, DMSO-d6) δ[ppm]: 0.803 (3.84), 0.851 (1.24), 1.019 (0.43), 1.026 (1.05), 1.041 (1.05), 1.049 (0.56), 1.084 (0.93), 1.137 (1.92), 1.154 (3.97), 1.173 (2.23), 1.232 (2.42), 1.314 (1.86), 1.330 (1.86), 1.432 (1.05), 1.548 (0.81), 1.907 (0.87), 1.993 (0.50), 2.046 (0.68), 2.057 (0.74), 2.061 (0.81), 2.069 (0.68), 2.083 (0.62), 2.181 (2.79), 2.200 (3.66), 2.214 (3.04), 2.318 (1.43), 2.322 (2.91), 2.326 (3.91), 2.332 (2.91), 2.336 (1.55), 2.518 (16.00), 2.522 (10.23), 2.539 (6.57), 2.633 (10.79), 2.660 (2.48), 2.664 (3.84), 2.669 (5.02), 2.673 (3.78), 2.678 (2.23), 2.736 (0.74), 2.902 (0.62), 2.920 (0.93), 2.933 (0.99), 2.951 (1.18), 2.994 (1.24), 3.302 (4.03), 3.319 (3.04), 3.722 (2.11), 3.754 (2.54), 3.956

(8.50), 4.206 (3.84), 4.416 (0.93), 4.578 (1.12), 6.879 (2.11), 7.308 (1.24), 7.330 (1.24), 7.367 (1.98), 7.374 (2.23), 7.390 (3.04), 7.396 (3.35), 7.412 (2.17), 7.418 (2.60), 7.437 (4.40), 7.444 (6.26), 7.450 (10.29), 7.464 (0.99), 7.653 (3.35), 7.660 (3.47), 7.679 (3.41), 7.686 (3.41), 7.836 (1.30), 7.857 (1.18), 8.233 (1.30), 8.255 (1.61), 8.270 (1.30), 10.323 (0.62).

Example 71

(−)-4-chloro-3-ethyl-7-{3-[(6-fluoro-1-naphthyl)oxy]propyl}-2,14-dimethyl-17-(morpholin-4-yl)-11,12,14,15,16,17-hexahydro-2H,10H-pyrazolo[3',4':6,7][1,2,10]thiadiazacyclotridecino[8,9,10-hi]indole-8-carboxylic acid 13,13-dioxide trifluoroacetate salt (Enantiomer 2)

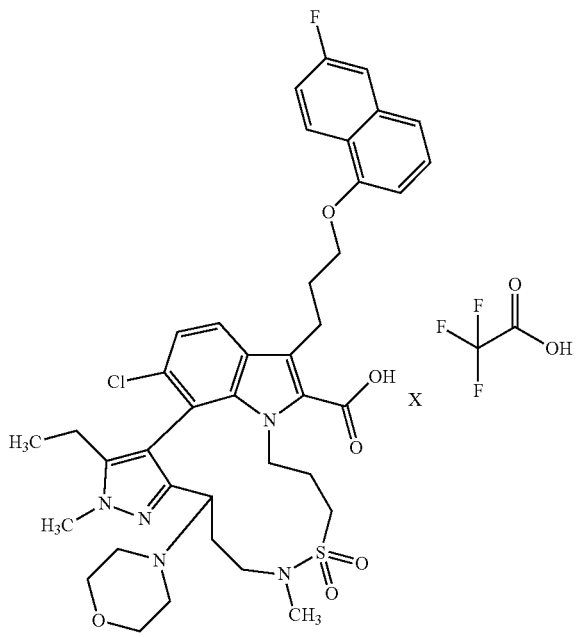

For the preparation of the racemic title compound see Example 69. Separation of enantiomers by preparative chiral HPLC (method see Example 69) gave the title compound (97.5 mg, 98% purity, 40% yield).

Analytical Chiral HPLC (method see Example 69): $R_t$=4.36 min.

LC-MS (Method 1): $R_t$=1.39 min; MS (ESIpos): m/z=766 [M+H]$^+$

Specific Optical Rotation (Method O1): −31.7° (c=10 mg/mL, DMSO)

$^1$H-NMR (400 MHz, DMSO-d6) δ[ppm]: 0.804 (6.13), 0.850 (2.11), 0.934 (1.02), 1.026 (2.66), 1.041 (2.72), 1.084 (1.23), 1.137 (0.95), 1.155 (1.57), 1.173 (1.16), 1.232 (3.81), 1.315 (2.31), 1.330 (2.04), 1.440 (1.70), 1.553 (1.29), 1.907 (1.57), 1.993 (0.82), 2.046 (0.82), 2.062 (1.29), 2.069 (1.09), 2.083 (0.95), 2.182 (4.49), 2.199 (5.79), 2.215 (4.83), 2.322 (3.34), 2.327 (4.56), 2.332 (3.68), 2.522 (13.00), 2.635 (16.00), 2.665 (4.70), 2.669 (5.72), 2.673 (4.70), 2.990 (1.97), 3.302 (5.92), 3.543 (4.90), 3.718 (12.39), 3.957 (14.16), 4.130 (0.82), 4.207 (6.06), 4.416 (1.50), 4.577 (1.77), 6.879 (3.20), 7.310 (2.04), 7.331 (2.04), 7.367 (2.52), 7.374 (2.93), 7.390 (4.49), 7.397 (5.04), 7.412 (3.00), 7.418 (3.61), 7.437 (6.26), 7.444 (9.12), 7.451 (14.16), 7.653 (4.56), 7.660 (4.77), 7.679 (4.56), 7.686 (4.63), 7.838 (2.11), 7.858 (1.84), 8.233 (1.91), 8.255 (2.52), 8.271 (1.97), 10.343 (1.09), 13.526 (0.48).

Example 72

4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda6-pyrazolo[3',4':4,5][1,2,8]thiadiazacycloundecino[6,7,8-hi]indole-8-carboxylic acid (Mixture of Stereoisomers)

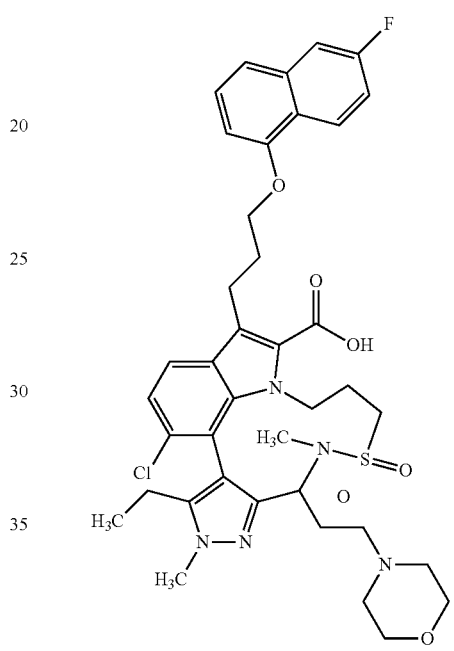

A solution of ethyl 13-chloro-12-ethyl-1-(3-((6-fluoronaphthalen-1-yl)oxy)propyl)-8,11-dimethyl-9-(2-morpholinoethyl)-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 143, 0.318 g, 400 μmol) in ethanol (2 mL) was treated with a 2 M aqueous solution of sodium hydroxide (600 μL, 1.20 mmol) and stirred at 60° C. for 24 h. After cooling to room temperature, the mixture was acidified with 1 N aqueous HCl and concentrated. The crude mixture was purified by reverse-phase flash chromatography on C18-silica gel (10-100% acetonitrile/water with 0.1% formic acid) to obtain, the title compound (0.134 g) as a ~2:1 mixture of diastereomers.

LC-MS (Method 5): $R_t$=1.31 min; MS (ESIneg): m/z=764 [M−H]$^-$ $^1$H NMR (DMSO-d6) δ: 8.32 (dt, 4H), 7.84 (d, 2H), 7.80 (d, 1H), 7.67 (dd, 3H), 7.50-7.35 (m, 11H), 7.29 (d, 2H), 7.21 (d, 1H), 6.85 (ddd, 4H), 5.24 (t, 1H), 4.53 (t, 2H), 4.45 (d, 3H), 4.18 (t, 7H), 4.08-3.95 (m, 3H), 3.88 (s, 7H), 3.82 (s, 3H), 3.55 (dd, 15H), 2.87 (s, 7H), 2.79 (dd, 2H), 2.55 (s, 8H), 2.36 (s, 12H), 2.27 (s, 20H), 2.22 (d, 5H), 2.22-2.02 (m, 6H), 1.94-1.85 (m, 2H), 1.83-1.68 (m, 11H), 0.82 (t, 3H), 0.76 (t, 8H).

The mixture of stereoisomers (127 mg) was separated into the racemate 2 (65 mg, see Example 74) and racemate 1 (12 mg, see Example 73) by preparative chiral HPLC.

Preparative Chiral HPLC Method:

Instrument: Labomatic HD5000, Labocord-5000; Gilson GX-241, Labcol Vario 4000, Column: Chiralpak IE 5µ 250×30 mm; Eluent A: MtBE+0.1 Vol-% Diethylamine (99%); Eluent B: Ethanol; Isocratic 90% A+10% B; Flow 50.0 mL/min; UV 254 nm Analytical Chiral HPLC Method:

Instrument: Agilent HPLC 1260; Column: Cellulose SC 3µ 100×4.6 mm; Eluent A: MtBE+0.1 Vol-% Diethylamine (99%); Eluent B: Ethanol; Gradient: isocratic, 90% A–10% B in 7 min; Flow 1.4 mL/min; Temperature: 25° C.; DAD 254 nm Example 73

(rac)-(4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid (Racemate 1)

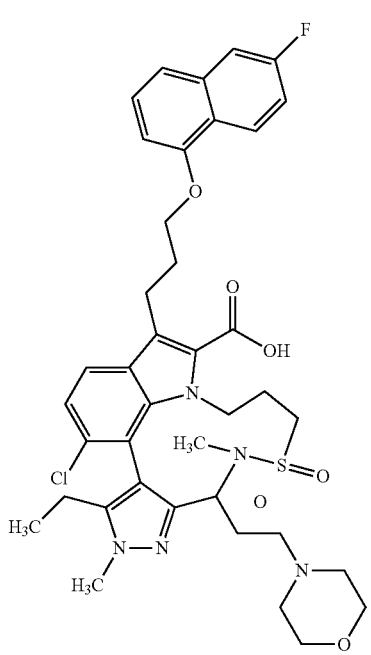

For the preparation of the mixture of stereoisomers see Example 72. Separation of this mixture into 2 diastereomers by preparative chiral HPLC (method see Example 72) gave racemate 1: 18 mg, 98% purity, 14% yield.

Analytical Chiral HPLC (method see Example 72): $R_t$=4.65 min.

LC-MS Method 2): $R_t$=0.94 min; MS (ESIpos): m/z=766 [M+H]$^+$ $^1$H-NMR (400 MHz, DMSO-d6) δ[ppm]: 0.760 (1.26), 0.779 (1.21), 0.823 (3.45), 0.842 (7.02), 0.860 (3.59), 0.995 (0.45), 1.107 (1.07), 1.138 (7.35), 1.156 (16.00), 1.175 (9.71), 1.231 (3.93), 1.332 (0.62), 1.348 (0.48), 1.629 (8.06), 1.822 (0.81), 1.841 (1.71), 1.858 (1.96), 1.876 (1.24), 1.906 (1.35), 2.191 (3.68), 2.199 (3.65), 2.210 (4.21), 2.227 (2.18), 2.255 (0.45), 2.322 (4.32), 2.326 (5.00), 2.331 (4.46), 2.518 (8.28), 2.522 (5.45), 2.539 (0.70), 2.664 (1.38), 2.668 (1.94), 2.673 (1.66), 2.713 (0.48), 2.876 (1.77), 2.894 (5.33), 2.912 (5.31), 2.931 (1.66), 3.195 (0.73), 3.212 (1.40), 3.231 (1.43), 3.250 (0.93), 3.504 (0.81), 3.533 (3.51), 3.544 (5.59), 3.556 (3.48), 3.785 (0.45), 3.805 (15.35), 3.867 (0.79), 3.884 (0.51), 4.100 (0.62), 4.107 (0.67), 4.124 (1.24), 4.136 (0.95), 4.152 (1.26), 4.168 (0.67), 4.176 (0.62), 4.294 (0.59), 4.329 (0.53), 5.186 (0.90), 5.206 (1.94), 5.226 (0.87), 6.789 (1.29), 6.793 (1.35), 6.806 (1.32), 6.810 (1.32), 7.100 (1.63), 7.121 (1.68), 7.368 (0.84), 7.374 (1.01), 7.380 (0.76), 7.390 (1.49), 7.397 (2.02), 7.401 (2.27), 7.418 (5.19), 7.438 (0.65), 7.636 (2.50), 7.642 (2.08), 7.662 (2.16), 7.668 (1.74), 8.297 (1.29), 8.311 (1.38), 8.319 (1.32), 8.335 (1.24).

Example 74

(rac) 4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda6-pyrazolo[3',4':4,5][1,2,8]thiadiazacycloundecino[6,7,8-hi]indole-8-carboxylic acid (Racemate 2)

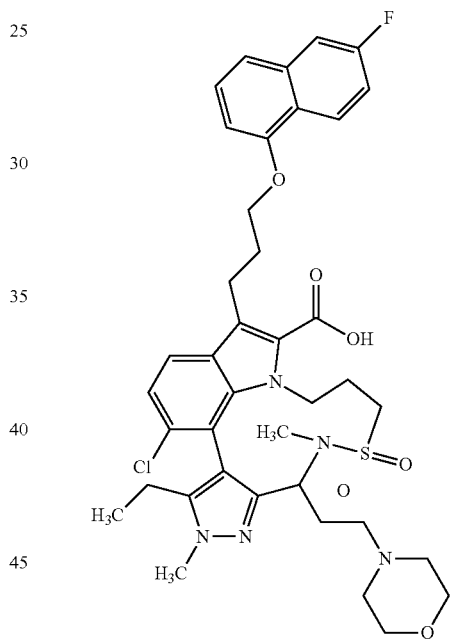

For the preparation of the mixture of stereoisomers see Example 72. Separation of this mixture into 2 diastereomers by preparative chiral HPLC (method see Example 72) gave racemate 2: 65 mg, 100% purity, 100% yield.

Analytical Chiral HPLC (method see Example 72): $R_t$=3.70. min.

LC-MS (Method 1): $R_t$=0.94 min; MS (ESIneg): m/z=764 [M−H]$^-$ $^1$H-NMR (600 MHz, DMSO-d$_6$): δ [ppm]=0.71-0.82 (m, 3H), 1.16 (t, 4H), 1.59-1.70 (m, 1H), 1.73-1.87 (m, 2H), 1.96-2.05 (m, 1H), 2.05-2.18 (m, 2H), 2.17-2.21 (m, 2H), 2.21-2.27 (m, 3H), 2.30 (br d, 3H), 2.84-2.91 (m, 5H), 3.51 (br s, 5H), 3.79-3.88 (m, 4H), 4.10-4.20 (m, 2H), 4.40-4.54 (m, 1H), 4.60 (br d, 1H), 6.82 (d, 1H), 7.16 (d, 1H), 7.29-7.50 (m, 3H), 7.57-7.76 (m, 2H), 8.31 (dd, 1H).

The title compound (59 mg) was separated into enantiomers by preparative chiral HPLC to give enantiomer 1 (27 mg, see Example 75) and enantiomer 2 (25 mg, see Example 76).

Preparative Chiral HPLC Method:
Instrument: Labomatic HD5000, Labocord-5000; Gilson GX-241, Labcol Vario 4000, Column: Cellulose SC 10µ 250×50 mm; Eluent A: Hexane+0.1 Vol-% Diethylamine (99%); Eluent B: Ethanol; Gradient: 20 50%, B in 15 min; Flow 100.0 mL/min; UV 254 nm.
Analytical Chiral HPLC Method:
Instrument: Agilent HPLC 1260; Column: Cellulose SC 3µ 100×4.6 mm; Eluent A: Hexane+0.1 Vol-% Diethylamine (99%); Eluent B: Ethanol; Gradient: 20 50% B; Flow 1.4 mL/min; Temperature: 25° C.; DAD 254 nm.

Example 75

4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid-N-ethylethanamine Salt (Enantiomer 1)

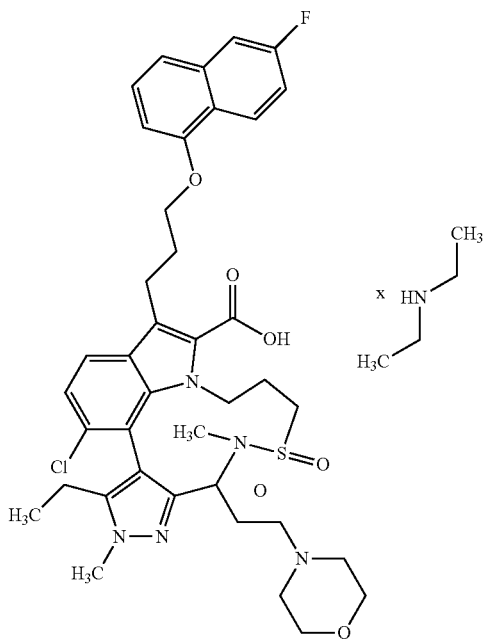

For the preparation of the racemic title compound see Example 74. Separation of enantiomers by preparative chiral HPLC (method see Example 74) gave the title compound (27 mg, 90% purity, 38% yield).

Analytical Chiral HPLC (method see Example 74): $R_t$=2.97 min.

LC-MS (Method 2): $R_t$=0.98 min; MS (ESIpos): m/z=766 [M+H]$^+$ $^1$H-NMR (400 MHz, DMSO-d6) δ[ppm]: 0.739 (3.43), 0.758 (7.49), 0.777 (3.59), 0.967 (0.97), 1.107 (9.40), 1.140 (6.07), 1.158 (14.14), 1.176 (6.44), 1.208 (0.57), 1.231 (1.31), 1.727 (1.40), 1.765 (0.57), 1.777 (0.55), 1.907 (0.92), 2.023 (0.85), 2.039 (0.83), 2.057 (0.94), 2.076 (1.10), 2.094 (0.87), 2.112 (0.48), 2.131 (0.87), 2.149 (1.10), 2.167 (1.15), 2.178 (1.33), 2.195 (2.11), 2.212 (1.84), 2.242 (3.03), 2.257 (1.26), 2.272 (1.13), 2.318 (2.07), 2.322 (2.30), 2.326 (2.48), 2.332 (1.84), 2.518 (5.59), 2.522 (3.47), 2.539 (0.67), 2.660 (0.48), 2.664 (0.99), 2.669 (1.38), 2.673 (1.03), 2.678 (0.51), 2.710 (0.48), 2.735 (0.44), 2.861 (11.84), 2.884 (1.61), 2.902 (4.67), 2.921 (4.46), 2.938 (1.38), 3.246 (0.78), 3.261 (1.10), 3.279 (1.91), 3.502 (3.03), 3.513 (4.92), 3.524 (3.01), 3.870 (16.00), 3.932 (0.51), 3.951 (0.46), 4.141 (1.15), 4.157 (2.25), 4.173 (1.15), 4.485 (1.08), 4.502 (1.61), 4.520 (1.24), 6.827 (1.31), 6.833 (1.38), 6.844 (1.29), 6.849 (1.38), 7.221 (2.05), 7.242 (2.05), 7.364 (0.87), 7.371 (1.03), 7.386 (1.43), 7.393 (2.00), 7.409 (1.15), 7.415 (3.06), 7.432 (4.48), 7.449 (0.55), 7.641 (1.59), 7.647 (1.61), 7.667 (1.59), 7.673 (1.56), 7.755 (1.29), 7.777 (1.17), 8.285 (1.38), 8.299 (1.45), 8.308 (1.40), 8.323 (1.31).

Example 76

4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda$^6$-pyrazolo[3',4':4,5][1,2,8]thiadiazacycloundecino[6,7,8-hi]indole-8-carboxylic acid-N-ethylethanamine Salt (Enantiomer 2)

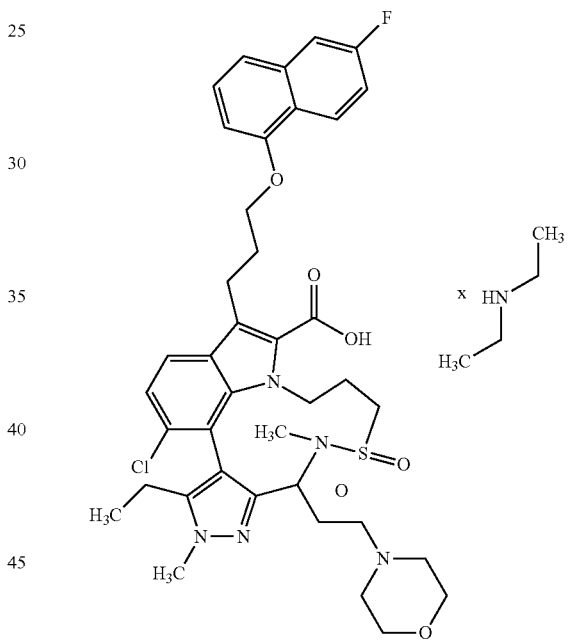

For the preparation of the racemic title compound see Example 74. Separation of enantiomers by preparative chiral HPLC (method see Example 74) gave the title compound (25 mg, 90% purity, 35% yield).

Analytical Chiral HPLC (method see Example 74): $R_t$=3.49 min.

LC-MS (Method 2): $R_t$=0.98 min; MS (ESIpos): m/z=766 [M+H]$^+$ $^1$H-NMR (400 MHz, DMSO-d6) δ[ppm]: 0.739 (3.47), 0.758 (7.44), 0.777 (3.61), 0.851 (0.41), 0.860 (0.41), 0.967 (0.77), 1.107 (6.46), 1.138 (6.19), 1.156 (13.72), 1.174 (6.52), 1.232 (1.69), 1.727 (1.39), 1.764 (0.59), 1.775 (0.59), 1.907 (0.95), 2.022 (0.86), 2.039 (0.83), 2.057 (0.92), 2.076 (1.13), 2.095 (0.86), 2.113 (0.50), 2.130 (0.89), 2.149 (1.10), 2.167 (1.13), 2.178 (1.36), 2.195 (2.13), 2.212 (1.87), 2.240 (3.11), 2.258 (1.27), 2.318 (2.13), 2.322 (2.58), 2.326 (2.87), 2.332 (2.10), 2.518 (8.59), 2.522 (5.57), 2.539 (1.04), 2.664 (1.33), 2.668 (1.81), 2.673 (1.36), 2.711 (0.47), 2.861

(11.47), 2.886 (1.57), 2.904 (4.56), 2.922 (4.44), 2.941 (1.36), 3.245 (0.68), 3.278 (1.72), 3.501 (3.02), 3.513 (4.95), 3.524 (3.05), 3.870 (16.00), 3.931 (0.47), 3.950 (0.47), 4.142 (1.13), 4.157 (2.25), 4.174 (1.16), 4.485 (1.07), 4.502 (1.66), 4.520 (1.24), 6.828 (1.30), 6.833 (1.33), 6.845 (1.24), 6.849 (1.36), 7.221 (1.90), 7.242 (1.81), 7.364 (0.86), 7.371 (1.01), 7.387 (1.39), 7.394 (1.99), 7.409 (1.10), 7.416 (3.08), 7.433 (4.59), 7.449 (0.56), 7.641 (1.54), 7.647 (1.54), 7.667 (1.54), 7.674 (1.54), 7.755 (1.07), 7.776 (0.98), 8.285 (1.36), 8.299 (1.45), 8.307 (1.39), 8.323 (1.33).

Example 77

(rac)-13-chloro-12-ethyl-1-(3-((6-fluoronaphthalen-1-yl)oxy)propyl)-11-methyl-8-(2-morpholinoethyl)-5,6,9,11-tetrahydro-4H,8H-pyrazolo[3',4':4,5][1]thia[2,8]diazacycloundecino[6,7,8-hi]indole-2-carboxylic acid 7,7-dioxide

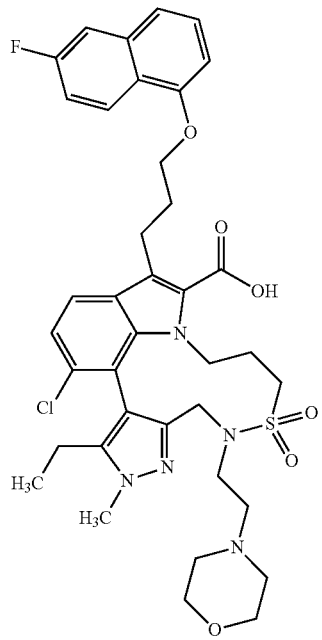 [SMILES: CCc1c2c(nn1C)CN(CCN1CCOCC1)S(=O)(=O)CCCn1c(C(=O)O)c(CCCOc3cccc4cc(F)ccc34)c3ccc(Cl)c-2c31]

A solution of ethyl 13-chloro-12-ethyl-1-(3-((6-fluoronaphthalen-1-yl)oxy)propyl)-11-methyl-8-(2-morpholinoethyl)-5,6,9,11-tetrahydro-4H,8H-pyrazolo[3',4':4,5][1]thia[2,8]diazacycloundecino[6,7,8-hi]indole-2-carboxylate 7,7-dioxide (Intermediate 148, 0.635 g, 813 μmol) in ethanol (5.41 mL) was treated with a solution of sodium hydroxide (2 M in water, 810 μL, 1.62 mmol, 2 eq) and stirred at 50° C. for 24 h. After cooling to room temperature, the mixture was acidified with 1 N aqueous HCl and concentrated. The crude mixture was purified by reverse-phase flash chromatography on C18-silica gel (10-100% acetonitrile/water with 0.1% formic acid) and concentrated to a residue that was triturated with acetonitrile to obtain, after filtration, the title compound (420 mg).

LC-MS (Method 7): $R_t$=2.51 min; MS (ESIneg): m/z=751 [M−H]−

$^1$H NMR (400 MHz, DMSO-d6) δ 13.34 (s, 1H), 8.31 (dd, 1H), 7.83 (d, 1H), 7.66 (dd, 1H), 7.51-7.35 (m, 3H), 7.27 (d, 1H), 6.85 (dd, 1H), 4.61-4.46 (m, 1H), 4.30 (d, 1H), 4.17 (t, 2H), 4.09 (d, 1H), 3.99-3.88 (m, 1H), 3.86 (s, 3H), 3.54 (t, 4H), 3.31 (s, 7H), 3.11 (s, 1H), 2.69-2.56 (m, 1H), 2.37 (s, 5H), 2.26-2.11 (m, 3H), 1.79 (s, 1H), 1.60 (s, 1H), 0.78 (t, 3H).

Experimental Section—Biological Assays

Examples were tested in selected biological assays one or more times. When tested more than once, data are reported as either average values, median values or as geometric mean values, wherein
  the average value, also referred to as the arithmetic mean value, represents the sum of the values obtained divided by the number of times tested,
  the median value represents the middle number of the group of values when ranked in ascending or descending order. If the number of values in the data set is odd, the median is the middle value. If the number of values in the data set is even, the median is the arithmetic mean of the two middle values, and
  the geometric mean value represents the nth root of the product of n numbers.

Examples were synthesized one or more times. When synthesized more than once, data from biological assays represent average values or median values calculated utilizing data sets obtained from testing of one or more synthetic batch.

An empty field in any of the following tables means that the respective compound has not been tested in that Assay.

The in vitro activity of the compounds of the present invention can be demonstrated in the following assays.

Assay 1
Protein-Protein Interaction Assay: MCL-1/Noxa BH3 Peptide (MCL-1 Assay)

The dose-dependent inhibition by the compounds described in this invention of the interaction between MCL-1 and the BH3 domain of Noxa (both human) was determined using a steady state binding competition assay with time-resolved fluorescence energy transfer (TR-FRET) readout. For that purpose MCL-1 (amino acids 173-329, N-terminal fused to Maltose Binding Protein (MBP) SEQ ID 1) and a synthetic Noxa BH3-derived peptide of sequence Biotin-PEG2-PEG2-PAELEVE-Nva-ATQLRRFGDKLN-FRQKLL-amide (SEQ ID 2) served as protein receptor and tracer ligand respectively. The MBP-MCL-1 was purchased from Beryllium (Bedford, Mass., USA). The expression and purification of this protein construct has been described elsewhere (DOI:10.1371/journal.pone.0125010). The Noxa BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 μM, 0.51 μM, 1.7 μM, 5.9 μM and 20 μM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 μl of a 2.5-fold concentrated MBP-MCL-1 solution (usually for a 1 nM end concentration in 5 μl reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between MBP-MCL-1 and the compounds. After that, 3 µl of a 1.67-fold concentrated solution (in assay buffer) consisting of Noxa BH3-derived peptide (1 nM end concentration) and TR-FRET detection reagents [1.67 nM anti-MBP-Eu cryptate and 1.67 nM streptavidin-XL665 (both from Cisbio Bioassays, Codolet, France)], were added.

The mixture was incubated in the dark for one hour at 22° C. and then overnight at 4° C. The formation of MCL-1/Noxa complexes was determined by measuring the resonance energy transfer of the anti-MBP-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of MCL-1/NOXA complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except MCL-1 were included. $IC_{50}$ values were determined by regression analysis based on a 4 parameter equation (minimum, maximum, $IC_{50}$, Hill; Y=Max+(Min−Max)/(1+(X/$IC_{50}$)^Hill) using the Screener Software (Genedata).

```
SEQ ID 1:
GKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTGSSELYRQSLEIISRYLREQATGAADTAPMGAS

GATSRKALETLRRVGDGVQRNHETAFQGMLRKLDIKNEDDVKSLSRVMIH

VFSDGVTNWGRIVTLISFGAFVAKHLKTINQESCIEPLAESITDVLVRTK

RDWLVKQRGWDGFVEFFHV

SEQ ID 2
Biotin-PEG2-PEG2-PAELEVE-Nva-ATQLRRFGDKLNFRQKLL-
amide
```

Assay 2
Protein-Protein Interaction Assay: BCL-XL/Bad BH3 Peptide (BCL-XL Assay)

The dose-dependent inhibition by the compounds described in this invention of the interaction between BCL-XL and the BH3 domain of Bad (both human) was determined using a steady state binding competition assay with time-resolved fluorescence energy transfer (TR-FRET) readout. For that purpose BCL-XL (amino acids 1-212, C-terminal fused to a hexahistidine (6×His) tag (SEQ ID 3) and a synthetic Bad BH3-derived peptide of sequence Biotin-PEG2-PEG2-NLWAAQRYGRELRR-Nle-SDEFVDSFKK-amide (SEQ ID 4) served as protein receptor and tracer ligand respectively. The recombinant BCL-XL protein (expressed in E. coli) was purchased from BPS Bioscience (San Diego, Calif., USA). The Bad BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 µl of a 2.5-fold concentrated His-BCL-XL solution (usually for a 1 nM end concentration in 5 µl reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between His-BCL-XL and the compounds. After that, 3 µl of a 1.67-fold concentrated solution (in assay buffer) consisting of Bad BH3-derived peptide (1 nM end concentration) and TR-FRET detection reagents [1.67 nM anti-His-Eu cryptate and 1.67 nM streptavidin-XL665 (both from Cisbio Bioassays, Codolet, France)], were added.

The mixture was incubated in the dark for one hour at 22° C. and then overnight at 4° C. The formation of BCL-XL/Bad complexes was determined by measuring the resonance energy transfer of the anti-His- Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of BCL-XL/Bad complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except BCL-XL were included. $IC_{50}$ values were determined by regression analysis based on a 4 parameter equation (minimum, maximum, $IC_{50}$, Hill; Y=Max+(Min−Max)/(1+(X/$IC_{50}$)^Hill) using the Screener Software (Genedata).

```
                                              SEQ ID 3
MSQSNRELVV DFLSYKLSQK GYSWSQFSDV EENRTEAPEG

TESEMETPSA INGNPSWHLA DSPAVNGATG HSSSLDAREV

IPMAAVKQAL REAGDEFELR YRRAFSDLTS QLHITPGTAY

QSFEQVVNEL FRDGVNWGRI VAFFSFGGAL CVESVDKEMQ

VLVSRIAAWM ATYLNDHLEP WIQENGGWDT FVELYGNNAA

AESRKGQERF NR

SEQ ID 4
Biotin-PEG2-PEG2-NLWAAQRYGRELRR-Nle-SDEFVDSFKK-
amide
```

Assay 3
Protein-Protein Interaction Assay: BCL-2/Bad BH3 Peptide (BCL-2 Assay)

The dose-dependent inhibition by the compounds described in this invention of the interaction between BCL-2 and the BH3 domain of Bad (both human) was determined using a steady state binding competition assay with time-resolved fluorescence energy transfer (TR-FRET) readout. For that purpose BCL-2 (amino acids 1-211, C-terminal fused to a hexahistidine (6×His) tag (SEQ ID 5) and a synthetic Bad BH3-derived peptide of sequence Biotin-PEG2-PEG2-NLWAAQRYGRELRR-Nle-SDEFVDSFKK-amide (SEQ ID 4) served as protein receptor and tracer ligand respectively. The recombinant BCL-2 protein (expressed in E. coli) was purchased from BPS Bioscience (San Diego, Calif., USA). The Bad BH3-derived peptide can be obtained from e.g. Biosyntan (Berlin, Germany).

In the assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were typically measured as duplicates in the same microtiter plate. For that, 100-fold concentrated DMSO solutions were prepared by serial dilutions (1:3.4) of a 2 mM stock solution in a clear, 384-well microtiter plate (Greiner Bio-One, Frickenhausen, Germany). From there, 50 nl were transferred in a dark test plate (Greiner Bio-One, Frickenhausen, Germany). The assay was initiated by addition of 2 µl of a 2.5-fold concentrated His-BCL-2 solution (usually for a 1 nM end concentration in 5 µl reaction volume) in aqueous assay buffer [50 mM Tris/HCl pH 7, 100 mM sodium chloride (NaCl), 50 mM potassium fluoride (KF), 0.005% Tween-20, 2 mM DTT, 0.1% bovine gamma globulin (BGG)] to the compounds in the assay plate. This was followed by a 10-minute incubation step at 22° C. for pre-equilibration of the putative complex between His-BCL-2 and the compounds. After that, 3 µl of a 1.67-fold concentrated solution (in assay buffer) consisting of Bad BH3-derived peptide (1 nM end concentration) and TR-FRET detection reagents [1.67 nM anti-His-Eu cryptate and 1.67 nM streptavidin-XL665 (both from Cisbio Bioassays, Codolet, France)], were added.

The mixture was incubated in the dark for one hour at 22° C. and then overnight at 4° C. The formation of BCL-2/Bad complexes was determined by measuring the resonance energy transfer of the anti-His-Eu-cryptate antibody to the streptavidin-XL665 present in the reaction. For that purpose, the fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of BCL-2/Bad complexes present.

The resulting data (ratio) were normalized, taking 0% inhibition as the mean value of control measurements (usually 32 data points) where all reagents were included. In this case 50 nl DMSO were used instead of compounds. A 100% inhibition corresponded to the mean value of control measurements (usually 32 data points) where all reagents except BCL-2 were included. $IC_{50}$ values were determined by regression analysis based on a 4 parameter equation (minimum, maximum, $IC_{50}$, Hill; $Y=Max+(Min-Max)/(1+(X/IC_{50})^{Hill})$ using the Screener Software (Genedata).

SEQ ID 5:
MAHAGRTGYD NREIVMKYIH YKLSQRGYEW DAGDVGAAPP

GAAPAPGIFS SQPGHTPHPA ASRDPVARTS PLQTPAAPGA

AAGPALSPVP PVVHLTLRQA GDDFSRRYRR DFAEMSSQLH

LTPFTARGRF ATVVEELFRD GVNWGRIVAF FEFGGVMCVE

SVNREMSPLV DNIALWMTEY LNRHLHTWIQ DNGGWDAFVE

LYGPSMRPLFD

TABLE 2

$IC_{50}$ values of selected examples in biochemical MCL-1 assay (Assay 1) and biochemical BCL-2 (Assay 3), BCL-XL Assay (Assay 2)

| Example | MCL-1 Assay [M] (median) | BCL-2 Assay [M] (median) | BCL-XL Assay [M] (median) |
|---|---|---|---|
| 1 | 6.2E-9 | >2.0E-5 | >2.0E-5 |
| 2 | 3.4E-9 | >2.0E-5 | >2.0E-5 |
| 3 | 2.7E-7 | >2.0E-5 | >2.0E-5 |
| 4 | 1.2E-9 | >2.0E-5 | >2.0E-5 |
| 5 | 5.2E-10 | >2.0E-5 | >2.0E-5 |
| 6 | 1.1E-8 | >2.0E-5 | 1.8E-5 |
| 7 | 1.3E-9 | 1.8E-5 | >2.0E-5 |
| 8 | 1.7E-9 | >2.0E-5 | >2.0E-5 |
| 9 | 3.4E-8 | >2.0E-5 | >2.0E-5 |
| 10 | 7.4E-9 | | |
| 11 | 2.2E-9 | >2.0E-5 | >2.0E-5 |
| 12 | 1.1E-7 | >2.0E-5 | 1.5E-5 |
| 13 | 6.3E-9 | >2.0E-5 | >2.0E-5 |
| 14 | 9.8E-9 | >2.0E-5 | >2.0E-5 |
| 15 | 5.6E-9 | >2.0E-5 | >2.0E-5 |
| 16 | 5.7E-9 | >2.0E-5 | >2.0E-5 |
| 17 | 8.1E-9 | >2.0E-5 | >2.0E-5 |
| 18 | 7.8E-9 | >2.0E-5 | >2.0E-5 |
| 19 | 1.8E-9 | >2.0E-5 | >2.0E-5 |
| 20 | 2.7E-9 | >2.0E-5 | >2.0E-5 |
| 21 | 1.7E-9 | >2.0E-5 | >2.0E-5 |
| 22 | 3.1E-9 | >2.0E-5 | >2.0E-5 |
| 23 | 3.3E-9 | 1.5E-5 | >2.0E-5 |
| 24 | 3.4E-9 | >2.0E-5 | >2.0E-5 |
| 25 | 1.7E-9 | >2.0E-5 5.1E-5 4.6E-5 | >2.0E-5 |
| 26 | 3.6E-9 | >2.0E-5 | >2.0E-5 |
| 27 | 2.1E-9 | >2.0E-5 | >2.0E-5 |
| 28 | 4.0E-9 | >2.0E-5 | >2.0E-5 |
| 29 | 3.1E-9 | >2.0E-5 | >2.0E-5 |
| 30 | 5.1E-9 | >2.0E-5 | >2.0E-5 |
| 31 | 3.6E-9 | >2.0E-5 | >2.0E-5 |
| 32 | 1.5E-9 | >2.0E-5 | >2.0E-5 |
| 33 | 4.2E-9 | >2.0E-5 | >2.0E-5 |
| 34 | 3.2E-9 | >2.0E-5 | >2.0E-5 |
| 35 | 3.5E-9 | >2.0E-5 | >2.0E-5 |
| 36 | 6.0E-10 | 1.8E-5 | >2.0E-5 |
| 37 | 1.1E-8 | 2.0E-5 | 1.8E-5 |
| 38 | 2.3E-8 | >2.0E-5 | >2.0E-5 |
| 39 | 8.9E-10 | >2.0E-5 | >2.0E-5 |
| 40 | 2.1E-9 | >2.0E-5 | 1.9E-5 |
| 41 | 1.3E-9 | 1.9E-5 | 1.9E-5 |
| 42 | 3.4E-10 | 1.2E-5 | 1.8E-5 |
| 43 | 6.2E-9 | >2.0E-5 | >2.0E-5 |
| 44 | 3.0E-9 | >2.0E-5 | >2.0E-5 |
| 45 | 3.3E-8 | >2.0E-5 | 1.8E-5 |
| 46 | 3.1E-10 | >2.0E-5 | >2.0E-5 |
| 47 | 8.0E-10 | >2.0E-5 | >2.0E-5 |
| 48 | 9.3E-10 | >2.0E-5 | >2.0E-5 |
| 49 | 3.2E-9 | 2.0E-5 | >2.0E-5 |
| 50 | 7.4E-10 | >2.0E-5 | >2.0E-5 |
| 51 | 9.6E-10 | >2.0E-5 | >2.0E-5 |
| 52 | 2.3E-8 | >2.0E-5 | 1.6E-5 |
| 53 | 1.7E-9 | 1.4E-5 | 1.6E-5 |
| 54 | 6.4E-10 | | 1.6E-5 |
| 55 | 1.6E-8 | 1.6E-5 | 1.3E-5 |

TABLE 2-continued $IC_{50}$ values of selected examples in biochemical MCL-1 assay (Assay 1) and biochemical BCL-2 (Assay 3), BCL-XL Assay (Assay 2)

| Example | MCL-1 Assay [M] (median) | BCL-2 Assay [M] (median) | BCL-XL Assay [M] (median) |
|---|---|---|---|
| 56 | 2.1E−9 | 1.4E−5 | 1.6E−5 |
| 57 | 4.8E−10 | 1.2E−5 | >2.0E−5 |
| 58 | 2.8E−8 | 1.3E−5 | 1.4E−5 |
| 59 | 1.9E−9 | 1.7E−5 | 1.6E−5 |
| 60 | 2.4E−9 | | >2.0E−5 |
| 61 | 9.4E−10 | 1.6E−5 | >2.0E−5 |
| 62 | 1.1E−7 | 1.4E−5 | 1.8E−5 |
| 63 | 1.1E−9 | 1.9E−5 | 1.9E−5 |
| 64 | 2.1E−8 | >2.0E−5 | >2.0E−5 |
| 65 | 9.4E−10 | >2.0E−5 | >2.0E−5 |
| 66 | 2.2E−8 | >2.0E−5 | >2.0E−5 |
| 67 | 4.0E−10 | | |
| 68 | 1.9E−9 | >2.0E−5 | >2.0E−5 |
| 69 | 1.5E−9 | | |
| 70 | 8.6E−8 | | |
| 71 | 8.0E−10 | | |
| 72 | 1.1E−9 | | |
| 73 | 3.4E−10 | | |
| 74 | 1.1E−9 | | |
| 75 | 1.5E−7 | | |
| 76 | 5.9E−10 | | |
| 77 | 6.2E−9 | >2.0E−5 | >2.0E−5 |

*single value

Cellular Assays

Assay 4

Induction of Caspase-3/7 Activity Upon Treatment of Cells with Selected Compounds The BH3-domain of MCL-1 sequesters pro-apoptotic proteins, thereby inhibiting apoptosis. In contrast, MCL-1 inhibitors are expected to antagonize this effect leading to an increase in apoptosis, which can be determined by measuring the activity of caspase-3/7.

The activity of caspase-3/7 was determined in DLBCL (Diffuse large B-cell lymphoma) cell lines (SUDHL5 and SUDHL10) upon treatment with different compounds, using the Caspase-Glo® 3/7 reagent from Promega (G8092).

The different cell lines were plated in culture medium (RPMI 1640 [GIBCO #22400-089] supplemented with 10% Fetal Bovine Serum) at a density of 3,300 cells in 30 μl/well in a sterile, solid black, flat bottom, polystyrene, TC-treated 384-well microplate (Corning #3571) using Multidrop Combi Reagent Dispenser. As a control, medium without cells was also added to the plate. Cells were incubated in a humidified incubator at 37° C. overnight.

On the next day, the cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 3 hours in a humidified incubator at 37° C. After this incubation, 30 μl of Caspase-Glo® 3/7 reagent (Promega G8092) was added to each well using the Multidrop Combi Reagent Dispenser, followed by 1 hour incubation at 37° C. Finally, luminescence was read at 0.1 ms, with a gain of 3000 using the PHERAstar FS microplate reader (BMG Labtech).

For the evaluation of the results, the background measured with "medium-only" was subtracted from all other values. Then, the values were normalized to DMSO-only treated cells (every value was divided by the mean of the DMSO control). The Bella DRC Master Sheet was used to calculate $EC_{50}$s, with fixed C0=1 and CI=plateau/max induction for the reference compound.

TABLE 3

$EC_{50}$ values of selected examples in cellular caspase induction assay (Assay 4)

| Example | Caspase SUDHL5 [M] (median) | Caspase SUDHL10 [M] (median) |
|---|---|---|
| 1 | 4.8E−6 | 1.4E−5 |
| 2 | 3.9E−6 | 1.1E−5 |
| 3 | >3.3E−5 | >3.3E−5 |
| 4 | 6.3E−7 | 1.6E−6 |
| 5 | 1.3E−7 | 5.9E−7 |
| 6 | 1.6E−5 | 1.4E−5 |
| 7 | 5.1E−7 | 7.4E−7 |
| 8 | 5.8E−7 | 1.0E−6 |
| 9 | 2.1E−5 | >3.3E−5 |
| 10 | 3.1E−6 | 1.4E−5 |
| 11 | 1.4E−6 | 3.1E−6 |
| 12 | 3.0E−5 | 3.0E−5 |
| 13 | 1.0E−5 | 1.6E−5 |
| 14 | 4.6E−6 | 9.2E−6 |
| 15 | 2.5E−6 | 6.4E−6 |
| 16 | 3.2E−5 | >3.3E−5 |
| 17 | 1.3E−5 | 2.1E−5 |
| 18 | 3.8E−6 | 8.4E−6 |
| 19 | 4.2E−7 | 6.1E−7 |
| 20 | 8.6E−7 | 2.1E−6 |
| 21 | 6.5E−7 | 1.4E−6 |
| 22 | 1.8E−6 | 3.3E−6 |
| 23 | 1.3E−6 | 2.3E−6 |
| 24 | 1.1E−6 | 2.3E−6 |
| 25 | 6.7E−7 | 1.5E−6 |
| 26 | 1.3E−6 | 3.5E−6 |
| 27 | 7.0E−7 | 2.4E−6 |
| 28 | 2.0E−6 | 1.1E−5 |
| 29 | 1.5E−6 | 4.5E−6 |
| 30 | 1.7E−6 | 5.6E−6 |
| 31 | 8.0E−7 | 1.9E−6 |
| 32 | 5.8E−7 | 1.1E−6 |
| 33 | 1.6E−6 | 5.1E−6 |
| 34 | 1.3E−6 | 3.6E−6 |
| 35 | 1.2E−6 | 2.6E−6 |
| 36 | 8.5E−8 | 2.0E−7 |
| 37 | 5.0E−6 | 1.2E−5 |
| 38 | 2.0E−5 | 2.2E−5 |
| 39 | 3.5E−7 | 7.3E−7 |
| 40 | 1.9E−6 | 3.3E−6 |
| 41 | 8.2E−7 | 1.6E−6 |
| 42 | 1.9E−7 | 2.9E−7 |
| 43 | 6.1E−6 | 9.4E−6 |
| 44 | 1.1E−6 | 1.7E−6 |
| 45 | 2.7E−5 | 2.3E−5 |
| 46 | 3.9E−7 | 3.8E−7 |
| 47 | 2.2E−7 | 3.2E−7 |
| 48 | 1.3E−8 | 9.7E−9 |
| 49 | 2.1E−7 | 2.7E−7 |
| 50 | 6.5E−7 | 2.8E−6 |
| 51 | 3.4E−7 | 4.9E−7 |
| 52 | 2.7E−5 | >3.3E−5 |
| 53 | 5.5E−7 | 7.7E−7 |
| 54 | 2.6E−7 | 5.2E−7 |
| 55 | 8.9E−7 | 1.3E−5 |
| 56 | 2.0E−7 | 1.6E−7 |
| 57 | 1.2E−7 | 1.1E−7 |
| 58 | 1.5E−5 | 3.2E−5 |
| 59 | 3.7E−8 | 7.8E−8 |
| 60 | 1.8E−8 | 3.2E−8 |
| 61 | 2.2E−8 | 2.4E−8 |
| 62 | 4.1E−6 | 6.8E−6 |
| 63 | 4.0E−8 | 4.2E−8 |
| 64 | 1.2E−6 | 1.6E−6 |
| 65 | 4.7E−8 | 6.0E−8 |
| 66 | 3.5E−6 | 6.0E−6 |
| 67 | 7.3E−9 | 1.2E−8 |
| 68 | 1.5E−6 | 1.7E−6 |
| 69 | 2.5E−7 | 6.5E−7 |

TABLE 3-continued

EC$_{50}$ values of selected examples in cellular
caspase induction assay (Assay 4)

| Example | Caspase SUDHL5 [M] (median) | Caspase SUDHL10 [M] (median) |
|---|---|---|
| 70 | 2.6E−6 | 4.4E−6 |
| 71 | 7.1E−8 | 1.4E−7 |
| 72 | 1.5E−8 | 2.7E−8 |
| 73 | 2.3E−8 | 2.3E−7 |
| 74 | 1.1E−8 | 1.4E−8 |
| 75 | 1.1E−5 | 3.5E−05 |
| 76 | 6.5E−09 | 5.5E−09 |
| 77 | 4.8E−6 | 1.4E−5 |

A further aspect of the invention are compounds which show an EC$_{50}$<3×E-5 in the Caspase SUDHL5 assay.

Yet a further aspect of the invention are compounds which show an EC$_{50}$<2×E-5 in the Caspase SUDHL5 assay.

Yet a further aspect of the invention are compounds which show an EC$_{50}$<9×E-6 in the Caspase SUDHL5 assay.

Yet a further aspect of the invention are compounds which show an EC$_{50}$<3×E-6 in the Caspase SUDHL5 assay.

Yet a further aspect of the invention are compounds which show an EC$_{50}$<3×E-7 in the Caspase SUDHL5 assay.

Yet a further aspect of the invention are compounds which show an EC$_{50}$<9×E-8 in the Caspase SUDHL5 assay.

Assay 5

PIxEL: Protein-Protein Interaction in Permeabilized Cells by ELISA

Most MCL1 protein molecules are localized at the mitochondria outer membrane and sequester pro-apoptotic proteins through binding of their BCL2 homology domain 3 (BH3 domain). MEB buffer (150 mM mannitol, 10 mM HEPES pH 7.5, 50 mM KCl, 20 μM EDTA, 20 μM EGTA, 5 mM potassium succinate, 0.1% protease-free BSA (SIGMA) with low dose digitonin (0.002%) permeabilizes plasma membrane while leaves live mitochondria, where MCL1 maintains its native localization and conformation. Unlike biophysical assays (e.g. TR-FRET) that use truncated recombinant MCL1 protein, this assay uses full length endogenous MCL1 protein at mitochondria outer membrane. It measures the interaction between MCL1 protein and biotinylated BIM BH3 peptide. Compounds can compete with BIM BH3 peptide to bind to MCL1 protein. This serum free assay measures the affinity between MCL1 protein and compound in permeabilized cells, therefore it is not affected by serum binding and cell permeability, and can measure the intrinsic compound affinity.

On day 1, RKO colon cancer cell line cells were plated at 0.8 million cells/ml, 100 μl/well in 96-well flat bottom TC plates (Corning). MCL1 antibody (Santa Cruz sc-12756) were diluted at 200 fold (final concentration 1 μg/ml) in carbonate buffer (Thermo Fisher Scientific, pH 9.6), and 50 μl of diluted antibody was added to each well of high bind ELISA plates (SARSTEDT). Each plate was tapped to make sure liquid covering entire bottom of wells and incubate at 37° C. overnight.

On the second day, MCL1 antibody was washed from ELISA plate. 250 μl Odyssey® Blocking Buffer (PBS) (Li-Cor) was added to each well, incubated at room temperature for at least 1 hour, then washed once with 250 μl 1×PBST. Plates with RKO cells were gently washed once with 100 μl/well PBS, once with 100 μl/well MEB buffer without digitonin, then 100 μl of MEB buffer with 0.002% digitonin was gently added to each well. Compounds were added with HP Tecan compound dispenser in 3-fold dilution series, highest dose 30 μM, 10-dose per compound in quadruplicates. Biotin-BIM peptide (synthesized by 21st Century) was added with HP Tecan compound dispenser at 0.2 μM immediately after the addition of compounds. Plates were rocked for 1 hour at room temperature. Then MEB buffer was aspirated and 50 μl of CHAPS buffer (50 mM Tris-Cl, pH 7.4, 150 mM NaCl, 1% CHAPS, 1 mM EDTA, 1 mM EGTA, cOmplete protease inhibitors (Roche), PhosSTOP (Roche)) was added to each well. Plates were rocked for 1 hour at 4° C., then 45 μl cell lysate from each well were transferred to ELISA plates coated with MCL1 antibody. Plates were incubated overnight in the cold room with rocking.

On the third day, ELISA plates were washed once with 250 μl 1×PBST. Streptavidin-poly-HRP (Thermo Fisher Scientific) was diluted to 20 ng/ml in Odyssey blocking buffer plus 0.05% Triton-100, and 100 μl was added to each well of the ELISA plate. Plates were incubated at room temperature for 1 hour with rocking, then washed with 100 μL 1×PBST for 3 times. Each SuperSignal ELISA Femto Maximum Sensitivity substrate was added to a 50-ml tube and mixed, then 100 μl of mixed substrate was added to each well. Plates were shaken for 1 minute then luminescence was measured by Envision plate reader (HP). Signal of each well were normalized by no-compound control and no-cell control. IC$_{50}$ was calculated using Graphic Pad PRISM software.

Table 4 shows the results of the protein-protein interaction in permeabilized cells by ELISA assay (Assay 5).

TABLE 4

IC50 values of selected examples in protein-protein interaction
in permeabilized cells byELISA assay (Assay 5)

| Example | PIXEL [M] (median) |
|---|---|
| 1 | |
| 2 | |
| 3 | |
| 4 | |
| 5 | 5.70E−07 |
| 6 | |
| 7 | |
| 8 | 5.52E−07 |
| 9 | |
| 10 | |
| 11 | 4.54E−06 |
| 12 | |
| 13 | |
| 14 | |
| 15 | |
| 16 | |
| 17 | |
| 18 | |
| 19 | |
| 20 | |
| 21 | |
| 22 | |
| 23 | |
| 24 | |
| 25 | |
| 26 | |
| 27 | |
| 28 | |
| 29 | |
| 30 | |
| 31 | |
| 32 | |
| 33 | |
| 34 | |
| 35 | |

TABLE 4-continued

IC50 values of selected examples in protein-protein interaction
in permeabilized cells byELISA assay (Assay 5)

| Example | PIXEL [M] (median) |
|---|---|
| 36 | 8.66E−08 |
| 37 | |
| 38 | |
| 39 | 5.06E−07 |
| 40 | 2.94E−05 |
| 41 | |
| 42 | 1.57E−07 |
| 43 | |
| 44 | |
| 45 | |
| 46 | 2.01E−07 |
| 47 | |
| 48 | 2.99E−08 |
| 49 | |
| 50 | |
| 51 | 4.58E−07 |
| 52 | |
| 53 | 3.29E−07 |
| 54 | 3.60E−07 |
| 55 | |
| 56 | 1.45E−07 |
| 57 | 7.48E−08 |
| 58 | |
| 59 | |
| 60 | |
| 61 | 1.42E−08 |
| 62 | |
| 63 | 2.20E−08 |
| 64 | |
| 65 | |
| 66 | |
| 67 | 8.74E−09 |
| 68 | 7.65E−07 |
| 69 | |
| 70 | |
| 71 | |
| 72 | |
| 73 | 3.31E−08 |
| 74 | |
| 75 | |
| 76 | |
| 77 | |

Assay 6

Induction of Cytotoxicity Upon Treatment of Cells with Selected Compounds

In principle, compounds that induce apoptosis will concomitantly induce cell cytotoxicity. Therefore, cytotoxicity assays were run in parallel in SUDHL5 and SUDHL10 cells.

The different cell lines were plated in culture medium (RPMI 1640 [GIBCO #22400-089] supplemented with 10% Fetal Bovine Serum) at a density of 3,300 cells in 30 μl/well in a sterile, solid black, flat bottom, polystyrene, TC-treated 384-well microplate (Corning #3571) using Multidrop Combi Reagent Dispenser. As a control, medium without cells was also added to the plate. Cells were incubated in a humidified incubator at 37° C. overnight. On the next day, the cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 5 hours in a humidified incubator at 37° C. After this incubation, 30 μl of CellTiter-Glo® Luminescent Cell Viability reagent (Promega, G7573) was added to each well using the Multidrop Combi Reagent Dispenser, followed by 15 minutes incubation on a shaker at room temperature. Finally, luminescence was read at 0.1 ms, with a gain of 3000 using the PHERAstar FS microplate reader (BMG Labtech).

For the evaluation of the results, each value was normalized to DMSO-only treated cells (every value was divided by the mean of the DMSO control). The Bella DRC Master Sheet was used to calculate $IC_{50}$s, with fixed CI=0 and C0=1.

Assay 7

Assessment of the Anti-Proliferative Effect of Compounds in Different Cell Lines The impact of compounds on the proliferation of different cell lines was assessed using the CellTiter-Glo® Luminescent Cell Viability reagent from Promega (G7573). The cell lines used for the proliferation assays are examples of tumor indications and listed in the table below.

TABLE 5 cell lines, sources and indications

| Cell line | Source | Indication |
|---|---|---|
| SUDHL5 | DSMZ | B-cell lymphoma (GC-DLBCL) |
| SUDHL10 | DSMZ | B-cell lymphoma (GC-DLBCL) |
| MV-4-11 | ATCC | Acute monocytic leukemia |
| HMC-1-8 | JCRB | Triple-negative Breast Cancer |
| SK-BR3 | ATCC | Her2-positive Breast Cancer |
| AMO-1 | DSMZ | Multiple Myeloma |
| A2058 | ATCC | Melanoma |
| NCI-H23 | ATCC | Non-Small Cell Lung Cancer |
| REC-1 | ATCC | Mantle cell lymphoma |
| A2780 | ECACC | Ovarian carcinoma |
| SNU-389 | ATCC | Liver Cancer |
| SK-MEL-2 | ATCC | Melanoma |
| SNU-16 | ATCC | Stomach Cancer |
| A-431 | ATCC | Squamous cell carcinoma |
| PA-1 | ECACC | Ovarian Cancer |
| DMS-114 | ATCC | Small Cell Lung Cancer |

The different cell lines were plated in culture medium (RPMI 1640 [Biochrom; #FG 1215] supplemented with 10% Fetal Calf Serum [Biochrom; #S 0415]) at a density of 3,300 cells (for suspension cells) or 800 cells (for adherent cells) in 30 μl/well in a sterile, solid black, flat bottom, polystyrene, TC-treated 384-well microplate (Corning #3571) using Multidrop Combi Reagent Dispenser. In parallel, cells were plated in a reference (day 0) plate for time zero determination. Cells were incubated in a humidified incubator at 37° C. overnight.

On the next day, cells were treated with compounds (stock solution, 10 mM in DMSO) using the HP D300 Digital Dispenser in a concentration range of 3.3×10e-5 M (33 μM) to 5×10e-9 M (5 nM) in a single-dot curve with at least 16 dilutions and a DMSO concentration of 0.33%. Rim wells were excluded. The cells were incubated for 72 hours in a humidified incubator at 37° C. The day 0 plate was measured by adding 30 μL/well of CTG solution (CellTiter-Glo® Luminescent Cell Viability reagent, Promega G7573) to time zero wells in the reference plate followed by a 10 minutes incubation and luminescence reading at 0.1 ms. using the PHERAstar FS microplate reader (BMG Labtech).

After 72 hours incubation, the treated plates were measured in the same way as the day 0 plate mentioned above. The Bella DRC Master Sheet was used to calculate $IC_{50}$s, with CI=day 0 values and C0=DMSO control values.

Table 6 shows the results of the SUDHL5 and SUDHL10 cytotoxicity and antiproliferation assays.

TABLE 6

IC$_{50}$ values of selected examples in cellular cytotoxicity induction assay (Assay 6) and antiproliferation assay (Assay 7)

| Example | Cytotox SUDHL5 [M] (median) | Cytotox SUDHL10 [M] (median) | Antiproli SUDHL5 [M] (median) | Antiproli SUDHL10 [M] (median) |
|---|---|---|---|---|
| 1 | 6.7E−6 | 1.3E−5 | 7.2E−6 | |
| 2 | 3.5E−6 | 9.8E−6 | 4.4E−6 | |
| 3 | >3.3E−5 | >3.3E−5 | 1.5E−5 | |
| 4 | 8.1E−7 | 1.2E−6 | 9.2E−7 | 5.6E−7 |
| 5 | 4.9E−7 | 7.1E−7 | 5.1E−7 | 4.4E−7 |
| 6 | 1.2E−5 | 1.7E−5 | 1.1E−5 | |
| 7 | 4.7E−7 | 9.1E−7 | 2.2E−7 | |
| 8 | 7.7E−7 | 1.1E−6 | 7.6E−7 | |
| 9 | 1.7E−5 | >3.3E−5 | 1.4E−5 | |
| 10 | 3.8E−6 | 1.2E−5 | 3.8E−6 | |
| 11 | 1.6E−6 | 3.7E−6 | 1.8E−6 | |
| 12 | 2.7E−5 | 2.7E−5 | 1.3E−5 | |
| 13 | 8.2E−6 | 1.7E−5 | 4.4E−6 | |
| 14 | 5.2E−6 | 8.5E−6 | 3.3E−6 | |
| 15 | 2.9E−6 | 6.3E−6 | 1.8E−6 | |
| 16 | 3.2E−5 | >3.3E−5 | 2.2E−5 | |
| 17 | 9.3E−6 | 1.6E−5 | 4.7E−6 | |
| 18 | 3.5E−6 | 9.2E−6 | 3.7E−6 | |
| 19 | 4.6E−7 | 8.5E−7 | 3.1E−7 | |
| 20 | 9.1E−7 | 1.7E−6 | 5.2E−7 | |
| 21 | 1.0E−6 | 1.8E−6 | 5.3E−7 | |
| 22 | 2.1E−6 | 3.6E−6 | 1.9E−6 | |
| 23 | 1.7E−6 | 2.5E−6 | 6.9E−7 | |
| 24 | 1.3E−6 | 2.4E−6 | 1.2E−6 | |
| 25 | 7.5E−7 | 2.0E−6 | 4.1E−7 | |
| 26 | 1.8E−6 | 3.4E−6 | 1.4E−6 | |
| 27 | 8.7E−7 | 2.1E−6 | 7.8E−7 | |
| 28 | 3.1E−6 | 8.0E−6 | 1.2E−6 | |
| 29 | 1.8E−6 | 3.8E−6 | 5.0E−7 | |
| 30 | 1.7E−6 | 4.4E−6 | 1.4E−6 | |
| 31 | 9.3E−7 | 1.9E−6 | 5.3E−7 | |
| 32 | 7.4E−7 | 1.2E−6 | 3.9E−7 | |
| 33 | 2.6E−6 | 6.4E−6 | | |
| 34 | 1.4E−6 | 2.4E−6 | 8.2E−7 | |
| 35 | 1.6E−6 | 2.7E−6 | 7.6E−7 | |
| 36 | 1.6E−7 | 2.4E−7 | 1.4E−7 | |
| 37 | 5.7E−6 | 9.0E−6 | 2.2E−6 | |
| 38 | 1.7E−5 | 2.1E−5 | 7.8E−6 | |
| 39 | 4.5E−7 | 6.7E−7 | 5.4E−7 | |
| 40 | 2.0E−6 | 3.9E−6 | 2.6E−6 | |
| 41 | 9.7E−7 | 1.7E−6 | 1.2E−6 | |
| 42 | 3.0E−7 | 3.5E−7 | 2.7E−7 | |
| 43 | 9.6E−6 | 1.3E−5 | 7.0E−6 | |
| 44 | 1.3E−6 | 2.6E−6 | 9.2E−7 | |
| 45 | 2.0E−5 | 1.7E−5 | 1.7E−5 | |
| 46 | 5.0E−7 | 6.1E−7 | 3.0E−7 | |
| 47 | 3.6E−7 | 3.4E−7 | 6.3E−7 | |
| 48 | 1.4E−8 | 1.2E−8 | 3.1E−8 | |
| 49 | 1.8E−7 | 2.2E−7 | 8.5E−7 | |
| 50 | 1.4E−6 | 3.8E−6 | 2.0E−6 | |
| 51 | 5.0E−7 | 9.8E−7 | 4.1E−7 | |
| 52 | 1.7E−5 | 1.7E−5 | 2.0E−5 | |
| 53 | 8.1E−7 | 9.0E−7 | 5.9E−7 | |
| 54 | 3.6E−7 | 6.5E−7 | 4.1E−7 | |
| 55 | 8.2E−6 | 1.3E−5 | 1.1E−5 | |
| 56 | 2.8E−7 | 2.5E−7 | 9.6E−8 | |
| 57 | 1.1E−7 | 1.4E−7 | 5.8E−8 | |
| 58 | 1.2E−5 | 1.8E−5 | 1.5E−5 | |
| 59 | 5.9E−8 | 1.0E−7 | 5.6E−8 | |
| 60 | 2.8E−8 | 3.9E−8 | 1.8E−8 | |
| 61 | 2.8E−8 | 4.9E−8 | 3.9E−8 | |
| 62 | 5.3E−6 | 9.7E−6 | 3.7E−6 | |
| 63 | 4.5E−8 | 8.6E−8 | 7.0E−8 | |
| 64 | 1.2E−6 | 2.9E−6 | 1.4E−6 | |
| 65 | 5.8E−8 | 1.0E−7 | 6.0E−8 | |
| 66 | 3.3E−6 | 8.5E−6 | 4.0E−6 | |
| 67 | 9.8E−9 | 1.8E−8 | 6.7E−9 | |
| 68 | 1.6E−6 | 2.9E−6 | 6.9E−6 | |
| 69 | 3.1E−7 | 1.3E−6 | | |
| 70 | 2.6E−6 | 4.7E−6 | 4.0E−6 | |
| 71 | 1.0E−7 | 1.5E−7 | 1.3E−7 | |
| 72 | 8.7E−9 | 3.4E−8 | | |
| 73 | 2.0E−8 | 1.9E−8 | 1.5E−8 | |
| 74 | 1.3E−8 | 1.7E−8 | 9.9E−9 | |
| 75 | 1.6E−5 | 1.6E−5 | 1.4E−5 | |
| 76 | 6.70E−09 | 8.2E−9 | 5.70E−09 | |
| 77 | 6.7E−6 | 1.3E−5 | 7.2E−6 | |

In one embodiment the invention covers compounds of formula (I) which show an IC$_{50}$ of 5×E-7 or <5×E-7 in the Antiproliferation Assay SUDHL5.

Table 7 shows the results of the MV-4-11, AMO-1, HMC-1-8 and A2780 antiproliferation assays.

TABLE 7

IC$_{50}$ values of selected examples in antiproliferation assay (Assay 7)

| Example | Antiproli MV-4-11 [M] | Antiproli AMO-1 [M] | Antiproli HMC-1-8 [M] | Antiproli A2780 [M] |
|---|---|---|---|---|
| 01 | 1.73E−5 | | | 3.21E−5 |
|  | 1.80E−5 | | | >3.30E−5 |
|  | 2.38E−5 | | | >3.30E−5 |
| 02 | 1.17E−5 | | | 2.66E−5 |
|  | 8.63E−6 | | | >3.30E−5 |
| 03 | 1.54E−5 | | | 2.11E−5 |
| 04 | 1.58E−6 | 2.5E−6 | | 1.22E−5 |
|  | 1.47E−6 | | | 1.66E−5 |
|  | 1.25E−6 | | | |
| 05 | 5.24E−7 | 1.5E−6 | | 9.33E−6 |
|  | 9.62E−7 | | | 1.13E−5 |
|  | 1.14E−6 | | | |
| 06 | 2.02E−5 | | | 1.19E−5 |
| 07 | 1.35E−6 | 2.0E−6 | | |
|  | 2.15E−6 | 2.2E−6 | | |
| 08 | 1.18E−6 | 1.5E−6 | 2.2E−6 | |
| 09 | 1.98E−5 | >3.3E−5 | | |
| 10 | 1.54E−5 | | | 1.68E−5 |
|  | 1.28E−5 | | | >3.30E−5 |
| 11 | 1.53E−5 | | | 1.62E−5 |
|  | 6.36E−6 | | | 2.49E−5 |
| 12 | 2.56E−5 | | | 1.23E−5 |
| 13 | 1.62E−5 | >3.3E−5 | | |
| 14 | 1.18E−5 | 1.9E−5 | | |
|  | 1.28E−5 | 1.7E−5 | | |
| 15 | 9.37E−6 | 1.2E−5 | | |
|  | 1.04E−5 | 1.2E−5 | | |
| 16 | >3.30E−5 | >3.3E−5 | | |
| 17 | 1.65E−5 | >3.3E−5 | | |
| 18 | 3.75E−6 | 9.6E−6 | | |
| 19 | 8.39E−7 | 1.5E−6 | | |
| 20 | 1.31E−6 | 2.8E−6 | | |
| 21 | 2.10E−6 | 2.6E−6 | | |
| 22 | 2.41E−6 | 2.6E−6 | | |
| 23 | 1.96E−6 | 3.8E−6 | | |
| 24 | 2.50E−6 | 4.3E−6 | | |
| 25 | 1.73E−6 | 4.1E−6 | | |
| 26 | 5.17E−7 | 7.1E−6 | | |
| 27 | 8.61E−7 | 2.5E−6 | | |
| 28 | 7.54E−6 | 1.2E−5 | | |

TABLE 7-continued

IC$_{50}$ values of selected examples in antiproliferation assay (Assay 7)

| Example | Antiproli MV-4-11 [M] | Antiproli AMO-1 [M] | Antiproli HMC-1-8 [M] | Antiproli A2780 [M] |
|---|---|---|---|---|
| 29 | 5.86E-6 | 7.1E-6 | | |
| 30 | 3.50E-6 | 7.0E-6 | | |
| 31 | 4.70E-6 | 4.2E-6 | | |
|  | 5.51E-6 | 3.9E-6 | | |
| 32 | 2.20E-6 | 2.4E-6 | | |
|  | 1.14E-6 | 3.9E-6 | | |
| 33 | 4.62E-6 | 4.8E-6 | | |
| 34 | 4.83E-6 | 6.3E-6 | | |
|  |  | 1.5E-6 | | |
| 35 | 4.34E-6 | 5.2E-6 | | |
|  | 8.18E-6 | 6.6E-6 | | |
| 36 |  | 4.5E-7 | 1.7E-6 | |
|  |  | 5.3E-7 | 1.9E-6 | |
| 37 |  | 2.8E-5 | 1.9E-5 | |
| 38 |  | 2.9E-5 | 2.7E-5 | |
| 39 |  | 1.4E-6 | 3.3E-6 | |
|  |  | 1.4E-6 | 5.1E-6 | |
| 40 |  | 4.9E-6 | 7.2E-6 | |
| 41 |  | 8.0E-6 | 3.9E-6 | |
| 42 |  | 2.6E-7 | 5.9E-6 | |
|  |  | 4.7E-7 | 3.8E-6 | |
| 43 |  | 1.1E-5 | >3.3E-5 | |
| 44 |  | 4.4E-6 | 1.2E-5 | |
| 45 |  | 1.5E-5 | >3.3E-5 | |
| 46 |  | 5.3E-7 | 9.4E-6 | |
|  |  | 5.0E-7 | 1.2E-5 | |
| 47 |  | 1.1E-6 | 8.0E-6 | |
|  |  | 4.2E-6 | 1.2E-5 | |
| 48 |  | 5.0E-8 | 9.8E-7 | |
|  |  | 1.2E-7 | 9.3E-7 | |
| 49 |  | 5.1E-7 | 7.8E-6 | |
|  |  | 1.6E-6 | 5.8E-6 | |
| 50 |  | 2.4E-6 | 3.0E-5 | |
|  |  | 7.1E-6 | 3.0E-5 | |
| 51 |  | 2.7E-6 | 1.4E-5 | |
|  |  | 1.3E-6 | 6.0E-6 | |
|  |  | 6.5E-7 | | |
| 52 |  | 1.1E-5 | >3.3E-5 | |
| 53 |  | 1.6E-6 | 5.0E-6 | |
|  |  | 5.9E-7 | 6.4E-6 | |
|  |  | 1.4E-6 | 7.7E-6 | |
|  |  | 7.5E-7 | | |
| 54 |  | 9.0E-7 | 2.2E-6 | |
|  |  | 3.8E-7 | 2.5E-6 | |
| 55 |  | >3.3E-5 | 2.1E-5 | |
| 56 |  | 4.5E-7 | 1.5E-6 | |
|  |  | 1.9E-7 | 2.3E-6 | |
|  |  | 3.2E-7 | 2.7E-6 | |
|  |  | 2.1E-7 | | |
| 57 |  | 1.6E-7 | 9.1E-7 | |
|  |  | 1.3E-7 | 1.3E-6 | |
| 58 |  | >3.3E-5 | 1.5E-5 | |
| 59 |  | 2.1E-7 | 6.0E-7 | |
| 60 |  | 4.4E-8 | 1.9E-7 | |
| 61 |  | 2.5E-8 | 3.6E-7 | |
|  |  | 2.8E-8 | 8.4E-8 | |
|  |  | 2.5E-8 | 1.6E-7 | |
| 62 |  | 3.8E-6 | 2.1E-5 | |
| 63 |  | 4.0E-8 | 5.5E-7 | |
|  |  | 4.5E-8 | 1.3E-7 | |
|  |  | 3.3E-8 | 3.4E-7 | |
| 64 |  | 1.0E-6 | 1.1E-5 | |
| 65 |  | 7.1E-8 | 1.5E-6 | |
| 66 |  | 3.7E-6 | >3.3E-5 | |
| 67 |  | 1.3E-7 | 2.6E-7 | |
|  |  | 9.4E-9 | 3.4E-8 | |
|  |  | 2.1E-8 | 1.4E-7 | |
| 68 |  | 1.0E-6 | 1.3E-5 | |
|  |  | 8.2E-7 | 1.8E-6 | |
| 69 |  |  | | |
| 70 |  | 7.3E-6 | 1.5E-5 | |
| 71 |  | 5.2E-7 | 3.2E-6 | |
|  |  | 1.3E-7 | | |
| 72 |  |  | | |
| 73 |  | 2.6E-8 | 1.0E-6 | |
|  |  | 2.5E-8 | | |
| 74 |  | 3.9E-8 | 3.2E-7 | |
| 75 |  | 2.1E-5 | >3.3E-5 | |
|  |  | 4.2E-6 | >3.3E-5 | |
| 76 |  | <5.0E-9 | 3.5E-7 | |
|  |  | 9.6E-9 | 4.1E-7 | |
|  |  | 1.4E-8 | | |
| 77 |  |  | | |

In one embodiment the invention covers compounds of formula (I) which show an IC$_{50}$ of 1×E-6 or <1×E-6 in the Antiproliferation Assay AMO-1.

In one embodiment the invention covers compounds of formula (I) which show an IC$_{50}$ of 3×E-6 or <3×E-6 in the Antiproliferation Assay HMC-1-8.

In one embodiment the invention covers compounds of formula (I) which show an IC$_{50}$ of 1×E-6 or <1×E-6 in the Antiproliferation Assay AMO-1 and/or an IC$_{50}$ of 3×E-6 or <3×E-6 in the Antiproliferation Assay HMC-1-8.

In one embodiment the invention covers compounds of formula (I) which show an IC$_{50}$ of 1×E-6 or <1×E-6 in the Antiproliferation Assay AMO-1 and an IC$_{50}$ of 3×E-6 or <3×E-6 in the Antiproliferation Assay HMC-1-8.

In one embodiment the invention covers compounds of formula (I) which show an IC$_{50}$ of 1×E-6 or <1×E-6 in the Antiproliferation Assay AMO-1 or an IC$_{50}$ of 3×E-6 or <3×E-6 in the Antiproliferation Assay HMC-1-8.

In one embodiment the invention covers compounds of formula (I) which show an IC$_{50}$ of 5×E-7 or <5×E-7 in the Antiproliferation Assay AMO-1 and an IC$_{50}$ of 2×E-6 or <2×E-6 in the Antiproliferation Assay HMC-1-8.

Table 8 shows the results of the SK-MEL-2, SNU-16, A-431, PA-1 and DM-S114 antiproliferation assays.

TABLE 8

IC$_{50}$ values of selected examples in antiproliferation assay (Assay 7)

| Example | Antiproli SK-MEL-2 [M] median | Antiproli SNU-16 [M] median | Antiproli A-431 [M] median | Antiproli PA-1 [M] median | Antiproli DM-S114 [M] median |
|---|---|---|---|---|---|
| 56 | 1.14E-6 | 1.05E-6 | 1.18E-6 | 7.07E-7 | 5.61E-7 |
| 57 | | | | | |
| 58 | | | | | |
| 59 | | | | | |
| 60 | 5.08E-6 | 2.54E-6 | 2.07E-6 | 1.84E-6 | |
| 61 | | | | | |
| 62 | | | | | |
| 63 | | | | | |
| 64 | | | | | |
| 65 | | | | | |
| 66 | | | | | |
| 67 | | | | | |
| 68 | | | | | |
| 69 | | | | | |
| 70 | | | | | |
| 71 | | | | | |
| 72 | | | | | |

TABLE 8-continued

IC$_{50}$ values of selected examples in antiproliferation assay (Assay 7)

| Example | Antiproli SK-MEL-2 [M] median | Antiproli SNU-16 [M] median | Antiproli A-431 [M] median | Antiproli PA-1 [M] median | Antiproli DM-S114 [M] median |
|---|---|---|---|---|---|
| 73 | | | | | |
| 74 | | | | | |
| 75 | 4.64E−7 | 1.26E−7 | 3.24E−7 | 3.20E−8 | 3.66E−8 |
| 76 | | | | | |
| 77 | | | | | |

Assay 8

Protein-Compound Interaction Assay (SPR Assay)

The ability of the compounds described in this invention to bind to MCL-1 may be determined using surface plasmon resonance (SPR). This allows for the quantification of binding in terms of the equilibrium dissociation constant (KD [M]), as well as association and dissociation rate constants (kon [1/M 1/s] and koff [1/s], respectively). The measurements may be performed using Biacore® T200 or Biacore® S200 instruments (GE Healthcare).

For SPR measurements, recombinant MCL-1 (amino acids 173-321, N-terminal fused to Maltose Binding Protein (MBP) (SEQ ID 1) purchased from Beryllium (Bedford, Mass., USA)) was immobilized using standard amine coupling (Johnsson B et al, Anal Biochem. 1991 Nov. 1; 198(2):268-77). Briefly, carboxymethylated dextran biosensor chips (Series S Sensor Chip CM5, GE Healthcare) were activated with 1-ethyl-3-(3-dimethylaminopropyl)-carbodiimide hydrochloride (EDC) and N-hydroxysuccinimide (NHS) according to the supplier's instructions. MBP-MCL-1 was diluted in 1×PBS-P+ (GE Healthcare) and injected on the activated chip surface. Subsequently, a solution of 1 M ethanolamine-HCl (GE Healthcare) was injected to block unreacted groups, resulting in approximately 400-2500 response units (RU) of immobilized protein. A reference surface was generated by treatment with NHS-EDC and ethanolamine-HCl. Compounds were dissolved in 100% dimethylsulfoxide (DMSO) to a concentration of 10 mM and subsequently diluted in running buffer (1×PBS-P+ (GE Healthcare) [generated from PBS-P+ Buffer 10× (GE Healthcare): 0.2 M phosphate buffer with 27 mM KCl, 1.37 M NaCl and 0.5% Surfactant P20 (Tween 20).], 1% v/v DMSO). For SPR binding-measurements, serial dilutions of compound (eight dilution steps, typically ranging from 0.2 nM up to 1 µM) were injected over immobilized protein. Binding affinity and kinetics were measured at 25° C. with a flow rate of 100 µl/min in running buffer. Compounds were injected for 60 s followed by a dissociation time of up to 1000 s.

The double-referenced sensorgrams were fit to a simple reversible Langmuir 1:1 reaction mechanism as implemented in the Biacore® T200 and S200 evaluation software (T200 evaluation software version 2.0 and S200 evaluation software version 1.0, GE Healthcare).

TABLE 9

$K_D$, $k_{on}$ and $k_{off}$ values (geometric mean values) of MCL-1 compound interactions of selected examples as determined in SPR assay 8

| Example | kon [1/Ms] | koff [1/s] | KD [M] |
|---|---|---|---|
| 1 | | | |
| 2 | | | |
| 3 | | | |
| 4 | | | |
| 5 | 3.2E6 | 7.9E−3 | 2.4E−9 |
| 6 | | | |
| 7 | | | |
| 8 | 2.2E6 | 8.0E−3 | 3.6E−9 |
| 9 | | | |
| 10 | | | |
| 11 | 4.2E6 | 1.1E−1 | 2.7E−8 |
| 12 | | | |
| 13 | | | |
| 14 | | | |
| 15 | | | |
| 16 | | | |
| 17 | | | |
| 18 | | | |
| 19 | | | |
| 20 | | | |
| 21 | | | |
| 22 | | | |
| 23 | | | |
| 24 | | | |
| 25 | | | |
| 26 | | | |
| 27 | | | |
| 28 | | | |
| 29 | | | |
| 30 | | | |
| 31 | | | |
| 32 | | | |
| 33 | | | |
| 34 | | | |
| 35 | | | |
| 36 | 1.0E6 | 4.0E−3 | 4.0E−9 |
| 37 | | | |
| 38 | | | |
| 39 | 3.4E6 | 1.8E−2 | 5.3E−9 |
| 40 | | | |
| 41 | | | |
| 42 | 2.1E6 | 1.6E−2 | 7.6E−9 |
| 43 | | | |
| 44 | | | |
| 45 | | | |
| 46 | 5.6E6 | 1.6E−2 | 2.8E−9 |
| 47 | | | |
| 48 | | | |
| 49 | | | |
| 50 | | | |
| 51 | | | |
| 52 | | | |
| 53 | | | |
| 54 | | | |
| 55 | | | |
| 56 | | | |
| 57 | | | |
| 58 | | | |
| 59 | | | |
| 60 | | | |
| 61 | 5.9E5 | 1.2E−3 | 1.9E−9 |
| 62 | | | |
| 63 | | | |
| 64 | | | |
| 65 | | | |
| 66 | | | |
| 67 | | | |
| 68 | | | |
| 69 | | | |
| 70 | | | |
| 71 | | | |
| 72 | | | |
| 73 | | | |

TABLE 9-continued

K$_D$, k$_{on}$ and k$_{off}$ values (geometric mean values) of MCL-1 compound
interactions of selected examples as determined in SPR assay 8

| Example | kon [1/Ms] | koff [1/s] | KD [M] |
|---|---|---|---|
| 74 | | | |
| 75 | | | |
| 76 | 7.3E6 | 2.5E−3 | 3.4E−10 |
| 77 | | | |

Assay 9
Equilibrium Shake Flask Solubility Assay

Thermodynamic solubility was determined by an equilibrium shake flask method [Edward H. Kerns and Li Di (2008) Solubility Methods in: Drug-like Properties: Concepts, Structure Design and Methods, p 276-286. Burlington, Mass.: Academic Press].

A saturated solution of the drug was prepared and the solution was mixed for 24 h to ensure that equilibrium has been reached. The solution was centrifuged to remove the insoluble fraction and the concentration of the compound in solution was determined using a standard calibration curve.

To prepare the sample, 2 mg solid compound was weighed in a 4 mL glass vial. 1 mL phosphate buffer pH 6.5 respectively borate Buffer pH 8 was added. The suspension was put on a stirrer and mixed for 24 hrs at room temperature. The solution was centrifuged afterwards. To prepare the sample for the standard calibration, 1-2 mg (accurate weight) solid sample was dissolved in acetonitrile/water 50:50 and diluted to 20 mL. Sample and standards were quantified by HPLC with UV-detection. For each sample two injection volumes (5 and 50 µL) in triplicates were made. Three injection volumes (5 µL, 10 µL and 20 µL) were made for the standard.

Chromatographic conditions were as follows:
HPLC column: Xterra MS C18 2.5 µm 4.6×30 mm
Injection volume: Sample: 3×5 µl and 3×50 µl
    Standard: 5 µl, 10 µl, 20 µl
Flow: 1.5 mL/min
Mobile phase: acidic gradient:
    A: Water/0.01% trifluoroacidic acid
    B: Acetonitrile/0.01% trifluoroacidic acid
    0 min→95% A 5% B
    0-3 min→35% A 65% B, linear gradient
    3-5 min→35% A 65% B, isocratic
    5-6 min→95% A 5% B, isocratic
UV detector: wavelength near the absorption maximum (between 200 and 400 nm)

The areas of sample- and standard injections as well as the calculation of the solubility value (in mg/L) were determined by using HPLC software (Waters Empower 2 FR).

Assay 10
CYP Inhibition Assay

The inhibitory potency of the test compounds towards cytochrome P450 dependent metabolic pathways was determined in human liver microsomes applying individual CYP isoform-selective standard probes (phenacetin, coumarin, bupropion, amodiaquine, diclofenac, S-mephenytoin, dextromethorphan, chlorzoxazone, midazolam, testosterone). Reference inhibitors were included as positive controls. Incubation conditions (protein and substrate concentration, incubation time) were optimized with regard to linearity of metabolite formation. The assay was processed by using Genesis Workstation (Tecan, Crailsheim, FRG) in 96-well plates at 37° C. After protein precipitation the metabolite formation was quantified by LC-MS/MS analysis followed by inhibition evaluation and IC$_{50}$ calculation.

The potential of an investigational drug to inhibit CYP enzymes, given by determined IC$_{50}$ values of test compounds in vitro, is a basic requirement in order to assess potential drug-drug interactions (DDI) with comedicated drugs which are relevant substrates of studied CYP isoforms. Such investigations are recommended by pertinent guidelines (i.e. EMA and FDA) for the evaluation of DDIs.

Assay 11
CYP Induction Assay

To evaluate the CYP induction potential in vitro, cultured human hepatocytes from three separate livers are treated once daily for three consecutive days with vehicle control, one of eight concentrations of test compound and known human CYP inducers (e.g. omeprazole, phenobarbital, and rifampin). After treatment, the cells are incubated in situ with the appropriate marker substrates for the analysis of CYP3A4, CYP2B6 and CYP1A2 activity by LC-MS/MS. Following the in situ incubation, the same hepatocytes from the same treatment groups are harvested for RNA isolation and analyzed by qRT-PCR to assess the effect of test compound on CYP1A2, CYP2B6 and CYP3A4 mRNA expression levels.

Assay 12
Caco-2 Permeation Assay

Caco-2 cells (purchased from DSMZ Braunschweig, Germany) were seeded at a density of 4.5×10$^4$ cell per well on 24 well insert plates, 0.4 µm pore size, and grown for 15 days in DMEM medium supplemented with 10% fetal bovine serum, 1% GlutaMAX (100×, GIBCO), 100 U/mL penicillin, 100 µg/mL streptomycin (GIBCO) and 1% non essential amino acids (100×). Cells were maintained at 37° C. in a humified 5% CO$_2$ atmosphere. Medium was changed every 2-3 day. Before running the permeation assay, the culture medium was replaced by an FCS-free hepes-carbonate transport puffer (pH 7.2). For assessment of monolayer integrity the transepithelial electrical resistance (TEER) was measured. Test compounds were predissolved in DMSO and added either to the apical or basolateral compartment in final concentration of 2 µM. Before and after 2h incubation at 37° C. samples were taken from both compartments. Analysis of compound content was done after precipitation with methanol by LC-MS/MS analysis. Permeability (Papp) was calculated in the apical to basolateral (A→B) and basolateral to apical (B→A) directions. The apparent permeability was calculated using following equation:

$$P_{app} = (V_r/P_o)(1/S)(P_2/t)$$

Where V$_r$ is the volume of medium in the receiver chamber, P$_o$ is the measured peak area of the test drug in the donor chamber at t=o, S the surface area of the monolayer, P2 is the measured peak area of the test drug in the acceptor chamber after 2 h of incubation, and t is the incubation time. The efflux ratio basolateral (B) to apical (A) was calculated by dividing the P$_{app}$ B-A by the P$_{app}$ A-B. In addition the compound recovery was calculated. As assay control reference compounds were analyzed in parallel.

Assay 13
Investigation of In Vitro Metabolic Stability in Rat Hepatocytes (Including Calculation of Hepatic In Vivo Blood Clearance (CL))

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold WME. The resulting cell suspension was filtered through sterile gaze in 50 mL falcon tubes and centrifuged at 50×g for 3 min at room temperature. The cell pellet was resuspended in 30 mL WME and centrifuged through a Percoll® gradient for 2 times at 100×g. The hepatocytes were washed again with Williams' medium E (WME) and resuspended in medium containing 5% FCS. Cell viability was determined by trypan blue exclusion.

For the metabolic stability assay liver cells were distributed in WME containing 5% FCS to glass vials at a density of $1.0 \times 10^6$ vital cells/mL. The test compound was added to a final concentration of 1 µM. During incubation, the hepatocyte suspensions were continuously shaken and aliquots were taken at 2, 8, 16, 30, 45 and 90 min, to which equal volumes of cold methanol were immediately added. Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro. The hepatic in vivo blood clearance (CL) and the maximal oral bioavailability ($F_{max}$) was calculated using the following formulae: CL'intrinsic [ml/(min*kg)]=kel [1/min]/((cellno/volume of incubation [ml])*fu,inc)*(cellno/liver weight [g])*(specific liver weight [g liver/kg body weight]); CLblood well-stirred [L/(h*kg)]=(QH [L/(h*kg)]*fu,blood*CL'intrinsic [L/(h*kg)])/(QH [L/(h*kg)]+fu,blood*CL'intrinsic [L/(h*kg)]); Fmax=1-CLblood/QH. The following parameter values were used: Liver blood flow 4.2 L/h/kg rat; specific liver weight 32 g/kg rat body weight; liver cells in vivo- $1.1 \times 10^8$ cells/g liver, liver cells in vitro $1.0 \times 10^6$/ml; fu,inc and fu,blood is taken as 1.

Assay 14
Investigation of In Vitro Metabolic Stability in Rat Hepatocytes in Liver Microsomes (Including Calculation of Hepatic In Vivo Blood Clearance (CL) and of Maximal Oral Bioavailability (Fmax))

The in vitro metabolic stability of test compounds is determined by incubating them at 1 µM in a suspension liver microsomes in 100 mM phosphate buffer, pH7.4 (sodium dihydrogen phosphate monohydrate+disodium hydrogen phosphate dihydrate) and at a protein concentration of 0.5 mg/mL at 37° C. The microsomes are activated by adding a co-factor mix containing 8 mM Glukose-6-Phosphat, 4 mM magnesium chloride; 0.5 mM NADP and 1 IU/ml G-6-P-Dehydrogenase in phosphate buffer, pH 7.4. The metabolic assay is started shortly afterwards by adding the test compound to the incubation at a final volume of 1 mL. Organic solvent in the incubations is limited to 0.01% dimethylsulfoxide (DMSO) and ≤1% acetonitrile. During incubation, the microsomal suspensions are continuously shaken at 580 rpm and aliquots are taken at 2, 8, 16, 30, 45 and 60 min, to which equal volumes of cold methanol are immediately added. Samples are frozen at −20° C. over night, subsequently centrifuged for 15 minutes at 3000 rpm and the supernatant is analyzed with an Agilent 1200 HPLC-system with LCMS/MS detection.

The half-life of a test compound is determined from the concentration-time plot. From the half-life the intrinsic clearances are calculated. Together with the additional parameters liver blood flow, specific liver weight and microsomal protein content the hepatic in vivo blood clearance (CL) and the maximal oral bioavailability ($F_{max}$) are calculated for the different species. The hepatic in vivo blood clearance (CLblood) and the maximal oral bioavailability ($F_{max}$) is calculated using the following formulae: CL'intrinsic [ml/(min*kg)]=kel [1/min]/((mg protein/volume of incubation [ml])*fu,inc)*(mg protein/liver weight [g])*(specific liver weight [g liver/kg body weight]); CLblood well-stirred [L/(h*kg)]=(QH [L/(h*kg)]*fu,blood*CL'intrinsic [L/(h*kg)])/(QH [L/(h*kg)]+fu,blood*CL'intrinsic [L/(h*kg)]); Fmax=1-CLblood/QH and using the following parameter values: Liver blood flow 1.32 L/h/kg (human), 2.1 L/h/kg (dog), 4.2 L/h/kg (rat); specific liver weight 21 g/kg (human), 39 g/kg (dog), 32 g/kg (rat); microsomal protein content ~40 mg/g.; fu,inc and fu,blood is taken as 1.

Assay 15
In Vivo Pharmacokinetics in Rats

For in vivo pharmacokinetic experiments test compounds were administered to male Wistar rats intravenously at doses of 0.3 to 1 mg/kg and intragastral at doses of 0.5 to 10 mg/kg formulated as solutions using solubilizers such as PEG400 in well-tolerated amounts.

For pharmacokinetics after intravenous administration test compounds were given as i.v. bolus and blood samples are taken at 2 min, 8 min, 15 min, 30 min, 45 min, 1 h, 2 h, 4 h, 6 h, 8 h and 24 h after dosing. Depending on the expected half-life additional samples were taken at later time points (e.g., 48 h, 72 h). For pharmacokinetics after intragastral administration test compounds were given intragastral to fasted rats and blood samples were taken at 5 min, 15 min, 30 min, 45 min, 1 h, 2 h, 4 h, 6 h, 8 h and 24 h after dosing. Depending on the expected half-life additional samples were taken at later time points (e.g., 48 h, 72 h). Blood was collected into Lithium-Heparintubes (Monovetten®, Sarstedt) and centrifuged for 15 min at 3000 rpm. An aliquot of 100 µL from the supernatant (plasma) was taken and precipitated by addition of 400 µL cold acetonitril and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood.

PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0-tlast) norm: Area under the concentration-time curve from t=0 h to the last time point for which plasma concentrations could be measured divided by the administered dose (in kg*h/L); t1/2: terminal half-life (in h); F: oral bioavailability: AUCnorm after intragastral administration divided by AUCnorm after intravenous administration (in %).

Assay 16
In Vivo Pharmacokinetics in Mouse

For in vivo pharmacokinetic experiments test compounds were administered to female CD1 mouse intravenously at doses of 0.3 to 1 mg/kg formulated as solutions using solubilizers such as PEG400 in well-tolerated amounts.

For pharmacokinetics after intravenous administration test compounds were given as i.v. bolus and blood samples were taken at 2 min, 5 min, 15 min, 30 min, 1 h, 2 h, 4 h, 7h, and 24 h after dosing. Blood was collected via a vena jugularis catheter into Lithium-Heparin coated tubes (Eppendorf) and centrifuged for 15 min at 3000 rpm. An aliquot from the supernatant (plasma) was taken and precipitated by addition of 1:10 (v/v) ice cold methanol and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t1/2: terminal half-life (in h); MRT iv (h): mean residence time.

Assay 17

In Vivo Pharmacokinetics in Dog

For in vivo pharmacokinetic experiments test compounds are administered to Beagle dogs intravenously at doses of 0.3 to 1 mg/kg formulated as solutions using solubilizers such as PEG400 in well-tolerated amounts.

For pharmacokinetics after intravenous administration test compounds are given in dogs as short term infusion (10 min). Blood samples are taken e.g. at 5 min, 10 min (end of short term infusion), 15 min, 30 min, 1 h, 2 h, 4 h, 6 h, 8 h and 24 h after dosing from the vena saphena. Blood is collected into K-EDTA (Monovetten®, Sarstedt) and centrifuged for 15 min at 3000 rpm. An aliquot of 100 μL from the supernatant (plasma) is taken and precipitated by addition of 400 μL cold acetonitrile and frozen at −20° C. over night. Samples are subsequently thawed and centrifuged at 3000 rpm, 4° C. for 20 minutes. Aliquots of the supernatants are taken for analytical testing using an Agilent HPLC-system with LCMS/MS detection. PK parameters are calculated by non-compartmental analysis using a PK calculation software (e.g. Phoenix WinNonlin®, Certara USA, Inc.).

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. AUCnorm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t1/2: terminal half-life (in h); MRT iv (h): mean residence time.

Assay 18

Assessment of the Anti-Proliferation Effect of Compounds in Tumor Xenografts

The suitability of the compounds of the present invention for the treatment of hyperproliferative disorders can be demonstrated in animal models of the following cancer types: breast cancer; esophageal cancer; liver cancer; lung cancer; lymphoma including non-Hodgkin-lymphoma type, diffuse large B-cell lymphoma subtype including GC-DLBCL* and ABC-DLBCL** subtypes, and mantle cell lymphoma; acute leukemia, acute myeloid leukemia type, acute monocytic leukemia; melanoma; multiple myeloma; melanoma; ovarian cancer; pancreas cancer leukemia, and leukemia. For this purpose, human tumor cells of the respective cancer type are injected subcutaneously into immunocompromised mice. Once the primary tumor growth is established the animals will be then randomized to receive treatment with either compound at maximum tolerated dose or vehicle control for a certain period of time. The difference between those groups in terms of the tumor growth will be used to access the treatment efficacy. The principles of such xenograft studies are summarized in Richmond, A.; Su, Y. (2008). "Mouse xenograft models vs GEM models for human cancer therapeutics". Disease Models and Mechanisms 1 (2-3): 78-82. doi:10.1242/dmm.000976.

The invention claimed is:

1. A compound of general formula (I):

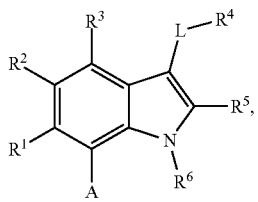

(I)

wherein

A is

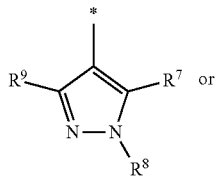

(A1)

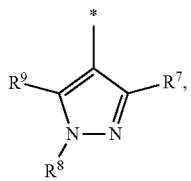

(A2)

A is
  wherein $R^6$ and $R^7$, together with two carbon atoms of the pyrazole ring, two carbon atoms of the indole moiety and the nitrogen atom to which $R^6$ is attached, form a 9-membered to 16-membered ring and * is the point of attachment of these moieties to the indole carbon atom bearing the A substituent;
  $R^1$ and $R^2$ are each independently selected from a hydrogen atom, a halogen atom, a cyano group, a $C_1$-$C_3$-alkyl group, and a $C_1$-$C_3$-alkoxy group;
  $R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group, a $C_1$-$C_3$-alkylthio group, a —S(O)—($C_1$-$C_3$-alkyl) group, a —S(O)$_2$—($C_1$-$C_3$-alkyl) group, a $C_1$-$C_3$-haloalkoxy group, a $C_1$-$C_3$-haloalkylthio group and a $C_3$-$C_5$-cycloalkyl group;
  $R^4$ is selected from an aryl group and a heteroaryl group, each of which is unsubstituted or substituted with one, two, three, four or five substituents and each substituent is independently selected from a halogen atom, a cyano group, a $C_1$-$C_3$-alkyl group, a $C_1$-$C_3$-haloalkyl group, a $C_1$-$C_3$-alkoxy group, a $C_1$-$C_3$-thioalkyl group, a $C_1$-$C_3$-haloalkoxy group, a ($C_1$-$C_3$)-haloalkyl-S—group and a $C_3$-$C_5$-cycloalkyl group;
  L is a group —(CH$_2$)$_m$-E- wherein any CH$_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group, or two substituents are optionally taken together with their intervening atoms to form a saturated or partially unsaturated 3-6-membered cycloalkyl ring, or a 3-8-membered saturated or partially unsaturated heterocyclic ring having 1-2 heteroatoms independently selected from an oxygen atom, a sulfur atom, a —S(O)— group, a —S(O)$_2$— group and a —NR$^{14}$— group;
  E is, an oxygen atom, a sulfur atom, a —S(O)— group, a —S(O)$_2$— group or a —NR$^{14}$— group and constitutes the connecting element to $R^4$;
  m is 2, 3, or 4;
  $R^5$ is selected from a COOH group, a

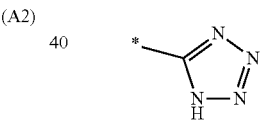

group, a —C(O)—NHS(O)$_2$($C_1$-$C_6$-alkyl) group, a —C(O)—NHS(O)$_2$($C_3$-$C_6$-cycloalkyl) group, a —C(O)—NHS(O)$_2$(aryl) group, a —C(O)—NHS(O)$_2$(CH$_2$)$_s$NHCO ($C_1$-$C_6$-alkyl) group, a —C(O)—NHS(O)$_2$(CH$_2$)$_s$NHCO ($C_3$-$C_6$-cycloalkyl) group and a —C(O)—NHS(O)$_2$ (CH$_2$)$_s$NHCO(aryl) group;
  —$R^6$-$R^7$— is $^{\#}$—(CH$_2$)$_n$—(B)$_t$—(CH$_2$)$_p$-$^{\#\#}$, wherein any —CH$_2$— group is unsubstituted or substituted with one or more substituents independently selected from a halogen atom, a hydroxyl group, a NR$^{16}$R$^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a heterocycloalkyl group and a (heterocycloalkyl)-($C_1$-$C_3$-alkylene)- group, and where a double bond in any alkenylene can be replaced by a 1,2-cyclopropyl group, and said 1,2-cyclopropyl group is unsubstituted or substituted one or two times with a halogen atom or a $C_1$-$C_2$-alkyl group, wherein $^{\#}$ is the point of attachment with the indole nitrogen atom and $^{\#\#}$ is the point of attachment with the pyrazole carbon atom bearing the $R^7$ substituent or
  —$R^6$-$R^7$— is $^{\#}$—(CH$_2$)$_n$—(B)$_t$—CR$^{22}$R$^{23}$—$^{\#\#}$ or $^{\#}$-(C$_2$-C$_9$-alkenylene)-(B)$_t$—CR$^{22}$R$^{23}$-$^{\#\#}$, wherein # is the point of attachment with the indole nitrogen atom and ## is the point of attachment with the pyrazole carbon atom bearing the $R^7$ substituent; and wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, a $C_1$-$C_3$-haloalkoxy group, a $C_3$-$C_6$-cycloalkyl group, and a (heterocycloalkyl)-($C_1$-$C_3$-alkylene)- group;

n is 1, 2, 3, 4, 5, 6, 7, or 8;
p is 1, 2, 3, 4, 5, 6, 7 or 8;
t is 1;
s is 0, 1 or 2;
where the integers selected for variables n, t, and p result in forming a 9-membered to 16-membered ring independent from the selection of variable A1 or A2;

B is independently selected from a —S(O)$NR^{15}$- group, a —$NR^{15}$S(O)— group, a —S(O)$_2NR^{15}$- group, and a —$NR^{15}$S(O)$_2$— group;

$R^8$ is selected from a hydrogen atom,
a $C_1$-$C_6$-alkyl group, which is unsubstituted or substituted with one or more substituents independently selected from
a halogen atom, a hydroxyl group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group, and
a $C_1$-$C_3$-haloalkyl group, a $C_3$-$C_6$-cycloalkyl group, or a $C_1$-$C_6$-alkyl group in which one or two not directly adjacent carbon atoms are independently replaced by a heteroatom independently selected from —O— and —NH— and $R^9$ is selected from a hydrogen atom,
a $C_1$-$C_4$-alkyl group,
a $C_1$-$C_3$-hydroxyalkyl group,
a $C_1$-$C_4$-haloalkyl group,
a $C_1$-$C_4$-haloalkyl-NH—C(O)—O—($C_1$-$C_3$-alkylene)- group,
a $C_2$-$C_6$-haloalkenyl group,
a $C_1$-$C_6$-alkyl-O- group,
a $C_1$-$C_4$-haloalkoxy group,
a $C_1$-$C_6$-alkyl-O—($C_1$-$C_3$-alkylene)- group,
a ($C_3$-$C_7$)-cycloalkyl group,
a ($C_3$-$C_7$)-cycloalkyl-O—($C_1$-$C_3$-alkylene)- group,
a phenyl-O—($C_1$-$C_3$-alkylene)- group,
a phenyl-($C_1$-$C_3$-alkylene)-O—($C_1$-$C_3$-alkylene)- group,
a $R^{18}$-(phenylene)-($C_1$-$C_3$-alkylene)-O—($C_1$-$C_3$-alkylene)- group,
a $R^{18}$-(phenylene)-O—($C_1$-$C_3$-alkylene)- group,
a $R^{18}$-(phenylene)-(heteroarylene)-O—($C_1$-$C_3$-alkylene)- group,
a ($R^{18}$)-(heterocycloalkylene)-($C_1$-$C_3$-alkylene)- group,
a ($R^{18}$)-(heterocycloalkylene)-(phenylene)-O—($C_1$-$C_3$-alkylene)- group,
a (heterocycloalkenyl)-(phenylene)-O—($C_1$-$C_3$-alkylene)- group,
a ($R^{18}$)-(heteroarylene)-($C_1$-$C_3$-alkylene)-O—($C_1$-$C_3$-alkylene)- group,
a ($R^{18}$)-(heteroarylene)-(phenylene)-O—($C_1$-$C_3$-alkylene)- group,
a ($R^{19}$)—S(O)$_2$-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—NH-(phenylene)-O—($C_1$-$C_3$-alkylene)- group,
a ($R^{19}$)—S(O)$_2$—N($C_1$-$C_6$-alkyl)-(phenylene)-O—($C_1$-$C_3$-alkylene)- group,
a ($R^{19}$)—S(O)$_2$-(heterocycloalkylene)-(phenylene)-O—($C_1$-$C_3$-alkylene)- group,
a ($R^{18}$)-(heterocycloalkylene)-(heteroarylene)-O—($C_1$-$C_3$-alkylene)- group,
a ($R^{19}$)-(heteroarylene)-O—($C_1$-$C_3$-alkylene)- group,
a ($R^{18}$)-(heteroarylene)-O—($C_1$-$C_3$-alkylene)- group,
a ($R^{19}$)—S(O)$_2$-(heteroarylene)-O—($C_1$-$C_3$-alkylene)- group,
a ($R^{19}$)—S(O)$_2$-(heterocycloalkylene)-(heteroarylene)-O—($C_1$-$C_3$-alkylene)- group,
a $NR^{20}R^{21}$—($C_1$-$C_3$-alkylene)- group,
a ($C_1$-$C_3$-alkyl)-NH—($C_1$-$C_3$-alkylene)- group,
a ($C_1$-$C_3$-haloalkyl)-($C_1$-$C_3$-alkylene)-NH—($C_1$-$C_3$-alkylene)- group,
a ($C_1$-$C_3$-haloalkyl)-NH—($C_1$-$C_3$-alkylene)- group,
a ($C_1$-$C_3$-alkyl)-NH—C(O)—($C_1$-$C_3$-alkylene)- group,
a ($C_1$-$C_3$-alkyl)-$NR^{15}$—C(O)—($C_1$-$C_3$-alkylene)- group,
a ($C_1$-$C_3$- alkyl)-C(O)—NH—($C_1$-$C_3$-alkylene)- group,
a ($C_1$-$C_3$- alkyl)-C(O)—$NR^{15}$—($C_1$-$C_3$-alkylene)- group,
a

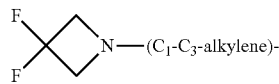

group, and a

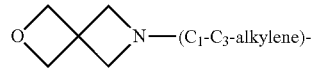

group, where the phenyl ring is unsubstituted or substituted with a halogen atom, a hydroxyl group, or a $C_1$-$C_3$-alkoxy group and
the heterocycloalkyl group is unsubstituted or substituted with an oxo (=O) group or is unsubstituted or substituted with one or more substituents independently selected from a halogen atom, a hydroxyl group, a $C_1$-$C_3$-alkyl group and a $C_1$-$C_3$-alkoxy group,
or $R^8$ and $R^9$ together form a 5- or 6-membered ring optionally comprising one or two heteroatoms independently selected from —O— and —$NR^{14}$—;

$R^{14}$ is a hydrogen atom or a $C_1$-$C_3$-alkyl group;
$R^{15}$ is independently selected from a hydrogen atom,
a $C_1$-$C_6$-alkyl group
which is unsubstituted or substituted with one or more substituents independently selected from a halogen atom, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a heterocycloalkyl group, an unsubstituted or substituted aryl group, a ($R^{18}$)-(heterocycloalkylene)-(arylene)-O—group, a (heterocycloalkyl)-(arylene)-O—group, an aryl-O- group, an aryl- ($C_1$-$C_3$-alkylene)-O- group, a ($R^{19}$)—S(O)$_2$-arylene-O- group, a ($R^{19}$)S(O)$_2$-heterocycloalkylene-arylene-O- group, an aryl-heteroarylene-O—group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-S(O)$_2$— group, and a heterocycloalkylene-heteroarylene-S(O)$_2$— group;

a ($C_3$-$C_7$)-cycloalkyl group and a phenyl group;

$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;

$R^{18}$ is independently selected from a hydrogen atom, a hydroxyl group, a cyano group, a $C_1$-$C_3$-alkyl group, a $C_1$-$C_6$-hydroxyalkyl group, a $C_1$-$C_3$-alkoxy group, a $R^{21}$OC(O)—($C_1$-$C_3$-alkylene)- group, a —C(O)O$R^{21}$ group, a —C(O)N$R^{20}R^{21}$ group, a ($C_1$-$C_3$-alkyl)-O—($C_1$-$C_3$-alkylene)-C(O)— group, a ($C_1$-$C_6$-alkyl)-C(O)— group and a $C_3$-$C_6$-cycloalkyl-C(O)— group;

$R^{19}$ is selected from a $C_1$-$C_3$-alkyl group, a $C_3$-$C_6$-cycloalkyl group and a N$R^{20}R^{21}$ group;

$R^{20}$ and $R^{21}$ are independently selected from a hydrogen atom and a $C_1$-$C_6$-alkyl group; and $R^{22}$ is independently selected from, a halogen atom and a $C_1$-$C_6$-alkyl group which is unsubstituted or substituted with one or more substituents selected from a halogen atom, a hydroxy group, a N$R^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, an aryl group, a ($R^{18}$)-(heterocycloalkylene)-(arylene)-O- group, a (heterocycloalkyl)-(arylene)-O— group, an aryl-O- group, an aryl-($C_1$-$C_3$-alkylene)-O- group, a ($R^{19}$)—S(O)$_2$-arylene-O- group, a ($R^{19}$)S(O)$_2$-heterocycloalkylene-arylene-O- group, an aryl-heteroarylene-O- group, an aryl-heteroarylene-O—($C_1$-$C_3$-alkylene)- group, a heterocycloalkyl-($C_1$-$C_3$-alkylene)-C(O)— group, a heterocycloalkyl-NH—C(O) group, an aryl-($C_1$-$C_3$-alkylene)-NH—C(O)— group, a heterocycloalkylene-($C_1$-$C_3$-alkylene)-S(O)$_2$— group, and a heterocycloalkylene-heteroarylene-S(O)$_2$— group and a $C_1$-$C_3$-alkyl-C(O)— group and $R^{23}$ is independently selected from a hydrogen atom, a halogen atom, a hydroxy group, a $C_1$-$C_6$-alkyl group, and a $C_1$-$C_6$-haloalkyl group, or $R^{22}$ and $R^{23}$ together with the carbon atom to which they are attached form a 3-6-membered carbocyclic ring or a 3-6-membered heterocyclic ring comprising one or two heteroatoms selected from nitrogen, oxygen or sulfur;

or a tautomer, an N-oxide, or a salt thereof, or a salt of a tautomer, or a salt of an N-oxide, or a mixture of same.

2. The compound of general formula (I) according to claim 1 wherein

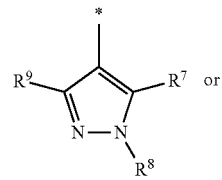

(A1)

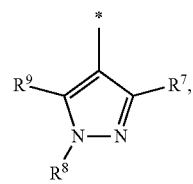

(A2)

A is wherein $R^6$ and $R^7$, together with two carbon atoms of the pyrazole ring, two carbon atoms of the indole moiety and the nitrogen atom to which $R^6$ is attached, form a 9-membered to 13-membered ring and * is the point of attachment of these moieties to the indole carbon atom bearing the A substituent;

$R^1$ and $R^2$ are each independently selected from a hydrogen atom, a halogen atom, a cyano group, a $C_1$-$C_3$-alkyl group and a $C_1$-$C_3$-alkoxy group;

$R^3$ is selected from a hydrogen atom, a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

$R^4$ is selected from an aryl group and a heteroaryl group, each of which is unsubstituted or substituted with one, two, or three substituents and each substituent is independently selected from a halogen atom, a cyano group, a $C_1$-$C_3$-alkyl group, a $C_1$-$C_3$-haloalkyl group, a $C_1$-$C_3$-alkoxy group and a $C_3$-$C_5$-cycloalkyl group;

L is a group —(CH$_2$)$_m$-E- wherein any CH$_2$ group is unsubstituted or substituted with one or two substituents and each substituent is independently selected from a halogen atom, a cyano group, a hydroxyl group, a $C_1$-$C_3$-alkyl group, and a $C_1$-$C_3$-alkoxy group;

E is a bond, an oxygen atom, a sulfur atom, or a —N$R^{14}$— group and constitutes the connecting element to $R^4$;

m is 2, 3, or 4;

$R^5$ is selected from a COOH group and a

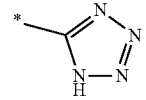

group;

—$R^6$-$R^7$— is #—(CH$_2$)$_n$—(B)$_t$—(CH$_2$)$_p$-##, wherein any —CH$_2$— group is unsubstituted or substituted with one or more substituents selected from a halogen atom, a hydroxyl group, a N$R^{16}R^{17}$ group, a $C_1$-$C_3$-alkyl group, a $C_1$-$C_3$-haloalkyl group, a heterocycloalkyl group and a $C_1$-$C_3$-alkoxy group, wherein # is the point of attachment with the indole nitrogen atom and ## is the point of attachment with the pyrazole carbon atom bearing the $R^7$ substituent or —$R^6$-$R^7$— is $^{\#}$—$(CH_2)_n$—$(B)_t$—$CR^{22}R^{23}$-$^{\#\#}$ or $^{\#}$-$(C_2$-$C_9$-alkenylene)-$(B)_t$—$CR^{22}R^{23}$-$^{\#\#}$, wherein $^{\#}$ is the point of attachment with the indole nitrogen atom and $^{\#\#}$ is the point of attachment with the pyrazole carbon atom bearing the $R^7$ substituent; and wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group;

n is 1, 2, 3, 4, or 5;

p is 1, 2, 3, or 4;

t is 1;

where the integers selected for variables n, t, and p result in forming a 9-membered to 13-membered ring independently from the selection of variable A1 or A2;

B is independently selected from a —$S(O)_2NR^{15}$- group and a —$NR^{15}S(O)_2$— group, $R^8$ is selected from a hydrogen atom and
  a $C_1$-$C_6$-alkyl group, which is unsubstituted or substituted with one or more substituents independently selected from
    a halogen atom, a hydroxy group, a $C_1$-$C_3$-alkoxy group, a $C_1$-$C_3$-haloalkoxy group, a $C_3$-$C_6$-cycloalkyl group, a heterocycloalkyl group, and a $NR^{20}R^{21}$ group;

$R^9$ is selected from a hydrogen atom,
  a $C_1$-$C_4$-alkyl group,
  a $C_1$-$C_3$-hydroxyalkyl group,
  a $C_1$-$C_4$-haloalkyl group,
  a $C_1$-$C_4$-haloalkyl-NH—C(O)—O—($C_1$-$C_3$-alkylene)-group,
  a $C_2$-$C_6$-haloalkenyl group,
  a $C_1$-$C_6$-alkyl-O- group,
  a $C_1$-$C_4$-haloalkoxy group,
  a $C_1$-$C_6$-alkyl-O—($C_1$-$C_3$-alkylene)- group,
  a ($C_1$-$C_3$-alkyl)-NH—($C_1$-$C_3$-alkylene)- group,
  a ($C_3$-$C_7$)-cycloalkyl group, and
  a ($C_3$-$C_7$)-cycloalkyl-O—($C_1$-$C_3$-alkylene)- group;

$R^{14}$ is a hydrogen atom or a $C_1$-$C_3$-alkyl group;

$R^{15}$ is independently selected from a hydrogen atom,
  a $C_1$-$C_6$-alkyl group
    which is unsubstituted or substituted with one or more substituents selected from a $C_1$-$C_3$-alkyl group, a heterocycloalkyl group, and an unsubstituted or substituted aryl group,
  a ($C_3$-$C_7$)-cycloalkyl group and
  a phenyl group;

$R^{16}$ and $R^{17}$ are each independently selected from a hydrogen atom, a $C_1$-$C_6$-alkyl group, a $C_1$-$C_6$-haloalkyl group, a $C_3$-$C_5$-cycloalkyl group, a $C_1$-$C_3$-alkyl-C(O)— group, a $C_1$-$C_3$-alkylS(O)$_2$— group and a $C_1$-$C_3$-alkyl-O—C(=O)— group;

$R^{19}$ is selected from a $C_1$-$C_3$-alkyl group, a $C_3$-$C_6$-cycloalkyl group and a $NR^{20}R^{21}$ group;

$R^{20}$ and $R^{21}$ are independently selected from a hydrogen atom and a $C_1$-$C_6$-alkyl group; and $R^{22}$ is independently selected from
  a halogen atom,
  a $C_1$-$C_6$-alkyl group which is unsubstituted or substituted with one or more substituents selected from a halogen atom, a hydroxy group, a $NR^{16}R^{17}$ group, a $C_1$-$C_3$-alkyl group, a $C_1$-$C_3$-haloalkyl group, a $C_1$-$C_3$-hydroxyalkyl group, a $C_1$-$C_3$-alkoxy group, a $C_1$-$C_3$-haloalkoxy group, a $C_3$-$C_6$-cycloalkyl group, a heterocycloalkyl group, and a phenyl group,
  a $C_3$-$C_6$-cycloalkyl group,
  a heterocycloalkyl group,
  a phenyl group, and
  a heteroaryl group and $R^{23}$ is independently selected from a hydrogen atom, a halogen atom, a hydroxy group, and a $C_1$-$C_4$-alkyl group, or $R^{22}$ and $R^{23}$ together with the carbon atom to which they are attached form a 3-6-membered carbocyclic ring or a 3-6-membered heterocyclic ring comprising one or two heteroatoms selected from nitrogen, oxygen or sulfur;

or a tautomer, an N-oxide, or a salt thereof, or a salt of a tautomer, or a salt of an N-oxide, or a mixture of same.

3. The compound of general formula (I) according to claim 1 wherein

A is

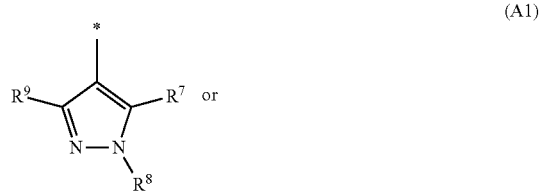

(A1)

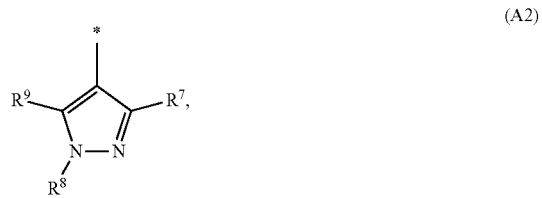

(A2)

wherein $R^6$ and $R^7$, together with two carbon atoms of the pyrazole ring, two carbon atoms of the indole moiety and the nitrogen atom to which $R^6$ is attached, form a 10-membered to 13-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group and a heteroaryl group, each of which is unsubstituted or substituted with one, two, or three substituents and each substituent is independently selected from a halogen atom and a $C_1$-$C_3$-alkyl group;

L is a group —$(CH_2)_m$-E-;

E is a bond or an oxygen atom and constitutes the connecting element to $R^4$;

m is 2, 3, or 4;

$R^5$ is a COOH group;

—$R^6$-$R^7$— is $^{\#}$—$(CH_2)_n$—$(B)_t$—$(CH_2)_p$-$^{\#\#}$, wherein any —$CH_2$— group is unsubstituted or substituted with one or more substituents selected from a halogen atom, a hydroxyl group, a $NR^{16}R^{17}$ group, a $C_1$-$C_3$-alkyl group, a $C_1$-$C_3$-haloalkyl group, a heterocycloalkyl group and a $C_1$-$C_3$-alkoxy group, wherein $^{\#}$ is the point of attachment with the indole nitrogen atom and $^{\#\#}$ is the point of attachment with the pyrazole carbon atom bearing the $R^7$ substituent or —$R^6$-$R^7$— is $^{\#}$—$(CH_2)_n$—$(B)_t$—$CR^{22}R^{23}$-$^{\#\#}$ or $^{\#}$-$(C_2$-$C_9$-alkenylene)-$(B)_t$—$CR^{22}R^{23}$-$^{\#\#}$, wherein $^{\#}$ is the point of attachment with the indole nitrogen atom and ## is the point of attachment with the pyrazole carbon atom bearing the $R^7$ substituent; and wherein one or more —$CH_2$— groups may be unsubstituted or substituted with one or more substituents independently selected from a halogen atom, a hydroxyl group, a $NR^{16}R^{17}$ group, a $C_1$-$C_3$-alkyl group, a $C_1$-$C_3$-haloalkyl group, a $C_1$-$C_3$-alkoxy group, and a $C_1$-$C_3$-haloalkoxy group;

n is 2, 3 or 4;

p is 1, 2, or 3;

t is 1;

where the integers selected for variables n, t, and p result in forming a 10-membered to 13-membered ring independently from the selection of variable A1 or A2;

B is selected from a —$S(O)_2NR^{15}$- group and a —$NR^{15}S(O)_2$— group;

$R^8$ is selected from a hydrogen atom and a $C_1$-$C_6$-alkyl group, which is unsubstituted or substituted with one or more substituents independently selected from a halogen atom, a hydroxy group, a $C_3$-$C_6$-cycloalkyl group and a heterocycloalkyl group;

$R^9$ is selected from a hydrogen atom, a $C_1$-$C_4$-alkyl group, a $C_1$-$C_3$-hydroxyalkyl group, a $C_1$-$C_4$-haloalkyl group, a $C_1$-$C_6$-alkyl-O- group, a $C_1$-$C_4$-haloalkoxy group, and a $C_1$-$C_6$-alkyl-O—($C_1$-$C_3$-alkylene)- group;

$R^{15}$ is independently selected from a hydrogen atom, a $C_1$-$C_6$-alkyl group which is unsubstituted or substituted with a substituent selected from a heterocycloalkyl group and an unsubstituted or substituted aryl group, and a ($C_3$-$C_7$)-cycloalkyl group;

$R^{16}$ and $R^{17}$ are each independently selected from a hydrogen atom, a $C_1$-$C_6$-alkyl group and a $C_1$-$C_6$-haloalkyl group; and $R^{22}$ is independently selected from a halogen atom, a $C_1$-$C_4$-alkyl group which is unsubstituted or substituted with a group selected from a hydroxy group, $NR^{16}R^{17}$ group, a $C_1$-$C_4$-alkoxy group, a $C_3$-$C_6$-cycloalkyl group, a heterocycloalkyl group and a phenyl group;

a phenyl group, a heteroaryl group, a $C_3$-$C_6$-cycloalkyl group, and a heterocycloalkyl group and $R^{23}$ is independently selected from a hydrogen atom, a halogen atom, a hydroxy group, and a $C_1$-$C_4$-alkyl group, or $R^{22}$ and $R^{23}$ together form a 3-6-membered carbocyclic ring;

or a tautomer, an N-oxide, or a salt thereof, or a salt of a tautomer, an N-oxide, or a mixture of same.

4. The compound of general formula (I) according to claim 1, wherein

A is

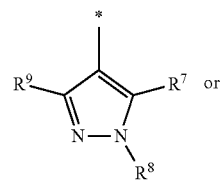

(A1)

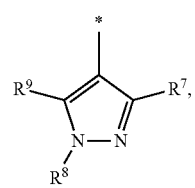

(A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;

$R^1$ and $R^2$ are each independently selected from a hydrogen atom and a halogen atom;

$R^3$ is a hydrogen atom;

$R^4$ is selected from an aryl group which is unsubstituted or substituted with one, two, or three substituents and each substituent is independently selected from a halogen atom and a $C_1$-$C_3$-alkyl group;

L is a group —$(CH_2)_m$-E-;

E is a bond or an oxygen atom and constitutes the connecting element to $R^4$;

m is 3;

$R^5$ is a COOH group;

—$R^6$-$R^7$— is $^{\#}$—$(CH_2)_n$—$(B)_t$—$(CH_2)_p$-$^{\#\#}$, wherein $^{\#}$ is the point of attachment with the indole nitrogen atom and $^{\#\#}$ is the point of attachment with the pyrazole carbon atom bearing the $R^7$ substituent or —$R^6$-$R^7$— is $^{\#}$—$(CH_2)_n$—$(B)_t$—$CR^{22}R^{23}$-$^{\#\#}$ or $^{\#}$-($C_2$-$C_9$-alkenylene)-$(B)_t$—$CR^{22}R^{23}$-$^{\#\#}$, wherein $^{\#}$ is the point of attachment with the indole nitrogen atom and $^{\#\#}$ is the point of attachment with the pyrazole carbon atom bearing the $R^7$ substituent;

n is 3;

t is 1;

p is 1;

where the integers selected for variables n, t, and p result in forming a 11-membered ring independently from the selection of variable A1 or A2;

B is a —$S(O)_2NR^{15}$- group;

$R^8$ is selected from a hydrogen atom and a $C_1$-$C_6$-alkyl group which is unsubstituted or substituted with a heterocycloalkyl group;

$R^9$ is selected from a hydrogen atom, a $C_1$-$C_4$-alkyl group, and a $C_1$-$C_6$-alkyl-O—($C_1$-$C_3$-alkylene)- group;

$R^{15}$ is independently selected from a hydrogen atom,
a $C_1$-$C_6$-alkyl group
which is unsubstituted or substituted with an unsubstituted or substituted aryl group or with a heterocycloalkyl group and
a $(C_3$-$C_7)$-cycloalkyl group; and
$R^{22}$ is independently selected from
a halogen atom,
a phenyl group,
a $C_3$-$C_6$-cycloalkyl group, and
a $C_1$-$C_3$-alkyl group which is unsubstituted or substituted with one or more substituents selected from a hydroxy group, a $NR^{17}R^{18}$ group, a $C_1$-$C_3$-haloalkyl group, a $C_1$-$C_3$-alkoxy group, a $C_3$-$C_6$-cycloalkyl group, a heterocycloalkyl group and a phenyl group and
$R^{23}$ is independently selected from a hydrogen atom, a halogen atom, a hydroxy group and a $C_1$-$C_3$-alkyl group,
or
$R^{22}$ and $R^{23}$ together form a 3-6-membered carbocyclic ring;
or a tautomer, an N-oxide, or a salt thereof, or a salt of a tautomer, or a salt of an N-oxide, or a mixture of same.

5. A compound according to general formula (I):

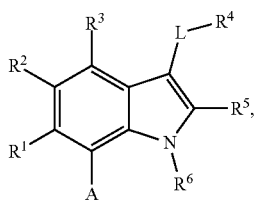

(I)

wherein
A is

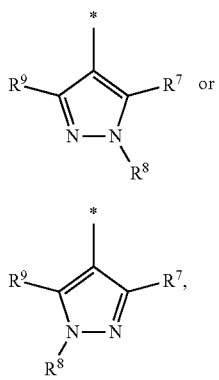

(A1)

or (A2)

wherein $R^6$ and $R^7$, together with two carbon atoms of the pyrazole ring, two carbon atoms of the indole moiety and the nitrogen atom to which $R^6$ is attached, form a 11-membered ring and * is the point of attachment of these moieties to the indole carbon atom bearing the A substituent;
$R^1$ is a hydrogen atom or a halogen atom;
$R^2$ is a hydrogen atom;
$R^3$ is a hydrogen atom;
$R^4$ is an aryl group, which is unsubstituted or substituted with one, two or three substituents independently selected from a halogen atom and a methyl group;
L is a group —$(CH_2)_3$—O—;
$R^5$ is a COOH group; —$R^6$-$R^7$— is $^{\#}$—$(CH_2)_n$—$S(O)_2NR^{15}$-$(CH_2)_p$-$^{\#\#}$, wherein $^{\#}$ is the point of attachment with the indole nitrogen atom and $^{\#\#}$ is the point of attachment with the pyrazole carbon atom bearing the $R^7$ substituent or
$R^6$-$R^7$— is $^{\#}$—$(CH_2)_n$—(B)$_t$—$CR^{22}R^{23}$-$^{\#\#}$,
wherein $^{\#}$ is the point of attachment with the indole nitrogen atom and $^{\#\#}$ is the point of attachment with the pyrazole carbon atom bearing the $R^7$ substituent;
n is 3;
t is 1;
p is 1;
where the integers selected for variables n, t and p result in forming a 11-membered ring independently from the selection of variable A1 or A2;
B is a —$S(O)_2NR^{15}$- group;
$R^8$ is a methyl group;
$R^9$ is selected from a methyl group and an ethyl group;
$R^{15}$ is independently selected from a hydrogen atom,
a $C_1$-$C_3$-alkyl group which is unsubstituted or substituted with an unsubstituted or a substituted aryl group or with an unsubstituted or substituted heterocycloalkyl group, and
a $(C_3$-$C_7)$-cycloalkyl group,
$R^{22}$ is independently selected from a $C_1$-$C_3$-haloalkyl group and a $C_1$-$C_3$-alkyl group which is unsubstituted or substituted with a hydroxyl group, a $C_3$-$C_5$-cycloalkyl group, or a heterocyclyl group; and
$R^{23}$ is a hydrogen atom;
or a tautomer, an N-oxide, or a salt thereof, or a salt of a tautomer, or a salt of an N-oxide, or a mixture of same.

6. The compound according to claim 1, which is selected from
(rac)-2,3-dimethyl-14-[2-(morpholin-4-yl)ethyl]-7- {3-[(naphthalen-1-yl)oxy]propyl}-13,13-dioxo-10,11,12,13,14,15-hexahydro-2H-13lambda$^6$-pyrazolo[3',4':4,5][1,2,8]thiadiazacycloundecino-[6,7,8-hi]indole-8-carboxylic acid,
2,3-dimethyl-14-[2-(morpholin-4-yl)ethyl]-7- {3-[(naphthalen-1-yl)oxy]propyl}-13,13-dioxo-10,11,12,13,14,15-hexahydro-2H-13lambda$^6$-pyrazolo[3',4':4,5] [1,2,8]thiadiazacycloundecino-[6,7,8-hi]indole-8-carboxylic acid-N-ethylethanamine (enantiomer 1),
2,3-dimethyl-14-[2-(morpholin-4-yl)ethyl]-7- {3-[(naphthalen-1-yl)oxy]propyl}-13,13-dioxo-10,11,12,13,14,15-hexahydro-2H-13lambda$^6$-pyrazolo[3',4':4,5] [1,2,8]thiadiazacycloundecino-[6,7,8-hi]indole-8-carboxylic acid-N-ethylethanamine (enantiomer 2),
(rac)-4-chloro-2,3,14-trimethyl-7-{3-[(naphthalen-1-yl)oxy]propyl}-13,13-dioxo-10,11,12,13,14,15-hexahydro-2H-13lambda$^6$-pyrazolo [3',4':4,5] [1,2,8]thiadiazacycloundecino-[6,7,8-hi]indole-8-carboxylic acid,
4-chloro-2,3,14-trimethyl-7-{3-[(naphthalen-1-yl)oxy]propyl}-13,13-dioxo-10,11,12,13,14,15-hexahydro-2H-13lambda$^6$-pyrazolo [3',4':4,5] [1,2,8]thiadiazacycloundecino[6,7,8-hi]indole-8-carboxylic acid-N-ethylethanamine (enantiomer 1),
4-chloro-2,3,14-trimethyl-7-{3-[(naphthalen-1-yl)oxy]propyl}-13,13-dioxo-10,11,12,13,14,15-hexahydro-2H-13lambda$^6$-pyrazolo [3',4':4,5] [1,2,8]thiadiazacycloundecino[6,7,8-hi]indole-8-carboxylic acid-N-ethylethanamine (enantiomer 2), (rac)-12-ethyl-13-fluoro-1-(3-((6-fluoronaphthalen-1-yl) oxy)propyl)-8,11-dimethyl-5,6,9,11-tetrahydro-4H, 8H-pyrazolo[3',4':4,5] [1] thia[2,8] diazacycloundecino [6,7,8-hi]indole-2-carboxylic acid 7,7-dioxide, 3-ethyl-4-fluoro-7-{3-[(6-fluoronaphthalen-1-yl)oxy] propyl}-2,14-dimethyl-13,13-dioxo-10,11,12,13,14, 15-hexahydro-2H-13lambda$^6$-pyrazolo [3',4':4,5] [1,2, 8]thiadiazacycloundecino-[6,7,8-hi]indole-8-carboxylic acid (enantiomer 1), 3-ethyl-4-fluoro-7-{3-[(6-fluoronaphthalen-1-yl)oxy] propyl}-2,14-dimethyl-13,13-dioxo-10,11,12,13,14, 15-hexahydro-2H-13lambda$^6$-pyrazolo [3',4':4,5] [1,2, 8]thiadiazacycloundecino-[6,7,8-hi]indole-8-carboxylic acid (enantiomer 2), (rac)-8,11,12-trimethyl-1-(3-(naphthalen-1-yloxy)propyl)-5,6,9,11-tetrahydro-4H,8H-pyrazolo[3',4':4,5] [1]thia[2,8]diazacycloundecino[6,7,8-hi]indole-2-carboxylic acid 7,7-dioxide, 2,3,14-trimethyl-7-{3-[(naphthalen-1-yl)oxy]propyl}-13, 13-dioxo-10,11,12,13,14,15-hexahydro-2H-13lambda$^6$-pyrazolo [3',4':4,5] [1,2,8]thiadiazacycloundecino[6,7,8-hi]indole-8-carboxylic acid-N-ethylethanamine (enantiomer1), 2,3,14-trimethyl-7-{3-[(naphthalen-1-yl)oxy]propyl}-13, 13-dioxo-10,11,12,13,14,15-hexahydro-2H-13lambda$^6$-pyrazolo [3',4':4,5] [1,2,8]thiadiazacycloundecino[6,7,8-hi]indole-8-carboxylic acid-N-ethylethanamine (enantiomer 2), (rac)-12-ethyl-11-methyl-1-(3-(naphthalen-1-yloxy)propyl)-8-(3-(2-oxopyrrolidin-1-yl)propyl)-5,6,9,11-tetrahydro-4H,8H-pyrazolo[3',4':4,5] [1] thia[2,8]diazacycloundecino [6,7,8-hi]indole-2-carboxylic acid 7,7-dioxide, (rac)-12-ethyl-11-methyl-1-(3-(naphthalen-1-yloxy)propyl)-8-(2-(piperidin-1-yl)ethyl)-4,5,6,8,9,11-hexahydropyrazolo [3',4': 4,5] [1,2,8] thiadiazacycloundecino [6,7,8-hi]indole-2-carboxylic acid 7,7-dioxide 2,2,2-trifluoroacetic acid salt, (rac)-12-ethyl-11-methyl-8-(3-morpholinopropyl)-1-(3-(naphthalen-1-yloxy)propyl)-4,5,6,8,9,11-hexahydropyrazolo [3',4': 4,5] [1,2,8] thiadiazacycloundecino [6,7,8-hi]indole-2-carboxylic acid 7,7-dioxide 2,2,2-trifluoroacetic acid salt, (rac)-12-ethyl-11-methyl-1-(3-(naphthalen-1-yloxy)propyl)-8-(3-(pyrrolidin-1-yl)propyl)-5,6,9,11-tetrahydro-4H,8H-pyrazolo[3',4':4,5] [1] thia[2,8]diazacycloundecino [6,7,8-hi]indole-2-carboxylic acid 7,7-dioxide, (rac)-12-ethyl-11-methyl-1-(3-(naphthalen-1-yloxy)propyl)-4,5,6,8,9,11-hexahydropyrazolo [3',4': 4,5] [1,2,8] thiadiazacycloundecino [6,7,8-hi] indole-2-carboxylic acid 7,7-dioxide, (rac)-12-ethyl-8,9,11-trimethyl-1-(3-(naphthalen-1-yloxy)propyl)-5,6,9,11-tetrahydro-4H,8H-pyrazolo[3', 4':4,5] [1] thia[2,8] diazacycloundecino [6,7,8-hi] indole-2-carboxylic acid 7,7-dioxide, (rac)-13-chloro-12-ethyl-1-(3-((6-fluoronaphthalen-1-yl) oxy)propyl)-8,11-dimethyl-5,6,9,11-tetrahydro-4H, 8H-pyrazolo [3',4':4,5] [1] thia[2,8] diazacycloundecino [6,7,8-hi] indole-2-carboxylic acid 7,7-dioxide, (rac)-13-chloro-12-ethyl-8,11-dimethyl-1-(3-(naphthalen-1-yloxy)propyl)-5,6,9,11-tetrahydro-4H,8H-pyrazolo[3',4':4,5] [1] thia[2,8] diazacycloundecino [6,7,8-hi] indole-2-carboxylic acid 7,7-dioxide, (rac)- 13-chloro- 1-(3-((2,3-dihydro-1H-inden-4-yl)oxy) propyl)-12-ethyl-8,11-dimethyl-5,6,9,11-tetrahydro-4H,8H-pyrazolo [3',4':4,5] [1] thia[2,8] diazacycloundecino [6,7,8-hi] indole-2-carboxylic acid 7,7-dioxide, (rac)-13-chloro-1-(3-(4-chloro-3 ,5-dimethylphenoxy) propyl)-12-ethyl-8,11-dimethyl-4,5,6,8,9,11-hexahydropyrazolo [3',4': 4,5] [1,2,8] thiadiazacycloundecino [6,7,8-hi] indole-2-carboxylic acid 7,7-dioxide, (rac)-13-chloro-12-ethyl-8,11-dimethyl-1-(3-((5,6,7,8-tetrahydronaphthalen-1-yl)oxy)propyl)-4,5,6,8,9,11-hexahydropyrazolo [3',4': 4,5] [1,2,8] thiadiazacycloundecino [6,7,8-hi] indole-2-carboxylic acid 7,7-dioxide, (rac)-13-chloro-12-ethyl- 1-(3-((4-fluoronaphthalen-1-yl) oxy)propyl)-8,11-dimethyl-4,5,6,8,9,11-hexahydropyrazolo [3',4':4,5] [1,2,8] thiadiazacycloundecino [6,7,8-hi] indole-2-carboxylic acid 7,7-dioxide, (rac)-13-fluoro- 1-(3-((6-fluoronaphthalen-1-yl)oxy)propyl)-8,11,12-trimethyl-5,6,9,11-tetrahydro-4H,8H-pyrazolo [3',4':4,5] [1] thia[2,8] diazacycloundecino [6,7,8-hi] indole-2-carboxylic acid 7,7-dioxide, (rac)-13-fluoro-8,11,12-trimethyl-1-(3-(naphthalen-1-yloxy)propyl)-5,6,9,11-tetrahydro-4H,8H-pyrazolo[3', 4':4,5] [1] thia[2,8] diazacycloundecino [6,7,8-hi] indole-2-carboxylic acid 7,7-dioxide, (rac)- 1-(3-((2,3-dihydro-1H-inden-4-yl)oxy)propyl)-13-fluoro-8, 11,12-trimethyl-5,6,9,11-tetrahydro-4H, 8H-pyrazolo [3',4':4,5] [1] thia[2,8] diazacycloundecino [6,7,8-hi] indole-2-carboxylic acid 7,7-dioxide, (rac)- 1-(3-(4-chloro-3 ,5-dimethylphenoxy)propyl)-13-fluoro-8, 11,12-trimethyl-5,6,9,11-tetrahydro-4H,8H-pyrazolo [3',4':4,5] [1] thia[2,8] diazacycloundecino [6,7,8-hi] indole-2-carboxylic acid 7,7-dioxide, (rac)-13-fluoro-8,11,12-trimethyl-1-(3-((5,6,7,8-tetrahydronaphthalen-1-yl)oxy)propyl)-5,6,9,11-tetrahydro-4H,8H-pyrazolo[3',4':4,5] [1] thia[2,8] diazacycloundecino [6,7,8-hi]indole-2-carboxylic acid 7,7-dioxide, (rac)-13-fluoro- 1-(3-((4-fluoronaphthalen-1-yl)oxy)propyl)-8,11,12-trimethyl-5,6,9,11-tetrahydro-4H,8H-pyrazolo [3',4':4,5] [1] thia[2,8] diazacycloundecino [6,7,8-hi]indole-2-carboxylic acid 7,7-dioxide, (rac)-12-ethyl- 13-fluoro-8,11-dimethyl- 1-(3-(naphthalen- 1-yloxy)propyl)-5,6,9,11-tetrahydro-4H,8H-pyrazolo [3',4':4,5] [1] thia[2,8] diazacycloundecino [6,7,8-hi]indole-2-carboxylic acid 7,7-dioxide, (rac)-1-(3-((2,3-dihydro-1H-inden-4-yl)oxy)propyl)-12-ethyl-13-fluoro-8,11-dimethyl-5,6,9,11-tetrahydro-4H, 8H-pyrazolo [3',4':4,5] [1] thia[2,8] diazacycloundecino [6,7,8-hi]indole-2-carboxylic acid 7,7-dioxide, (rac)-1-(3-(4-chloro-3 ,5-dimethylphenoxy)propyl)-12-ethyl-13-fluoro-8,11-dimethyl-5,6,9,11-tetrahydro-4H, 8H-pyrazolo [3',4':4,5] [1] thia[2,8] diazacycloundecino [6,7,8-hi]indole-2-carboxylic acid 7,7-dioxide, (rac)-12-ethyl-13-fluoro-8,11-dimethyl-1-(3-((5,6,7,8-tetrahydronaphthalen-1-yl)oxy)propyl)-5,6,9,11-tetrahydro-4H,8H-pyrazolo[3',4':4,5] [1] thia[2,8] diazacycloundecino [6,7,8-hi]indole-2-carboxylic acid 7,7-dioxide, (rac)-12-ethyl-13-fluoro-1-(3-((4-fluoronaphthalen-1-yl) oxy)propyl)-8,11-dimethyl-5,6,9,11-tetrahydro-4H, 8H-pyrazolo[3',4':4,5] [1] thia[2,8] diazacycloundecino [6,7,8-hi] indole-2-carboxylic acid 7,7-dioxide, (+)-4-chloro-3-ethyl-7-{3-[(6-fluoronaphthalen-1-yl) oxy]propyl}-2,14-dimethyl-13,13-dioxo-10,11,12,13, 14,15-hexahydro-2H-13lambda$^6$-pyrazolo [3',4':4,5] [1,2,8]thiadiazacycloundecino-[6,7,8-hi]indole-8-carboxylic acid (enantiomer 1), (−)-4-chloro-3-ethyl-7-{3-[(6-fluoronaphthalen-1-yl) oxy]propyl}-2,14-dimethyl-13,13-dioxo-10,11,12,13, 14,15-hexahydro-2H-13lambda$^6$-pyrazolo [3',4':4,5]

[1,2,8]thiadiazacycloundecino-[6,7,8-hi]indole-8-carboxylic acid (enantiomer 2), (−)-4-fluoro-7-{3-[(6-fluoronaphthalen-1-yl)oxy]propyl}-2,3,14-trimethyl-13,13-dioxo-10,11,12,13,14,15-hexahydro-2H-13lambda$^6$-pyrazolo[3',4':4,5][1,2,8]thiadiazacycloundecino-[6,7,8-hi]indole-8-carboxylic acid (enantiomer 1), (+)-4-fluoro-7-{3-[(6-fluoronaphthalen-1-yl)oxy]propyl}-2,3,14-trimethyl-13,13-dioxo-10,11,12,13,14,15-hexahydro-2H-13lambda$^6$-pyrazolo [3 ',4':4,5] [1,2,8] thiadiazacycloundecino- [6,7,8-hi] indole-8-carboxylic acid (enantiomer 2), (rac)-4-chloro-14-cyclopropyl-2,3-dimethyl-7-[3-(1-naphthyloxy)propyl]-11,12,14,15-tetrahydro-2H,10H-pyrazolo[3',4':4,5][1,2,8]thiadiazacycloundecino[6,7,8-hi]indole-8-carboxylic acid 13,13-dioxide, (rac)-4-chloro-14-cyclopropyl-7-{3-[(6-fluoro-1-naphthyl)oxy]propyl}-2,3-dimethyl-11,12,14,15-tetrahydro-2H,10H-pyrazolo[3',4':4,5][1,2,8]thiadiazacycloundecino[6,7,8-hi]indole-8-carboxylic acid 13,13-dioxide, (−)-4-chloro- 14-cyclopropyl-7-{3-[(6-fluoro-1-naphthyl)oxy]propyl}-2,3-dimethyl-11,12,14,15-tetrahydro-2H,10H-pyrazolo [3 ',4':4,5] [1,2,8]thiadiazacycloundecino [6,7,8-hi] indole- 8-carboxylic acid 13,13-dioxide N-diethylamine salt (enantiomer 1), (+)-4-chloro-14-cyclopropyl-7-{3-[(6-fluoro-1-naphthyl)oxy]propyl}-2,3-dimethyl-11,12,14,15-tetrahydro-2H,10H-pyrazolo [3 ',4':4,5] [1,2,8]thiadiazacycloundecino [6,7,8-hi] indole- 8-carboxylic acid 13,13-dioxide N-diethylamine salt (enantiomer 2), (rac)-2,3,14-trimethyl- 15-[2-(morpholin-4-yl)ethyl]-7-[3-(1-naphthyloxy)propyl]-11,12,14,15-tetrahydro-2H,10H-pyrazolo [3 ',4':4,5] [1,2,8]thiadiazacycloundecino [6,7,8-hi] indole- 8-carboxylic acid 13,13-dioxide, 2,3,14-trimethyl-15-[2-(morpholin-4-yl)ethyl]-7-{3-[(naphthalen-1-yl)oxy]propyl}-13,13-dioxo-10,11,12,13,14,15-hexahydro-2H-13lambda$^6$-pyrazolo[3',4':4,5][1,2,8]thiadiazacycloundecino [6,7,8-hi] indole-8-carboxylic acid N-ethylethanamine salt (enantiomer 1), 2,3,14-trimethyl-15-[2-(morpholin-4-yl)ethyl]-7-{3-[(naphthalen-1-yl)oxy]propyl}-13,13-dioxo-10,11,12,13,14,15-hexahydro-2H-13lambda$^6$-pyrazolo[3',4':4,5][1,2,8]thiadiazacycloundecino [6,7,8-hi] indole-8-carboxylic acid N-ethylethanamine salt (enantiomer 2), (rac)-4-chloro-7-{3-[(6-fluoro-1-naphthyl)oxy]propyl}-2,3,14-trimethyl-15-[2-(morpholin-4-yl)ethyl]-11,12,14,15-tetrahydro-2H,10H-pyrazolo [3',4':4,5] [1,2,8] thiadiazacycloundecino [6,7,8-hi] indole-8-carboxylic acid 13,13-dioxide, (rac)-4-chloro-7-{3-[(6-fluoro-1-naphthyl)oxy]propyl}-2,3,14-trimethyl-15-[2-(morpholin-4-yl)ethyl]-11,12,14,15-tetrahydro-2H,10H-pyrazolo [3',4':4,5] [1,2,8] thiadiazacycloundecino [6,7,8-hi] indole-8-carboxylic acid 13,13-dioxide, (rac)-4-chloro-14-(2,4-dimethoxybenzyl)-7-{3-[(6-fluoro-1-naphthyl)oxy]propyl}-2,3-dimethyl-11,12,14,15-tetrahydro-2H,10H-pyrazolo [3',4':4,5] [1,2,8]thiadiazacycloundecino [6,7,8-hi] indole-8-carboxylic acid 13,13-dioxide, (rac)-4-chloro-7-{3-[(6-fluoro-1-naphthyl)oxy]propyl}-2,3-dimethyl-11,12,14,15-tetrahydro-2H,10H-pyrazolo [3',4':4,5] thiadiazacycloundecino [6,7,8-hi] indole-8-carboxylic acid 13,13-dioxide, 4-chloro-7-{3-[(6-fluoronaphthalen-1-yl)oxy]propyl}-2,3-dimethyl-13,13-dioxo-10,11,12,13,14,15-hexahydro-2H-13lambda$^6$-pyrazolo[3',4':4,5] [1,2,8]thiadiazacycloundecino [6,7,8-hi] indole-8-carboxylic acid (enantiomer 1), 4-chloro-7-{3-[(6-fluoronaphthalen-1-yl)oxy]propyl}-2,3-dimethyl-13,13-dioxo-10,11,12,13,14,15-hexahydro-2H-13lambda$^6$-pyrazolo [3',4':4,5] [1,2,8]thiadiazacycloundecino [6,7,8-hi] indole-8-carboxylic acid (enantiomer 2), (rac)-4-chloro-14-cyclopropyl-3-ethyl-7-{3-[(6-fluoro-1-naphthyl)oxy]propyl}-2-methyl-11,12,14,15-tetrahydro-2H,10H-pyrazolo [3',4':4,5] [1,2,8]thiadiazacycloundecino [6,7,8-hi] indole-8-carboxylic acid 13,13-dioxide, (−) 4-chloro-14-cyclopropyl-3-ethyl-7-{3-[(6-fluoronaphthalen-1-yl)oxy]propyl}-2-methyl-13,13-dioxo-10,11,12,13,14,15-hexahydro-2H-13lambda$^6$-pyrazolo [3',4':4,5] [1,2,8]thiadiazacycloundecino [6,7,8-hi] indole-8-carboxylic acid N-ethylethanamine salt (enantiomer 1), (+)4-chloro-14-cyclopropyl-3-ethyl-7-{3-[(6-fluoronaphthalen-1-yl)oxy]propyl}-2-methyl-13,13-dioxo-10,11,12,13,14,15-hexahydro-2H-13lambda$^6$-pyrazolo [3',4':4,5] [1,2,8]thiadiazacycloundecino [6,7,8-hi] indole-8-carboxylic acid N-ethylethanamine salt (enantiomer 2), (rac)-4-chloro-3,14-diethyl-7-{3-[(6-fluoro-1-naphthyl)oxy]propyl}-2-methyl-11,12,14,15-tetrahydro-2H,10H-pyrazolo [3',4':4,5] [1,2,8]thiadiazacycloundecino [6,7,8-hi] indole-8-carboxylic acid 13,13-dioxide, (+)-4-chloro-3,14-diethyl-7-{3-[(6-fluoronaphthalen-1-yl)oxy]propyl}-2-methyl-13,13-dioxo-10,11,12,13,14,15-hexahydro-2H-13lambda$^6$-pyrazolo [3',4':4,5] [1,2,8]thiadiazacycloundecino [6,7,8-hi] indole-8-carboxylic acid N-ethylethanamine salt (enantiomer 1), (−)-4-chloro-3,14-diethyl-7-{3-[(6-fluoronaphthalen-1-yl)oxy]propyl}-2-methyl-13,13-dioxo-10,11,12,13,14,15-hexahydro-2H-13lambda$^6$-pyrazolo [3',4':4,5] [1,2,8]thiadiazacycloundecino[6,7,8-hi]indole-8-carboxylic acid N-ethylethanamine salt (enantiomer 2), (rac)-4-chloro-3-ethyl-7-{3-[(6-fluoro-1-naphthyl)oxy]propyl}-2,14-dimethyl-15-[2-(tetrahydro-2H-pyran-4-yl)ethyl]-11,12,14,15-tetrahydro-2H,10H-pyrazolo[3',4':4,5] [1,2,8]thiadiazacycloundecino[6,7,8-hi]indole-8-carboxylic acid 13,13-dioxide (racemate 2), (rac)-4-chloro-3-ethyl-7-{3-[(6-fluoro-1-naphthyl)oxy]propyl}-2,14-dimethyl-15-[2-(tetrahydro-2H-pyran-4-yl)ethyl]-11,12,14,15-tetrahydro-2H,10H-pyrazolo[3',4':4,5] [1,2,8]thiadiazacycloundecino[6,7,8-hi]indole-8-carboxylic acid 13,13-dioxide (racemate 1), (+)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5] [1,2,8]thiadiazacycloundecino[6,7,8-hi]indole-8-carboxylic acid (enantiomer 1), (−)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5] [1,2,8]thiadiazacycloundecino[6,7,8-hi]indole-8-carboxylic acid (enantiomer 2), (+)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda$^6$-pyrazolo[3',4':4,5] [1,2,8] thiadiazacycloundecino[6,7,8-hi]indole-8-carboxylic acid (enantiomer 3), (−)-4-chloro-3-ethyl-7-{3-[(6-fluoronaphthalen-1-yl)oxy]propyl}-2,14-dimethyl-15-[2-(oxan-4-yl)ethyl]-13,13-dioxo-10,11,12,13,14,15-hexahydro-2H-13lambda⁶-pyrazolo[3',4':4,5] [1,2,8]thiadiazacycloundecino [6,7,8-hi] indole-8-carboxylic acid (enantiomer 4), (rac)-4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda⁶-pyrazolo [3',4':4,5] [1,2,8] thiadiazacycloundecino [6,7,8-hi] indole-8-carboxylic acid, 4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda⁶-pyrazolo [3',4':4,5] [1,2,8]thiadiazacycloundecino [6,7,8-hi] indole-8-carboxylic acid (enantiomer 1), 4-chloro-7-{3-[(6-fluoronaphthalen-1-yl)oxy]propyl}-2,3,14-trimethyl-15-[2-(morpholin-4-yl)ethyl]-13,13-dioxo-10,11,12,13,14,15-hexahydro-2H-13lambda⁶-pyrazolo [3',4':4,5] [1,2,8]thiadiazacycloundecino [6,7,8-hi] indole-8-carboxylic acid (enantiomer 2), (rac)4-chloro-3-ethyl-7-{3-[(6-fluoro-1-naphthyl)oxy]propyl}-2,14-dimethyl-11,12,14,15-tetrahydro-2H,10H-pyrazolo [3',4':4,5] [1,2,8]thiadiazacycloundecino [6,7,8-hi] indole-8-carboxylic acid 13,13-dioxide, (rac)-15-chloro-14-ethyl-1-(3-((6-fluoronaphthalen-1-yl)oxy)propyl)-8,13-dimethyl-11-morpholino-5,6,9,10,11,13-hexahydro-4H,8H-pyrazolo[3',4':6,7] [1] thia[2,10] diazacyclotridecino [8,9,10-hi] indole-2-carboxylic acid 7,7-dioxide, (+)-4-chloro-3-ethyl-7-{3-[(6-fluoro-1-naphthyl)oxy]propyl}-2,14-dimethyl-17-(morpholin-4-yl)-11,12,14,15,16,17-hexahydro-2H,10H-pyrazolo[3',4':6,7] [1,2,10] thiadiazacyclotridecino [8,9,10-hi] indole-8-carboxylic acid 13,13-dioxide trifluoroacetate salt (enantiomer 1), (−)-4-chloro-3-ethyl-7- {3-[(6-fluoro-1-naphthyl)oxy]propyl}-2,14-dimethyl- 17-(morpholin-4-yl)- 11,12,14, 15,16,17-hexahydro-2H,10H-pyrazolo [3 ',4': 6,7] [ 1,2, 10] thiadiazacyclotridecino [ 8,9, 10-hi] indole-8-carboxylic acid 13,13-dioxide trifluoroacetate salt (enantiomer 2), (rac) 4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda⁶-pyrazolo [3 ',4':4,5] [1,2,8] thiadiazacycloundecino [6,7,8-hi] indole-8-carboxylic acid, (15S)-4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda⁶-pyrazolo [3',4':4,5] [1,2,8] thiadiazacycloundecino [6,7,8-hi] indole-8-carboxylic acid, (rac) 4-chloro-3-ethyl-7-{3-[(6-fluoronaphthalen-1-yl)oxy]propyl}-2,14-dimethyl-15-[2-(morpholin-4-yl)ethyl]-13,13-dioxo-10,11,12,13,14,15-hexahydro-2H-13lambda⁶-pyrazolo [3 ',4':4,5] [1,2,8] thiadiazacycloundecino [6,7,8-hi] indole-8-carboxylic acid, 4-chloro-3-ethyl-7-{3-[(6-fluoronaphthalen- 1-yl)oxy] propyl}-2,14-dimethyl- 15-[2-(morpholin-4-yl)ethyl]-13,13-dioxo- 10, 11,12,13,14,15-hexahydro- 2H-13lambda⁶-pyrazolo [3 ',4':4,5] [1,2,8]thiadiazacycloundecino [6,7,8-hi] indole- 8-carboxylic acid-N-ethylethanamine salt (enantiomer 1), 4-chloro-3-ethyl-7-{3-[(6-fluoronaphthalen- 1-yl)oxy] propyl}-2,14-dimethyl- 15-[2-(morpholin-4-yl)ethyl]-13,13-dioxo- 10, 11,12,13,14,15-hexahydro- 2H-13lambda⁶-pyrazolo [3 ',4':4,5] [1,2,8]thiadiazacycloundecino [6,7,8-hi] indole- 8-carboxylic acid-N-ethylethanamine salt (enantiomer 2) and (rac)-13-chloro-12-ethyl- 1-(3-((6-fluoronaphthalen-1-yl)oxy)propyl)- 11-methyl- 8-(2-morpholinoethyl)-5,6,9, 11-tetrahydro-4H,8H-pyrazolo[3',4':4,5][1]thia[2,8]diazacycloundecino[6,7,8-hi]indole-2-carboxylic acid 7,7-dioxide;

wherein lambda⁶ means λ6;

or a tautomer, an N-oxide, or a salt thereof, or a salt of a tautomer, or a salt of an N-oxide, or a mixture of same.

7. A method of preparing a compound of general formula (I) according to claim 1, said method comprising the step of reacting an intermediate compound of general formula (II):

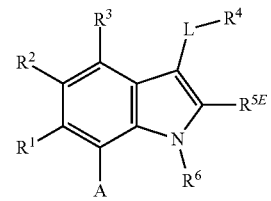

wherein $R^1$, $R^2$, $R^3$, $R^4$, $R^6$, A and L are as defined for the compound of general formula (I) according to claim 1, and $R^{5E}$ represents a carboxylic ester group or a benzyl ester group, with an alkali hydroxide in a mixture of water and THF and/or an aliphatic alcohol of formula $C_1$-$C_3$-alkyl-OH, at a temperature from 0° C. to 100° C., to transform the group $R^{SE}$ into a group $R^5$ as defined for the compounds of general formula (I), and subsequently optionally converting the free acid group $R^5$ into a pharmaceutically acceptable salt thereof to obtain a compound of general formula (I)

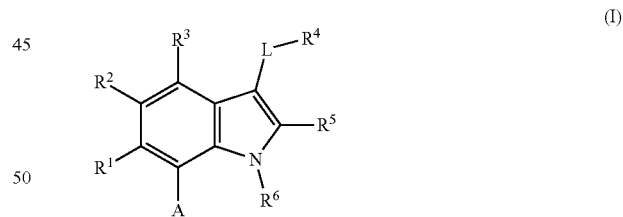

wherein $R^1$, $R^2$, $R^3$, $R^4$, $R^5$, $R^6$, A and L are as defined for the compound of general formula (I) according to claim 1 or a stereoisomer, a tautomer, an N-oxide, a hydrate, a solvate, or a salt thereof, or a mixture of same, and subsequently, or as a step preceding the salt conversion, optionally separating enantiomers by preparative HPLC on a chiral stationary phase.

8. A method of inhibiting proliferation of a cell and/or inducing apoptosis in a cell, comprising contacting the cell with a compound of general formula (I) according to claim 1.

9. A method of treating a disease, comprising administering a compound of general formula (I) according to claim 1, wherein the disease is a hyperproliferative disease.

10. The method according to claim 9, wherein the hyperproliferative disease is cancer.

11. The method according to claim 10, wherein the cancer is selected from breast cancer, leukemia, liver cancer, lung cancer, lymphoma, melanoma, multiple myeloma, squamous cell carcinoma, stomach cancer and ovarian cancer.

12. A pharmaceutical composition comprising a compound of general formula (I) according to claim 1 and one or more pharmaceutically acceptable excipients.

13. A pharmaceutical combination comprising:
   one or more compounds of general formula (I) according to claim 1, and
   one or more further anti-cancer agents.

* * * * *

UNITED STATES PATENT AND TRADEMARK OFFICE
CERTIFICATE OF CORRECTION

PATENT NO. : 11,401,278 B2
APPLICATION NO. : 16/764672
DATED : August 2, 2022
INVENTOR(S) : Laura Furst et al.

Page 1 of 1

It is certified that error appears in the above-identified patent and that said Letters Patent is hereby corrected as shown below:

In the Claims

In Claim 7, at Column 410, Line number 39:
"group R5E into a group R5 as defined for the compounds of"
Should read:
--group $R^{5E}$ into a group R5 as defined for the compounds of--

Signed and Sealed this
Fifteenth Day of November, 2022

Katherine Kelly Vidal
*Director of the United States Patent and Trademark Office*